(12) United States Patent
Goff et al.

(10) Patent No.: US 8,987,303 B2
(45) Date of Patent: Mar. 24, 2015

(54) AMPK-ACTIVATING HETEROCYCLIC COMPOUNDS AND METHODS FOR USING THE SAME

(71) Applicant: Rigel Pharmaceuticals, Inc., South San Francisco, CA (US)

(72) Inventors: Dane Goff, Redwood City, CA (US); Donald Payan, Hillsborough, CA (US); Rajinder Singh, Belmont, CA (US); Simon Shaw, Oakland, CA (US); David Carroll, San Francisco, CA (US); Yasumichi Hitoshi, Brisbane, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 93 days.

(21) Appl. No.: 13/801,030

(22) Filed: Mar. 13, 2013

(65) Prior Publication Data

US 2013/0267701 A1 Oct. 10, 2013

Related U.S. Application Data

(63) Continuation of application No. 13/194,810, filed on Jul. 29, 2011.

(60) Provisional application No. 61/368,928, filed on Jul. 29, 2010.

(51) Int. Cl.

| A61K 31/4427 | (2006.01) |
|---|---|
| C07D 401/14 | (2006.01) |
| C07D 487/04 | (2006.01) |
| C07D 213/82 | (2006.01) |
| C07D 401/06 | (2006.01) |
| C07D 401/12 | (2006.01) |
| C07D 405/14 | (2006.01) |
| C07D 409/12 | (2006.01) |
| C07D 409/14 | (2006.01) |
| C07D 413/14 | (2006.01) |
| C07D 417/14 | (2006.01) |
| C07D 451/06 | (2006.01) |
| C07D 471/10 | (2006.01) |
| C07D 495/04 | (2006.01) |
| C07D 405/12 | (2006.01) |
| C07D 213/81 | (2006.01) |
| C07D 213/56 | (2006.01) |

(52) U.S. Cl.
CPC ............ *C07D 487/04* (2013.01); *C07D 213/82* (2013.01); *C07D 401/06* (2013.01); *C07D 401/12* (2013.01); *C07D 401/14* (2013.01); *C07D 405/14* (2013.01); *C07D 409/12* (2013.01); *C07D 409/14* (2013.01); *C07D 413/14* (2013.01); *C07D 417/14* (2013.01); *C07D 451/06* (2013.01); *C07D 471/10* (2013.01); *C07D 495/04* (2013.01); *C07D 405/12* (2013.01); *C07D 213/81* (2013.01); *C07D 213/56* (2013.01)

USPC ........... 514/318; 546/184; 546/186; 546/187; 514/315; 514/316

(58) Field of Classification Search
CPC .......................... A61K 31/4427; C07D 401/14
USPC .......... 546/184, 186, 187; 514/315, 316, 317, 514/318
See application file for complete search history.

(56) References Cited

U.S. PATENT DOCUMENTS

| 8,569,340 B2 * | 10/2013 | Hong et al. ................... 514/316 |
|---|---|---|
| 2009/0163511 A1 | 6/2009 | Darwish et al. |
| 2009/0170829 A1 | 7/2009 | Hong et al. |
| 2009/0186894 A1 | 7/2009 | Singh et al. |
| 2009/0275609 A1 | 11/2009 | Yu et al. |
| 2010/0190802 A1 | 7/2010 | Darwish et al. |
| 2012/0028954 A1 | 2/2012 | Goff |
| 2013/0203987 A1 | 8/2013 | Goff |
| 2013/0267702 A1 | 10/2013 | Goff |

FOREIGN PATENT DOCUMENTS

| EP | 1669350 A1 | 6/2006 |
|---|---|---|
| EP | 1932834 A1 | 6/2008 |
| WO | 2005/014571 A1 | 2/2005 |
| WO | 2009/026204 A1 | 2/2009 |
| WO | 2009/132136 A1 | 10/2009 |

OTHER PUBLICATIONS

Fairlamb, et al., "Alkoxy- and amidocarbonylation of functionalised aryl and heteroaryl halides catalysed by a Bedford palladacycle and dppf: a comparison with the primary Pd(ii) precursos (PhCN)2PdCl2 and Pd(OAc)2", Dalton Transactions, No. 8, Jan. 1, 2007, p. 859.

(Continued)

*Primary Examiner* — Golam M M Shameem
(74) *Attorney, Agent, or Firm* — McDonnell Boehnen Hulbert & Berghoff LLP; Travis Young

(57) ABSTRACT

Disclosed are substituted pyridine compounds as well as pharmaceutical compositions and methods of use. One embodiment is a compound having the structure

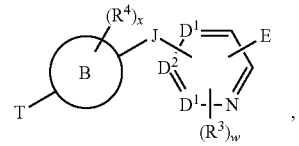

wherein E, J, T, the ring system denoted by "B", T, $R^3$, $R^4$, w and x are as described herein. In certain embodiments, a compound disclosed herein activates the AMPK pathway, and can be used to treat metabolism-related disorders and conditions.

24 Claims, No Drawings

(56) References Cited

OTHER PUBLICATIONS

Guo, et al., "A novel method for the mild and selective amidation of diesters and the amidation of monoesters," Tetrahedron Letters, Elsevier, Amsterdam, NL, vol. 42, No. 10, Mar. 4, 2011, pp. 1843-1845.

Database Registry [Online] Chemical Abstracts Service, Columbus, Ohio, US, Registry Nos. 548781-51-7, 548781-09-5 and 548779-43-7 (Jul. 16, 2003); 548468-29-7, 548456-28-6, 548451-66-7, 548440-29-5 and 548437-90-7 (Jul. 15, 2003); 547724-15-2 and 547712-96-9 (Jul. 14, 2003); and 546118-92-7, 546092-83-5, 546092-74-4 and 546082-00-2 (Jul. 11, 2003).

Wu, et al., "Novel 2,2-Bipyridine Ligand for Palladium-Catalyzed Regioselective Carbonylation," Organic Letters, vol. 1, No. 5, Sep. 1, 1999, pp. 745-747.

\* cited by examiner

AMPK-ACTIVATING HETEROCYCLIC COMPOUNDS AND METHODS FOR USING THE SAME

CROSS-REFERENCE TO RELATED APPLICATIONS

This application is a continuation of U.S. patent application Ser. No. 13/194,810, filed Jul. 29, 2011, which in turn claims the benefit of the earlier filing date of U.S. Provisional Patent Application Ser. No. 61/368,928, filed Jul. 29, 2010, each of which is hereby incorporated herein by reference in its entirety.

BACKGROUND

1. Field

This disclosure relates generally to compounds, pharmaceutical compositions and methods of use of the compounds and compositions containing them. This disclosure relates more particularly to certain substituted pyridine compounds and pharmaceutical compositions thereof, and to methods of treating and preventing metabolic disorders such as type II diabetes, atherosclerosis and cardiovascular disease using certain substituted pyridine compounds.

2. Technical Background

The kinase 5"-AMP-activated protein kinase (AMPK) is well established as an important sensor and regulator of cellular energy homeostasis. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Activation of the AMPK pathway improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, activation of the AMPK pathway decreases glycogen concentration by reducing the activity of glycogen synthase. Activation of the AMPK pathway also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis.

What is needed are compounds, pharmaceutical compositions and methods of using them to treat disease states wherein AMPK activation is beneficial, such as type II diabetes, atherosclerosis and cardiovascular disease.

SUMMARY

Disclosed herein are compounds having structural formula (I)

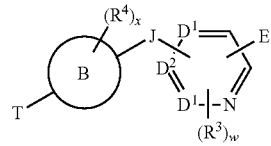

and pharmaceutically acceptable salts, prodrugs and N-oxides thereof (and solvates and hydrates thereof), in which
  0 or 1 of $D^1$, $D^2$ and $D^3$ is N, with the others independently being CH or C substituted by one of the w $R^3$;
  E is —$R^2$, —C(O)$NR^1R^2$, —$NR^1R^2$ or —$NR^1C(O)R^2$, in which $R^1$ and $R^2$ together with the nitrogen to which they are bound form Hca, or $R^1$ is H, —($C_1$-$C_4$ alkyl), —C(O)—($C_1$-$C_4$ alkyl) or —C(O)O—($C_1$-$C_4$ alkyl), and $R^2$ is —C(O)Hca, —($C_0$-$C_3$ alkyl)-Ar, —($C_0$-$C_3$ alkyl)-Het, —($C_0$-$C_3$ alkyl)-Cak or —($C_0$-$C_3$ alkyl)-Hca;
  each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;
  w is 0, 1, 2 or 3;
  each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^4$ on the same carbon optionally combine to form oxo, and two $R^4$ on different carbons optionally combine to form a —($C_0$-$C_4$ alkylene)- bridge;
  x is 0, 1, 2, 3 or 4;
  J is absent, —C(O)—, —$NR^{13}$—, —$NR^{13}C(O)$— or —C(O)$NR^{13}$—, in which $R^{13}$ is selected from —H, —($C_1$-$C_4$ alkyl), —C(O)—($C_1$-$C_4$ alkyl) and —C(O)O—($C_1$-$C_4$ alkyl);
the ring system denoted by "B" is absent, arylene, heteroarylene,

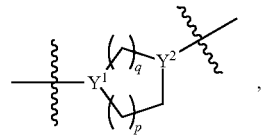

wherein each of $Y^1$ and $Y^2$ is N, C or CH, provided that at least one of $Y^1$ and $Y^2$ is N, p is 0, 1, 2, 3 or 4, q is 1, 2, 3 or 4, and the sum of p and q is 1, 2, 3, 4, 5 or 6, or

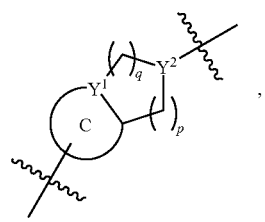

wherein $Y^1$ is N or C and $Y^2$ is N, C or CH, provided that at least one of $Y^1$ and $Y^2$ is N, the ring system denoted by "C" is an arylene or a heteroarylene, p is 0, 1, 2, 3 or 4, q is 1, 2, 3 or 4, and the sum of p and q is 1, 2, 3, 4, 5 or 6;

T is H, —($C_1$-$C_6$ alkyl), —($C_1$-$C_6$ alkyl)-$R^{23}$ in which $R^{23}$ is Het or Ar and in which one or more non-adjacent carbons of the alkyl is optionally replaced by —O— or —S—, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$ or

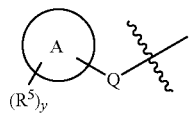

wherein

Q is —O—($C_0$-$C_3$ alkyl)-, —S(O)$_2$—, -L- or ($C_0$-$C_3$ alkyl)-, in which each carbon of the —($C_0$-$C_3$ alkyl)- is optionally and independently substituted with one or two $R^{16}$;

the ring system denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$N_3$, —$SF_5$, —$NO_2$ and —CN; and y is 0, 1, 2, 3 or 4;

in which each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —S(O)$_{0-2}$—, —C(O)O—, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9$SO$_2$—, —SO$_2$$NR^9$— and —$NR^9$SO$_2$$NR^9$—, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted.

Also disclosed herein are pharmaceutical compositions. Examples of such compositions include those having at least one pharmaceutically acceptable carrier, diluent or excipient; and a compound, pharmaceutically acceptable salt, prodrug or N-oxide (or solvate or hydrate) disclosed herein.

Another aspect of the present disclosure includes methods for modulating metabolism in subjects. Accordingly, also disclosed are methods for treating metabolic disorders using the presently disclosed compounds and pharmaceutical compositions.

Another aspect of the present disclosure includes methods for modulating sphingolipid metabolism, for example modulating ceramide signalling in subjects. In one aspect, modulating sphingolipid metabolism includes modulating ceramidase activity, for example by up-regulating ceramidase function. Accordingly, also disclosed are methods for treating ceramide-linked diseases and disorders using the presently disclosed compounds and pharmaceutical compositions.

DETAILED DESCRIPTION

One aspect of the disclosure provides compounds having structural formula (I):

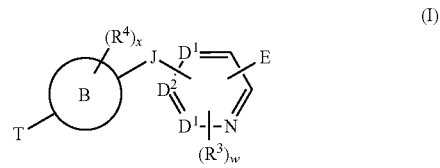

and pharmaceutically acceptable salts, prodrugs and N-oxides thereof (and solvates and hydrates thereof), in which 0 or 1 of $D^1$, $D^2$ and $D^3$ is N, with the others independently being CH or C substituted by one of the w $R^3$;

E is —$R^2$, —C(O)$NR^1R^2$, —$NR^1R^2$ or —$NR^1$C(O)$R^2$, in which $R^1$ and $R^2$ together with the nitrogen to which they are bound form Hca, or $R^1$ is H, —($C_1$-$C_4$ alkyl), —C(O)—($C_1$-$C_4$ alkyl) or —C(O)O—($C_1$-$C_4$ alkyl), and $R^2$ is —C(O)Hca, —($C_0$-$C_3$ alkyl)-Ar, —($C_1$-$C_3$ alkyl)-O—Ar, —($C_1$-$C_3$ alkyl)-O-Het, —($C_0$-$C_3$ alkyl)-Het, —($C_0$-$C_3$ alkyl)-Cak or —($C_0$-$C_3$ alkyl)-Hca;

each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;

w is 0, 1, 2 or 3;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^4$ on the same carbon optionally combine to form oxo, and two $R^4$ on different carbons optionally combine to form a —($C_0$-$C_4$ alkylene)- bridge;

x is 0, 1, 2, 3 or 4;

J is absent, —C(O)—, —$NR^{13}$—, —$NR^{13}$C(O)— or —C(O)$NR^{13}$—, in which $R^{13}$ is selected from —H, —($C_1$-$C_4$ alkyl), —C(O)—($C_1$-$C_4$ alkyl) and —C(O)O—($C_1$-$C_4$ alkyl);

the ring system denoted by "B" is absent, arylene, heteroarylene.

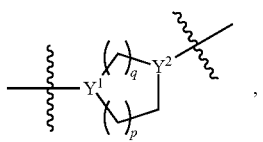

wherein each of $Y^1$ and $Y^2$ is N, C or CH, provided that at least one of $Y^1$ and $Y^2$ is N; p is 0, 1, 2, 3 or 4, q is 1, 2, 3 or 4, and the sum of p and q is 1, 2, 3, 4, 5 or 6, or

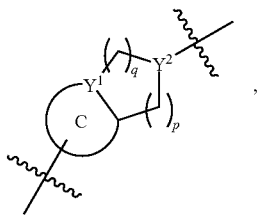

wherein $Y^1$ is N or C and $Y^2$ is N, C or CH, provided that at least one of $Y^1$ and $Y^2$ is N, the ring system denoted by "C" is an arylene or a heteroarylene, p is 0, 1, 2, 3 or 4, q is 1, 2, 3 or 4, and the sum of p and q is 1, 2, 3, 4, 5 or 6;

T is H, —($C_1$-$C_6$ alkyl), —($C_1$-$C_6$ alkyl)-$R^{23}$ in which $R^{23}$ is Het or Ar and in which one or more non-adjacent carbons of the alkyl is optionally replaced by —O— or —S—, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$ or

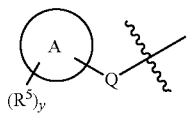

wherein
Q is —O—($C_0$-$C_3$ alkyl)-, —S(O)$_2$—, -L- or ($C_0$-$C_3$ alkyl)-, in which each carbon of the —($C_0$-$C_3$ alkyl)- is optionally and independently substituted with one or two $R^{16}$;
the ring system denoted by "A" is heteroaryl, aryl, cycloalkyl or heterocycloalkyl;
each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$N_3$, —$SF_5$, —$NO_2$ and —CN; and
y is 0, 1, 2, 3 or 4;
in which
each L is independently selected from —$NR^9$C(O)O—, —OC(O)$NR^9$—, —$NR^9$C(O)$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9SO_2$—, —SO$_2NR^9$— and —$NR^9SO_2NR^9$—, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

In certain embodiments of the presently disclosed compounds of structural formula (I) as described above, the compound has structural formula (II):

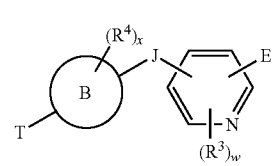

(II)

and pharmaceutically acceptable salts, prodrugs and N-oxides thereof (and solvates and hydrates thereof), in which E is —$R^2$, —C(O)$NR^1R^2$, —$NR^1R^2$, —$NR^1$C(O)$R^2$, in which $R^1$ and $R^2$ together with the nitrogen to which they are bound form Hca, or $R^1$ is H, —($C_1$-$C_4$ alkyl), —C(O)—($C_1$-$C_4$ alkyl) or —C(O)O—($C_1$-$C_4$ alkyl), and $R^2$ is —C(O)Hca, —($C_0$-$C_3$ alkyl)-Ar, —($C_0$-$C_3$ alkyl)-Het, —($C_0$-$C_3$ alkyl)-Cak or —($C_0$-$C_3$ alkyl)-Hca;

each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;

w is 0, 1, 2 or 3;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^4$ on the same carbon optionally combine to form oxo;

x is 0, 1, 2, 3 or 4;

J is absent, —C(O)—, —$NR^{13}$—, —$NR^{13}$C(O)— or —C(O)$NR^{13}$—, in which $R^{13}$ is selected from —H, —($C_1$-$C_4$ alkyl), —C(O)—($C_1$-$C_4$ alkyl) and —C(O)O—($C_1$-$C_4$ alkyl);

the ring system denoted by "B" is absent, arylene, heteroarylene, or

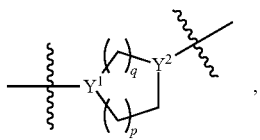

wherein each of $Y^1$ and $Y^2$ is N, C or CH, provided that at least one of $Y^1$ and $Y^2$ is N; p is 0, 1, 2, 3 or 4, q is 1, 2, 3 or 4, and the sum of p and q is 2, 3, 4, 5 or 6;

T is H, —($C_1$-$C_6$ alkyl), —($C_1$-$C_6$ alkyl)-$R^{23}$ in which $R^{23}$ is Het or Ar and in which one or more non-adjacent carbons of the alkyl is optionally replaced by —O— or —S—, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$ or

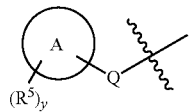

wherein
Q is —O—($C_0$-$C_3$ alkyl)-, —S(O)$_2$—, -L- or ($C_0$-$C_3$ alkyl)-, in which each carbon of the —($C_0$-$C_3$ alkyl)- is optionally and independently substituted with one or two $R^{16}$.

the ring system denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN; and y is 0, 1, 2, 3 or 4;

in which
each L is independently selected
from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9SO_2$—, —$SO_2NR^9$— and —$NR^9SO_2NR^9$—, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted.

In certain embodiments of the presently disclosed compounds of structural formula (I), the compound is not 5-(4-(4-cyanobenzyl)piperazine-1-carbonyl)-N-(1-(4-cyanobenzyl)piperidin-4-yl)picolinamide;

N-(1-(4-cyanobenzyl)piperidin-4-yl)-5-(4-(4-fluorobenzyl)piperazine-1-carbonyl)picolinamide;

N-(1-(4-cyanobenzyl)piperidin-4-yl)-5-(4-(4-(trifluoromethyl)benzyl)piperazine-1-carbon yl)picolinamide (S)-5-(4-(4-chlorophenyl)piperazine-1-carbonyl)-N-(1-(4-fluorobenzyl)pyrrolidin-3-yl)picolinamide;

(S)-5-(4-(4-chlorophenyl)piperazine-1-carbonyl)-N-(1-(pyridin-4-ylmethyl)pyrrolidin-3-yl)picolinamide;

(S)-5-(4-(4-chlorophenyl)piperazine-1-carbonyl)-N-(1-(4-cyanobenzyl)pyrrolidin-3-yl)picolinamide;

N-(1-(4-chlorobenzyl)pyrrolidin-3-yl)-5-(4-(4-chlorophenyl)piperazine-1-carbonyl)picolinamide; or 5-(4-(4-chlorophenyl)piperazine-1-carbonyl)-N-(1-(4-(trifluoromethyl)benzyl)pyrrolidin-3-yl)picolinamide.

In one embodiment, the presently disclosed compounds are not compounds disclosed in Darwish et al., International Patent Application no. PCT/US10/22411, filed Jan. 28, 2010, which is hereby incorporated by reference in its entirety.

In certain embodiments of the presently disclosed compounds of structural formula (I) and (II) as described above, $D^1$, $D^2$ and $D^3$ are independently CH or C substituted by one of the w $R^3$. In other embodiments, $D^1$ is N and $D^2$ and $D^3$ are independently CH or C substituted by one of the w $R^3$. In other embodiments, $D^2$ is N and $D^1$ and $D^3$ are independently CH or C substituted by one of the w $R^3$. In other embodiments, $D^3$ is N and $D^1$ and $D^2$ are independently CH or C substituted by one of the w $R^3$.

In certain embodiments of the presently disclosed compounds of structural formula (I) and (II) as described above, J is —C(O)—, —$NR^{13}$—, —$NR^{13}$C(O)— or —C(O)$NR^{13}$—, in which $R^{13}$ is selected from —H, —($C_1$-$C_4$ alkyl), —C(O)—($C_1$-$C_4$ alkyl) and —C(O)O—($C_1$-$C_4$ alkyl). In certain embodiments of the compounds of structural formula (I) and (II) as described above, $R^{13}$ is H. In other embodiments, $R^{13}$ is unsubstituted ($C_1$-$C_4$ alkyl). In certain embodiments of the compounds of structural formula (I) and (II) as described above, J is —C(O)—. In other embodiments, J is —$NR^{13}$— (for example, —NH—). In still other embodiments, J is —$NR^{13}$C(O)— (for example, —NHC(O)—). In other embodiments, J is —C(O)$NR^{13}$— (for example, —C(O)NH—). In still other embodiments, J is absent.

In the presently disclosed compounds of structural formula (I) and (II) as described above, the ring system denoted by "B" is absent, arylene, heteroarylene,

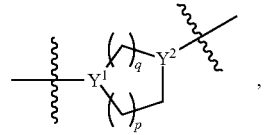

in which each of $Y^1$ and $Y^2$ is N, C or CH, provided that at least one of $Y^1$ and $Y^2$ is N; p is 0, 1, 2, 3 or 4, q is 1, 2, 3 or 4, and the sum of p and q is 1, 2, 3, 4, 5 or 6,

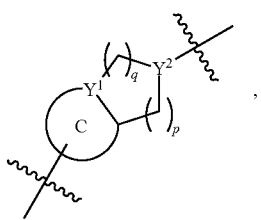

wherein $Y^1$ is N or C and $Y^2$ is N, C or CH, provided that at least one of $Y^1$ and $Y^2$ is N, the ring system denoted by "C" is an arylene or a heteroarylene, p is 0, 1, 2, 3 or 4, q is 1, 2, 3 or 4, and the sum of p and q is 1, 2, 3, 4, 5 or 6.

For example, in certain embodiments of the presently disclosed compounds of structural formula (I) and (II) as described above, (for example, those described below with respect to structural formula (IV)), the ring system denoted by "B" is arylene or heteroarylene. In certain embodiments, the ring system denoted by "B" is arylene (for example, phenylene such as 1,4-phenylene). In other embodiments, the ring system denoted by "B" is heteroarylene (for example, 1H-pyrazolylene, 1H-1,2,3-triazolylene, pyridylene, furanylene or thienylene). In certain embodiments of the presently disclosed compounds of structural formula (I) as described above, the ring system denoted by "B" is monocyclic arylene or heteroarylene.

In certain embodiments of the presently disclosed compounds of structural formula (I) and (II) as described above, the ring system denoted by "B" is absent.

In certain embodiments of the presently disclosed compounds of structural formula (I) and (II) as described above, the ring system denoted by "B" is

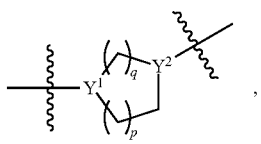

wherein each of $Y^1$ and $Y^2$ is N, C or CH, provided that at least one of $Y^1$ and $Y^2$ is N; p is 0, 1, 2, 3 or 4, q is 1, 2, 3 or 4, and the sum of p and q is 2, 3, 4, 5 or 6. For example, in certain embodiments, $Y^1$ is N and $Y^2$ is C or CH. (When $Y^1$ or $Y^2$ is C, it is substituted by one of the x $R^4$.) In other embodiments, $Y^1$ is C or CH and $Y^2$ is N. In other embodiments, $Y^1$ is CF and $Y^2$ is N. In other embodiments, $Y^1$ and $Y^2$ are each N. In certain embodiments of the presently disclosed compounds of structural formula (I) and (II) as described above, p is 1 and q is 2. For example, in one embodiment, the ring system denoted by "B" is a piperidine linked to the T moiety through its nitrogen atom. In another embodiment, the ring system denoted by "B" is a piperidine linked to the J moiety through its piperidine nitrogen. In another embodiment, the ring system denoted by "B" is a piperazine. In other embodiments of the presently disclosed compounds of structural formula (I) and (II) as described above, p is 1 and q is 1. For example, in certain embodiments, the ring system denoted by "B" is a pyrrolidine, for example, linked to the J moiety through its pyrrolidine nitrogen. In still other embodiments of the presently disclosed compounds of structural formula (I) and (II) as described above, p is 0 and q is 1. For example, in certain embodiments, the ring system denoted by "B" is an azetidine, for example, linked to the J moiety through its azetidine nitrogen.

In certain embodiments of the presently disclosed compounds of structural formula (I) as described above, the ring system denoted by "B" is

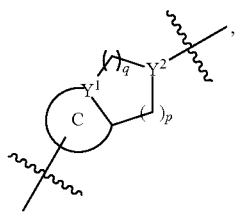

wherein $Y^1$ is N or C and $Y^2$ is N, C or CH, provided that at least one of $Y^1$ and $Y^2$ is N, the ring system denoted by "C" is an arylene or a heteroarylene, p is 0, 1, 2, 3 or 4, q is 1, 2, 3 or 4, and the sum of p and q is 1, 2, 3, 4, 5 or 6. For example, in certain embodiments, $Y^1$ is N and $Y^2$ is C or CH. (When $Y^2$ is C, it can be substituted by one of the x $R^4$.) In other embodiments, $Y^1$ is C and $Y^2$ is N. In other embodiments, $Y^1$ and $Y^2$ are each N. In certain embodiments of the presently disclosed compounds of structural formula (I) and (II) as described above, p is 1 and q is 2. In other embodiments of the presently disclosed compounds of structural formula (I) as described above, p is 1 and q is 1. The heteroarylene can be, for example, a pyridine, a pyrazine, a pyrimidine, a triazine, a pyrrole, a pyrazole, an imidazole, or a triazole. In one example, the ring system denoted by "B" is

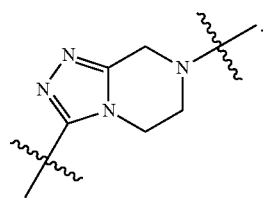 [SMILES: *c1nnc2n1CCN(*)C2]

In the presently disclosed compounds of structural formula (I) and (II) as described above, x, the number of substituents on the ring system denoted by "B", is 0, 1, 2, 3 or 4. In one embodiment, x is 0, 1, 2 or 3. For example, in certain embodiments, x is 0. In other embodiments, x can be 1 or 2.

In certain embodiments of the presently disclosed compounds of structural formula (I) and (II) as described above (for example, when the ring system denoted by "B" is

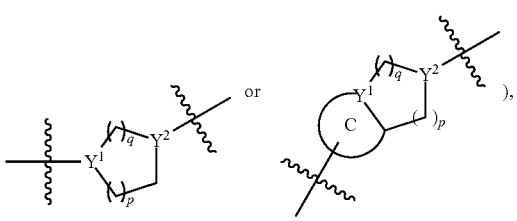

two $R^4$ groups combine to form an oxo. The oxo can be bound, for example, at the position alpha to a nitrogen atom of the ring system. In other embodiments, no two $R^4$ groups combine to form an oxo.

In certain embodiments of the presently disclosed compounds of structural formula (I) and (II) as described above (for example, when the ring system denoted by "B" is

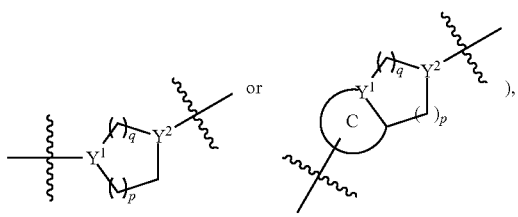

two R$^4$ groups on different carbons combine to form a —(C$_0$-C$_4$ alkylene)- bridge. The alkylene bridge can form bicyclic system, for example, a [3.2.1] system, a [3.2.0] system, a [3.1.0] system, [2.2.2] system, a [2.2.1] system, a [2.1.1] system, a [2.2.0] system or a [2.1.0] system. For example, in one embodiment, ring system denoted by "B" is substituted with R$^4$ groups to form

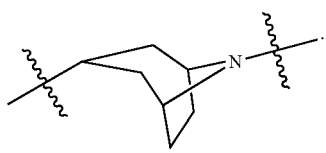 [SMILES: *C1CC2CCC(C1)N2*]

In certain embodiments the —(C$_0$-C$_4$ alkylene)- bridge is unsubstituted. In other embodiments, it is substituted only with one or more halogens.

In certain embodiments of the presently disclosed compounds of structural formula (I) and (II) as described above (for example, when the ring system denoted by "B" is

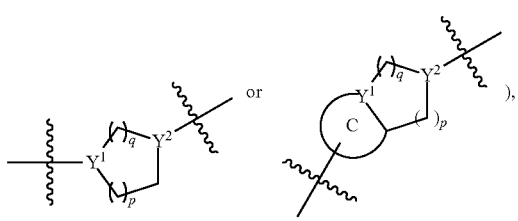

two R$^4$ moieties (for example, on the same carbon) are (C$_1$-C$_4$ alkyl) (for example, methyl), as described below.

In certain embodiments of the presently disclosed compounds of structural formula (I) and (II) as described above, when x is 4, not all four R$^4$ groups are (C$_1$-C$_6$ alkyl).

In certain embodiments of the presently disclosed compounds of structural formula (I) and (II) as described above, each R$^4$ is independently selected from —(C$_1$-C$_6$ alkyl), —(C$_1$-C$_6$ haloalkyl) (for example, difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O) R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)— (C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^4$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O) R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)— (C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, each R$^4$ is independently halogen (e.g., F, Cl), unsubstituted (C$_1$-C$_6$ alkoxy) (e.g., methoxy, ethoxy), —(C$_1$-C$_6$ haloalkoxy) (e.g., trifluoromethoxy), —SH, —S(unsubstituted C$_1$-C$_6$ alkyl), —S(C$_1$-C$_6$ haloalkyl), —OH, —CN, —NO$_2$, —NH$_2$, —NH(unsubstituted C$_1$-C$_4$ alkyl), —N(unsubstituted C$_1$-C$_4$ alkyl)$_2$, —N$_3$, —SF$_5$, —C(O)—NH$_2$, C(O)NH(unsubstituted C$_1$-C$_4$ alkyl), C(O)N(unsubstituted C$_1$-C$_4$ alkyl)$_2$, —C(O)OH, C(O)O(unsubstituted C$_1$-C$_6$ alkyl), —(NH)$_{0-1}$SO$_2$R$^{33}$, —(NH)$_{0-1}$COR$^{33}$, heterocycloalkyl optionally substituted with an (unsubstituted C$_1$-C$_6$ alkyl) and heteroaryl optionally substituted with an (unsubstituted C$_1$-C$_6$ alkyl), in which each R$^{33}$ is (unsubstituted C$_1$-C$_6$ alkyl), (C$_1$-C$_6$ haloalkyl(unsubstituted C$_3$-C$_8$ cycloalkyl) or (C$_3$-C$_8$ heterocycloalkyl) optionally substituted with an (unsubstituted C$_1$-C$_6$ alkyl), and two R$_4$ optionally come together to form oxo. In certain embodiments, each R$^4$ is independently methyl, ethyl, n-propyl, iso-propyl, trifluoromethyl, pentafluoroethyl, acetyl, —NH$_2$, —OH, methoxy, ethoxy, trifluoromethoxy, —SO$_2$Me, -halogen, —NO$_2$ or —CN, and two R$_4$ optionally come together to form oxo.

In the presently disclosed compounds of structural formula (I) and (II) as described above, E is —R$^2$, —C(O)NR$^1$R$^2$, —NR$^1$R$^2$ or —NR$^1$C(O)R$^2$, in which R$^1$ and R$^2$ together with the nitrogen to which they are bound form Hca, or R$^1$ is H, —(C$_1$-C$_4$ alkyl), —C(O)—(C$_1$-C$_4$ alkyl) or —C(O)O—(C$_1$-C$_4$ alkyl); and R$^2$ is —C(O)Hca, —(C$_0$-C$_3$ alkyl)-Ar, —(C$_0$-C$_3$ alkyl)-Het, —(C$_0$-C$_3$ alkyl)-Cak or —(C$_0$-C$_3$ alkyl)-Hca. In certain embodiments, E is —C(O)NR$^1$R$^2$. In other embodiments, E is —NR$^1$R$^2$. In other embodiments, E is —R$^2$. In still other embodiments, E is —NR$^1$C(O)R$^2$.

In certain embodiments of the compounds of structural formula (I) and (II) as described above, R$^1$ is H, —(C$_1$-C$_4$ alkyl), —C(O)—(C$_1$-C$_4$ alkyl) or —C(O)O—(C$_1$-C$_4$ alkyl); and R$^2$ is —C(O)Hca, —(C$_0$-C$_3$ alkyl)-Ar, —(C$_0$-C$_3$ alkyl)-Het, —(C$_0$-C$_3$ alkyl)-Cak or —(C$_0$-C$_3$ alkyl)-Hca. In certain of the compounds of structural formula (I) as described above, R$^1$ is H. In other embodiments, R$^1$ is (C$_1$-C$_4$ alkyl), for example methyl, ethyl, n-propyl or isopropyl. In still other embodiments, R$^1$ is —C(O)—O—(C$_1$-C$_4$ alkyl), for example —C(O)OCH$_3$ or —C(O)—O-t-butyl. In certain embodiments, no alkyl of R$^1$ is substituted with an aryl-, heteroaryl-, cycloalkyl- or heterocycloalkyl-containing group. In certain embodiments, any alkyl of R$^1$ is unsubstituted.

In certain of the compounds of structural formula (I) and (II) as described above, R$^2$ is -Hca. In certain embodiments, R$^2$ is an optionally-substituted monocyclic heterocycloalkyl. By way of example, such optionally substituted R$^2$ moieties include, without limitation, -(optionally-substituted azetidinyl), -(optionally-substituted pyrrolidinyl), -(optionally-substituted piperidinyl), -(optionally-substituted piperazinyl) or -(optionally-substituted azepanyl). For example, in one embodiment, R$^2$ can be -(optionally substituted piperidinyl) or -(optionally substituted pyrrolidinyl). In one embodiment, R$^2$ is -(optionally substituted piperidinyl). In another embodiment, R$^2$ is -(optionally substituted pyrrolidinyl). In another embodiment, R$^2$ is -(optionally substituted piperazinyl).

In certain particular embodiments of the presently disclosed compounds of structural formula (I) and (II) as described above, R$^2$ is -(optionally-substituted azetidin-3-yl), -(optionally substituted piperidin-4-yl), -(optionally substituted piperazin-4-yl), -(optionally substituted pyrrolidin-3-yl) or -(optionally-substituted azepan-4-yl). For example, in one embodiment, $R^2$ is -(optionally substituted piperidin-4-yl).

In another embodiment, $R^2$ is -(optionally substituted pyrrolidin-3-yl). In another embodiment, $R^2$ is -(optionally substituted piperazin-4-yl).

In certain particular embodiments, when $R^2$ is -(optionally substituted piperidin-4-yl), it is unsubstituted at its 2- and 3-positions.

In other embodiments, when $R^2$ is -(optionally substituted piperidin-4-yl), it is substituted with F at a 3-position. For example, $R^2$ can be

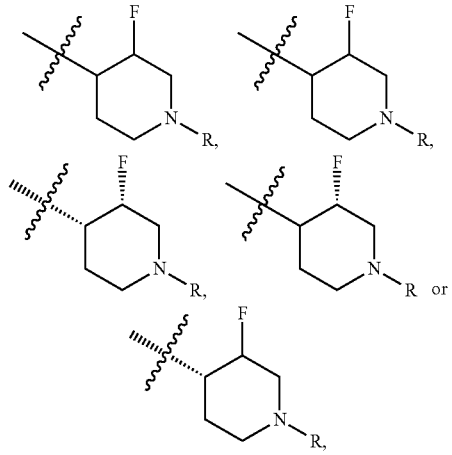

in which the R group is a further substituent, for example, as described below. Such compounds can be provided as mixtures of diastereomers or enantiomers, or in diastereomerically and/or enantiomerically enriched form. In certain embodiments, the compound is provided in substantially diastereomerically pure form, for example, as substantially diastereomerically pure cis compound, or diastereomerically pure trans compound. In certain embodiments, a compound is provided in substantially enantiomerically pure form.

In certain embodiments of the presently disclosed compounds of structural formula (I) and (II) as described above, the azetidinyl, pyrrolidinyl, piperidinyl, piperazinyl and azepanyl $R^2$ moieties described above are substituted, for example, at their 1-positions. In certain alternative embodiments, they can be substituted at their 4-positions (e.g., when a piperidin-1-yl) or 3 positions (e.g., when a pyrrolidin-5-yl). For example, in one embodiment, $R^2$ is substituted (e.g., at its 1-position) with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl, piperazinyl or azepanyl $R^2$ moiety is substituted (e.g., at its 1-position) with an optionally substituted benzyl or an optionally substituted phenyl. In another embodiment, the azetidinyl, pyrrolidinyl, piperidinyl, piperazinyl or azepanyl $R^2$ moiety is substituted (e.g., at its 1-position) with a benzyl substituted with an electron withdrawing group; or a phenyl substituted with an electron withdrawing group. For example, the benzyl or phenyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), SF$_5$, NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl, piperazinyl or azepanyl $R^2$ moiety is substituted (e.g., at its 1-position) with an unsubstituted benzyl or an unsubstituted phenyl. In other embodiments, the azetidinyl, pyrrolidinyl, piperidinyl, piperazinyl or azepanyl $R^2$ moiety is substituted (e.g., at its 1-position) with —CH(CH$_3$)Ar, CH(C(O)OCH$_3$)Ar or —C(CH$_3$)$_2$Ar.

In other embodiments of the compounds disclosed herein of structural formula (I) and (II) as described above, the azetidinyl, pyrrolidinyl, piperidinyl, piperazinyl or azepanyl $R^2$ moiety is substituted (e.g., at its 1-position) with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl, piperazinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein of structural formula (I) and (II) as described above, the azetidinyl, pyrrolidinyl, piperidinyl, piperazinyl or azepanyl $R^2$ moiety is substituted (e.g., at its 1-position) with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—NR$^9$—, such as —C(O)—NH—. In other embodiments of the presently disclosed compounds of structural formula (I) as described above, the azetidinyl, pyrrolidinyl, piperidinyl, piperazinyl or azepanyl $R^2$ moiety is substituted (e.g., at its 1-position) with —C(O)—O($C_0$-$C_6$ alkyl), —C(O)—Het, —C(O)—Ar, —S(O)$_2$-Het, —S(O)$_2$—Ar or —S(O)$_2$—O ($C_0$-$C_6$ alkyl), in which Ar and Het can be, for example, as described above with reference to —($C_0$-$C_3$ alkyl)-Ar or —($C_0$-$C_3$ alkyl)-Het. In one embodiment, the azetidinyl, pyrrolidinyl, piperidinyl, piperazinyl or azepanyl $R^2$ moiety is substituted (e.g., at its 1-position) with —C(O)—Het or —C(O)—Ar; in another embodiment, it is substituted (e.g., at its 1-position) with —S(O)$_2$-Het or —S(O)$_2$—Ar. For example, in certain embodiments, the azetidinyl, pyrrolidinyl, piperidinyl, piperazinyl or azepanyl $R^2$ moiety is substituted (e.g., at its 1-position) with an optionally-substituted benzoyl (for example, substituted with an electron withdrawing group as described above); or with an optionally-substituted nicotinyl, isonicotinyl or picolinyl (for example, optionally substituted with an electron withdrawing group as described above). In other embodiments, the azetidinyl, pyrrolidinyl, piperidinyl, piperazinyl or azepanyl $R^2$ moiety is substituted (e.g., at its 1-position) with an unsubstituted benzoyl; or an unsubstituted nicotinoyl, isonicotinoyl or picolinoyl.

In other embodiments of the presently disclosed compounds of structural formula (I) and (II) as described above, the azetidinyl, pyrrolidinyl, piperidinyl, piperazinyl or azepanyl $R^2$ moiety is substituted (e.g., at its 1-position) with —($C_0$-$C_3$ alkyl)-Cak, for example -(unsubstituted $C_0$-$C_3$ alkyl)-Cak (e.g, —CH$_2$-Cak) or —C(O)—Cak.

In one embodiment, $R^2$ is not an oxo-substituted heterocycloalkyl. In another embodiment, $R^2$ is not a tetramethyl-substituted heterocycloalkyl.

In certain embodiments of the compounds of structural formula (I) and (II) as described above (for example, those in which E is —C(O)NR$^1$R$^2$), R$^1$ and R$^2$ together with the nitrogen to which they are bound form Hca. In such embodiments, Hca can be, for example, an optionally-substituted piperidinyl, an optionally-substituted pyrrolidinyl, or an optionally-substituted piperazinyl. When R$^1$ and R$^2$ together to form Hca, it can be defined and substituted as described above for R$^2$ wherein it is Hca.

In certain embodiments of the compounds of structural formula (I) and (II) as described above (for example, those in which E is —R$^2$, or —NR$^1$R$^2$), R$^2$ is —C(O)Hca. In certain such embodiments, the Hca is linked to the —C(O)— through a nitrogen. In other such embodiments, the Hca can be linked to the —C(O)— through a carbon atom. The Hca can be defined and substituted, for example, as described above with respect to R$^2$ when it is Hca.

In certain embodiments of the compounds of structural formula (I) as described above (for example, those in which E is —R$^2$, —NR$^1$R$^2$ or —C(O)NR$^1$R$^2$), R$^2$ is —(C$_0$-C$_3$ alkyl)-Ar or —(C$_0$-C$_3$ alkyl)-Het. For example, in certain embodiments, R$^2$ is Ar, in which the Ar can be, for example, monocyclic, such as optionally-substituted phenyl. In other embodiments, R$^2$ is —(C$_1$-C$_3$ alkyl)-(optionally-substituted phenyl), for example optionally-substituted benzyl. In other embodiments, R$^2$ is Het, in which the Het can be, for example, monocyclic, such as optionally-substituted pyridinyl or optionally-substituted 1H-pyrazolyl. In other embodiments of the compounds of structural formula (I) as described above (for example, those in which E is —C(O)NR$^1$R$^2$), R$^2$ is —(C$_0$-C$_3$ alkyl)-Cak, in which the Cak can be, for example, monocyclic, such as optionally-substituted cyclohexyl. The aryl, heteroaryl or cycloalkyl of R$^2$ can be substituted, for example, as described above with reference to R$^2$ when it is Hca. For example, in certain embodiments, the aryl, heteroaryl or cycloalkyl of R$^2$ is substituted with —(C$_0$-C$_3$ alkyl)-Ar or —(C$_0$-C$_3$ alkyl)-Het, substituted as described above. In other embodiments, the aryl, heteroaryl or cycloalkyl of R$^2$ is substituted with —O—(C$_0$-C$_3$ alkyl)-Ar or —O—(C$_0$-C$_3$ alkyl)-Het. In other embodiments, the aryl, heteroaryl or cycloalkyl of R$^2$ is substituted with an optionally-substituted heterocycloalkyl, such as a mopholin-1-yl, a 4-methylpiperazin-1-yl, or a pyrrolidin-1-yl. The ring system of the R$^2$ moiety can be substituted at any position. For example, in certain embodiments, the ring of a monocyclic R$^2$ moiety is substituted at the 4-position, as counted from the attachment to the central pyridine, pyrazine, pyridazine or pyrimidine, or the nitrogen or carbonyl of the E moiety. In other embodiments, the ring of a monocyclic R$^2$ moiety is substituted at the 3-position, as counted from the attachment to the central pyridine, pyrazine, pyridazine or pyrimidine, or the nitrogen or carbonyl of the E moiety.

In certain embodiments of the presently disclosed compounds of structural formula (I) and (II) as described above, the compound has structural formula (III)

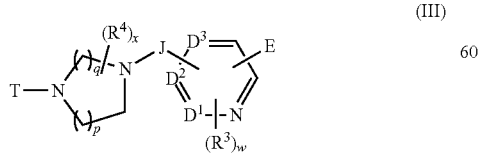

(III)

in which E is —R$^2$, —C(O)NR$^1$R$^2$, —NR$^1$R$^2$ or —NR$^1$C(O)R$^2$, in which R$^1$ and R$^2$ together with the nitrogen to which they are bound form Hca, or R$^1$ is H, —(C$_1$-C$_4$ alkyl), —C(O)—(C$_1$-C$_4$ alkyl) or —C(O)O—(C$_1$-C$_4$ alkyl); and R$^2$ is —C(O)Hca, —(C$_0$-C$_3$ alkyl)-Ar, —(C$_0$-C$_3$ alkyl)-Het, —(C$_0$-C$_3$ alkyl)-Cak or —(C$_0$-C$_3$ alkyl)-Hca. All other variables are as described above with reference to structural formulae (I) and (II). In certain such embodiments, E is R$^2$, —NR$^1$R$^2$ or —NR$^1$C(O)R$^2$. In certain embodiments of the compounds of structural formula (III), J is —C(O)—.

In certain embodiments of compounds of structural formulae (I) —(III) as described above, (for example, those in which E is —C(O)NR$^1$R$^2$), when R$^2$ is Hca (for example, pyrrolidine or piperidine), it is substituted with at least one fluorine, and further optionally substituted, for example, as described below. In certain embodiments of compounds of structural formula (III) (for example, those in which E is —C(O)NR$^1$R$^2$), when R$^2$ is Hca (for example, pyrollidine or piperazine), it is substituted (for example, at the nitrogen) with —C(O)—R$^{22}$, —S(O)$_2$—R$^{22}$, —C(O)—Cak, —CH$_2$-Cak, —CH(CH$_3$)—R$^{22}$, —C(CH$_3$)$_2$—R$^{22}$, —CH(C(O)—O (C$_1$-C$_4$ alkyl))Het, in which R$^{22}$ is Ar or Het, and further optionally substituted, for example, as described below.

In certain embodiments of the compounds of structural formulae (I) —(III) as described above, (for example, those in which E is —C(O)NR$^1$R$^2$), R$^1$ and R$^2$ together with the nitrogen to which they are bound form Hca, as described below. For example, R$^1$ and R$^2$ can together to form an optionally substituted piperazine or an optionally-substituted pyrrolidine, as described below. In other embodiments, R$^1$ and R$^2$ together with the nitrogen to which they are bound form an optionally-substituted spirocyclic heterocycloalkyl (for example, 2,8-diazaspiro[4.5]decanyl), as described below.

In certain embodiments of the compounds of structural formulae (I) —(III) as described above, (for example, those in which E is —C(O)NR$^1$Hca), T is H, —C(O)—(C$_1$-C$_6$ alkyl) or (C$_1$-C$_6$ alkyl), for example, as described below. In other embodiments of the compounds of structural formula (III) (for example, those in which E is —C(O)NR$^1$Hca), T is —C(CH$_3$)$_2$Ar, —CH$_2$-Het, -Het, —CH$_2$-Cak or Hca, for example, as described below. In other embodiments of the compounds of structural formula (III) (for example, those in which E

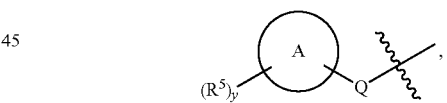

is —C(O)NR$^1$Hca), T is in which Q is —C(O)— or —S(O)$_2$—, for example, as described below.

In certain embodiments of the presently disclosed compounds of structural formula (I) and (II) as described above, the compound has structural formula (IV)

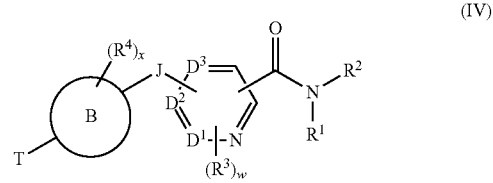

(IV)

in which J is absent, —NR$^{13}$—, —NR$^{13}$C(O)— or —C(O) NR$^{13}$—; and the ring system denoted by "B" is arylene, heteroarylene, or absent, and all other variables are as described with respect to structural formulae (I) —(III). For example, in certain embodiments of the compounds of structural formula (IV) as described above, J is absent. In other embodiments, J is —NR$^{13}$—, such as —NH—. In other embodiments, J is —NR$^{13}$C(O)—, such as —NHC(O)—. In certain embodiments, the ring system denoted by "B" is arylene, such as phenylene); or heteroarylene, such as 1H-pyrazolylene, 1H-1,2,3-triazolylene), with particular examples being described below. In other embodiments, the ring system denoted by "B" is absent, with particular examples being described below. In certain embodiments of the compounds of structural formula (IV), (for example, those in which E is —C(O)NR$^1$R$^2$), R$^2$ is Hca, such as piperidinyl, with particular examples being described below.

In certain embodiments of the presently disclosed compounds of structural formula (I) and (II) as described above, the compound has structural formula (V)

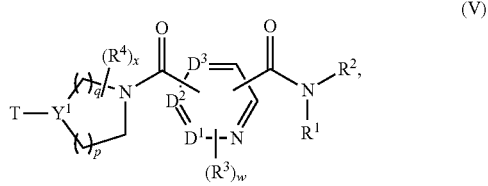

(V)

in which the variables are as described above with reference to structural formulae (I) —(III). In certain embodiments of the compounds of structural formula (V), R$^2$ is Hca (for example, pyrrolidine or piperidine), for example, described below. In other embodiments of the compounds of structural formula (IV), R$^2$ is Cak, such as cyclohexyl, for example, described below.

In certain embodiments of the presently disclosed compounds of structural formula (I) and (II) as described above, the compound has structural formula (VI)

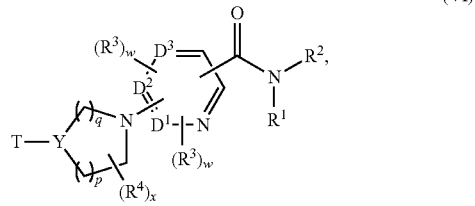

(VI)

in which Y is N, C, CF or CH, and all other variables are as described above with reference to structural formulae (I) —(III). For example, in certain embodiments, Y is N. In other embodiments, Y is CF or CH. In certain embodiments of the compounds of structural formula (VI), p is 1 and q is 2. In other embodiments (for example, when Y is C, CF or CH), q is 1 and p is 1. In certain embodiments of the compounds of structural formula (VI), R$^2$ is Hca, such as pyrrolidine or piperidine.

In certain embodiments of the presently disclosed compounds of structural formula (I) and (II) as described above, the compound has structural formula (VII)

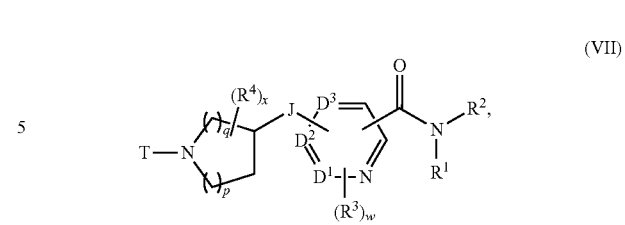

(VII)

in which J is absent, —NR$^{13}$—, —NR$^{13}$C(O)— or —C(O)NR$^{13}$—, and all other variables are as described above with reference to structural formulae (I)(III). For example, in one embodiment, J is —NR$^{13}$—C(O)—. In other embodiments, J is —NR$^{13}$—. In certain embodiments of the compounds of structural formula (VII), p is 1 and q is 2. In other embodiments, q is 1 and p is 1. In other embodiments (for example, when Y is C, CF or CH), q is 1 and p is 0. In certain embodiments of the compounds of structural formula (VII), R$^2$ is Hca, such as pyrrolidine or piperidine, particular examples of which are further described below.

In certain embodiments of the presently disclosed compounds of structural formula (I) and (II) as described above, the compound has structural formula (VIII)

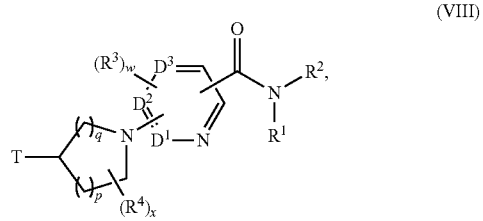

(VIII)

in which the variables are as described above with reference to structural formulae (I) —(III). In certain embodiments of the compounds of structural formula (VIII), p is 1 and q is 2. In other embodiments, q is 1 and p is 1. In other embodiments (for example, when Y is C, CF or CH), q is 1 and p is 0. In certain embodiments of the compounds of structural formula (VIII), R$^2$ is Hca.

In certain embodiments of the presently disclosed compounds of structural formulae (I)-(VIII) as described above, T is

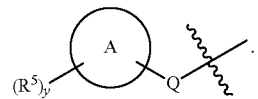

In such embodiments, Q is —O—(C$_0$-C$_3$ alkyl)-, —S(O)$_2$—, L or —(C$_0$-C$_3$ alkyl)- in which each carbon of the (C$_0$-C$_3$ alkyl) is optionally and independently substituted with one or two R$^{16}$, in which each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo. In certain embodiments, each R$^{16}$ is independently selected from —(C$_1$-C$_6$ alkyl), —(C$_1$-C$_6$ haloalkyl) (for example, difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-

$C_6$ alkyl)-C(O)$R^{10}$—($C_0$-$C_6$ alkyl)-S(O)$_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in particular compounds, each $R^{16}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, each $R^{16}$ is independently methyl, ethyl, n-propyl, isopropyl, trifluoromethyl, pentafluoroethyl, acetyl, —$NH_2$, —OH, methoxy, ethoxy, trifluoromethoxy, —$SO_2$Me, -halogen, —$NO_2$, $N_3$, —$SF_5$, or —CN, and two $R^{16}$ optionally come together to form oxo. In certain embodiments, Q has at most one $R^{16}$ or an oxo substituted thereon. Q can be, for example, an unsubstituted —($C_0$-$C_3$ alkyl)- (for example, a single bond, —$CH_2$— or —$CH_2$—$CH_2$—). In other embodiments, Q is a ($C_1$-$C_3$ alkyl) having as its only substitution a single oxo group. For example, in certain embodiments of the compounds of structural formulae (I)-(VII) as described above, Q is —$CH_2$—; —$CH_2CH_2$—; —$OCH_2CH_2$—; O; a single bond; —$S(O)_2$—; —$C(O)$—; —CHF—; —CH(OH)—, —$C(CH_3)_2$—, or —$CH(CH_3)$—.

In certain embodiments of the compounds of structural formulae (I)-(VIII) as described above, T is

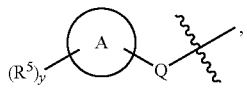

in which Q is —C(O)— or —$S(O)_2$—. In other embodiments, T is

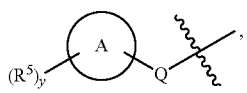

in which Q is —$C(CH_3)_2$—, —$CH_2CH_2$—, —$CH(CH_3)$—, —CH(OH)— or —CHF—.

In certain embodiments of the compounds of structural formulae (I)-(VIII) as described above (for example, those in which T is not bound to a nitrogen), T is

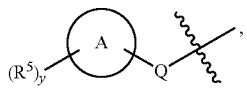

in which Q is O.

In certain embodiments of the compounds of structural formulae (I)-(VIII) as described above (for example, those in which the ring system denoted by "B" is absent), T is

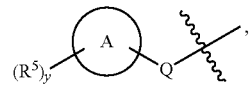

in which Q is —O—($C_1$-$C_3$ alkyl)-, for example, —$OCH_2$— or —$OCH_2CH_2$—.

The number of substituents, y, on the ring system denoted by "A", is 0, 1, 2, 3 or 4. For example, in some embodiments of the presently disclosed compounds of structural formulae (I)-(VIII) as described above, y is 0, 1, 2 or 3, such as 1. In one embodiment, y is not zero and at least one $R^5$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —$N_3$, —$SF_5$, $NO_2$ or —C(O)—Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formulae (I)-(VIII) as described above, each $R^5$ is independently selected from —($C_1$-$C_6$ alkyl), —($C_1$-$C_6$ haloalkyl) (for example, difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$N_3$, —$SF_5$, —$NO_2$ and —CN, in which each $R^7$, $R^8$ and $R^{10}$ is independently selected from H, —($C_1$-$C_6$ alkyl), —($C_1$-$C_6$ haloalkyl) (for example, difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^5$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$N_3$, —$SF_5$, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, each $R^5$ is independently halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —$N_3$, —$SF_5$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}SO_2R^{33}$, —(NH)$_{0-1}COR^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, each $R^5$ is independently methyl, ethyl, n-propyl, isopropyl, trifluoromethyl, pentafluoroethyl, acetyl, —$NH_2$, —OH, methoxy, ethoxy, trifluoromethoxy, —$SO_2Me$, -halogen, —$NO_2$, $N_3$, —$SF_5$, or —CN.

In one embodiment of the compounds of structural formulae (I)-(VIII) as described above, y is 0. In another embodiment, y is 1. In another embodiment, y is 2.

In the presently disclosed compounds of structural formulae (I)-(VIII) as described above, the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, the ring system denoted by "A" is an aryl or a heteroaryl and Q is —$CH_2$—; —$CH_2CH_2$—; a single bond; —$S(O)_2$—; —C(O)—; or —$CH(CH_3)$—. In other embodiments, the ring system denoted by "A" is an aryl or a heteroaryl and Q is —CF—, —CH(OH)— or —$C(CH_3)_2$—. In other embodiments, the ring system denoted by "A" is an aryl or a heteroaryl and Q is —O—, —$OCH_2$— or —$OCH_2CH_2$—.

For example, in certain embodiments of the presently disclosed compounds of structural formulae (I)-(VIII) as described above, the ring system denoted by "A" is monocyclic aryl, such as phenyl. In one embodiment, y is 1 and $R^5$ is attached to the phenyl in the para position relative to Q. In one embodiment, y is 1 and $R^5$ is attached to the phenyl in the meta position relative to Q. In certain embodiments, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —$N_3$, $SF_5$, —C(O)$CH_3$, —C(O)OH, —C(O)$NH_2$, methoxy, trifluoromethyl, difluoromethyl, difluoromethoxy or trifluoromethoxy. In another embodiment, the

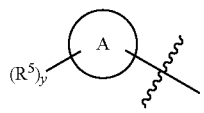

moiety is a 3,4-dihalophenyl, a 3,5-dihalophenyl, a 3-cyano-5-methoxyphenyl, a 4-cyano-3-halophenyl, or a 3-halo-4-methoxyphenyl.

In another embodiment of the presently disclosed compounds of structural formulae (I)-(VIII) as described above, the ring system denoted by "A" is a heteroaryl. For example, in certain embodiments, the ring system denoted by "A" is a pyridyl, a thienyl, or a furanyl. In another embodiment, the ring system denoted by "A" is an isoxazolyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, the ring system denoted by "A" is an aryl or a heteroaryl and Q is —$CH_2$—; a single bond; —$S(O)_2$—; —C(O)—; or —$CH(CH_3)$—. In other embodiments, the ring system denoted by "A" is an aryl or a heteroaryl and Q is —O—, —CF—, —CH(OH)— or —$C(CH_3)_2$—. In other embodiments, the ring system denoted by "A" is an aryl or a heteroaryl and Q is —O—, —$OCH_2$— or —$OCH_2CH_2$—.

In another embodiment of the presently disclosed compounds of formulae (I)-(VIII) as described above, the ring system denoted by "A" is a heterocycloalkyl. For example, in certain embodiments, the ring system denoted by "A" is a tetrahydro-2H-pyranyl or a morpholino. In one such embodiment, when the "A" ring system is a heterocycloalkyl, Q is a single bond. In another such embodiment, Q is —$CH_2$— or —C(O)—. In another such embodiment, Q is —O—, —$OCH_2$— or —$OCH_2CH_2$—.

In another embodiment of the presently disclosed compounds of formulae (I)-(VIII) as described above, the ring system denoted by "A" is a cycloalkyl. For example, in certain embodiments, the ring system denoted by "A" is a cyclohexyl. In one such embodiment, when the "A" ring system is a cycloalkyl, Q is —$CH_2$— or —C(O)—. In another such embodiment, Q is a single bond. In another such embodiment, Q is —O—, —$OCH_2$— or —$OCH_2CH_2$—.

In certain embodiments of the compounds of formulae (I)-(VIII) as described above, T is H, —($C_1$-$C_6$ alkyl) or —C(O)($C_1$-$C_6$ alkyl). In certain such embodiments, the alkyl moieties of T are unsubstituted. In other such embodiments, the alkyl moieties of T are optionally substituted as described below. For example, in certain embodiments, T is H, ispropyl, or —C(O)-t-butyl.

In certain embodiments of the compounds of formulae (I)-(VIII) as described above, T is —$C(CH_3)_2Ar$, —$CH_2$-Het, -Het, —$CH_2$-Cak or -Hca. The —Ar, -Het, -Cak and -Hca moieties can, for example, be substituted with y $R^5$ moieties, as described above with reference to the ring system denoted by "A".

In certain embodiments of the presently disclosed compounds of structural formulae (I)-(VIII) as described above, the T moiety is selected from the group consisting of

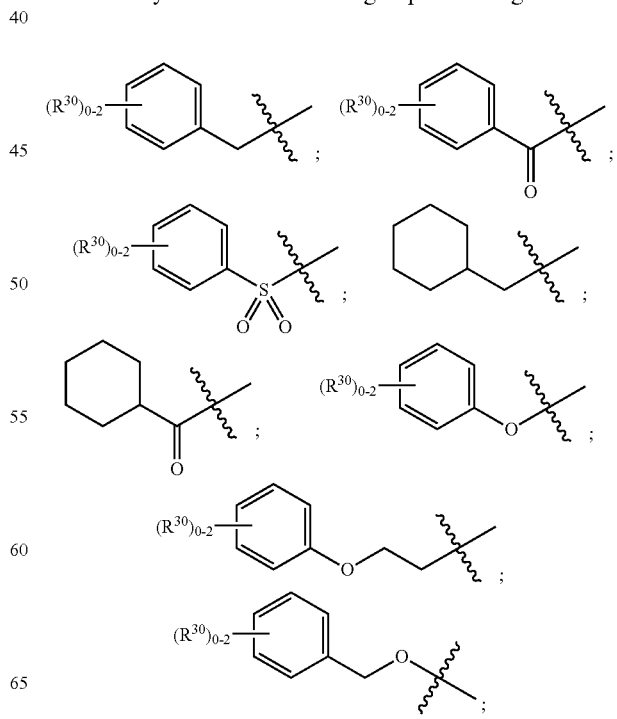

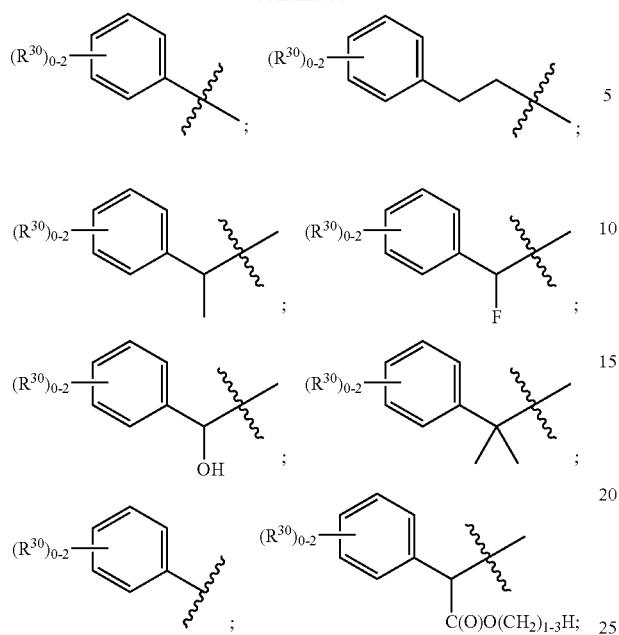

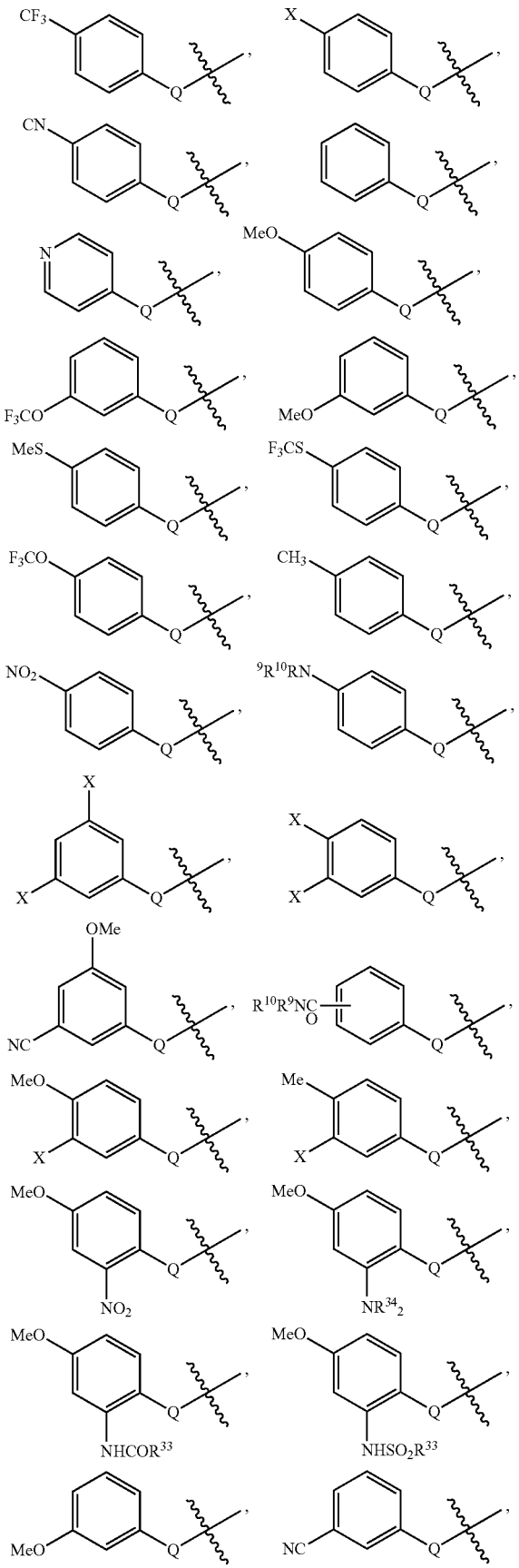

monocyclic heterocycloalkyl (for example, tetrahydropyranyl, morpholinyl, piperidinyl, piperazinyl) substituted with 0, 1 or 2 $R^{30}$, monocyclic heteroaryl (for example, pyridyl, isoxazolyl, oxazolyl, pyrrolyl, thienyl) substituted with 0, 1 or 2 $R^{30}$; monocyclic heteroarylmethyl- (for example, pyridylmethyl, isoxazolylmethyl, oxazolylmethyl, pyrrolylmethyl, thienylmethyl), in which the heteroaryl is substituted with 0, 1 or 2 $R^{30}$; or monocyclic heteroaryloxy- (for example, pyridyloxy, isoxazolyloxy, oxazolyloxy, pyrrolyloxy, thienyloxy), in which the heteroaryl is substituted with 0, 1 or 2 $R^{30}$; in which each $R^{30}$ is independently selected from halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —$N_3$, —$SF_5$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}$$SO_2R^{33}$, —(NH)$_{0-1}$COR$^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, no $R^{30}$ is substituted on the ring of the T moiety. In other embodiments, one $R^{30}$ is substituted on the ring of the T moiety, for example, at a para-position of a phenyl, a meta-position of a phenyl, or at a 3- or 4-position of a heteroaryl or heterocycloalkyl (as counted from the attachment point of the ring system denoted by "B"). Certain particular identities of the T moiety will be found by the person of skill in the art in the compounds described below with respect to Table 1. Those of skill in the art will understand that combinations of such T moieties with other subcombinations of features disclosed herein is specifically contemplated.

For example, in certain embodiments of the compounds of formulae (I)-(VIII) as

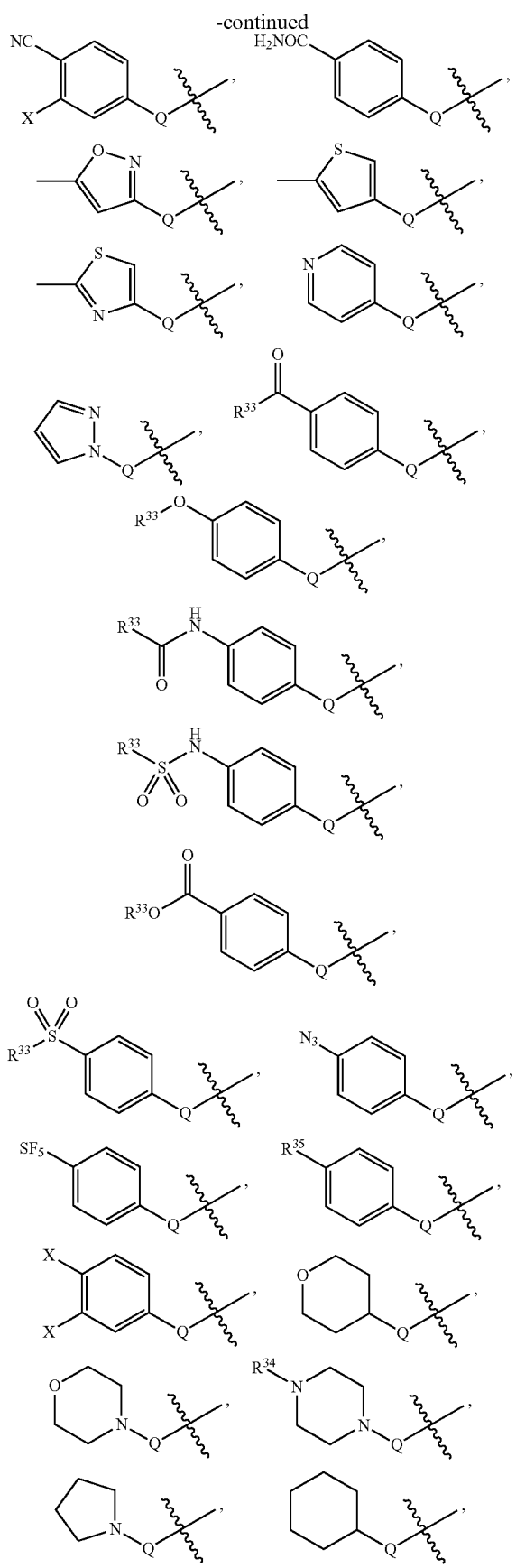

described above, the T moiety is selected from heterocycloalkyl optionally substituted by alkyl and/or halogen, -Q-heteroaryl optionally substituted by unsubstituted ($C_1$-$C_4$ alkyl) and/or halogen, H, C(O)tBu and isopropyl, in which each X is independently F, Cl or Br (preferably F or Cl), each $R^{33}$ is unsubstituted ($C_1$-$C_4$ alkyl), unsubstituted ($C_1$-$C_4$ haloalkyl) or cycloalkyl optionally substituted with unsubstituted alkyl, unsubstituted ($C_1$-$C_4$ alkyl), unsubstituted ($C_1$-$C_4$ haloalkyl) or cycloalkyl optionally substituted with unsubstituted alkyl, and each $R^{35}$ is heterocycloalkyl, optionally substituted with unsubstituted alkyl. In certain such embodiments, Q is a single bond, —$CH_2$—, —$CH_2O$—, —$OCH_2CH_2$—, —$CH_2CH_2$—, —O—, —CHF—, —CH($CH_3$)—, —C($CH_3$)$_2$—, —CH(OH)—, —CH(COOMe)-, —CH(COOEt)-, —C(O)— or —S(O)$_2$—.

In one embodiment of the presently disclosed compounds of structural formulae (I)-(VII) as described above, the compound has structural formula (IX):

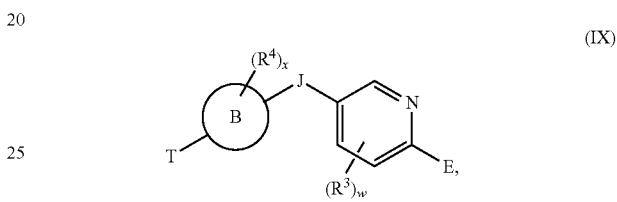

(IX)

in which the variables are defined as described above with reference to any of structural formulae (I)-(VIII).

In another embodiment of the presently disclosed compounds of structural formulae (I)-(VIII) as described above, the compound has structural formula (X):

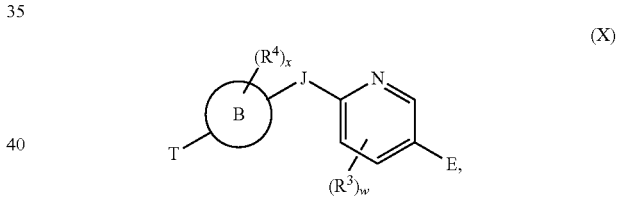

(X)

in which the variables are defined as described above with reference to any of structural formulae (I)-(VIII). For example, in certain embodiments, $R^2$ can be

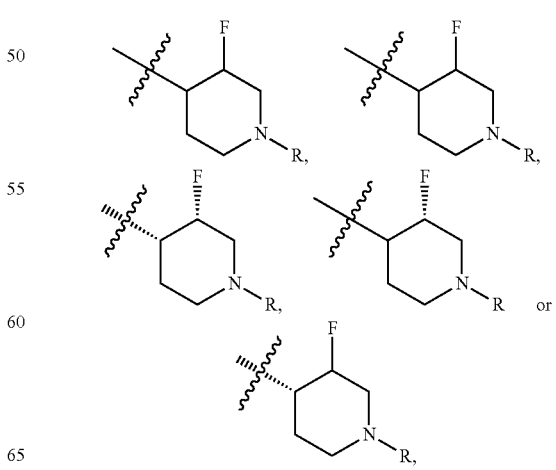

in which the R group is a further substituent, for example, as described herein.

In another embodiment of the presently disclosed compounds of structural formulae (I)-(VIII) as described above, the compound has structural formula (XI):

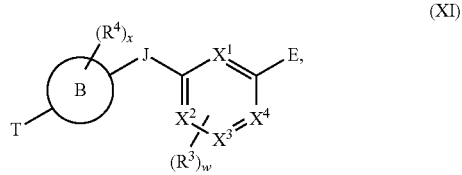

(XI)

in which one of $X^1$, $X^2$, $X^3$ and $X^4$ are N, and the others are carbons (for example, independently CH or C substituted with one of the w $R^3$ groups), and all other variables are defined as described above with reference to any of structural formulae (I)-(VIII). For example, in one embodiment, $X^1$ is N and $X^2$, $X^3$ and $X^4$ are carbons. In another embodiment, $X^2$ is N and $X^1$, $X^3$ and $X^4$ are carbons. In another embodiment, $X^3$ is N and $X^1$, $X^2$ and $X^4$ are carbons. In another embodiment, $X^4$ is N and $X^1$, $X^2$ and $X^3$ are carbons.

In another embodiment of the presently disclosed compounds of structural formulae (I)-(VIII) as described above, the compound has structural formula (XII):

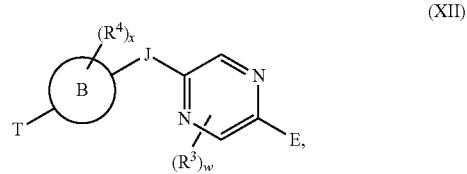

(XII)

in which the variables are defined as described above with reference to any of structural formulae (I)-(VIII).

In another embodiment of the presently disclosed compounds of structural formulae (I)-(VIII) as described above, the compound has structural formula (XIII):

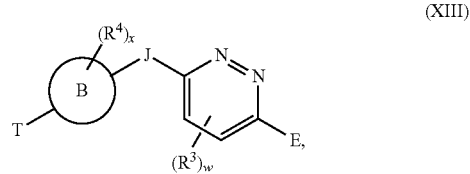

(XIII)

in which the variables are defined as described above with reference to any of structural formulae (I)-(VIII).

In the compounds of any of structural formulae (I)-(XIII) as described above, w, the number of substituents on the central pyridine, pyridazine, pyrazine or pyrimidine, is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (for example, chloro) or —($C_1$-$C_4$ alkyl) (for example, methyl, ethyl or propyl). In certain embodiments, an $R^3$ is substituted on the central pyridine, pyrazine, pyridazine or pyrimidine in the meta position relative to the J moiety.

In certain embodiments of the compounds of any of structural formulae (I)-(XIII) as described above, each $R^3$ is independently selected from —($C_1$-$C_6$ alkyl), —($C_1$-$C_6$ haloalkyl) (for example, difluoromethyl, trifluoromethyl and the like), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, in which each R$^7$, R$^8$ and R$^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, in which each R$^7$, R$^8$ and R$^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (for example, chloro) or —($C_1$-$C_4$ alkyl) (for example, methyl, ethyl or propyl). In certain embodiments, each $R^3$ is independently halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —NO$_2$, —NH$_2$, —NH(unsubstituted $C_1$-$C_4$ alkyl), —N(unsubstituted $C_1$-$C_4$ alkyl)$_2$, —N$_3$, —SF$_5$, —C(O)—NH$_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}$SO$_2$R$^{33}$, —(NH)$_{0-1}$COR$^{33}$, heterocycloalkyl optionally substituted with an (unsubstituted $C_1$-$C_6$ alkyl) and heteroaryl optionally substituted with an (unsubstituted $C_1$-$C_6$ alkyl), in which each R$^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, each $R^3$ is independently methyl, ethyl, n-propyl, isopropyl, trifluoromethyl, pentafluoroethyl, acetyl, —NH$_2$, —OH, methoxy, ethoxy, trifluoromethoxy, —SO$_2$Me, -halogen, —NO$_2$ or —CN.

In certain embodiments of the compounds of any of structural formulae (I)-(XIII) as described above, w is at least one, and at least one $R^3$ is —NR$^8$R$^9$. For example, in one embodiment, w is 1. In certain such embodiments, an $R^3$ is substituted on the central pyridine, pyrazine, pyridazine or pyrimidine in the meta position relative to the J moiety.

In other embodiments of the compounds of any of structural formulae (I)-(XIII) as described above, w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —NR$^9$—. For example, in one embodiment, w is 1. In certain such embodiments, $R^3$ is substituted on the central pyridine, pyrazine, pyridazine or pyrimidine in the meta position relative to the J moiety. In one particular embodiment, $R^3$ is —$CH_2$—$N(CH_3)$—$CH_2$—$C(O)$—$OCH_3$.

In certain embodiments of the presently disclosed compounds of structural formulae (I)-(XIII) as described above, the compound has the structural formula (XIV):

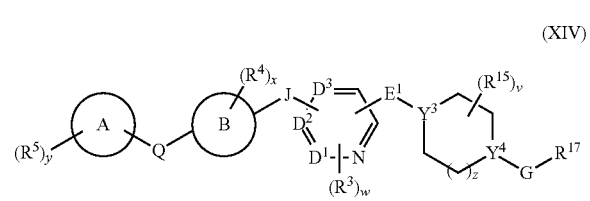

(XIV)

in which $E^1$ is absent, —C(O)—, —C(O)$NR^1$— or —$NR^1$C(O)—; z is 0 or 1; $Y^3$ is N, C or CH and $Y^4$ is N, C or CH; Q and G are each independently a single bond, —$CH_2$—, —$C(H)(R^{16})$—, —$C(R^{16})_2$—, —$CH_2CH_2$—, L (for example, —C(O)—$NR^9$— or —$NR^9$—C(O)—), -L-$C(R^{16})_2$—, —O—($C_0$-$C_3$ alkyl)- in which the ($C_0$-$C_3$ alkyl) is bound to the $R^{17}$ moiety or the ring system denoted by "A", or —$S(O)_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, and two $R^{15}$ on the same carbon optionally combine to form oxo; and $R^{17}$ is Het or Ar, and all other variables are defined as described above with reference to any of structural formula (I)-(XIII).

In certain embodiments of the presently disclosed compounds of structural formula (XIV) as described above (for example, those in which $E^1$ is —C(O)— or absent, $Y^3$ is N and $Y^4$ is N. In other embodiments, (for example, those in which $E^1$ is —C(O)—$NR^1$—), $Y^3$ is C or CH and $Y^4$ is N. In other embodiments, $Y^3$ is N and $Y^4$ is C or CH. In other embodiments, $Y^3$ is C or CH and $Y^4$ is C or CH; in such embodiments, the $E^1$ and G moieties can be disposed, for example, cis to one another on the cycloalkyl ring. In certain embodiments of the presently disclosed compounds of structural formula (XIV) as described above, z is 1. In other embodiments, z is 0.

In certain embodiments of the presently disclosed compounds of structural formulae (I)-(XIV) as described above, $D^1$, $D^2$ and $D^3$ are all CH or C substituted by one of the w $R^3$, and the $R^2$ moiety is an optionally-substituted piperidine. For example, in one embodiment, a compound has structural formula (XV):

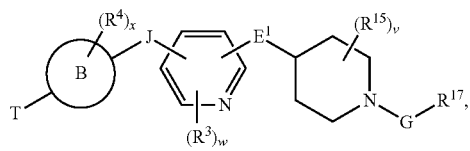

(XV)

in which all variables are and all as described above with respect to any of structural formulae (I)-(XIV). In one such embodiment, v is 0.

In other embodiments of compounds according to structural formula (XV), one of the $R^{15}$ is F. For example, the F can be substituted at the carbon alpha to the $E^1$ moiety. Accordingly, in certain embodiments, a compound has structural formula (XVI):

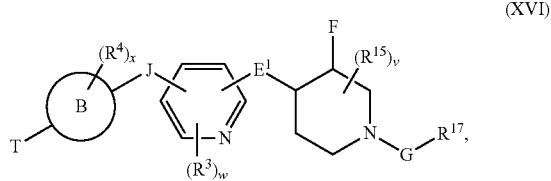

(XVI)

in which v is 0, 1, 2 or 3 and all other variables are as described above with respect to any of structural formulae (I)-(XIV). In certain such embodiments, v is 0. In one embodiment, the $E^1$ moiety and the F are disposed in a cis relationship to one another. In other embodiment, the $E^1$ moiety and the F are disposed in a trans relationship to one another. For example, the compound of structural formula (XVI) can be provided as any of the four diastereomers of structural formulae (XVII)-(XX):

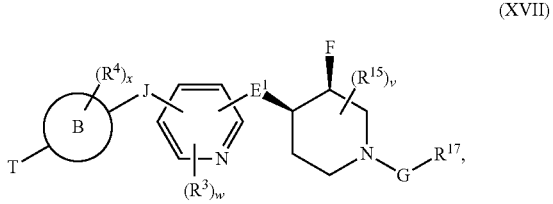

(XVII)

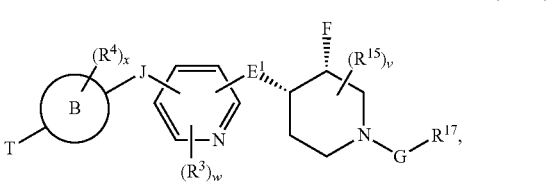

(XVIII)

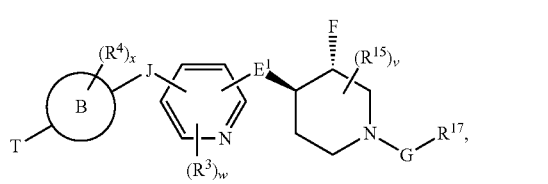

(XIX)

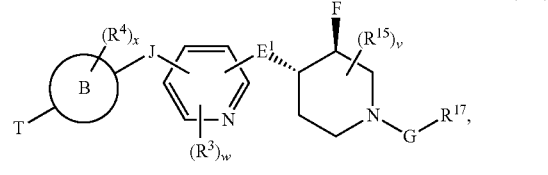

(XX)

in which v is 0, 1, 2 or 3 (e.g., 0), and all other variables are and all as described above with respect to any of structural formulae (I)-(XVI). Compounds can be provided as mixtures of diastereomers or enantiomers, or in diastereomerically and/or enantiomerically enriched form. In certain embodiments, the compound is provided in substantially diastereomerically pure form, for example, as substantially diastereomerically pure cis compound, or diastereomerically pure trans compound. In certain embodiments, a compound is provided in substantially enantiomerically pure form, for example, as one of the compounds of structural formulae (XVII)-(XX).

In certain embodiments of the compounds of structural formulae (XV)-(XX), the compound has structural formula (XXI):

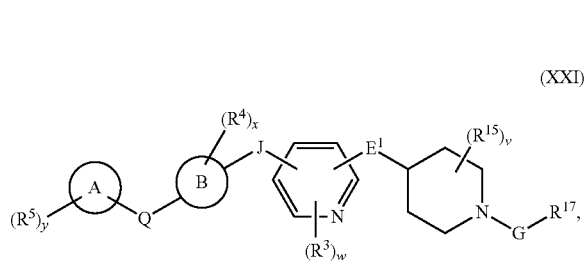

(XXI)

in which all variables are as described above with respect to any of structural formulae (I)-(XX). For example, the

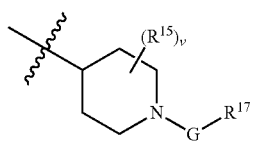

moiety can be selected from

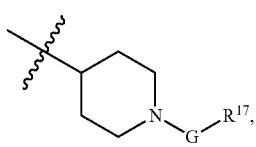 

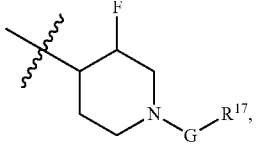 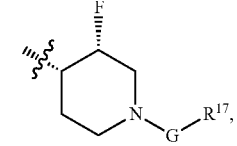

in which the G-R$^{17}$ group is as described herein. Such compounds can be provided as mixtures of diastereomers or enantiomers, or in diastereomerically and/or enantiomerically enriched form. In certain embodiments, the compound is provided in substantially diastereomerically pure form, for example, as substantially diastereomerically pure cis compound, or diastereomerically pure trans compound. In certain embodiments, a compound is provided in substantially enantiomerically pure form.

In the compounds of structural formulae (XV)-(XXI), the regiochemistry around the central pyridine can be as described with respect to any of claims (IX)-(XI). Moreover, the E$^1$ moiety of any such compounds can be absent, —C(O)—, —C(O)NR$^1$— or —NR$^1$C(O)—. In one such embodiment, a compound of any of structural formula (XV)-(XXI) is of structural formula (XXII):

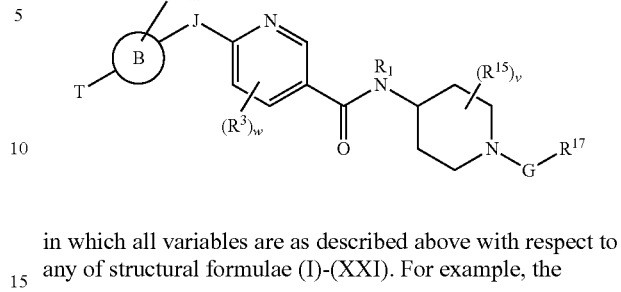

(XXII)

in which all variables are as described above with respect to any of structural formulae (I)-(XXI). For example, the

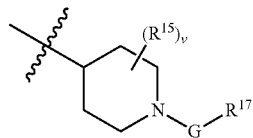

moiety can be selected from

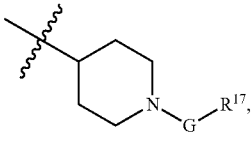 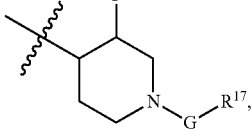

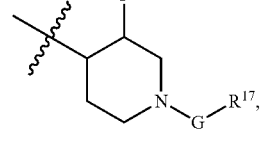 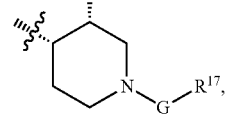

in which the G-R$^{17}$ group is as described herein.

In certain embodiments of the compounds according to structural formula (XV)-(XXII), the ring denoted by "B" is

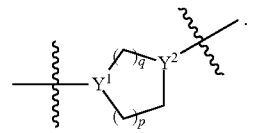

In certain such embodiments, Y$^2$ is N and Y$^1$ is CH or C substituted by one of the x R$^4$. In other such embodiments, both Y$^1$ and Y$^2$ are N. For example, in certain embodiments, compounds according to structural formulae (XV)-(XXII) have structural formula (XXIII):

(XXIII)

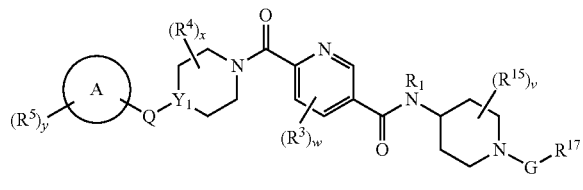

in which in which all variables are as described above with respect to any of structural formulae (I)-(XXII). In one embodiment, $Y^1$ is N. In another embodiment, $Y^1$ is CH, or is C substituted by one of the x $R^4$. For example, in certain embodiments, compounds have one of structural formulae (XXIV)-(XXIX):

(XXIV)

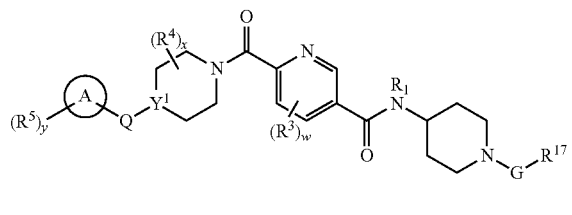

(XXV)

(XXVI)

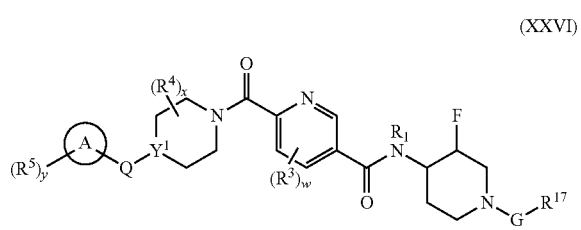

(XXVII)

(XXVIII)

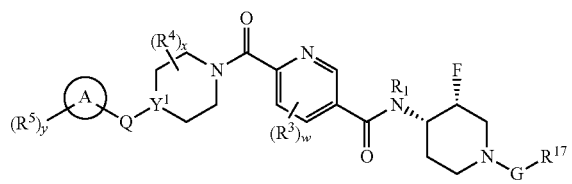

(XXIX)

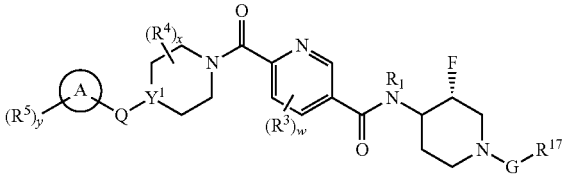

in which in which all variables are as described above with respect to any of structural formulae (I)-(XXII). In certain embodiments of the compounds of structural formulae (XXIV)-(XXIX), $Y^1$ is CH or C substituted by one of the x $R^4$. In certain embodiments of the compounds of structural formulae (XXIV)-(XXIX), w is 0. In other such embodiments, x is 0. In still other such embodiments, both w and x are 0. In any such embodiments, $R^1$ can be, for example, H, or unsubstituted ($C_1$-$C_4$ alkyl) such as methyl. Compounds according to structural formulae (XXVI)-(XXIX) can be provided as mixtures of diastereomers or enantiomers, or in diastereomerically and/or enantiomerically enriched form. In certain embodiments, the compound is provided in substantially diastereomerically pure form, for example, as substantially diastereomerically pure cis compound, or diastereomerically pure trans compound. In certain embodiments, a compound is provided in substantially enantiomerically pure form.

In the compounds of structural formulae (XV)-(XXIX) as described above, G and Q can be as described above with reference to structural formulae (I)-(XIV). For example, in certain embodiments, G is $CH_2$, CO, or $SO_2$. In certain embodiments, Q is $CH_2$, CO, $SO_2$ or O.

In the compounds of structural formulae (XV)-(XXIX) as described above, $R^{17}$ and T can be as described above with reference to structural formulae (I)-(XIV). For example, in certain embodiments, $R^{17}$ is an optionally substituted phenyl, for example, substituted with 0-2 $R^{30}$ groups as described above. In other embodiments, $R^{17}$ is an optionally substituted heteroaryl, for example, substituted with 0-2 $R^{30}$ groups as described above. In certain embodiments, T is

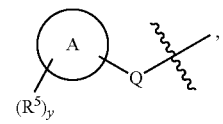

in which Q is as described above. The ring system denoted by A and its optional $R^5$ substituents can be, for example, phenyl substituted by 0-2 $R^{30}$ groups as described above. In other embodiments, ring system denoted by A and its optional $R^5$ substituents are heteroaryl, for example, substituted with 0-2 $R^{30}$ groups as described above.

As examples, in certain embodiments, the compounds have one of structural formulae (XXX)-(XXXV):

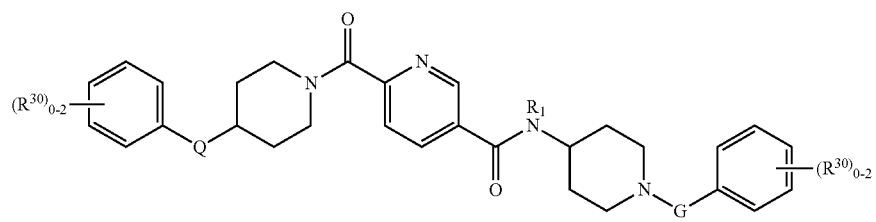

(XXX)

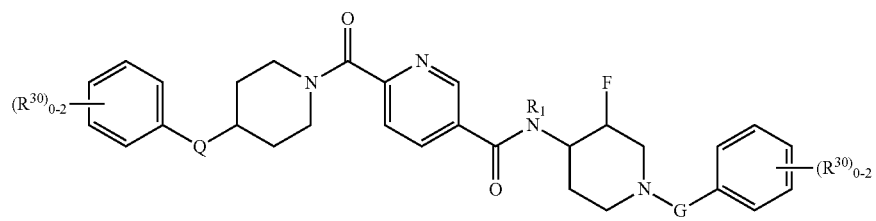

(XXXI)

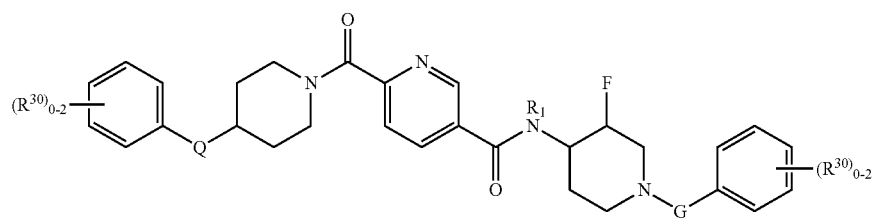

(XXXII)

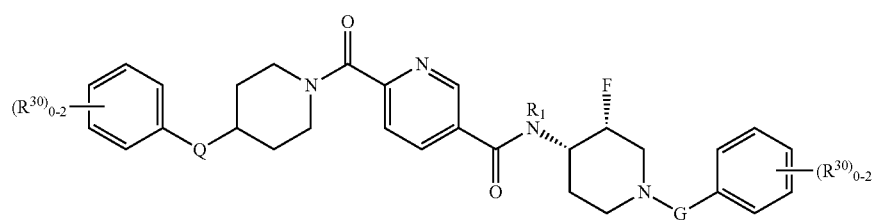

(XXXIII)

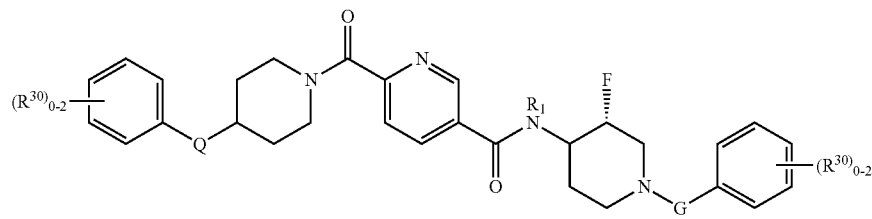

(XXXIV)

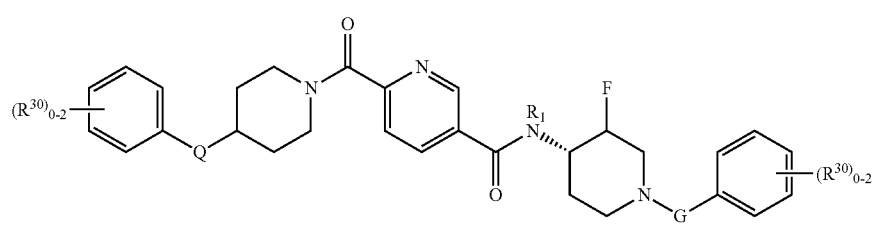

(XXXV)

in which Q, G, $R^1$ and $R^{30}$ are as described above with reference to structural formulae (I)-(XXIX). In certain such embodiments, $R^1$ is H. In certain embodiments, G is $CH_2$, CO, or $SO_2$. In certain embodiments, Q is $CH_2$, CO, $SO_2$ or O. Compounds according to structural formulae (XXX)-(XXXV) can be provided as mixtures of diastereomers or enantiomers, or in diastereomerically and/or enantiomerically enriched form. In certain embodiments, the compound is provided in substantially diastereomerically pure form, for example, as substantially diastereomerically pure cis compound, or diastereomerically pure trans compound. In certain embodiments, a compound is provided in substantially enantiomerically pure form.

In other embodiments of the presently disclosed compounds of structural formulae (I)-(XIII) as described above, the compound has the structural formula (XXXVI):

(XXXVI)

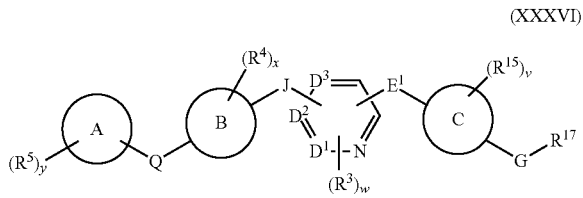

in which the ring system denoted by "C" is a monocyclic arylene or heteroarylene, or a monocyclic arylene fused to a heterocycloalkyl, and all other variables are as defined above with respect to any of structural formulae (I)-(XIV). For example, in certain embodiments, the ring system denoted by "C" is a phenylene, for example, a 1,4-phenylene. In other embodiments, the ring system denoted by "C" is a monocyclic heteroarylene, such as a pyridylene (for example, a 2,5-pyridylene); a 1,3-pyrazolylene (for example, a 1,3-pyrazolylene); a furanylene (for example, a 2,4-furanylene); or a thienylene (for example, a 2,4-thienylene). In other embodiments, the ring system denoted by "C" is a 1,2,3,4-tetrahydroisoquinolinylene (for example, a 1,2,3,4-tetrahydroisoquinolin-2,6-ylene).

In other embodiments of the presently disclosed compounds of structural formulae (I)-(XIII) as described above, the compound has the structural formula (XVI):

(XXXVII)

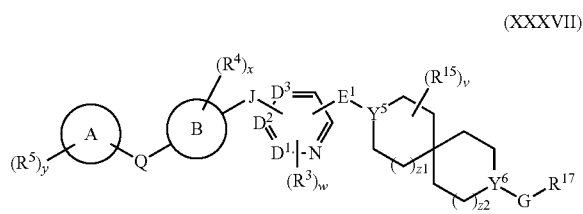

in which z1 is 0 or 1; z2 is 0 or 1; $Y^5$ is N, C or CH; $Y^6$ is N, C or CH; each of the v $R^{15}$ can be disposed either spiro-fused ring; and all other variables are as defined above with respect to any of structural formulae (I)-(XIV).

In certain embodiments of the presently disclosed compounds of structural formula (XXXVII) as described above (for example, those in which $E^1$ is —C(O)— or absent), $Y^5$ is N and $Y^6$ is N. In other embodiments, (for example, those in which $E^1$ is —C(O)—$NR^1$—), $Y^5$ is C or CH and $Y^6$ is N. In other embodiments, $Y^5$ is N and $Y^6$ is C or CH. In other embodiments, $Y^5$ is C or CH and $Y^6$ is C or CH. In certain embodiments of the presently disclosed compounds of structural formula (XXXVII) as described above, z1 is 1 and z2 is 0. In other embodiments, z1 is 0 and z2 is 1.

In one embodiment of the compounds of structural formula (XIV)-(XXXVII) as described above, Q is a single bond. In another embodiment, Q is —$CH_2$—. In other embodiments, Q is —C(O)— or —$S(O)_2$—. In other embodiments, Q is —NH—C(O)— or —$CH_2$—NH—C(O)—. In other embodiments, Q is —$C(CH_3)_2$—, —$CH_2CH_2$—, —$CH(CH_3)$—, —CH(OH)— or —CHF—. In other embodiments, Q is —O—. In other embodiments, Q is —$CH_2O$— or —$OCH_2CH_2$—. In other embodiments, Q is —CH(COOMe)- or —CH(COOEt)-.

In one embodiment of the compounds of structural formula (XIV)-(XXXVII) as described above, G is —$CH_2$—. In other embodiments, G is —C(O)— or —$S(O)_2$—. In other embodiments, G is —$CH(CH_3)$— or —$C(CH_3)_2$—. In other embodiments, G is —O—. In other embodiments, G is —C(O)—NH— or —C(O)—NH—$CH_2$—. In other embodiments, G is —$CH_2CH_2$—. In other embodiments, G is a single bond. In other embodiments, G is —O—. In other embodiments, G is —$OCH_2$— or —$CH_2CH_2O$—. In other embodiments, G is —CH(COOMe)- or —CH(COOEt)-.

In the presently disclosed compounds of structural formulae (XIV)-(XXXVII) as described above, the above-described Q and G moieties can be combined in any possible combination. For example, in one embodiment, Q is a single bond and G is —$CH_2$— or —C(O)—. In another embodiment, Q is —$CH_2$— or —C(O)— and G is a single bond. In yet another embodiment, Q is —$CH_2$— or —C(O)— and G is —$CH_2$— or —C(O)—.

In certain embodiments of the compounds of structural formulae (XIV)-(XXXVII) as described above, the ring system denoted by "A" is aryl or heteroaryl, as described above. In one embodiment, the ring system denoted by "A" is substituted with one or more electron-withdrawing groups as described above. In another embodiment, $R^{17}$ is substituted with one or more electron-withdrawing groups as described above. In certain embodiments, the ring system denoted by "A", $R^{17}$ or both are not substituted with an aryl, heteroaryl, cycloalkyl or heterocycloalkyl-containing group. In certain embodiments, the azacycloalkyl to which -G-$R^{17}$ is bound is a piperidinyl; in other embodiments, it is a pyrrolidinyl.

In the presently disclosed compounds of structural formulae (XIV)-(XXXVII) as described above, v is 0, 1, 2, 3 or 4. In one embodiment, v is 0, 1, 2 or 3. For example, v can be 0, or can be 1 or 2.

In certain embodiments of the presently disclosed compounds of structural formulae (XIV)-(XXXVII) as described above, two $R^{15}$ groups combine to form an oxo. The oxo can be bound, for example, at the position alpha relative to the nitrogen of an azacycloalkyl ring. In other embodiments, no two $R^{15}$ groups combine to form an oxo.

In certain embodiments of the presently disclosed compounds of structural formulae (XIV)-(XXXVII) as described above, v is at least 1 (for example, 1) and at least one $R^{15}$ is F. In certain embodiments, the F can be, for example, disposed at a position alpha to the $E^1$ moiety. When the F and $E^1$ are both disposed on saturated carbons, they can be disposed in a cis relationship with respect to one another. For example, in certain embodiments, a compound has structural formula (XXXVIII)

(XXXVIII)

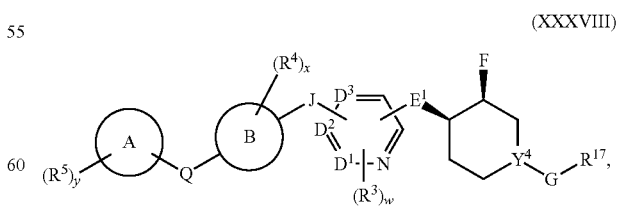

in which $Y^4$ is N or CH and all variables are defined as described above with respect to structural formulae (I)-(XIV). In other embodiments, a compound has structural formula (XXXIX)

(XXXIX)

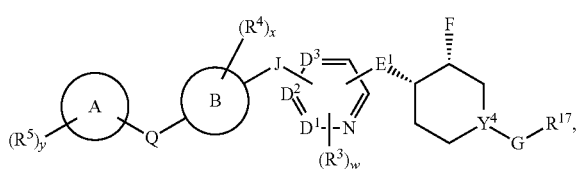

in which $Y^4$ is N or CH and all variables are defined as described above with respect to structural formulae (I)-(XIV). In other embodiments, when the F and $E^1$ are both disposed on saturated carbons, they can be disposed in a trans relationship with respect to one another. For example, in one embodiment, a compound has structural formula (XL)

(XL)

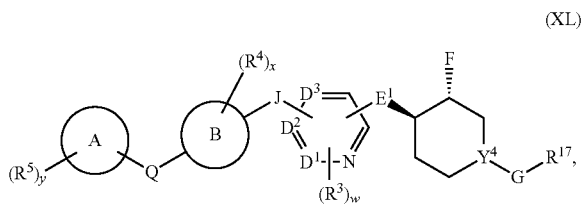

in which $Y^4$ is N or CH and all variables are defined as described above with respect to structural formulae (I)-(XIV). In another embodiment, a compound has structural formula (XLI)

(XLI)

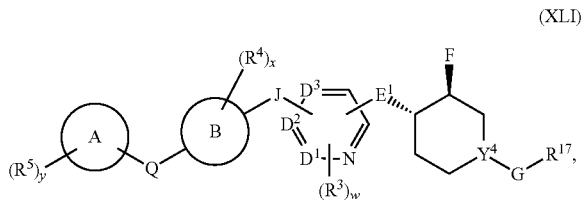

in which $Y^4$ is N or CH and all variables are defined as described above with respect to structural formulae (I)-(XIV). Compounds according to structural formulae (XXX-VIII)-(XII) can be provided as mixtures of diastereomers or enantiomers, or in diastereomerically and/or enantiomerically enriched form. In certain embodiments, the compound is provided in substantially diastereomerically pure form, for example, as substantially diastereomerically pure cis compound, or diastereomerically pure trans compound. In certain embodiments, a compound is provided in substantially enantiomerically pure form.

In certain embodiments of the presently disclosed compounds of structural formulae (XIV)-(XLI) as described above, when v is 4, not all four $R^{15}$ moieties are ($C_1$-$C_6$ alkyl).

In certain embodiments of the presently disclosed compounds of structural formulae (XIV)-(XLI) as described above, each $R^{15}$ is independently selected from —($C_1$-$C_6$ alkyl), —($C_1$-$C_6$ haloalkyl) (for example, difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, each $R^{15}$ is independently halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —$N_3$, —$SF_5$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}SO_2R^{33}$, —(NH)$_{0-1}COR^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl), and two $R_4$ optionally come together to form oxo. In certain embodiments, each $R^{15}$ is independently methyl, ethyl, n-propyl, isopropyl, trifluoromethyl, pentafluoroethyl, acetyl, —$NH_2$, —OH, methoxy, ethoxy, trifluoromethoxy, —$SO_2Me$, -halogen, —$NO_2$, $N_3$, —$SF_5$, or —CN, and two $R^{15}$ on the same carbon optionally combine to form oxo. In some embodiments, one $R^{15}$ is —C(O)$NR^9R^7$, which can be bound, for example, at a position alpha relative to the piperidine nitrogen, or at the position linked to the $E^1$ moiety.

In certain embodiments of the presently disclosed compounds of structural formulae (XIV)-(XLI) as described above, $R^{17}$ is an unsubstituted aryl or heteroaryl. In other embodiments, the $R^{17}$Ar or Het is substituted with 1, 2 or 3 substituents independently selected from —($C_1$-$C_6$ alkyl), —($C_1$-$C_6$ haloalkyl) (for example, difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, the $R^{17}$Ar or Het is substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S (O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, R$^{17}$ is substituted with 1, 2 or 3 substituents selected from halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which no alkyl or haloalkyl is substituted with an aryl-, heteroaryl-, cycloalkyl- or heterocycloalkyl-containing group. In certain embodiments, R$^{17}$ is substituted with 1, 2 or 3 substituents selected from halogen (e.g., F, Cl), unsubstituted (C$_1$-C$_6$ alkoxy) (e.g., methoxy, ethoxy), —(C$_1$-C$_6$ haloalkoxy) (e.g., trifluoromethoxy), —SH, —S(unsubstituted C$_1$-C$_6$ alkyl), —S(C$_1$-C$_6$ haloalkyl), —OH, —CN, —NO$_2$, —NH$_2$, —NH(unsubstituted C$_1$-C$_4$ alkyl), —N(unsubstituted C$_1$-C$_4$ alkyl)$_2$, —N$_3$, —SF$_5$, —C(O)—NH$_2$, C(O)NH(unsubstituted C$_1$-C$_4$ alkyl), C(O)N(unsubstituted C$_1$-C$_4$ alkyl)$_2$, —C(O)OH, C(O)O(unsubstituted C$_1$-C$_6$ alkyl), —(NH)$_{0-1}$SO$_2$R$^{33}$, —(NH)$_{0-1}$COR$^{33}$, heterocycloalkyl optionally substituted with an (unsubstituted C$_1$-C$_6$ alkyl) and heteroaryl optionally substituted with an (unsubstituted C$_1$-C$_6$ alkyl), in which each R$^{33}$ is (unsubstituted C$_1$-C$_6$ alkyl), (C$_1$-C$_6$ haloalkyl(unsubstituted C$_3$-C$_8$ cycloalkyl) or (C$_3$-C$_8$ heterocycloalkyl) optionally substituted with an (unsubstituted C$_1$-C$_6$ alkyl), and two R$_4$ optionally come together to form oxo. In certain embodiments, each R$^{17}$ is substituted with 1, 2 or 3 substituents selected from methyl, ethyl, n-propyl, isopropyl, trifluoromethyl, pentafluoroethyl, acetyl, —NH$_2$, —OH, methoxy, ethoxy, trifluoromethoxy, —SO$_2$Me, -halogen, —NO$_2$, N$_3$, —SF$_5$, or —CN. R$^{17}$ can be substituted with, for example, one such substituent, or two such substituents.

In certain embodiments of the presently disclosed compounds of structural formulae (XIV)-(XLI) as described above, at least one of R$^{17}$ and the ring system denoted by "A" is substituted with —C(O)NR$^{27}$R$^{29}$, in which R$^{27}$ is selected from H, —(C$_1$-C$_6$ alkyl), —(C$_1$-C$_6$ haloalkyl) (for example, difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)— (C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —C(O)—(C$_1$-C$_4$ alkyl) or —C(O)—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca (for example, morpholino, piperazinyl, pyrrolidinyl or piperidinyl). In certain embodiments, heterocycloalkyl, alkyl or haloalkyl groups of R$^{27}$ and R$^{29}$ are substituted with 1, 2 or 3 substituents selected from halogen (e.g., F, Cl), unsubstituted (C$_1$-C$_6$ alkoxy) (e.g., methoxy, ethoxy), —(C$_1$-C$_6$ haloalkoxy) (e.g., trifluoromethoxy), —SH, —S(unsubstituted C$_1$-C$_6$ alkyl), —S(C$_1$-C$_6$ haloalkyl), —OH, —CN, —NO$_2$, —NH$_2$, —NH(unsubstituted C$_1$-C$_4$ alkyl), —N(unsubstituted C$_1$-C$_4$ alkyl)$_2$, —N$_3$, —SF$_5$, —C(O)—NH$_2$, C(O)NH(unsubstituted C$_1$-C$_4$ alkyl), C(O)N(unsubstituted C$_1$-C$_4$ alkyl)$_2$, —C(O)OH, C(O)O(unsubstituted C$_1$-C$_6$ alkyl), —(NH)$_{0-1}$SO$_2$R$^{33}$, —(NH)$_{0-1}$COR$^{33}$, heterocycloalkyl optionally substituted with an (unsubstituted C$_1$-C$_6$ alkyl) and heteroaryl optionally substituted with an (unsubstituted C$_1$-C$_6$ alkyl), in which each R$^{33}$ is (unsubstituted C$_1$-C$_6$ alkyl), (C$_1$-C$_6$ haloalkyl(unsubstituted C$_3$-C$_8$ cycloalkyl) or (C$_3$-C$_8$ heterocycloalkyl) optionally substituted with an (unsubstituted C$_1$-C$_6$ alkyl), and two R$_4$ optionally come together to form oxo. In certain embodiments, the heterocycloalkyl, alkyl or haloalkyl groups of R$^{27}$ and R$^{29}$ are optionally substituted with acetyl, —NH$_2$, —OH, methoxy, ethoxy, trifluoromethoxy, —SO$_2$Me, -halogen, —NO$_2$, N$_3$, —SF$_5$, or —CN. In one embodiment, R$^{27}$ and R$^{29}$ are both H. In another embodiment, R$^{27}$ is CH$_3$ and R$^{29}$ is H.

In certain embodiments of the presently disclosed compounds of structural formulae (XIV)-(XLI) as described above, the -G-R$^{17}$ moiety is selected from the group consisting of

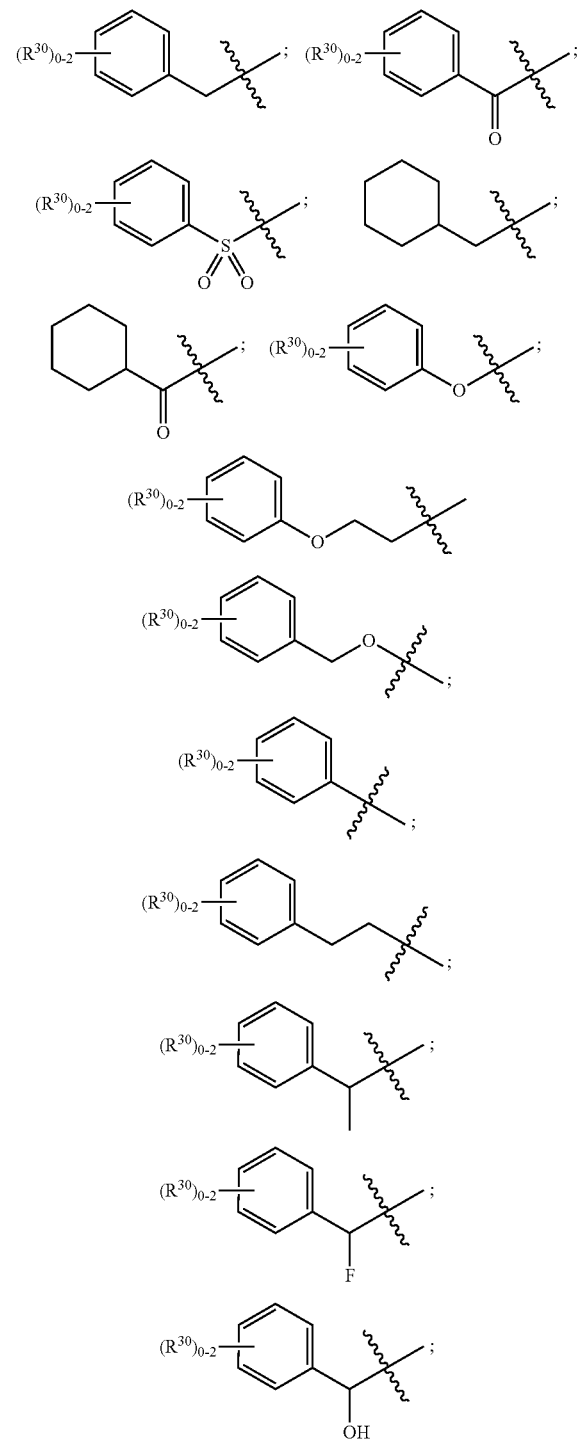

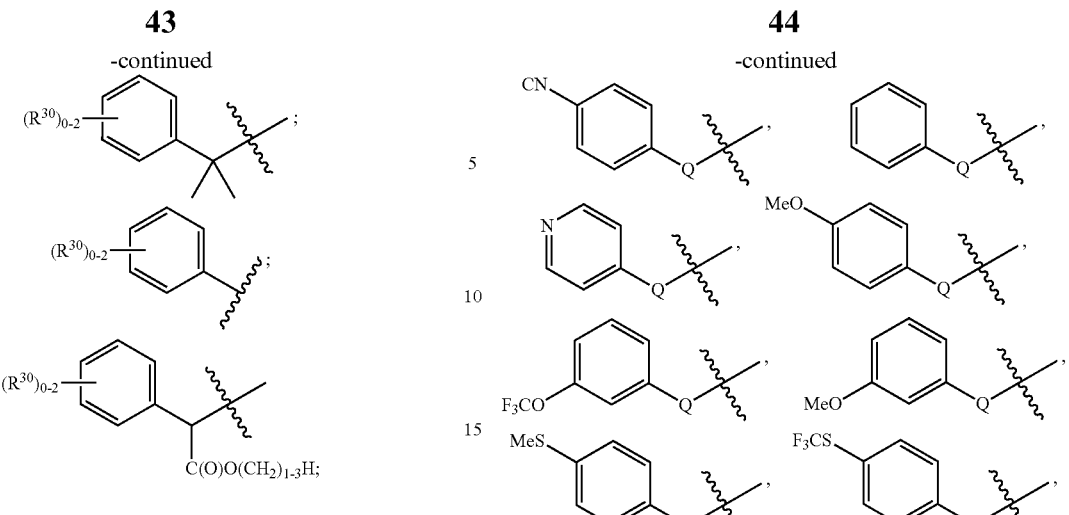

monocyclic heterocycloalkyl (for example, tetrahydropyranyl, morpholinyl, piperidinyl, piperazinyl) substituted with 0, 1 or 2 $R^{30}$, monocyclic heteroaryl (for example, pyridyl, isoxazolyl, oxazolyl, pyrrolyl, thienyl) substituted with 0, 1 or 2 $R^{30}$; monocyclic heteroarylmethyl- (for example, pyridylmethyl, isoxazolylmethyl, oxazolylmethyl, pyrrolylmethyl, thienylmethyl), in which the heteroaryl is substituted with 0, 1 or 2 $R^{30}$; or monocyclic heteroaryloxy- (for example, pyridyloxy, isoxazolyloxy, oxazolyloxy, pyrrolyloxy, thienyloxy), in which the heteroaryl is substituted with 0, 1 or 2 $R^{30}$; in which each $R^{30}$ is independently selected from halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —$N_3$, —$SF_5$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}$$SO_2R^{33}$, —(NH)$_{0-1}$$COR^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, no $R^{30}$ is substituted on the ring of $R^{17}$. In other embodiments, one $R^{30}$ is substituted on the ring, for example, at a para-position of a phenyl, a meta-position of a phenyl, or at a 3- or 4-position of a heteroaryl or heterocycloalkyl (as counted from the attachment point of the $Y^4$, $Y^6$ or the ring system denoted by "C"). Certain particular identities of the -G-$R^{17}$ moiety will be found by the person of skill in the art in the compounds described below with respect to Table 1. Those of skill in the art will understand that combinations of such -G-$R^{17}$ moieties with other subcombinations of features disclosed herein is specifically contemplated.

For example, in certain embodiments of the compounds of formulae (XIV)-(XLI) as described above, the -G-$R^{17}$ moiety is selected from

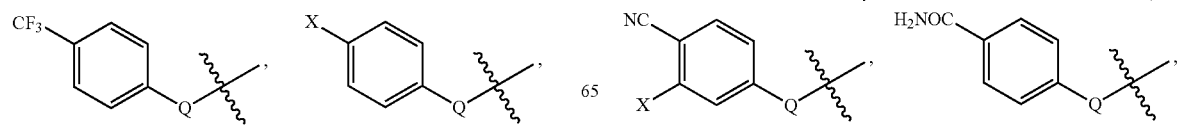

-continued

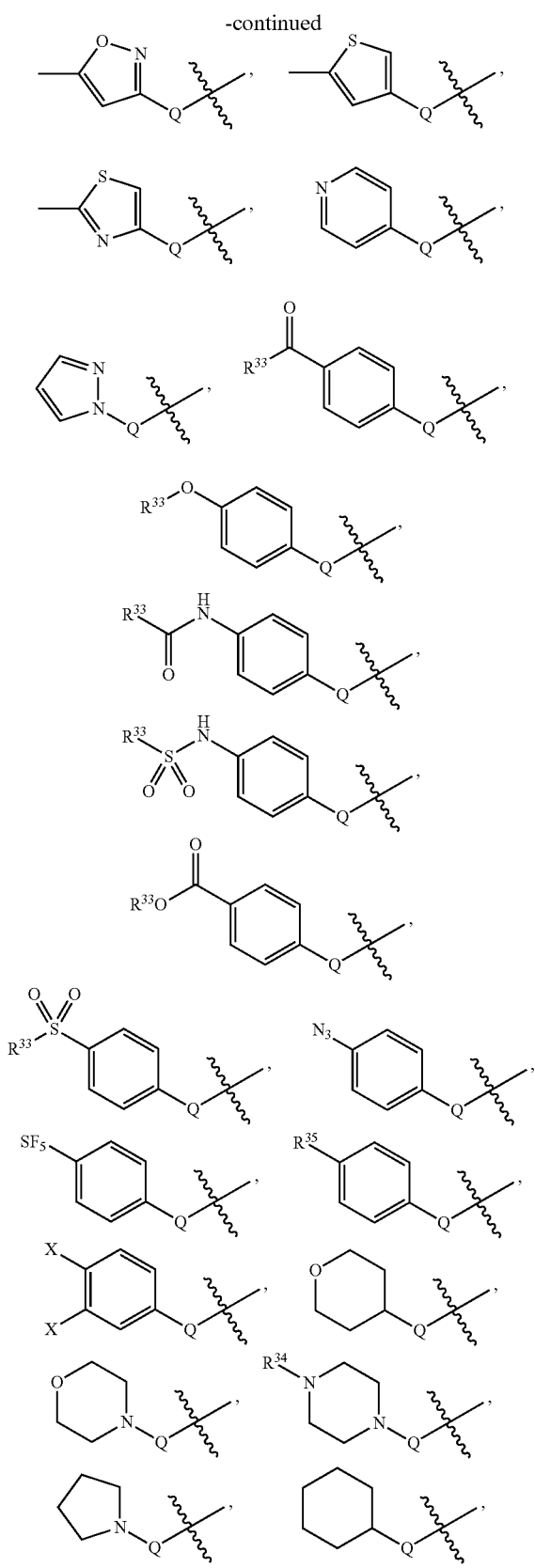

heterocycloalkyl optionally substituted by alkyl and/or halogen, -Q-heteroaryl optionally substituted by unsubstituted ($C_1$-$C_4$ alkyl) and/or halogen, H, C(O)tBu and isopropyl, in which each X is independently F, Cl or Br (preferably F or Cl), each $R^{33}$ is unsubstituted ($C_1$-$C_4$ alkyl), unsubstituted ($C_1$-$C_4$ haloalkyl) or cycloalkyl optionally substituted with unsubstituted alkyl, unsubstituted ($C_1$-$C_4$ alkyl), unsubstituted ($C_1$-$C_4$ haloalkyl) or cycloalkyl optionally substituted with unsubstituted alkyl, and each $R^{35}$ is heterocycloalkyl, optionally substituted with unsubstituted alkyl. In certain such embodiments, Q is a single bond, —$CH_2$—, —$CH_2O$—, —$OCH_2CH_2$—, —$CH_2CH_2$—, —O—, —CHF—, —CH($CH_3$)—, —C($CH_3$)_2—, —CH(OH)—, —CH(COOMe)-, —CH(COOEt)-, —C(O)— or —S(O)_2—. As the person of skill in the art will appreciate, the

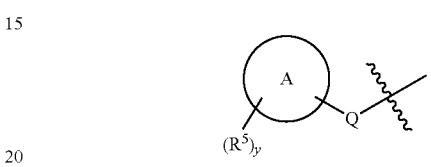

moiety and G-$R^{17}$ moieties described above can be combined in virtually any combination, and such combinations are specifically contemplated by this disclosure. For example, in certain embodiments of the presently disclosed compounds of structural formulae (XIV)-(XX) as described above, both the

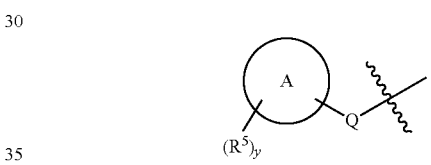

moiety and the -G-$R^{17}$ moiety are

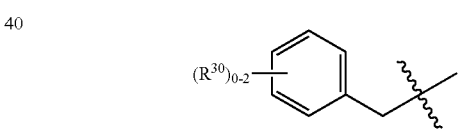

(for example, 4-fluorobenzyl or 4-cyanobenzyl). In other embodiments, the

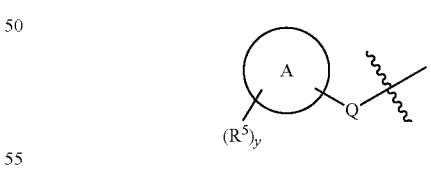

moiety is

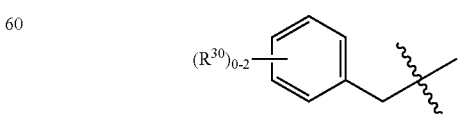

(for example, 4-fluorobenzyl or 4-cyanobenzyl), and the -G-$R^{17}$ moiety is

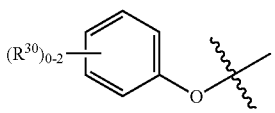

(for example, 4-methylphenoxy, 4-methoxyphenoxy, 4-chlorophenoxy, 4-cyanophenoxy, 4-cyano-2-methoxyphenoxy, 3-methylphenoxy, 3-methoxyphenoxy, 3-fluorophenoxy or 3-cyanophenoxy). Of course, the person of skill in the art will recognize that other combinations of

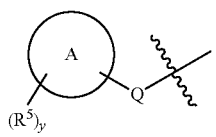

and -G-$R^{17}$ can be used. Such combinations of

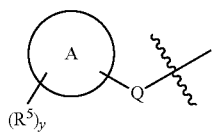

and -G-$R^{17}$ in combination with other combinations of features described herein is specifically contemplated by this disclosure.

In certain embodiments, the presently disclosed compounds have the structural formula (XLII):

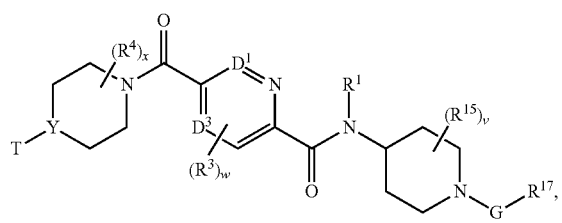

(XLII)

in which the variables are independently defined as described above with respect to structural formulae (I)-(XLI). In certain embodiments of the compounds of structural formula (XXI), T is H. In certain embodiments of the compounds of structural formula (XLII), T is

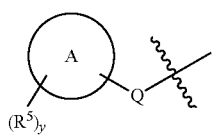

as described above with respect to structural formulae (I)-(XLI), and -G-$R^{17}$ is benzoyl, benzenesulfonyl, phenyl, 1-phenylethyl, 1-methyl-1-phenylethyl, —CH(CO(O)(CH$_2$)$_{1-3}$H)-phenyl substituted with 0, 1 or 2 $R^{30}$ as described above, or 4-methoxybenzyl, —C(O)—Cak or —CH$_2$-Cak. In certain embodiments, G-$R^{17}$ is as described above with respect to structural formulae (I)-(XLII), and T is benzoyl, benzenesulfonyl, 1-methyl-1-phenylethyl, heterocycloalkyl, heteroarylmethyl or heteroaryl substituted with 0, 1 or 2 $R^{30}$ as described above, or 3,5-difluorobenzyl, —C(O)—Cak, ($C_1$-$C_6$ alkyl)C(O)— or ($C_1$-$C_6$ alkyl). In certain embodiments, Y is N. In other embodiments, Y is CH or C substituted by one of the x $R^4$.

In certain embodiments, the presently disclosed compounds have the structural formula (XLIII):

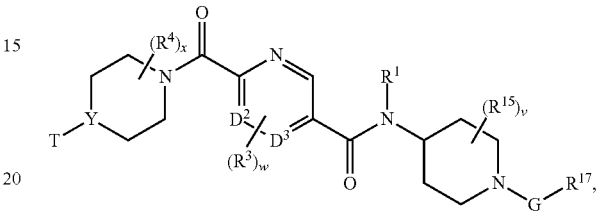

(XLIII)

in which the variables are independently defined as described above with respect to structural formulae (I)-(XLII). In certain embodiments of the compounds of structural formula (XLIII), T is H. In certain embodiments of the compounds of structural formula (XLIII), T is

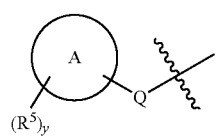

as described above with respect to structural formulae (I)-(XLII), and -G-$R^{17}$ is benzoyl, benzenesulfonyl, phenyl, 1-phenylethyl, 1-methyl-1-phenylethyl, —CH(CO(O)(CH$_2$)$_{1-3}$H)-phenyl substituted with 0, 1 or 2 $R^{30}$ as described above, or 4-methoxybenzyl, —C(O)—Cak or —CH$_2$-Cak. In certain embodiments, G-$R^{17}$ is as described above with respect to structural formulae (I)-(XLII), and T is benzoyl, benzenesulfonyl, 1-methyl-1-phenylethyl, heterocycloalkyl, heteroarylmethyl or heteroaryl substituted with 0, 1 or 2 $R^{30}$ as described above, or 3,5-difluorobenzyl, —C(O)—Cak, ($C_1$-$C_6$ alkyl)C(O)— or ($C_1$-$C_6$ alkyl). In certain embodiments, Y is N. In other embodiments, Y is CH or C substituted by one of the x $R^4$.

In certain embodiments, the presently disclosed compounds have the structural formula (XLIV):

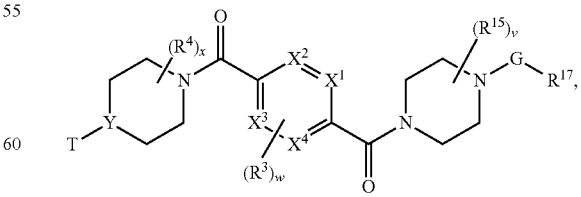

(XLIV)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, T is ($C_1$-$C_6$ alkyl). In other embodiments,

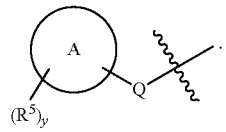

In certain embodiments, the T moiety and the G-$R^{17}$ moiety are independently benzyl, 2-phenylethyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (XLV):

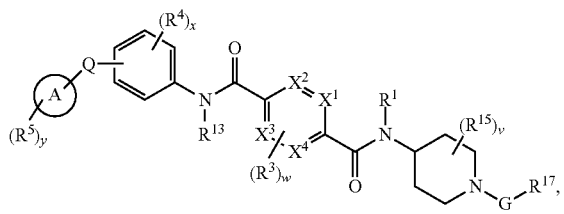

(XLV)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

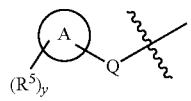

moiety and the G-$R^{17}$ moiety are independently benzyl or phenyl substituted with 0, 1 or 2 $R^{30}$ as described above. In certain embodiments, the Q and the $NR^{13}$ are substituted para from one another on the phenylene. In other embodiments, the Q and the $NR^{13}$ are substituted meta from one another on the phenylene.

In certain embodiments, the presently disclosed compounds have the structural formula (XLVI):

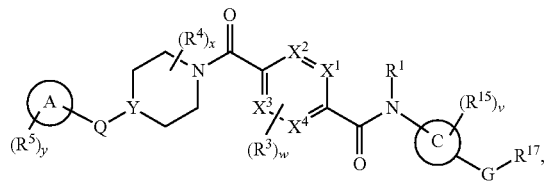

(XLVI)

in which the ring system denoted by "C" is heteroarylene (for example, monocyclic heteroarylene), one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

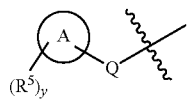

moiety and the G-$R^{17}$ moiety are independently benzyl or phenyl substituted with 0, 1 or 2 $R^{30}$ as described above. In certain embodiments, the ring system denoted by "C" is a pyrazolylene (for example, a 1,3-pyrazolylene), a pyridylene (for example, a 2,5-pyridylene). In certain embodiments, Y is N. In other embodiments, Y is CH or C substituted by one of the x $R^4$.

In certain embodiments, the presently disclosed compounds have the structural formula (XLVII):

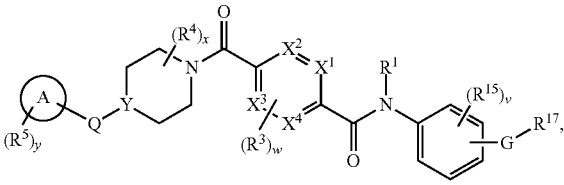

(XLVII), in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

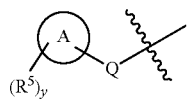

moiety and the G-$R^{17}$ moiety are independently benzyl, phenylmethoxy, —C(O)NHCH$_2$-phenyl, heteroaryl, or phenyl substituted with 0, 1 or 2 $R^{30}$ as described above. In certain embodiments, the G and the $NR^1$ are substituted para with respect to one another on the phenylene. In other embodiments, the G and the $NR^1$ are substituted meta with respect to one another on the phenylene. In other embodiments, the G and the $NR^1$ are substituted ortho with respect to one another on the phenylene. In certain embodiments, Y is N. In other embodiments, Y is CH or C substituted by one of the x $R^4$.

In certain embodiments, the presently disclosed compounds have the structural formula (XLVIII):

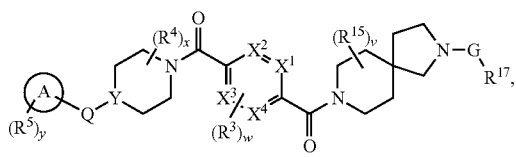
(XLVIII)

in which one or two of $X^1$, $X^2$, $X^3$ and $X^4$ are N, and the others are CH or C substituted by one of the w $R^3$; each of the v $R^{15}$ can be disposed either spiro-fused ring; and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

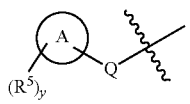

moiety and the G-$R^{17}$ moiety are independently benzyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (XLIX):

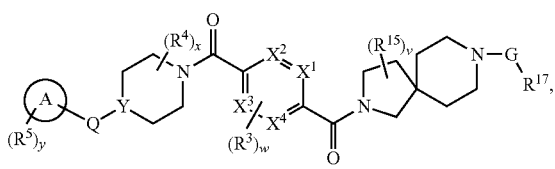
(XLIX)

in which one or two of $X^1$, $X^2$, $X^3$ and $X^4$ are N, and the others are CH or C substituted by one of the w $R^3$; each of the v $R^{15}$ can be disposed either spiro-fused ring; and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

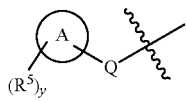

moiety and the G-$R^{17}$ moiety are independently benzyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (L):

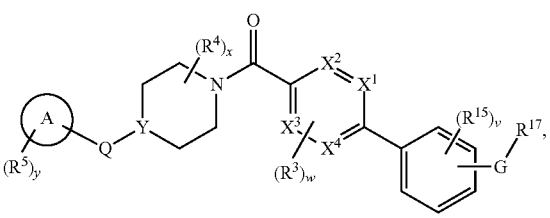
(L)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

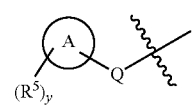

moiety and the G-$R^{17}$ moiety are independently benzyl, phenylmethoxy, —C(O)NHCH$_2$-phenyl or phenyl substituted with 0, 1 or 2 $R^{30}$ as described above. In certain embodiments, the G and the NR$^1$ are substituted para with respect to one another on the phenylene. In other embodiments, the G and the NR$^1$ are substituted meta with respect to one another on the phenylene. In other embodiments, the G and the NR$^1$ are substituted ortho with respect to one another on the phenylene. In certain embodiments, Y is N. In other embodiments, Y is CH or C substituted by one of the x $R^4$.

In certain embodiments, the presently disclosed compounds have the structural formula (LI):

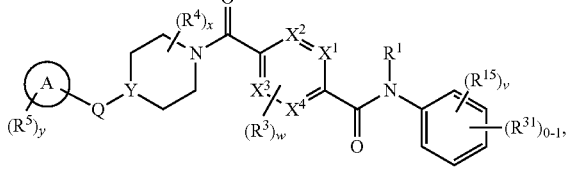
(LI)

in which one or two of $X^1$, $X^2$, $X^3$ and $X^4$ are N, and the others are CH or C substituted by one of the w $R^3$, $R^{31}$ is defined as described above for $R^{30}$ with respect to the

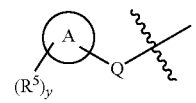

moiety and all other variables are independently defined as described above with respect to structural formulae (I)-(XLIII). In one embodiment, $X^1$ is N and $X^2$, $X^3$ and $X^4$ are CH or C substituted by one of the w $R^3$. In certain embodiments, $R^{31}$ is Br. In certain embodiments, the

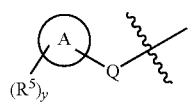

moiety is benzyl with 0, 1 or 2 $R^{30}$ as described above. In certain embodiments, the G and the $NR^1$ are substituted para with respect to one another on the phenylene. In other embodiments, the G and the $NR^1$ are substituted meta with respect to one another on the phenylene. In other embodiments, the G and the $NR^1$ are substituted ortho with respect to one another on the phenylene. In certain embodiments, Y is N. In other embodiments, Y is CH or C substituted by one of the x $R^4$.

In certain embodiments, the presently disclosed compounds have the structural formula (LII):

(LII)

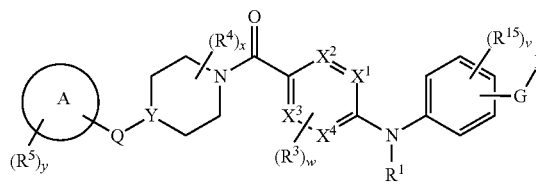

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

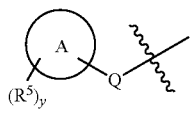

moiety and the G-$R^{17}$ moiety are independently benzyl, phenoxy, phenylmethoxy, —C(O)NHCH$_2$-phenyl or phenyl substituted with 0, 1 or 2 $R^{30}$ as described above. In certain embodiments, the G and the $NR^1$ are substituted para with respect to one another on the phenylene. In other embodiments, the G and the $NR^1$ are substituted meta with respect to one another on the phenylene. In other embodiments, the G and the $NR^1$ are substituted ortho with respect to one another on the phenylene. In certain embodiments, Y is N. In other embodiments, Y is CH or C substituted by one of the x $R^4$.

In certain embodiments, the presently disclosed compounds have the structural formula (LIII):

(LIII)

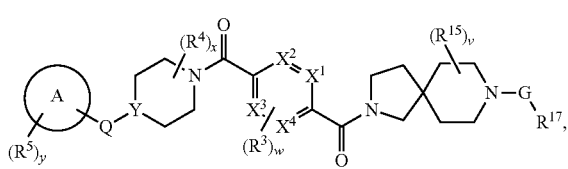

in which one or two of $X^1$, $X^2$, $X^3$ and $X^4$ are N; each of the v $R^{15}$ can be disposed either spiro-fused ring; and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

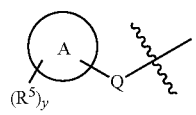

moiety and the G-$R^{17}$ moiety are independently benzyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (LIV):

(LIV)

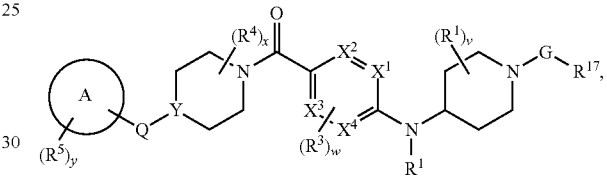

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

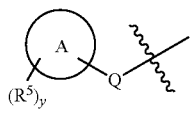

moiety and the G-$R^{17}$ moiety are independently benzyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (LV):

(LV)

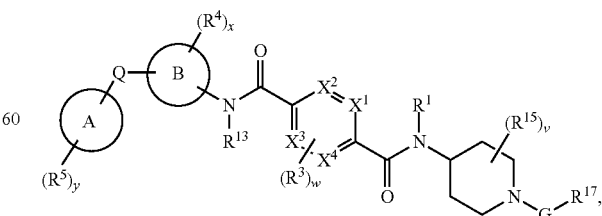

in which the ring system denoted by "B" is a heteroarylene, one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

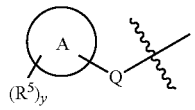

moiety and the G-$R^{17}$ moiety are independently benzyl or phenyl substituted with 0, 1 or 2 $R^{30}$ as described above. In certain embodiments, the ring system denoted by "B" is a pyrazolylene (for example, a 1,3-pyrazolylene).

In certain embodiments, the presently disclosed compounds have the structural formula (LVI):

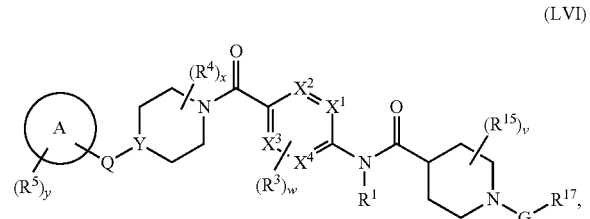

(LVI)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

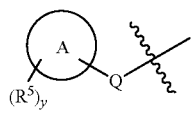

moiety and the G-$R^{17}$ moiety are independently benzyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (LVII):

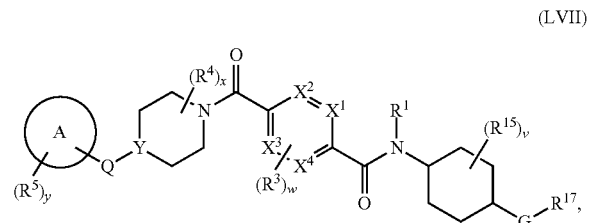

(LVII)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

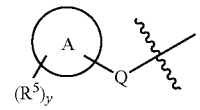

moiety and the G-$R^{17}$ moiety are independently benzyl or phenyl substituted with 0, 1 or 2 $R^{30}$ as described above. The $NR^1$ and G-$R^{17}$ moieites can, for example, be substituted cis with respect to one another on the cyclohexane ring. In other embodiments, the $NR^1$ and G-$R^{17}$ moieites are substituted trans with respect to one another on the cyclohexane ring. In certain embodiments, Y is N. In other embodiments, Y is CH or C substituted by one of the x $R^4$.

certain embodiments, the presently disclosed compounds have the structural formula (LVIII):

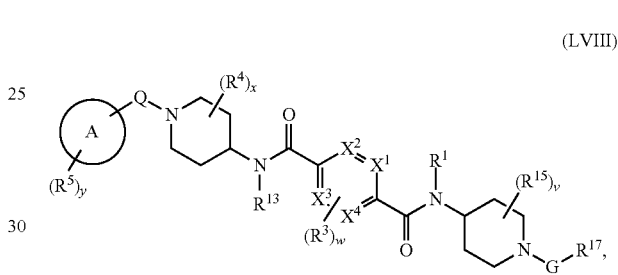

(LVIII)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

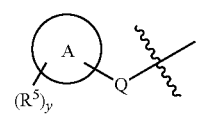

moiety and the G-$R^{17}$ moiety are independently benzyl, phenoxy or phenyl substituted with 0, 1 or 2 $R^{30}$ as described above.

In certain embodiments, the presently disclosed compounds have the structural formula (LIX):

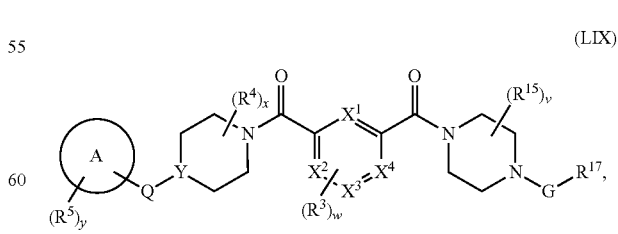

(LIX)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

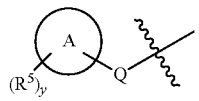

moiety and the G-$R^{17}$ moiety are independently benzyl, 2-phenylethyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (LX):

(LX)

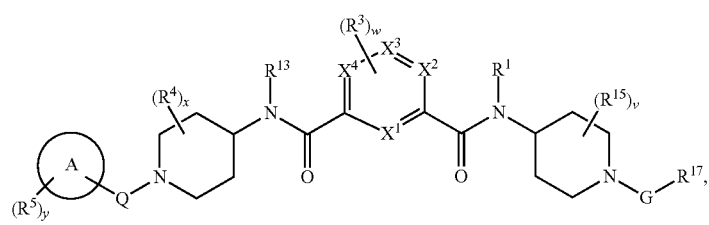

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

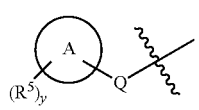

moiety and the G-$R^{17}$ moiety are independently benzyl or phenyl substituted with 0, 1 or 2 $R^{30}$ as described above.

In certain embodiments, the presently disclosed compounds have the structural formula (LXI):

(LXI)

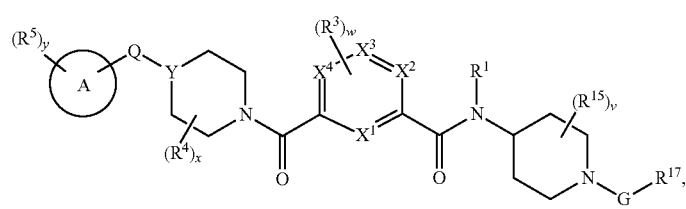

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

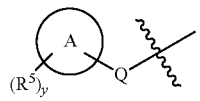

moiety and the G-$R^{17}$ moiety are independently benzyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (LXII):

(LXII)

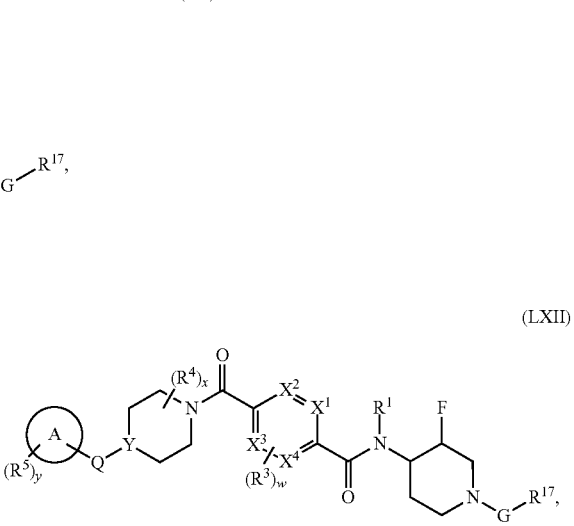

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. In certain embodiments, the fluorine atom and the —N$R^1$— are disposed cis with respect to one another on the piperidine. In certain embodiments, the

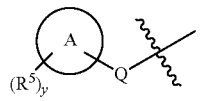

moiety and the G-R$^{17}$ moiety are independently benzyl or phenyl substituted with 0, 1 or 2 R$^{30}$ as described above. In certain embodiments, Y is N. In other embodiments, Y is CH or C substituted by one of the x R$^4$.

In certain embodiments, the presently disclosed compounds have the structural formula (LXIII):

(LXIII)

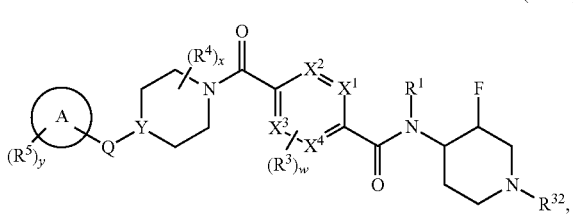

in which R$^{32}$ is —H, —(C$_1$-C$_4$ alkyl), —C(O)—(C$_1$-C$_4$ alkyl) or —C(O)O—(C$_1$-C$_4$ alkyl), one or two of X$^1$, X$^2$, X$^3$ and X$^4$ are N, and the others are CH or C substituted by one of the w R$^3$, and all other variables are independently defined as described above with respect to structural formulae (I)-(XLIII). In one embodiment, X$^1$ is N and X$^2$, X$^3$ and X$^4$ are CH or C substituted by one of the w R$^3$. and the other variables are independently defined as described above with respect to structural formulae (I)-(XIV). In certain embodiments, R$^{32}$ is H or methyl. In certain embodiments, the fluorine atom and the —NR$^1$— are disposed cis with respect to one another on the piperidine. In certain embodiments, the

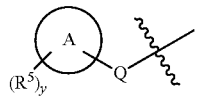

moiety and the G-R$^{17}$ moiety are independently benzyl or phenyl substituted with 0, 1 or 2 R$^{30}$ as described above. In certain embodiments, Y is N. In other embodiments, Y is CH or C substituted by one of the x R$^4$.

In certain embodiments, the presently disclosed compounds have the structural formula (LXIV):

(LXIV)

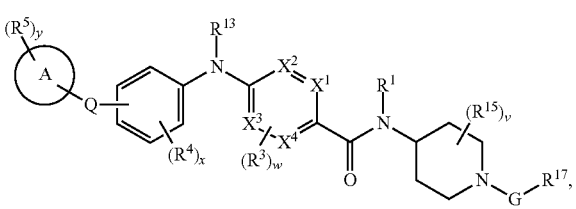

in which one or two of X$^1$, X$^2$, X$^3$ and X$^4$ are N, and the others are CH or C substituted by one of the w R$^3$, and all other variables are independently defined as described above with respect to structural formulae (I)-(XLIII). In one embodiment, X$^1$ is N and X$^2$, X$^3$ and X$^4$ are CH or C substituted by one of the w R$^3$. For example, in certain embodiments, the

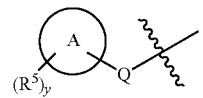

moiety and the G-R$^{17}$ moiety are independently benzyl, phenoxy or phenyl substituted with 0, 1 or 2 R$^{30}$ as described above. In certain embodiments, the Q and the NR$^{13}$ are substituted para from one another on the phenylene. In other embodiments, the Q and the NR$^{13}$ are substituted meta from one another on the phenylene.

In certain embodiments, the presently disclosed compounds have the structural formula (LXV):

(LXV)

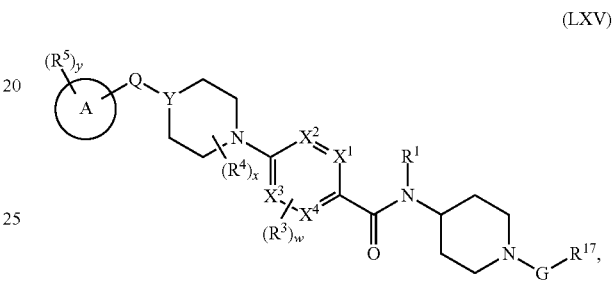

in which one or two of X$^1$, X$^2$, X$^3$ and X$^4$ are N, and the others are CH or C substituted by one of the w R$^3$, and all other variables are independently defined as described above with respect to structural formulae (I)-(XLIII). In one embodiment, X$^1$ is N and X$^2$, X$^3$ and X$^4$ are CH or C substituted by one of the w R$^3$. In certain embodiments, the

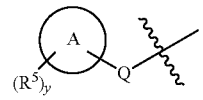

moiety and the G-R$^{17}$ moiety are independently benzyl or phenyl substituted with 0, 1 or 2 R$^{30}$ as described above. In certain embodiments, Y is N. In other embodiments, Y is CH or C substituted by one of the x R$^4$.

In certain embodiments, the presently disclosed compounds have the structural formula (LXVI):

(LXVI)

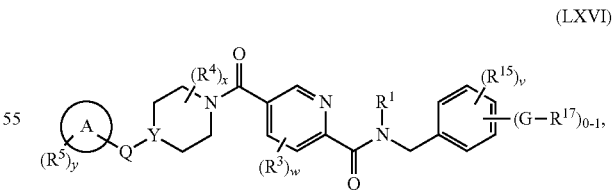

in which one or two of X$^1$, X$^2$, X$^3$ and X$^4$ are N, and the others are CH or C substituted by one of the w R$^3$, and all other variables are independently defined as described above with respect to structural formulae (I)-(XLIII), and the G-R$^{17}$ moiety is optional. In one embodiment, X$^1$ is N and X$^2$, X$^3$ and X$^4$ are CH or C substituted by one of the w R$^3$. For example, in certain embodiments, the G-R$^{17}$ moiety is absent. In certain embodiments, the

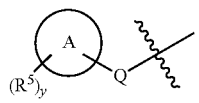

moiety and the G-R$^{17}$ moiety (if present) are independently benzyl or phenyl substituted with 0, 1 or 2 R$^{30}$ as described above. In certain embodiments, Y is N. In other embodiments, Y is CH or C substituted by one of the x R$^4$.

In certain embodiments, the presently disclosed compounds have the structural formula (LXVII):

(LXVII)

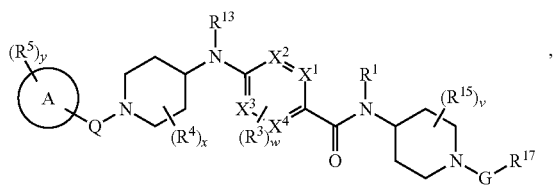

in which one or two of X$^1$, X$^2$, X$^3$ and X$^4$ are N, and the others are CH or C substituted by one of the w R$^3$, and all other variables are independently defined as described above with respect to structural formulae (I)-(XLIII). In one embodiment, X$^1$ is N and X$^2$, X$^3$ and X$^4$ are CH or C substituted by one of the w R$^3$. For example, in certain embodiments, the

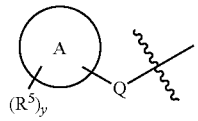

moiety and the G-R$^{17}$ moiety are independently benzyl or phenyl substituted with 0, 1 or 2 R$^{30}$ as described above.

In certain embodiments, the presently disclosed compounds have the structural formula (LXVIII):

(LXVII)

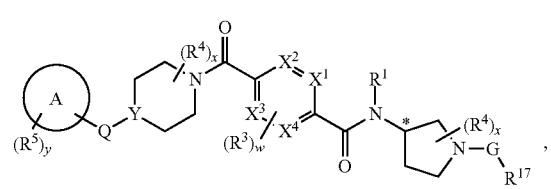

in which one or two of X$^1$, X$^2$, X$^3$ and X$^4$ are N, and the others are CH or C substituted by one of the w R$^3$, and all other variables are independently defined as described above with respect to structural formulae (I)-(XLIII). In one embodiment, X$^1$ is N and X$^2$, X$^3$ and X$^4$ are CH or C substituted by one of the w R$^3$. For example, in certain embodiments, the

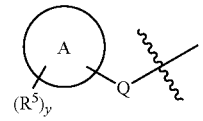

moiety and the G-R$^{17}$ moiety are independently benzyl or phenyl substituted with 0, 1 or 2 R$^{30}$ as described above. In certain embodiments, the stereogenic center indicated by "*" is racemic. In other embodiments, it is enantiomerically enriched, for example, in the (R)-configuration (i.e., the carbon-NR$^1$ bond disposed above the plane of the page). In other embodiments, it is enantiomerically enriched, for example, in the (S)-configuration (i.e., the carbon-NR$^1$ bond disposed below the plane of the page). In certain embodiments, Y is N. In other embodiments, Y is CH or C substituted by one of the x R$^4$.

In certain embodiments, the presently disclosed compounds have the structural formula (LXVIII):

(LXVIII)

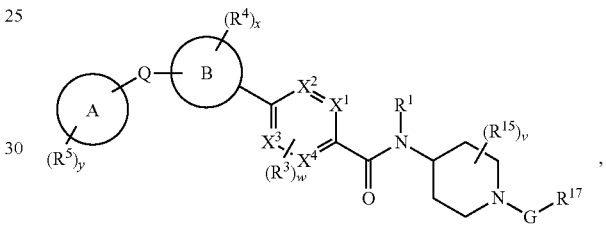

in which the ring system denoted by "B" is a heteroarylene, one or two of X$^1$, X$^2$, X$^3$ and X$^4$ are N, and the others are CH or C substituted by one of the w R$^3$, and all other variables are independently defined as described above with respect to structural formulae (I)-(XLIII). In one embodiment, X$^1$ is N and X$^2$, X$^3$ and X$^4$ are CH or C substituted by one of the w R$^3$. For example, in certain embodiments, the

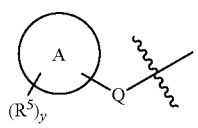

moiety and the G-R$^{17}$ moiety are independently benzyl or phenyl substituted with 0, 1 or 2 R$^{30}$ as described above. In certain embodiments, the ring system denoted by "B" is a triazolylene (for example, a 1,2,3-triazol-1,4-ylene).

In certain embodiments, the presently disclosed compounds have the structural formula (LXIX):

(LXIX)

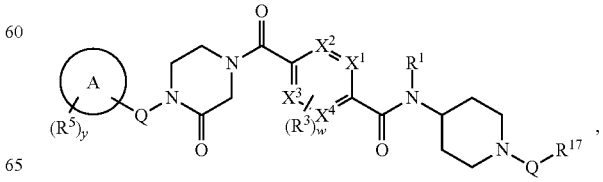

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

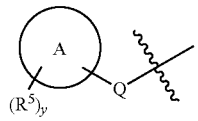

moiety and the G-$R^{17}$ moiety are independently benzyl or phenyl substituted with 0, 1 or 2 $R^{30}$ as described above.

In certain embodiments, the presently disclosed compounds have the structural formula (LXX):

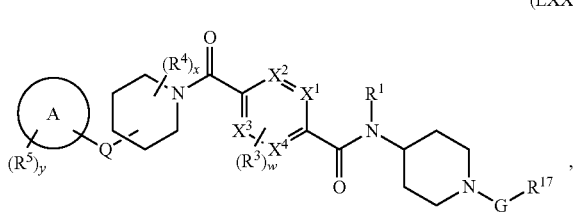

(LXX)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

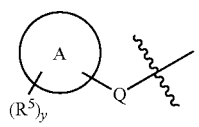

moiety and the G-$R^{17}$ moiety are independently benzyl, benzoyl, 1-fluoro-1-phenylmethyl, phenoxy or phenyl substituted with 0, 1 or 2 $R^{30}$ as described above. In certain embodiments, the

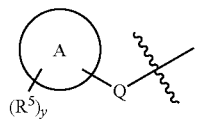

moiety is bound at the 4-position of the piperidine. In other embodiments, it is bound at the 3-position of the piperidine. In other embodiments, it is bound at the 2-position of the piperidine.

In certain embodiments, the presently disclosed compounds have the structural formula (LXXI):

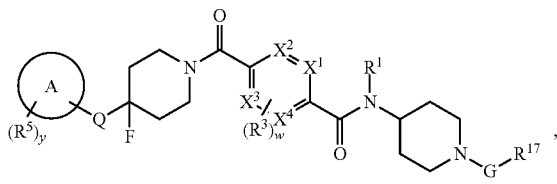

(LXXI)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the moiety and the G-$R^{17}$ moiety are independently benzyl, benzoyl, 1-fluoro-1-phenylmethyl, phenoxy or phenyl substituted with 0, 1 or 2 $R^{30}$ as described above.

In certain embodiments, the presently disclosed compounds have the structural formula (LXXII):

(LXXII)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the moiety and the G-$R^{17}$ moiety are independently benzyl or phenyl substituted with 0, 1 or 2 $R^{30}$ as described above.

In certain embodiments, the presently disclosed compounds have the structural formula (LXXIII):

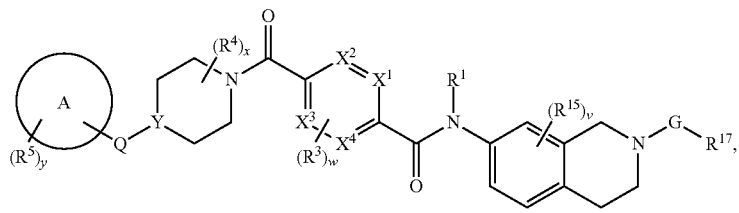

(LXXIII)

in which one or two of $X^1$, $X^2$, $X^3$ and $X^4$ are N and the others are CH or C substituted by one of the w $R^3$; each of the $R^{15}$ is substituted on either ring of the 1,2,3,4-tetrahydroisoquinoline; and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

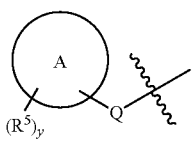

moiety and the G-$R^{17}$ moiety are independently benzyl or phenyl substituted with 0, 1 or 2 $R^{30}$ as described above. In certain embodiments, Y is N. In other embodiments, Y is CH or C substituted by one of the x $R^4$.

In certain embodiments, the presently disclosed compounds have the structural formula (LXXIV):

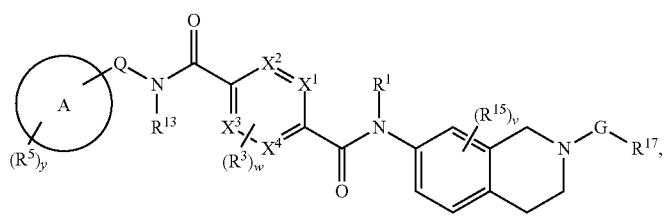

(LXXIV)

in which one or two of $X^1$, $X^2$, $X^3$ and $X^4$ are N, and the others are CH or C substituted by one of the w $R^3$; each of the $R^{15}$ is substituted on either ring of the 1,2,3,4-tetrahydroisoquinoline; and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

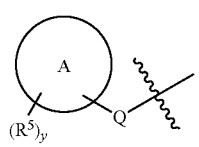

moiety and the G-$R^{17}$ moiety are independently benzyl or phenyl substituted with 0, 1 or 2 $R^{30}$ as described above.

In certain embodiments, the presently disclosed compounds have the structural formula (LXXV):

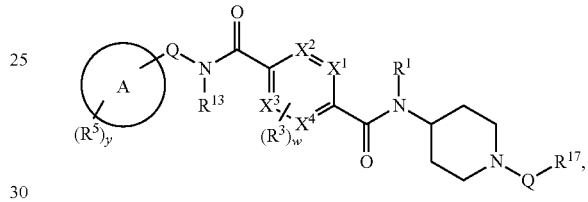

(LXXV)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

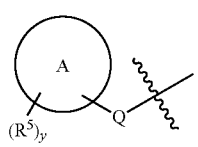

moiety and the G-$R^{17}$ moiety are independently benzyl or phenyl substituted with 0, 1 or 2 $R^{30}$ as described above. In other embodiments, the Q moiety is —O—CH$_2$—CH$_2$—.

In certain embodiments, the presently disclosed compounds have the structural formula (LXXVI):

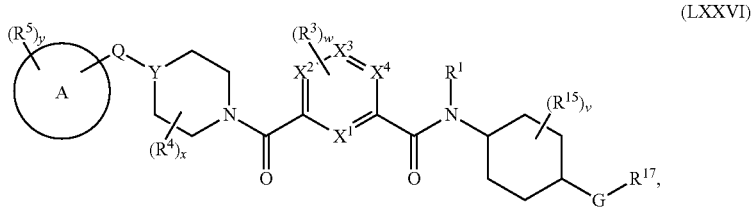

(LXXVI)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

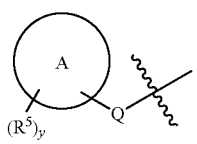

moiety and the G-$R^{17}$ moiety are independently benzyl or phenyl substituted with 0, 1 or 2 $R^{30}$ as described above. In certain embodiments, the $NR^1$ and the -G-$R^{17}$ are disposed cis with respect to one another on the cyclohexane ring. In other embodiments, the $NR^1$ and the -G-$R^{17}$ are disposed trans with respect to one another on the cyclohexane ring. In certain embodiments, Y is N. In other embodiments, Y is CH or C substituted by one of the x $R^4$.

In certain embodiments, the presently disclosed compounds have the structural formula (LXXVII):

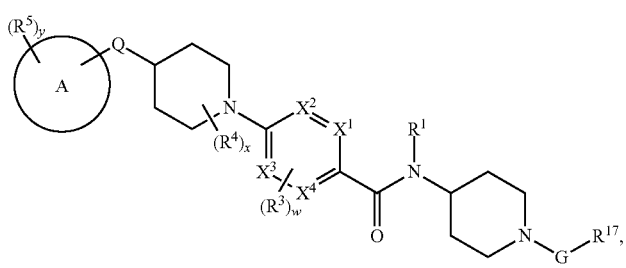

(LXXVII)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. For example, in certain embodiments, the

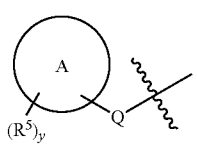

moiety and the G-$R^{17}$ moiety are independently benzyl, phenoxy or phenyl substituted with 0, 1 or 2 $R^{30}$ as described above.

In certain embodiments, the presently disclosed compounds have the structural formula (LXXVIII):

(LXXVIII)

[structural formula LXXVIII]

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. The E moiety can be, for example, as described with reference to any of structural formulae (XIII)-(LXXVIII). For example, in certain embodiments, the

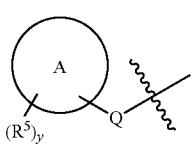

moiety and the E moiety are independently benzyl, phenoxy or phenyl substituted with 0, 1 or 2 $R^{30}$ as described above.

In certain embodiments, the presently disclosed compounds have the structural formula (LXXIX):

(LXXIX)

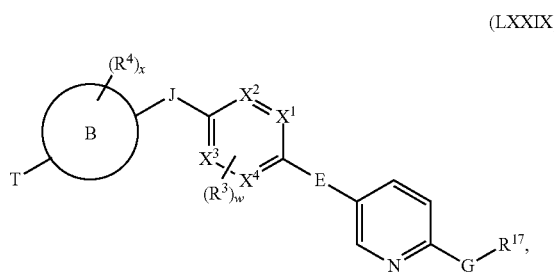

in which one or two of $X^1$, $X^2$, $X^3$ and $X^4$ are N, and the others are CH or C substituted by one of the w $R^3$, $E^2$ is —CONR$^1$— (for example, —CONH—) or —NR$^1$CO— (for example, —NHCO—), and all other variables are independently defined as described above with respect to structural formulae (I)-(XLIII). In one embodiment, $X^1$ is N and $X^2$, $X^3$ and $X^4$ are CH or C substituted by one of the w $R^3$. The -G-$R^{17}$ moiety can be, for example, as described with reference to any of structural formulae (XIII)-(LXXVIII). Independently, the

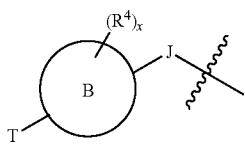

moiety can be, for example, as described with reference to any of structural formulae (XIII)-(LXXVIII). For example, in certain embodiments, the T moiety and the G-$R^{17}$ moiety are independently benzyl, phenoxy or phenyl substituted with 0, 1 or 2 $R^{30}$ as described above. In other embodiments, G is O, CH$_2$, or SO$_2$.

In certain embodiments, the presently disclosed compounds have the structural formula (LXXX):

(LXXX)

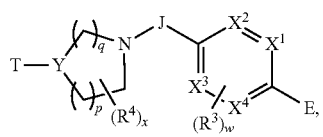

in which two $R^4$ on different carbons combine to form a (C$_1$-C$_4$ alkylene) bridge, one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. The E moiety can be, for example, as described with reference to any of structural formulae (XIII)-(LXXVIII). Independently, the T moiety can be, for example, as described with reference to any of structural formulae (XIII)-(LVII). For example, in certain embodiments, the T moiety is independently benzyl, phenoxy or phenyl substituted with 0, 1 or 2 $R^{30}$ as described above. In certain embodiments, Y is N. In other embodiments, Y is CH or C substituted by one of the x $R^4$. In certain embodiments, the

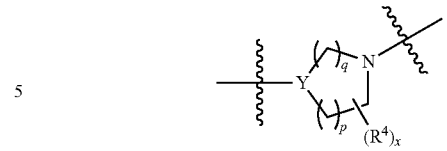

moiety is

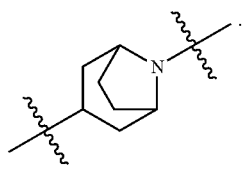 [SMILES: *C1CC2CCC(C1)N2*]

In certain embodiments, the presently disclosed compounds have the structural formula (LXXXI):

(LXXXI)

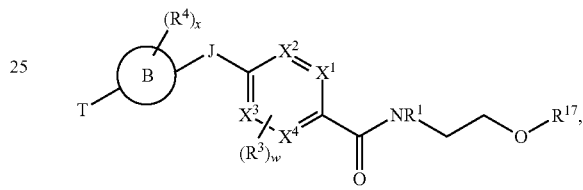

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. In one embodiment, $R^1$ is H. The —$R^{17}$ moiety can be, for example, as described with reference to any of structural formulae (XIII)-(LXXVIII). Independently, the

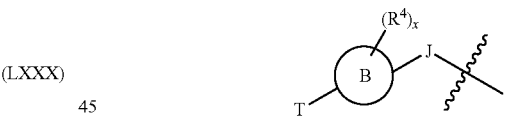

moiety can be, for example, as described with reference to any of structural formulae (XIII)-(LXXVIII). For example, in certain embodiments, the T moiety is benzyl, phenoxy or phenyl substituted with 0, 1 or 2 $R^{30}$ as described above; and the $R^{17}$ moiety is phenyl substituted with 0, 1 or 2 $R^{30}$ as described above.

In certain embodiments, the presently disclosed compounds have the structural formula (LXXXII):

(LXXXII)

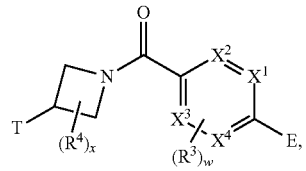

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. The E moiety can be, for example, as described with reference to any of structural formulae (XIII)-(LXXVIII). Independently, the T moiety can be, for example, as described with reference to any of structural formulae (XIII)-(LXXVIII). For example, in certain embodiments, the T moiety is benzyl, phenoxy or phenyl substituted with 0, 1 or 2 $R^{30}$ as described above.

In certain embodiments, the presently disclosed compounds have the structural formula (LXXXIII):

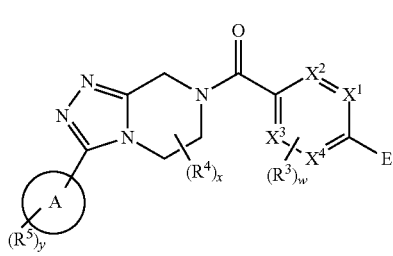

(LXIII)

in which one or two of $X^1$, $X^2$, $X^3$ and $X^4$ are N, and the others are CH or C substituted by one of the w $R^3$, and all other variables are independently defined as described above with respect to structural formulae (I)-(XLIII). In one embodiment, $X^1$ is N and $X^2$, $X^3$ and $X^4$ are CH or C substituted by one of the w $R^3$. The E moiety can be, for example, as described with reference to any of structural formulae (XIII)-(LXXVIII). The A-$(R^5)_y$ moiety independently be, for example, described reference to any of structural formulae (XIII)-(LXXVIII). For example, in certain embodiments, the T moiety is benzyl, phenoxy or phenyl substituted with 0, 1 or 2 $R^{30}$ as described above.

In certain embodiments, the presently disclosed compounds have the structural formula (LXXXIV):

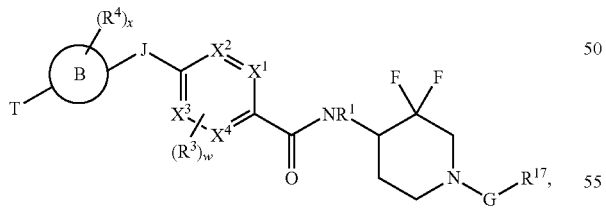

(LXXXIV)

in which one or two of $X^1$, $X^2$, $X^3$ and $X^4$ are N, and the others are CH or C substituted by one of the w $R^3$, and all other variables are independently defined as described above with respect to structural formulae (I)-(XXII). In one embodiment, $X^1$ is N and $X^2$, $X^3$ and $X^4$ are CH or C substituted by one of the w $R^3$. In one embodiment, $R^1$ is H. The -G-$R^{17}$ moiety can be, for example, as described with reference to any of structural formulae (XIII)-(LXXVIII). Independently, the

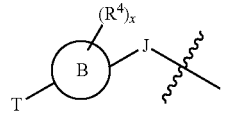

moiety can be, for example, as described with reference to any of structural formulae (XIII)-(LXXVIII). For example, in certain embodiments, the T moiety is benzyl, phenoxy or phenyl substituted with 0, 1 or 2 $R^{30}$ as described above; and the $R^{17}$ moiety is phenyl substituted with 0, 1 or 2 $R^{30}$ as described above.

In certain embodiments of compounds having structural formulae (XIII)-(LXXVIII), the

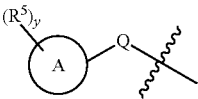

moiety is p-(trifluoromethyl)phenyl, p-fluorophenoxy, m-chloro-p-cyanophenoxy, p-trifluoromethylphenoxy, m,p-difluorophenoxy, m-cyanophenoxy, p-chlorobenzoyl, 2-(p-fluorophenoxy)ethyl, m-methoxyphenyl, m-fluoro-p-methoxybenzyl, p-methylbenzyl, α,p-difluorobenzyl, p-fluoro-α-hydroxybenzyl, 1-methyl-1-phenylethyl, p-chlorophenyl, p-cyanophenoxy, benzenesulfonyl, tetrahydro-2H-pyran-4-yl, 5-methylisoxazol-3-yl, p-fluorobenzenesulfonyl, p-methoxybenzenesulfonyl, benzyl, p-cyano-o-methoxyphenoxy, p-methoxybenzoyl, p-methoxyphenoxy, benzoyl, p-fluorobenzoyl, cyclohexanecarbonyl, p-methoxybenzoyl, cyclohexylmethyl, pyrid-4-yl, pyrid-4-ylmethyl, phenoxy, phenyl, phenethyl, p-methoxyphenyl, p-fluorophenyl, p-cyanophenyl, p-(trifluoromethyl)benzyl, p-methoxybenzyl, p-fluorobenzyl, m,m-difluorobenzyl, p-carbamoylbenzyl, p-(pentafluorosulfanyl)benzyl, p-(pentafluorosulfanyl)phenoxy, p-(cyclopropylsulfonyl)phenoxy, p-(cyclopropylsulfonyl)benzyl, p-(methylsulfonyl)benzyl, p-(methylsulfonyl)phenoxy, p-(trifluoromethylsulfonyl)phenoxy, p-(trifluoromethylsulfonyl)phenyl, p-(methylsulfonyl)phenyl, p-(dimethylcarbamoyl)benzyl, p-(isopropylsulfonyl)phenyl, p-(cyclopropylsulfonyl)phenyl, p-azidobenzoyl, o,p-difluorobenzoyl, o,p-difluorobenzoxy, pyridin-3-yloxy, pyridin-4-yloxy, m,p-difluorobenzoyl, p-fluorobenzyloxy, p-(1-pyrrolidinyl)benzoyl, p-(trifluoromethylthio)phenoxy, m-(cyclopropanecarboxamido)phenoxy, p-acetamidophenoxy, m-acetamidophenoxy, p-cyclopropancarboxamidphenoxy, p-morpholinobenzoyl, p-(4-methylpiperzine-1-yl)benzoyl, p-methoxy-o-nitrophenoxy, p-(methylsulfinyl)benzoyl, p-(methylsulfonamido)benzoxy, p-nitrophenoxy, p-aminophenoxy or p-cyanobenzyl.

Another aspect of the disclosure provides compounds of structural formula (LXXXV):

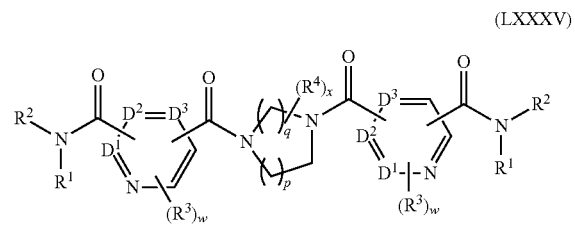

(LXXXV)

in which each of the variables is independently defined as described above with respect to structural formulae (I)-(LXXXIV). For example, in certain embodiments, a compound has structural formula (LXXXVI):

(LXXXVI)

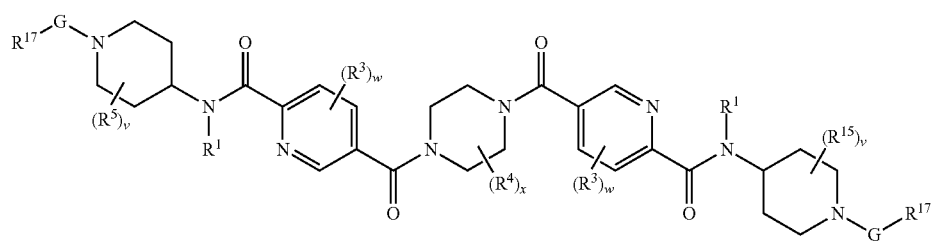

in which each of the variables is independently defined as described above with respect to structural formulae (I)-(LXXVIII).

In certain embodiments of compounds having structural formulae (XIII)-(LXXVI) as described above, the -G-$R^{17}$ moiety is p-chlorobenzyl, p-fluorobenzyl, p-cyanobenzyl, p-cyano-m-fluorobenzyl, p-cyanobenzoyl, p-cyanobenzenesulfonyl, cyclohexanecarbonyl, benzoyl, benzyl, phenyl, cyclohexylmethyl, phenoxy, phenylmethoxy, 1-phenylethyl, p-nitrophenyl, cyanophenyl, p-(trifluoromethyl)phenyl, p-bromophenyl, 1H-pyrrol-3-yl, 4-morpholinyl, 4-methylpiperazin-1-yl, p-cyanobenzylcarbamoyl, m,m-difluorobenzyl, p-fluoro-m-methylbenzyl, p-methoxybenzyl, p-chlorobenzyl, p-methylbenzoxy, m-fluorophenoxy, p-fluorophenoxy, m-cyanophenoxy, m-methoxyphenoxy, m-methylphenoxy, p-cyanophenoxy, p-fluorophenoxy, pyrid-3-yl, thien-3-yl, phenethyl, α-carboethoxybenzyl, pyrid-4-ylmethyl, 1-(p-cyanophenyl)-1-methylethyl, p-(trifluoromethyl)benzenesulfonyl, p-(trifluoromethyl)phenoxy, p-(trifluoromethyl)benzyl, m-(trifluoromethyl)benzyl, p-methylsulfonylbenxyl, p-methylsulfonylphenoxy, p-acetylphenoxy, p-pyrrolidinylbenzyl, or p-methoxybenzyl, As the person of skill in the art will recognize, the various embodiments and features described above can be combined to form other embodiments contemplated by the disclosure. For example, in one embodiment of the compounds of certain of structural formulae (I)-(LXXV) as described above, Q is —$CH_2$—, as described above, and G is —$CH_2$—, as described above. In another embodiment of the compounds of certain of structural formulae (I)-(LXXV) as described above, x is 0 and each w is 0. In another embodiment of the compounds of certain of structural formulae (I)-(LXXVI), x is 0, each w is 0 and each v is 0.

Moreover, the various -E moieties and T-("B" ring system)-J- moieties described above with respect to any of structural formulae (I)-(LXXVI) can be combined around the central pyridine, pyrazine, pyridazine or pyrimidine (for example, in any of the ways described with respect to structural formulae (IX)-(XIII)) to form additional embodiments of compounds specifically contemplated by this disclosure.

Examples of compounds according to structural formula (I) include those listed in Table 1. These compounds can be made according to the general schemes described below, for example using procedures analogous to those described below in the Examples.

TABLE 1

| No. | Name | Structure |
|---|---|---|
| 1 | N-(4-(4-cyanobenzyl)piperadin-4-yl)-6-(4-(4-fluorobenzyl)piperizine-1-carbonyl)picolinamide | 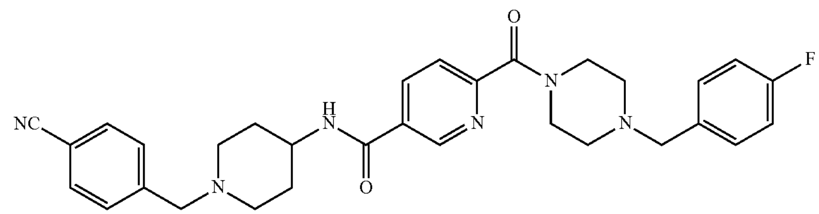 [SMILES: N#Cc1ccc(CN2CCC(NC(=O)c3ccc(C(=O)N4CCN(Cc5ccc(F)cc5)CC4)nc3)CC2)cc1] |
| 2 | N-(1-(4-cyanobenzyl)piperidin-4-yl)-5-(piperazine-1-carbonyl)picolinamide | 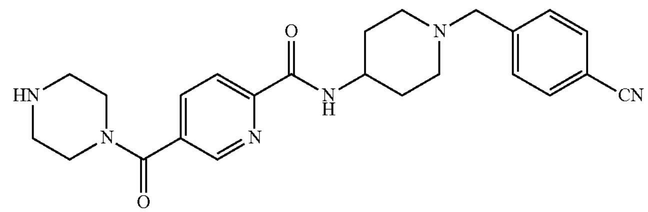 [SMILES: N#Cc1ccc(CN2CCC(NC(=O)c3ccc(C(=O)N4CCNCC4)cn3)CC2)cc1] |
| 3 | pyridine-2,5-diylbis((4-(4-fluorobenzyl)piperazin-1-yl)methanone) | 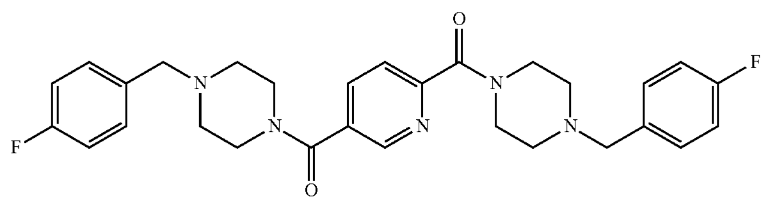 [SMILES: O=C(c1ccc(C(=O)N2CCN(Cc3ccc(F)cc3)CC2)nc1)N1CCN(Cc2ccc(F)cc2)CC1] |
| 4 | N-(1-(4-cyanobenzoyl)piperidin-4-yl)-5-(4-(4-fluorobenzyl)piperazine-1-carbonyl)picolinamide | 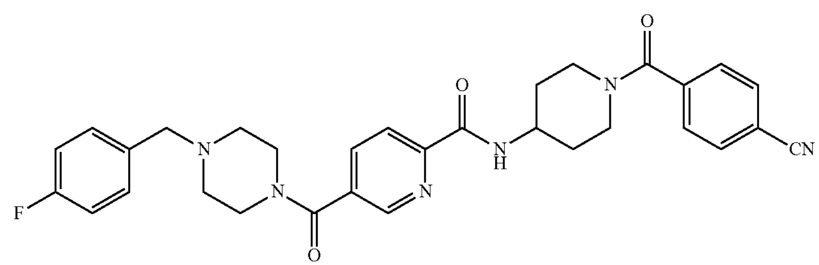 [SMILES: N#Cc1ccc(C(=O)N2CCC(NC(=O)c3ccc(C(=O)N4CCN(Cc5ccc(F)cc5)CC4)cn3)CC2)cc1] |

TABLE 1-continued

| No. | Name | Structure |
|---|---|---|
| 5 | N²-(1-(4-cyanobenzyl)piperidin-4-yl)-N⁵-(3-benzylphenyl)pyridine-2,5-dicarboxamide | 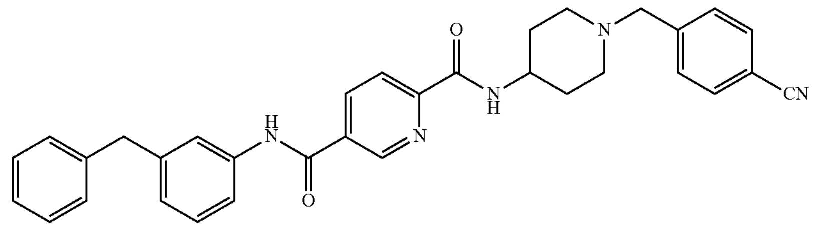 [SMILES: N#Cc1ccc(CN2CCC(NC(=O)c3ccc(C(=O)Nc4cccc(Cc5ccccc5)c4)cn3)CC2)cc1] |
| 6 | N-(4-((4-cyanophenyl)sulfonyl)piperidin-4-yl)-5-(4-(4-fluorobenzyl)piperazine-1-carbonyl)picolinamide | 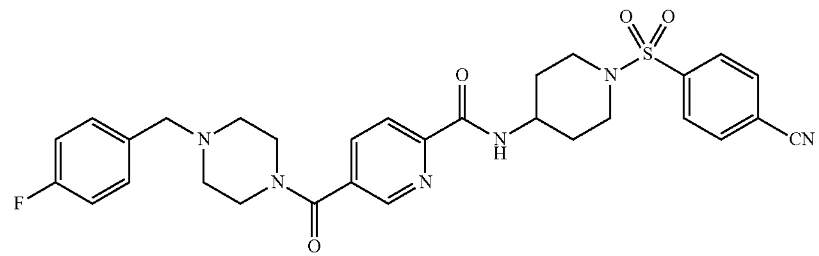 [SMILES: N#Cc1ccc(S(=O)(=O)N2CCC(NC(=O)c3ccc(C(=O)N4CCN(Cc5ccc(F)cc5)CC4)cn3)CC2)cc1] |
| 7 | N-(1-(cyclohexanecarbonyl)piperidin-4-yl)-5-(4-(4-fluorobenzyl)piperazine-1-carbonyl)picolinamide | 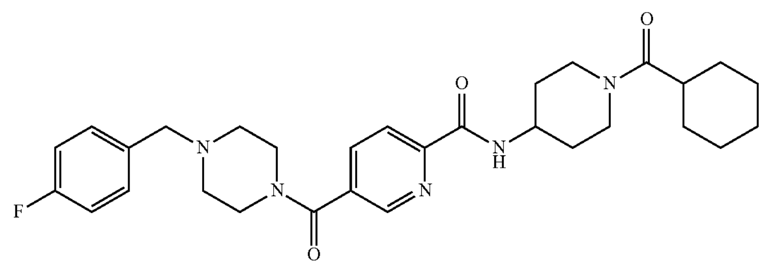 [SMILES: O=C(NC1CCN(C(=O)C2CCCCC2)CC1)c1ccc(C(=O)N2CCN(Cc3ccc(F)cc3)CC2)cn1] |
| 8 | N-(1-(benzoyl)piperidin-4-yl)-5-(4-(4-fluorobenzyl)piperazine-1-carbonyl)picolinamide |

TABLE 1-continued

| No. | Name | Structure |
|---|---|---|
| 9 | N-(1-(4-cyanobenzyl)-1H-pyrazol-3-yl)-5-(4-(4-fluorobenzyl)piperazine-1-carbonyl)picolinamide | 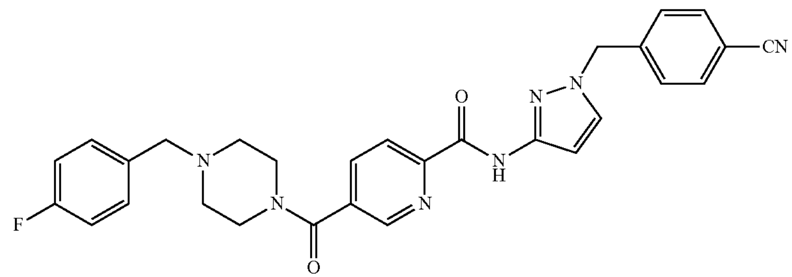 [SMILES: N#Cc1ccc(Cn2ccc(NC(=O)c3ccc(C(=O)N4CCN(Cc5ccc(F)cc5)CC4)cn3)n2)cc1] |
| 10 | N-(4-benzylphenyl)-5-(4-(4-fluorobenzyl)piperazine-1-carbonyl)picolinamide | 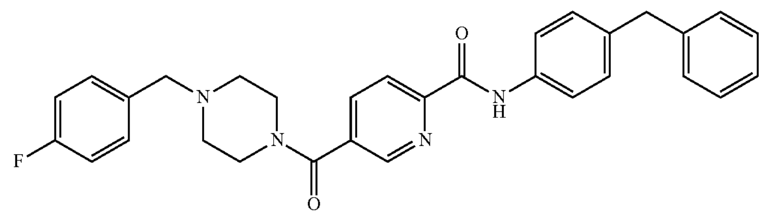 [SMILES: O=C(Nc1ccc(Cc2ccccc2)cc1)c1ccc(C(=O)N2CCN(Cc3ccc(F)cc3)CC2)cn1] |
| 11 | 5-(4-(4-fluorobenzyl)piperazine-1-carbonyl-N-(4-phenylphenyl)picolinamide | 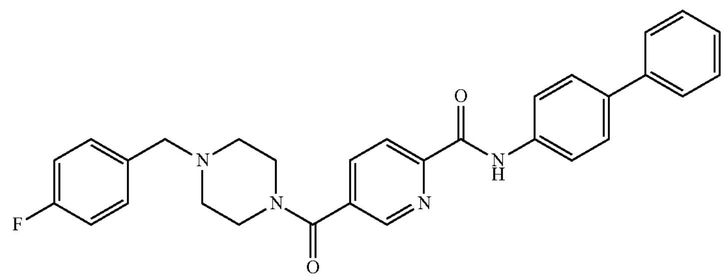 [SMILES: O=C(Nc1ccc(-c2ccccc2)cc1)c1ccc(C(=O)N2CCN(Cc3ccc(F)cc3)CC2)cn1] |
| 12 | 5-(4-(4-fluorobenzyl)piperazine-1-carbonyl-N-(3-phenylphenyl)picolinamide | 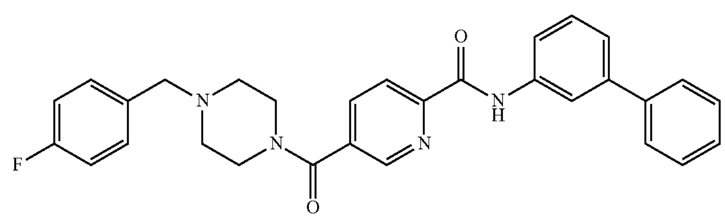 [SMILES: O=C(Nc1cccc(-c2ccccc2)c1)c1ccc(C(=O)N2CCN(Cc3ccc(F)cc3)CC2)cn1] |

TABLE 1-continued

| No. | Name | Structure |
|-----|------|-----------|
| 13 | N-(1-(cyclohexylmethyl)piperidin-4-yl)-5-(4-(4-fluorobenzyl)piperazine-1-carbonyl)picolinamide | 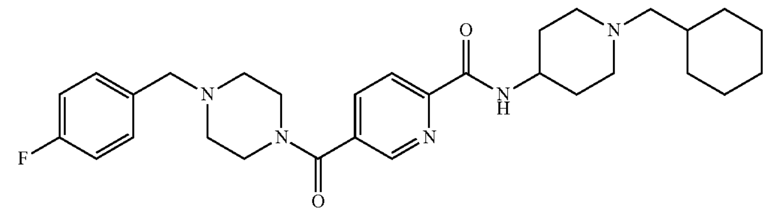 [SMILES: O=C(NC1CCN(CC2CCCCC2)CC1)c1ccc(C(=O)N2CCN(Cc3ccc(F)cc3)CC2)cn1] |
| 14 | 5-(4-(4-fluorobenzyl)piperazine-1-carbonyl)-N-(1-(phenyl)piperidin-4-yl)picolinamide | 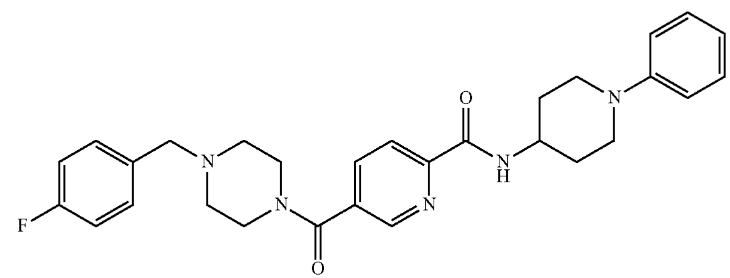 [SMILES: O=C(NC1CCN(c2ccccc2)CC1)c1ccc(C(=O)N2CCN(Cc3ccc(F)cc3)CC2)cn1] |
| 15 | 4-((8-(5-(4-(4-fluorobenzyl)piperazine-1-carbonyl)picolinoyl)-2,8-diazaspiro[4.5]decan-2-yl)methyl)benzonitrile | 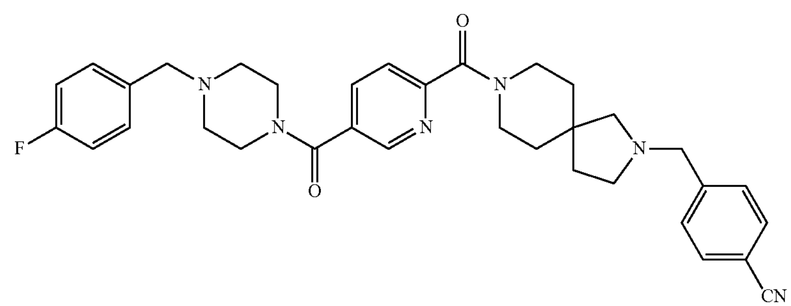 [SMILES: N#Cc1ccc(CN2CCC3(CCN(C(=O)c4ccc(C(=O)N5CCN(Cc6ccc(F)cc6)CC5)cn4)CC3)C2)cc1] |
| 16 | 5-(4-(4-fluorobenzyl)piperazine-1-carbonyl)-N-(4-phenoxyphenyl)picolinamide | 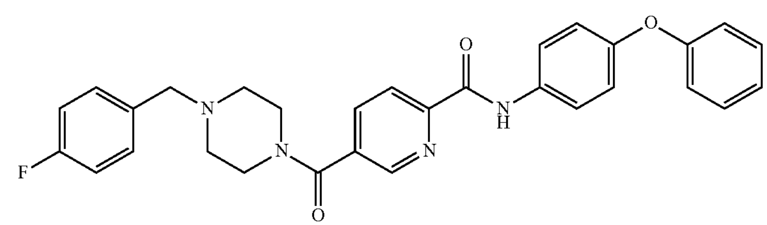 [SMILES: O=C(Nc1ccc(Oc2ccccc2)cc1)c1ccc(C(=O)N2CCN(Cc3ccc(F)cc3)CC2)cn1] |

TABLE 1-continued
| No. | Name | Structure |
|---|---|---|
| 17 | (4-(4-fluorobenzyl)piperazin-1-yl)(6-(4-(benzyloxy)phenyl)pyridin-3-yl)methanone | 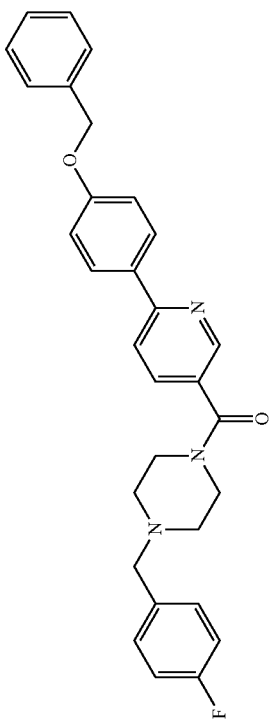 |
| 18 | 5-(4-(4-fluorobenzyl)piperazine-1-carbonyl)-N-(1-phenylethyl)piperidin-4-yl)picolinamide | 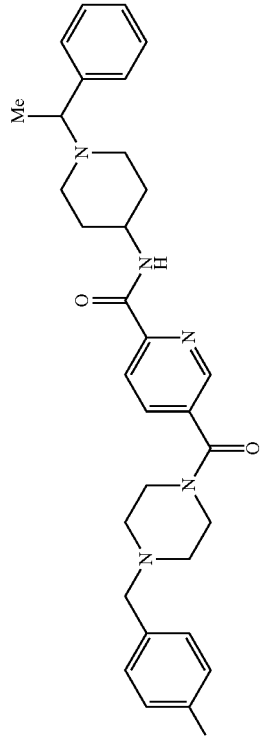 |
| 19 | 5-(4-(4-fluorobenzyl)piperazine-1-carbonyl)-N-(2-phenylphenyl)picolinamide | 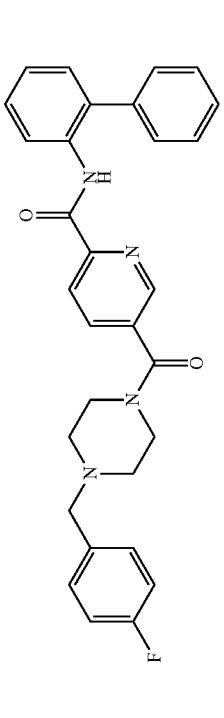 |
| 20 | 5-(4-(4-fluorobenzyl)piperazine-1-carbonyl)-N-(4-(4-nitrophenyl)phenyl)picolinamide | 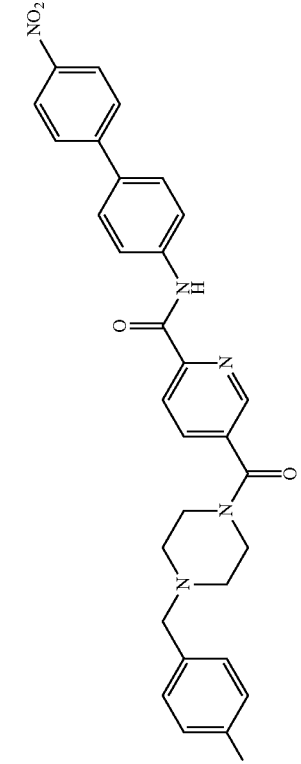 |

TABLE 1-continued

| No. | Name | Structure |
|-----|------|-----------|
| 21 | 5-(4-(4-fluorobenzyl)piperazine-1-carbonyl)-N-(3-phenoxyphenyl)picolinamide | 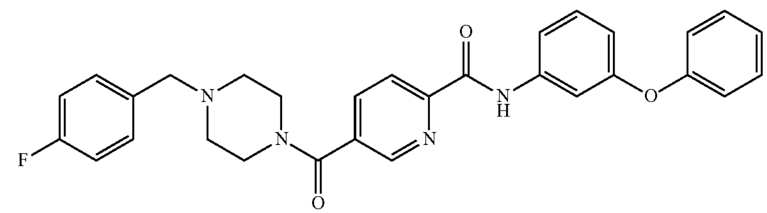 [SMILES: O=C(Nc1cccc(Oc2ccccc2)c1)c1ccc(C(=O)N2CCN(Cc3ccc(F)cc3)CC2)cn1] |
| 22 | (6-(3-(benzyloxy)phenyl)pyridin-3-yl)(4-(4-fluorobenzyl)piperazin-1-yl)methanone | 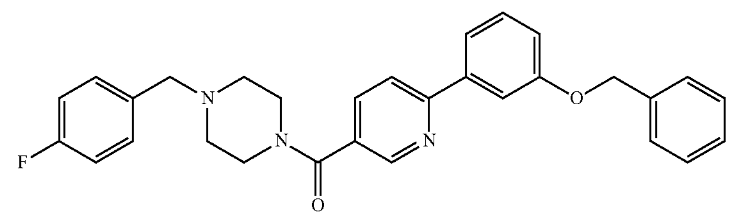 [SMILES: O=C(c1ccc(-c2cccc(OCc3ccccc3)c2)nc1)N1CCN(Cc2ccc(F)cc2)CC1] |
| 23 | N-(1-(4-cyanobenzyl)-1H-pyrazol-4-yl)-5-(4-(4-fluorobenzyl)piperazine-1-carbonyl)picolinamide | 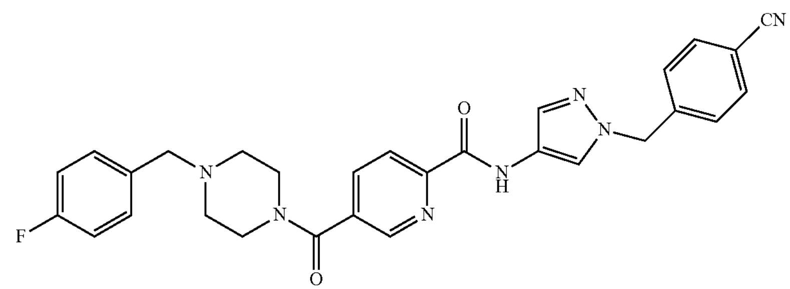 [SMILES: N#Cc1ccc(Cn2cc(NC(=O)c3ccc(C(=O)N4CCN(Cc5ccc(F)cc5)CC4)cn3)cn2)cc1] |
| 24 | N-(4-(4-cyanophenyl)phenyl)-5-(4-(4-fluorobenzyl)piperazine-1-carbonyl)picolinamide | 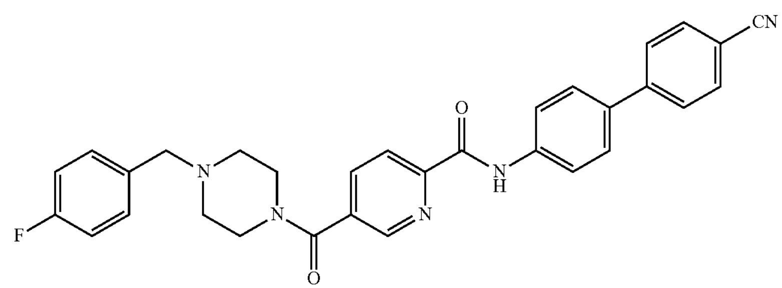 [SMILES: O=C(Nc1ccc(-c2ccc(C(F)(F)F)cc2)cc1)c1ccc(C(=O)N2CCN(Cc3ccc(F)cc3)CC2)cn1] |

TABLE 1-continued

| No. | Name | Structure |
|---|---|---|
| 25 | 5-(4-(4-fluorobenzyl)piperazine-1-carbonyl)-N-(4-(4-trifluoromethylphenyl)phenyl)picolinamide | 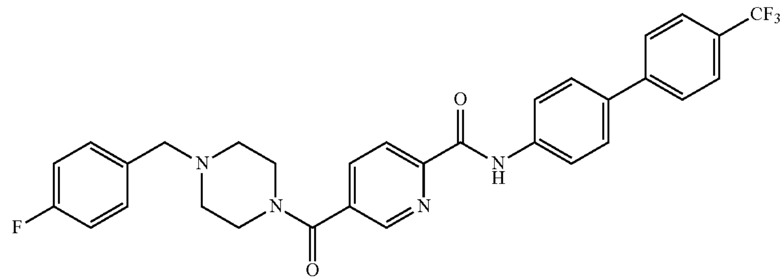 |
| 26 | N-(4-benzoylphenyl)-5-(4-(4-fluorobenzyl)piperazine-1-carbonyl)picolinamide | 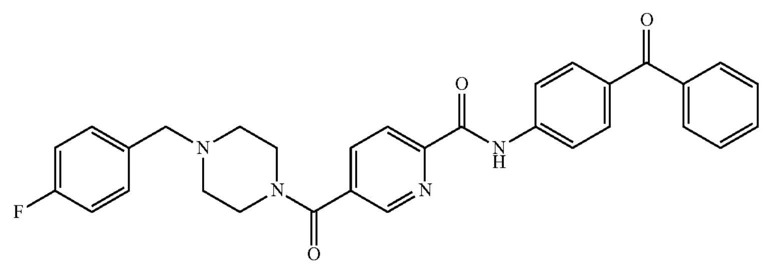 [SMILES: O=C(c1ccccc1)c1ccc(NC(=O)c2ccc(C(=O)N3CCN(Cc4ccc(F)cc4)CC3)cn2)cc1] |
| 27 | N-(4-benzyloxyphenyl)-5-(4-(4-fluorobenzyl)piperazine-1-carbonyl)picolinamide | 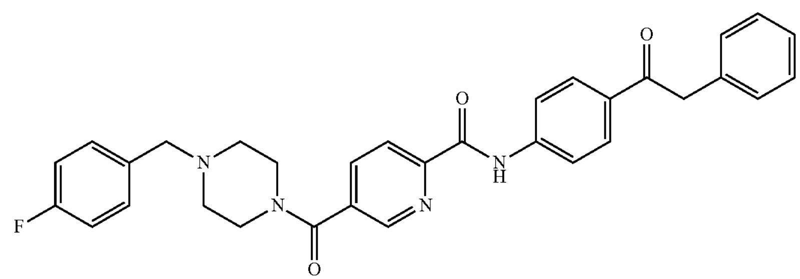 [SMILES: O=C(Cc1ccccc1)c1ccc(NC(=O)c2ccc(C(=O)N3CCN(Cc4ccc(F)cc4)CC3)cn2)cc1] |
| 28 | N-(4-bromophenyl)-5-(4-(4-fluorobenzyl)piperazine-1-carbonyl)picolinamide | 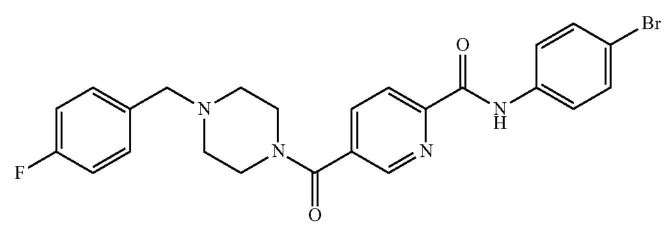 [SMILES: O=C(Nc1ccc(Br)cc1)c1ccc(C(=O)N2CCN(Cc3ccc(F)cc3)CC2)cn1] |

TABLE 1-continued

| No. | Name | Structure |
|---|---|---|
| 29 | N-(4'-methoxyphenyl)phenyl)-5-(4-(4-fluorobenzyl)piperazine-1-carbonyl)picolinamide | 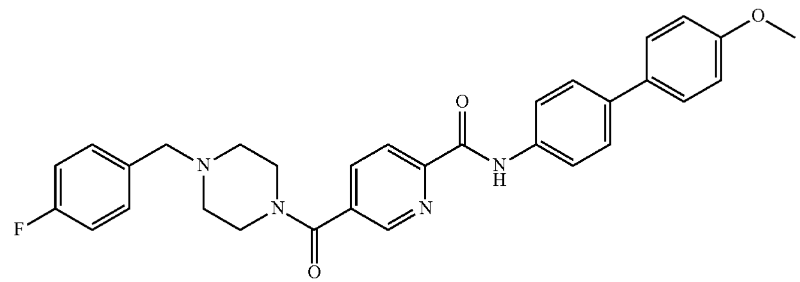 [SMILES: COc1ccc(-c2ccc(NC(=O)c3ccc(C(=O)N4CCN(Cc5ccc(F)cc5)CC4)cn3)cc2)cc1] |
| 30 | (6-(4-benzylphenylamino)pyridin-3-yl)(4-(4-fluorobenzyl)piperazin-1-yl)methanone | 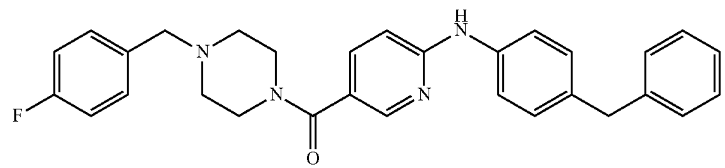 [SMILES: O=C(c1ccc(Nc2ccc(Cc3ccccc3)cc2)nc1)N1CCN(Cc2ccc(F)cc2)CC1] |
| 31 | 4-((2-(5-(4-(4-fluorobenzyl)piperazine-1-carbonyl)pyridin-2-yl)-2,8-diazaspiro[4.5]decan-8-yl)methyl)benzonitrile | 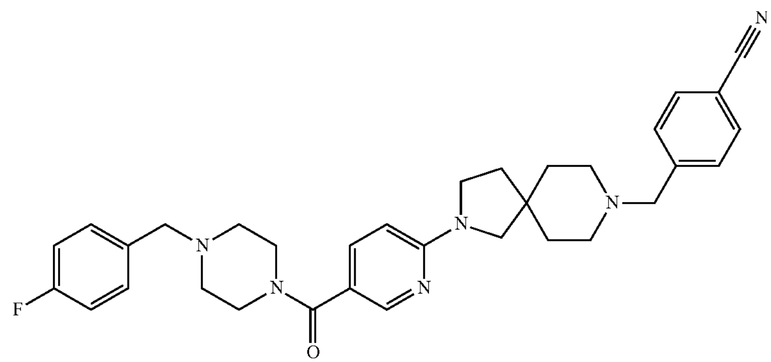 [SMILES: N#Cc1ccc(CN2CCC3(CC2)CCN(c2ccc(C(=O)N4CCN(Cc5ccc(F)cc5)CC4)cn2)C3)cc1] |

TABLE 1-continued

| No. | Name | Structure |
|---|---|---|
| 32 | N-(4-(3-cyanophenyl)phenyl)-5-(4-(4-fluorobenzyl)piperazine-1-carbonyl)picolinamide | 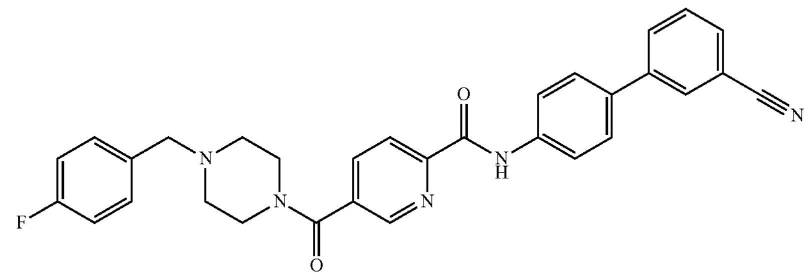 [SMILES: N#Cc1cccc(-c2ccc(NC(=O)c3ccc(C(=O)N4CCN(Cc5ccc(F)cc5)CC4)cn3)cc2)c1] |
| 33 | (6-(3-phenylphenylamino)pyridin-3-yl)(4-(4-fluorobenzyl)piperazin-1-yl)methanone | 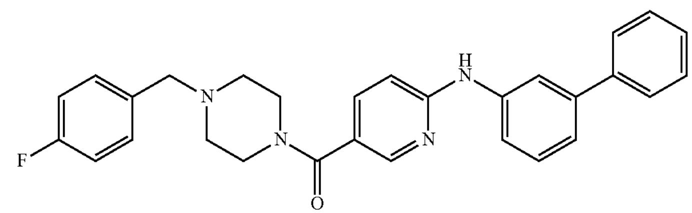 [SMILES: O=C(c1ccc(Nc2cccc(-c3ccccc3)c2)nc1)N1CCN(Cc2ccc(F)cc2)CC1] |
| 34 | (4-(4-fluorobenzyl)piperazin-1-yl)(6-(4-phenoxyphenylamino)pyridin-3-yl)methanone | 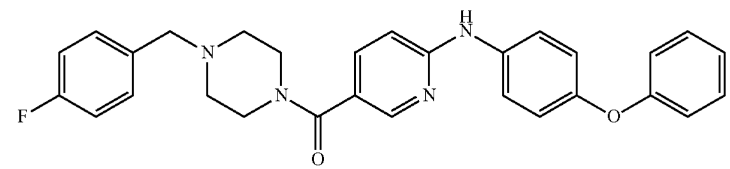 [SMILES: O=C(c1ccc(Nc2ccc(Oc3ccccc3)cc2)nc1)N1CCN(Cc2ccc(F)cc2)CC1] |
| 35 | (6-(4-(4-cyanobenzylcarbamoyl)phenyl)pyridin-3-yl)(4-(4-fluorobenzyl)piperazin-1-yl)methanone | 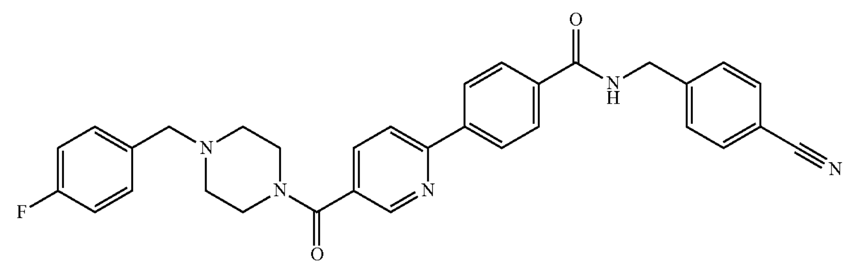 [SMILES: N#Cc1ccc(CNC(=O)c2ccc(-c3ccc(C(=O)N4CCN(Cc5ccc(F)cc5)CC4)cn3)cc2)cc1] |

TABLE 1-continued

| No. | Name | Structure |
|---|---|---|
| 36 | (6-(4-(cyanobenzyl)piperidin-4-ylamino)pyridin-3-yl)(4-(4-fluorobenzyl)piperazin-1-yl)methanone | 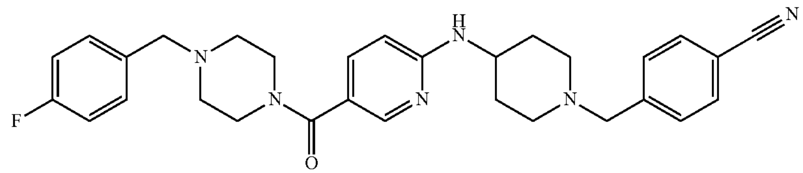 [SMILES: N#Cc1ccc(CN2CCC(Nc3ccc(C(=O)N4CCN(Cc5ccc(F)cc5)CC4)cn3)CC2)cc1] |
| 37 | (6-(4-phenylphenylamino)pyridin-3-yl)(4-(4-fluorobenzyl)piperazin-1-yl)methanone | 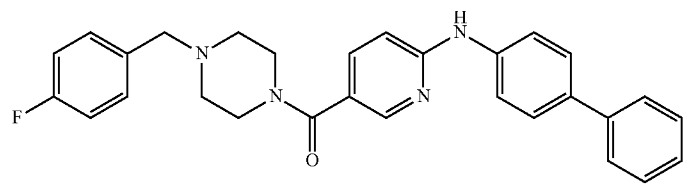 [SMILES: O=C(c1ccc(Nc2ccc(-c3ccccc3)cc2)nc1)N1CCN(Cc2ccc(F)cc2)CC1] |
| 38 | N⁵-(1-(4-cyanobenzyl)-1H-pyrazol-3-yl)-N²-(1-(4-cyanobenzyl)piperidin-4-yl)pyridine-2,5-dicarboxamide | 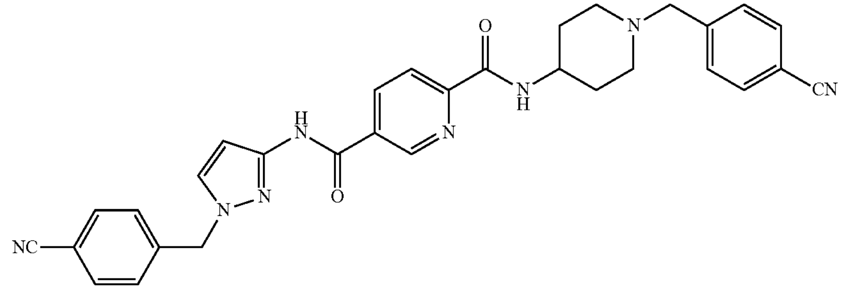 [SMILES: N#Cc1ccc(CN2CCC(NC(=O)c3ccc(C(=O)Nc4ccn(Cc5ccc(C#N)cc5)n4)cn3)CC2)cc1] |
| 39 | 5-(4-(4-fluorobenzyl)piperazine-1-carbonyl)-N-(4-(1H-pyrrol-3-yl)phenyl)picolinamide | 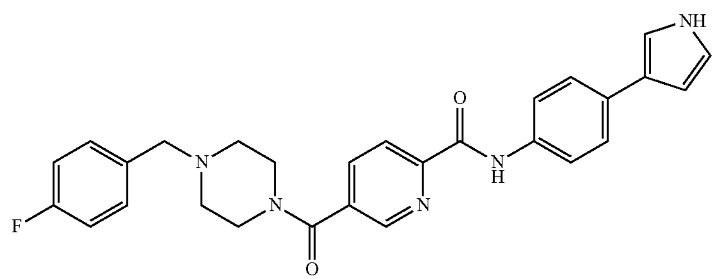 [SMILES: O=C(Nc1ccc(-c2cc[nH]c2)cc1)c1ccc(C(=O)N2CCN(Cc3ccc(F)cc3)CC2)cn1] |

TABLE 1-continued

| No. | Name | Structure |
|---|---|---|
| 40 | 5-(4-(4-fluorobenzyl)piperazine-1-carbonyl)-N-(4-morpholinophenyl)picolinamide | 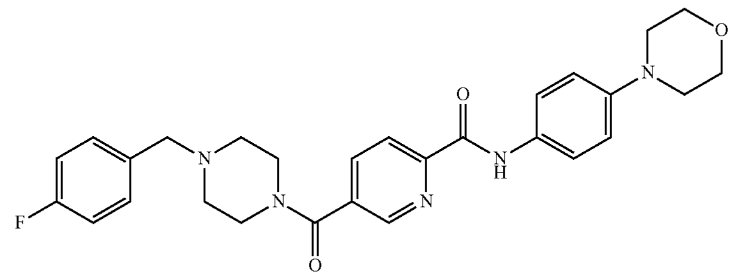 [SMILES: O=C(Nc1ccc(N2CCOCC2)cc1)c1ccc(C(=O)N2CCN(Cc3ccc(F)cc3)CC2)cn1] |
| 41 | 5-(4-(4-fluorobenzyl)piperazine-1-carbonyl)-N-(4-(4-methylpiperazin-1-yl)phenyl)picolinamide | 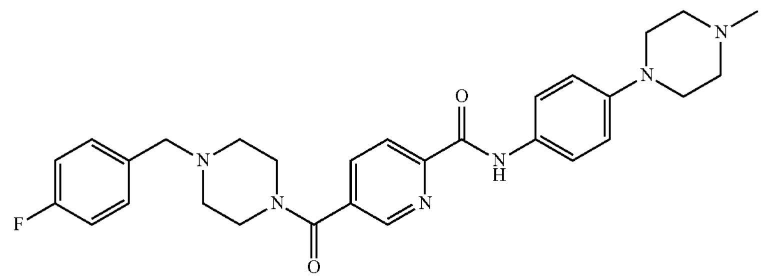 [SMILES: CN1CCN(c2ccc(NC(=O)c3ccc(C(=O)N4CCN(Cc5ccc(F)cc5)CC4)cn3)cc2)CC1] |
| 42 | (6-(3-(4-cyanobenzylcarbamoyl)phenyl)pyridin-3-yl)(4-(4-fluorobenzyl)piperazin-1-yl)methanone | 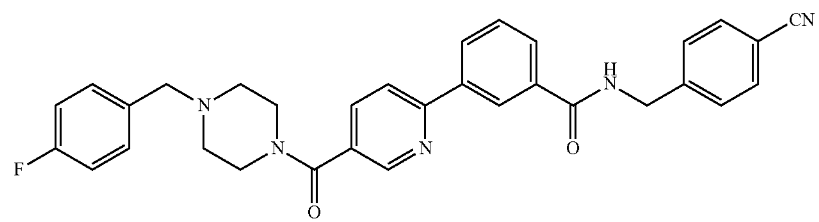 [SMILES: N#Cc1ccc(CNC(=O)c2cccc(-c3ccc(C(=O)N4CCN(Cc5ccc(F)cc5)CC4)cn3)c2)cc1] |

TABLE 1-continued

| No. | Name | Structure |
|---|---|---|
| 43 | N⁵-(1-(4-cyanobenzyl)-1H-pyrazol-4-yl)-N²-(1-(4-cyanobenzyl)piperidin-4-yl)pyridine-2,5-dicarboxamide | 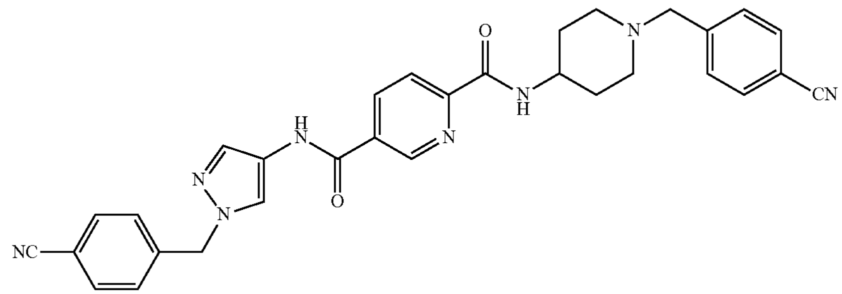 [SMILES: N#Cc1ccc(CN2CCC(NC(=O)c3ccc(C(=O)Nc4cnn(Cc5ccc(C#N)cc5)c4)cn3)CC2)cc1] |
| 44 | (6-(1-(4-fluorobenzyl)-1H-pyrazol-4-ylamino)pyridin-3-yl)(4-(4-fluorobenzyl)piperazin-1-yl)methanone | 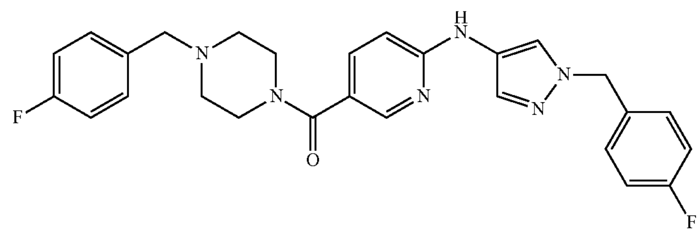 [SMILES: O=C(c1ccc(Nc2cnn(Cc3ccc(F)cc3)c2)nc1)N1CCN(Cc2ccc(F)cc2)CC1] |
| 45 | N-(1-(4-cyanobenzyl)piperidin-4-yl)-5-(1-(4-fluorobenzyl)-1H-pyrazol-4-ylamino)picolinamide | 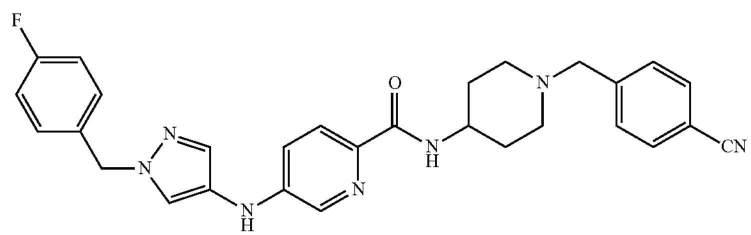 [SMILES: N#Cc1ccc(CN2CCC(NC(=O)c3ccc(Nc4cnn(Cc5ccc(F)cc5)c4)cn3)CC2)cc1] |
| 46 | (6-(1-(4-cyanobenzyl)piperidine-4-carboxamido)pyridin-3-yl)(4-(4-fluorobenzyl)piperazin-1-yl)methanone | 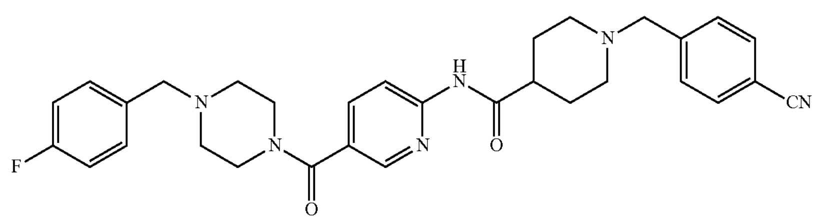 [SMILES: N#Cc1ccc(CN2CCC(C(=O)Nc3ccc(C(=O)N4CCN(Cc5ccc(F)cc5)CC4)cn3)CC2)cc1] |

TABLE 1-continued

| No. | Name | Structure |
|---|---|---|
| 47 | N-(4-(4-cyanobenzylcarbamoyl)phenyl)-5-(4-(4-fluorobenzyl)piperazine-1-carbonyl)picolinamide | 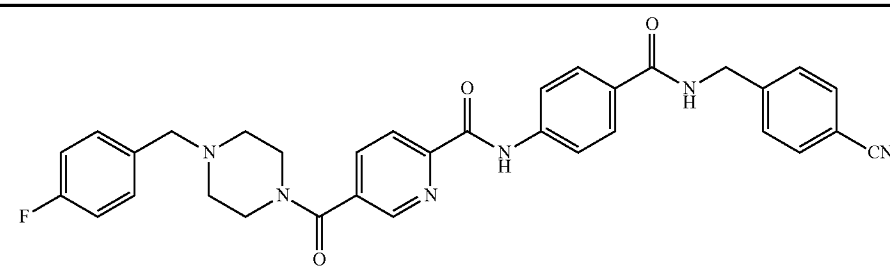 |
| 48 | (6-(4-(4-cyanobenzylcarbamoyl)phenylamino)pyridin-3-yl)(4-(4-fluorobenzyl)piperazin-1-yl)methanone | 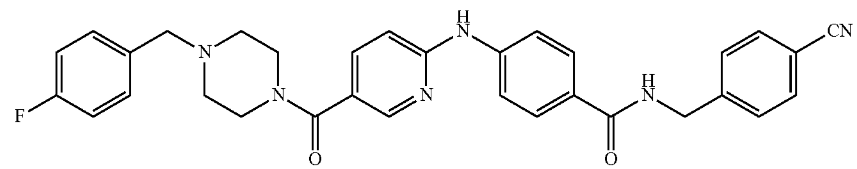 [SMILES: N#Cc1ccc(CNC(=O)c2ccc(Nc3ccc(C(=O)N4CCN(Cc5ccc(F)cc5)CC4)cn3)cc2)cc1] |
| 49 | N-(1-(3,5-difluorobenzyl)piperidin-4-yl)-5-(4-(4-fluorobenzyl)piperazine-1-carbonyl)picolinamide | 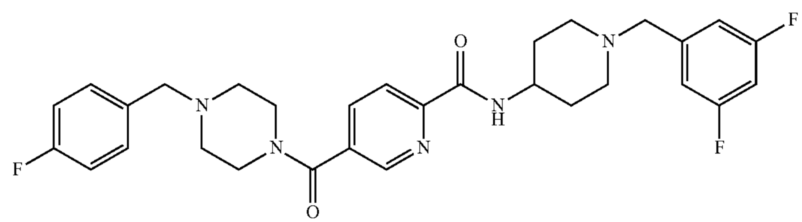 [SMILES: O=C(NC1CCN(Cc2cc(F)cc(F)c2)CC1)c1ccc(C(=O)N2CCN(Cc3ccc(F)cc3)CC2)cn1] |
| 50 | 5-(4-(4-fluorobenzyl)piperazine-1-carbonyl)-N-(1-(4-fluoro-3-methylbenzyl)piperidin-4-yl)picolinamide | 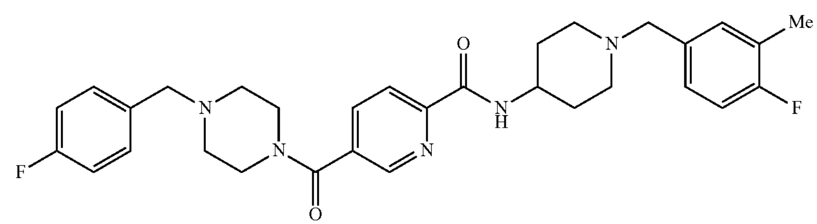 [SMILES: Cc1cc(CN2CCC(NC(=O)c3ccc(C(=O)N4CCN(Cc5ccc(F)cc5)CC4)cn3)CC2)ccc1F] |

TABLE 1-continued

| No. | Name | Structure |
|---|---|---|
| 51 | N-(1-(4-chlorobenzyl)piperidin-4-yl)-5-(4-(4-fluorobenzyl)piperazine-1-carbonyl)picolinamide | 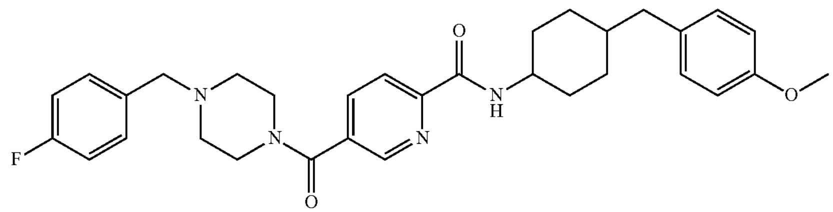 [SMILES: COc1ccc(CC2CCC(NC(=O)c3ccc(C(=O)N4CCN(Cc5ccc(F)cc5)CC4)cn3)CC2)cc1] |
| 52 | N-(1-(4-chlorobenzyl)piperidin-4-yl)-5-(4-(4-fluorobenzyl)piperazine-1-carbonyl)picolinamide | 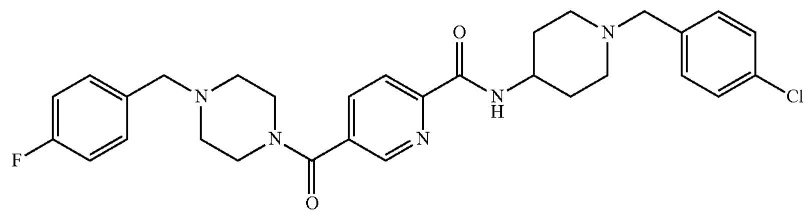 [SMILES: O=C(NC1CCN(Cc2ccc(Cl)cc2)CC1)c1ccc(C(=O)N2CCN(Cc3ccc(F)cc3)CC2)cn1] |
| 53 | 5-(4-(4-fluorobenzyl)piperazine-1-carbonyl)-N-(4-(4-methylphenoxy)phenyl)picolinamide | 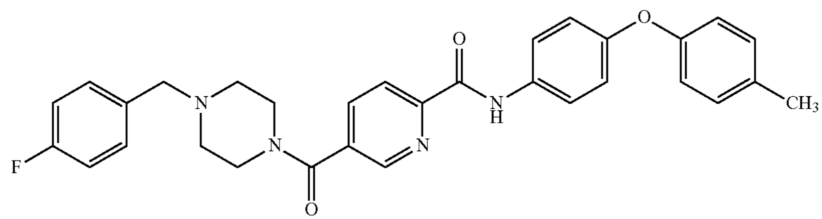 [SMILES: Cc1ccc(Oc2ccc(NC(=O)c3ccc(C(=O)N4CCN(Cc5ccc(F)cc5)CC4)cn3)cc2)cc1] |
| 54 | 5-(4-(4-fluorobenzyl)piperazine-1-carbonyl)-N-(4-(4-methoxyphenoxy)phenyl)picolinamide | 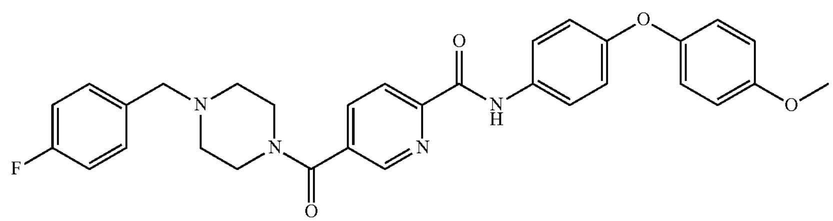 [SMILES: COc1ccc(Oc2ccc(NC(=O)c3ccc(C(=O)N4CCN(Cc5ccc(F)cc5)CC4)cn3)cc2)cc1] |

TABLE 1-continued

| No. | Name | Structure |
|---|---|---|
| 55 | 5-(4-(4-fluorobenzyl)piperazine-1-carbonyl)-N-(4-(3-fluorophenoxy)phenyl)picolinamide | 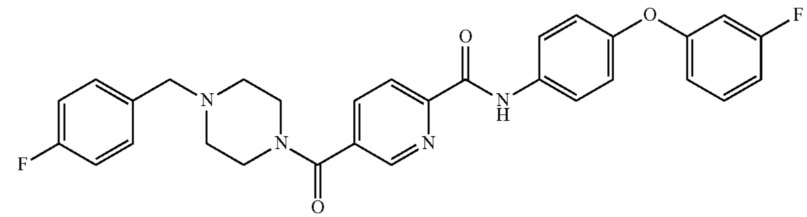 [SMILES: O=C(Nc1ccc(Oc2cccc(F)c2)cc1)c1ccc(C(=O)N2CCN(Cc3ccc(F)cc3)CC2)cn1] |
| 56 | N-(4-(3-cyanophenoxy)phenyl)-5-(4-(4-fluorobenzyl)piperazine-1-carbonyl)picolinamide | 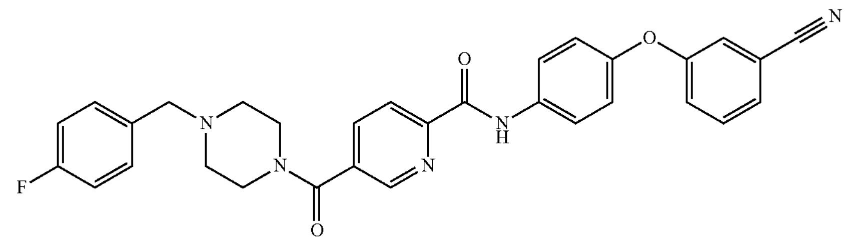 [SMILES: N#Cc1cccc(Oc2ccc(NC(=O)c3ccc(C(=O)N4CCN(Cc5ccc(F)cc5)CC4)cn3)cc2)c1] |
| 57 | 5-(4-(4-fluorobenzyl)piperazine-1-carbonyl)-N-(4-(3-methoxyphenoxy)phenyl)picolinamide | 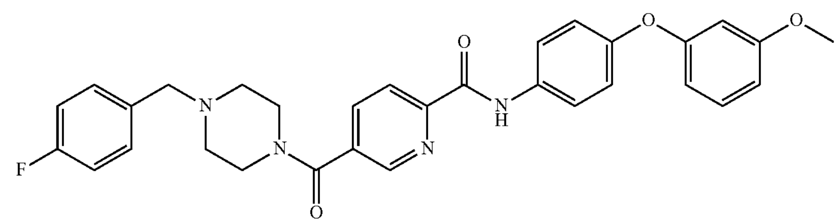 [SMILES: COc1cccc(Oc2ccc(NC(=O)c3ccc(C(=O)N4CCN(Cc5ccc(F)cc5)CC4)cn3)cc2)c1] |
| 58 | 5-(4-(4-fluorobenzyl)piperazine-1-carbonyl)-N-(4-(3-methylphenoxy)phenyl)picolinamide | 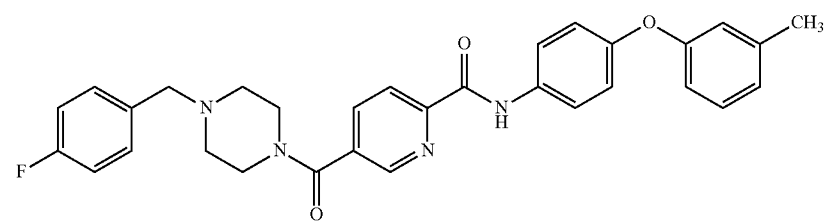 [SMILES: Cc1cccc(Oc2ccc(NC(=O)c3ccc(C(=O)N4CCN(Cc5ccc(F)cc5)CC4)cn3)cc2)c1] |

TABLE 1-continued

| No. | Name | Structure |
|---|---|---|
| 59 | N-(4-(4-cyanophenoxy)phenyl)-5-(4-(4-fluorobenzyl)piperazine-1-carbonyl)picolinamide | 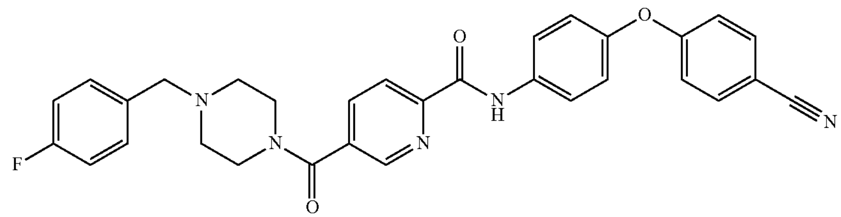 [SMILES: N#Cc1ccc(Oc2ccc(NC(=O)c3ccc(C(=O)N4CCN(Cc5ccc(F)cc5)CC4)cn3)cc2)cc1] |
| 60 | 5-(4-(4-fluorobenzyl)piperazine-1-carbonyl)-N-(4-(4-fluorophenoxy)phenyl)picolinamide | 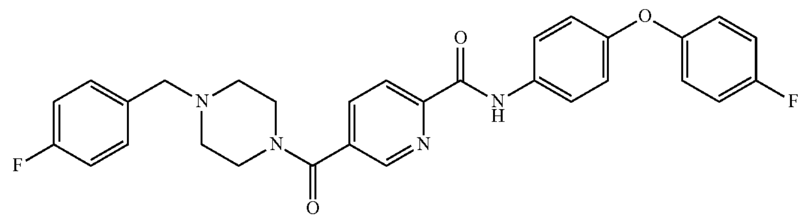 [SMILES: O=C(Nc1ccc(Oc2ccc(F)cc2)cc1)c1ccc(C(=O)N2CCN(Cc3ccc(F)cc3)CC2)cn1] |
| 61 | 5-(4-(4-fluorobenzyl)piperazine-1-carbonyl)-N-(4-(pyridine-3-yl)phenyl)picolinamide | 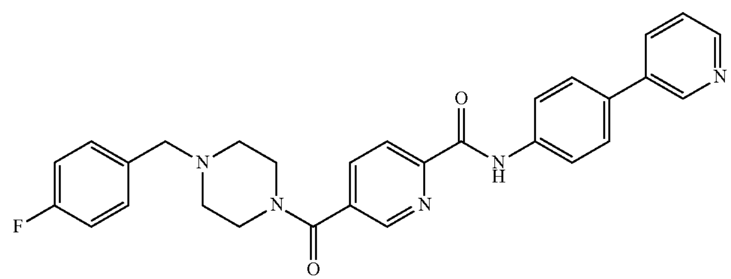 [SMILES: O=C(Nc1ccc(-c2cccnc2)cc1)c1ccc(C(=O)N2CCN(Cc3ccc(F)cc3)CC2)cn1] |
| 62 | 5-(4-(4-fluorobenzyl)piperazine-1-carbonyl)-N-(4-(thiophen-3-yl)phenyl)picolinamide | 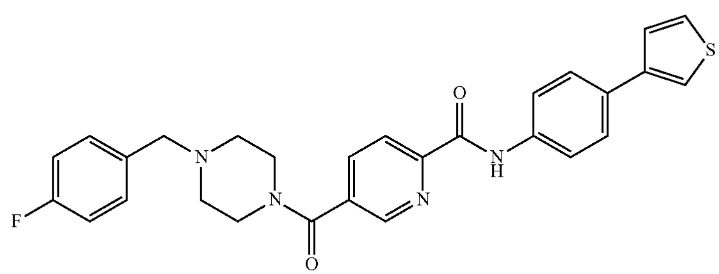 [SMILES: O=C(Nc1ccc(-c2ccsc2)cc1)c1ccc(C(=O)N2CCN(Cc3ccc(F)cc3)CC2)cn1] |

TABLE 1-continued

| No. | Name | Structure |
|---|---|---|
| 63 | 5-(4-(4-fluorobenzyl)piperazine-1-carbonyl)-(6-(4-cyanophenoxy)pyridin-3-yl)picolinamide | 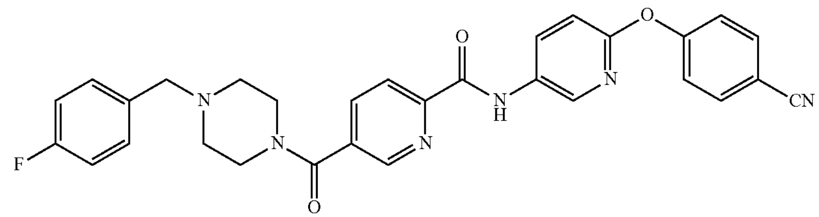 [SMILES: N#Cc1ccc(Oc2ccc(NC(=O)c3ccc(C(=O)N4CCN(Cc5ccc(F)cc5)CC4)cn3)cn2)cc1] |
| 64 | 5-(4-(4-fluorobenzyl)piperazine-1-carbonyl)-(6-(3-cyanophenoxy)pyridin-3-yl)picolinamide | 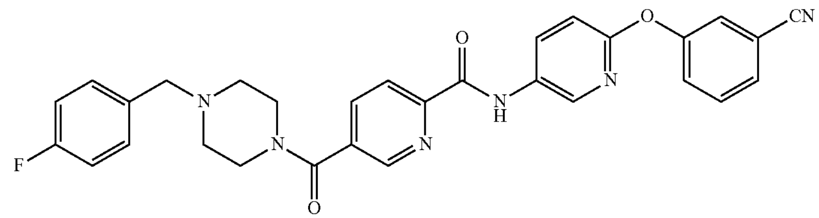 [SMILES: N#Cc1cccc(Oc2ccc(NC(=O)c3ccc(C(=O)N4CCN(Cc5ccc(F)cc5)CC4)cn3)cn2)c1] |
| 65 | 5-(4-(4-fluorobenzyl)piperazine-1-carbonyl)-N-(6-(4-fluorophenoxy)pyridin-3-yl)picolinamide | 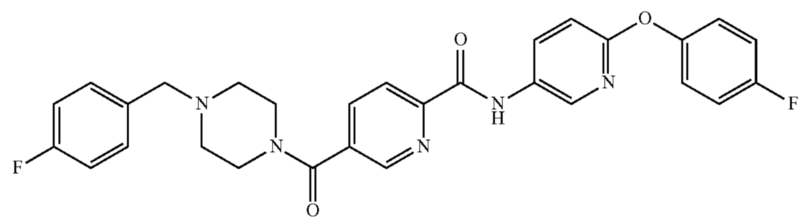 [SMILES: O=C(Nc1ccc(Oc2ccc(F)cc2)nc1)c1ccc(C(=O)N2CCN(Cc3ccc(F)cc3)CC2)cn1] |
| 66 | 5-(4-(4-cyano-2-methoxyphenoxy)piperidine-1-carbonyl)-N-(1-(4-cyanobenzyl)piperidin-4-yl)picolinamide | 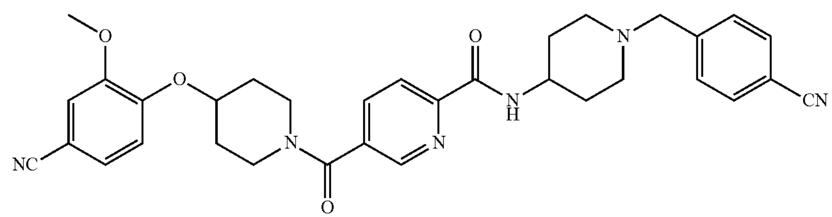 [SMILES: COc1cc(C#N)ccc1OC1CCN(C(=O)c2ccc(C(=O)NC3CCN(Cc4ccc(C#N)cc4)CC3)nc2)CC1] |

TABLE 1-continued

| No. | Name | Structure |
|-----|------|-----------|
| 67 | 5-(4-(4-fluoro-4-fluorobenzoyl)piperidine-1-carbonyl)-N-(6-(4-fluorophenoxy)pyridin-3-yl)picolinamide | 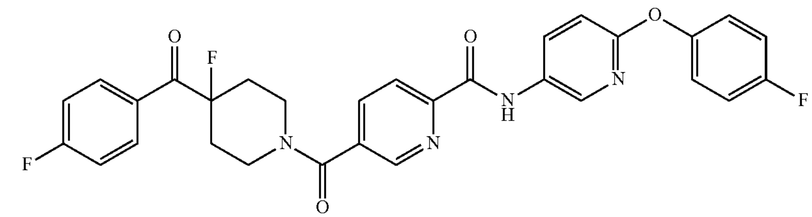 [SMILES: O=C(Nc1ccc(Oc2ccc(F)cc2)nc1)c1ccc(C(=O)N2CCC(F)(C(=O)c3ccc(F)cc3)CC2)cn1] |
| 68 | N-(1-(4-cyanobenzyl)piperidin-4-yl)-5-(4-(4-fluoro-4-fluorobenzoyl)piperidine-1-carbonyl)picolinamide | 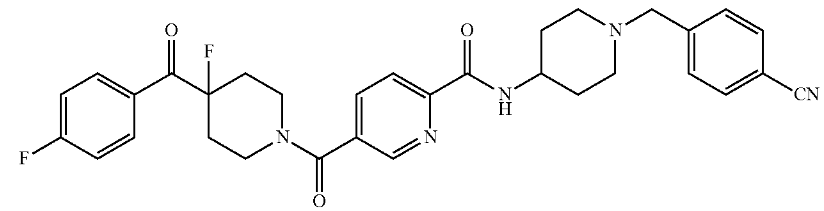 [SMILES: N#Cc1ccc(CN2CCC(NC(=O)c3ccc(C(=O)N4CCC(F)(C(=O)c5ccc(F)cc5)CC4)cn3)CC2)cc1] |
| 69 | 5-(4-(4-methoxybenzoyl)piperidine-1-carbonyl)-N-(6-(4-fluorophenoxy)pyridin-3-yl)picolinamide | 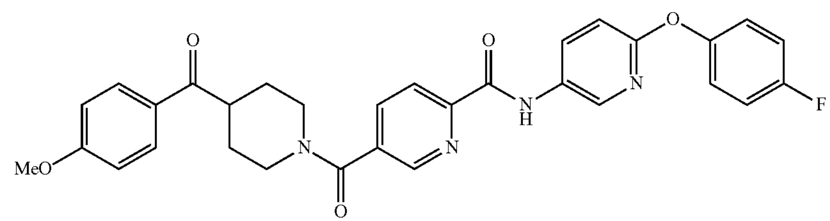 [SMILES: COc1ccc(C(=O)C2CCN(C(=O)c3ccc(C(=O)Nc4ccc(Oc5ccc(F)cc5)nc4)nc3)CC2)cc1] |
| 70 | 5-(4-(4-methoxyphenoxy)piperidine-1-carbonyl)-N-(6-(4-fluorophenoxy)pyridin-3-yl)picolinamide | 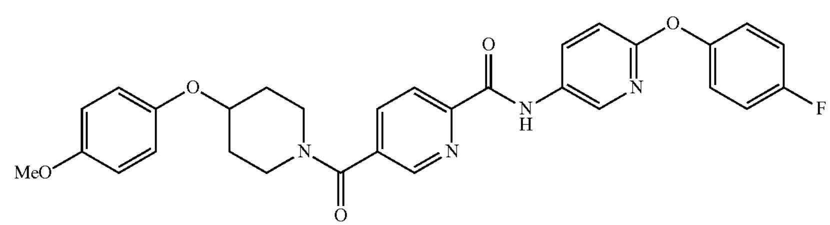 [SMILES: COc1ccc(OC2CCN(C(=O)c3ccc(C(=O)Nc4ccc(Oc5ccc(F)cc5)nc4)nc3)CC2)cc1] |

TABLE 1-continued

| No. | Name | Structure |
|---|---|---|
| 71 | trans-N-(4-(4-cyanophenoxy)cyclohexyl)-5-(4-(4-fluorobenzyl)piperazine-1-carbonyl)picolinamide | 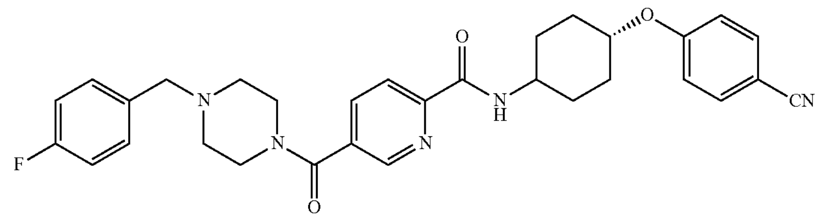 |
| 72 | 5-(4-benzylpiperazine-1-carbonyl)-N-(1-benzylpiperidin-4-yl)picolinamide | 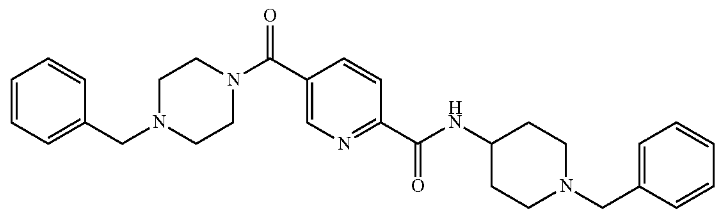 [SMILES: O=C(NC1CCN(Cc2ccccc2)CC1)c1ccc(C(=O)N2CCN(Cc3ccccc3)CC2)cn1] |
| 73 | pyridine-2,5-diylbis((4-benzylpiperazin-1-yl)methanone) | 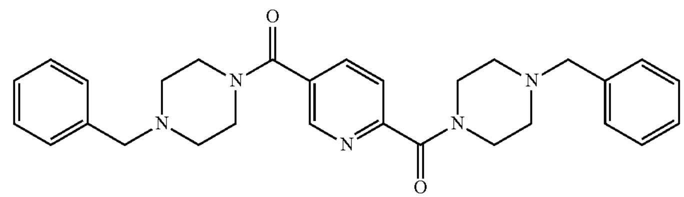 [SMILES: O=C(c1ccc(C(=O)N2CCN(Cc3ccccc3)CC2)nc1)N1CCN(Cc2ccccc2)CC1] |
| 74 | 6-(4-benzylpiperazine-1-carbonyl)-N-(1-benzylpiperidin-4-yl)nicotinamide | 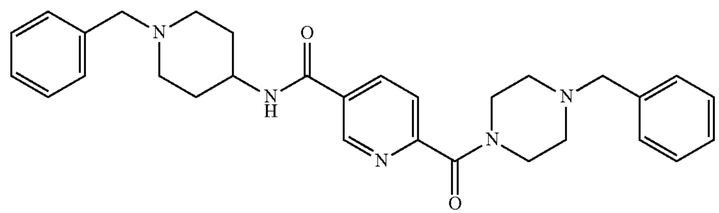 [SMILES: O=C(NC1CCN(Cc2ccccc2)CC1)c1ccc(C(=O)N2CCN(Cc3ccccc3)CC2)nc1] |

TABLE 1-continued

| No. | Name | Structure |
|-----|------|-----------|
| 75 | 5,5'-(piperazine-1,4-diylbis(oxomethylene))bis(N-(1-(4-cyanobenzyl)piperidin-4-yl)picolinamide) | 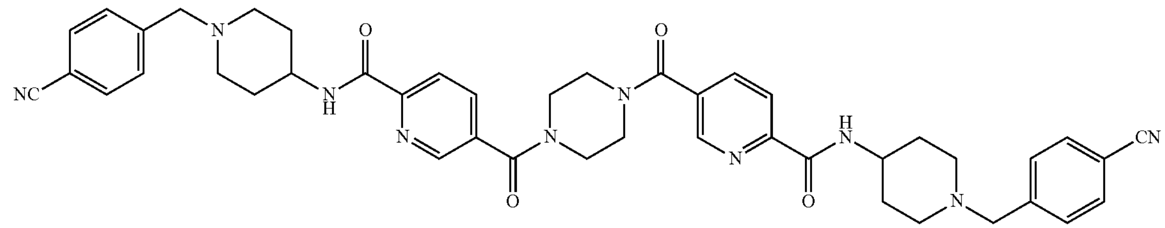 [SMILES: N#Cc1ccc(CN2CCC(NC(=O)c3ccc(C(=O)N4CCN(C(=O)c5ccc(C(=O)NC6CCN(Cc7ccc(C#N)cc7)CC6)nc5)CC4)cn3)CC2)cc1] |
| 76 | N-(1-(4-cyanobenzyl)piperidin-4-yl)-5-(4-(4-fluorobenzoyl)piperazine-1-carbonyl)picolinamide | 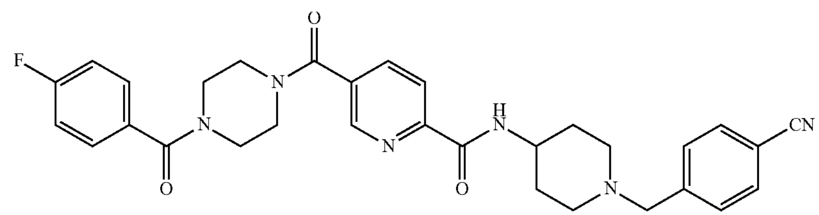 [SMILES: N#Cc1ccc(CN2CCC(NC(=O)c3ccc(C(=O)N4CCN(C(=O)c5ccc(F)cc5)CC4)cn3)CC2)cc1] |
| 77 | N-(1-(4-cyanobenzyl)piperidin-4-yl)-5-(4-(4-methoxybenzoyl)piperazine-1-carbonyl)picolinamide | 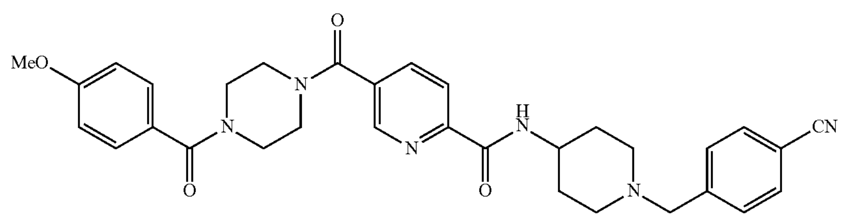 [SMILES: COc1ccc(C(=O)N2CCN(C(=O)c3ccc(C(=O)NC4CCN(Cc5ccc(C#N)cc5)CC4)nc3)CC2)cc1] |
| 78 | N-(1-(4-cyanobenzyl)piperidin-4-yl)-5-(4-(4-fluorophenylsulfonyl)piperazine-1-carbonyl)picolinamide | 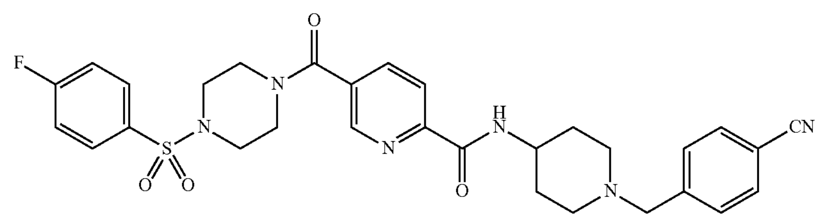 [SMILES: N#Cc1ccc(CN2CCC(NC(=O)c3ccc(C(=O)N4CCN(S(=O)(=O)c5ccc(F)cc5)CC4)cn3)CC2)cc1] |

TABLE 1-continued

| No. | Name | Structure |
|---|---|---|
| 79 | N-(1-(4-cyanobenzyl)piperidin-4-yl)-5-(4-(4-methoxyphenylsulfonyl)piperazine-1-carbonyl)picolinamide | 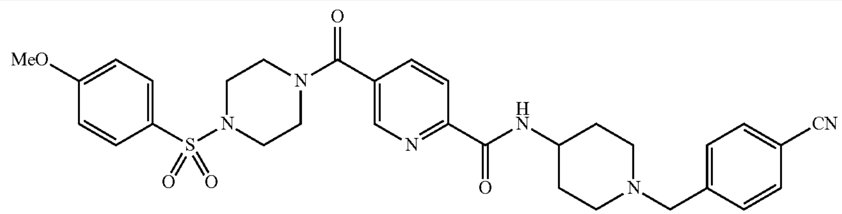 [SMILES: COc1ccc(S(=O)(=O)N2CCN(C(=O)c3ccc(C(=O)NC4CCN(Cc5ccc(C#N)cc5)CC4)nc3)CC2)cc1] |
| 80 | 5-(4-benzoylpiperazine-1-carbonyl)-N-(1-(4-cyanobenzyl)piperidin-4-yl)picolinamide | 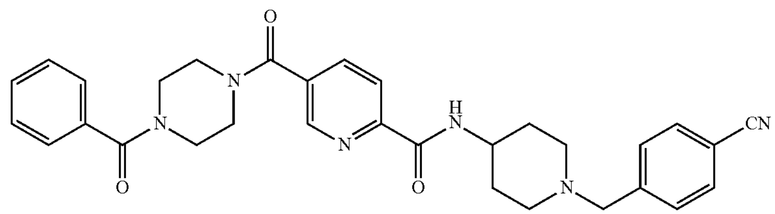 [SMILES: N#Cc1ccc(CN2CCC(NC(=O)c3ccc(C(=O)N4CCN(C(=O)c5ccccc5)CC4)cn3)CC2)cc1] |
| 81 | N-(1-(4-cyanobenzyl)piperidin-4-yl)-5-(4-pivaloylpiperazine-1-carbonyl)picolinamide | 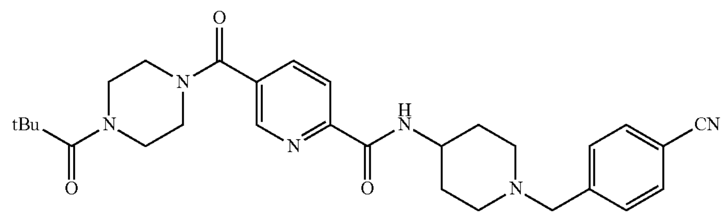 [SMILES: CC(C)(C)C(=O)N1CCN(C(=O)c2ccc(C(=O)NC3CCN(Cc4ccc(C#N)cc4)CC3)nc2)CC1] |
| 82 | N-(1-(4-cyanobenzyl)piperidin-4-yl)-5-(4-(phenylsulfonyl)piperazine-1-carbonyl)picolinamide | 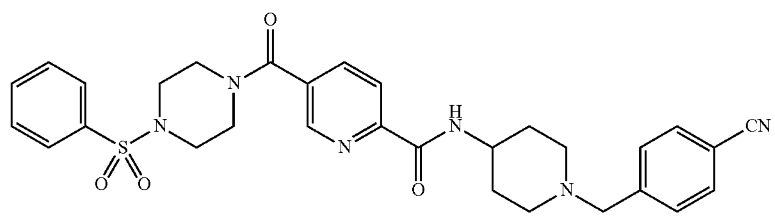 [SMILES: N#Cc1ccc(CN2CCC(NC(=O)c3ccc(C(=O)N4CCN(S(=O)(=O)c5ccccc5)CC4)cn3)CC2)cc1] |

TABLE 1-continued

| No. | Name | Structure |
|---|---|---|
| 83 | N-(1-(4-cyanobenzyl)piperidin-4-yl)-5-(4-(tetrahydro-2H-pyran-4-yl)piperazine-1-carbonyl)picolinamide | 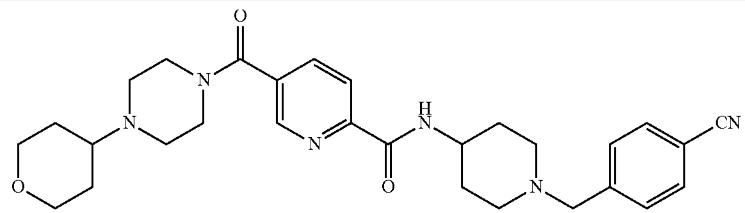 [SMILES: N#Cc1ccc(CN2CCC(NC(=O)c3ccc(C(=O)N4CCN(C5CCOCC5)CC4)cn3)CC2)cc1] |
| 84 | N-(1-(4-cyanobenzyl)piperidin-4-yl)-5-(4-isopropylpiperazine-1-carbonyl)picolinamide | 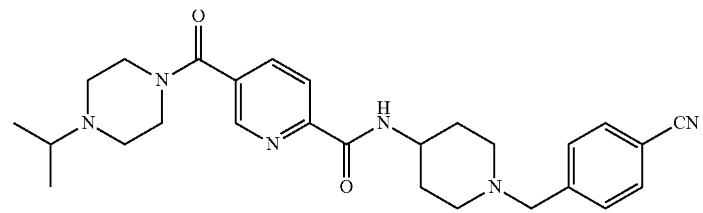 [SMILES: CC(C)N1CCN(C(=O)c2ccc(C(=O)NC3CCN(Cc4ccc(C#N)cc4)CC3)nc2)CC1] |
| 85 | N-(1-benzylpiperidin-4-yl)-5-(4-((5-methylisoxazol-3-yl)methyl)piperazine-1-carbonyl)picolinamide | 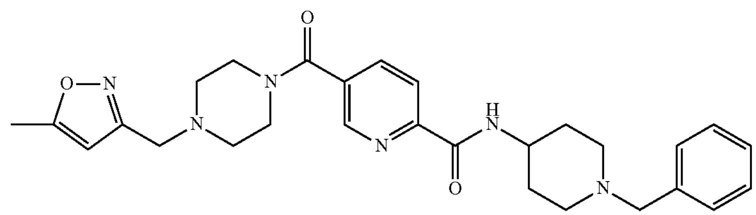 [SMILES: Cc1cc(CN2CCN(C(=O)c3ccc(C(=O)NC4CCN(Cc5ccccc5)CC4)nc3)CC2)no1] |
| 86 | N2,N6-bis(1-(4-cyanobenzyl)piperidin-4-yl)pyridine-2,6-dicarboxamide | 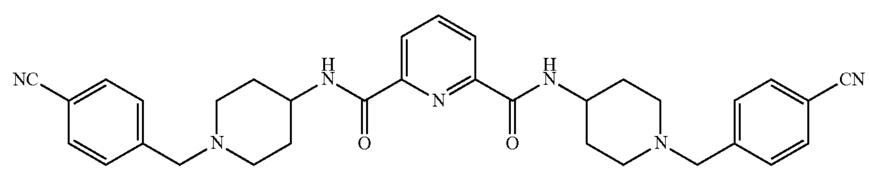 [SMILES: N#Cc1ccc(CN2CCC(NC(=O)c3cccc(C(=O)NC4CCN(Cc5ccc(C#N)cc5)CC4)n3)CC2)cc1] |
| 87 | N2,N6-bis(1-(4-fluorobenzyl)piperidin-4-yl)pyridine-2,6-dicarboxamide | 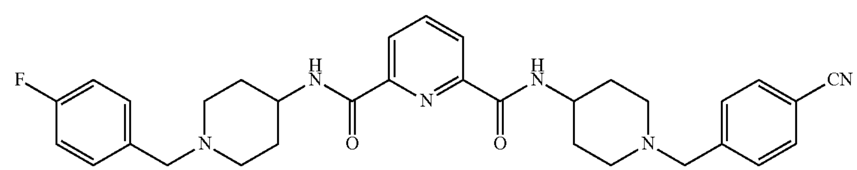 [SMILES: N#Cc1ccc(CN2CCC(NC(=O)c3cccc(C(=O)NC4CCN(Cc5ccc(F)cc5)CC4)n3)CC2)cc1] |

TABLE 1-continued

| No. | Name | Structure |
|---|---|---|
| 88 | (4-(4-fluorobenzyl)piperazin-1-yl)(6-(4-phenethylpiperazine-1-carbonyl)pyridin-3-yl)methanone | 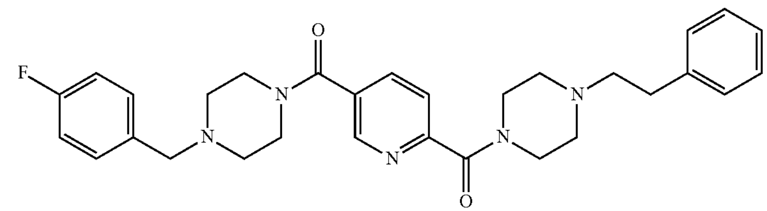 [SMILES: O=C(c1ccc(C(=O)N2CCN(CCc3ccccc3)CC2)nc1)N1CCN(Cc2ccc(F)cc2)CC1] |
| 89 | N-(1-(4-cyanobenzyl)piperidin-4-yl)-5-(4-(cyclohexanecarbonyl)piperazine-1-carbonyl)picolinamide | 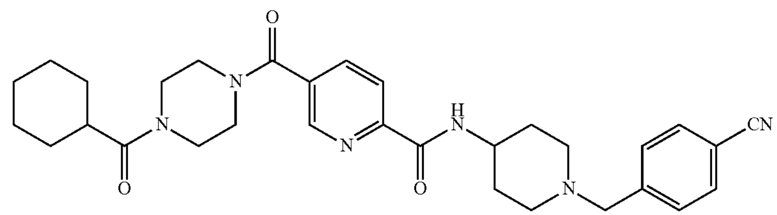 [SMILES: N#Cc1ccc(CN2CCC(NC(=O)c3ccc(C(=O)N4CCN(C(=O)C5CCCCC5)CC4)cn3)CC2)cc1] |
| 90 | (4-phenethylpiperazin-1-yl)(5-(4-phenylpiperazine-1-carbonyl)pyridin-2-yl)methanone | 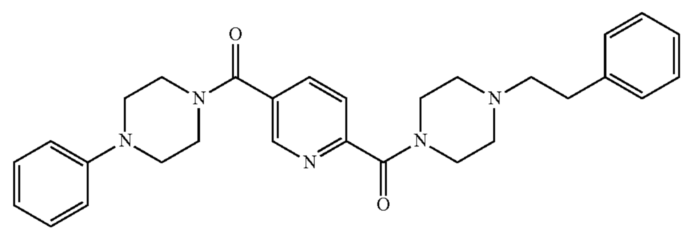 [SMILES: O=C(c1ccc(C(=O)N2CCN(CCc3ccccc3)CC2)nc1)N1CCN(c2ccccc2)CC1] |
| 91 | (4-isopropylpiperazin-1-yl)(6-(4-phenethylpiperazine-1-carbonyl)pyridin-3-yl)methanone | 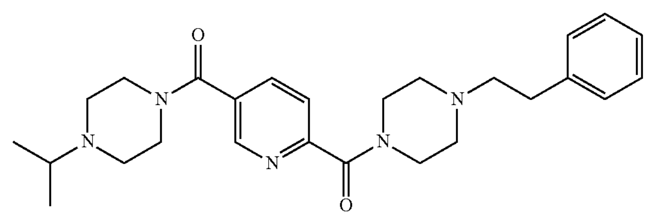 [SMILES: CC(C)N1CCN(C(=O)c2ccc(C(=O)N3CCN(CCc4ccccc4)CC3)nc2)CC1] |

TABLE 1-continued

| No. | Name | Structure |
|---|---|---|
| 92 | pyridine-2,5-diylbis((4-phenethylpiperazin-1-yl)methanone) | 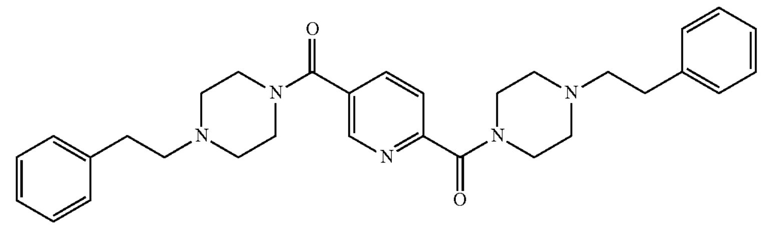 [SMILES: O=C(c1ccc(C(=O)N2CCN(CCc3ccccc3)CC2)nc1)N1CCN(CCc2ccccc2)CC1] |
| 93 | (4-(4-fluorobenzyl)piperazin-1-yl)(6-(4-phenethylpiperazine-1-carbonyl)pyridin-2-yl)methanone | 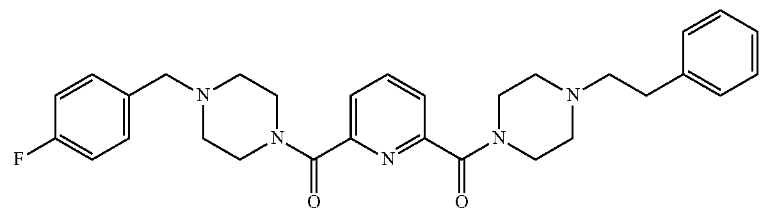 [SMILES: O=C(c1cccc(C(=O)N2CCN(Cc3ccc(F)cc3)CC2)n1)N1CCN(CCc2ccccc2)CC1] |
| 94 | (4-(4-fluorobenzyl)piperazin-1-yl)(6-(4-phenylpiperazine-1-carbonyl)pyridin-2-yl)methanone | 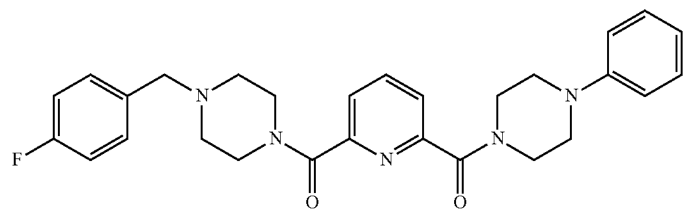 [SMILES: O=C(c1cccc(C(=O)N2CCN(c3ccccc3)CC2)n1)N1CCN(Cc2ccc(F)cc2)CC1] |
| 95 | N-(1-(4-cyanobenzyl)piperidin-4-yl)-5-(4-(cyclohexylmethyl)piperazine-1-carbonyl)picolinamide | 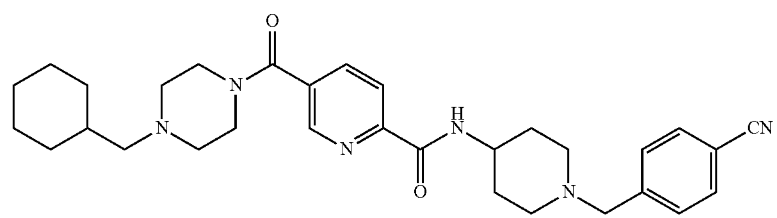 [SMILES: N#Cc1ccc(CN2CCC(NC(=O)c3ccc(C(=O)N4CCN(CC5CCCCC5)CC4)cn3)CC2)cc1] |

TABLE 1-continued

| No. | Name | Structure |
|---|---|---|
| 96 | N-(1-benzylpiperidin-4-yl)-5-(4-(pyridin-4-yl)piperazine-1-carbonyl)picolinamide | 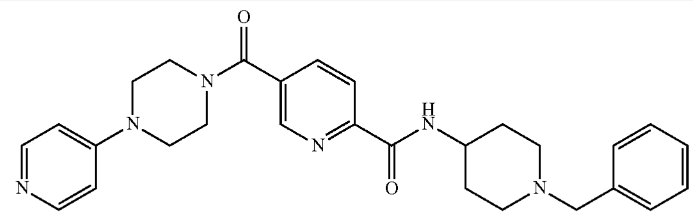 [SMILES: O=C(NC1CCN(Cc2ccccc2)CC1)c1ccc(C(=O)N2CCN(c3ccncc3)CC2)cn1] |
| 97 | N-(1-benzylpiperidin-4-yl)-5-(4-phenylpiperazine-1-carbonyl)picolinamide | 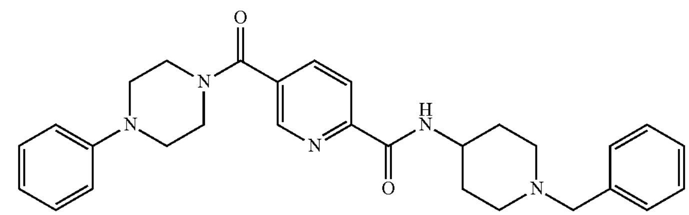 [SMILES: O=C(NC1CCN(Cc2ccccc2)CC1)c1ccc(C(=O)N2CCN(c3ccccc3)CC2)cn1] |
| 98 | ethyl 2-(4-(5-(4-(4-fluorobenzyl)piperazine-1-carbonyl)picolinamido)piperidin-1-yl)-2-phenylacetate | 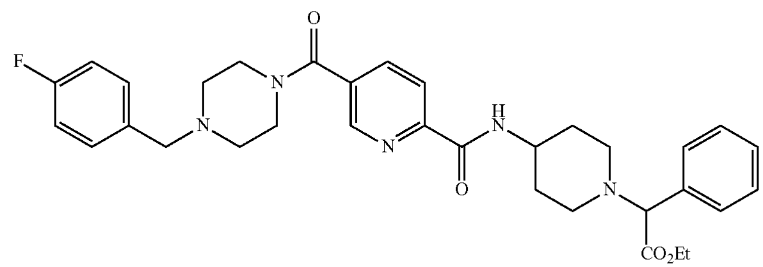 [SMILES: CCOC(=O)C(c1ccccc1)N1CCC(NC(=O)c2ccc(C(=O)N3CCN(Cc4ccc(F)cc4)CC3)cn2)CC1] |
| 99 | N-(4-(4-cyanobenzyl)cyclohexyl)-6-(4-(4-fluorobenzyl)piperazine-1-carbonyl)picolinamide | 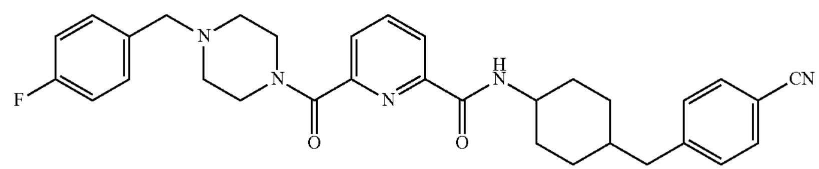 [SMILES: N#Cc1ccc(CC2CCC(NC(=O)c3cccc(C(=O)N4CCN(Cc5ccc(F)cc5)CC4)n3)CC2)cc1] |

TABLE 1-continued

| No. | Name | Structure |
|-----|------|-----------|
| 100 | cis-1-(4-cyanobenzyl)-3-fluoropiperidin-4-yl)-5-(4-(4-fluorobenzyl)piperazine-1-carbonyl)picolinamide | 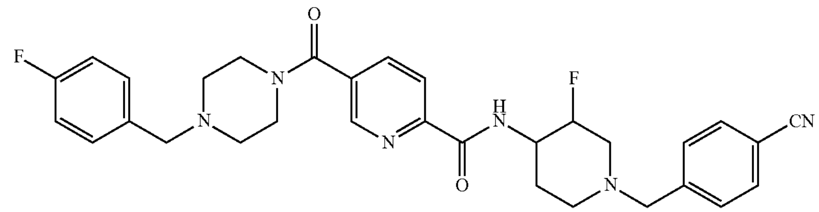 [SMILES: N#Cc1ccc(CN2CCC(NC(=O)c3ccc(C(=O)N4CCN(Cc5ccc(F)cc5)CC4)cn3)C(F)C2)cc1] |
| 101 | N-(1-(4-cyanobenzyl)piperidin-4-yl)-5-(4-(4-methoxybenzyl)piperazine-1-carbonyl)picolinamide | 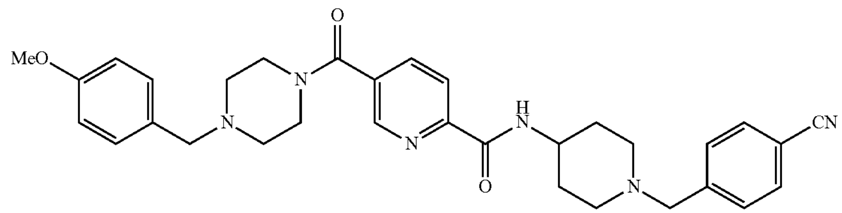 [SMILES: COc1ccc(CN2CCN(C(=O)c3ccc(C(=O)NC4CCN(Cc5ccc(C#N)cc5)CC4)nc3)CC2)cc1] |
| 102 | 5-(4-(4-fluorobenzyl)piperazine-1-carbonyl)-N-(cis-3-fluoropiperidin-4-yl)picolinamide | 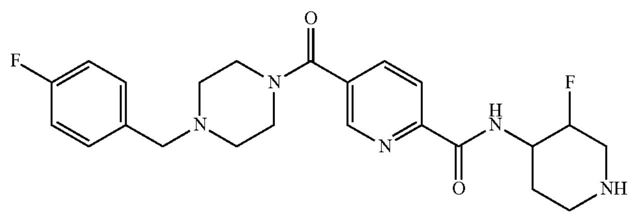 [SMILES: O=C(NC1CCNCC1F)c1ccc(C(=O)N2CCN(Cc3ccc(F)cc3)CC2)cn1] |
| 103 | N-(1-(4-cyanobenzyl)piperidin-4-yl)-5-(4-(pyridin-4-ylmethyl)piperazine-1-carbonyl)picolinamide | 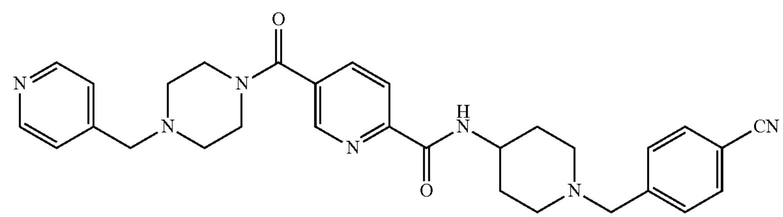 [SMILES: N#Cc1ccc(CN2CCC(NC(=O)c3ccc(C(=O)N4CCN(Cc5ccncc5)CC4)cn3)CC2)cc1] |

TABLE 1-continued

| No. | Name | Structure |
|-----|------|-----------|
| 104 | N-(cis-3-fluoro-1-(pyridin-4-ylmethyl)piperidin-4-yl)-5-(4-(4-fluorobenzyl)piperazine-1-carbonyl)picolinamide | 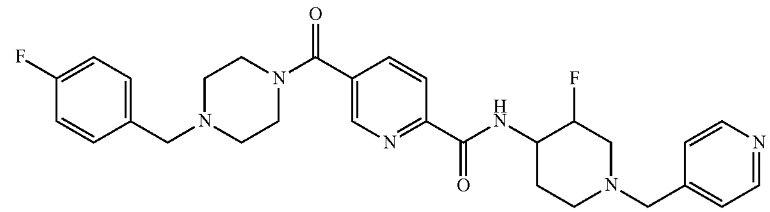 [SMILES: O=C(NC1CCN(Cc2ccncc2)CC1F)c1ccc(C(=O)N2CCN(Cc3ccc(F)cc3)CC2)cn1] |
| 105 | N2-(1-benzylpiperidin-4-yl)-N5-(biphenyl-4-yl)pyridine-2,5-dicarboxamide | 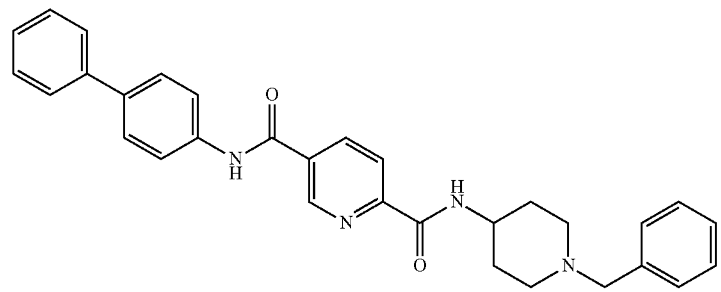 [SMILES: O=C(Nc1ccc(-c2ccccc2)cc1)c1ccc(C(=O)NC2CCN(Cc3ccccc3)CC2)nc1] |
| 106 | N2-(1-benzylpiperidin-4-yl)-N5-(biphenyl-3-yl)pyridine-2,5-dicarboxamide | 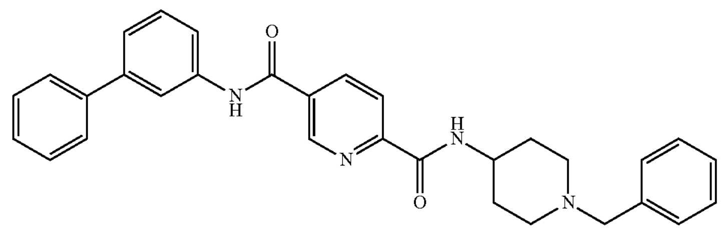 [SMILES: O=C(Nc1cccc(-c2ccccc2)c1)c1ccc(C(=O)NC2CCN(Cc3ccccc3)CC2)nc1] |
| 107 | 5-(4-(4-fluorobenzyl)piperazine-1-carbonyl)-N-phenylpicolinamide | 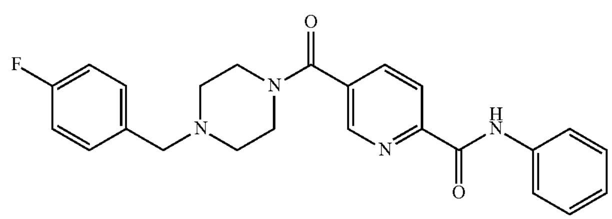 [SMILES: O=C(Nc1ccccc1)c1ccc(C(=O)N2CCN(Cc3ccc(F)cc3)CC2)cn1] |

TABLE 1-continued

| No. | Name | Structure |
|---|---|---|
| 108 | 5-(4-benzylphenylamino)-N-(1-(4-cyanobenzyl)piperidin-4-yl)picolinamide | 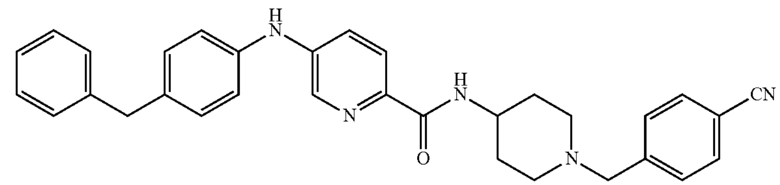 [SMILES: N#Cc1ccc(CN2CCC(NC(=O)c3ccc(Nc4ccc(Cc5ccccc5)cc4)cn3)CC2)cc1] |
| 109 | 5-(biphenyl-4-ylamino)-N-(1-(4-cyanobenzyl)piperidin-4-yl)picolinamide | 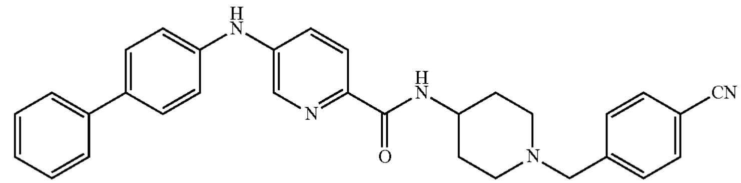 [SMILES: N#Cc1ccc(CN2CCC(NC(=O)c3ccc(Nc4ccc(-c5ccccc5)cc4)cn3)CC2)cc1] |
| 110 | 5-(4-benzylpiperazin-1-yl)-N-(1-(4-cyanobenzyl)piperidin-4-yl)picolinamide | 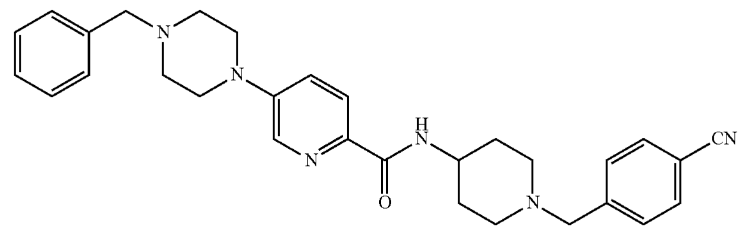 [SMILES: N#Cc1ccc(CN2CCC(NC(=O)c3ccc(N4CCN(Cc5ccccc5)CC4)cn3)CC2)cc1] |
| 111 | N-(1-(2-(4-cyanophenyl)propan-2-yl)piperidin-4-yl)-5-(4-(4-fluorobenzyl)piperazine-1-carbonyl)picolinamide | 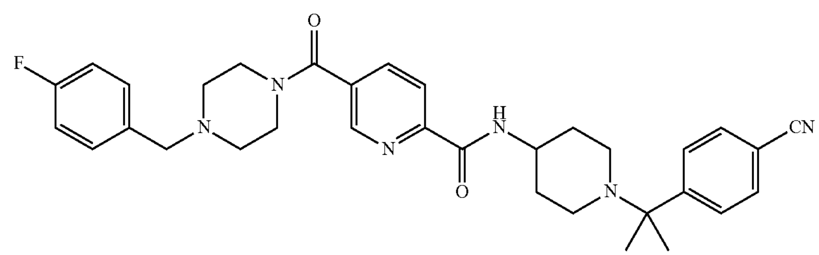 [SMILES: CC(C)(c1ccc(C#N)cc1)N1CCC(NC(=O)c2ccc(C(=O)N3CCN(Cc4ccc(F)cc4)CC3)cn2)CC1] |
| 112 | N-(1-benzylpiperidin-4-yl)-5-(3-phenoxyphenylamino)picolinamide | 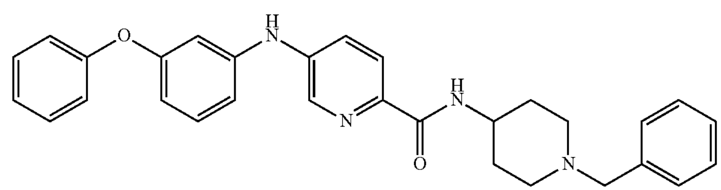 [SMILES: O=C(NC1CCN(Cc2ccccc2)CC1)c1ccc(Nc2cccc(Oc3ccccc3)c2)cn1] |

TABLE 1-continued

| No. | Name | Structure |
|---|---|---|
| 113 | N-(1-benzylpiperidin-4-yl)-5-(4-phenoxyphenylamino)picolinamide | 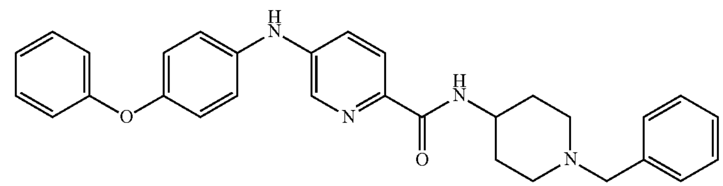 [SMILES: O=C(NC1CCN(Cc2ccccc2)CC1)c1ccc(Nc2ccc(Oc3ccccc3)cc2)cn1] |
| 114 | N-(1-benzylpiperidin-4-yl)-5-(biphenyl-3-ylamino)picolinamide | 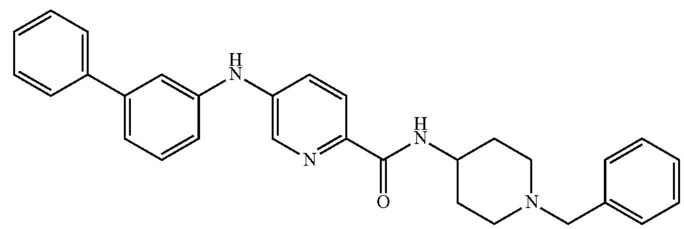 [SMILES: O=C(NC1CCN(Cc2ccccc2)CC1)c1ccc(Nc2cccc(-c3ccccc3)c2)cn1] |
| 115 | N-benzyl-5-(4-(4-fluorobenzyl)piperazine-1-carbonyl)picolinamide | 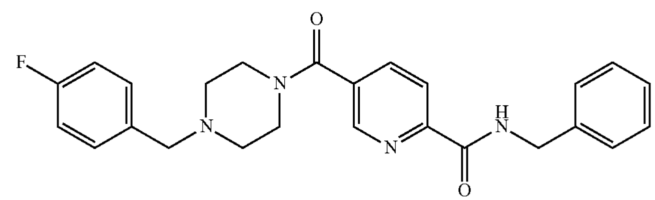 [SMILES: O=C(NCc1ccccc1)c1ccc(C(=O)N2CCN(Cc3ccc(F)cc3)CC2)cn1] |
| 116 | N-benzyl-5-(4-benzylpiperazine-1-carbonyl)picolinamide | 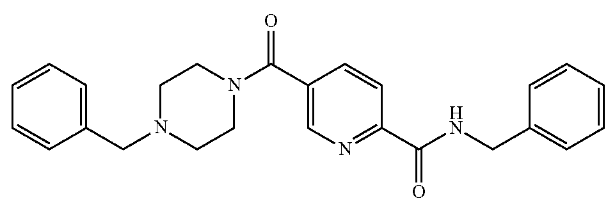 [SMILES: O=C(NCc1ccccc1)c1ccc(C(=O)N2CCN(Cc3ccccc3)CC2)cn1] |
| 117 | 5-(4-(4-fluorobenzyl)piperazine-1-carbonyl)-N-(1-(4-methoxybenzyl)piperidin-4-yl)picolinamide | 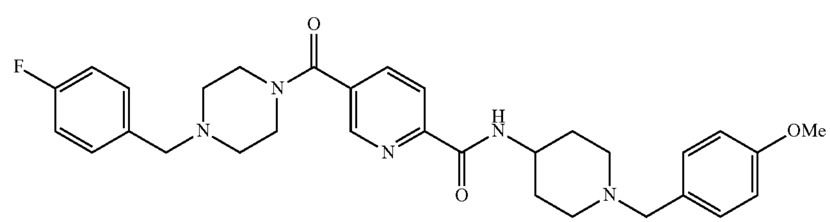 [SMILES: COc1ccc(CN2CCC(NC(=O)c3ccc(C(=O)N4CCN(Cc5ccc(F)cc5)CC4)cn3)CC2)cc1] |

TABLE 1-continued

| No. | Name | Structure |
|---|---|---|
| 118 | (R)-N-(1-(4-cyanobenzyl)pyrrolidin-3-yl)-5-(4-(4-fluorobenzyl)piperazine-1-carbonyl)picolinamide | 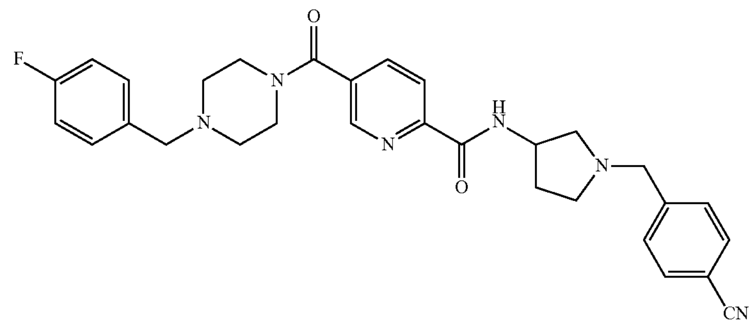 [SMILES: N#Cc1ccc(CN2CCC(NC(=O)c3ccc(C(=O)N4CCN(Cc5ccc(F)cc5)CC4)cn3)C2)cc1] |
| 119 | N-(1-benzylpiperidin-4-yl)-5-(4'-cyanobiphenyl-4-ylamino)picolinamide | 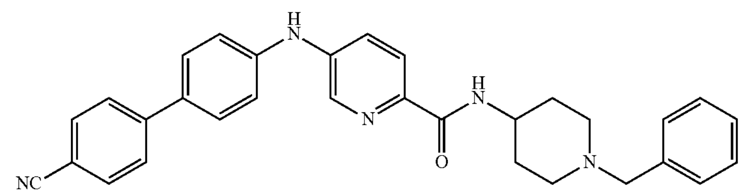 [SMILES: N#Cc1ccc(-c2ccc(Nc3ccc(C(=O)NC4CCN(Cc5ccccc5)CC4)nc3)cc2)cc1] |
| 120 | N-(1-benzylpiperidin-4-yl)-5-(4'-methoxybiphenyl-4-ylamino)picolinamide | 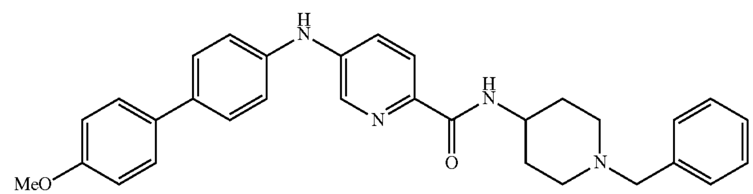 [SMILES: COc1ccc(-c2ccc(Nc3ccc(C(=O)NC4CCN(Cc5ccccc5)CC4)nc3)cc2)cc1] |
| 121 | 5-(1-benzyl-1H-1,2,3-triazol-4-yl)-N-(1-(4-cyanobenzyl)piperidin-4-yl)picolinamide | 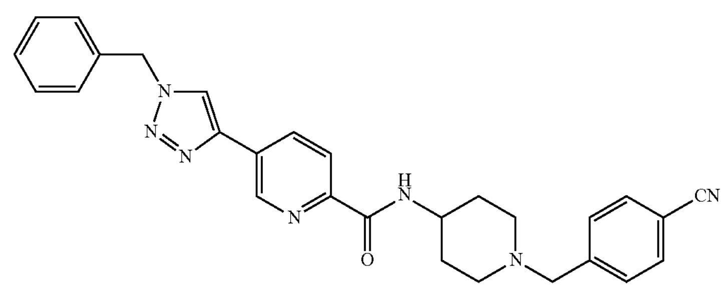 [SMILES: N#Cc1ccc(CN2CCC(NC(=O)c3ccc(-c4cn(Cc5ccccc5)nn4)cn3)CC2)cc1] |

TABLE 1-continued

| No. | Name | Structure |
|---|---|---|
| 122 | 5-(1-benzyl-1H-1,2,3-triazol-4-yl)-N-(1-(4-cyanobenzyl)piperidin-4-yl)picolinamide | 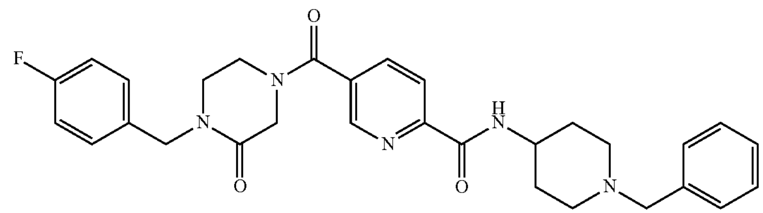 [SMILES: O=C(NC1CCN(Cc2ccccc2)CC1)c1ccc(C(=O)N2CCN(Cc3ccc(F)cc3)C(=O)C2)cn1] |
| 123 | (S)-N-(1-(4-cyanobenzyl)pyrrolidin-3-yl)-5-(4-(4-fluorobenzyl)piperazine-1-carbonyl)picolinamide | 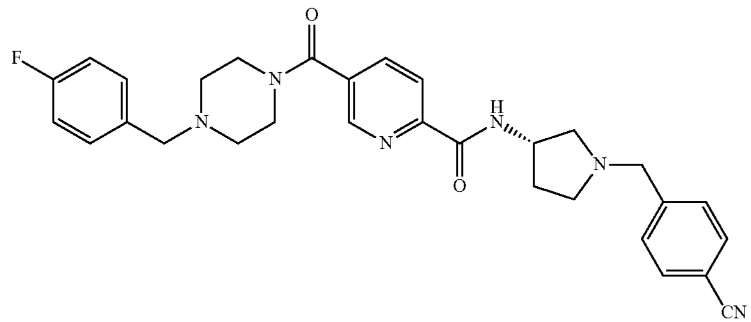 [SMILES: N#Cc1ccc(CN2CC[C@H](NC(=O)c3ccc(C(=O)N4CCN(Cc5ccc(F)cc5)CC4)cn3)C2)cc1] |
| 124 | 5-(4-benzylpiperidine-1-carbonyl)-N-(1-(4-cyanobenzyl)piperidin-4-yl)picolinamide | 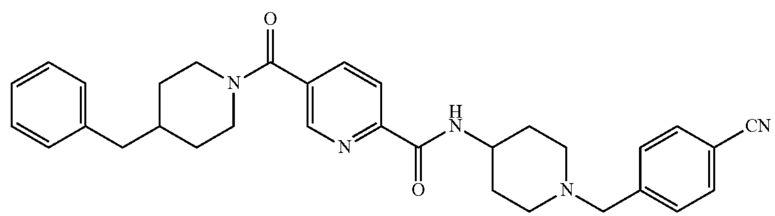 [SMILES: N#Cc1ccc(CN2CCC(NC(=O)c3ccc(C(=O)N4CCC(Cc5ccccc5)CC4)cn3)CC2)cc1] |
| 125 | N-(1-(4-cyanobenzyl)piperidin-4-yl)-5-(4-(4-fluorobenzyl)-3,3-dimethylpiperazine-1-carbonyl)picolinamide | 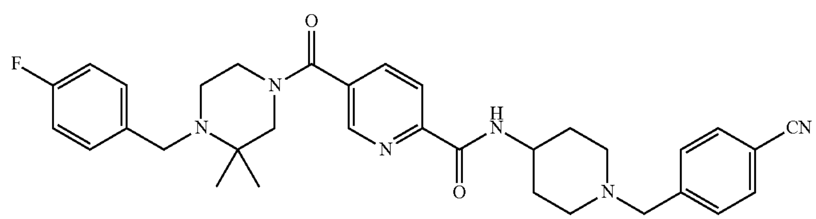 [SMILES: CC1(C)CN(C(=O)c2ccc(C(=O)NC3CCN(Cc4ccc(C#N)cc4)CC3)nc2)CCN1Cc1ccc(F)cc1] |

TABLE 1-continued

| No. | Name | Structure |
|-----|------|-----------|
| 126 | N-(1-(4-cyanobenzyl)piperidin-4-yl)-5-(1-phenylpiperidin-4-ylamino)picolinamide | 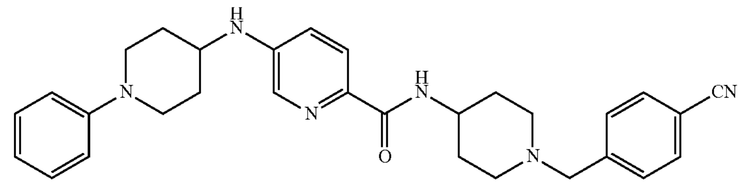 [SMILES: N#Cc1ccc(CN2CCC(NC(=O)c3ccc(NC4CCN(c5ccccc5)CC4)cn3)CC2)cc1] |
| 127 | N-(cis-1-(4-chlorobenzyl)-3-fluoropiperidin-4-yl)-5-(4-(4-fluorobenzyl)piperazine-1-carbonyl)picolinamide | 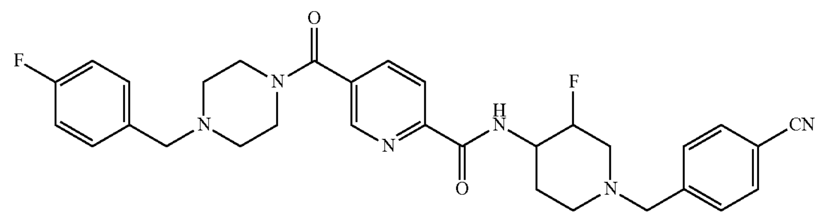 [SMILES: N#Cc1ccc(CN2CCC(NC(=O)c3ccc(C(=O)N4CCN(Cc5ccc(F)cc5)CC4)cn3)C(F)C2)cc1] |
| 128 | N-(1-(4-cyanobenzyl)piperidin-4-yl)-5-(4-(4-cyanobenzyl)piperidine-1-carbonyl)picolinamide | 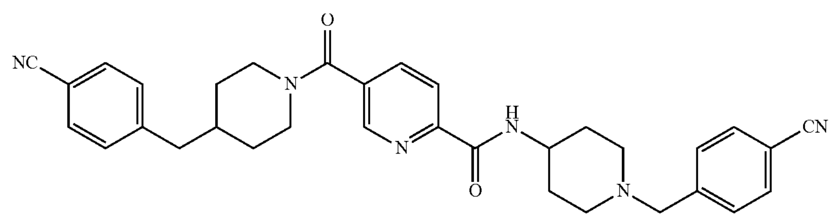 [SMILES: N#Cc1ccc(CC2CCN(C(=O)c3ccc(C(=O)NC4CCN(Cc5ccc(C#N)cc5)CC4)nc3)CC2)cc1] |
| 129 | N-(1-(4-cyanobenzyl)piperidin-4-yl)-5-(4-(4-methoxybenzoyl)piperidine-1-carbonyl)picolinamide | 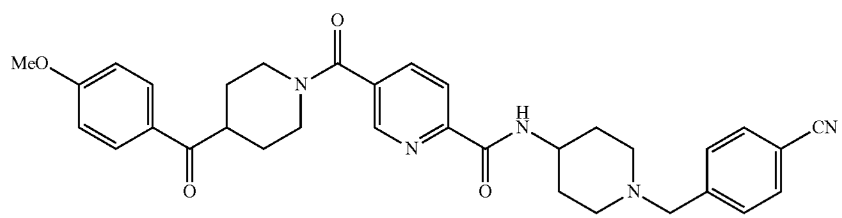 [SMILES: COc1ccc(C(=O)C2CCN(C(=O)c3ccc(C(=O)NC4CCN(Cc5ccc(C#N)cc5)CC4)nc3)CC2)cc1] |
| 130 | N-(1-(4-cyanobenzyl)piperidin-4-yl)-5-(4-(4-fluorobenzyl)piperidine-1-carbonyl)picolinamide | 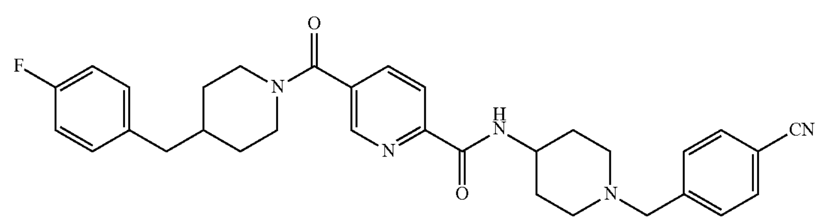 [SMILES: N#Cc1ccc(CN2CCC(NC(=O)c3ccc(C(=O)N4CCC(Cc5ccc(F)cc5)CC4)cn3)CC2)cc1] |

TABLE 1-continued

| No. | Name | Structure |
|---|---|---|
| 131 | N-(1-(4-cyanobenzyl)piperidin-4-yl)-5-(4-(4-methoxybenzyl)piperidine-1-carbonyl)picolinamide | 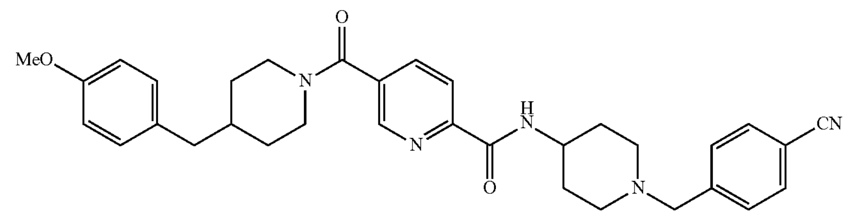 [SMILES: COc1ccc(CC2CCN(C(=O)c3ccc(C(=O)NC4CCN(Cc5ccc(C#N)cc5)CC4)nc3)CC2)cc1] |
| 132 | N-(2-(4-cyanobenzyl)-1,2,3,4-tetrahydroisoquinolin-7-yl)-5-(4-(4-fluorobenzyl)piperazine-1-carbonyl)picolinamide | 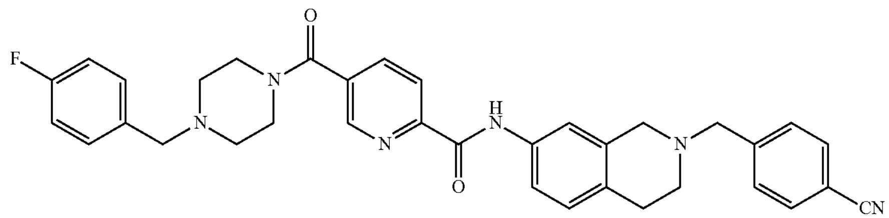 [SMILES: N#Cc1ccc(CN2CCc3ccc(NC(=O)c4ccc(C(=O)N5CCN(Cc6ccc(F)cc6)CC5)cn4)cc3C2)cc1] |
| 133 | N-(1-(4-cyanobenzyl)piperidin-4-yl)-5-(4-(2-phenylpropan-2-yl)piperazine-1-carbonyl)picolinamide | 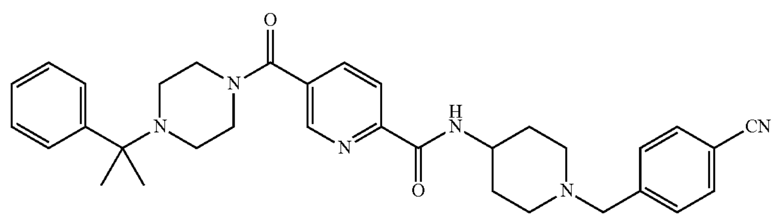 [SMILES: CC(C)(c1ccccc1)N1CCN(C(=O)c2ccc(C(=O)NC3CCN(Cc4ccc(C#N)cc4)CC3)nc2)CC1] |
| 134 | 5-(4-(4-chlorophenyl)piperidine-1-carbonyl)-N-(1-(4-cyanobenzyl)piperidin-4-yl)picolinamide | 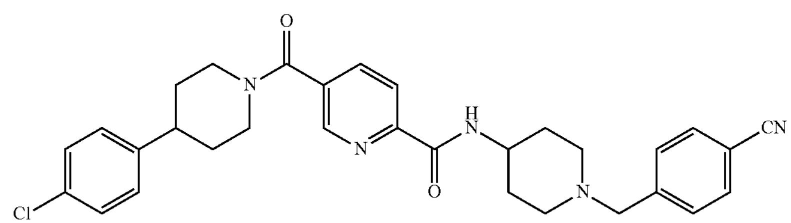 [SMILES: N#Cc1ccc(CN2CCC(NC(=O)c3ccc(C(=O)N4CCC(c5ccc(Cl)cc5)CC4)cn3)CC2)cc1] |

TABLE 1-continued

| No. | Name | Structure |
|---|---|---|
| 135 | N-(1-(4-cyanobenzyl)piperidin-4-yl)-5-(4-(4-cyanophenoxy)piperidine-1-carbonyl)picolinamide | 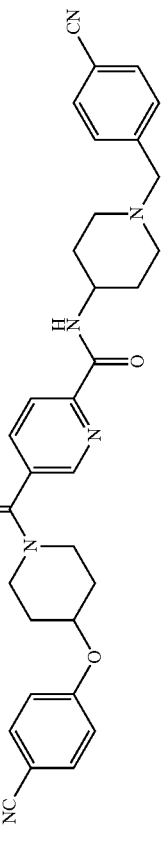 |
| 136 | N-(1-(4-cyanobenzyl)piperidin-4-yl)-5-(4-(4-fluorobenzoyl)piperidine-1-carbonyl)picolinamide | 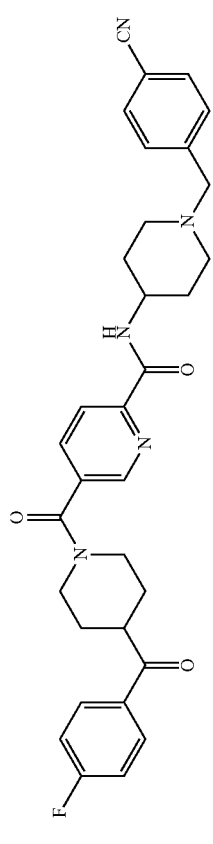 |
| 137 | N-(1-(4-cyanobenzyl)piperidin-4-yl)-5-(3-(4-cyanophenoxy)piperidine-1-carbonyl)picolinamide | 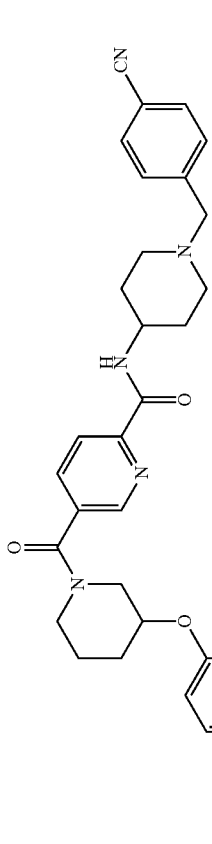 |
| 138 | N-(1-(4-cyanobenzyl)piperidin-4-yl)-5-(4-(fluoro(4-fluorophenyl)methyl)piperidine-1-carbonyl)picolinamide | 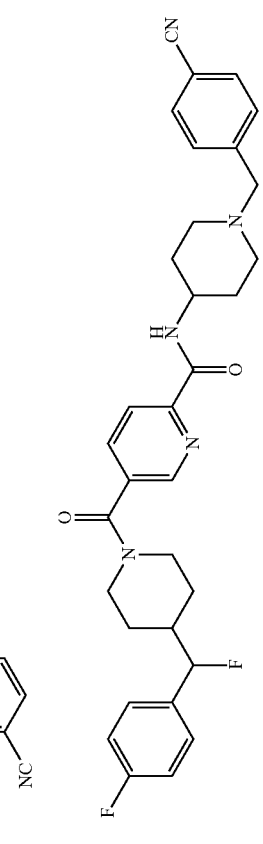 |

TABLE 1-continued

| No. | Name | Structure |
|---|---|---|
| 139 | 5-(1-(4-chlorophenyl)piperidin-4-ylamino)-N-(1-(4-cyanobenzyl)piperidin-4-yl)picolinamide | 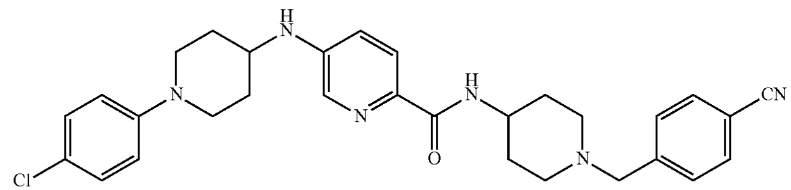 [SMILES: N#Cc1ccc(CN2CCC(NC(=O)c3ccc(NC4CCN(c5ccc(Cl)cc5)CC4)cn3)CC2)cc1] |
| 140 | N-(1-(4-cyanobenzyl)piperidin-4-yl)-5-(4-(3,5-difluorobenzyl)piperazine-1-carbonyl)picolinamide | 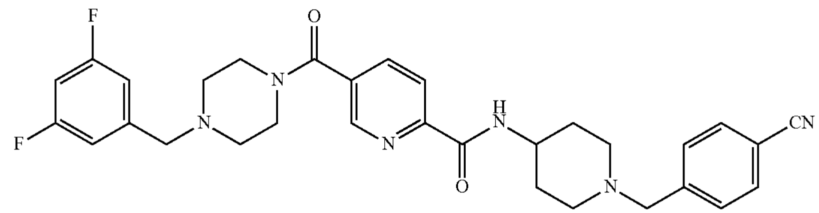 [SMILES: N#Cc1ccc(CN2CCC(NC(=O)c3ccc(C(=O)N4CCN(Cc5cc(F)cc(F)c5)CC4)cn3)CC2)cc1] |
| 141 | 5-(4-(4-carbamoylbenzyl)piperidine-1-carbonyl)-N-(1-(4-cyanobenzyl)piperidin-4-yl)picolinamide | 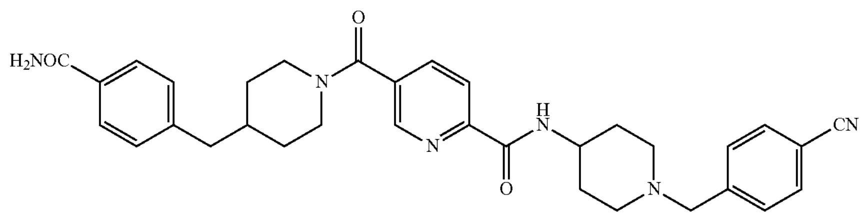 [SMILES: N#Cc1ccc(CN2CCC(NC(=O)c3ccc(C(=O)N4CCC(Cc5ccc(C(N)=O)cc5)CC4)cn3)CC2)cc1] |
| 142 | N-(1-(4-cyanobenzyl)piperidin-4-yl)-5-(4-((4-fluorophenyl)(hydroxy)methyl)piperidine-1-carbonyl)picolinamide | 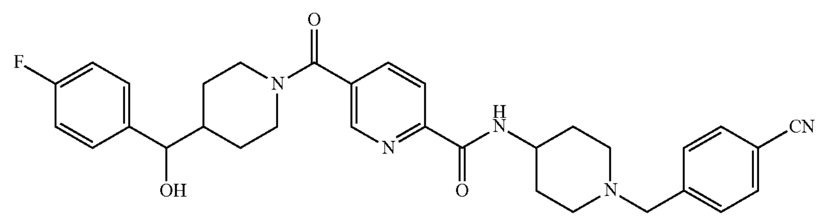 [SMILES: N#Cc1ccc(CN2CCC(NC(=O)c3ccc(C(=O)N4CCC(C(O)c5ccc(F)cc5)CC4)cn3)CC2)cc1] |

TABLE 1-continued

| No. | Name | Structure |
|-----|------|-----------|
| 143 | N-(1-(4-cyanobenzyl)piperidin-4-yl)-5-(4-(4-methoxyphenoxy)piperidine-1-carbonyl)picolinamide | 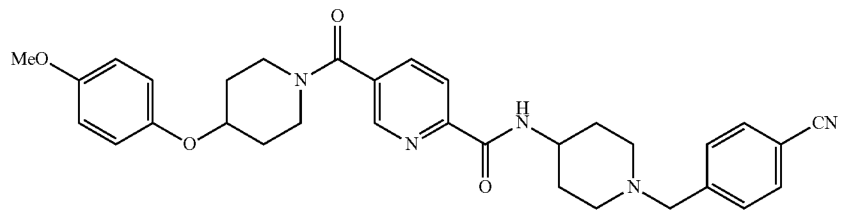 [SMILES: COc1ccc(OC2CCN(C(=O)c3ccc(C(=O)NC4CCN(Cc5ccc(C#N)cc5)CC4)nc3)CC2)cc1] |
| 144 | N2-(2-(4-cyanobenzyl)-1,2,3,4-tetrahydroisoquinolin-7-yl)-N5-(4-fluorobenzyl)pyridine-2,5-dicarboxamide | 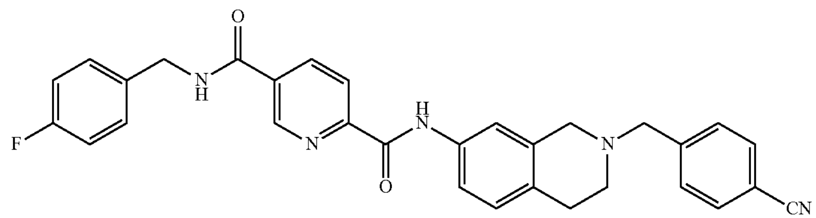 [SMILES: N#Cc1ccc(CN2CCc3ccc(NC(=O)c4ccc(C(=O)NCc5ccc(F)cc5)cn4)cc3C2)cc1] |
| 145 | N-(1-(4-cyanobenzyl)piperidin-4-yl)-5-(4-(4-methylbenzyl)piperidine-1-carbonyl)picolinamide | 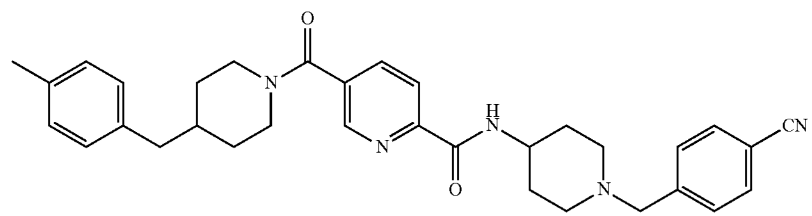 [SMILES: Cc1ccc(CC2CCN(C(=O)c3ccc(C(=O)NC4CCN(Cc5ccc(C#N)cc5)CC4)nc3)CC2)cc1] |
| 146 | N-(1-(4-cyanobenzyl)piperidin-4-yl)-5-(4-(3-fluoro-4-methoxybenzyl)piperidine-1-carbonyl)picolinamide | 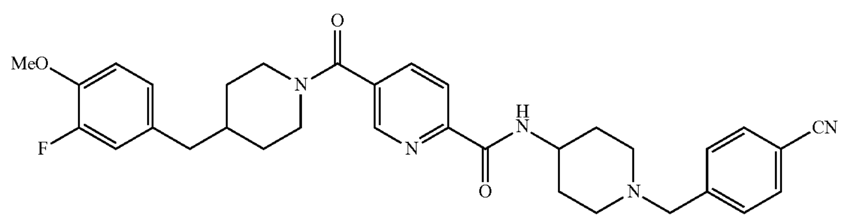 [SMILES: COc1ccc(CC2CCN(C(=O)c3ccc(C(=O)NC4CCN(Cc5ccc(C#N)cc5)CC4)nc3)CC2)cc1F] |

TABLE 1-continued

| No. | Name | Structure |
|---|---|---|
| 147 | N-(1-(4-cyanobenzyl)piperidin-4-yl)-5-(4-(3-methoxybenzyl)piperidine-1-carbonyl)picolinamide | 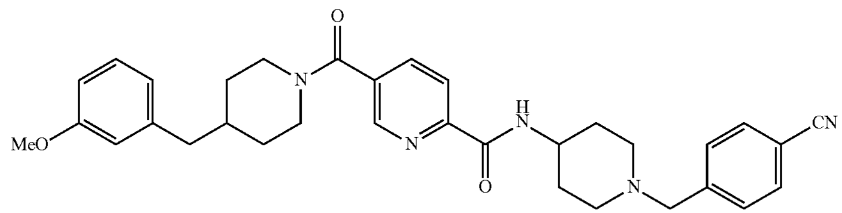 [SMILES: COc1cccc(CC2CCN(C(=O)c3ccc(C(=O)NC4CCN(Cc5ccc(C#N)cc5)CC4)nc3)CC2)c1] |
| 148 | N-(1-(4-cyanobenzyl)piperidin-4-yl)-5-(4-(4-fluorophenoxy)piperidine-1-carbonyl)picolinamide | 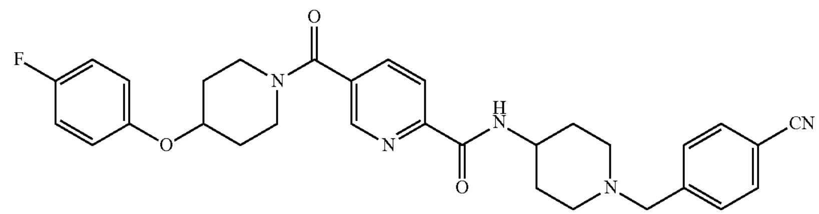 [SMILES: N#Cc1ccc(CN2CCC(NC(=O)c3ccc(C(=O)N4CCC(Oc5ccc(F)cc5)CC4)cn3)CC2)cc1] |
| 149 | N2-(1-(4-cyanobenzyl)piperidin-4-yl)-N5-(2-(4-fluorophenoxy)ethyl)pyridine-2,5-dicarboxamide | 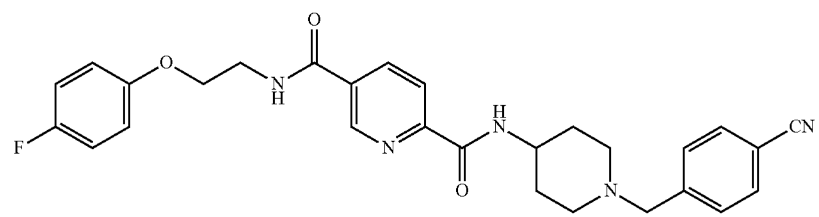 [SMILES: N#Cc1ccc(CN2CCC(NC(=O)c3ccc(C(=O)NCCOc4ccc(F)cc4)cn3)CC2)cc1] |
| 150 | N-(cis-4-(4-cyanophenoxy)cyclohexyl)-5-(4-(4-fluorobenzyl)piperazine-1-carbonyl)picolinamide | 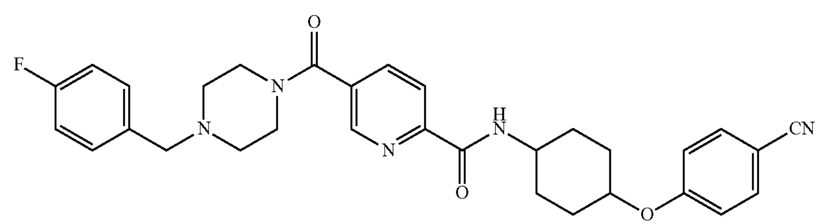 [SMILES: N#Cc1ccc(OC2CCC(NC(=O)c3ccc(C(=O)N4CCN(Cc5ccc(F)cc5)CC4)cn3)CC2)cc1] |

TABLE 1-continued

| No. | Name | Structure |
|---|---|---|
| 151 | N-(trans-4-(4-cyanophenoxy)cyclohexyl)-5-(4-(4-fluorobenzoyl)piperazine-1-carbonyl)picolinamide | 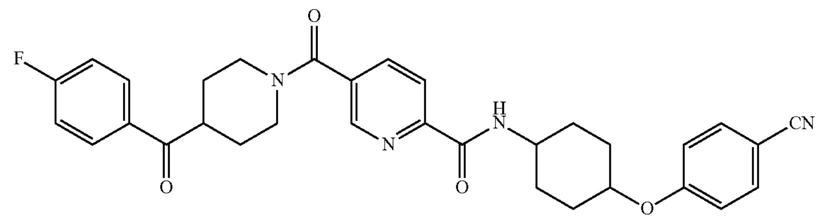 [SMILES: N#Cc1ccc(OC2CCC(NC(=O)c3ccc(C(=O)N4CCC(C(=O)c5ccc(F)cc5)CC4)cn3)CC2)cc1] |
| 152 | N-(1-(4-cyanobenzyl)piperidin-4-yl)-5-(3-(4-fluorobenzyl)piperidine-1-carbonyl)picolinamide | 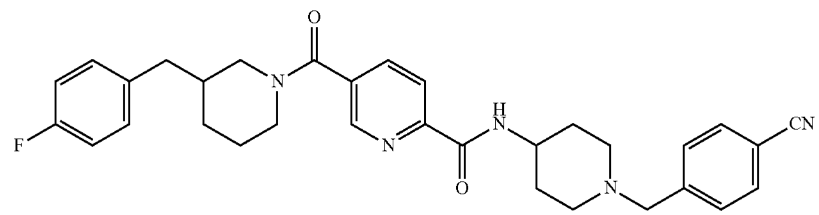 [SMILES: N#Cc1ccc(CN2CCC(NC(=O)c3ccc(C(=O)N4CCCC(Cc5ccc(F)cc5)C4)cn3)CC2)cc1] |
| 153 | N-(1-(4-cyanobenzyl)piperidin-4-yl)-5-(2-(4-fluorobenzyl)piperidine-1-carbonyl)picolinamide | 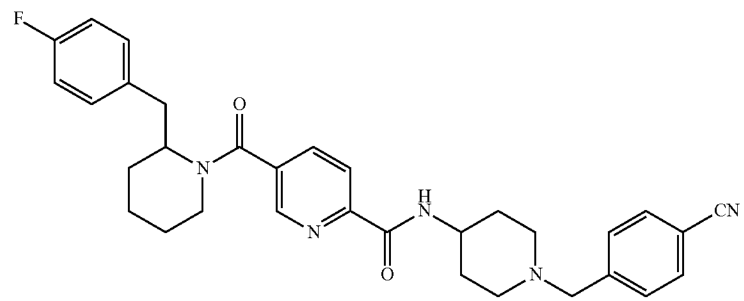 [SMILES: N#Cc1ccc(CN2CCC(NC(=O)c3ccc(C(=O)N4CCCCC4Cc4ccc(F)cc4)cn3)CC2)cc1] |
| 154 | 5-(4-(4-chlorobenzoyl)piperidine-1-carbonyl)-N-(1-(4-cyanobenzyl)piperidin-4-yl)picolinamide | 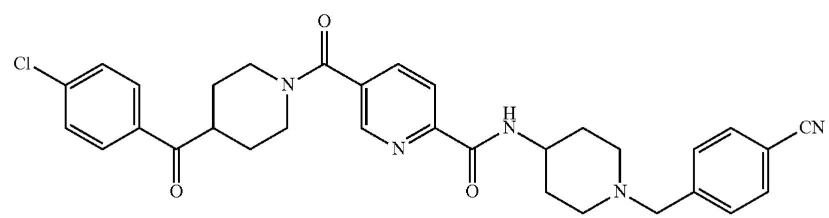 [SMILES: N#Cc1ccc(CN2CCC(NC(=O)c3ccc(C(=O)N4CCC(C(=O)c5ccc(Cl)cc5)CC4)cn3)CC2)cc1] |

TABLE 1-continued

| No. | Name | Structure |
|---|---|---|
| 155 | N-(1-(4-cyanobenzyl)piperidin-4-yl)-5-(4-(3-cyanophenoxy)piperidine-1-carbonyl)picolinamide | 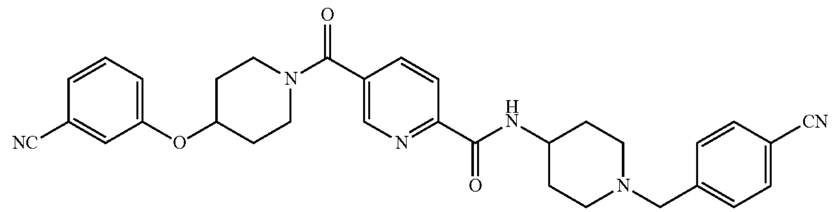 [SMILES: N#Cc1ccc(CN2CCC(NC(=O)c3ccc(C(=O)N4CCC(Oc5cccc(C#N)c5)CC4)cn3)CC2)cc1] |
| 156 | 5-(4-(3-chloro-4-cyanophenoxy)piperidine-1-carbonyl)-N-(1-(4-cyanobenzyl)piperidin-4-yl)picolinamide | 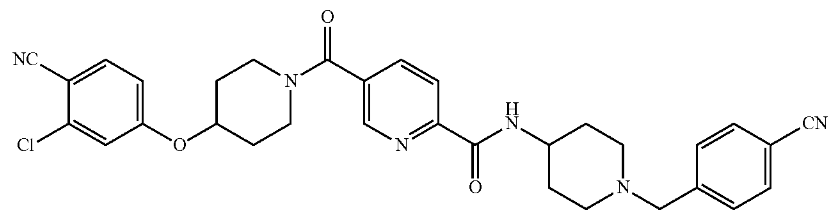 [SMILES: N#Cc1ccc(CN2CCC(NC(=O)c3ccc(C(=O)N4CCC(Oc5ccc(C#N)c(Cl)c5)CC4)cn3)CC2)cc1] |
| 157 | N-(1-(4-cyanobenzyl)piperidin-4-yl)-5-(4-(4-(trifluoromethyl)phenoxy)piperidine-1-carbonyl)picolinamide | 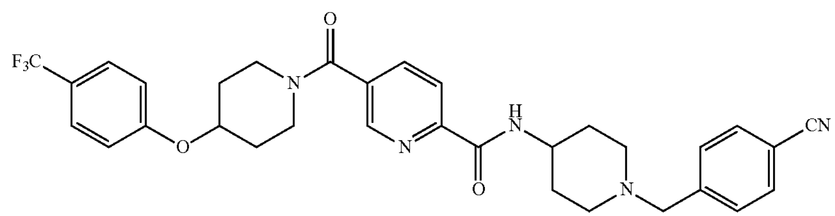 [SMILES: N#Cc1ccc(CN2CCC(NC(=O)c3ccc(C(=O)N4CCC(Oc5ccc(C(F)(F)F)cc5)CC4)cn3)CC2)cc1] |
| 158 | N-(1-(4-cyanobenzyl)piperidin-4-yl)-5-(4-(3,4-difluorophenoxy)piperidine-1-carbonyl)picolinamide | 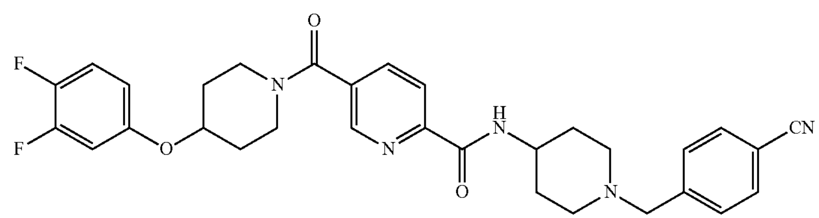 [SMILES: N#Cc1ccc(CN2CCC(NC(=O)c3ccc(C(=O)N4CCC(Oc5ccc(F)c(F)c5)CC4)cn3)CC2)cc1] |

TABLE 1-continued

| No. | Name | Structure |
|-----|------|-----------|
| 159 | N-(1-(4-cyanobenzyl)piperidin-4-yl)-3-(5,20-dioxo-24-((3aS,4S,6aR)-2-oxohexahydro-1H-thieno[3,4-d]imidazol-4-yl)-7,10,13,16-tetraoxa-4,19-diazatetracos-1-ynyl)-5-(4-(4-fluorobenzyl)piperazine-1-carbonyl)picolinamide | 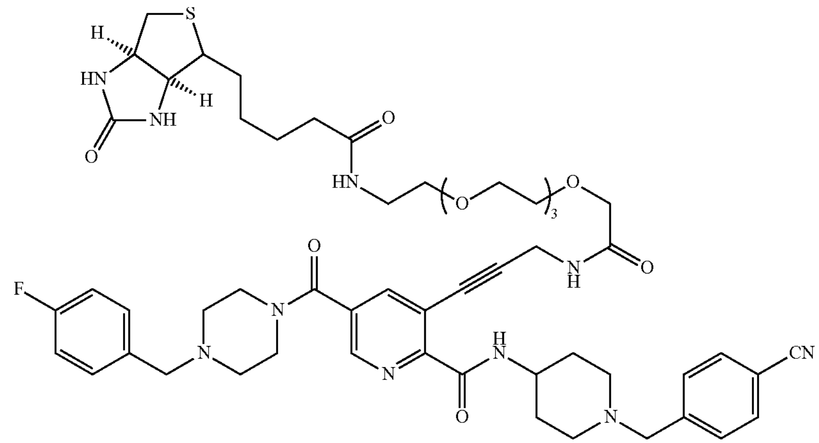 |
| 160 | 5-(4-(4-fluorobenzoyl)piperidine-1-carbonyl)-N-(1-(4-methoxybenzyl)piperidin-4-yl)picolinamide | 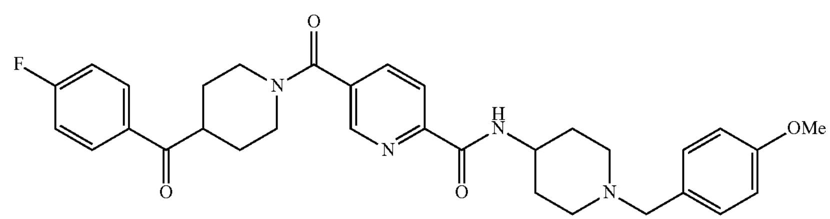 [SMILES: COc1ccc(CN2CCC(NC(=O)c3ccc(C(=O)N4CCC(C(=O)c5ccc(F)cc5)CC4)cn3)CC2)cc1] |
| 161 | 5-(4-(4-fluorophenoxy)piperidine-1-carbonyl)-N-(1-(4-methoxybenzyl)piperidin-4-yl)picolinamide | 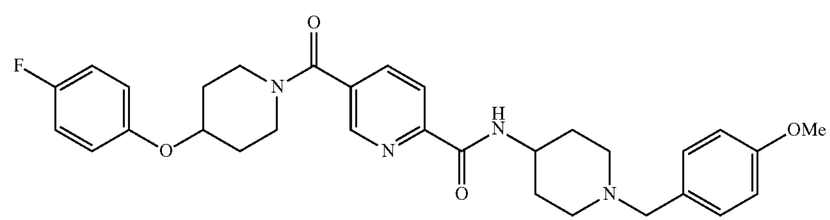 [SMILES: COc1ccc(CN2CCC(NC(=O)c3ccc(C(=O)N4CCC(Oc5ccc(F)cc5)CC4)cn3)CC2)cc1] |

TABLE 1-continued

| No. | Name | Structure |
|---|---|---|
| 162 | 5-(4-(4-cyanophenoxy)piperidine-1-carbonyl)-N-(1-(4-methoxybenzyl)piperidin-4-yl)picolinamide | 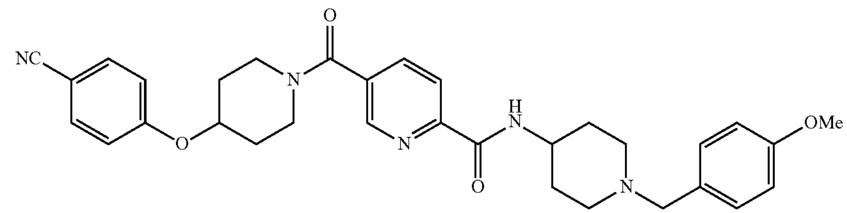 [SMILES: COc1ccc(CN2CCC(NC(=O)c3ccc(C(=O)N4CCC(Oc5ccc(C#N)cc5)CC4)cn3)CC2)cc1] |
| 163 | 5-(4-(4-methoxybenzoyl)piperidine-1-carbonyl)-N-(1-(4-methoxybenzyl)piperidin-4-yl)picolinamide | 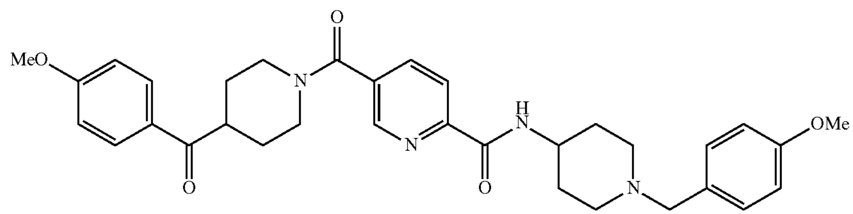 [SMILES: COc1ccc(CN2CCC(NC(=O)c3ccc(C(=O)N4CCC(C(=O)c5ccc(OC)cc5)CC4)cn3)CC2)cc1] |
| 164 | tert-butyl 3-(2-(1-(4-cyanobenzyl)piperidin-4-ylcarbamoyl)-5-(4-(4-fluorobenzyl)piperazine-1-carbonyl)pyridin-3-yl)prop-2-ynylcarbamate | 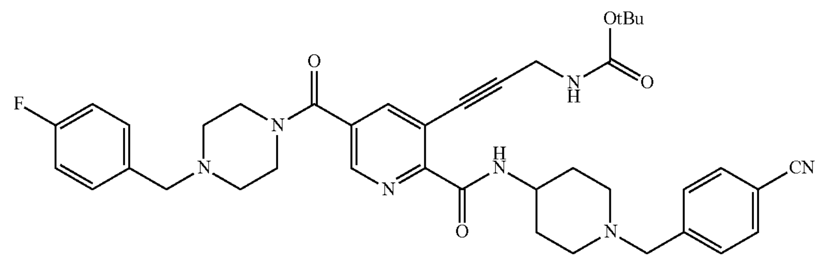 [SMILES: CC(C)(C)OC(=O)NCC#Cc1cc(C(=O)N2CCN(Cc3ccc(F)cc3)CC2)cnc1C(=O)NC1CCN(Cc2ccc(C#N)cc2)CC1] |
| 165 | N-(1-(4-cyanobenzyl)piperidin-4-yl)-5-(4-(4-cyanophenoxy)piperidin-1-yl)picolinamide | 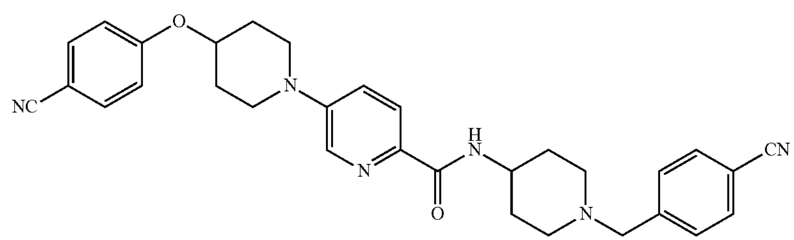 [SMILES: N#Cc1ccc(CN2CCC(NC(=O)c3ccc(N4CCC(Oc5ccc(C#N)cc5)CC4)cn3)CC2)cc1] |

TABLE 1-continued

| No. | Name | Structure |
|---|---|---|
| 166 | N2-(1-(4-cyanobenzyl)piperidin-4-yl)-N5-(1-(4-cyanophenyl)piperidin-4-yl)pyridine-2,5-dicarboxamide | 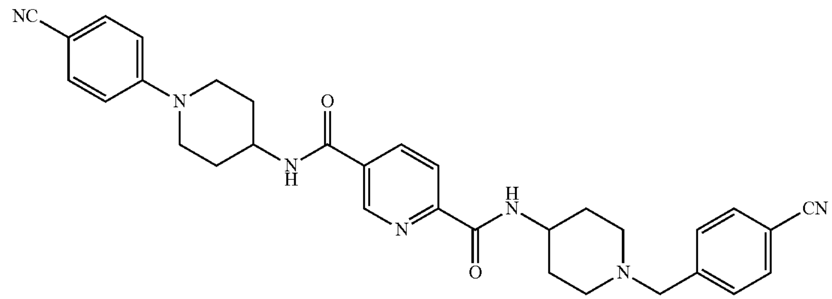 [SMILES: N#Cc1ccc(CN2CCC(NC(=O)c3ccc(C(=O)NC4CCN(c5ccc(C#N)cc5)CC4)cn3)CC2)cc1] |
| 167 | N-((cis)-4-(4-cyanophenoxy)cyclohexyl)-5-(4-(4-fluorophenyl)piperidine-1-carbonyl)picolinamide | 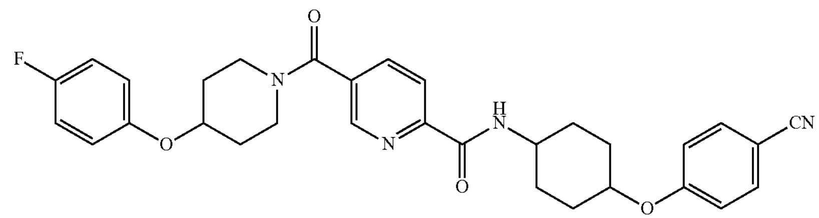 [SMILES: N#Cc1ccc(OC2CCC(NC(=O)c3ccc(C(=O)N4CCC(Oc5ccc(F)cc5)CC4)cn3)CC2)cc1] |
| 168 | N-((trans)-4-(4-cyanophenoxy)cyclohexyl)-5-(4-(4-fluorobenzoyl)piperidine-1-carbonyl)picolinamide | 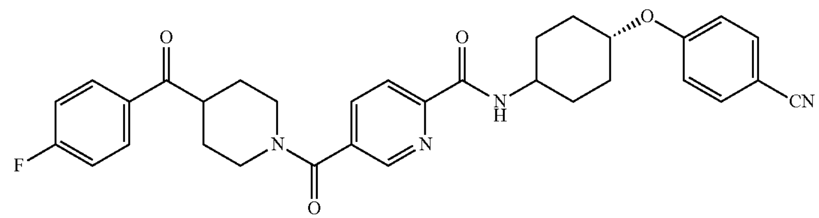 |
| 169 | N-((trans)-4-(4-cyanophenoxy)cyclohexyl)-5-(4-(4-fluorophenoxy)piperidine-1-carbonyl)picolinamide | 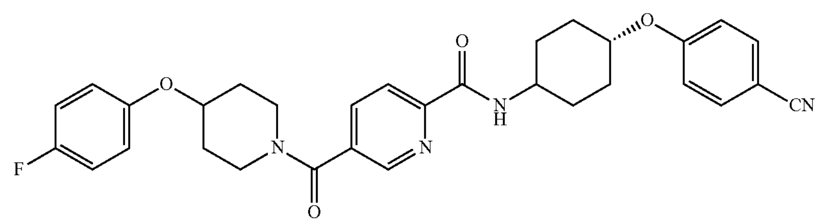 |

TABLE 1-continued

| No. | Name | Structure |
|---|---|---|
| 170 | N-(5-(4-(4-fluorobenzyl)piperazine-1-carbonyl)pyridin-2-yl)biphenyl-4-carboxamide | 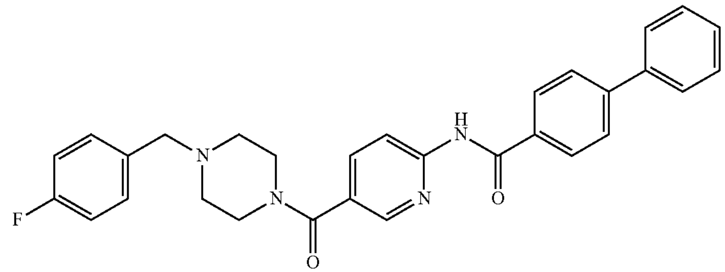 [SMILES: O=C(Nc1ccc(C(=O)N2CCN(Cc3ccc(F)cc3)CC2)cn1)c1ccc(-c2ccccc2)cc1] |
| 171 | N-((cis)-4-(4-cyanophenoxy)cyclohexyl)-5-(4-(4-methoxybenzoyl)piperidine-1-carbonyl)picolinamide | 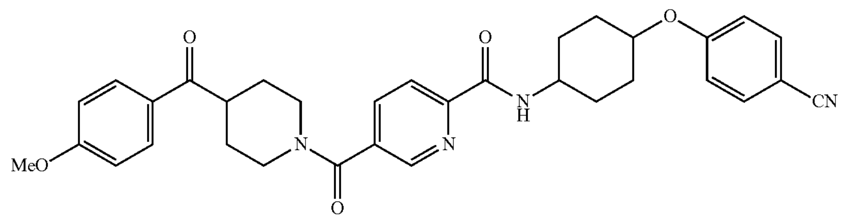 |
| 172 | N-((trans)-4-(4-cyanophenoxy)cyclohexyl)-5-(4-(4-methoxyphenoxy)piperidine-1-carbonyl)picolinamide | 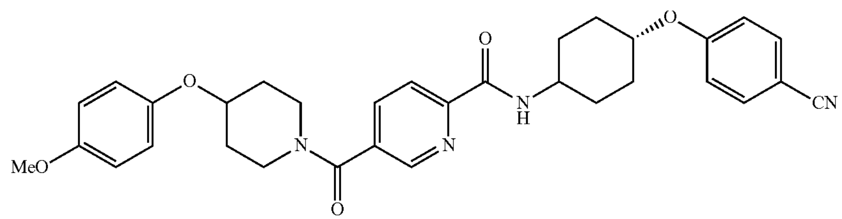 |
| 173 | 1-(4-cyanobenzyl)-N-(5-(4-(4-fluorophenoxy)piperidine-1-carbonyl)pyridin-2-yl)piperidine-4-carboxamide | 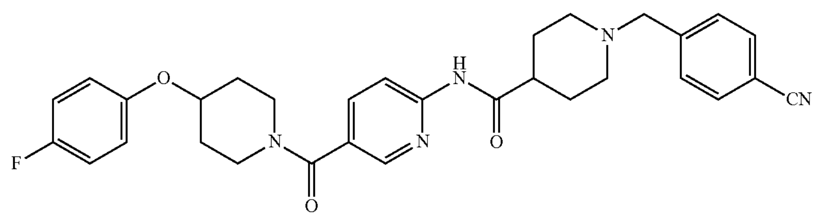 [SMILES: N#Cc1ccc(CN2CCC(C(=O)Nc3ccc(C(=O)N4CCC(Oc5ccc(F)cc5)CC4)cn3)CC2)cc1] |

TABLE 1-continued

| No. | Name | Structure |
|---|---|---|
| 174 | N-((cis)-4-(4-cyanophenoxy)cyclohexyl)-5-(4-(4-methoxyphenoxy)piperidine-1-carbonyl)picolinamide | 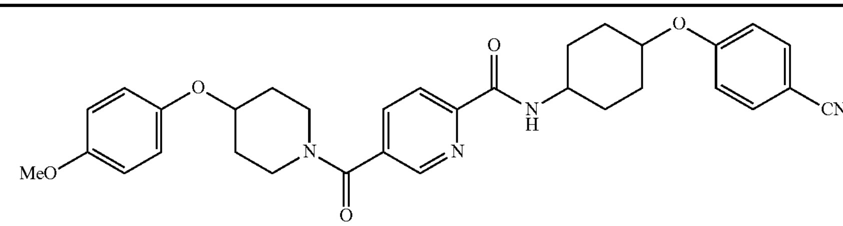 |
| 175 | 1-(4-cyanobenzyl)-N-(5-(4-(4-fluorobenzoyl)piperidine-1-carbonyl)pyridin-2-yl)piperidine-4-carboxamide | 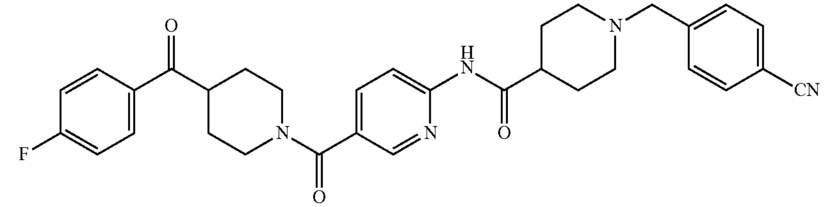 [SMILES: N#Cc1ccc(CN2CCC(C(=O)Nc3ccc(C(=O)N4CCC(C(=O)c5ccc(F)cc5)CC4)cn3)CC2)cc1] |
| 176 | N-((cis)-4-(4-cyanophenoxy)cyclohexyl)-5-((S)-3-(4-fluorophenoxy)pyrrolidine-1-carbonyl)picolinamide | 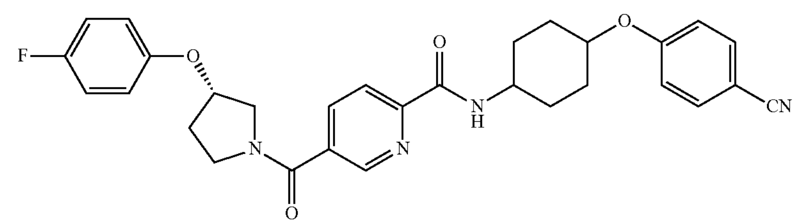 [SMILES: N#Cc1ccc(OC2CCC(NC(=O)c3ccc(C(=O)N4CC[C@H](Oc5ccc(F)cc5)C4)cn3)CC2)cc1] |
| 177 | N-(5-(4-(4-fluorobenzyl)piperazine-1-carbonyl)pyridin-2-yl)-6-(4-fluorophenoxy)nicotinamide | 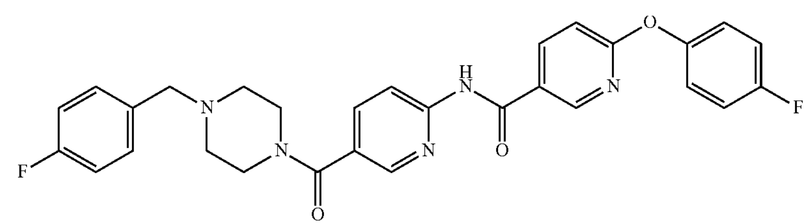 [SMILES: O=C(Nc1ccc(C(=O)N2CCN(Cc3ccc(F)cc3)CC2)cn1)c1ccc(Oc2ccc(F)cc2)nc1] |

TABLE 1-continued

| No. | Name | Structure |
|---|---|---|
| 178 | N-(1-(4-fluorobenzyl)piperidin-4-yl)-5-(4-(4-methoxybenzoyl)piperidine-1-carbonyl)picolinamide | 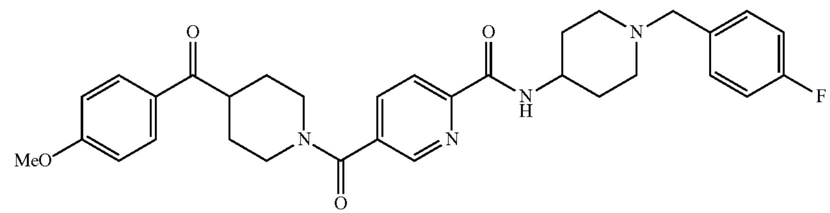 [SMILES: COc1ccc(C(=O)C2CCN(C(=O)c3ccc(C(=O)NC4CCN(Cc5ccc(F)cc5)CC4)nc3)CC2)cc1] |
| 179 | N-(1-(4-fluorobenzyl)piperidin-4-yl)-5-(4-(4-(trifluoromethyl)phenoxy)piperidine-1-carbonyl)picolinamide | 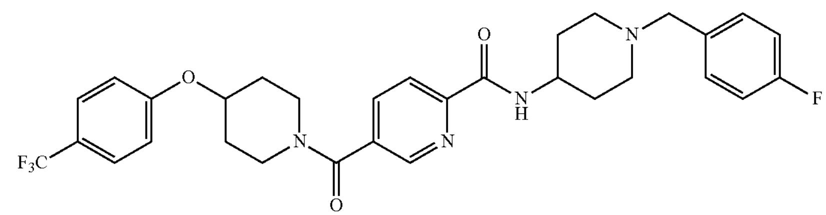 [SMILES: O=C(NC1CCN(Cc2ccc(F)cc2)CC1)c1ccc(C(=O)N2CCC(Oc3ccc(C(F)(F)F)cc3)CC2)cn1] |
| 180 | N-(1-(4-fluorobenzyl)piperidin-4-yl)-5-(4-(4-fluorophenoxy)piperidine-1-carbonyl)picolinamide | 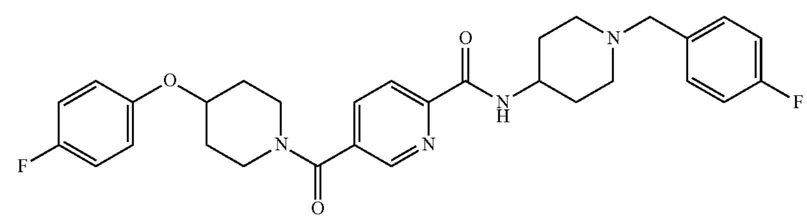 [SMILES: O=C(NC1CCN(Cc2ccc(F)cc2)CC1)c1ccc(C(=O)N2CCC(Oc3ccc(F)cc3)CC2)cn1] |
| 181 | 5-(4-(4-fluorobenzoyl)piperidine-1-carbonyl)-N-(1-(4-fluorobenzyl)piperidin-4-yl)picolinamide | 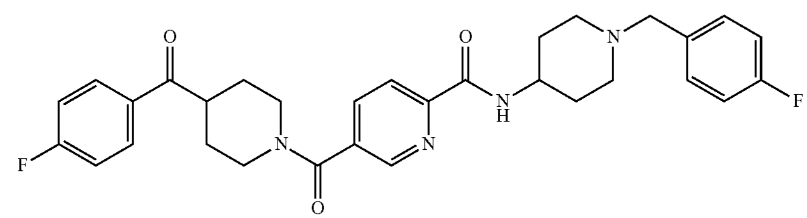 [SMILES: O=C(NC1CCN(Cc2ccc(F)cc2)CC1)c1ccc(C(=O)N2CCC(C(=O)c3ccc(F)cc3)CC2)cn1] |

TABLE 1-continued

| No. | Name | Structure |
|-----|------|-----------|
| 182 | (S)-N-(1-(4-fluorobenzyl)piperidin-4-yl)-5-(3-(4-fluorophenoxy)pyrrolidine-1-carbonyl)picolinamide | 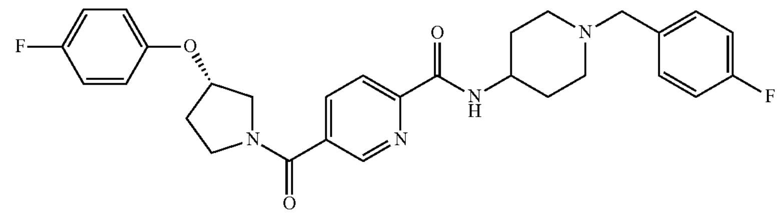 [SMILES: O=C(NC1CCN(Cc2ccc(F)cc2)CC1)c1ccc(C(=O)N2CC[C@H](Oc3ccc(F)cc3)C2)cn1] |
| 183 | N-(1-(4-fluorobenzyl)piperidin-4-yl)-5-(4-(4-methoxyphenoxy)piperidine-1-carbonyl)picolinamide | 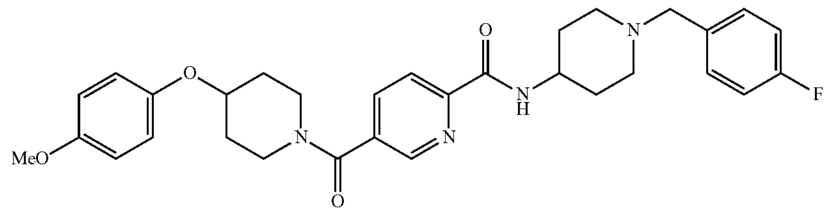 [SMILES: COc1ccc(OC2CCN(C(=O)c3ccc(C(=O)NC4CCN(Cc5ccc(F)cc5)CC4)nc3)CC2)cc1] |
| 184 | 5-(4-(4-methoxybenzoyl)piperidine-1-carbonyl)-N-((cis)-4-(4-methoxyphenoxy)cyclohexyl)picolinamide | 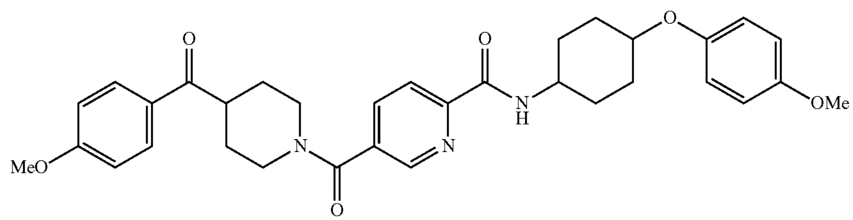 [SMILES: COc1ccc(OC2CCC(NC(=O)c3ccc(C(=O)N4CCC(C(=O)c5ccc(OC)cc5)CC4)cn3)CC2)cc1] |
| 185 | N-((cis)-4-(4-methoxyphenoxy)cyclohexyl)-5-(4-(4-(trifluoromethyl)phenoxy)piperidine-1-carbonyl)picolinamide | 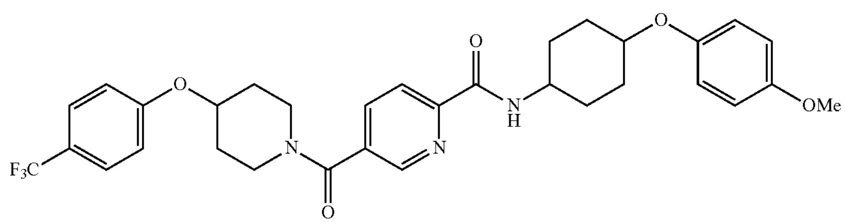 [SMILES: COc1ccc(OC2CCC(NC(=O)c3ccc(C(=O)N4CCC(Oc5ccc(C(F)(F)F)cc5)CC4)cn3)CC2)cc1] |

TABLE 1-continued

| No. | Name | Structure |
|---|---|---|
| 186 | N-((cis)-4-(4-methoxyphenoxy)cyclohexyl)-5-(4-(4-methoxyphenoxy)piperidine-1-carbonyl)picolinamide | 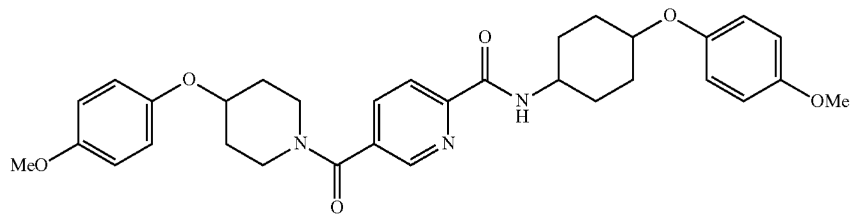 [SMILES: COc1ccc(OC2CCC(NC(=O)c3ccc(C(=O)N4CCC(Oc5ccc(OC)cc5)CC4)cn3)CC2)cc1] |
| 187 | (4-(4-fluorobenzyl)piperazin-1-yl)(6-(4-(4-(trifluoromethyl)phenoxy)piperidin-1-yl)pyridin-3-yl)methanone | 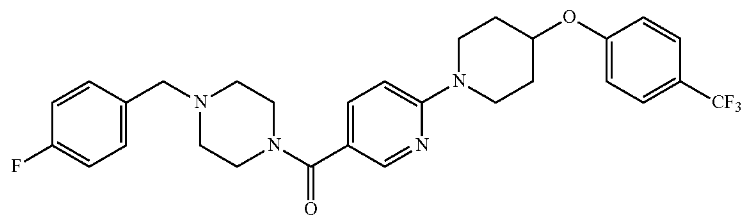 |
| 188 | 4-(1-(5-(4-(4-fluorobenzyl)piperazine-1-carbonyl)pyridin-2-yl)piperidin-4-yloxy)benzonitrile | 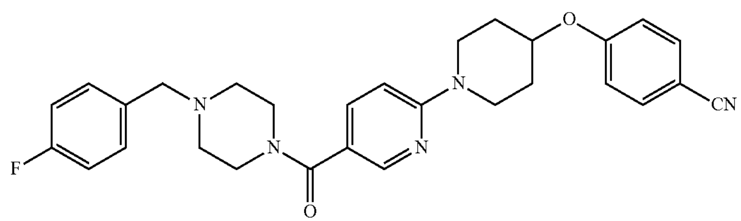 [SMILES: O=C(c1ccc(N2CCC(Oc3ccc(C(F)(F)F)cc3)CC2)nc1)N1CCN(Cc2ccc(F)cc2)CC1] |
| 189 | (4-(4-fluorobenzyl)piperazin-1-yl)(6-(4-(4-methoxybenzoyl)piperidin-1-yl)pyridin-3-yl)methanone | 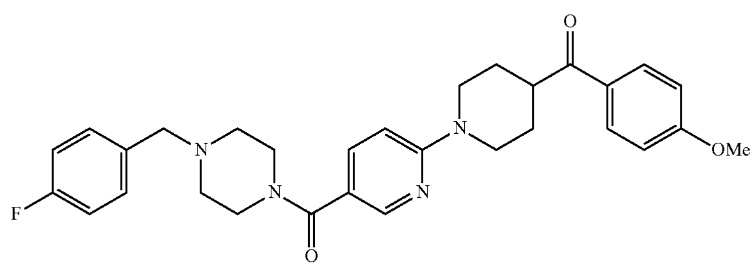 [SMILES: COc1ccc(C(=O)C2CCN(c3ccc(C(=O)N4CCN(Cc5ccc(F)cc5)CC4)cn3)CC2)cc1] |

TABLE 1-continued

| No. | Name | Structure |
|---|---|---|
| 190 | N-((cis)-4-(4-cyanophenoxy)cyclohexyl)-5-(4-(4-(trifluoromethyl)phenoxy)piperidine-1-carbonyl)picolinamide | 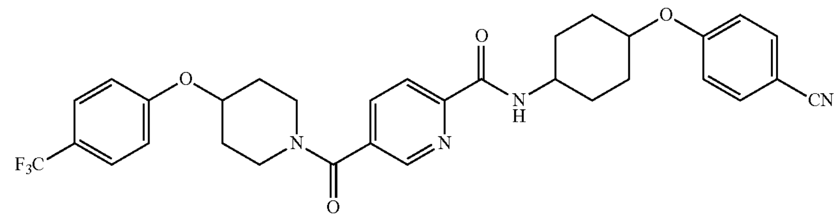 [SMILES: N#Cc1ccc(OC2CCC(NC(=O)c3ccc(C(=O)N4CCC(Oc5ccc(C(F)(F)F)cc5)CC4)cn3)CC2)cc1] |
| 191 | 5-(4-(4-methoxyphenoxy)piperidine-1-carbonyl)-N-((cis)-4-(4-(trifluoromethyl)phenoxy)cyclohexyl)picolinamide | 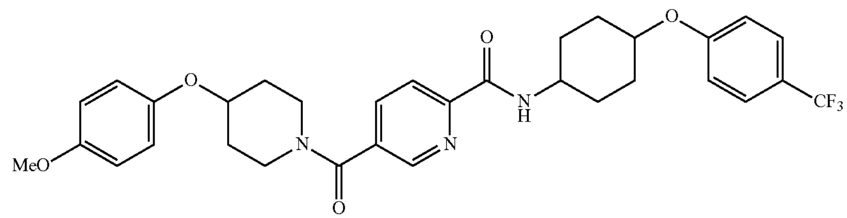 [SMILES: COc1ccc(OC2CCN(C(=O)c3ccc(C(=O)NC4CCC(Oc5ccc(C(F)(F)F)cc5)CC4)nc3)CC2)cc1] |
| 192 | 5-(4-(4-methoxybenzoyl)piperidine-1-carbonyl)-N-((cis)-4-(4-(trifluoromethyl)phenoxy)cyclohexyl)picolinamide | 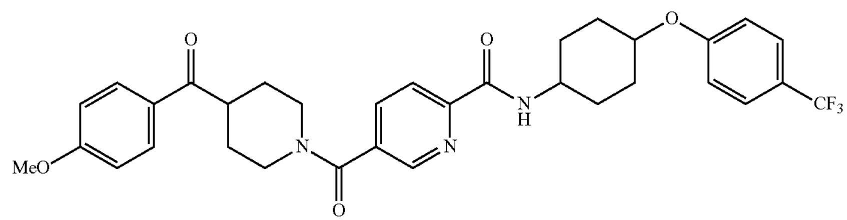 [SMILES: COc1ccc(C(=O)C2CCN(C(=O)c3ccc(C(=O)NC4CCC(Oc5ccc(C(F)(F)F)cc5)CC4)nc3)CC2)cc1] |
| 193 | 5-(4-(4-cyanophenoxy)piperidine-1-carbonyl)-N-((cis)-4-(4-(trifluoromethyl)phenoxy)cyclohexyl)picolinamide | 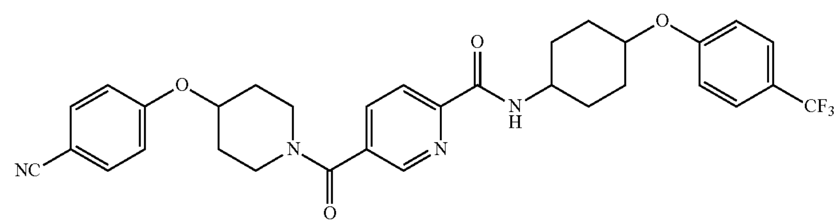 [SMILES: N#Cc1ccc(OC2CCN(C(=O)c3ccc(C(=O)NC4CCC(Oc5ccc(C(F)(F)F)cc5)CC4)nc3)CC2)cc1] |

TABLE 1-continued

| No. | Name | Structure |
|-----|------|-----------|
| 194 | 5-(4-(4-methoxybenzoyl)piperidine-1-carbonyl)-N-(1-(4-(pyrrolidin-1-yl)benzyl)piperidin-4-yl)picolinamide | 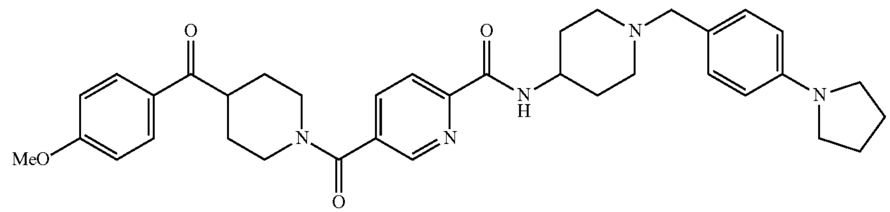 [SMILES: COc1ccc(C(=O)C2CCN(C(=O)c3ccc(C(=O)NC4CCN(Cc5ccc(N6CCCC6)cc5)CC4)nc3)CC2)cc1] |
| 195 | 5-(4-(4-methoxyphenoxy)piperidine-1-carbonyl)-N-(1-(4-(pyrrolidin-1-yl)benzyl)piperidin-4-yl)picolinamide | 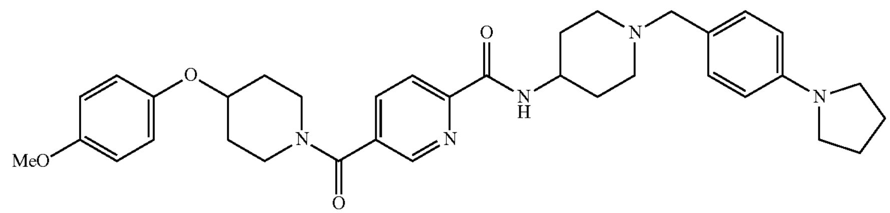 [SMILES: COc1ccc(OC2CCN(C(=O)c3ccc(C(=O)NC4CCN(Cc5ccc(N6CCCC6)cc5)CC4)nc3)CC2)cc1] |
| 196 | 5-(4-(4-fluorophenoxy)piperidine-1-carbonyl)-N-(1-(4-(pyrrolidin-1-yl)benzyl)piperidin-4-yl)picolinamide | 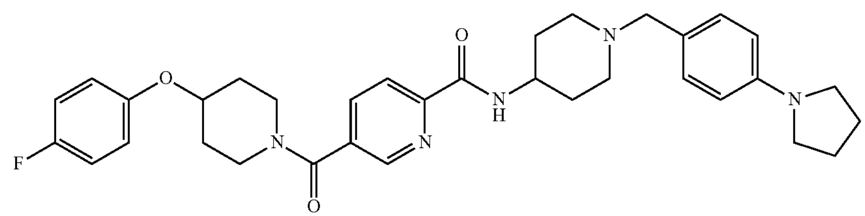 [SMILES: O=C(NC1CCN(Cc2ccc(N3CCCC3)cc2)CC1)c1ccc(C(=O)N2CCC(Oc3ccc(F)cc3)CC2)cn1] |
| 197 | 5-(4-(4-cyanophenoxy)piperidine-1-carbonyl)-N-(1-(4-(pyrrolidin-1-yl)benzyl)piperidin-4-yl)picolinamide | 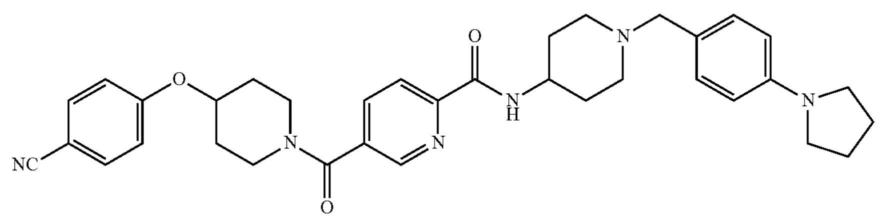 [SMILES: N#Cc1ccc(OC2CCN(C(=O)c3ccc(C(=O)NC4CCN(Cc5ccc(N6CCCC6)cc5)CC4)nc3)CC2)cc1] |

TABLE 1-continued

| No. | Name | Structure |
|-----|------|-----------|
| 198 | N-((cis)-4-(4-cyano-3-fluorophenoxy)cyclohexyl)-5-(4-(4-methoxybenzoyl)piperidine-1-carbonyl)picolinamide | 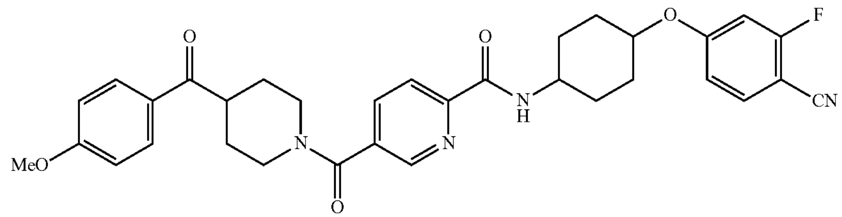 [SMILES: COc1ccc(C(=O)C2CCN(C(=O)c3ccc(C(=O)NC4CCC(Oc5ccc(C#N)c(F)c5)CC4)nc3)CC2)cc1] |
| 199 | N-((cis)-4-(4-cyano-3-fluorophenoxy)cyclohexyl)-5-(4-(4-(trifluoromethyl)phenoxy)piperidine-1-carbonyl)picolinamide | 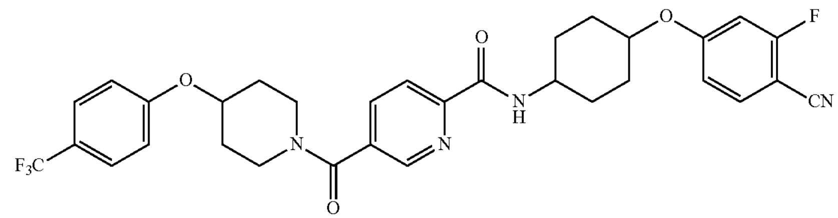 [SMILES: N#Cc1ccc(OC2CCC(NC(=O)c3ccc(C(=O)N4CCC(Oc5ccc(C(F)(F)F)cc5)CC4)cn3)CC2)cc1F] |
| 200 | 5-(4-(4-cyanophenoxy)piperidine-1-carbonyl)-N-(1-(4-fluorobenzyl)piperidin-4-yl)picolinamide | 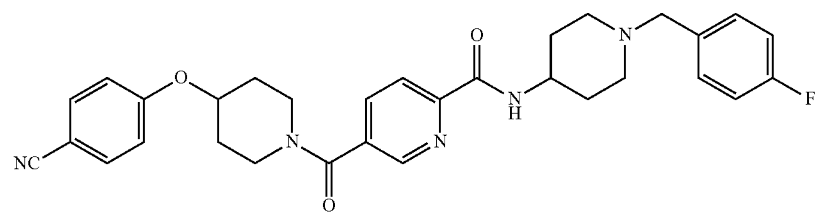 [SMILES: N#Cc1ccc(OC2CCN(C(=O)c3ccc(C(=O)NC4CCN(Cc5ccc(F)cc5)CC4)nc3)CC2)cc1] |
| 201 | N-(1-(4-carbamoylbenzyl)piperidin-4-yl)-5-(4-(4-fluorobenzyl)piperazine-1-carbonyl)picolinamide | 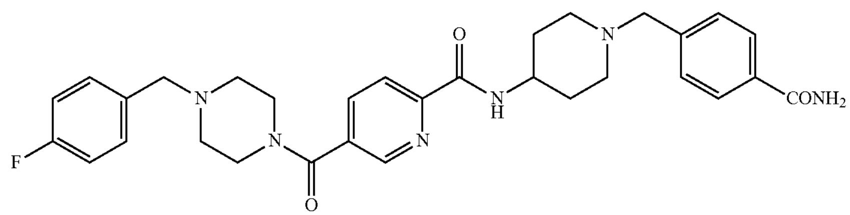 [SMILES: NC(=O)c1ccc(CN2CCC(NC(=O)c3ccc(C(=O)N4CCN(Cc5ccc(F)cc5)CC4)cn3)CC2)cc1] |

TABLE 1-continued

| No. | Name | Structure |
|---|---|---|
| 202 | N-(1-(4-methoxybenzyl)piperidin-4-yl)-5-(4-(4-(methylsulfonyl)phenoxy)piperidine-1-carbonyl)picolinamide | 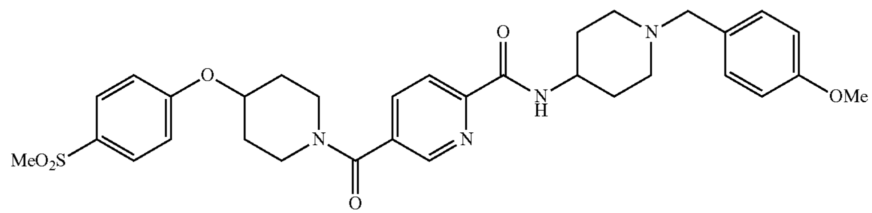 [SMILES: COc1ccc(CN2CCC(NC(=O)c3ccc(C(=O)N4CCC(Oc5ccc(S(C)(=O)=O)cc5)CC4)cn3)CC2)cc1] |
| 203 | N-(1-(3,5-difluorobenzyl)piperidin-4-yl)-5-(4-(4-(methylsulfonyl)phenoxy)piperidine-1-carbonyl)picolinamide | 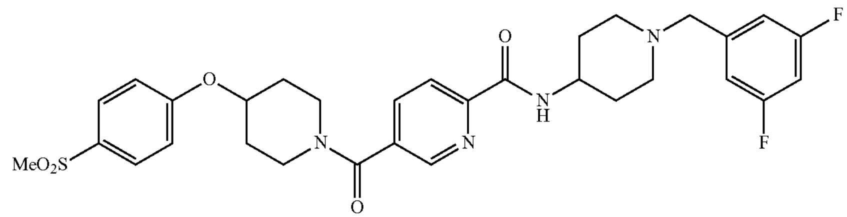 [SMILES: CS(=O)(=O)c1ccc(OC2CCN(C(=O)c3ccc(C(=O)NC4CCN(Cc5cc(F)cc(F)c5)CC4)nc3)CC2)cc1] |
| 204 | N-(6-(4-fluorophenoxy)pyridin-3-yl)-5-(4-(4-methoxybenzoyl)piperidine-1-carbonyl)pyrazine-2-carboxamide | 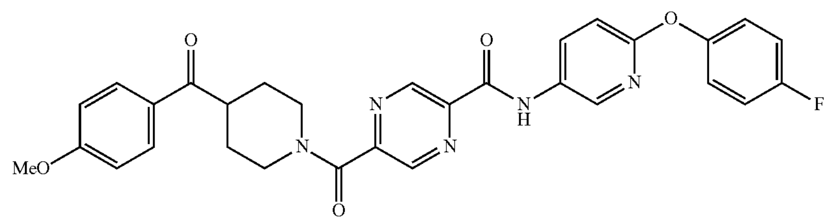 [SMILES: COc1ccc(C(=O)C2CCN(C(=O)c3cnc(C(=O)Nc4ccc(Oc5ccc(F)cc5)nc4)cn3)CC2)cc1] |
| 205 | N-(6-(4-fluorophenoxy)pyridin-3-yl)-5-(4-(4-(trifluoromethyl)phenoxy)piperidine-1-carbonyl)pyrazine-2-carboxamide | 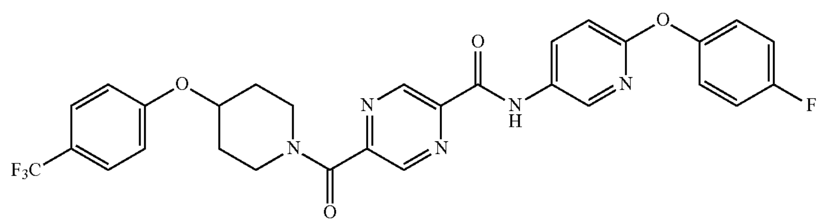 [SMILES: O=C(Nc1ccc(Oc2ccc(F)cc2)nc1)c1cnc(C(=O)N2CCC(Oc3ccc(C(F)(F)F)cc3)CC2)cn1] |

| No. | Name | Structure |
|---|---|---|
| 206 | 5-(4-(2,4-difluorobenzoyl)piperidine-1-carbonyl)-N-(6-(4-fluorophenoxy)pyridin-3-yl)pyrazine-2-carboxamide | 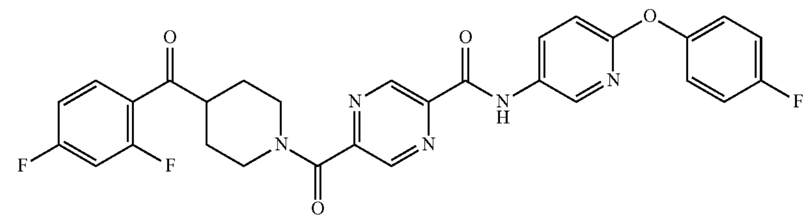 [SMILES: O=C(Nc1ccc(Oc2ccc(F)cc2)nc1)c1cnc(C(=O)N2CCC(C(=O)c3ccc(F)cc3F)CC2)cn1] |
| 207 | N-(6-(4-fluorophenoxy)pyridin-3-yl)-5-(4-(4-(methylsulfonyl)phenoxy)piperidine-1-carbonyl)pyrazine-2-carboxamide | 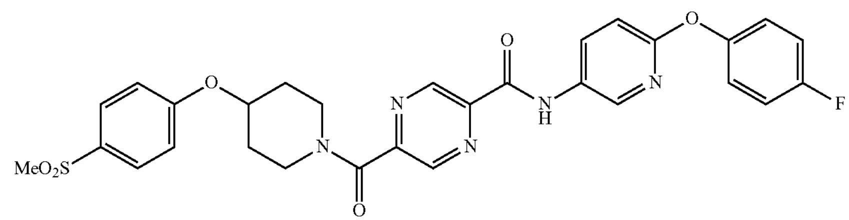 [SMILES: CS(=O)(=O)c1ccc(OC2CCN(C(=O)c3cnc(C(=O)Nc4ccc(Oc5ccc(F)cc5)nc4)cn3)CC2)cc1] |
| 208 | 5-(4-(4-(methylsulfonyl)phenoxy)piperidine-1-carbonyl)-N-(1-(4-(pyrrolidin-1-yl)benzyl)piperidin-4-yl)picolinamide | 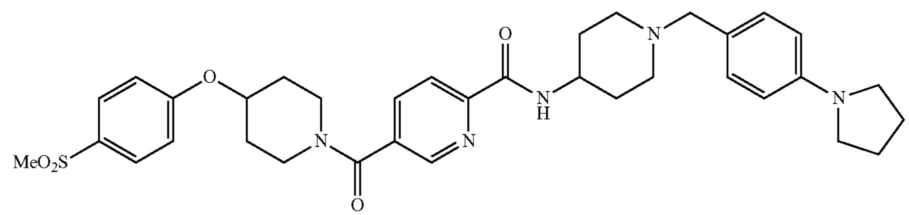 [SMILES: CS(=O)(=O)c1ccc(OC2CCN(C(=O)c3ccc(C(=O)NC4CCN(Cc5ccc(N6CCCC6)cc5)CC4)nc3)CC2)cc1] |
| 209 | N-(1-(4-cyanobenzyl)piperidin-4-yl)-5-(3-(4-cyanophenoxy)azetidine-1-carbonyl)picolinamide | 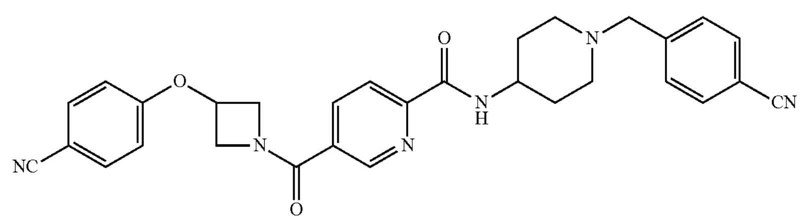 [SMILES: N#Cc1ccc(CN2CCC(NC(=O)c3ccc(C(=O)N4CC(Oc5ccc(C#N)cc5)C4)cn3)CC2)cc1] |

TABLE 1-continued

| No. | Name | Structure |
|---|---|---|
| 210 | 5-(3-(4-cyanophenoxy)azetidine-1-carbonyl)-N-(6-(4-fluorophenoxy)pyridin-3-yl)picolinamide | 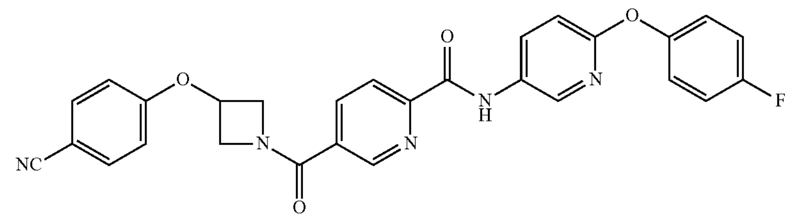 [SMILES: N#Cc1ccc(OC2CN(C(=O)c3ccc(C(=O)Nc4ccc(Oc5ccc(F)cc5)nc4)nc3)C2)cc1] |
| 211 | N-(1-(4-cyanobenzyl)piperidin-4-yl)-5-(4-(4-methoxybenzoyl)piperidine-1-carbonyl)pyrazine-2-carboxamide | 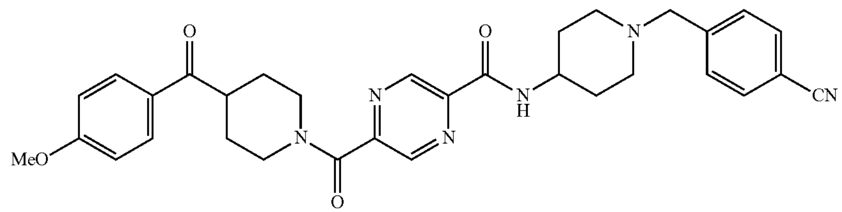 [SMILES: COc1ccc(C(=O)C2CCN(C(=O)c3cnc(C(=O)NC4CCN(Cc5ccc(C#N)cc5)CC4)cn3)CC2)cc1] |
| 212 | N-(1-(4-cyanobenzyl)piperidin-4-yl)-5-(4-(4-(trifluoromethyl)phenoxy)piperidine-1-carbonyl)pyrazine-2-carboxamide | 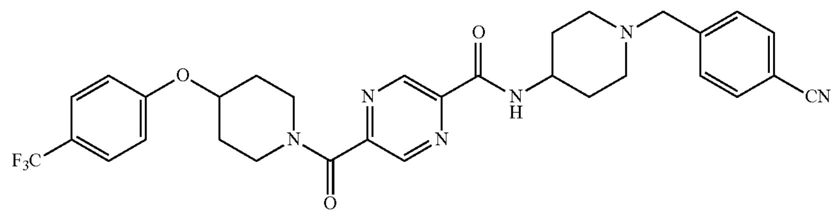 [SMILES: N#Cc1ccc(CN2CCC(NC(=O)c3cnc(C(=O)N4CCC(Oc5ccc(C(F)(F)F)cc5)CC4)cn3)CC2)cc1] |
| 213 | 6-(4-(2,4-difluorobenzoyl)piperidine-1-carbonyl)-N-(1-(4-(methylsulfonyl)benzyl)piperidin-4-yl)nicotinamide | 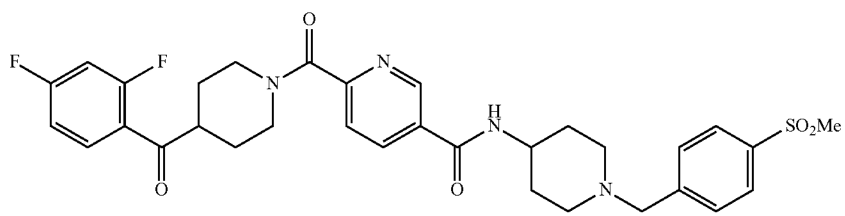 [SMILES: CS(=O)(=O)c1ccc(CN2CCC(NC(=O)c3ccc(C(=O)N4CCC(C(=O)c5ccc(F)cc5F)CC4)nc3)CC2)cc1] |

TABLE 1-continued

| No. | Name | Structure |
|---|---|---|
| 214 | 6-(4-(4-cyanophenoxy)piperidine-1-carbonyl)-N-(1-(4-(methylsulfonyl)benzyl)piperidin-4-yl)nicotinamide | 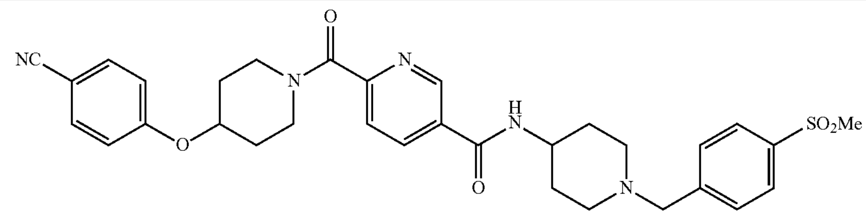 [SMILES: CS(=O)(=O)c1ccc(CN2CCC(NC(=O)c3ccc(C(=O)N4CCC(Oc5ccc(C#N)cc5)CC4)nc3)CC2)cc1] |
| 215 | 6-(4-(4-methoxybenzoyl)piperidine-1-carbonyl)-N-(1-(4-(methylsulfonyl)benzyl)piperidin-4-yl)nicotinamide | 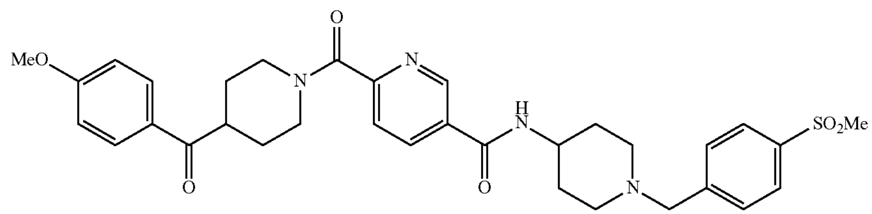 [SMILES: COc1ccc(C(=O)C2CCN(C(=O)c3ccc(C(=O)NC4CCN(Cc5ccc(S(C)(=O)=O)cc5)CC4)cn3)CC2)cc1] |
| 216 | 6-(4-(2,4-difluorobenzoyl)piperidine-1-carbonyl)-N-(1-(4-(methylsulfonamido)benzyl)piperidin-4-yl)nicotinamide | 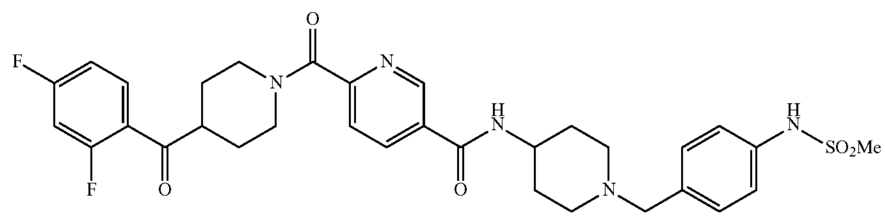 [SMILES: CS(=O)(=O)Nc1ccc(CN2CCC(NC(=O)c3ccc(C(=O)N4CCC(C(=O)c5ccc(F)cc5F)CC4)nc3)CC2)cc1] |
| 217 | 6-(4-(4-cyanophenoxy)piperidine-1-carbonyl)-N-(1-(4-(methylsulfonamido)benzyl)piperidin-4-yl)nicotinamide | 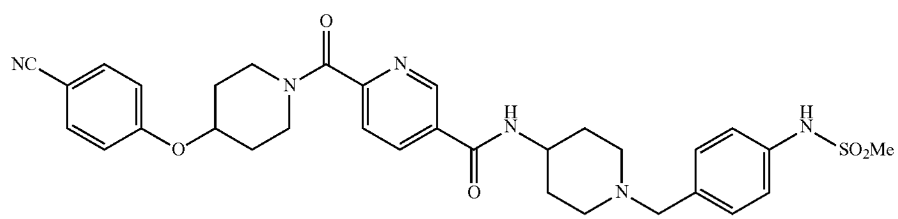 [SMILES: CS(=O)(=O)Nc1ccc(CN2CCC(NC(=O)c3ccc(C(=O)N4CCC(Oc5ccc(C#N)cc5)CC4)nc3)CC2)cc1] |

TABLE 1-continued

| No. | Name | Structure |
|---|---|---|
| 218 | N-(1-(4-cyanobenzyl)piperidin-4-yl)-5-(4-(4-(methylsulfonyl)phenoxy)piperidine-1-carbonyl)pyrazine-2-carboxamide | 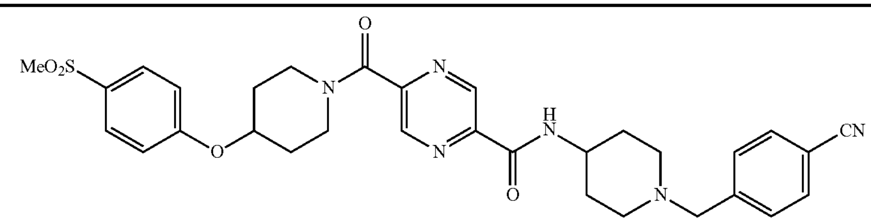 |
| 219 | N-(1-(4-cyanobenzyl)piperidin-4-yl)-5-(4-(4-(pyrrolidin-1-yl)benzoyl)piperidine-1-carbonyl)pyrazine-2-carboxamide | 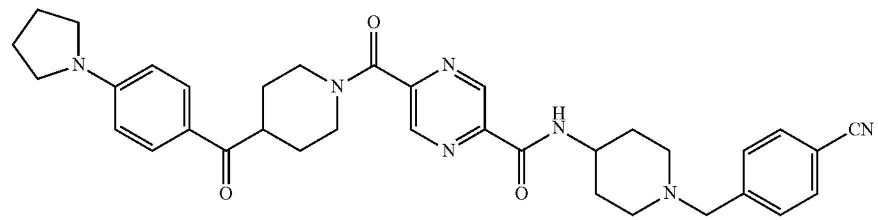 [SMILES: N#Cc1ccc(CN2CCC(NC(=O)c3cnc(C(=O)N4CCC(C(=O)c5ccc(N6CCCC6)cc5)CC4)cn3)CC2)cc1] |
| 220 | N-(1-(4-cyanobenzyl)piperidin-4-yl)-5-(4-(4-(4-methylpiperazin-1-yl)benzoyl)piperidine-1-carbonyl)pyrazine-2-carboxamide | 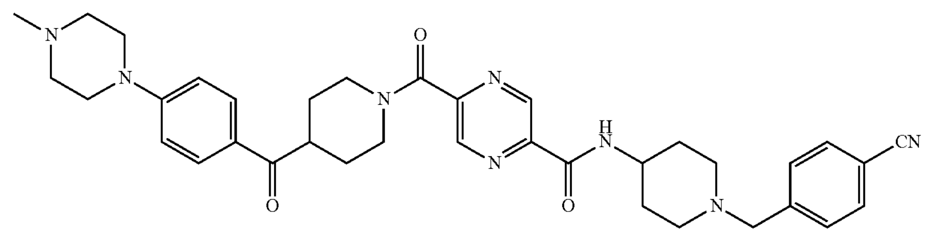 [SMILES: CN1CCN(c2ccc(C(=O)C3CCN(C(=O)c4cnc(C(=O)NC5CCN(Cc6ccc(C#N)cc6)CC5)cn4)CC3)cc2)CC1] |
| 221 | N-(1-(4-cyanobenzyl)piperidin-4-yl)-6-(4-(4-(methylsulfonyl)benzoyl)piperidine-1-carbonyl)nicotinamide | 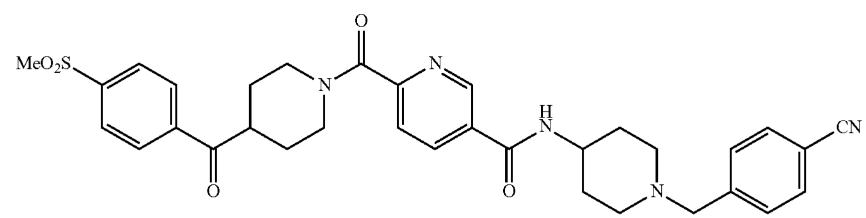 [SMILES: CS(=O)(=O)c1ccc(C(=O)C2CCN(C(=O)c3ccc(C(=O)NC4CCN(Cc5ccc(C#N)cc5)CC4)cn3)CC2)cc1] |

TABLE 1-continued

| No. | Name | Structure |
|---|---|---|
| 222 | N-(1-(4-fluorobenzyl)piperidin-4-yl)-6-(4-(4-(methylsulfonyl)benzoyl)piperidine-1-carbonyl)nicotinamide | 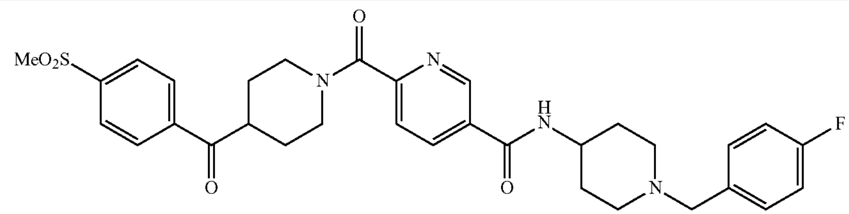 [SMILES: CS(=O)(=O)c1ccc(C(=O)C2CCN(C(=O)c3ccc(C(=O)NC4CCN(Cc5ccc(F)cc5)CC4)cn3)CC2)cc1] |
| 223 | N-(1-(4-methoxybenzyl)piperidin-4-yl)-6-(4-(4-(methylsulfonyl)benzoyl)piperidine-1-carbonyl)nicotinamide | 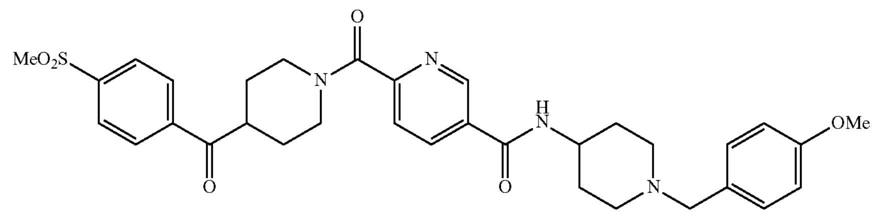 [SMILES: COc1ccc(CN2CCC(NC(=O)c3ccc(C(=O)N4CCC(C(=O)c5ccc(S(C)(=O)=O)cc5)CC4)nc3)CC2)cc1] |
| 224 | N-(6-(4-fluorophenoxy)pyridin-3-yl)-6-(4-(4-(methylsulfonyl)benzoyl)piperidine-1-carbonyl)nicotinamide | 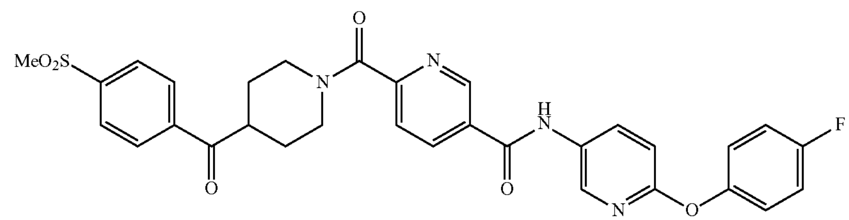 [SMILES: CS(=O)(=O)c1ccc(C(=O)C2CCN(C(=O)c3ccc(C(=O)Nc4ccc(Oc5ccc(F)cc5)nc4)cn3)CC2)cc1] |
| 225 | N-(1-(4-fluorobenzyl)piperidin-4-yl)-5-(4-(4-(methylsulfonyl)benzoyl)piperidine-1-carbonyl)picolinamide | 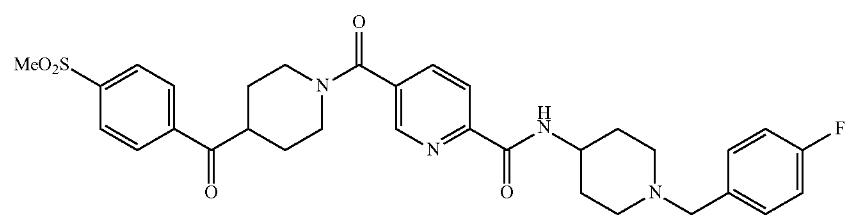 [SMILES: CS(=O)(=O)c1ccc(C(=O)C2CCN(C(=O)c3ccc(C(=O)NC4CCN(Cc5ccc(F)cc5)CC4)nc3)CC2)cc1] |

TABLE 1-continued

| No. | Name | Structure |
|---|---|---|
| 226 | N-(1-(4-fluorobenzyl)piperidin-4-yl)-5-(4-(4-(methylsulfonyl)phenoxy)piperidine-1-carbonyl)picolinamide | 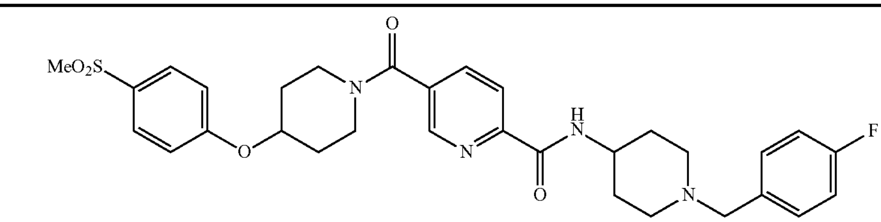 |
| 227 | N-(1-(4-cyanobenzyl)piperidin-4-yl)-5-(4-(4-(methylsulfonyl)phenoxy)piperidine-1-carbonyl)picolinamide | 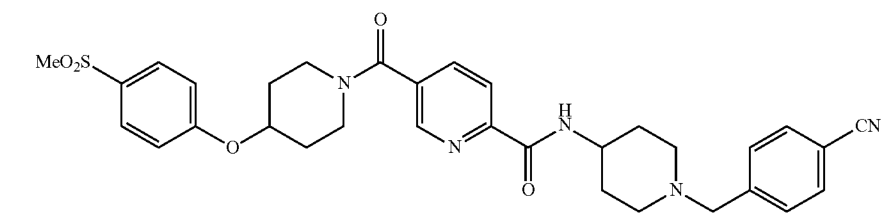 |
| 228 | N-(1-(4-cyanobenzyl)piperidin-4-yl)-5-(4-(4-(methylsulfonyl)benzoyl)piperidine-1-carbonyl)picolinamide | 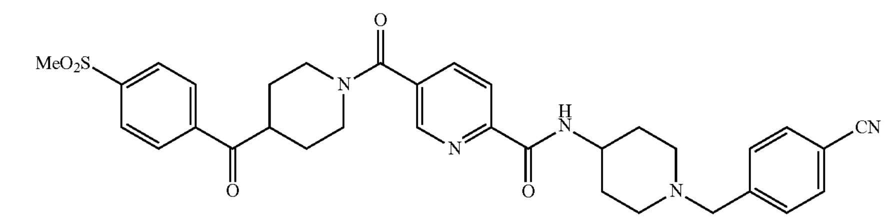 [SMILES: CS(=O)(=O)c1ccc(C(=O)C2CCN(C(=O)c3ccc(C(=O)NC4CCN(Cc5ccc(C#N)cc5)CC4)nc3)CC2)cc1] |
| 229 | 6-(4-(4-(methylsulfonyl)benzoyl)piperidine-1-carbonyl)-N-(1-(4-(pyrrolidin-1-yl)benzyl)piperidin-4-yl)nicotinamide | 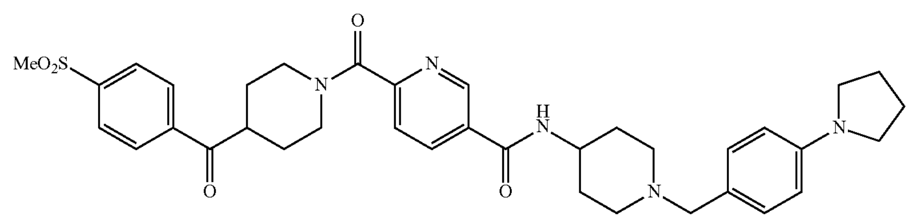 [SMILES: CS(=O)(=O)c1ccc(C(=O)C2CCN(C(=O)c3ccc(C(=O)NC4CCN(Cc5ccc(N6CCCC6)cc5)CC4)cn3)CC2)cc1] |

TABLE 1-continued

| No. | Name | Structure |
|---|---|---|
| 230 | 6-(4-(4-(methylsulfonyl)phenoxy)piperidine-1-carbonyl)-N-(1-(4-(pyrrolidin-1-yl)benzyl)piperidin-4-yl)nicotinamide | 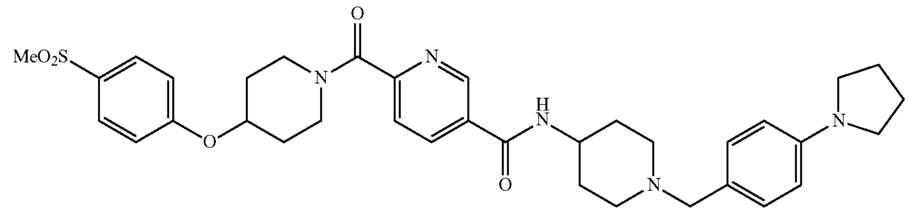 [SMILES: CS(=O)(=O)c1ccc(OC2CCN(C(=O)c3ccc(C(=O)NC4CCN(Cc5ccc(N6CCCC6)cc5)CC4)cn3)CC2)cc1] |
| 231 | N-(6-(4-fluorophenoxy)pyridin-3-yl)-5-(4-(4-(methylsulfonyl)phenoxy)piperidine-1-carbonyl)picolinamide | 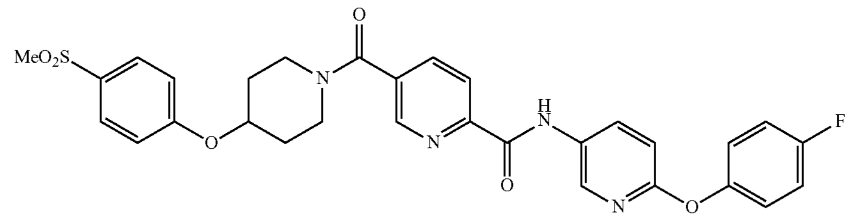 [SMILES: CS(=O)(=O)c1ccc(OC2CCN(C(=O)c3ccc(C(=O)Nc4ccc(Oc5ccc(F)cc5)nc4)nc3)CC2)cc1] |
| 232 | N-(6-(4-fluorophenoxy)pyridin-3-yl)-5-(4-(4-(methylsulfonyl)benzoyl)piperidine-1-carbonyl)picolinamide | 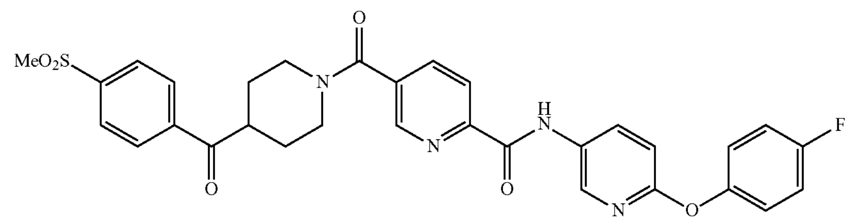 [SMILES: CS(=O)(=O)c1ccc(C(=O)C2CCN(C(=O)c3ccc(C(=O)Nc4ccc(Oc5ccc(F)cc5)nc4)nc3)CC2)cc1] |
| 233 | 5-(4-(4-(methylsulfonyl)benzoyl)piperidine-1-carbonyl)-N-(1-(4-(pyrrolidin-1-yl)benzyl)piperidin-4-yl)picolinamide | 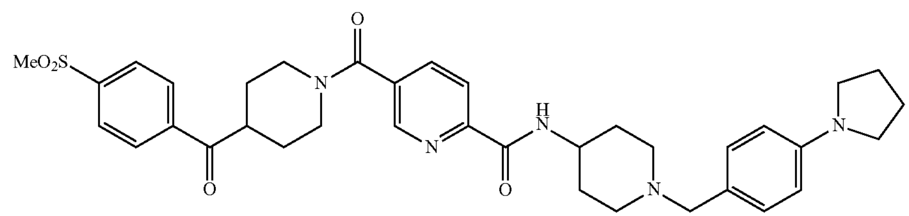 [SMILES: CS(=O)(=O)c1ccc(C(=O)C2CCN(C(=O)c3ccc(C(=O)NC4CCN(Cc5ccc(N6CCCC6)cc5)CC4)nc3)CC2)cc1] |

TABLE 1-continued

| No. | Name | Structure |
|-----|------|-----------|
| 234 | N-(1-(4-methoxybenzyl)piperidin-4-yl)-5-(4-(4-(methylsulfonyl)benzoyl)piperidine-1-carbonyl)picolinamide | 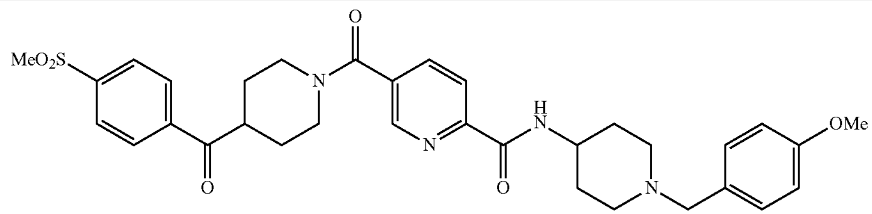 [SMILES: COc1ccc(CN2CCC(NC(=O)c3ccc(C(=O)N4CCC(C(=O)c5ccc(S(C)(=O)=O)cc5)CC4)cn3)CC2)cc1] |
| 235 | N-(6-(4-fluorophenoxy)pyridin-3-yl)-6-(4-(4-(methylsulfonyl)phenoxy)piperidine-1-carbonyl)nicotinamide | 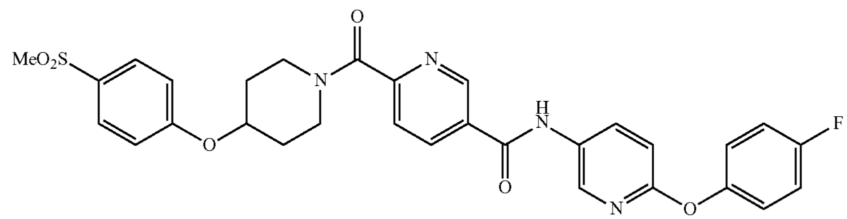 [SMILES: CS(=O)(=O)c1ccc(OC2CCN(C(=O)c3ccc(C(=O)Nc4ccc(Oc5ccc(F)cc5)nc4)cn3)CC2)cc1] |
| 236 | N-(1-(3,5-difluorobenzyl)piperidin-4-yl)-6-(4-(4-(methylsulfonyl)phenoxy)piperidine-1-carbonyl)nicotinamide | 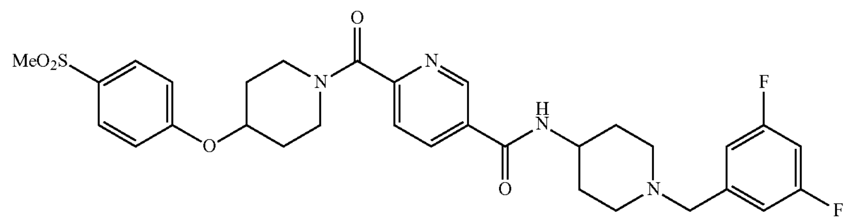 [SMILES: CS(=O)(=O)c1ccc(OC2CCN(C(=O)c3ccc(C(=O)NC4CCN(Cc5cc(F)cc(F)c5)CC4)cn3)CC2)cc1] |
| 237 | N-(1-(4-methoxybenzyl)piperidin-4-yl)-6-(4-(4-(methylsulfonyl)phenoxy)piperidine-1-carbonyl)nicotinamide | 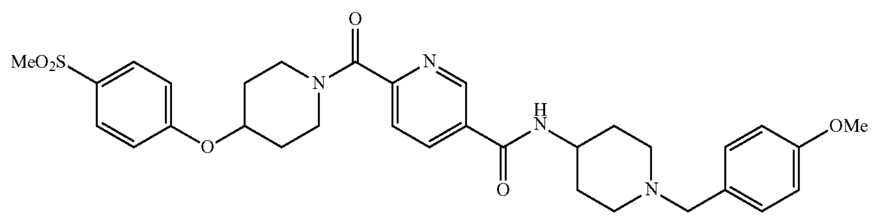 [SMILES: COc1ccc(CN2CCC(NC(=O)c3ccc(C(=O)N4CCC(Oc5ccc(S(C)(=O)=O)cc5)CC4)nc3)CC2)cc1] |

TABLE 1-continued

| No. | Name | Structure |
|---|---|---|
| 238 | N-(1-(3-methoxybenzyl)piperidin-4-yl)-6-(4-(4-(methylsulfonyl)phenoxy)piperidine-1-carbonyl)nicotinamide | 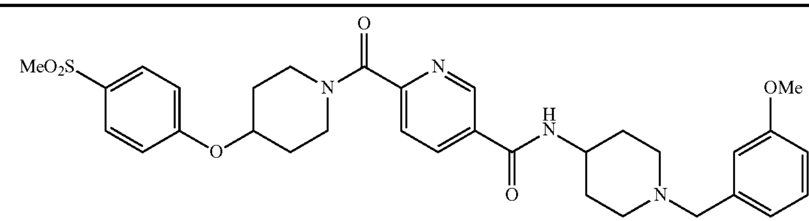 |
| 239 | 6-(4-(4-(methylsulfonyl)phenoxy)piperidine-1-carbonyl)-N-(1-(3-(trifluoromethoxy)benzyl)piperidin-4-yl)nicotinamide | 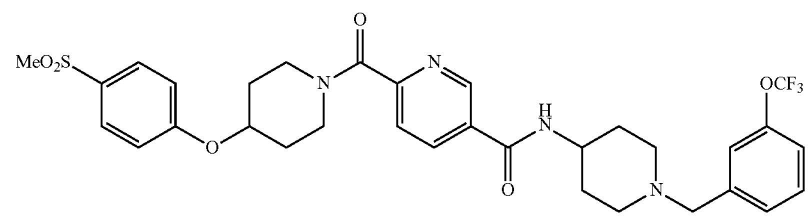 [SMILES: CS(=O)(=O)c1ccc(OC2CCN(C(=O)c3ccc(C(=O)NC4CCN(Cc5cccc(OC(F)(F)F)c5)CC4)cn3)CC2)cc1] |
| 240 | 6-(4-(4-azidobenzoyl)piperidine-1-carbonyl)-N-(1-(4-cyanobenzyl)piperidin-4-yl)nicotinamide | 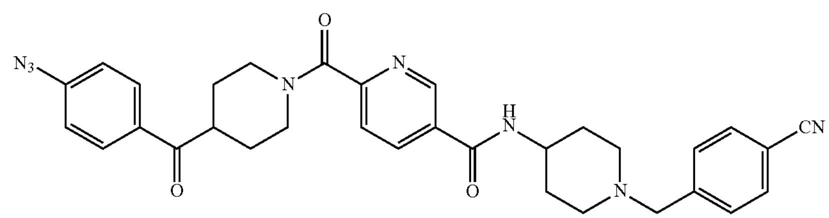 [SMILES: N#Cc1ccc(CN2CCC(NC(=O)c3ccc(C(=O)N4CCC(C(=O)c5ccc(N=[N+]=[N-])cc5)CC4)nc3)CC2)cc1] |
| 241 | N-(1-(3-methoxybenzyl)piperidin-4-yl)-5-(4-(4-(methylsulfonyl)phenoxy)piperidine-1-carbonyl)picolinamide | 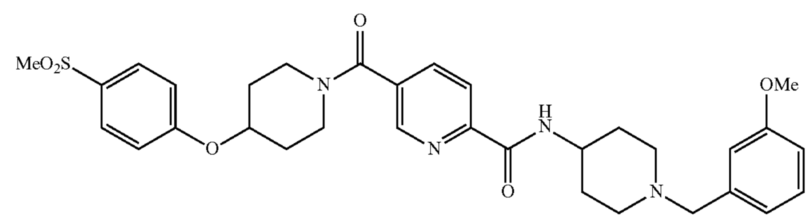 [SMILES: COc1cccc(CN2CCC(NC(=O)c3ccc(C(=O)N4CCC(Oc5ccc(S(C)(=O)=O)cc5)CC4)cn3)CC2)c1] |

TABLE 1-continued

| No. | Name | Structure |
|---|---|---|
| 242 | 5-(4-(4-(methylsulfonyl)phenoxy)piperidine-1-carbonyl)-N-(1-(3-(trifluoromethoxy)benzyl)piperidin-4-yl)picolinamide | 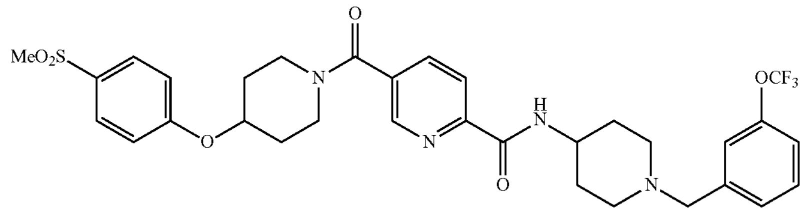 [SMILES: CS(=O)(=O)c1ccc(OC2CCN(C(=O)c3ccc(C(=O)NC4CCN(Cc5cccc(OC(F)(F)F)c5)CC4)nc3)CC2)cc1] |
| 243 | N-(1-(4-cyanobenzyl)piperidin-4-yl)-6-(4-(4-(4-methylpiperazin-1-yl)benzoyl)piperidine-1-carbonyl)nicotinamide | 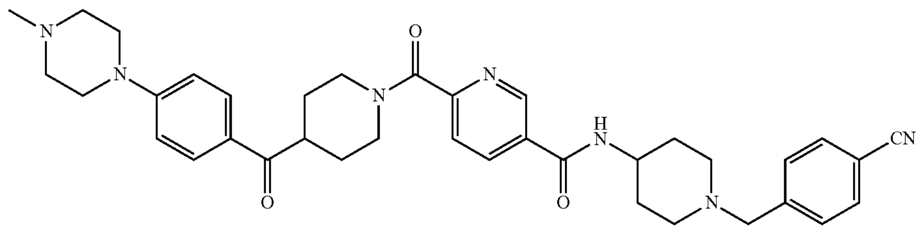 [SMILES: CN1CCN(c2ccc(C(=O)C3CCN(C(=O)c4ccc(C(=O)NC5CCN(Cc6ccc(C#N)cc6)CC5)cn4)CC3)cc2)CC1] |
| 244 | 6-(4-(4-(4-methylpiperazin-1-yl)benzoyl)piperidine-1-carbonyl)-N-(1-(4-(trifluoromethoxy)benzyl)piperidin-4-yl)nicotinamide | 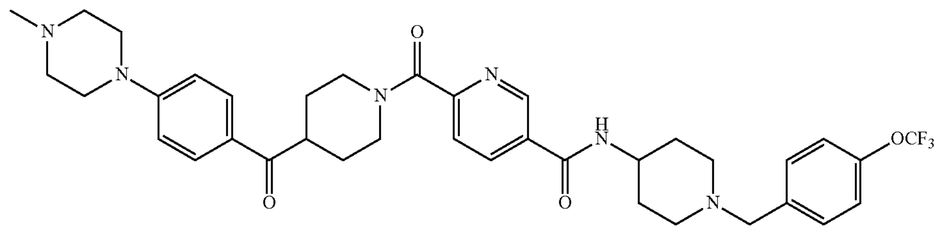 [SMILES: CN1CCN(c2ccc(C(=O)C3CCN(C(=O)c4ccc(C(=O)NC5CCN(Cc6ccc(OC(F)(F)F)cc6)CC5)cn4)CC3)cc2)CC1] |
| 245 | N-(6-(4-fluorophenoxy)pyridin-3-yl)-6-(4-(4-(4-methylpiperazin-1-yl)benzoyl)piperidine-1-carbonyl)nicotinamide | 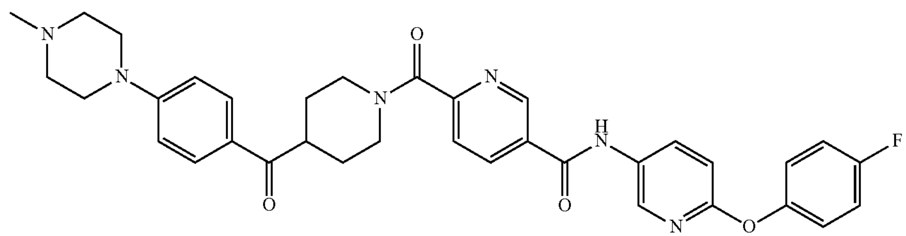 [SMILES: CN1CCN(c2ccc(C(=O)C3CCN(C(=O)c4ccc(C(=O)Nc5ccc(Oc6ccc(F)cc6)nc5)cn4)CC3)cc2)CC1] |

TABLE 1-continued

| No. | Name | Structure |
|---|---|---|
| 246 | N-(1-(4-cyanobenzyl)piperidin-4-yl)-6-(4-(4-(cyclopropyl)sulfonyl)phenoxy)piperidine-1-carbonyl)nicotinamide | 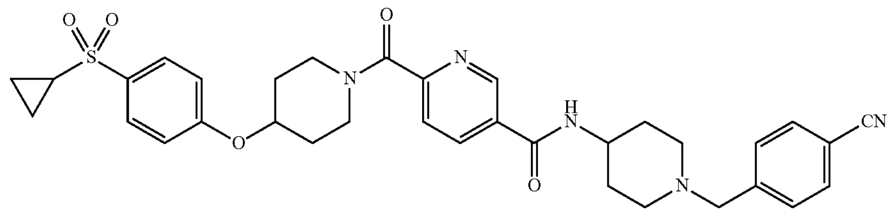 [SMILES: N#Cc1ccc(CN2CCC(NC(=O)c3ccc(C(=O)N4CCC(Oc5ccc(S(=O)(=O)C6CC6)cc5)CC4)nc3)CC2)cc1] |
| 247 | 6-(4-(4-(cyclopropylsulfonyl)phenoxy)piperidine-1-carbonyl)-N-(6-(4-fluorophenoxy)pyridin-3-yl)nicotinamide | 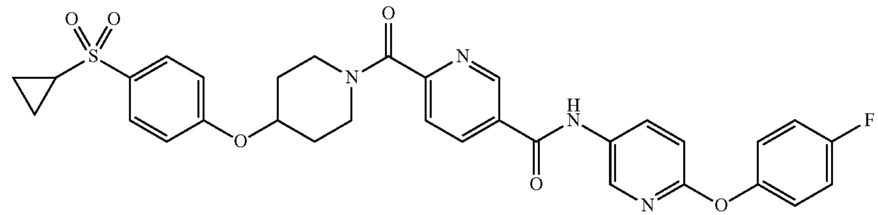 [SMILES: O=C(Nc1ccc(Oc2ccc(F)cc2)nc1)c1ccc(C(=O)N2CCC(Oc3ccc(S(=O)(=O)C4CC4)cc3)CC2)nc1] |
| 248 | 6-(4-(4-(cyclopropylsulfonyl)phenoxy)piperidine-1-carbonyl)-N-(1-(4-(pyrrolidin-1-yl)benzyl)piperidin-4-yl)nicotinamide | 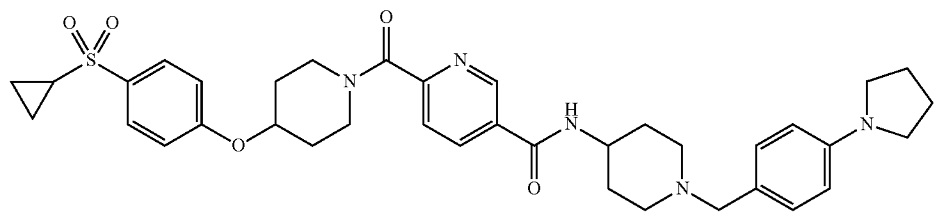 [SMILES: O=C(NC1CCN(Cc2ccc(N3CCCC3)cc2)CC1)c1ccc(C(=O)N2CCC(Oc3ccc(S(=O)(=O)C4CC4)cc3)CC2)nc1] |
| 249 | 6-(4-(4-(cyclopropylsulfonyl)phenoxy)piperidine-1-carbonyl)-N-(1-(4-(trifluoromethoxy)benzyl)piperidin-4-yl)nicotinamide | 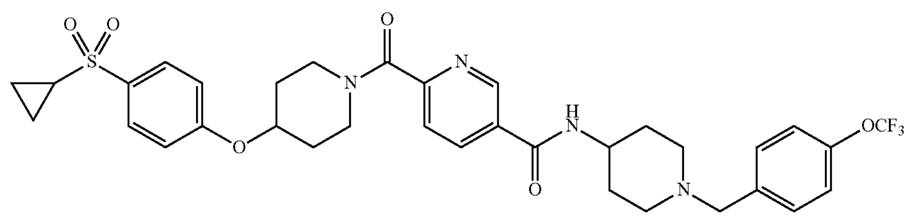 [SMILES: O=C(NC1CCN(Cc2ccc(OC(F)(F)F)cc2)CC1)c1ccc(C(=O)N2CCC(Oc3ccc(S(=O)(=O)C4CC4)cc3)CC2)nc1] |

TABLE 1-continued

| No. | Name | Structure |
|---|---|---|
| 250 | N-(1-(4-cyanobenzyl)piperidin-4-yl)-5-(4-(4-(methylsulfonyl)phenyl)piperazine-1-carbonyl)picolinamide | 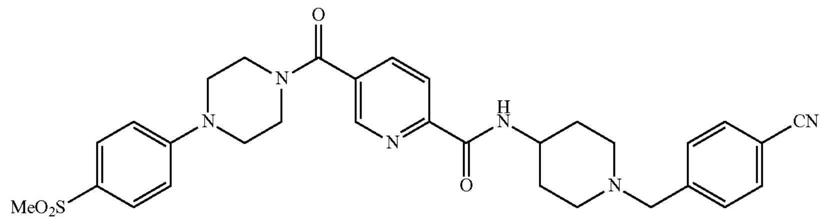 [SMILES: CS(=O)(=O)c1ccc(N2CCN(C(=O)c3ccc(C(=O)NC4CCN(Cc5ccc(C#N)cc5)CC4)nc3)CC2)cc1] |
| 251 | N-(1-(4-cyanobenzyl)piperidin-4-yl)-5-(4-(4-(isopropylsulfonyl)phenyl)piperazine-1-carbonyl)picolinamide | 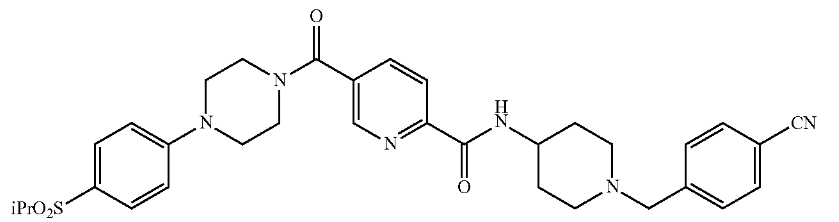 |
| 252 | N-((trans)-1-(4-cyanobenzyl)-3-fluoropiperidin-4-yl)-5-(4-(4-(methylsulfonyl)benzoyl)piperidine-1-carbonyl)picolinamide | 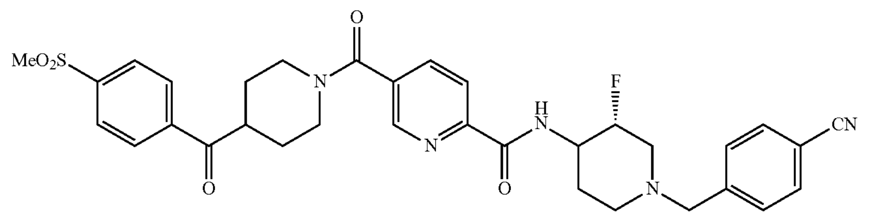 [SMILES: CS(=O)(=O)c1ccc(C(=O)C2CCN(C(=O)c3ccc(C(=O)NC4CCN(Cc5ccc(C#N)cc5)C[C@H]4F)nc3)CC2)cc1] |
| 253 | N-((trans)-3-fluoro-1-(4-(trifluoromethoxy)benzyl)piperidin-4-yl)-5-(4-(4-(methylsulfonyl)benzoyl)piperidine-1-carbonyl)picolinamide | 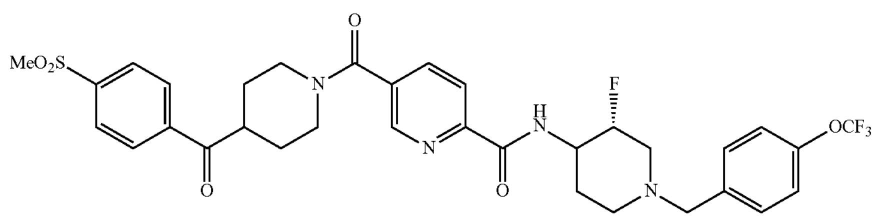 [SMILES: CS(=O)(=O)c1ccc(C(=O)C2CCN(C(=O)c3ccc(C(=O)NC4CCN(Cc5ccc(OC(F)(F)F)cc5)C[C@H]4F)nc3)CC2)cc1] |

TABLE 1-continued

| No. | Name | Structure |
|---|---|---|
| 254 | N-((trans)-1-(4-cyanobenzyl)-3-fluoropiperidin-4-yl)-5-(4-(4-(methylsulfonyl)phenoxy)piperidine-1-carbonyl)picolinamide | 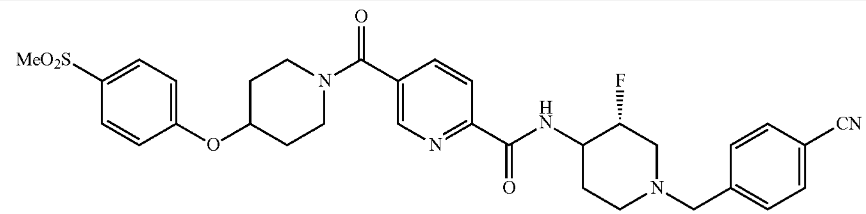 [SMILES: CS(=O)(=O)c1ccc(OC2CCN(C(=O)c3ccc(C(=O)NC4CCN(Cc5ccc(C#N)cc5)C[C@H]4F)nc3)CC2)cc1] |
| 255 | N-((trans)-3-fluoro-1-(4-(trifluoromethoxy)benzyl)piperidin-4-yl)-5-(4-(4-(methylsulfonyl)phenoxy)piperidine-1-carbonyl)picolinamide | 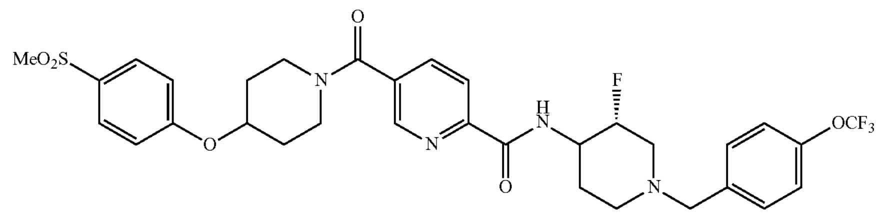 [SMILES: CS(=O)(=O)c1ccc(OC2CCN(C(=O)c3ccc(C(=O)NC4CCN(Cc5ccc(OC(F)(F)F)cc5)C[C@H]4F)nc3)CC2)cc1] |
| 256 | N-(1-(4-cyanobenzyl)piperidin-4-yl)-5-(4-(4-(cyclopropylsulfonyl)phenyl)piperazine-1-carbonyl)picolinamide | 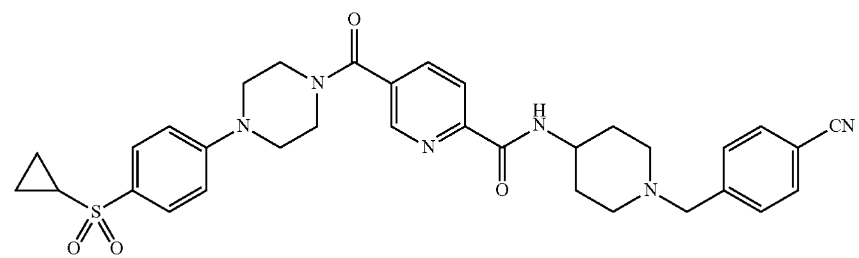 [SMILES: N#Cc1ccc(CN2CCC(NC(=O)c3ccc(C(=O)N4CCN(c5ccc(S(=O)(=O)C6CC6)cc5)CC4)cn3)CC2)cc1] |
| 257 | N-(1-(4-cyanobenzyl)piperidin-4-yl)-5-(4-(4-(trifluoromethylsulfonyl)phenyl)piperazine-1-carbonyl)picolinamide | 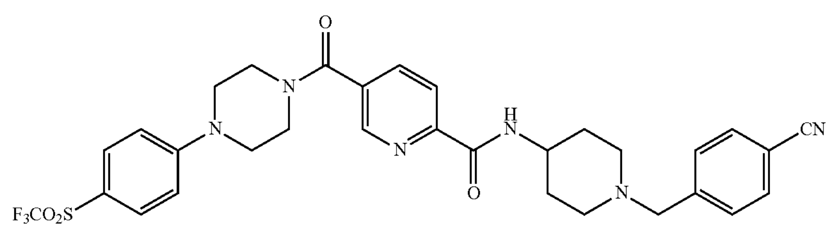 |

TABLE 1-continued

| No. | Name | Structure |
|---|---|---|
| 258 | N-(1-(4-cyanobenzyl)piperidin-4-yl)-5-(4-(4-(cyclopropanecarbonyl)phenyl)piperazine-1-carbonyl)picolinamide | 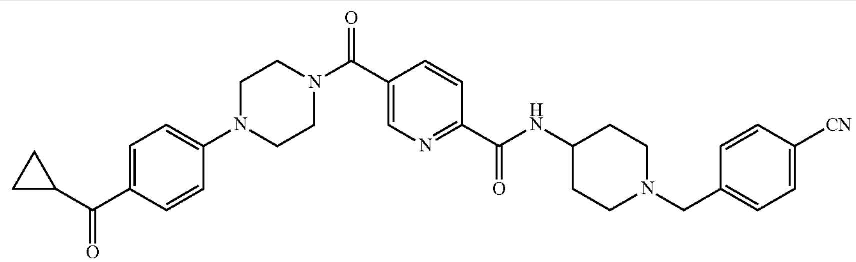 [SMILES: N#Cc1ccc(CN2CCC(NC(=O)c3ccc(C(=O)N4CCN(c5ccc(C(=O)C6CC6)cc5)CC4)cn3)CC2)cc1] |
| 259 | N-(6-(4-acetylphenoxy)pyridin-3-yl)-5-(4-(4-(methylsulfonyl)phenoxy)piperidine-1-carbonyl)picolinamide | 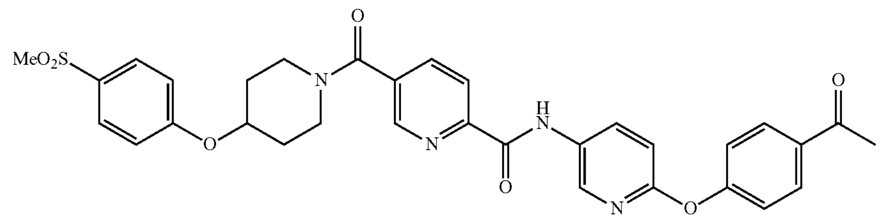 [SMILES: CC(=O)c1ccc(Oc2ccc(NC(=O)c3ccc(C(=O)N4CCC(Oc5ccc(S(C)(=O)=O)cc5)CC4)cn3)cn2)cc1] |
| 260 | N-(1-(4-cyanobenzyl)piperidin-4-yl)-5-(4-(4-(ethylsulfonyl)benzoyl)piperidine-1-carbonyl)picolinamide | 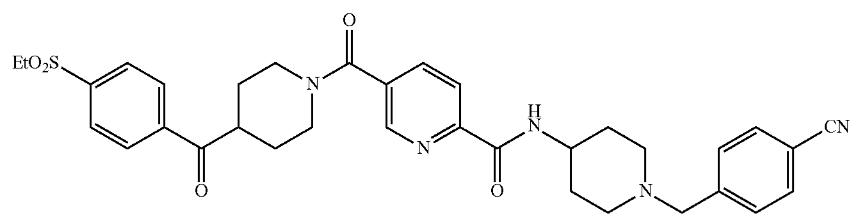 |
| 261 | N-(6-(4-fluorophenylsulfonyl)pyridin-3-yl)-5-(4-(4-(methylsulfonyl)phenoxy)piperidine-1-carbonyl)picolinamide | 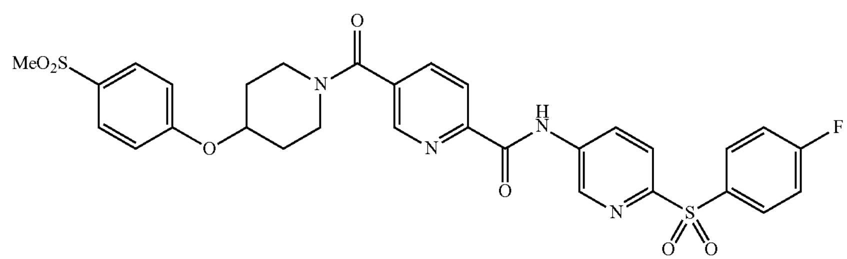 [SMILES: CS(=O)(=O)c1ccc(OC2CCN(C(=O)c3ccc(C(=O)Nc4ccc(S(=O)(=O)c5ccc(F)cc5)nc4)nc3)CC2)cc1] |

TABLE 1-continued

| No. | Name | Structure |
|---|---|---|
| 262 | N-(1-(4-cyanobenzyl)piperidin-4-yl)-5-(4-(4-fluorophenylsulfonyl)piperidine-1-carbonyl)picolinamide | 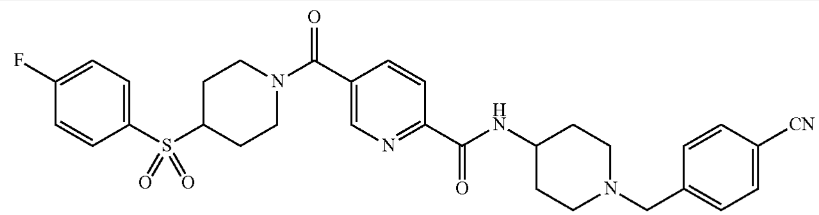 [SMILES: N#Cc1ccc(CN2CCC(NC(=O)c3ccc(C(=O)N4CCC(S(=O)(=O)c5ccc(F)cc5)CC4)cn3)CC2)cc1] |
| 263 | N-(1-(4-cyanobenzyl)piperidin-4-yl)-5-(4-(4-(2,2,2-trifluoroacetyl)phenyl)piperazine-1-carbonyl)picolinamide | 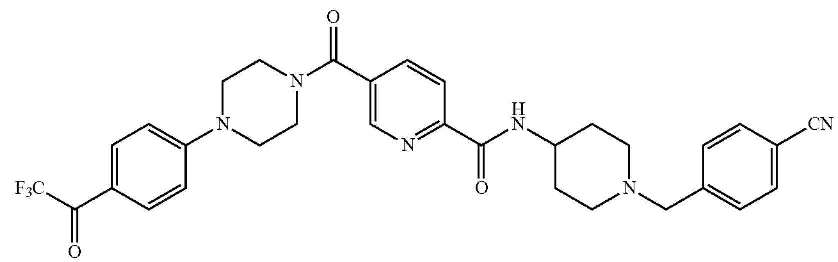 [SMILES: N#Cc1ccc(CN2CCC(NC(=O)c3ccc(C(=O)N4CCN(c5ccc(C(=O)C(F)(F)F)cc5)CC4)cn3)CC2)cc1] |
| 264 | N2,N5-bis(1-benzylpiperidin-4-yl)pyridine-2,5-dicarboxamide | 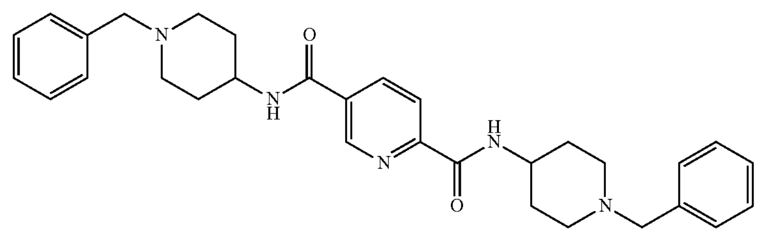 [SMILES: O=C(NC1CCN(Cc2ccccc2)CC1)c1ccc(C(=O)NC2CCN(Cc3ccccc3)CC2)nc1] |
| 265 | N-(1-(4-cyanobenzyl)piperidin-4-yl)-5-(3-(4-cyanophenoxy)piperidin-1-yl)picolinamide | 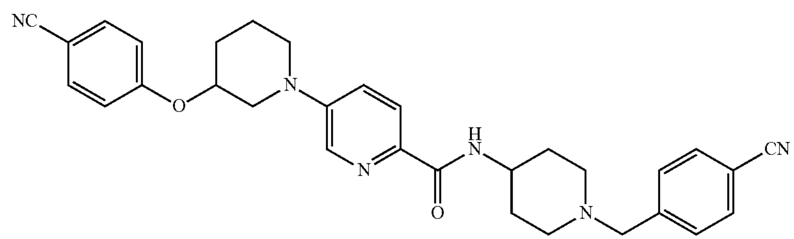 [SMILES: N#Cc1ccc(CN2CCC(NC(=O)c3ccc(N4CCCC(Oc5ccc(C#N)cc5)C4)cn3)CC2)cc1] |

TABLE 1-continued

| No. | Name | Structure |
|---|---|---|
| 266 | 5-(4-(4-chlorobenzoyl)piperidin-1-yl)-N-(1-(4-cyanobenzyl)piperidin-4-yl)picolinamide | 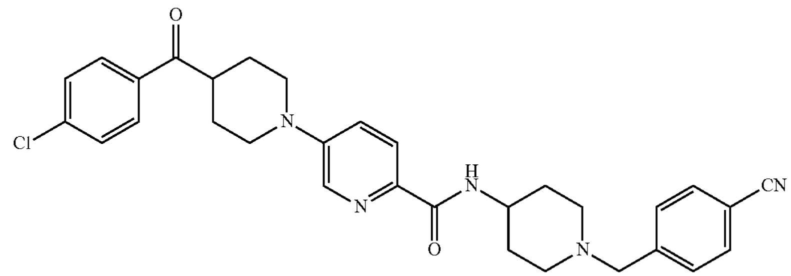 [SMILES: N#Cc1ccc(CN2CCC(NC(=O)c3ccc(N4CCC(C(=O)c5ccc(Cl)cc5)CC4)cn3)CC2)cc1] |
| 267 | N-(1-(4-cyanobenzyl)piperidin-4-yl)-5-(1-(4-cyanophenyl)piperidin-4-ylamino)picolinamide | 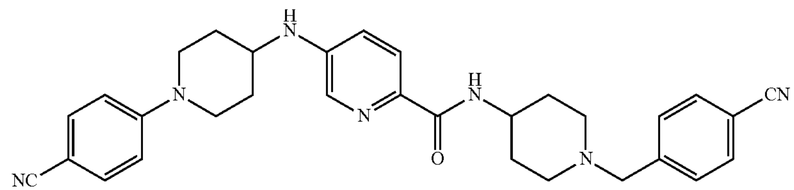 [SMILES: N#Cc1ccc(CN2CCC(NC(=O)c3ccc(NC4CCN(c5ccc(C#N)cc5)CC4)cn3)CC2)cc1] |
| 268 | N-(1-(4-cyanobenzyl)piperidin-4-yl)-5-(4-(2-(4-fluorophenyl)propan-2-yl)piperazine-1-carbonyl)picolinamide | 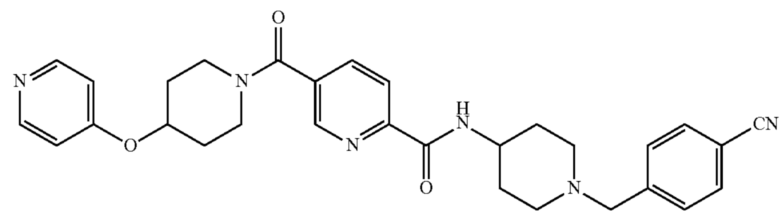 [SMILES: N#Cc1ccc(CN2CCC(NC(=O)c3ccc(C(=O)N4CCC(Oc5ccncc5)CC4)cn3)CC2)cc1] |
| 269 | N-(1-(4-cyanobenzyl)piperidin-4-yl)-5-(4-(pyridin-4-yloxy)piperidine-1-carbonyl)picolinamide | 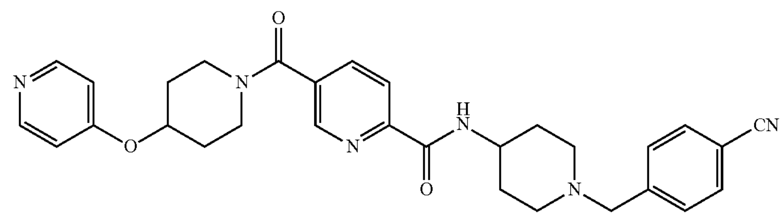 [SMILES: N#Cc1ccc(CN2CCC(NC(=O)c3ccc(C(=O)N4CCC(Oc5ccncc5)CC4)cn3)CC2)cc1] |

TABLE 1-continued

| No. | Name | Structure |
|-----|------|-----------|
| 270 | (S)-N-(1-(4-cyanobenzyl)piperidin-4-yl)-5-(3-(4-fluorophenoxy)pyrrolidine-1-carbonyl)picolinamide | 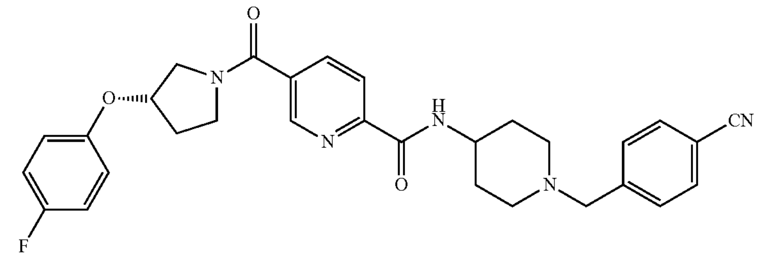 |
| 271 | N-(1-(4-cyanobenzyl)piperidin-4-yl)-5-(4-(2,4-difluorobenzoyl)piperidine-1-carbonyl)picolinamide | 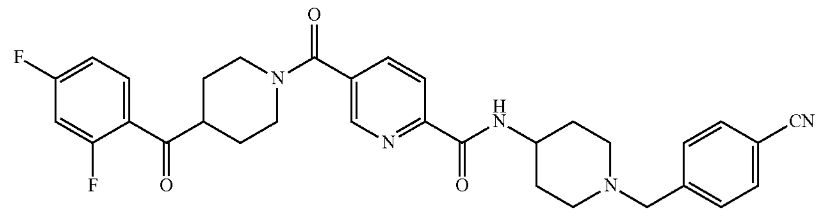 [SMILES: N#Cc1ccc(CN2CCC(NC(=O)c3ccc(C(=O)N4CCC(C(=O)c5ccc(F)cc5F)CC4)cn3)CC2)cc1] |
| 272 | 5-(4-(4-fluorobenzoyl)piperidine-1-carbonyl)-N-(6-(4-fluorophenoxy)pyridin-3-yl)picolinamide | 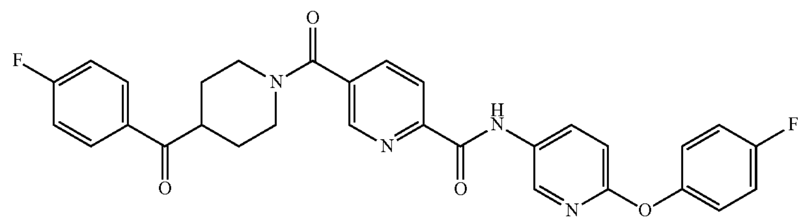 [SMILES: O=C(Nc1ccc(Oc2ccc(F)cc2)nc1)c1ccc(C(=O)N2CCC(C(=O)c3ccc(F)cc3)CC2)cn1] |
| 273 | 5-(4-(4-fluorophenoxy)piperidine-1-carbonyl)-N-(6-(4-fluorophenoxy)pyridin-3-yl)picolinamide | 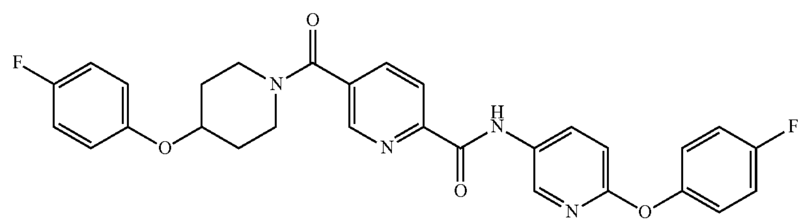 [SMILES: O=C(Nc1ccc(Oc2ccc(F)cc2)nc1)c1ccc(C(=O)N2CCC(Oc3ccc(F)cc3)CC2)cn1] |

TABLE 1-continued

| No. | Name | Structure |
|---|---|---|
| 274 | N-(1-(4-cyanobenzyl)piperidin-4-yl)-5-(3-(4-methoxyphenoxy)piperidine-1-carbonyl)picolinamide | 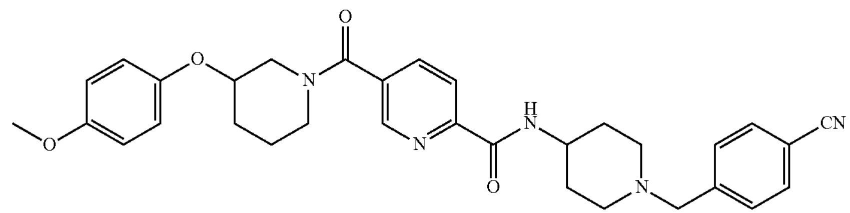 [SMILES: COc1ccc(OC2CCCN(C(=O)c3ccc(C(=O)NC4CCN(Cc5ccc(C#N)cc5)CC4)nc3)C2)cc1] |
| 275 | N-(1-(4-cyanobenzyl)piperidin-4-yl)-5-(1-(4-methoxyphenyl)piperidin-4-ylamino)picolinamide | 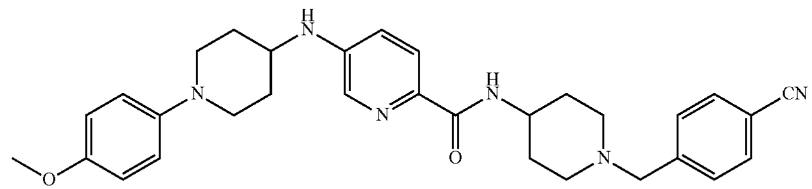 [SMILES: COc1ccc(N2CCC(Nc3ccc(C(=O)NC4CCN(Cc5ccc(C#N)cc5)CC4)nc3)CC2)cc1] |
| 276 | N-(1-(4-cyanobenzyl)piperidin-4-yl)-5-(1-(4-fluorophenyl)piperidin-4-ylamino)picolinamide | 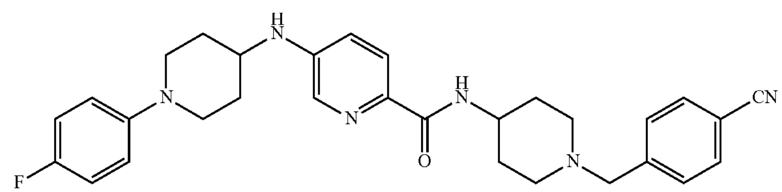 [SMILES: N#Cc1ccc(CN2CCC(NC(=O)c3ccc(NC4CCN(c5ccc(F)cc5)CC4)cn3)CC2)cc1] |
| 277 | N-(1-(4-cyanobenzyl)piperidin-4-yl)-5-(3-(3-methoxyphenoxy)piperidine-1-carbonyl)picolinamide | 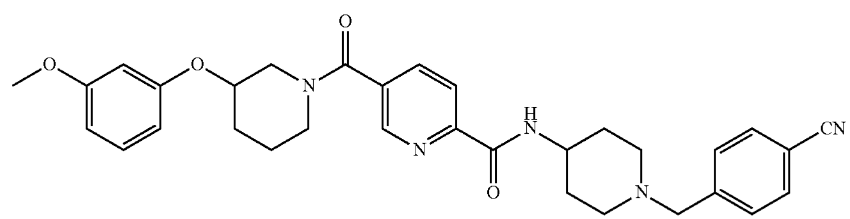 [SMILES: COc1cccc(OC2CCCN(C(=O)c3ccc(C(=O)NC4CCN(Cc5ccc(C#N)cc5)CC4)nc3)C2)c1] |

TABLE 1-continued

| No. | Name | Structure |
|---|---|---|
| 278 | (R)-N-(1-(4-cyanobenzyl)piperidin-4-yl)-5-(3-(4-fluorophenoxy)pyrrolidine-1-carbonyl)picolinamide | 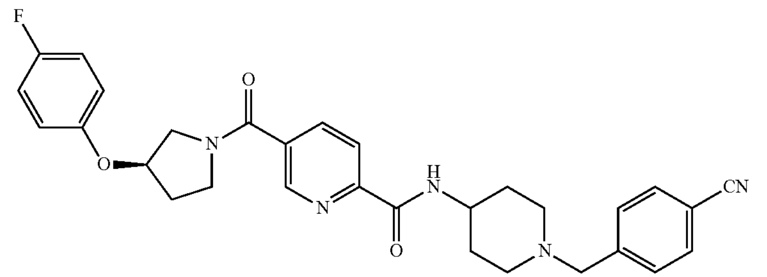 [SMILES: N#Cc1ccc(CN2CCC(NC(=O)c3ccc(C(=O)N4CC[C@@H](Oc5ccc(F)cc5)C4)cn3)CC2)cc1] |
| 279 | N-(1-(4-cyanobenzyl)piperidin-4-yl)-5-((trans)-4-(4-cyanophenoxy)-3-fluoropiperidine-1-carbonyl)picolinamide | 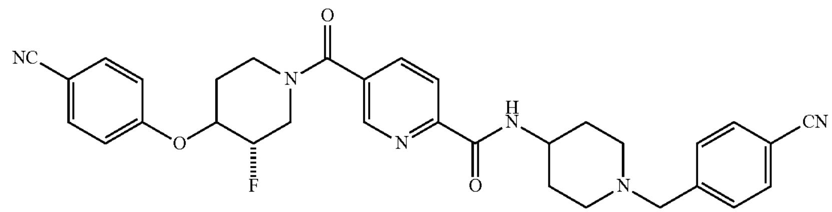 [SMILES: N#Cc1ccc(CN2CCC(NC(=O)c3ccc(C(=O)N4CCC(Oc5ccc(C#N)cc5)[C@@H](F)C4)cn3)CC2)cc1] |
| 280 | N-(1-(4-cyanobenzyl)piperidin-4-yl)-5-(((1R,3r,5S)-3-(4-cyanophenoxy)-8-azabicyclo[3.2.1]octane-8-carbonyl)picolinamide | 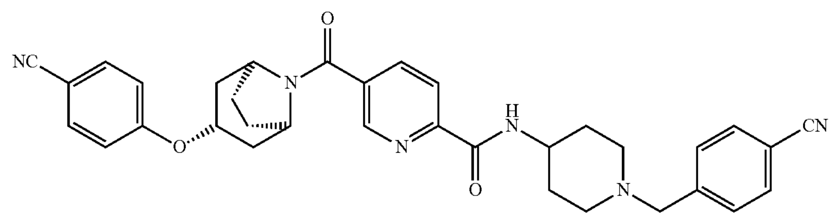 |
| 281 | N-(1-(4-cyanobenzyl)piperidin-4-yl)-5-(4-(3,4-difluorobenzoyl)piperidine-1-carbonyl)picolinamide | 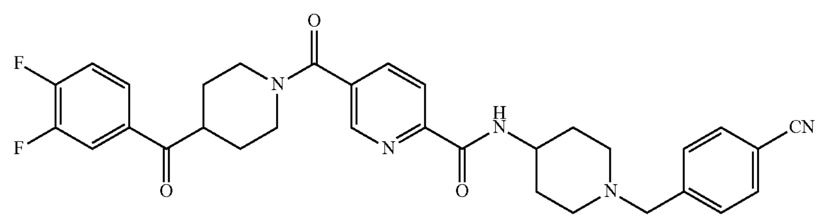 [SMILES: N#Cc1ccc(CN2CCC(NC(=O)c3ccc(C(=O)N4CCC(C(=O)c5ccc(F)c(F)c5)CC4)cn3)CC2)cc1] |

TABLE 1-continued

| No. | Name | Structure |
|---|---|---|
| 282 | N-(1-(4-cyanobenzyl)piperidin-4-yl)-5-(4-(2,4-difluorophenoxy)piperidine-1-carbonyl)picolinamide | 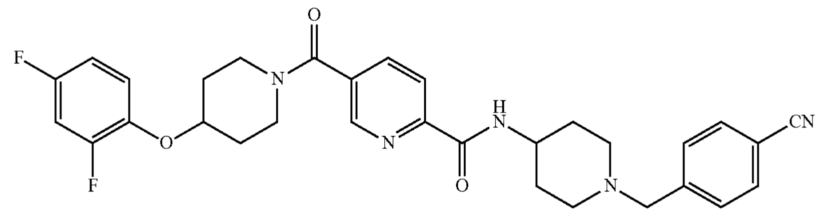 [SMILES: N#Cc1ccc(CN2CCC(NC(=O)c3ccc(C(=O)N4CCC(Oc5ccc(F)cc5F)CC4)cn3)CC2)cc1] |
| 283 | N-(1-(4-cyanobenzyl)piperidin-4-yl)-5-(4-(pyridin-3-yloxy)piperidine-1-carbonyl)picolinamide | 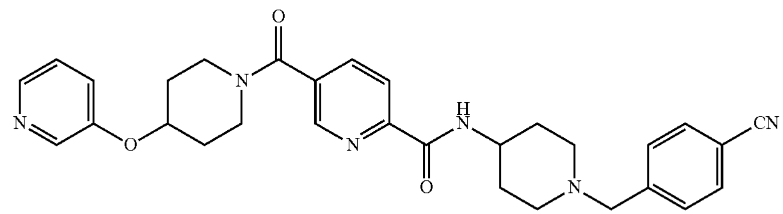 [SMILES: N#Cc1ccc(CN2CCC(NC(=O)c3ccc(C(=O)N4CCC(Oc5cccnc5)CC4)cn3)CC2)cc1] |
| 284 | ethyl 4-(1-(6-(1-(4-cyanobenzyl)piperidin-4-ylcarbamoyl)nicotinoyl)piperidin-4-yloxy)benzoate | 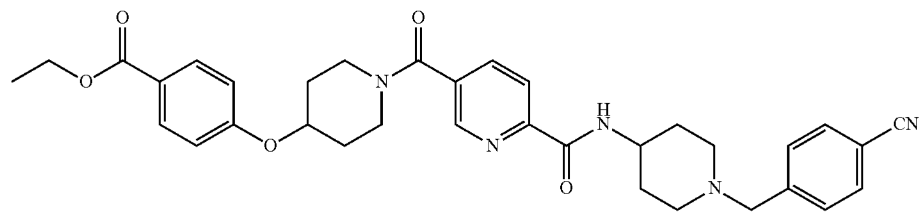 [SMILES: CCOC(=O)c1ccc(OC2CCN(C(=O)c3ccc(C(=O)NC4CCN(Cc5ccc(C#N)cc5)CC4)nc3)CC2)cc1] |
| 285 | 5-(4-(4-cyanobenzyl)piperazine-1-carbonyl)-N-(1-(4-methoxybenzyl)piperidin-4-yl)picolinamide | 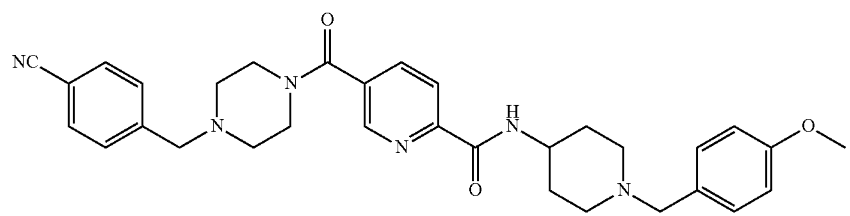 [SMILES: COc1ccc(CN2CCC(NC(=O)c3ccc(C(=O)N4CCN(Cc5ccc(C#N)cc5)CC4)cn3)CC2)cc1] |

TABLE 1-continued

| No. | Name |
|-----|------|
| 286 | 5-(4-(4-cyano-2-methoxyphenoxy)piperidin-1-yl)-N-(1-(4-cyanobenzyl)piperidin-4-yl)picolinamide |
| 287 | N-(1-(3,5-difluorobenzyl)piperidin-4-yl)-5-(4-(4-methoxybenzoyl)piperidine-1-carbonyl)picolinamide |
| 288 | N-(1-(3,5-difluorobenzyl)piperidin-4-yl)-5-(4-(4-fluorobenzoyl)piperidine-1-carbonyl)picolinamide |
| 289 | 5-(4-(4-cyanophenoxy)piperidine-1-carbonyl)-N-(1-(3,5-difluorobenzyl)piperidin-4-yl)picolinamide |

TABLE 1-continued

| No. | Name | Structure |
|---|---|---|
| 290 | tert-butyl 3-(2-((1-(4-cyanobenzyl)piperidin-4-yl)carbamoyl)-5-(4-(4-fluorobenzyl)piperazine-1-carbonyl)pyridin-3-yl)propylcarbamate | 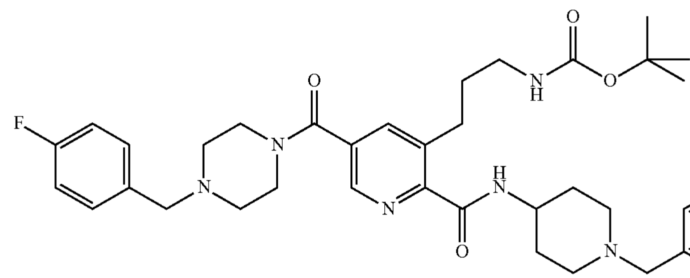 |
| 291 | N-(1-(4-cyanobenzyl)piperidin-4-yl)-3-(5,21-dioxo-25-((3aS,4S,6aR)-2-oxohexahydro-1H-thieno[3,4-d]imidazol-4-yl)-8,11,14,17-tetraoxa-4,20-diazapentacosyl)-5-(4-(4-fluorobenzyl)piperazine-1-carbonyl)picolinamide | 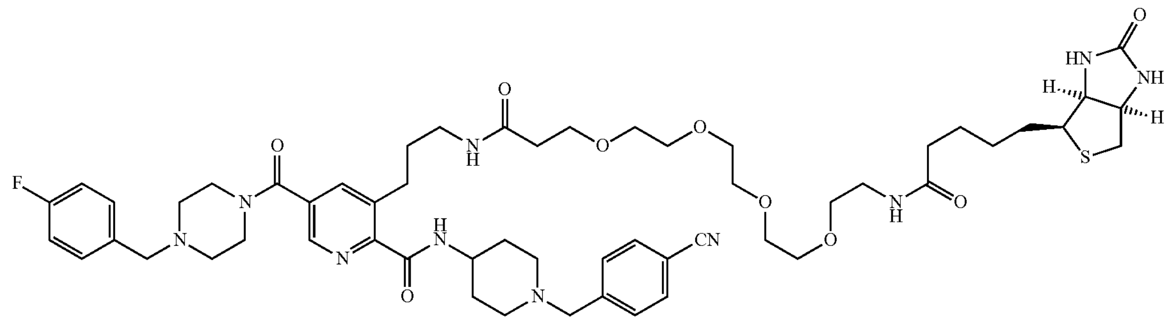 |
| 292 | N-(1-(3,5-difluorobenzyl)piperidin-4-yl)-5-(((S)-3-(4-fluorophenoxy)pyrrolidine-1-carbonyl)picolinamide | 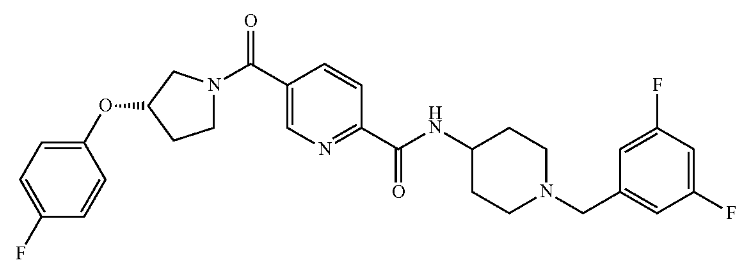 |

TABLE 1-continued

| No. | Name | Structure |
|---|---|---|
| 293 | N-(1-(3,5-difluorobenzyl)piperidin-4-yl)-5-(4-(p-tolyloxy)piperidine-1-carbonyl)picolinamide | 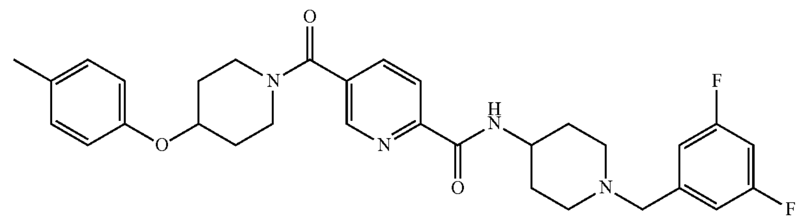 [SMILES: Cc1ccc(OC2CCN(C(=O)c3ccc(C(=O)NC4CCN(Cc5cc(F)cc(F)c5)CC4)nc3)CC2)cc1] |
| 294 | N-(1-(3,5-difluorobenzyl)piperidin-4-yl)-5-(4-(4-(trifluoromethyl)phenoxy)piperidine-1-carbonyl)picolinamide | 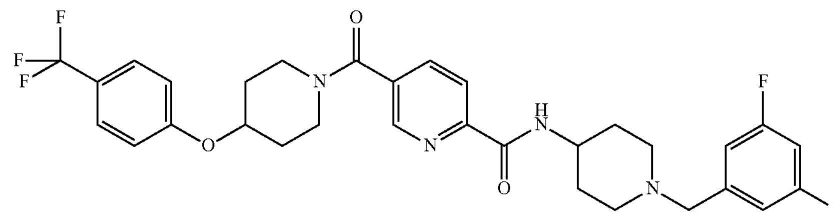 |
| 295 | N-(1-(3,5-difluorobenzyl)piperidin-4-yl)-5-(4-(4-fluorophenoxy)piperidine-1-carbonyl)picolinamide | 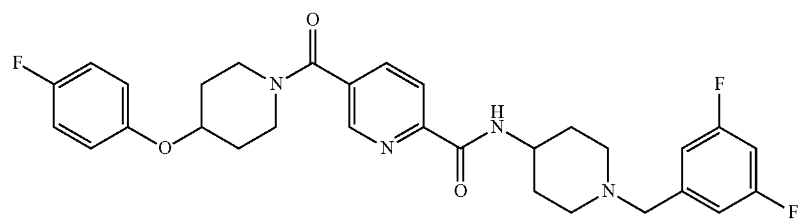 [SMILES: O=C(NC1CCN(Cc2cc(F)cc(F)c2)CC1)c1ccc(C(=O)N2CCC(Oc3ccc(F)cc3)CC2)cn1] |
| 296 | N-(1-(3,5-difluorobenzyl)piperidin-4-yl)-5-(4-(4-methoxyphenoxy)piperidine-1-carbonyl)picolinamide | 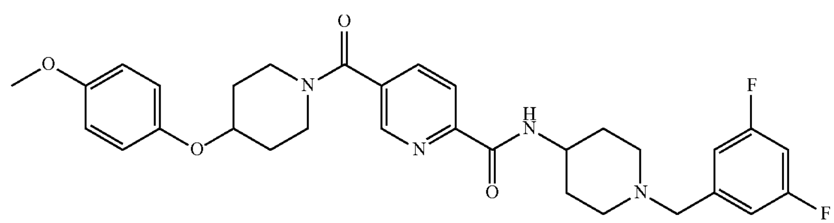 [SMILES: COc1ccc(OC2CCN(C(=O)c3ccc(C(=O)NC4CCN(Cc5cc(F)cc(F)c5)CC4)nc3)CC2)cc1] |

TABLE 1-continued

| No. | Name | Structure |
|-----|------|-----------|
| 297 | N-(1-(3,5-difluorobenzyl)piperidin-4-yl)-5-(4-(3,4-difluorophenoxy)piperidine-1-carbonyl)picolinamide | 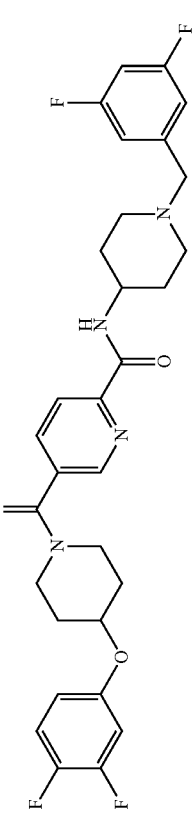 |
| 298 | 5-(4-(3,4-difluorobenzoyl)piperidine-1-carbonyl)-N-(1-(3,5-difluorobenzyl)piperidin-4-yl)picolinamide | 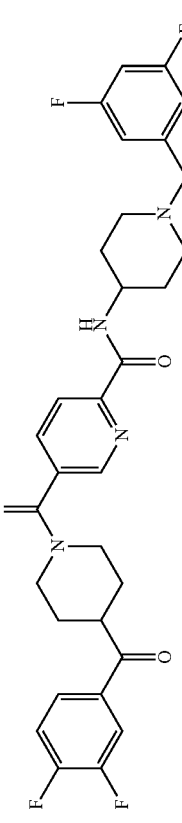 |
| 299 | N-((cis)-4-(3,5-difluorophenoxy)cyclohexyl)-5-(4-(4-fluorophenoxy)piperidine-1-carbonyl)picolinamide | 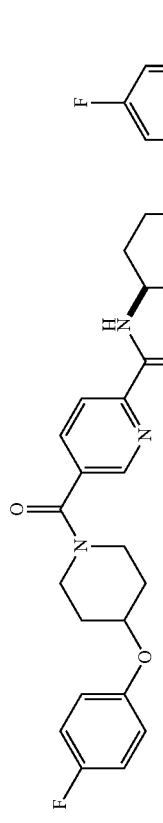 |
| 300 | N-((cis)-4-(3,5-difluorophenoxy)cyclohexyl)-5-(4-(4-methoxybenzoyl)piperidine-1-carbonyl)picolinamide | 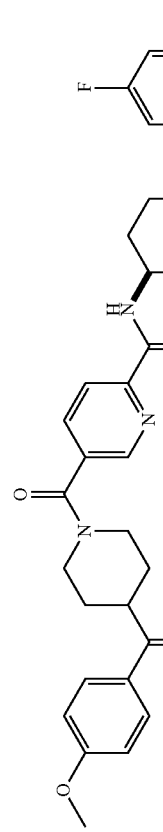 |

TABLE 1-continued

| No. | Name | Structure |
|---|---|---|
| 301 | N-(1-(4-cyanobenzyl)piperidin-4-yl)-5-(4-(4-(trifluoromethyl)phenoxy)piperidin-1-yl)picolinamide | 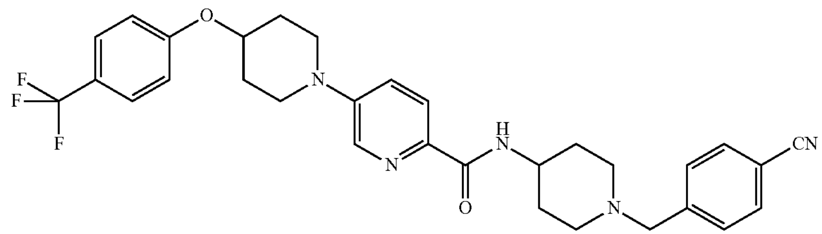 [SMILES: N#Cc1ccc(CN2CCC(NC(=O)c3ccc(N4CCC(Oc5ccc(C(F)(F)F)cc5)CC4)cn3)CC2)cc1] |
| 302 | N-(1-(4-cyanobenzyl)piperidin-4-yl)-5-(4-(4-methoxybenzoyl)piperidin-1-yl)picolinamide | 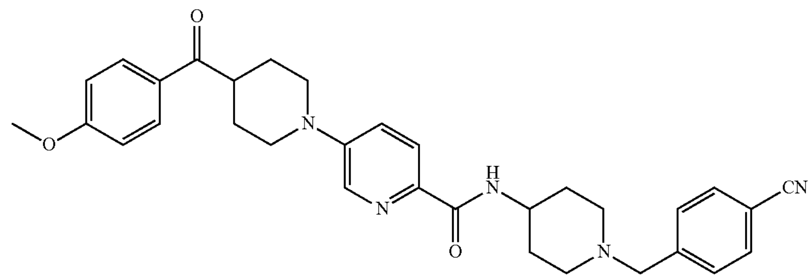 |
| 303 | 5-(4-(4-cyanophenoxy)piperidine-1-carbonyl)-N-((cis)-4-(4-fluorophenoxy)cyclohexyl)picolinamide | 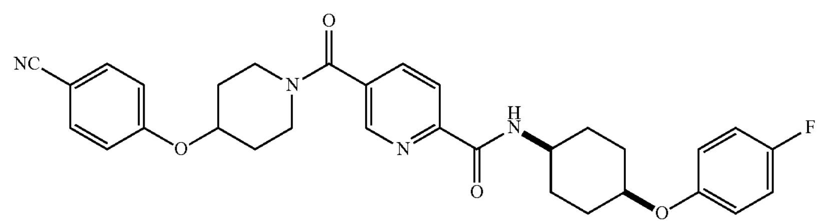 |
| 304 | 5-(4-(4-fluorobenzoyl)piperidine-1-carbonyl)-N-((cis)-4-(4-fluorophenoxy)cyclohexyl)picolinamide | 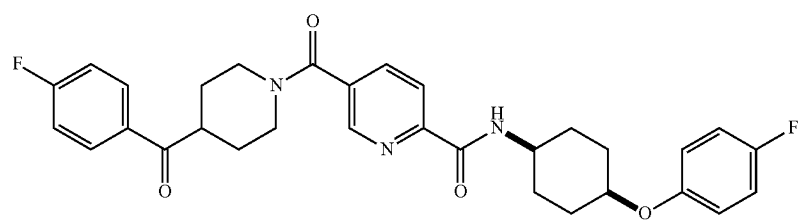 |

TABLE 1-continued

| No. | Name | Structure |
|-----|------|-----------|
| 305 | N-(2-(4-fluorophenoxy)ethyl)-5-(4-(4-methoxybenzoyl)piperidine-1-carbonyl)picolinamide | 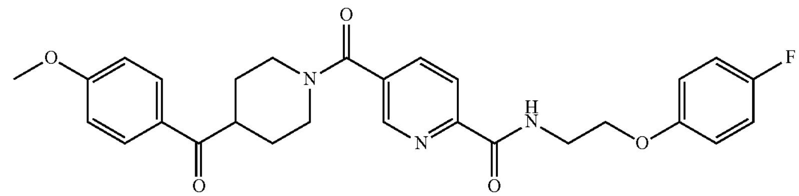 [SMILES: COc1ccc(C(=O)C2CCN(C(=O)c3ccc(C(=O)NCCOc4ccc(F)cc4)nc3)CC2)cc1] |
| 306 | 5-(4-(4-cyanophenoxy)piperidine-1-carbonyl)-N-(2-(4-fluorophenoxy)ethyl)picolinamide | 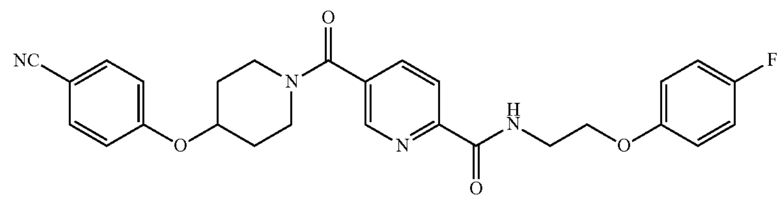 [SMILES: N#Cc1ccc(OC2CCN(C(=O)c3ccc(C(=O)NCCOc4ccc(F)cc4)nc3)CC2)cc1] |
| 307 | N-(1-(4-cyanobenzyl)piperidin-4-yl)-5-(3-(4-fluorobenzyloxy)azetidine-1-carbonyl)picolinamide | 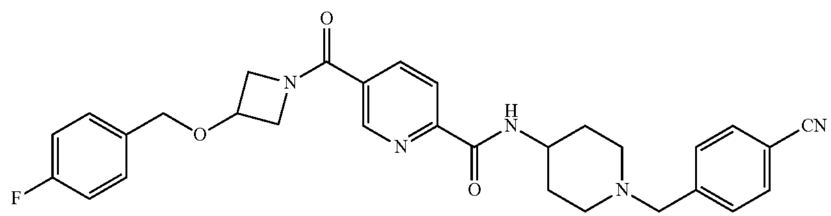 [SMILES: N#Cc1ccc(CN2CCC(NC(=O)c3ccc(C(=O)N4CC(OCc5ccc(F)cc5)C4)cn3)CC2)cc1] |
| 308 | N-(1-(3,5-difluorobenzyl)piperidin-4-yl)-5-(3-(4-fluorobenzyloxy)azetidine-1-carbonyl)picolinamide | 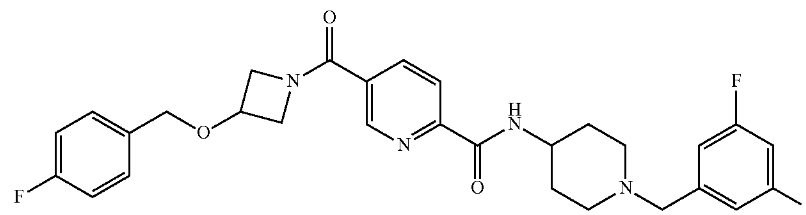 |
| 309 | N-(1-(4-cyanobenzyl)piperidin-4-yl)-6-(4-(4-methoxybenzoyl)piperidine-1-carbonyl)nicotinamide | 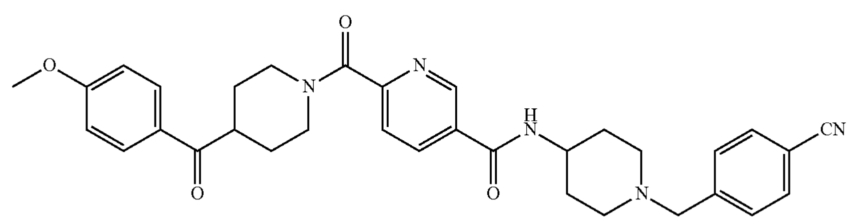 [SMILES: COc1ccc(C(=O)C2CCN(C(=O)c3ccc(C(=O)NC4CCN(Cc5ccc(C#N)cc5)CC4)cn3)CC2)cc1] |

TABLE 1-continued

| No. | Name | Structure |
|---|---|---|
| 310 | N-(1-(3,5-difluorobenzyl)piperidin-4-yl)-6-(4-(4-methoxybenzoyl)piperidine-1-carbonyl)nicotinamide | 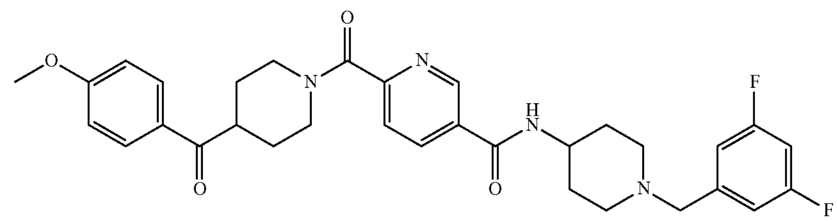 [SMILES: COc1ccc(C(=O)C2CCN(C(=O)c3ccc(C(=O)NC4CCN(Cc5cc(F)cc(F)c5)CC4)cn3)CC2)cc1] |
| 311 | N-((cis)-4-(4-fluorophenoxy)cyclohexyl)-5-(4-(4-methoxybenzoyl)piperidine-1-carbonyl)picolinamide | 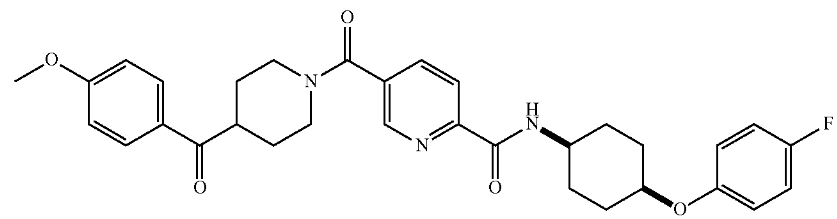 |
| 312 | N-((cis)-4-(4-fluorophenoxy)cyclohexyl)-5-(4-(4-fluorophenoxy)piperidine-1-carbonyl)picolinamide | 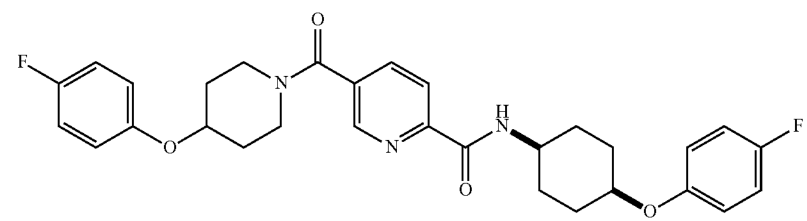 |
| 313 | 5-(3-(4-cyanophenoxy)azetidine-1-carbonyl)-N-(1-(3,5-difluorobenzyl)piperidin-4-yl)picolinamide | 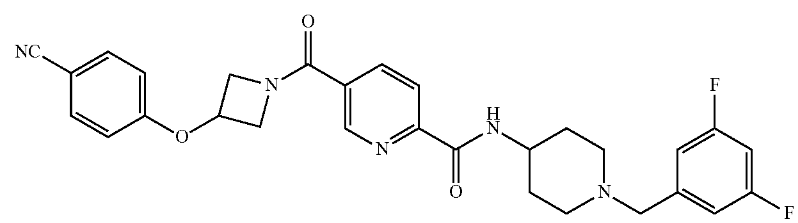 [SMILES: N#Cc1ccc(OC2CN(C(=O)c3ccc(C(=O)NC4CCN(Cc5cc(F)cc(F)c5)CC4)nc3)C2)cc1] |

TABLE 1-continued

| No. | Name | Structure |
|---|---|---|
| 314 | 5-(3-(4-cyanophenyl)-5,6,7,8-tetrahydro-[1,2,4]triazolo[4,3-a]pyrazine-7-carbonyl)-N-(1-(3,5-difluorobenzyl)piperidin-4-yl)picolinamide | 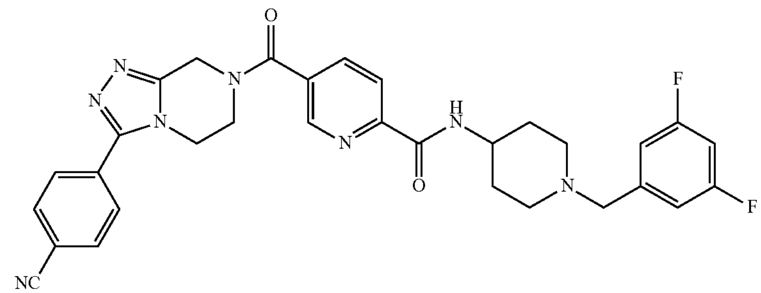 [SMILES: N#Cc1ccc(-c2nnc3n2CCN(C(=O)c2ccc(C(=O)NC4CCN(Cc5cc(F)cc(F)c5)CC4)nc2)C3)cc1] |
| 315 | N-((1s,4s)-4-(4-cyanophenoxy)cyclohexyl)-6-(4-(4-methoxybenzoyl)piperidine-1-carbonyl)nicotinamide | 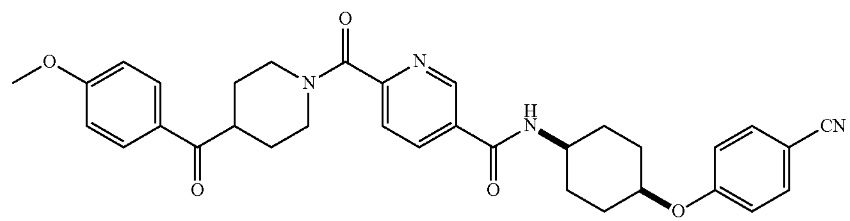 |
| 316 | N-(cis)-4-(4-fluorophenoxy)cyclohexyl)-6-(4-(4-methoxybenzoyl)piperidine-1-carbonyl)nicotinamide | 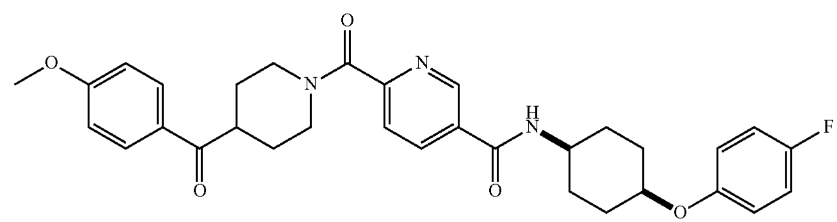 |
| 317 | N-(1-(4-fluorobenzyl)piperidin-4-yl)-6-(4-(4-methoxybenzoyl)piperidine-1-carbonyl)nicotinamide | 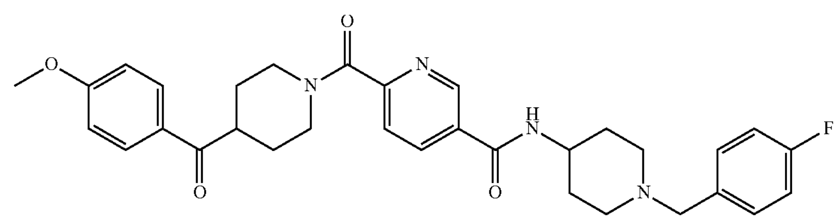 [SMILES: COc1ccc(C(=O)C2CCN(C(=O)c3ccc(C(=O)NC4CCN(Cc5ccc(F)cc5)CC4)cn3)CC2)cc1] |

TABLE 1-continued

| No. | Name | Structure |
|---|---|---|
| 318 | 6-(4-(4-methoxybenzoyl)piperidine-1-carbonyl)-N-(1-(4-methoxybenzyl)piperidin-4-yl)nicotinamide | 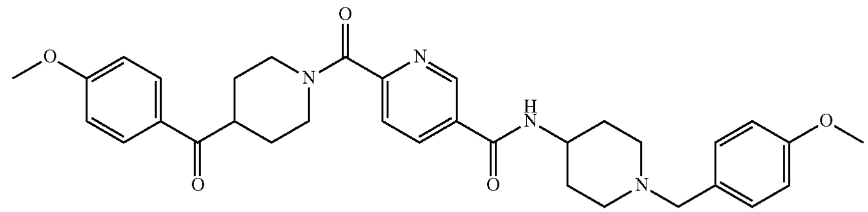 |
| 319 | 6-(4-(4-cyanophenoxy)piperidine-1-carbonyl)-N-(1-(4-methoxybenzyl)piperidin-4-yl)nicotinamide | 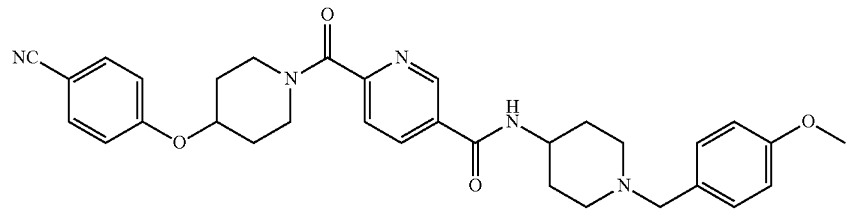 [SMILES: COc1ccc(CN2CCC(NC(=O)c3ccc(C(=O)N4CCC(Oc5ccc(C#N)cc5)CC4)nc3)CC2)cc1] |
| 320 | 6-(4-(4-cyanophenoxy)piperidine-1-carbonyl)-N-(1-(4-fluorobenzyl)piperidin-4-yl)nicotinamide | 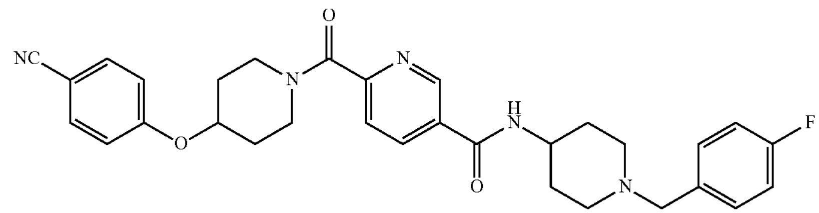 [SMILES: N#Cc1ccc(OC2CCN(C(=O)c3ccc(C(=O)NC4CCN(Cc5ccc(F)cc5)CC4)cn3)CC2)cc1] |
| 321 | N-((cis)-4-(4-cyanophenoxy)cyclohexyl)-6-(4-(4-cyanophenoxy)piperidine-1-carbonyl)nicotinamide | 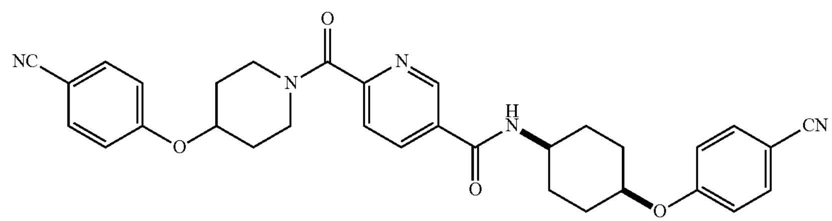 |

TABLE 1-continued

| No. | Name | Structure |
|---|---|---|
| 322 | 6-(4-(4-cyanophenoxy)piperidine-1-carbonyl)-N-(1-(3,5-difluorobenzyl)piperidin-4-yl)nicotinamide | 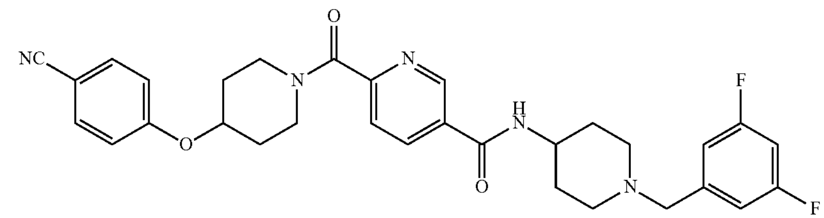 [SMILES: N#Cc1ccc(OC2CCN(C(=O)c3ccc(C(=O)NC4CCN(Cc5cc(F)cc(F)c5)CC4)cn3)CC2)cc1] |
| 323 | N-(1-(4-cyanobenzyl)piperidin-4-yl)-6-(4-(4-cyanophenoxy)piperidine-1-carbonyl)nicotinamide | 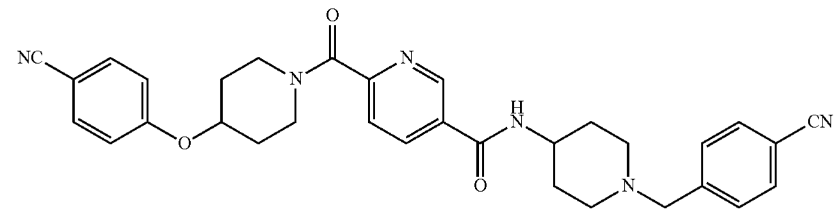 [SMILES: N#Cc1ccc(CN2CCC(NC(=O)c3ccc(C(=O)N4CCC(Oc5ccc(C#N)cc5)CC4)nc3)CC2)cc1] |
| 324 | 6-(4-(4-cyanophenoxy)piperidine-1-carbonyl)-N-((cis)-4-(4-fluorophenoxy)cyclohexyl)nicotinamide | 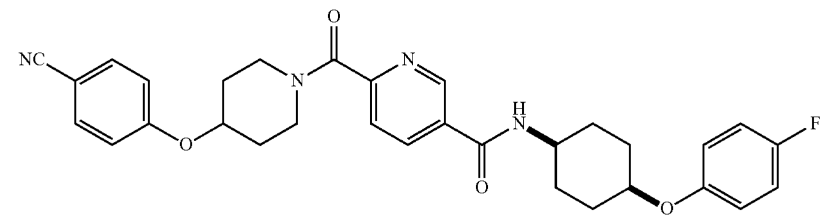 |
| 325 | N-(6-(4-fluorophenoxy)pyridin-3-yl)-6-(4-(4-methoxybenzoyl)piperidine-1-carbonyl)nicotinamide | 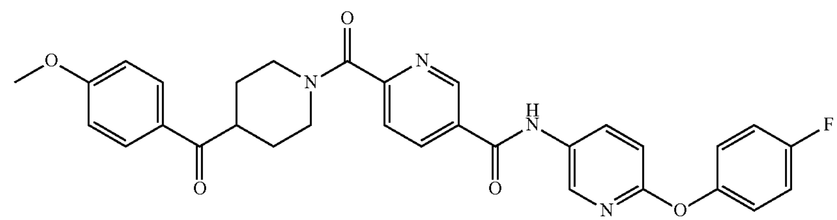 [SMILES: COc1ccc(C(=O)C2CCN(C(=O)c3ccc(C(=O)Nc4ccc(Oc5ccc(F)cc5)nc4)cn3)CC2)cc1] |

TABLE 1-continued

| No. | Name | Structure |
|---|---|---|
| 326 | 6-(4-(4-cyanophenoxy)piperidine-1-carbonyl)-N-(6-(4-fluorophenoxy)pyridin-3-yl)nicotinamide | 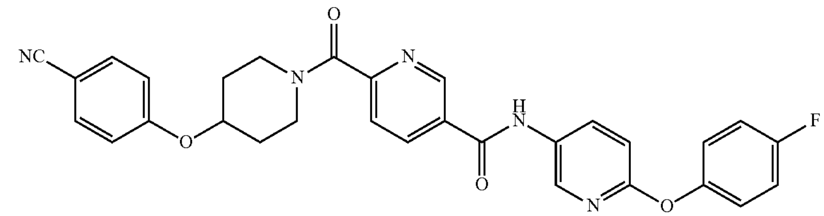 [SMILES: N#Cc1ccc(OC2CCN(C(=O)c3ccc(C(=O)Nc4ccc(Oc5ccc(F)cc5)nc4)cn3)CC2)cc1] |
| 327 | 6-(4-(4-fluorobenzyl)piperazine-1-carbonyl)-N-(1-(4-methoxybenzyl)piperidin-4-yl)nicotinamide | 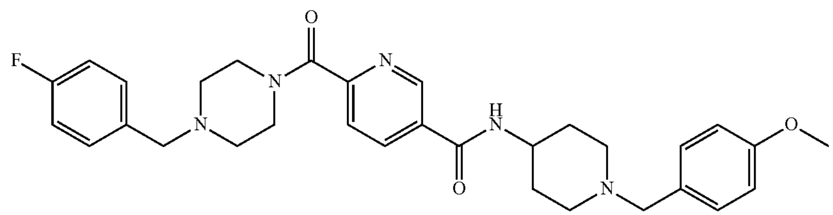 [SMILES: COc1ccc(CN2CCC(NC(=O)c3ccc(C(=O)N4CCN(Cc5ccc(F)cc5)CC4)nc3)CC2)cc1] |
| 328 | 6-(4-(4-fluorobenzyl)piperazine-1-carbonyl)-N-(1-(4-fluorobenzyl)piperidin-4-yl)nicotinamide | 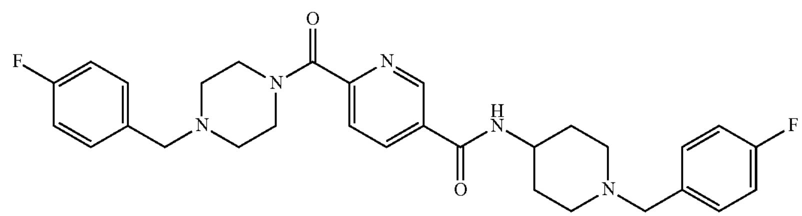 [SMILES: O=C(NC1CCN(Cc2ccc(F)cc2)CC1)c1ccc(C(=O)N2CCN(Cc3ccc(F)cc3)CC2)nc1] |
| 329 | 5-(4-(3,4-difluorobenzoyl)piperidine-1-carbonyl)-N-(1-(4-methoxybenzyl)piperidin-4-yl)picolinamide | 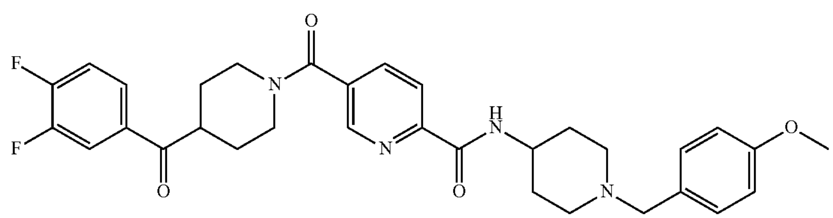 [SMILES: COc1ccc(CN2CCC(NC(=O)c3ccc(C(=O)N4CCC(C(=O)c5ccc(F)c(F)c5)CC4)cn3)CC2)cc1] |

TABLE 1-continued

| No. | Name | Structure |
|---|---|---|
| 330 | 5-(4-(3,4-difluorobenzoyl)piperidine-1-carbonyl)-N-(6-(4-fluorophenoxy)pyridin-3-yl)picolinamide | 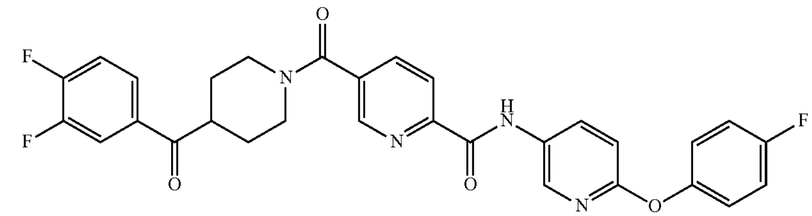 [SMILES: O=C(Nc1ccc(Oc2ccc(F)cc2)nc1)c1ccc(C(=O)N2CCC(C(=O)c3ccc(F)c(F)c3)CC2)cn1] |
| 331 | 5-(4-(2,4-difluorobenzoyl)piperidine-1-carbonyl)-N-(1-(4-methoxybenzyl)piperidin-4-yl)picolinamide | 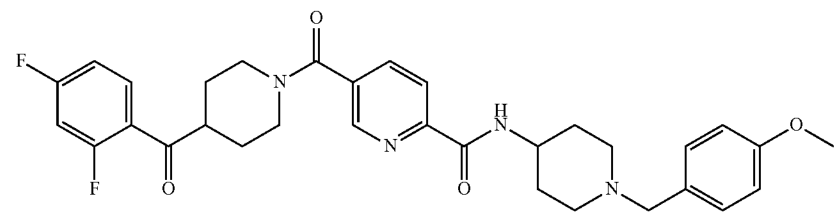 [SMILES: COc1ccc(CN2CCC(NC(=O)c3ccc(C(=O)N4CCC(C(=O)c5ccc(F)cc5F)CC4)cn3)CC2)cc1] |
| 332 | N-((cis)-4-(4-cyanophenoxy)cyclohexyl)-6-(4-(4-fluorobenzyl)piperazine-1-carbonyl)nicotinamide | 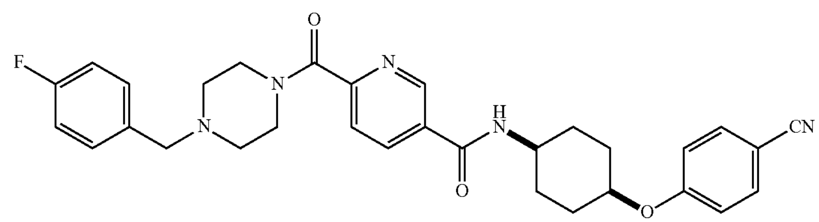 |
| 333 | tert-butyl 4-(6-(4-(4-cyanophenoxy)piperidine-1-carbonyl)nicotinamido)piperidine-1-carboxylate | 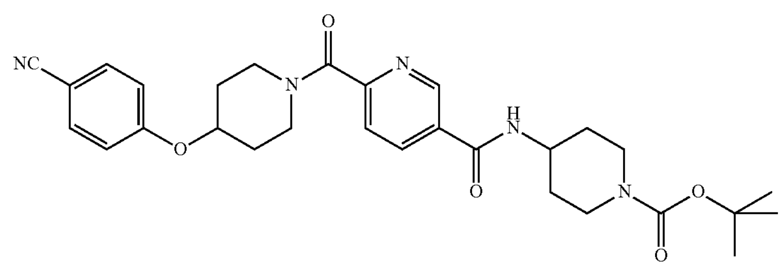 [SMILES: CC(C)(C)OC(=O)N1CCC(NC(=O)c2ccc(C(=O)N3CCC(Oc4ccc(C#N)cc4)CC3)nc2)CC1] |

TABLE 1-continued

| No. | Name | Structure |
|---|---|---|
| 334 | 6-(4-(4-fluorobenzyl)piperazine-1-carbonyl)-N-(6-(4-fluorophenoxy)pyridin-3-yl)nicotinamide | 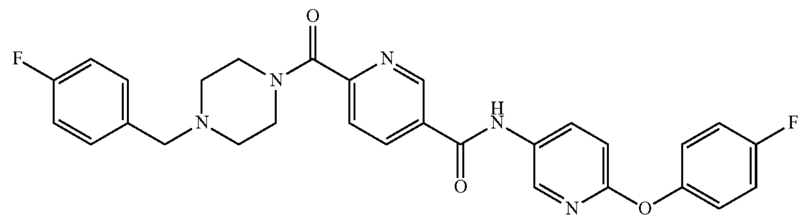 [SMILES: O=C(Nc1ccc(Oc2ccc(F)cc2)nc1)c1ccc(C(=O)N2CCN(Cc3ccc(F)cc3)CC2)nc1] |
| 335 | 6-(4-(4-cyanophenoxy)piperidine-1-carbonyl)-N-(piperidin-4-yl)nicotinamide | 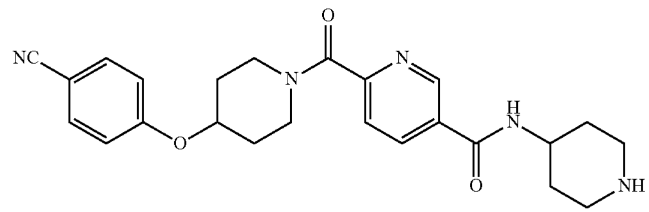 [SMILES: N#Cc1ccc(OC2CCN(C(=O)c3ccc(C(=O)NC4CCNCC4)cn3)CC2)cc1] |
| 336 | 6-(4-(4-cyanophenoxy)piperidine-1-carbonyl)-N-(1-(4-(pyrrolidin-1-yl)benzyl)piperidin-4-yl)nicotinamide | 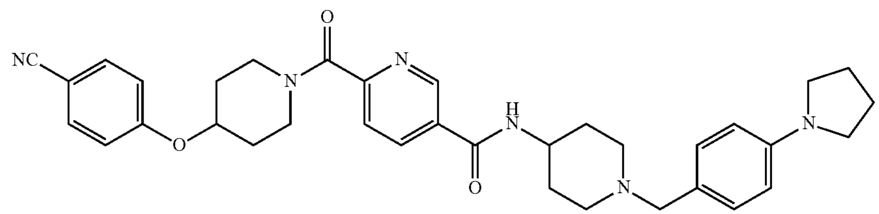 [SMILES: N#Cc1ccc(OC2CCN(C(=O)c3ccc(C(=O)NC4CCN(Cc5ccc(N6CCCC6)cc5)CC4)cn3)CC2)cc1] |
| 337 | 6-(4-(4-cyanophenoxy)piperidine-1-carbonyl)-N-(1-(4-morpholinobenzyl)piperidin-4-yl)nicotinamide | 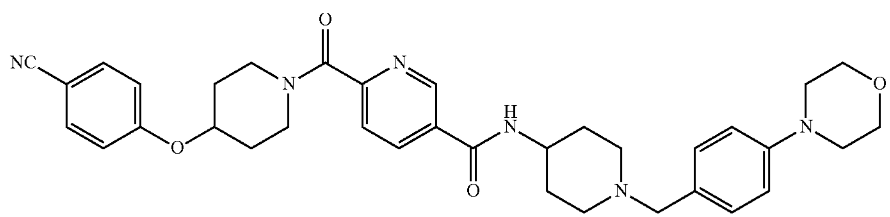 [SMILES: N#Cc1ccc(OC2CCN(C(=O)c3ccc(C(=O)NC4CCN(Cc5ccc(N6CCOCC6)cc5)CC4)cn3)CC2)cc1] |

TABLE 1-continued

| No. | Name | Structure |
|---|---|---|
| 338 | 6-(4-(4-cyanophenoxy)piperidine-1-carbonyl)-N-(1-(4-(trifluoromethoxy)benzyl)piperidin-4-yl)nicotinamide | 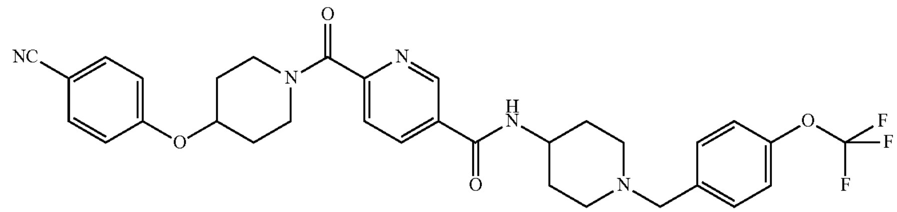 [SMILES: N#Cc1ccc(OC2CCN(C(=O)c3ccc(C(=O)NC4CCN(Cc5ccc(OC(F)(F)F)cc5)CC4)cn3)CC2)cc1] |
| 339 | N-(1-(4-cyanobenzyl)piperidin-4-yl)-5-(4-(4-(trifluoromethyl)phenyl)piperazine-1-carbonyl)picolinamide | 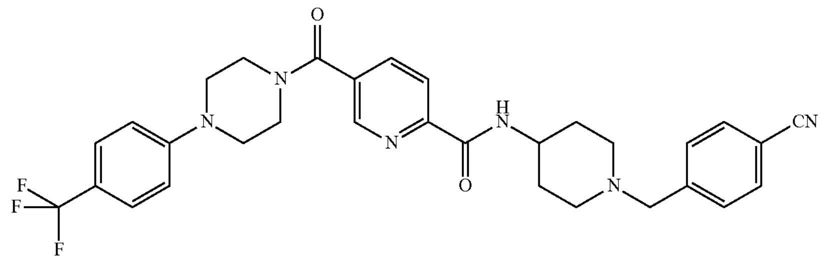 [SMILES: N#Cc1ccc(CN2CCC(NC(=O)c3ccc(C(=O)N4CCN(c5ccc(C(F)(F)F)cc5)CC4)cn3)CC2)cc1] |
| 340 | N-(1-(4-cyanobenzyl)piperidin-4-yl)-5-(4-(4-cyanophenyl)piperazine-1-carbonyl)picolinamide | 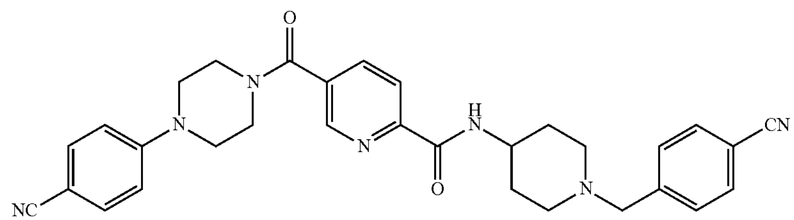 [SMILES: N#Cc1ccc(CN2CCC(NC(=O)c3ccc(C(=O)N4CCN(c5ccc(C#N)cc5)CC4)cn3)CC2)cc1] |
| 341 | N-(1-(4-cyanobenzyl)piperidin-4-yl)-5-(4-(4-fluorophenyl)piperazine-1-carbonyl)picolinamide | 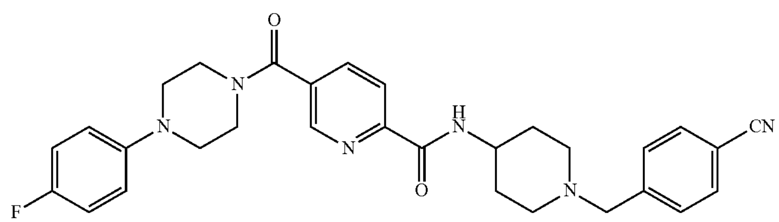 [SMILES: N#Cc1ccc(CN2CCC(NC(=O)c3ccc(C(=O)N4CCN(c5ccc(F)cc5)CC4)cn3)CC2)cc1] |

TABLE 1-continued

| No. | Name | Structure |
|-----|------|-----------|
| 342 | 5-(4-(2,4-difluorobenzoyl)piperidine-1-carbonyl)-N-(6-(4-fluorophenoxy)pyridin-3-yl)picolinamide | 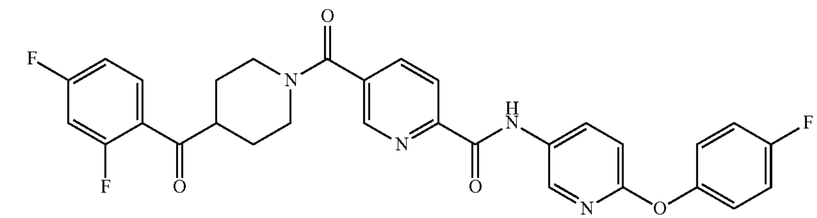 [SMILES: O=C(Nc1ccc(Oc2ccc(F)cc2)nc1)c1ccc(C(=O)N2CCC(C(=O)c3ccc(F)cc3F)CC2)cn1] |
| 343 | 6-(4-(2,4-difluorophenoxy)piperidine-1-carbonyl)-N-(6-(4-fluorophenoxy)pyridin-3-yl)nicotinamide | 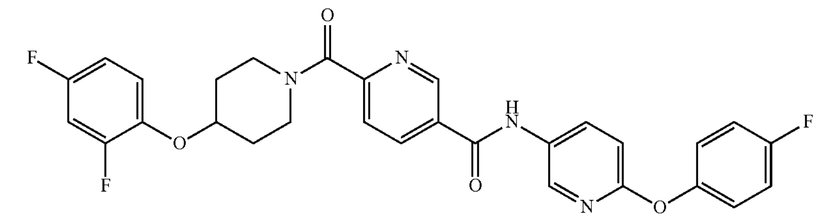 [SMILES: O=C(Nc1ccc(Oc2ccc(F)cc2)nc1)c1ccc(C(=O)N2CCC(Oc3ccc(F)cc3F)CC2)nc1] |
| 344 | 6-(4-(2,4-difluorophenoxy)piperidine-1-carbonyl)-N-(1-(4-methoxybenzyl)piperidin-4-yl)nicotinamide | 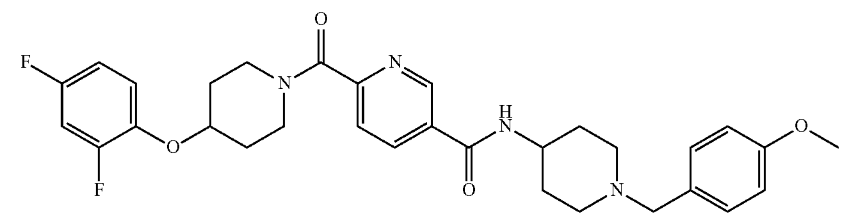 [SMILES: COc1ccc(CN2CCC(NC(=O)c3ccc(C(=O)N4CCC(Oc5ccc(F)cc5F)CC4)nc3)CC2)cc1] |
| 345 | N-(1-(4-cyanobenzyl)piperidin-4-yl)-6-(4-(2,4-difluorophenoxy)piperidine-1-carbonyl)nicotinamide | 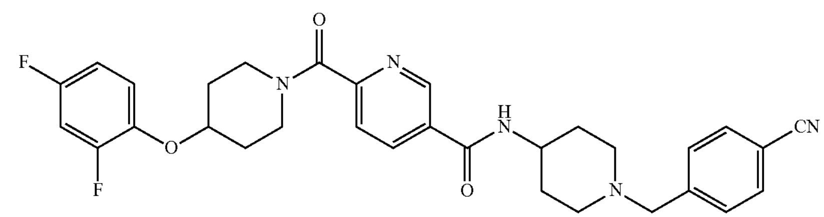 [SMILES: N#Cc1ccc(CN2CCC(NC(=O)c3ccc(C(=O)N4CCC(Oc5ccc(F)cc5F)CC4)nc3)CC2)cc1] |

TABLE 1-continued

| No. | Name | Structure |
|---|---|---|
| 346 | N-(1-(4-cyanobenzyl)piperidin-4-yl)-6-(4-(2,4-difluorobenzoyl)piperidine-1-carbonyl)nicotinamide | 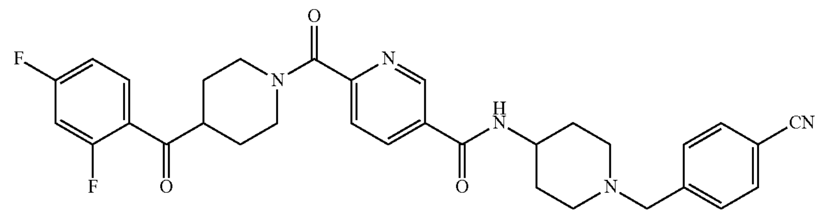 [SMILES: N#Cc1ccc(CN2CCC(NC(=O)c3ccc(C(=O)N4CCC(C(=O)c5ccc(F)cc5F)CC4)nc3)CC2)cc1] |
| 347 | 6-(4-(2,4-difluorobenzoyl)piperidine-1-carbonyl)-N-(1-(4-methoxybenzyl)piperidin-4-yl)nicotinamide | 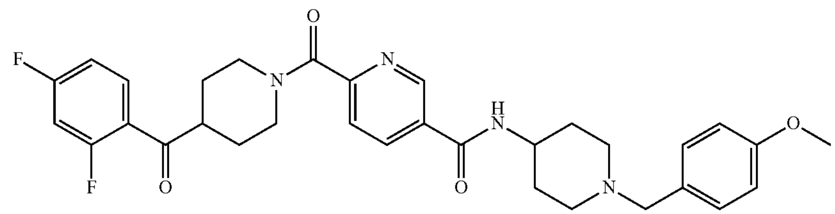 [SMILES: COc1ccc(CN2CCC(NC(=O)c3ccc(C(=O)N4CCC(C(=O)c5ccc(F)cc5F)CC4)nc3)CC2)cc1] |
| 348 | 6-(4-(2,4-difluorobenzoyl)piperidine-1-carbonyl)-N-(6-(4-fluorophenoxy)pyridin-3-yl)nicotinamide | 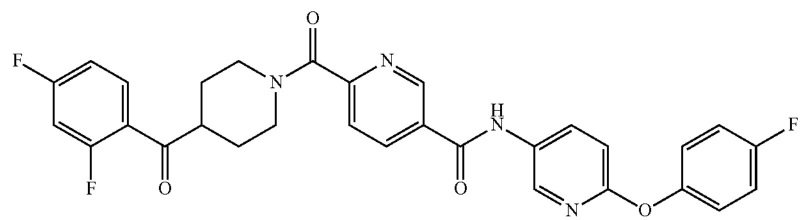 [SMILES: O=C(Nc1ccc(Oc2ccc(F)cc2)nc1)c1ccc(C(=O)N2CCC(C(=O)c3ccc(F)cc3F)CC2)nc1] |
| 349 | N-((trans)-1-(4-cyanobenzyl)-3-fluoropiperidin-4-yl)-6-(4-(4-methoxybenzoyl)piperidine-1-carbonyl)nicotinamide | 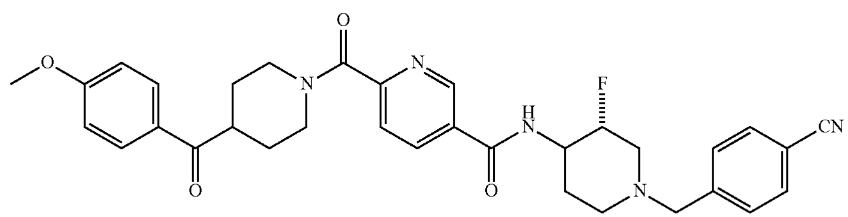 [SMILES: COc1ccc(C(=O)C2CCN(C(=O)c3ccc(C(=O)NC4CCN(Cc5ccc(C#N)cc5)C[C@H]4F)cn3)CC2)cc1] |

TABLE 1-continued

| No. | Name | Structure |
|-----|------|-----------|
| 350 | N-((trans)-3-fluoro-1-(4-(trifluoromethoxy)benzyl)piperidin-4-yl)-6-(4-(4-methoxybenzoyl)piperidine-1-carbonyl)nicotinamide | 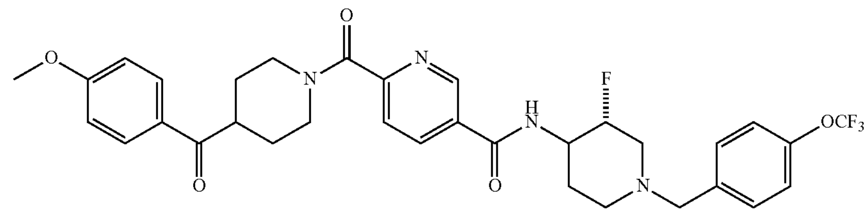 [SMILES: COc1ccc(C(=O)C2CCN(C(=O)c3ccc(C(=O)NC4CCN(Cc5ccc(OC(F)(F)F)cc5)C[C@H]4F)cn3)CC2)cc1] |
| 351 | N-(1-(4-cyanobenzyl)piperidin-4-yl)-6-(4-(4-cyanophenoxy)piperidin-1-yl)pyridazine-3-carboxamide | 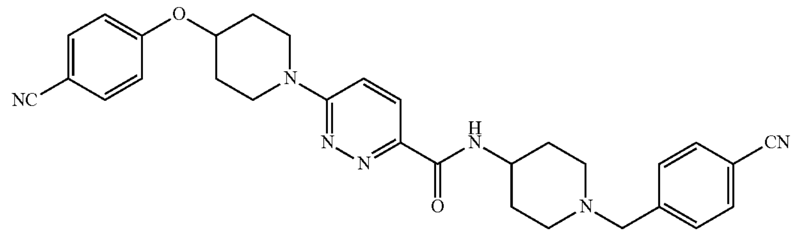 |
| 352 | N-((trans)-3-fluoro-1-(4-(pyrrolidin-1-yl)benzyl)piperidin-4-yl)-6-(4-(4-methoxybenzoyl)piperidine-1-carbonyl)nicotinamide | 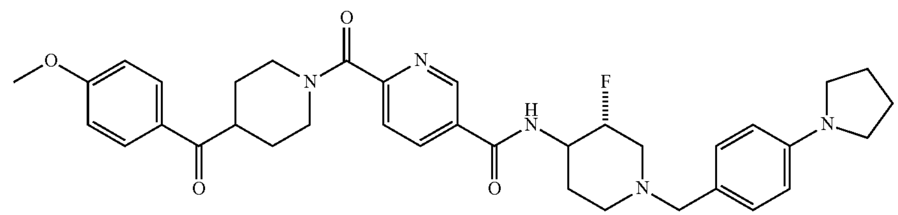 [SMILES: COc1ccc(C(=O)C2CCN(C(=O)c3ccc(C(=O)NC4CCN(Cc5ccc(N6CCCC6)cc5)C[C@H]4F)cn3)CC2)cc1] |
| 353 | N-((trans)-3-fluoro-1-(4-isopropoxybenzyl)piperidin-4-yl)-6-(4-(4-methoxybenzoyl)piperidine-1-carbonyl)nicotinamide | 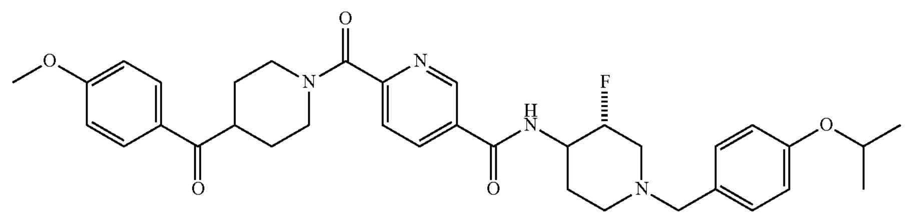 [SMILES: COc1ccc(C(=O)C2CCN(C(=O)c3ccc(C(=O)NC4CCN(Cc5ccc(OC(C)C)cc5)C[C@H]4F)cn3)CC2)cc1] |

TABLE 1-continued

| No. | Name | Structure |
|---|---|---|
| 354 | N-((trans)-1-(4-cyano-3-fluorobenzyl)-3-fluoropiperidin-4-yl)-6-(4-(4-methoxybenzoyl)piperidine-1-carbonyl)nicotinamide | 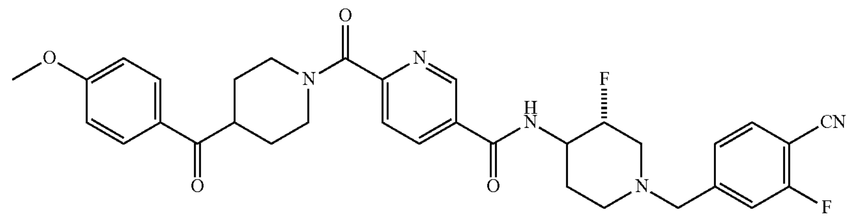 [SMILES: COc1ccc(C(=O)C2CCN(C(=O)c3ccc(C(=O)NC4CCN(Cc5ccc(C#N)c(F)c5)C[C@H]4F)cn3)CC2)cc1] |
| 355 | 6-(4-(4-cyanophenoxy)piperidine-1-carbonyl)-N-(1-(oxazol-4-ylmethyl)piperidin-4-yl)nicotinamide | 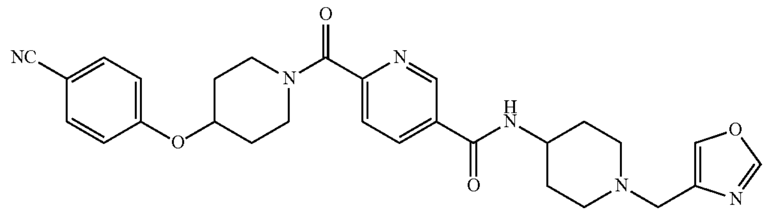 [SMILES: N#Cc1ccc(OC2CCN(C(=O)c3ccc(C(=O)NC4CCN(Cc5cocn5)CC4)cn3)CC2)cc1] |
| 356 | 6-(4-(4-cyanophenoxy)piperidine-1-carbonyl)-N-(1-(thiazol-2-ylmethyl)piperidin-4-yl)nicotinamide | 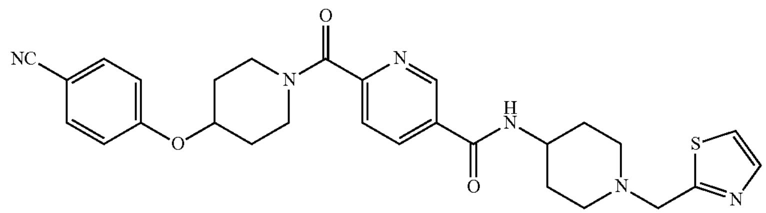 [SMILES: N#Cc1ccc(OC2CCN(C(=O)c3ccc(C(=O)NC4CCN(Cc5nccs5)CC4)cn3)CC2)cc1] |
| 357 | N-(1-(4-cyanobenzyl)piperidin-4-yl)-5-(4-(4-(dimethylcarbamoyl)phenoxy)piperidine-1-carbonyl)picolinamide | 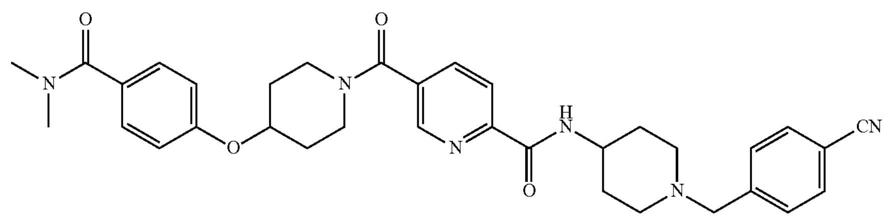 [SMILES: CN(C)C(=O)c1ccc(OC2CCN(C(=O)c3ccc(C(=O)NC4CCN(Cc5ccc(C#N)cc5)CC4)nc3)CC2)cc1] |

TABLE 1-continued

| No. | Name | Structure |
|---|---|---|
| 358 | 5-(4-(4-acetylphenoxy)piperidine-1-carbonyl)-N-(1-(4-cyanobenzyl)piperidin-4-yl)picolinamide | 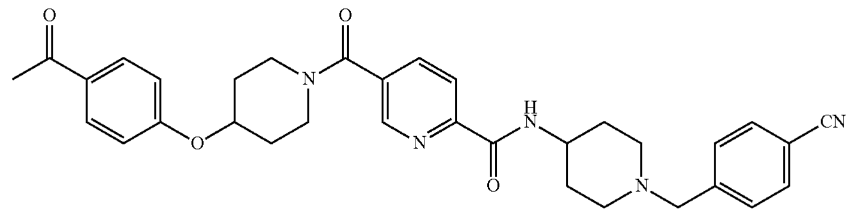 [SMILES: CC(=O)c1ccc(OC2CCN(C(=O)c3ccc(C(=O)NC4CCN(Cc5ccc(C#N)cc5)CC4)nc3)CC2)cc1] |
| 359 | 5-(4-(4-acetylphenoxy)piperidine-1-carbonyl)-N-(6-(4-fluorophenoxy)pyridin-3-yl)picolinamide | 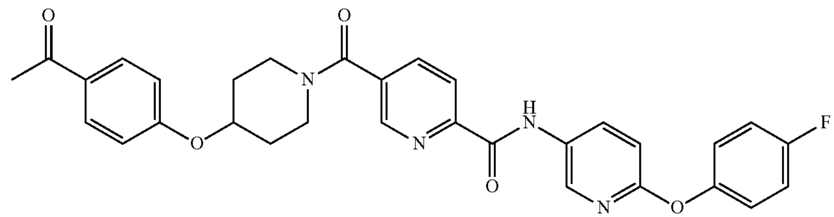 [SMILES: CC(=O)c1ccc(OC2CCN(C(=O)c3ccc(C(=O)Nc4ccc(Oc5ccc(F)cc5)nc4)nc3)CC2)cc1] |
| 360 | 5-(4-(4-(dimethylcarbamoyl)phenoxy)piperidine-1-carbonyl)-N-(6-(4-fluorophenoxy)pyridin-3-yl)picolinamide | 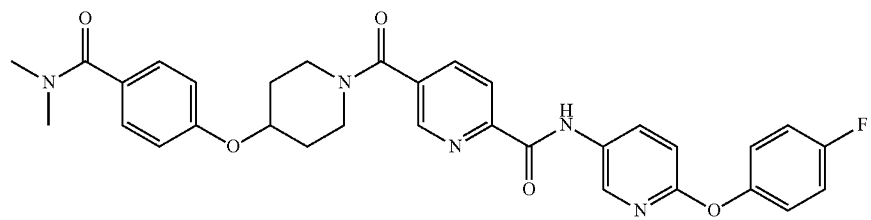 [SMILES: CN(C)C(=O)c1ccc(OC2CCN(C(=O)c3ccc(C(=O)Nc4ccc(Oc5ccc(F)cc5)nc4)nc3)CC2)cc1] |
| 361 | N-(1-(4-cyanobenzyl)piperidin-4-yl)-6-(4-(4-(trifluoromethyl)phenoxy)piperidin-1-yl)pyridazine-3-carboxamide | 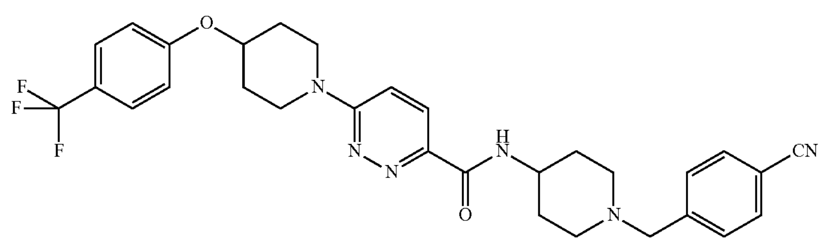 |

TABLE 1-continued

| No. | Name | Structure |
|---|---|---|
| 362 | N-(1-(4-cyanobenzyl)piperidin-4-yl)-6-(4-(4-methoxybenzoyl)piperidin-1-yl)pyridazine-3-carboxamide | 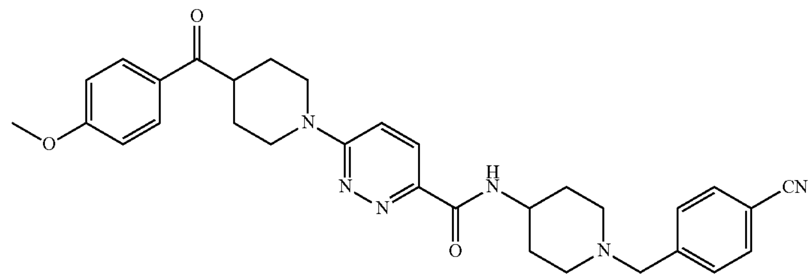 [SMILES: COc1ccc(C(=O)C2CCN(c3ccc(C(=O)NC4CCN(Cc5ccc(C#N)cc5)CC4)nn3)CC2)cc1] |
| 363 | N-(1-(4-cyanobenzyl)piperidin-4-yl)-6-(4-(4-nitrophenoxy)piperidine-1-carbonyl)nicotinamide | 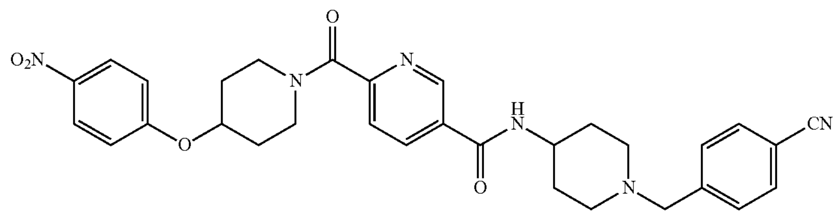 [SMILES: N#Cc1ccc(CN2CCC(NC(=O)c3ccc(C(=O)N4CCC(Oc5ccc([N+](=O)[O-])cc5)CC4)nc3)CC2)cc1] |
| 364 | 6-(4-(4-aminophenoxy)piperidine-1-carbonyl)-N-(1-(4-cyanobenzyl)piperidin-4-yl)nicotinamide | 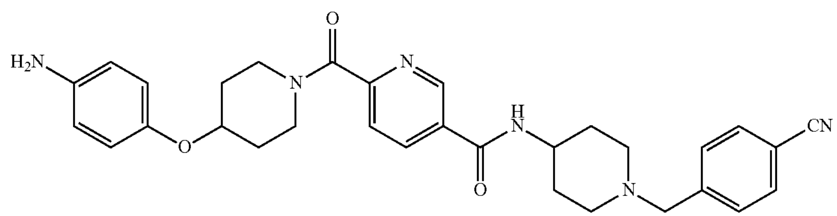 |
| 365 | N-(1-(4-cyanobenzyl)piperidin-4-yl)-5-(4-(4-(pyrrolidin-1-yl)benzoyl)piperidine-1-carbonyl)picolinamide | 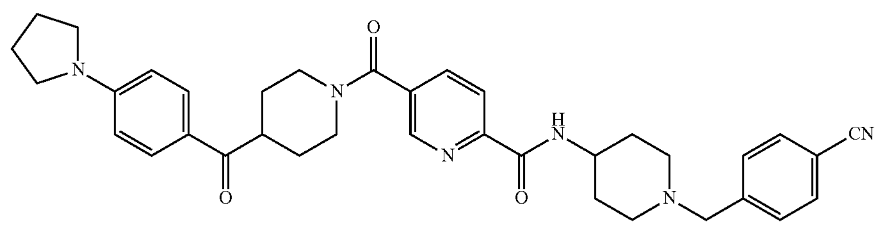 [SMILES: N#Cc1ccc(CN2CCC(NC(=O)c3ccc(C(=O)N4CCC(C(=O)c5ccc(N6CCCC6)cc5)CC4)cn3)CC2)cc1] |

TABLE 1-continued

| No. | Name | Structure |
|---|---|---|
| 366 | 6-(4-(4-acetamidophenoxy)piperidine-1-carbonyl)-N-(1-(4-cyanobenzyl)piperidin-4-yl)nicotinamide | 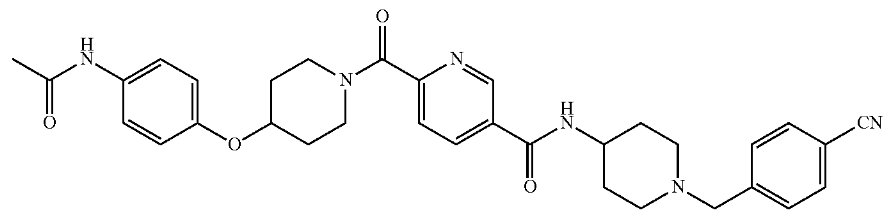 [SMILES: CC(=O)Nc1ccc(OC2CCN(C(=O)c3ccc(C(=O)NC4CCN(Cc5ccc(C#N)cc5)CC4)cn3)CC2)cc1] |
| 367 | N-(1-(4-cyanobenzyl)piperidin-4-yl)-6-(4-(4-(methylsulfonamido)phenoxy)piperidine-1-carbonyl)nicotinamide | 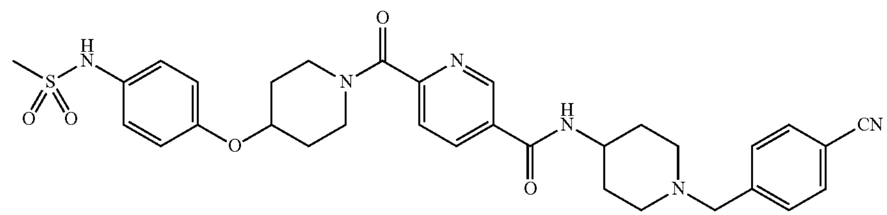 [SMILES: CS(=O)(=O)Nc1ccc(OC2CCN(C(=O)c3ccc(C(=O)NC4CCN(Cc5ccc(C#N)cc5)CC4)cn3)CC2)cc1] |
| 368 | N-(6-(4-fluorophenoxy)pyridin-3-yl)-5-(4-(4-(pyrrolidin-1-yl)benzoyl)piperidine-1-carbonyl)picolinamide | 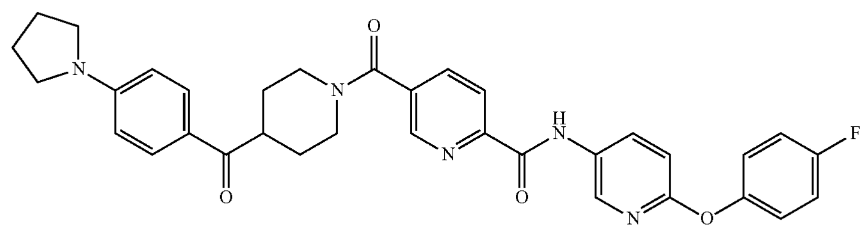 [SMILES: O=C(Nc1ccc(Oc2ccc(F)cc2)nc1)c1ccc(C(=O)N2CCC(C(=O)c3ccc(N4CCCC4)cc3)CC2)cn1] |
| 369 | 5-(4-(4-cyanobenzoyl)piperidine-1-carbonyl)-N-(1-(4-cyanobenzyl)piperidin-4-yl)picolinamide | 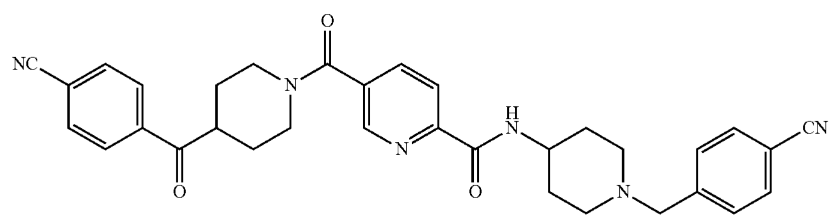 [SMILES: N#Cc1ccc(CN2CCC(NC(=O)c3ccc(C(=O)N4CCC(C(=O)c5ccc(C#N)cc5)CC4)cn3)CC2)cc1] |

TABLE 1-continued

| No. | Name | Structure |
|---|---|---|
| 370 | N-(1-(4-cyanobenzyl)piperidin-4-yl)-6-(4-(4-(dimethylamino)phenoxy)piperidine-1-carbonyl)nicotinamide | 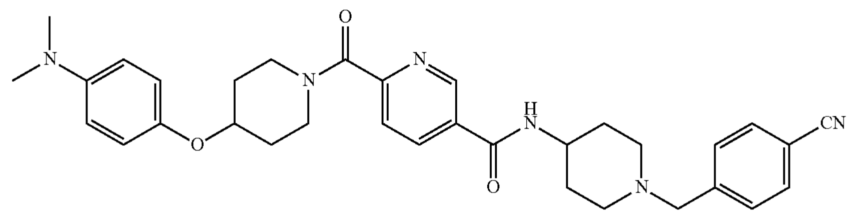 [SMILES: CN(C)c1ccc(OC2CCN(C(=O)c3ccc(C(=O)NC4CCN(Cc5ccc(C#N)cc5)CC4)cn3)CC2)cc1] |
| 371 | N-(1-(4-cyanobenzyl)piperidin-4-yl)-6-(4-(4-(17-oxo-1-((3aS,4S,6aR)-2-oxohexahydro-1H-thieno[3,4-d]imidazol-4-yl)-4,7,10,13-tetraoxa-16-azaicosanamido)phenoxy)piperidine-1-carbonyl)nicotinamide | 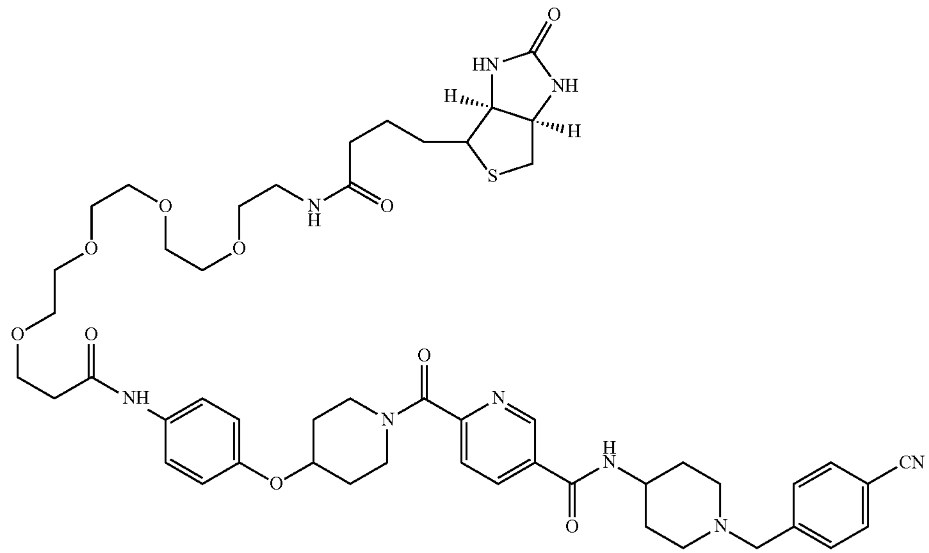 [SMILES: N#Cc1ccc(CN2CCC(NC(=O)c3ccc(C(=O)N4CCC(Oc5ccc(NC(=O)CCOCCOCCOCCOCCNC(=O)CCCC6SC[C@@H]7NC(=O)N[C@H]67)cc5)CC4)nc3)CC2)cc1] |
| 372 | N-(1-(4-cyanobenzyl)piperidin-4-yl)-5-(4-(4-(methylthio)benzoyl)piperidine-1-carbonyl)picolinamide | 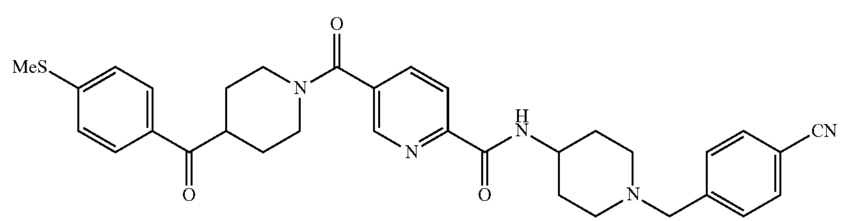 [SMILES: CSc1ccc(C(=O)C2CCN(C(=O)c3ccc(C(=O)NC4CCN(Cc5ccc(C#N)cc5)CC4)nc3)CC2)cc1] |

TABLE 1-continued

| No. | Name | Structure |
|---|---|---|
| 373 | 6-(4-(4-methoxybenzoyl)piperidine-1-carbonyl)-N-(1-(4-nitrobenzyl)piperidin-4-yl)nicotinamide | 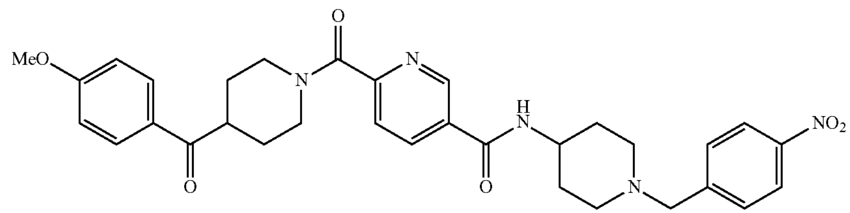 [SMILES: COc1ccc(C(=O)C2CCN(C(=O)c3ccc(C(=O)NC4CCN(Cc5ccc([N+](=O)[O-])cc5)CC4)cn3)CC2)cc1] |
| 374 | 1-(4-cyanobenzyl)-4-(5-(4-(methylsulfinyl)benzoyl)piperidine-1-carbonyl)picolinamido)piperidine 1-oxide | 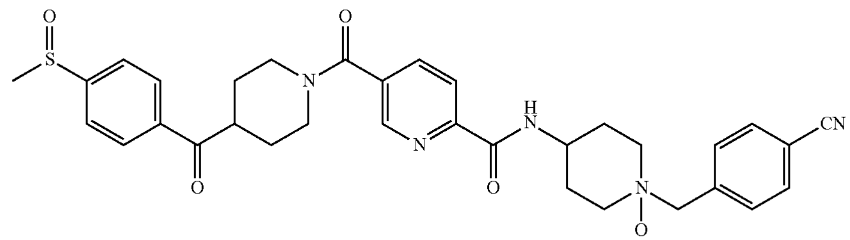 |
| 375 | 5-(4-(4-(1H-pyrazol-1-yl)benzoyl)piperidine-1-carbonyl)-N-(1-(4-cyanobenzyl)piperidin-4-yl)picolinamide | 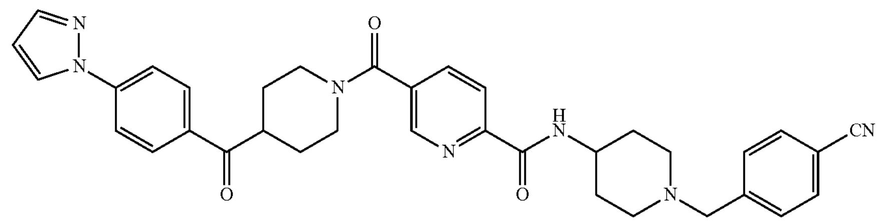 [SMILES: N#Cc1ccc(CN2CCC(NC(=O)c3ccc(C(=O)N4CCC(C(=O)c5ccc(-n6cccn6)cc5)CC4)cn3)CC2)cc1] |
| 376 | N-(1-(4-cyanobenzyl)piperidin-4-yl)-5-(4-(4-morpholinobenzoyl)piperidine-1-carbonyl)picolinamide | 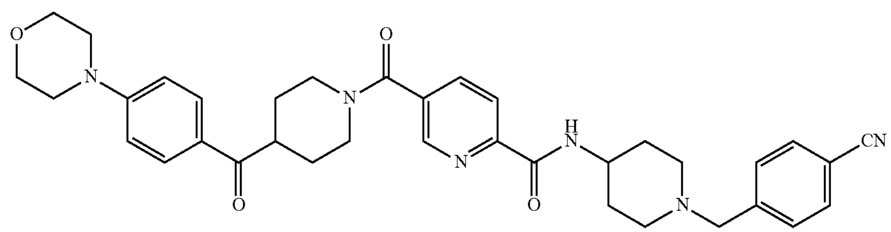 [SMILES: N#Cc1ccc(CN2CCC(NC(=O)c3ccc(C(=O)N4CCC(C(=O)c5ccc(N6CCOCC6)cc5)CC4)cn3)CC2)cc1] |

TABLE 1-continued

| No. | Name | Structure |
|-----|------|-----------|
| 377 | N-(1-(4-cyanobenzyl)piperidin-4-yl)-6-(4-(4-(pyrrolidin-1-yl)benzoyl)piperidine-1-carbonyl)nicotinamide | 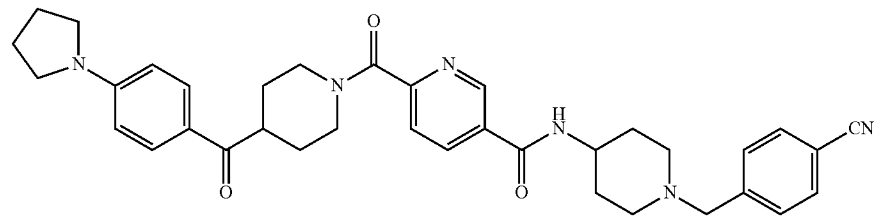 [SMILES: N#Cc1ccc(CN2CCC(NC(=O)c3ccc(C(=O)N4CCC(C(=O)c5ccc(N6CCCC6)cc5)CC4)nc3)CC2)cc1] |
| 378 | N-(1-(4-cyanobenzyl)piperidin-4-yl)-6-(4-(4-methoxy-2-nitrophenoxy)piperidine-1-carbonyl)nicotinamide | 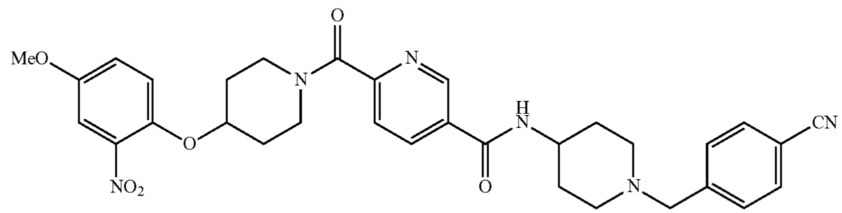 [SMILES: COc1ccc(OC2CCN(C(=O)c3ccc(C(=O)NC4CCN(Cc5ccc(C#N)cc5)CC4)cn3)CC2)c([N+](=O)[O-])c1] |
| 379 | N-(6-(4-fluorophenoxy)pyridin-3-yl)-5-(4-(4-morpholinobenzoyl)piperidine-1-carbonyl)picolinamide | 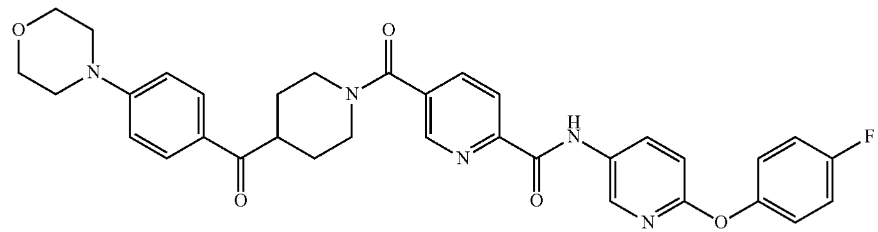 [SMILES: O=C(Nc1ccc(Oc2ccc(F)cc2)nc1)c1ccc(C(=O)N2CCC(C(=O)c3ccc(N4CCOCC4)cc3)CC2)cn1] |
| 380 | N-(1-(4-cyanobenzyl)piperidin-4-yl)-5-(4-(4-(4-methylpiperazin-1-yl)benzoyl)piperidine-1-carbonyl)picolinamide | 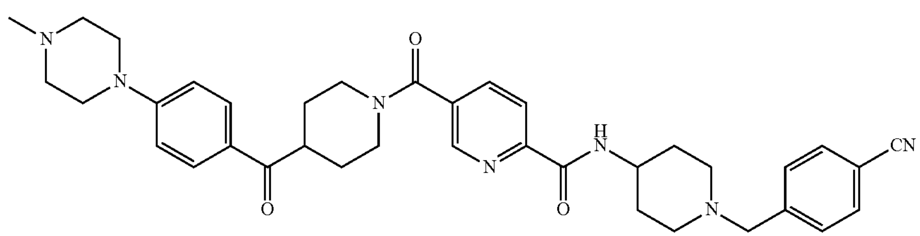 [SMILES: CN1CCN(c2ccc(C(=O)C3CCN(C(=O)c4ccc(C(=O)NC5CCN(Cc6ccc(C#N)cc6)CC5)nc4)CC3)cc2)CC1] |

| No. | Name | Structure |
|---|---|---|
| 381 | N-(1-(4-fluorobenzyl)piperidin-4-yl)-6-(4-(4-(pyrrolidin-1-yl)benzoyl)piperidine-1-carbonyl)nicotinamide | 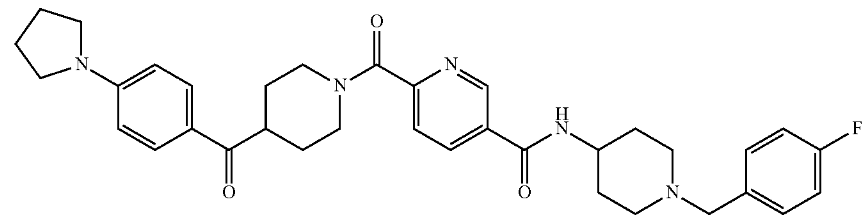 [SMILES: O=C(NC1CCN(Cc2ccc(F)cc2)CC1)c1ccc(C(=O)N2CCC(C(=O)c3ccc(N4CCCC4)cc3)CC2)nc1] |
| 382 | N-(6-(4-fluorophenoxy)pyridin-3-yl)-6-(4-(4-(pyrrolidin-1-yl)benzoyl)piperidine-1-carbonyl)nicotinamide | 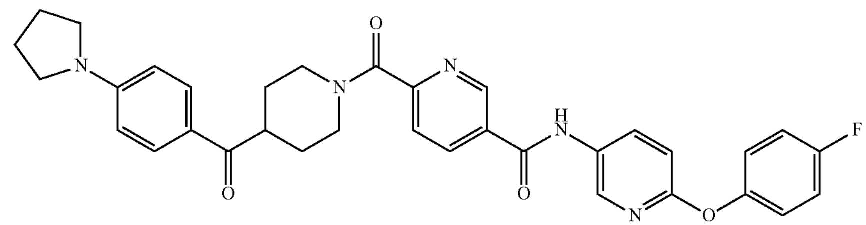 [SMILES: O=C(Nc1ccc(Oc2ccc(F)cc2)nc1)c1ccc(C(=O)N2CCC(C(=O)c3ccc(N4CCCC4)cc3)CC2)nc1] |
| 383 | 6-(4-(2-acetamido-4-methoxyphenoxy)piperidine-1-carbonyl)-N-(1-(4-cyanobenzyl)piperidin-4-yl)nicotinamide | 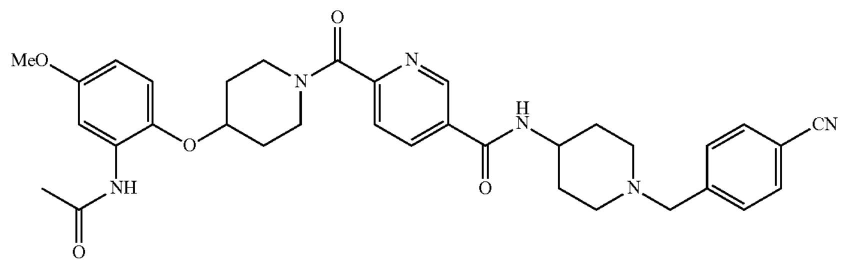 [SMILES: COc1ccc(OC2CCN(C(=O)c3ccc(C(=O)NC4CCN(Cc5ccc(C#N)cc5)CC4)cn3)CC2)c(NC(C)=O)c1] |
| 384 | 6-(4-(2-amino-4-methoxyphenoxy)piperidine-1-carbonyl)-N-(1-(4-cyanobenzyl)piperidin-4-yl)nicotinamide | 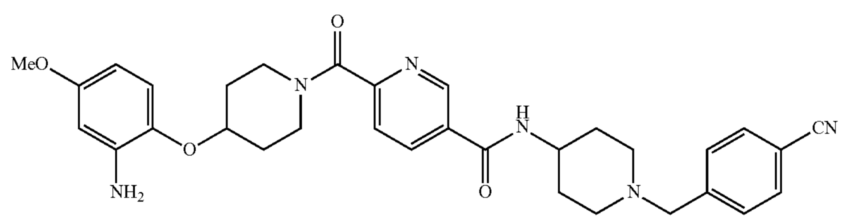 |

TABLE 1-continued

| No. | Name | Structure |
|---|---|---|
| 385 | N-(1-(4-cyanobenzyl)piperidin-4-yl)-6-(4-(2-(dimethylamino)-4-methoxyphenoxy)piperidine-1-carbonyl)nicotinamide | 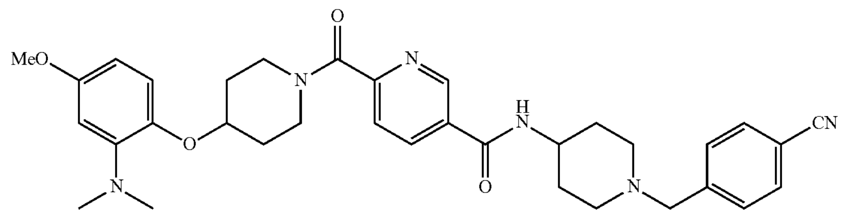 [SMILES: COc1ccc(OC2CCN(C(=O)c3ccc(C(=O)NC4CCN(Cc5ccc(C#N)cc5)CC4)cn3)CC2)c(N(C)C)c1] |
| 386 | N3,N6-bis(1-(4-cyanobenzyl)piperidin-4-yl)pyridazine-3,6-dicarboxamide | 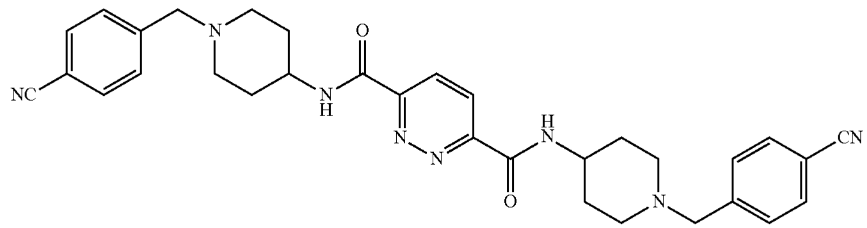 [SMILES: N#Cc1ccc(CN2CCC(NC(=O)c3ccc(C(=O)NC4CCN(Cc5ccc(C#N)cc5)CC4)nn3)CC2)cc1] |
| 387 | N-(1-(4-cyanobenzyl)piperidin-4-yl)-6-(4-(4-methoxybenzoyl)piperidine-1-carbonyl)pyridazine-3-carboxamide | 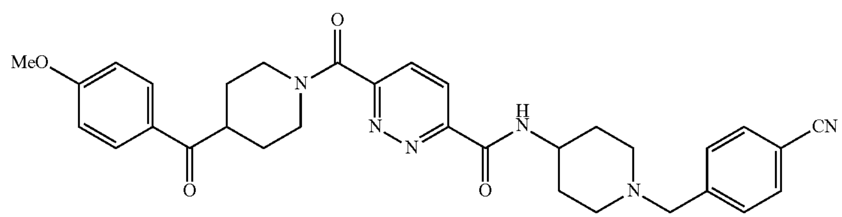 [SMILES: COc1ccc(C(=O)C2CCN(C(=O)c3ccc(C(=O)NC4CCN(Cc5ccc(C#N)cc5)CC4)nn3)CC2)cc1] |
| 388 | N-(1-(4-cyanobenzyl)piperidin-4-yl)-6-(4-(4-cyanophenoxy)piperidine-1-carbonyl)pyridazine-3-carboxamide | 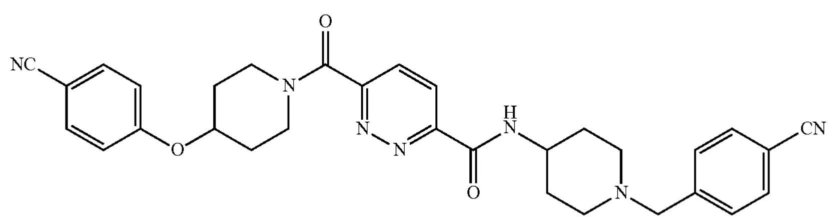 [SMILES: N#Cc1ccc(CN2CCC(NC(=O)c3ccc(C(=O)N4CCC(Oc5ccc(C#N)cc5)CC4)nn3)CC2)cc1] |

TABLE 1-continued

| No. | Name | Structure |
|---|---|---|
| 389 | N-(1-(4-cyanobenzyl)piperidin-4-yl)-6-(4-(4-methoxy-2-(methylsulfonamido)phenoxy)piperidine-1-carbonyl)nicotinamide | 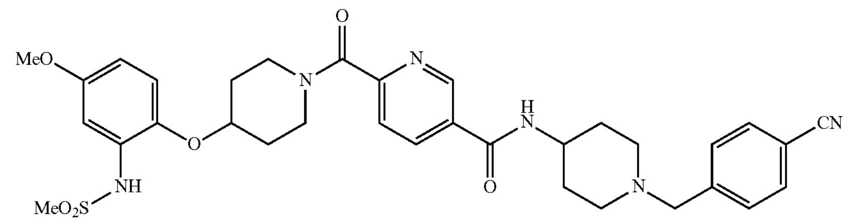 [SMILES: COc1ccc(OC2CCN(C(=O)c3ccc(C(=O)NC4CCN(Cc5ccc(C#N)cc5)CC4)cn3)CC2)c(NS(C)(=O)=O)c1] |
| 390 | 6-(4-(4-acetylphenoxy)piperidine-1-carbonyl)-N-(1-(4-cyanobenzyl)piperidin-4-yl)nicotinamide | 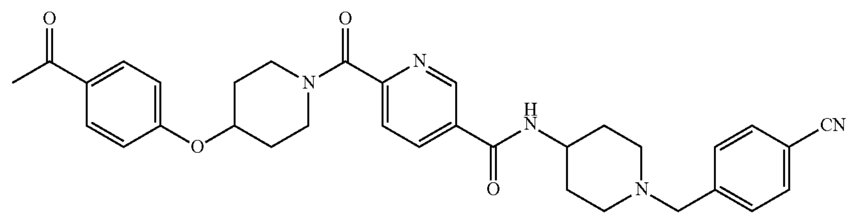 |
| 391 | 6-(4-(4-acetylphenoxy)piperidine-1-carbonyl)-N-(1-(4-fluorobenzyl)piperidin-4-yl)nicotinamide | 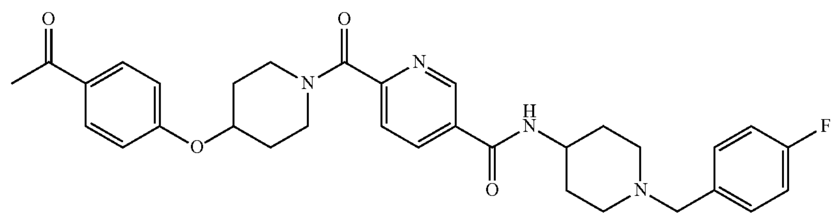 [SMILES: CC(=O)c1ccc(OC2CCN(C(=O)c3ccc(C(=O)NC4CCN(Cc5ccc(F)cc5)CC4)cn3)CC2)cc1] |
| 392 | 6-(4-(4-(1H-pyrazol-1-yl)benzoyl)piperidine-1-carbonyl)-N-(1-(4-fluorobenzyl)piperidin-4-yl)nicotinamide | 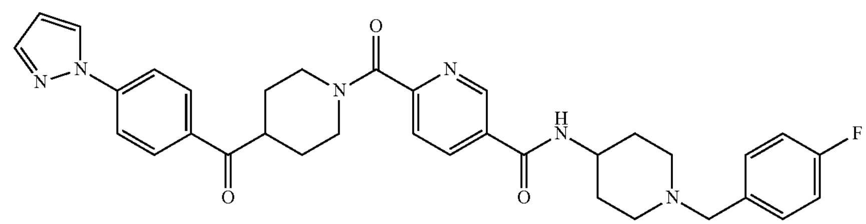 [SMILES: O=C(NC1CCN(Cc2ccc(F)cc2)CC1)c1ccc(C(=O)N2CCC(C(=O)c3ccc(-n4cccn4)cc3)CC2)nc1] |

TABLE 1-continued

| No. | Name | Structure |
|-----|------|-----------|
| 393 | 6-(4-(4-(1H-pyrazol-1-yl)benzoyl)piperidine-1-carbonyl)-N-(1-(4-cyanobenzyl)piperidin-4-yl)nicotinamide | 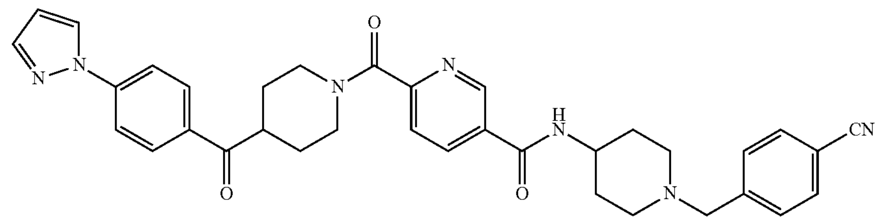 [SMILES: N#Cc1ccc(CN2CCC(NC(=O)c3ccc(C(=O)N4CCC(C(=O)c5ccc(-n6cccn6)cc5)CC4)nc3)CC2)cc1] |
| 394 | N-(1-(4-cyanobenzyl)piperidin-4-yl)-6-(4-(4-methoxy-2-(17-oxo-21-((3aS,4S,6aR)-2-oxohexahydro-1H-thieno[3,4-d]imidazol-4-yl)-4,7,10,13-tetraoxa-16-azahenicosanamido)phenoxy)piperidine-1-carbonyl)nicotinamide | 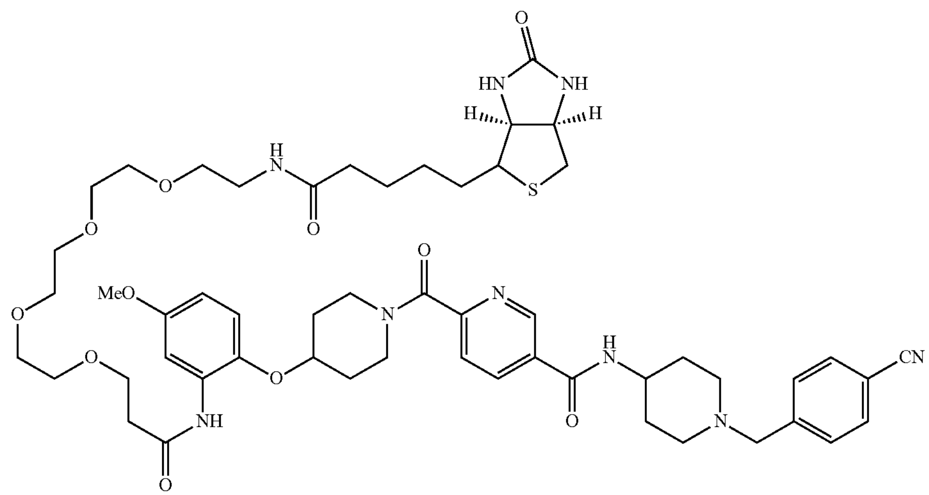 [SMILES: COc1ccc(OC2CCN(C(=O)c3ccc(C(=O)NC4CCN(Cc5ccc(C#N)cc5)CC4)cn3)CC2)c(NC(=O)CCOCCOCCOCCOCCNC(=O)CCCCC2SC[C@@H]3NC(=O)N[C@H]23)c1] |
| 395 | 6-(4-(4-acetylphenoxy)piperidine-1-carbonyl)-N-(6-(4-fluorophenoxy)pyridin-3-yl)nicotinamide | 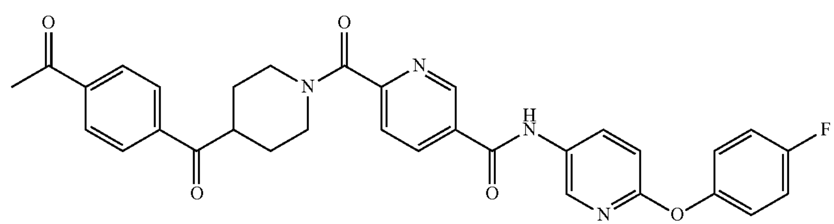 [SMILES: CC(=O)c1ccc(C(=O)C2CCN(C(=O)c3ccc(C(=O)Nc4ccc(Oc5ccc(F)cc5)nc4)cn3)CC2)cc1] |

TABLE 1-continued

| No. | Name | Structure |
|-----|------|-----------|
| 396 | N-(1-(4-fluorobenzyl)piperidin-4-yl)-6-(4-(4-(methylsulfonyl)phenoxy)piperidine-1-carbonyl)nicotinamide | 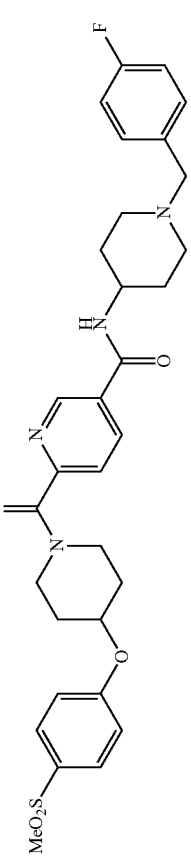 |
| 397 | N-(1-(4-cyanobenzyl)piperidin-4-yl)-6-(4-(4-(methylsulfonyl)phenoxy)piperidine-1-carbonyl)nicotinamide | 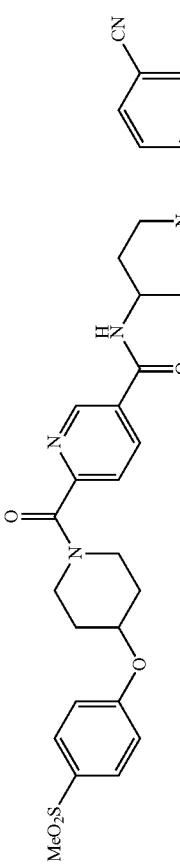 |
| 398 | N-(4-(4-cyanophenoxy)cyclohexyl)-6-(4-(4-(methylsulfonyl)phenoxy)piperidine-1-carbonyl)nicotinamide | 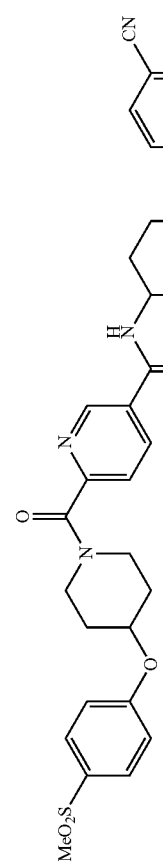 |
| 399 | N-(1-(4-cyanobenzyl)piperidin-4-yl)-6-(4-(4-(methylsulfonyl)phenoxy)piperidine-1-carbonyl)pyridazine-3-carboxamide | 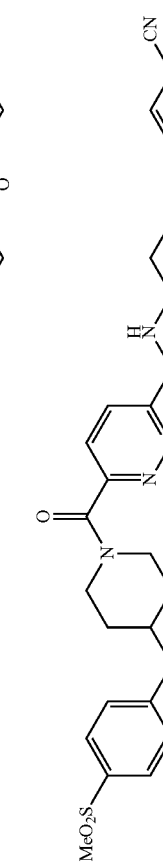 |

TABLE 1-continued

| No. | Name | Structure |
|---|---|---|
| 400 | N-(1-(4-aminobenzyl)piperidin-4-yl)-6-(4-(4-methoxybenzoyl)piperidine-1-carbonyl)nicotinamide | 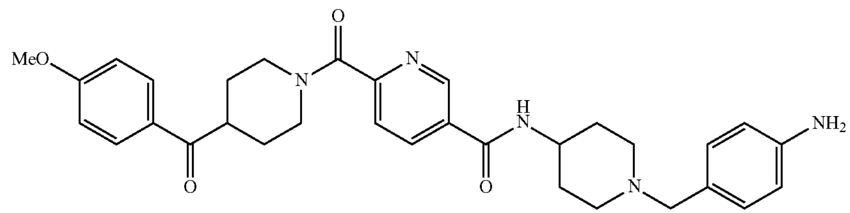 [SMILES: COc1ccc(C(=O)C2CCN(C(=O)c3ccc(C(=O)NC4CCN(Cc5ccc(N)cc5)CC4)cn3)CC2)cc1] |
| 401 | N-(1-(4-acetamidobenzyl)piperidin-4-yl)-6-(4-(4-methoxybenzoyl)piperidine-1-carbonyl)nicotinamide | 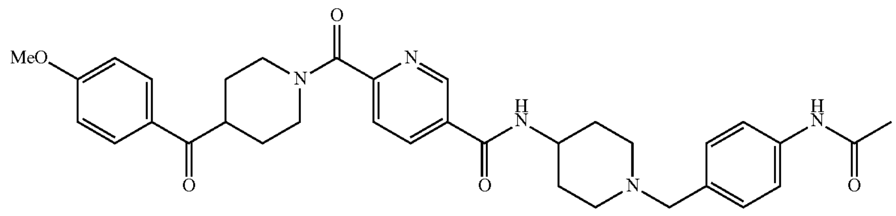 [SMILES: COc1ccc(C(=O)C2CCN(C(=O)c3ccc(C(=O)NC4CCN(Cc5ccc(NC(C)=O)cc5)CC4)cn3)CC2)cc1] |
| 402 | 6-(4-(4-acetylphenoxy)piperidine-1-carbonyl)-N-(4-(4-cyanophenoxy)cyclohexyl)nicotinamide | 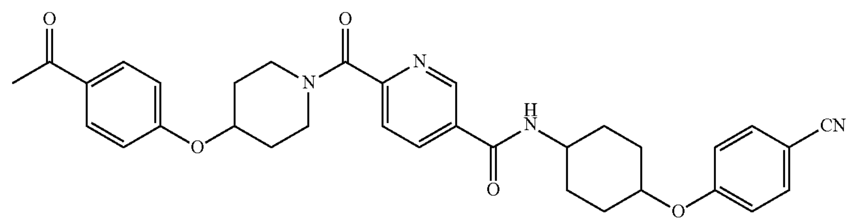 [SMILES: CC(=O)c1ccc(OC2CCN(C(=O)c3ccc(C(=O)NC4CCC(Oc5ccc(C#N)cc5)CC4)cn3)CC2)cc1] |
| 403 | 5-(4-(4-methoxybenzoyl)piperidine-1-carbonyl)-N-(1-(4-(14-oxo-18-((3aS,4S,6aR)-2-oxohexahydro-1H-thieno[3,4-d]imidazol-4-yl)-4,7,10-trioxa-13-azaoctadecanamido)benzyl)piperidin-4-yl)picolinamide | 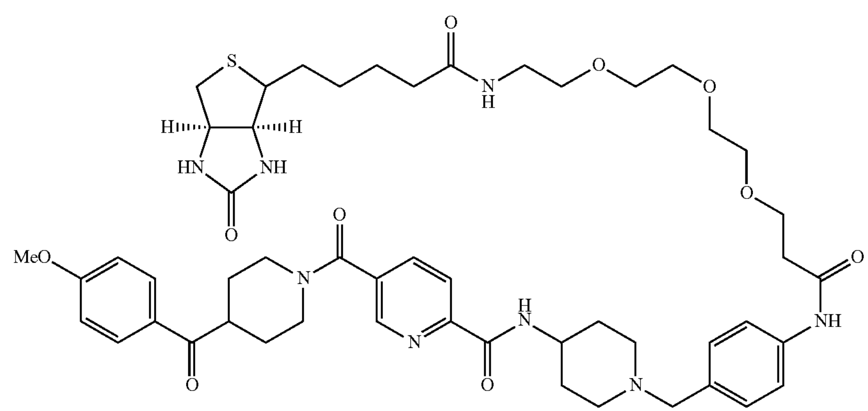 [SMILES: COc1ccc(C(=O)C2CCN(C(=O)c3ccc(C(=O)NC4CCN(Cc5ccc(NC(=O)CCOCCOCCOCCNC(=O)CCCCC6SC[C@@H]7NC(=O)N[C@H]67)cc5)CC4)nc3)CC2)cc1] |

TABLE 1-continued

| No. | Name | Structure |
|---|---|---|
| 404 | 6-(4-(4-fluorobenzyl)piperazine-1-carbonyl)-N-(1-(4-fluorophenyl)piperidin-4-yl)nicotinamide | 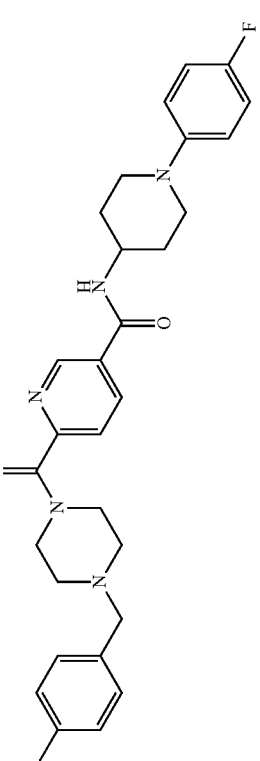 |
| 405 | 6-(4-(4-fluorobenzyl)piperazine-1-carbonyl)-N-(1-(4-methoxyphenyl)piperidin-4-yl)nicotinamide | 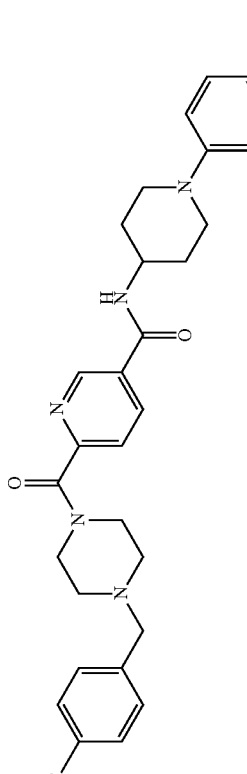 |
| 406 | 6-(4-(4-acetamidophenoxy)piperidine-1-carbonyl)-N-(1-(4-fluorobenzyl)piperidin-4-yl)nicotinamide | 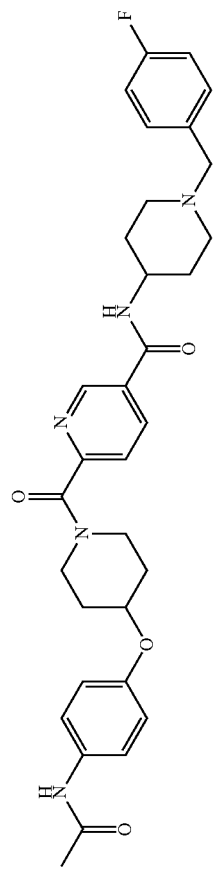 |
| 407 | 6-(4-(4-acetamidophenoxy)piperidine-1-carbonyl)-N-(1-(4-methoxybenzyl)piperidin-4-yl)nicotinamide | 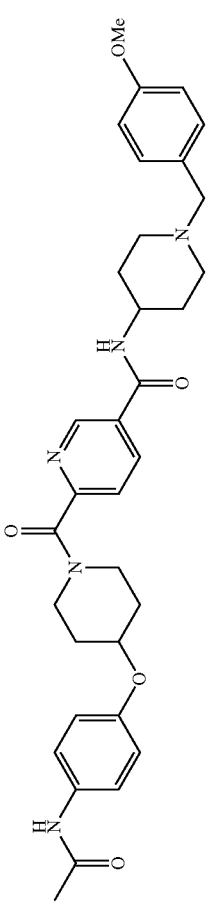 |

TABLE 1-continued

| No. | Name | Structure |
|---|---|---|
| 408 | 5-(4-(4-acetamidophenoxy)piperidine-1-carbonyl)-N-(6-(4-fluorophenoxy)pyridin-3-yl)picolinamide | 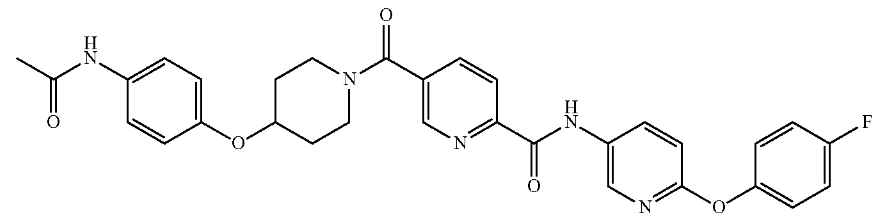 [SMILES: CC(=O)Nc1ccc(OC2CCN(C(=O)c3ccc(C(=O)Nc4ccc(Oc5ccc(F)cc5)nc4)nc3)CC2)cc1] |
| 409 | N-(1-(4-cyanobenzyl)piperidin-4-yl)-6-(4-(cyclopropanecarboxamido phenoxy)piperidine-1-carbonyl)nicotinamide | 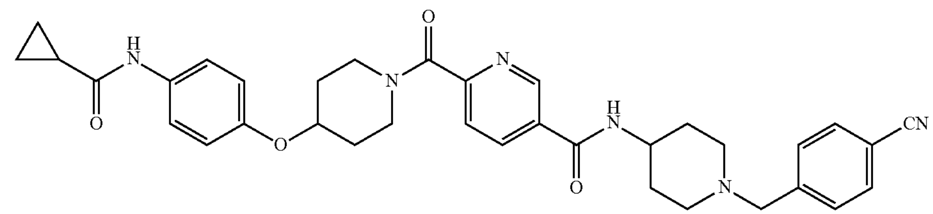 [SMILES: N#Cc1ccc(CN2CCC(NC(=O)c3ccc(C(=O)N4CCC(Oc5ccc(NC(=O)C6CC6)cc5)CC4)nc3)CC2)cc1] |
| 410 | N-(1-(4-cyanobenzyl)piperidin-4-yl)-5-(4-(4-(trifluoromethylthio)phenoxy)piperidine-1-carbonyl)picolinamide | 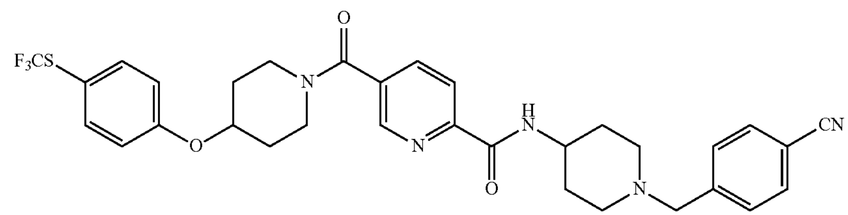 |
| 411 | 6-(4-(3-acetamidophenoxy)piperidine-1-carbonyl)-N-(1-(4-cyanobenzyl)piperidin-4-yl)nicotinamide | 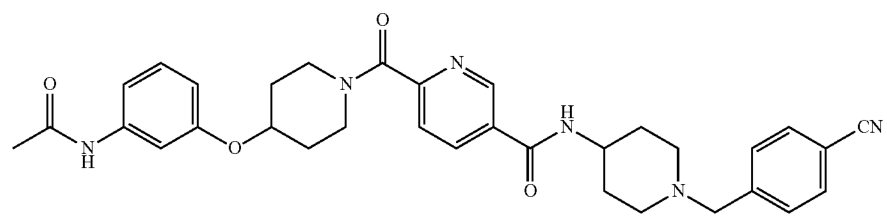 [SMILES: CC(=O)Nc1cccc(OC2CCN(C(=O)c3ccc(C(=O)NC4CCN(Cc5ccc(C#N)cc5)CC4)cn3)CC2)c1] |

TABLE 1-continued

| No. | Name | Structure |
|---|---|---|
| 412 | 6-(4-(3-acetamidophenoxy)piperidine-1-carbonyl)-N-(1-(4-methoxybenzyl)piperidin-4-yl)nicotinamide | 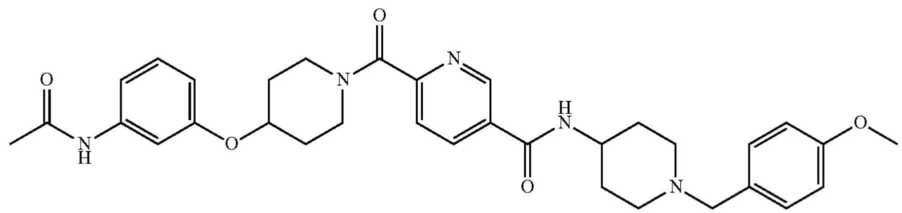 [SMILES: COc1ccc(CN2CCC(NC(=O)c3ccc(C(=O)N4CCC(Oc5cccc(NC(C)=O)c5)CC4)nc3)CC2)cc1] |
| 413 | 6-(4-(3-acetamidophenoxy)piperidine-1-carbonyl)-N-(1-(4-fluorobenzyl)piperidin-4-yl)nicotinamide | 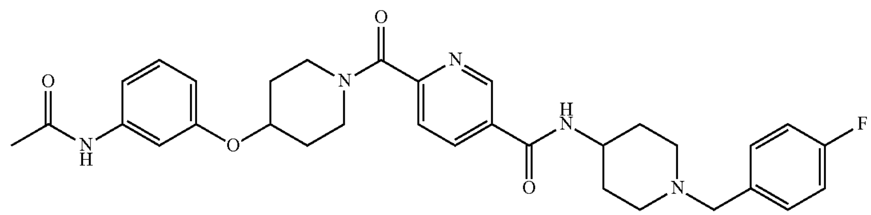 [SMILES: CC(=O)Nc1cccc(OC2CCN(C(=O)c3ccc(C(=O)NC4CCN(Cc5ccc(F)cc5)CC4)cn3)CC2)c1] |
| 414 | 6-(4-(3-acetamidophenoxy)piperidine-1-carbonyl)-N-(6-(4-fluorophenoxy)pyridin-3-yl)nicotinamide | 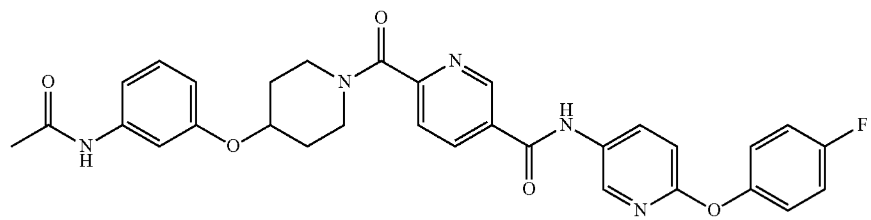 [SMILES: CC(=O)Nc1cccc(OC2CCN(C(=O)c3ccc(C(=O)Nc4ccc(Oc5ccc(F)cc5)nc4)cn3)CC2)c1] |
| 415 | N-(1-(4-cyanobenzyl)piperidin-4-yl)-5-(4-(4-(trifluoromethylsulfonyl)phenoxy)piperidine-1-carbonyl)picolinamide | 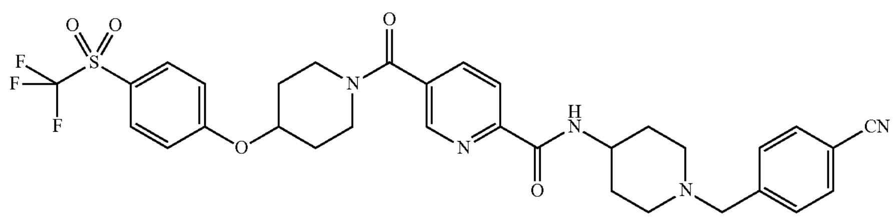 [SMILES: N#Cc1ccc(CN2CCC(NC(=O)c3ccc(C(=O)N4CCC(Oc5ccc(S(=O)(=O)C(F)(F)F)cc5)CC4)cn3)CC2)cc1] |

TABLE 1-continued

| No. | Name | Structure |
|---|---|---|
| 416 | tert-butyl 3-(5-(1-(4-cyanobenzyl)piperidin-4-ylcarbamoyl)-2-(4-(4-methoxybenzoyl)piperidine-1-carbonyl)pyridin-3-yl)propylcarbamate | 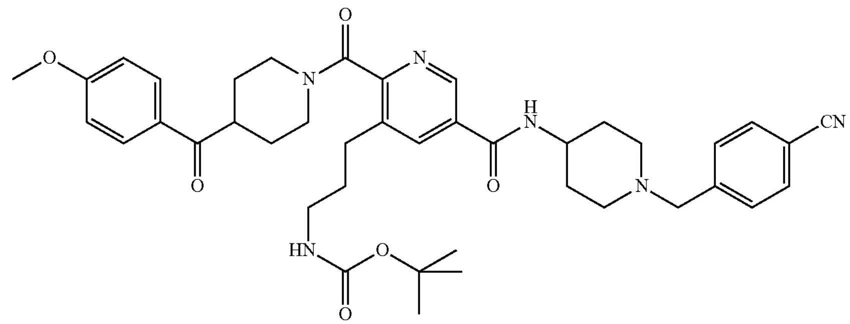 [SMILES: COc1ccc(C(=O)C2CCN(C(=O)c3ncc(C(=O)NC4CCN(Cc5ccc(C#N)cc5)CC4)cc3CCCNC(=O)OC(C)(C)C)CC2)cc1] |
| 417 | N-(1-(4-cyanophenyl)piperidin-4-yl)-6-(4-(4-fluorobenzyl)piperazine-1-carbonyl)nicotinamide | 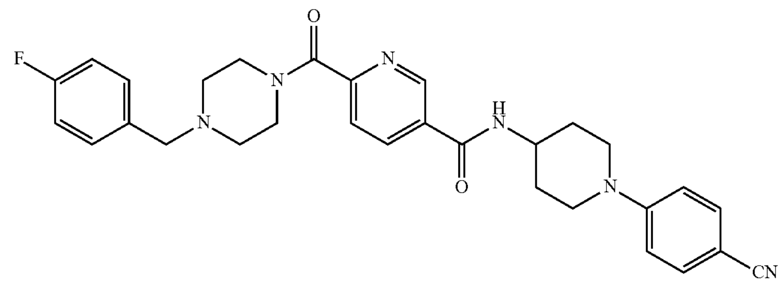 [SMILES: N#Cc1ccc(N2CCC(NC(=O)c3ccc(C(=O)N4CCN(Cc5ccc(F)cc5)CC4)nc3)CC2)cc1] |
| 418 | 6-(4-(4-cyanophenoxy)piperidine-1-carbonyl)-N-(1-(4-cyanophenyl)piperidin-4-yl)nicotinamide | 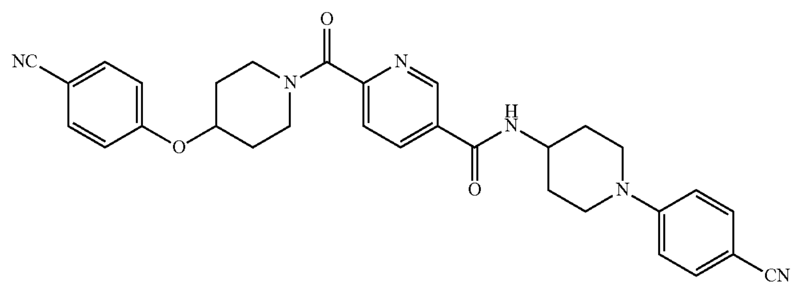 [SMILES: N#Cc1ccc(OC2CCN(C(=O)c3ccc(C(=O)NC4CCN(c5ccc(C#N)cc5)CC4)cn3)CC2)cc1] |

TABLE 1-continued

| No. | Name | Structure |
|-----|------|-----------|
| 419 | N-(1-(4-cyanobenzyl)piperidin-4-yl)-5-(4-(thiophene-2-carbonyl)piperidine-1-carbonyl)picolinamide | 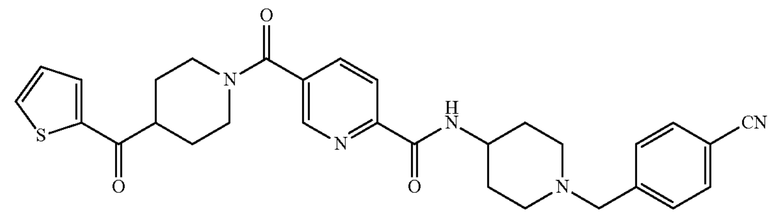 [SMILES: N#Cc1ccc(CN2CCC(NC(=O)c3ccc(C(=O)N4CCC(C(=O)c5cccs5)CC4)cn3)CC2)cc1] |
| 420 | 6-(4-(4-cyanophenoxy)piperidine-1-carbonyl)-N-(1-(4-(methylsulfonyl)phenyl)piperidin-4-yl)nicotinamide | 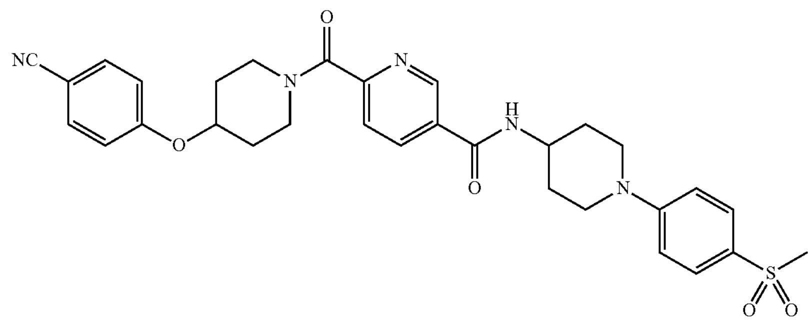 [SMILES: CS(=O)(=O)c1ccc(N2CCC(NC(=O)c3ccc(C(=O)N4CCC(Oc5ccc(C#N)cc5)CC4)nc3)CC2)cc1] |
| 421 | 6-(4-(4-fluorobenzyl)piperazine-1-carbonyl)-N-(1-(4-(methylsulfonyl)phenyl)piperidin-4-yl)nicotinamide | 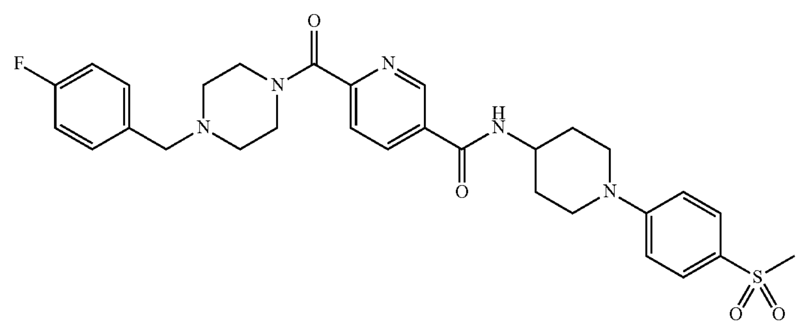 [SMILES: CS(=O)(=O)c1ccc(N2CCC(NC(=O)c3ccc(C(=O)N4CCN(Cc5ccc(F)cc5)CC4)nc3)CC2)cc1] |

TABLE 1-continued

| No. | Name | Structure |
|---|---|---|
| 422 | 6-(4-(4-cyanophenoxy)piperidine-1-carbonyl)-N-(1-(4-fluorophenyl)piperidin-4-yl)nicotinamide | 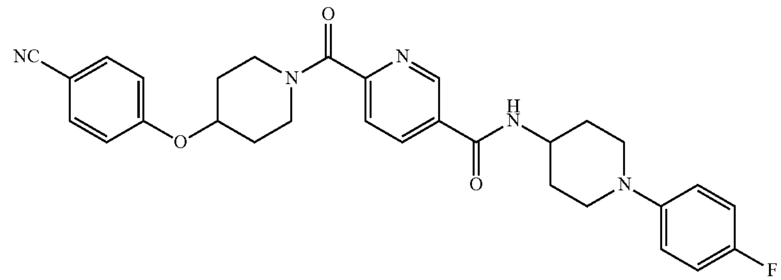 [SMILES: N#Cc1ccc(OC2CCN(C(=O)c3ccc(C(=O)NC4CCN(c5ccc(F)cc5)CC4)cn3)CC2)cc1] |
| 423 | 6-(4-(4-cyanophenoxy)piperidine-1-carbonyl)-N-(1-(4-methoxyphenyl)piperidin-4-yl)nicotinamide | 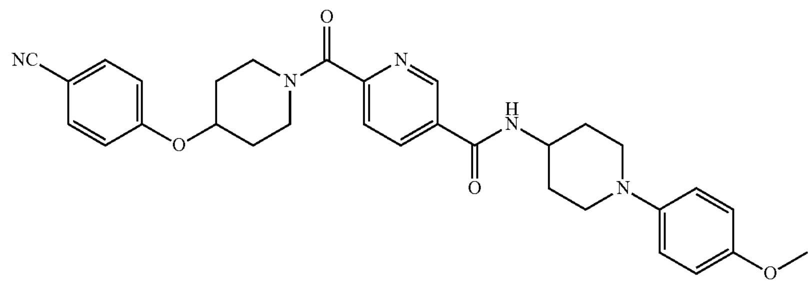 [SMILES: COc1ccc(N2CCC(NC(=O)c3ccc(C(=O)N4CCC(Oc5ccc(C#N)cc5)CC4)nc3)CC2)cc1] |
| 424 | 6-(4-(4-methoxybenzoyl)piperidine-1-carbonyl)-N-(1-(3-(trifluoromethoxy)benzyl)piperidin-4-yl)nicotinamide | 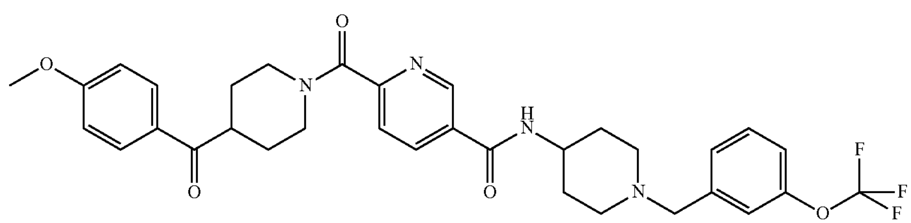 [SMILES: COc1ccc(C(=O)C2CCN(C(=O)c3ccc(C(=O)NC4CCN(Cc5cccc(OC(F)(F)F)c5)CC4)cn3)CC2)cc1] |
| 425 | 6-(4-(4-methoxybenzoyl)piperidine-1-carbonyl)-N-(1-(3-methoxybenzyl)piperidin-4-yl)nicotinamide | 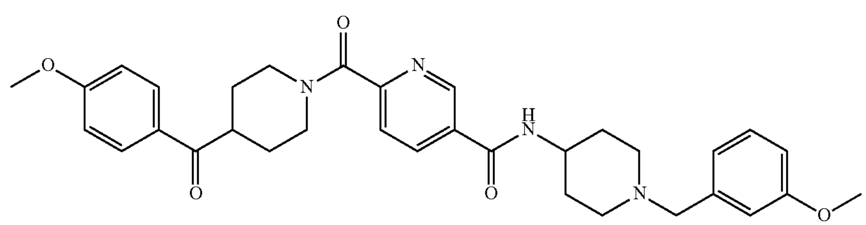 |

TABLE 1-continued

| No. | Name | Structure |
|---|---|---|
| 426 | N-((3S,4R)-3-fluoro-1-((5-methylisoxazol-3-yl)methyl)piperidin-4-yl)-6-(4-(4-methoxybenzoyl)piperidine-1-carbonyl)nicotinamide | 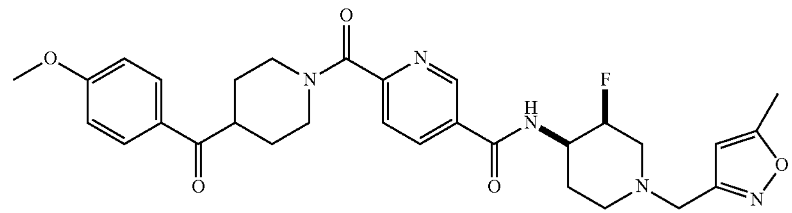 |
| 427 | N-((3S,4R)-3-fluoro-1-((2-methylthiazol-4-yl)methyl)piperidin-4-yl)-6-(4-(4-methoxybenzoyl)piperidine-1-carbonyl)nicotinamide | 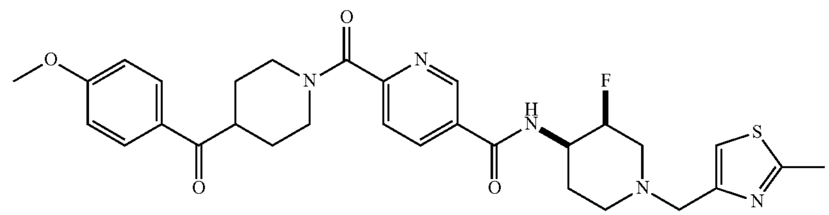 |
| 428 | 6-(4-(4-acetamidophenoxy)piperidine-1-carbonyl)-N-(1-(3-(trifluoromethoxy)benzyl)piperidin-4-yl)nicotinamide | 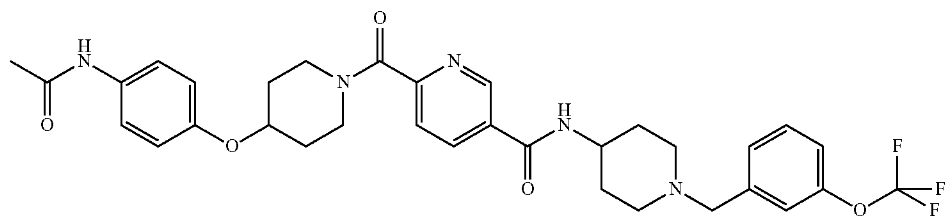 [SMILES: CC(=O)Nc1ccc(OC2CCN(C(=O)c3ccc(C(=O)NC4CCN(Cc5cccc(OC(F)(F)F)c5)CC4)cn3)CC2)cc1] |
| 429 | 6-(4-(3-acetamidophenoxy)piperidine-1-carbonyl)-N-(1-(3-(trifluoromethoxy)benzyl)piperidin-4-yl)nicotinamide | 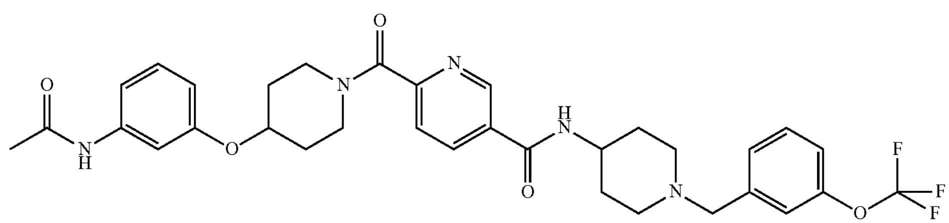 [SMILES: CC(=O)Nc1cccc(OC2CCN(C(=O)c3ccc(C(=O)NC4CCN(Cc5cccc(OC(F)(F)F)c5)CC4)cn3)CC2)c1] |

TABLE 1-continued

| No. | Name | Structure |
|-----|------|-----------|
| 430 | 6-(4-(4-methoxybenzoyl)piperidine-1-carbonyl)-N-(1-(4-(trifluoromethoxy)benzyl)piperidin-4-yl)nicotinamide | 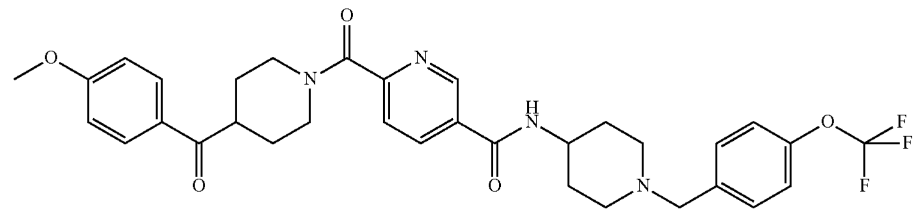 [SMILES: COc1ccc(C(=O)C2CCN(C(=O)c3ccc(C(=O)NC4CCN(Cc5ccc(OC(F)(F)F)cc5)CC4)cn3)CC2)cc1] |
| 431 | N-(1-(4-cyanobenzyl)piperidin-4-yl)-6-(4-(3-(cyclopropanecarboxamido)phenoxy)piperidine-1-carbonyl)nicotinamide | 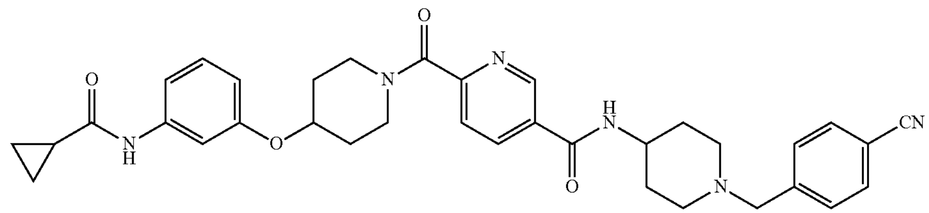 [SMILES: N#Cc1ccc(CN2CCC(NC(=O)c3ccc(C(=O)N4CCC(Oc5cccc(NC(=O)C6CC6)c5)CC4)nc3)CC2)cc1] |
| 432 | 6-(4-(3-(cyclopropanecarboxamido)phenoxy)piperidine-1-carbonyl)-N-(1-(4-fluorobenzyl)piperidin-4-yl)nicotinamide | 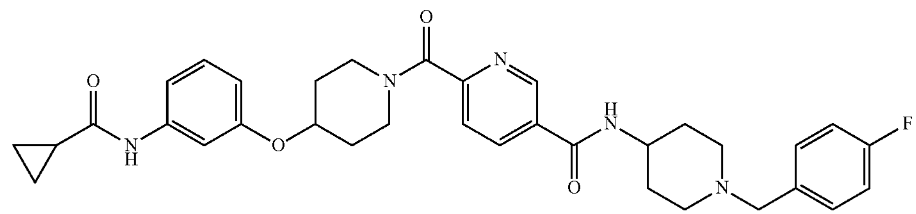 [SMILES: O=C(NC1CCN(Cc2ccc(F)cc2)CC1)c1ccc(C(=O)N2CCC(Oc3cccc(NC(=O)C4CC4)c3)CC2)nc1] |
| 433 | 6-(4-(3-(cyclopropanecarboxamido)phenoxy)piperidine-1-carbonyl)-N-(6-(4-fluorophenoxy)pyridin-3-yl)nicotinamide | 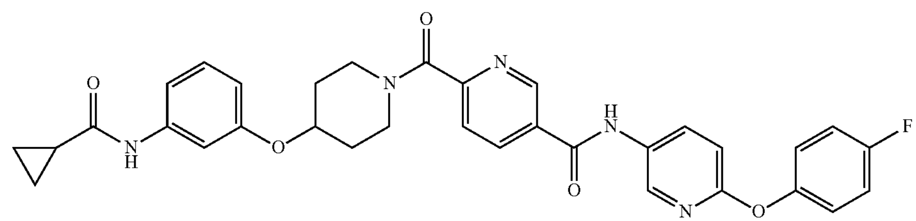 [SMILES: O=C(Nc1ccc(Oc2ccc(F)cc2)nc1)c1ccc(C(=O)N2CCC(Oc3cccc(NC(=O)C4CC4)c3)CC2)nc1] |

TABLE 1-continued

| No. | Name | Structure |
|---|---|---|
| 434 | N-((cis)-4-(4-cyanophenoxy)cyclohexyl)-6-(4-(3-(cyclopropanecarboxamido)phenoxy)piperidine-1-carbonyl)nicotinamide | 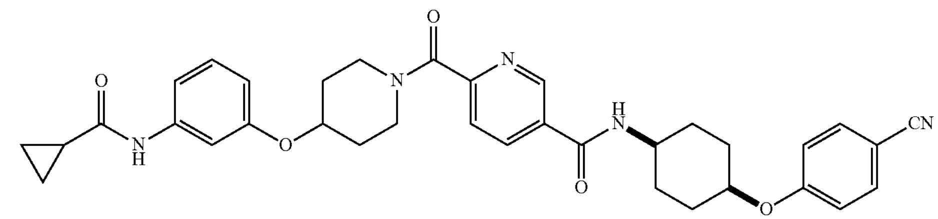 |
| 435 | 6-(4-(3-(cyclopropanecarboxamidophenoxy)piperidine-1-carbonyl)-N-(1-(4-methoxybenzyl)piperidin-4-yl)nicotinamide | 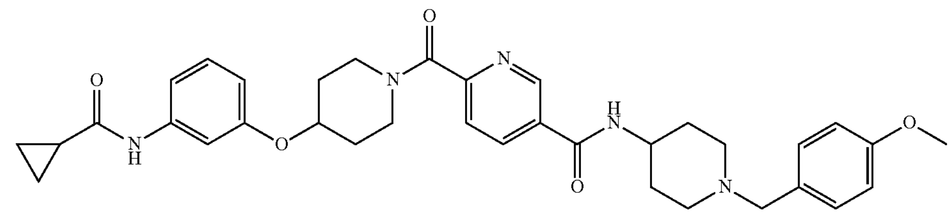 [SMILES: COc1ccc(CN2CCC(NC(=O)c3ccc(C(=O)N4CCC(Oc5cccc(NC(=O)C6CC6)c5)CC4)nc3)CC2)cc1] |
| 436 | N-(1-(4-cyanobenzyl)piperidin-4-yl)-6-(4-(4-(trifluoromethylthio)phenoxy)piperidine-1-carbonyl)pyridazine-3-carboxamide | 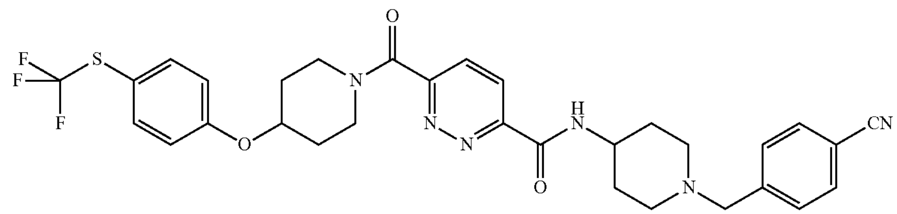 [SMILES: N#Cc1ccc(CN2CCC(NC(=O)c3ccc(C(=O)N4CCC(Oc5ccc(SC(F)(F)F)cc5)CC4)nn3)CC2)cc1] |
| 437 | 6-(4-(4-acetylphenoxy)piperidine-1-carbonyl)-N-(1-(4-cyanobenzyl)piperidin-4-yl)pyridazine-3-carboxamide | 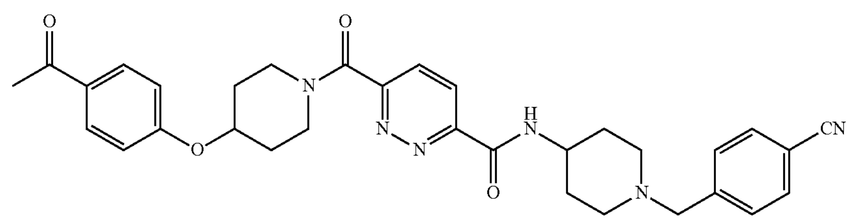 |

TABLE 1-continued

| No. | Name | Structure |
|---|---|---|
| 438 | 6-(4-(3-(cyclopropanecarboxamido)phenoxy)piperidine-1-carbonyl)-N-(1-(4-(trifluoromethoxy)benzyl)piperidin-4-yl)nicotinamide | 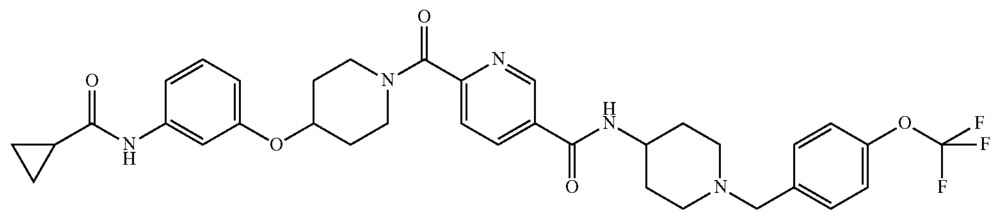 [SMILES: O=C(NC1CCN(Cc2ccc(OC(F)(F)F)cc2)CC1)c1ccc(C(=O)N2CCC(Oc3cccc(NC(=O)C4CC4)c3)CC2)nc1] |
| 439 | N-(1-(4-methoxybenzyl)piperidin-4-yl)-6-(4-(4-(pyrrolidin-1-yl)benzoyl)piperidine-1-carbonyl)nicotinamide | 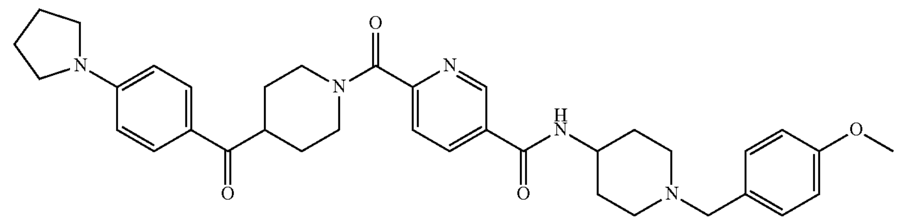 [SMILES: COc1ccc(CN2CCC(NC(=O)c3ccc(C(=O)N4CCC(C(=O)c5ccc(N6CCCC6)cc5)CC4)nc3)CC2)cc1] |
| 440 | 6-(4-(4-(pyrrolidin-1-yl)benzoyl)piperidine-1-carbonyl)-N-(1-(4-(trifluoromethoxy)benzyl)piperidin-4-yl)nicotinamide | 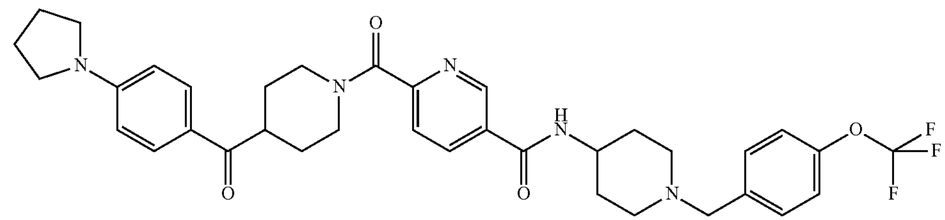 [SMILES: O=C(NC1CCN(Cc2ccc(OC(F)(F)F)cc2)CC1)c1ccc(C(=O)N2CCC(C(=O)c3ccc(N4CCCC4)cc3)CC2)nc1] |
| 441 | 6-(4-(4-(pyrrolidin-1-yl)benzoyl)piperidine-1-carbonyl)-N-(1-(3-(trifluoromethoxy)benzyl)piperidin-4-yl)nicotinamide | 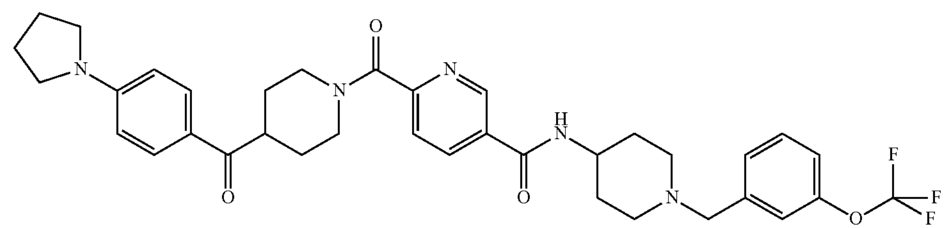 [SMILES: O=C(NC1CCN(Cc2cccc(OC(F)(F)F)c2)CC1)c1ccc(C(=O)N2CCC(C(=O)c3ccc(N4CCCC4)cc3)CC2)nc1] |

TABLE 1-continued

| No. | Name | Structure |
|---|---|---|
| 442 | N-((cis)-4-(4-cyanophenoxy)cyclohexyl)-6-(4-(4-(pyrrolidin-1-yl)benzoyl)piperidine-1-carbonyl)nicotinamide | 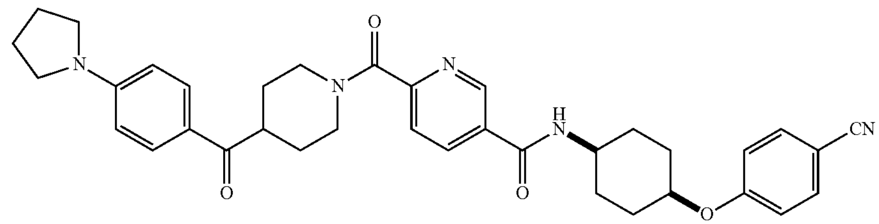 |
| 443 | N-(1-(3-fluoro-4-methoxybenzyl)piperidin-4-yl)-6-(4-(4-(pyrrolidin-1-yl)benzoyl)piperidine-1-carbonyl)nicotinamide | 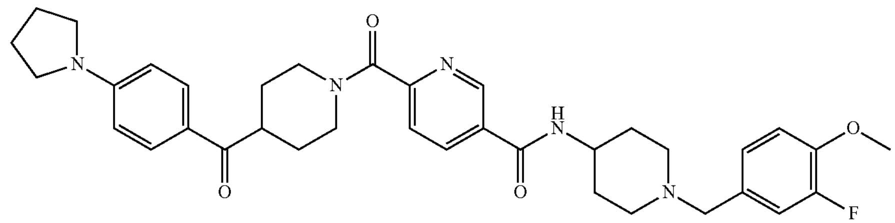 [SMILES: COc1ccc(CN2CCC(NC(=O)c3ccc(C(=O)N4CCC(C(=O)c5ccc(N6CCCC6)cc5)CC4)nc3)CC2)cc1F] |
| 444 | 6-(4-(4-(pyrrolidin-1-yl)benzoyl)piperidine-1-carbonyl)-N-(1-(4-(pyrrolidin-1-yl)benzyl)piperidin-4-yl)nicotinamide | 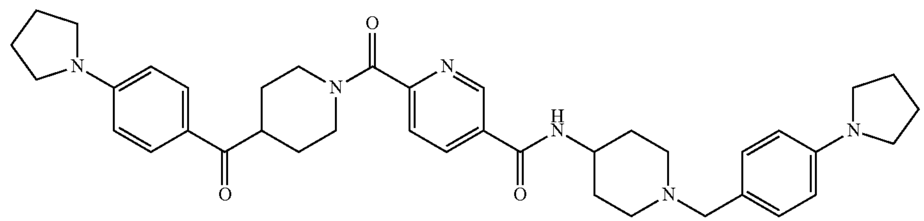 [SMILES: O=C(NC1CCN(Cc2ccc(N3CCCC3)cc2)CC1)c1ccc(C(=O)N2CCC(C(=O)c3ccc(N4CCCC4)cc3)CC2)nc1] |
| 445 | 6-(4-(4-methoxybenzoyl)piperidine-1-carbonyl)-N-(piperidin-4-yl)nicotinamide | 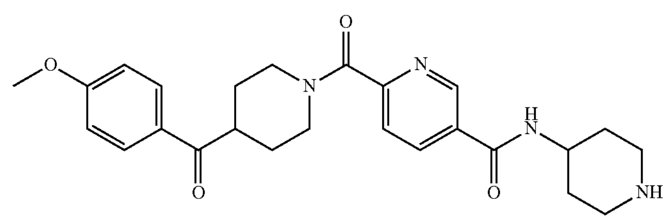 [SMILES: COc1ccc(C(=O)C2CCN(C(=O)c3ccc(C(=O)NC4CCNCC4)cn3)CC2)cc1] |

TABLE 1-continued

| No. | Name | Structure |
|-----|------|-----------|
| 446 | N-(1-(4-isopropoxybenzyl)piperidin-4-yl)-6-(4-(4-(pyrrolidin-1-yl)benzoyl)piperidine-1-carbonyl)nicotinamide | 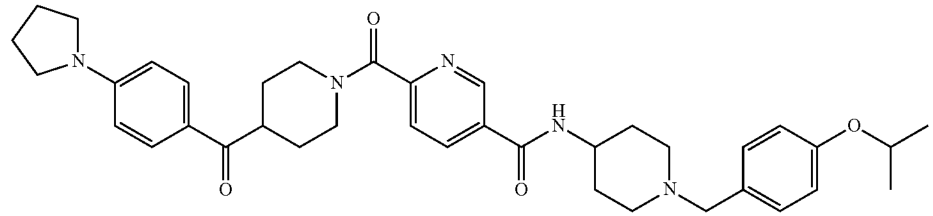 [SMILES: CC(C)Oc1ccc(CN2CCC(NC(=O)c3ccc(C(=O)N4CCC(C(=O)c5ccc(N6CCCC6)cc5)CC4)nc3)CC2)cc1] |
| 447 | N-(1-(4-cyano-3-fluorobenzyl)piperidin-4-yl)-6-(4-(4-(pyrrolidin-1-yl)benzoyl)piperidine-1-carbonyl)nicotinamide | 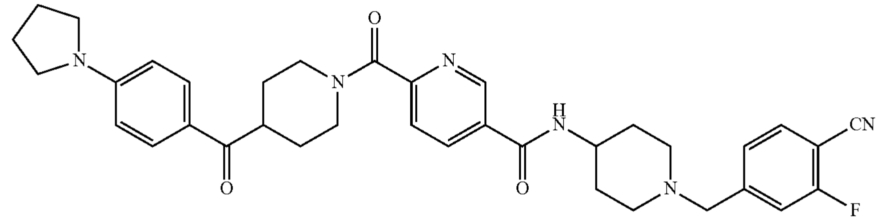 [SMILES: N#Cc1ccc(CN2CCC(NC(=O)c3ccc(C(=O)N4CCC(C(=O)c5ccc(N6CCCC6)cc5)CC4)nc3)CC2)cc1F] |
| 448 | N-(1-(4-cyanobenzyl)piperidin-4-yl)-6-(4-(4-(cyclopropanesulfonamido)phenoxy)piperidine-1-carbonyl)nicotinamide | 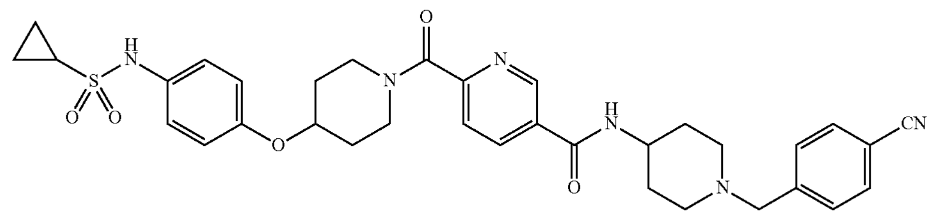 [SMILES: N#Cc1ccc(CN2CCC(NC(=O)c3ccc(C(=O)N4CCC(Oc5ccc(NS(=O)(=O)C6CC6)cc5)CC4)nc3)CC2)cc1] |
| 449 | 6-(4-(4-(cyclopropanesulfonamido)phenoxy)piperidine-1-carbonyl)-N-(6-(4-fluorophenoxy)pyridin-3-yl)nicotinamide | 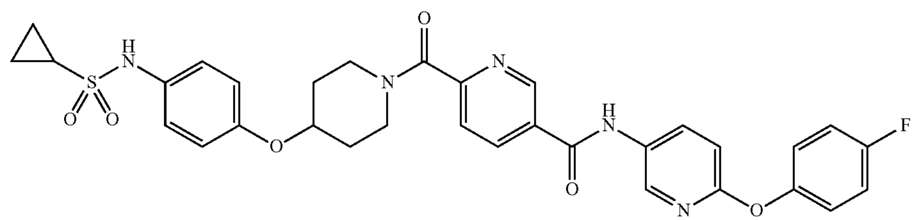 [SMILES: O=C(Nc1ccc(Oc2ccc(F)cc2)nc1)c1ccc(C(=O)N2CCC(Oc3ccc(NS(=O)(=O)C4CC4)cc3)CC2)nc1] |

| No. | Name | Structure |
|---|---|---|
| 450 | N-(1-(4-cyanobenzyl)piperidin-4-yl)-6-(4-(4-(trifluoromethylsulfonyl)phenoxy)piperidine-1-carbonyl)nicotinamide | 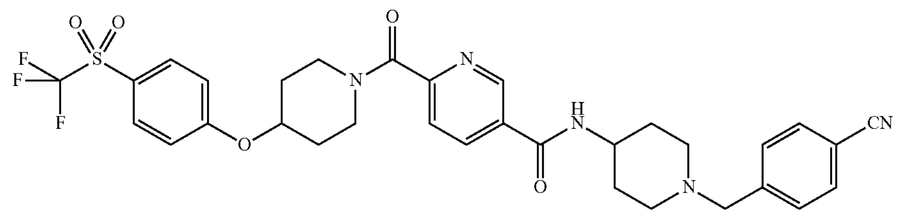 [SMILES: N#Cc1ccc(CN2CCC(NC(=O)c3ccc(C(=O)N4CCC(Oc5ccc(S(=O)(=O)C(F)(F)F)cc5)CC4)nc3)CC2)cc1] |
| 451 | N-((trans)-1-(4-cyanobenzyl)-3-fluoropiperidin-4-yl)-6-(4-(4-(trifluoromethylsulfonyl)phenoxy)piperidine-1-carbonyl)nicotinamide | 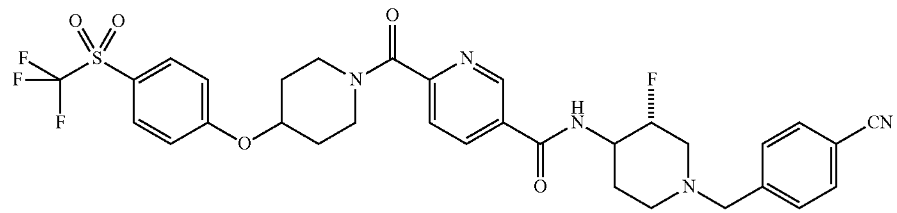 [SMILES: N#Cc1ccc(CN2CCC(NC(=O)c3ccc(C(=O)N4CCC(Oc5ccc(S(=O)(=O)C(F)(F)F)cc5)CC4)nc3)[C@H](F)C2)cc1] |
| 452 | N-((3R,4R)-1-(4-cyanobenzyl)-3-fluoropiperidin-4-yl)-6-(4-(4-methoxybenzoyl)piperidine-1-carbonyl)nicotinamide | 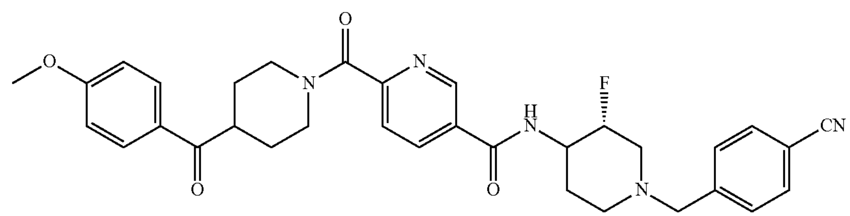 [SMILES: COc1ccc(C(=O)C2CCN(C(=O)c3ccc(C(=O)NC4CCN(Cc5ccc(C#N)cc5)C[C@H]4F)cn3)CC2)cc1] |
| 453 | N-((3S,4S)-1-(4-cyanobenzyl)-3-fluoropiperidin-4-yl)-6-(4-(4-methoxybenzoyl)piperidine-1-carbonyl)nicotinamide | 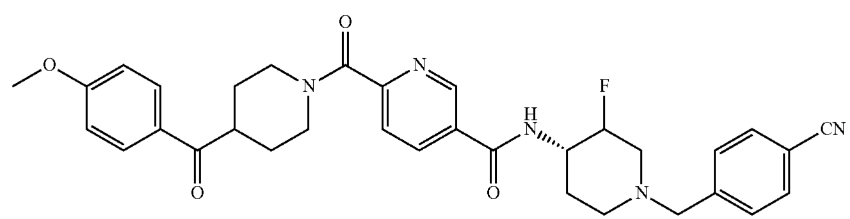 |

TABLE 1-continued

| No. | Name | Structure |
|---|---|---|
| 454 | N-((cis)-1-(4-cyanobenzyl)-3-fluoropiperidin-4-yl)-6-(4-(4-methoxybenzoyl)piperidine-1-carbonyl)nicotinamide | 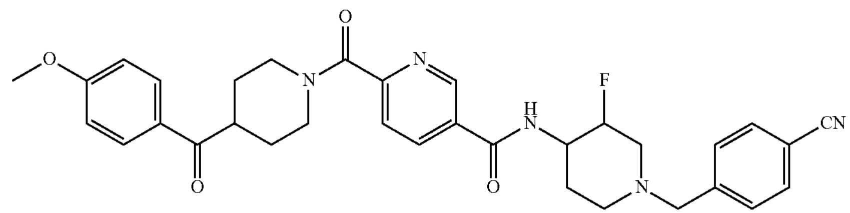 |
| 455 | 6-(4-(4-(cyclopropanecarbonyl)phenoxy)piperidine-1-carbonyl)-N-(1-(4-(trifluoromethoxy)benzyl)piperidin-4-yl)nicotinamide | 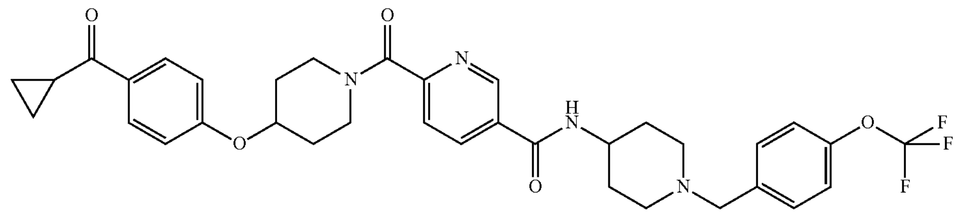 [SMILES: O=C(NC1CCN(Cc2ccc(OC(F)(F)F)cc2)CC1)c1ccc(C(=O)N2CCC(Oc3ccc(C(=O)C4CC4)cc3)CC2)nc1] |
| 456 | N-(1-(4-cyanobenzyl)piperidin-4-yl)-6-(4-(4-(cyclopropanecarbonyl)phenoxy)piperidine-1-carbonyl)nicotinamide | 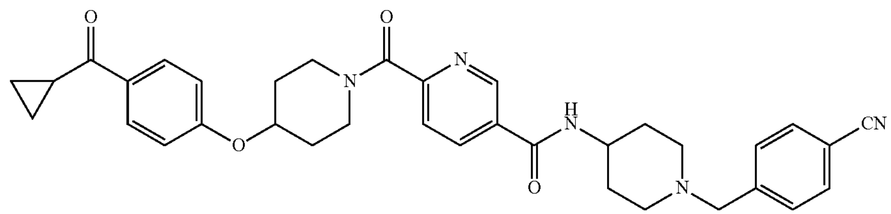 [SMILES: N#Cc1ccc(CN2CCC(NC(=O)c3ccc(C(=O)N4CCC(Oc5ccc(C(=O)C6CC6)cc5)CC4)nc3)CC2)cc1] |
| 457 | 6-(4-(4-(cyclopropanecarbonyl)phenoxy)piperidine-1-carbonyl)-N-(6-(4-fluorophenoxy)pyridin-3-yl)nicotinamide | 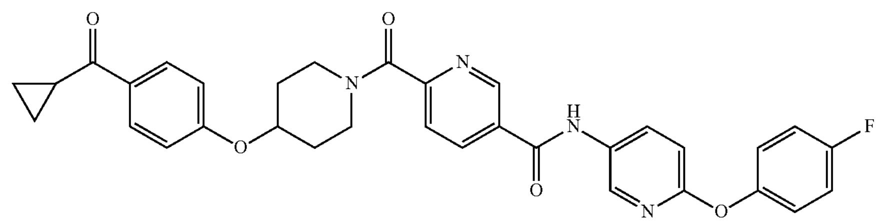 [SMILES: O=C(Nc1ccc(Oc2ccc(F)cc2)nc1)c1ccc(C(=O)N2CCC(Oc3ccc(C(=O)C4CC4)cc3)CC2)nc1] |

TABLE 1-continued

| No. | Name | Structure |
|---|---|---|
| 458 | 6-(4-(4-(cyclopropanecarbonyl)phenoxy)piperidine-1-carbonyl)-N-(1-(4-methoxybenzyl)piperidin-4-yl)nicotinamide | 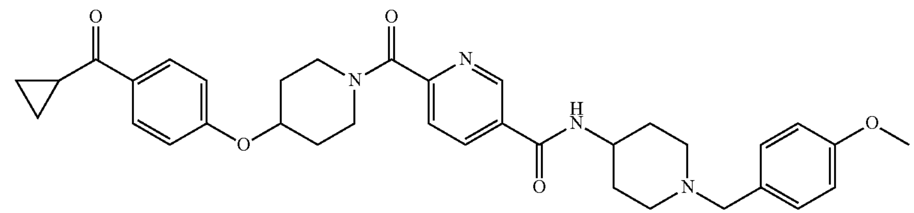 [SMILES: COc1ccc(CN2CCC(NC(=O)c3ccc(C(=O)N4CCC(Oc5ccc(C(=O)C6CC6)cc5)CC4)nc3)CC2)cc1] |
| 459 | N-(6-(4-cyanophenoxy)pyridin-3-yl)-6-(4-(4-(methylsulfonyl)phenoxy)piperidine-1-carbonyl)nicotinamide | 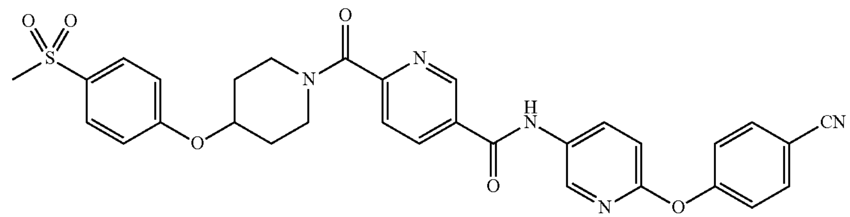 [SMILES: CS(=O)(=O)c1ccc(OC2CCN(C(=O)c3ccc(C(=O)Nc4ccc(Oc5ccc(C#N)cc5)nc4)cn3)CC2)cc1] |
| 460 | N-(6-(4-cyanophenoxy)pyridin-3-yl)-6-(4-(4-methoxybenzoyl)piperidine-1-carbonyl)nicotinamide | 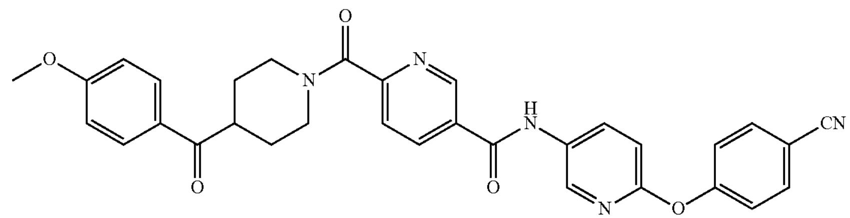 [SMILES: COc1ccc(C(=O)C2CCN(C(=O)c3ccc(C(=O)Nc4ccc(Oc5ccc(C#N)cc5)nc4)cn3)CC2)cc1] |
| 461 | N-((cis)-3-fluoro-1-(4-(trifluoromethoxy)benzyl)piperidin-4-yl)-6-(4-(4-methoxybenzoyl)piperidine-1-carbonyl)nicotinamide | 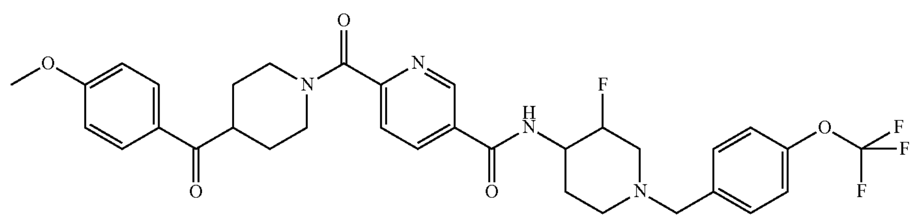 [SMILES: COc1ccc(C(=O)C2CCN(C(=O)c3ccc(C(=O)NC4CCN(Cc5ccc(OC(F)(F)F)cc5)CC4F)cn3)CC2)cc1] |

TABLE 1-continued

| No. | Name | Structure |
|-----|------|-----------|
| 462 | N-(6-(4-acetylphenoxy)pyridin-3-yl)-6-(4-(4-methoxybenzoyl)piperidine-1-carbonyl)nicotinamide | 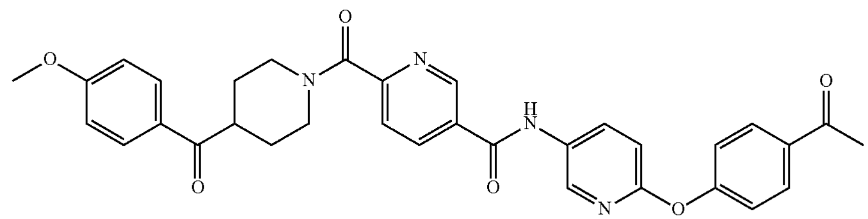 [SMILES: COc1ccc(C(=O)C2CCN(C(=O)c3ccc(C(=O)Nc4ccc(Oc5ccc(C(C)=O)cc5)nc4)cn3)CC2)cc1] |
| 463 | N-(6-(4-cyanophenoxy)pyridin-3-yl)-6-(4-(2,4-difluorobenzoyl)piperidine-1-carbonyl)nicotinamide | 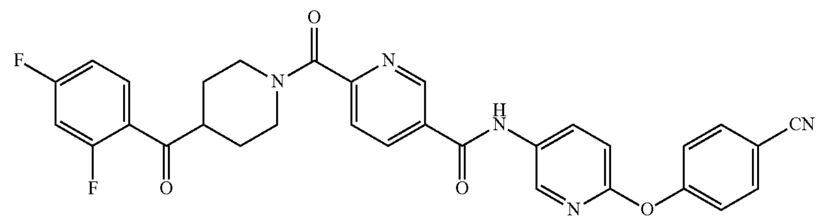 |
| 464 | N-(6-(4-acetylphenoxy)pyridin-3-yl)-6-(4-(2,4-difluorobenzoyl)piperidine-1-carbonyl)nicotinamide | 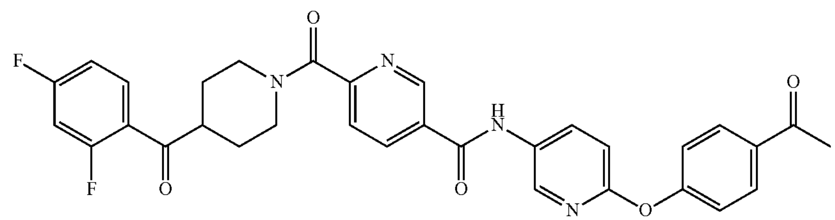 [SMILES: CC(=O)c1ccc(Oc2ccc(NC(=O)c3ccc(C(=O)N4CCC(C(=O)c5ccc(F)cc5F)CC4)nc3)cn2)cc1] |
| 465 | 6-(4-(4-methoxybenzoyl)piperidine-1-carbonyl)-N-(6-(4-(methylsulfonyl)phenoxy)pyridin-3-yl)nicotinamide | 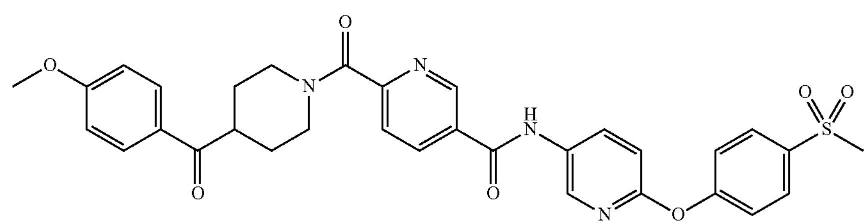 |

TABLE 1-continued

| No. | Name | Structure |
|---|---|---|
| 466 | 6-(4-(2,4-difluorobenzoyl)piperidine-1-carbonyl)-N-(6-(4-(methylsulfonyl)phenoxy)pyridin-3-yl)nicotinamide | 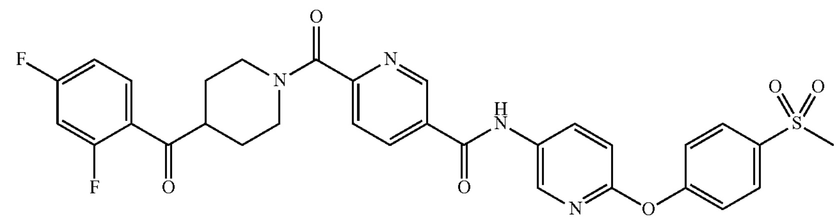 [SMILES: CS(=O)(=O)c1ccc(Oc2ccc(NC(=O)c3ccc(C(=O)N4CCC(C(=O)c5ccc(F)cc5F)CC4)nc3)cn2)cc1] |
| 467 | N-(6-(4-fluorophenylsulfonyl)pyridin-3-yl)-6-(4-(4-methoxybenzoyl)piperidine-1-carbonyl)nicotinamide | 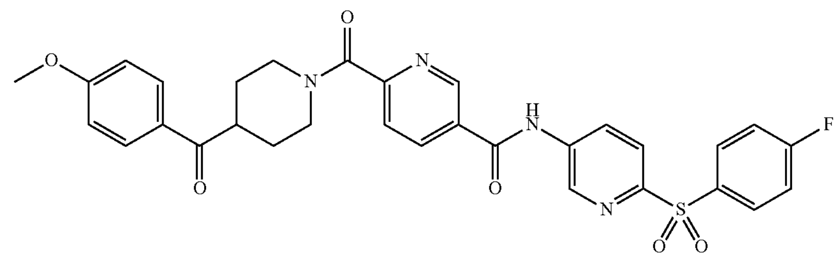 [SMILES: COc1ccc(C(=O)C2CCN(C(=O)c3ccc(C(=O)Nc4ccc(S(=O)(=O)c5ccc(F)cc5)nc4)cn3)CC2)cc1] |
| 468 | N-(5-(4-cyanophenoxy)pyridin-2-yl)-6-(4-(4-methoxybenzoyl)piperidine-1-carbonyl)nicotinamide | 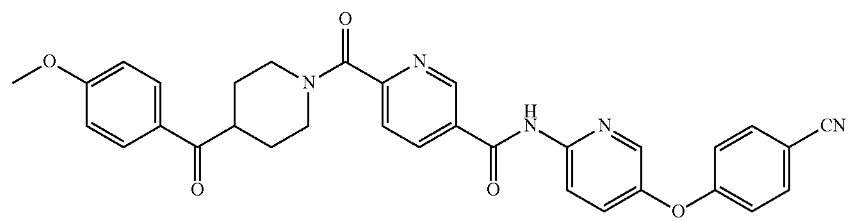 [SMILES: COc1ccc(C(=O)C2CCN(C(=O)c3ccc(C(=O)Nc4ccc(Oc5ccc(C#N)cc5)cn4)cn3)CC2)cc1] |
| 469 | N-(5-(4-cyanophenoxy)pyridin-2-yl)-6-(4-(2,4-difluorobenzoyl)piperidine-1-carbonyl)nicotinamide | 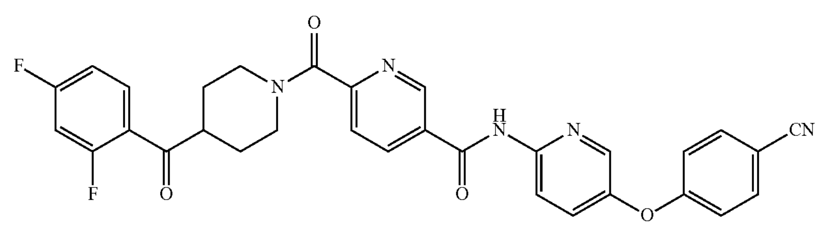 [SMILES: N#Cc1ccc(Oc2ccc(NC(=O)c3ccc(C(=O)N4CCC(C(=O)c5ccc(F)cc5F)CC4)nc3)nc2)cc1] |

TABLE 1-continued

| No. | Name | Structure |
|-----|------|-----------|
| 470 | 6-(4-(4-fluorophenylsulfonyl)piperidine-1-carbonyl)-N-(1-(4-(trifluoromethoxy)benzyl)piperidin-4-yl)nicotinamide | 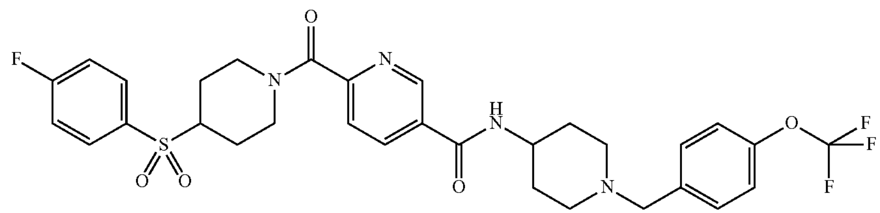 [SMILES: O=C(NC1CCN(Cc2ccc(OC(F)(F)F)cc2)CC1)c1ccc(C(=O)N2CCC(S(=O)(=O)c3ccc(F)cc3)CC2)nc1] |
| 471 | N-(1-(4-cyanobenzyl)piperidin-4-yl)-6-(4-(4-fluorophenylsulfonyl)piperidine-1-carbonyl)nicotinamide | 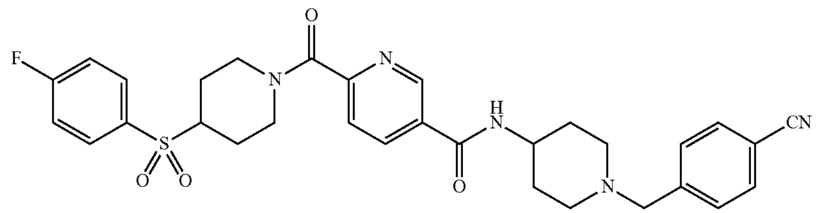 [SMILES: N#Cc1ccc(CN2CCC(NC(=O)c3ccc(C(=O)N4CCC(S(=O)(=O)c5ccc(F)cc5)CC4)nc3)CC2)cc1] |
| 472 | N-(6-(4-cyanophenoxy)pyridin-3-yl)-6-(4-(4-fluorophenylsulfonyl)piperidine-1-carbonyl)nicotinamide | 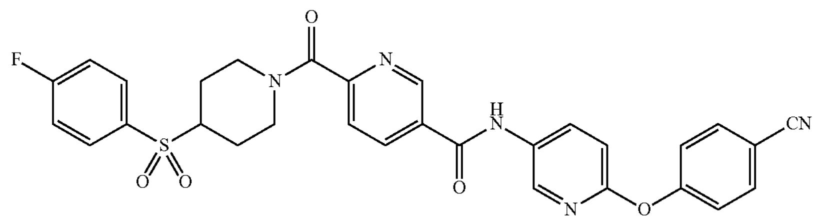 [SMILES: N#Cc1ccc(Oc2ccc(NC(=O)c3ccc(C(=O)N4CCC(S(=O)(=O)c5ccc(F)cc5)CC4)nc3)cn2)cc1] |
| 473 | N-(6-(4-acetylphenoxy)pyridin-3-yl)-6-(4-(4-fluorophenylsulfonyl)piperidine-1-carbonyl)nicotinamide | 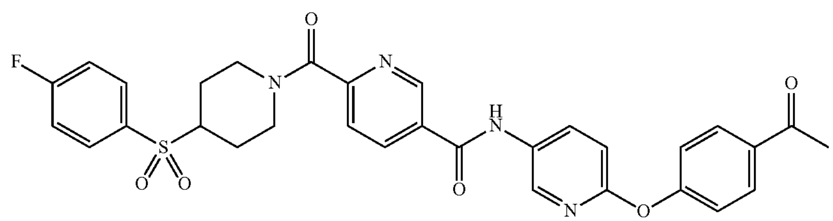 [SMILES: CC(=O)c1ccc(Oc2ccc(NC(=O)c3ccc(C(=O)N4CCC(S(=O)(=O)c5ccc(F)cc5)CC4)nc3)cn2)cc1] |

TABLE 1-continued

| No. | Name | Structure |
|---|---|---|
| 474 | 6-(4-(4-fluorophenylsulfonyl)piperidine-1-carbonyl)-N-(1-(4-methoxybenzyl)piperidin-4-yl)nicotinamide | 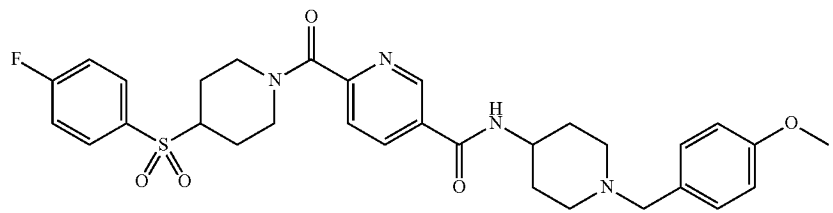 [SMILES: COc1ccc(CN2CCC(NC(=O)c3ccc(C(=O)N4CCC(S(=O)(=O)c5ccc(F)cc5)CC4)nc3)CC2)cc1] |
| 475 | 6-(4-(4-fluorophenylsulfonyl)piperidine-1-carbonyl)-N-(1-(3-methoxybenzyl)piperidin-4-yl)nicotinamide | 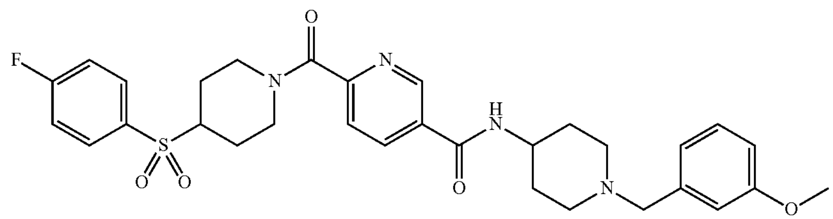 [SMILES: COc1cccc(CN2CCC(NC(=O)c3ccc(C(=O)N4CCC(S(=O)(=O)c5ccc(F)cc5)CC4)nc3)CC2)c1] |
| 476 | N-(6-(4-cyanophenoxy)pyridin-3-yl)-6-(4-(4-fluorobenzyl)piperazine-1-carbonyl)nicotinamide | 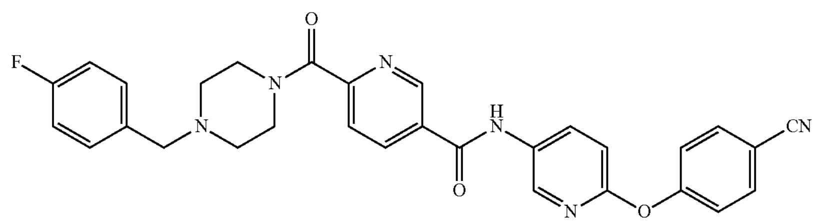 [SMILES: N#Cc1ccc(Oc2ccc(NC(=O)c3ccc(C(=O)N4CCN(Cc5ccc(F)cc5)CC4)nc3)cn2)cc1] |
| 477 | N-(6-(4-acetylphenoxy)pyridin-3-yl)-6-(4-(4-fluorobenzyl)piperazine-1-carbonyl)nicotinamide | 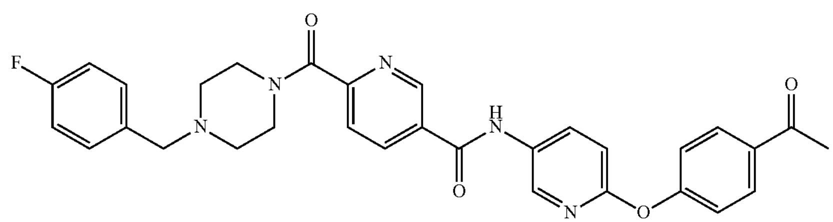 [SMILES: CC(=O)c1ccc(Oc2ccc(NC(=O)c3ccc(C(=O)N4CCN(Cc5ccc(F)cc5)CC4)nc3)cn2)cc1] |

TABLE 1-continued

| No. | Name | Structure |
|-----|------|-----------|
| 478 | N-(6-(4-cyanophenoxy)-2-methylpyridin-3-yl)-6-(4-(4-methoxybenzoyl)piperidine-1-carbonyl)nicotinamide | 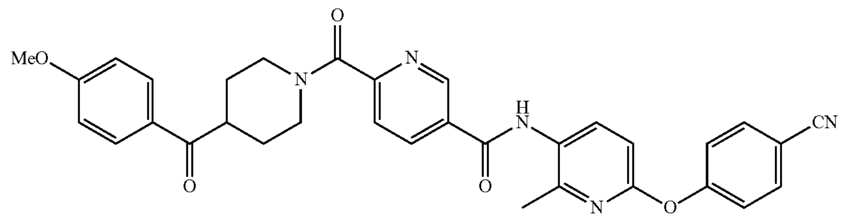 [SMILES: COc1ccc(C(=O)C2CCN(C(=O)c3ccc(C(=O)Nc4ccc(Oc5ccc(C#N)cc5)nc4C)cn3)CC2)cc1] |
| 479 | N-(6-(4-cyanophenoxy)-2-methylpyridin-3-yl)-6-(4-(2,4-difluorobenzoyl)piperidine-1-carbonyl)nicotinamide | 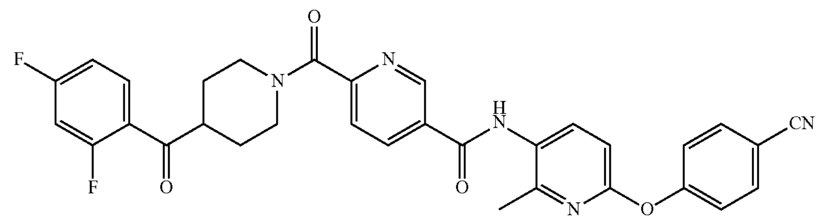 [SMILES: Cc1nc(Oc2ccc(C#N)cc2)ccc1NC(=O)c1ccc(C(=O)N2CCC(C(=O)c3ccc(F)cc3F)CC2)nc1] |
| 480 | N-(6-(4-(dimethylcarbamoyl)phenoxy)pyridin-3-yl)-6-(4-(4-methoxybenzoyl)piperidine-1-carbonyl)nicotinamide | 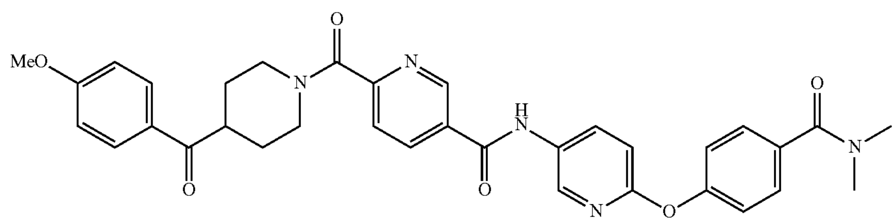 [SMILES: COc1ccc(C(=O)C2CCN(C(=O)c3ccc(C(=O)Nc4ccc(Oc5ccc(C(=O)N(C)C)cc5)nc4)cn3)CC2)cc1] |
| 481 | 6-(4-(2,4-difluorobenzoyl)piperidine-1-carbonyl)-N-(6-(4-(dimethylcarbamoyl)phenoxy)pyridin-3-yl)nicotinamide | 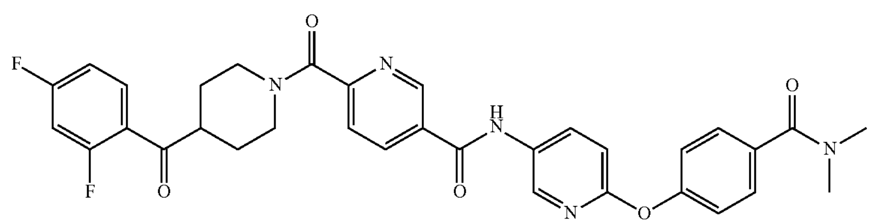 [SMILES: CN(C)C(=O)c1ccc(Oc2ccc(NC(=O)c3ccc(C(=O)N4CCC(C(=O)c5ccc(F)cc5F)CC4)nc3)cn2)cc1] |

TABLE 1-continued

| No. | Name | Structure |
|---|---|---|
| 482 | N-(1-(4-cyanobenzyl)piperidin-4-yl)-6-(4-(4-methoxybenzoyl)piperidine-1-carbonyl)-N-methylnicotinamide | 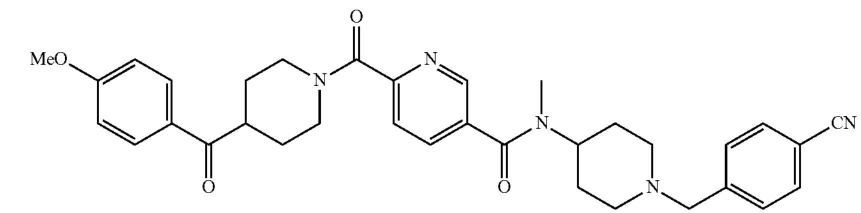 [SMILES: COc1ccc(C(=O)C2CCN(C(=O)c3ccc(C(=O)N(C)C4CCN(Cc5ccc(C#N)cc5)CC4)cn3)CC2)cc1] |
| 483 | 6-(4-(4-methoxybenzoyl)piperidine-1-carbonyl)-N-methyl-N-(1-(4-(trifluoromethoxy)benzyl)piperidin-4-yl)nicotinamide | 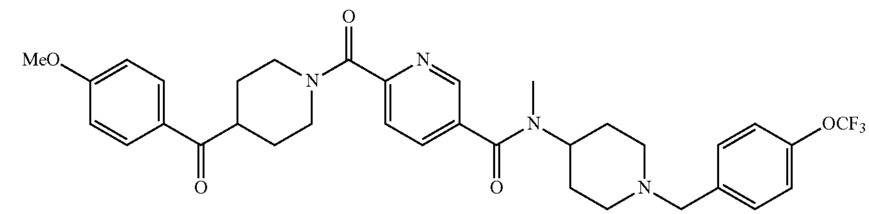 [SMILES: COc1ccc(C(=O)C2CCN(C(=O)c3ccc(C(=O)N(C)C4CCN(Cc5ccc(OC(F)(F)F)cc5)CC4)cn3)CC2)cc1] |
| 484 | 6-(4-(4-methoxybenzoyl)piperidine-1-carbonyl)-N-(1-(4-methoxybenzyl)piperidin-4-yl)-N-methylnicotinamide | 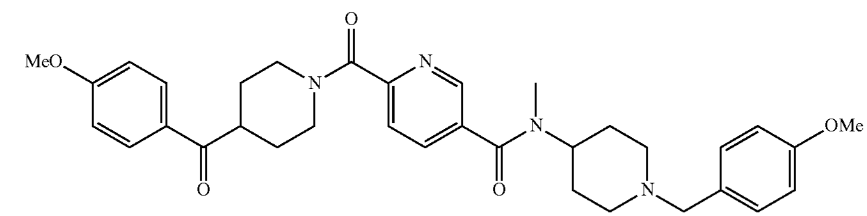 [SMILES: COc1ccc(CN2CCC(N(C)C(=O)c3ccc(C(=O)N4CCC(C(=O)c5ccc(OC)cc5)CC4)nc3)CC2)cc1] |
| 485 | N-(6-(4-acetylphenoxy)pyridin-3-yl)-6-(4-(4-(methylsulfonyl)phenoxy)piperidine-1-carbonyl)nicotinamide | 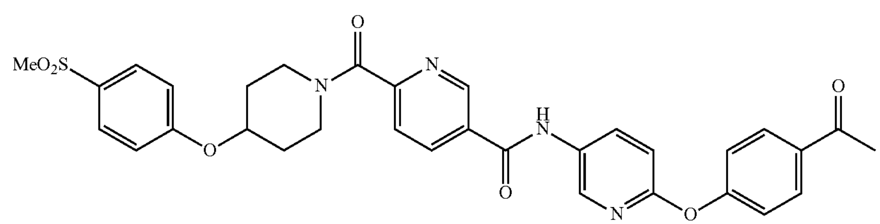 [SMILES: CC(=O)c1ccc(Oc2ccc(NC(=O)c3ccc(C(=O)N4CCC(Oc5ccc(S(C)(=O)=O)cc5)CC4)nc3)cn2)cc1] |

TABLE 1-continued

| No. | Name | Structure |
|---|---|---|
| 486 | N-(6-(4-acetylphenoxy)pyridin-3-yl)-6-(4-(4-(cyclopropylsulfonyl)phenoxy)piperidine-1-carbonyl)nicotinamide | 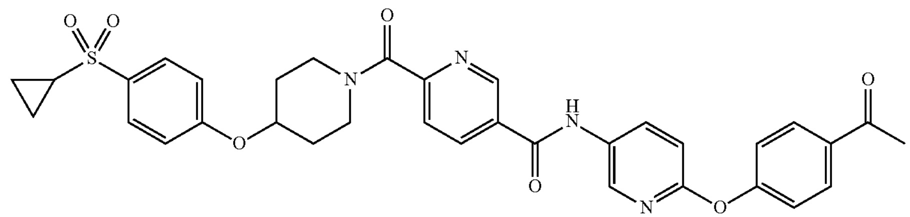 [SMILES: CC(=O)c1ccc(Oc2ccc(NC(=O)c3ccc(C(=O)N4CCC(Oc5ccc(S(=O)(=O)C6CC6)cc5)CC4)nc3)cn2)cc1] |
| 487 | N-(6-(4-acetylphenoxy)pyridin-3-yl)-6-(4-(4-(methylsulfonyl)phenyl)piperazine-1-carbonyl)nicotinamide | 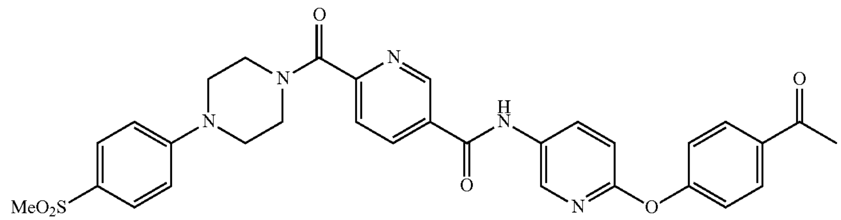 [SMILES: CC(=O)c1ccc(Oc2ccc(NC(=O)c3ccc(C(=O)N4CCN(c5ccc(S(C)(=O)=O)cc5)CC4)nc3)cn2)cc1] |
| 488 | N-(6-(4-acetylphenoxy)pyridin-3-yl)-6-(4-(4-(dimethylcarbamoyl)phenoxy)piperidine-1-carbonyl)nicotinamide | 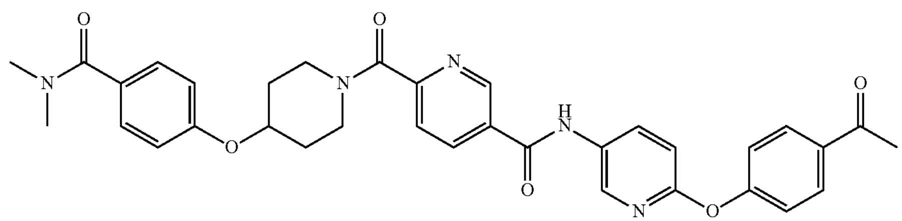 [SMILES: CC(=O)c1ccc(Oc2ccc(NC(=O)c3ccc(C(=O)N4CCC(Oc5ccc(C(=O)N(C)C)cc5)CC4)nc3)cn2)cc1] |
| 489 | N-(6-(4-acetylphenoxy)pyridin-3-yl)-6-(4-(4-(isopropylsulfonyl)phenyl)piperazine-1-carbonyl)nicotinamide | 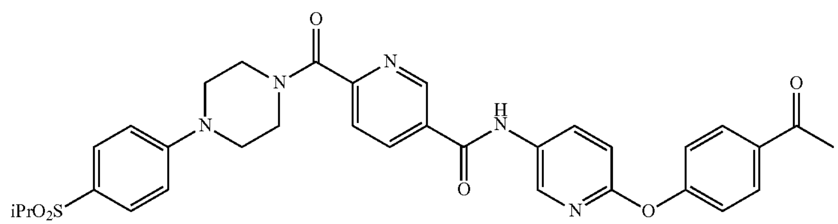 |

TABLE 1-continued

| No. | Name | Structure |
|-----|------|-----------|
| 490 | N-(1-(4-(dimethylcarbamoyl)benzyl)piperidin-4-yl)-6-(4-(4-methoxybenzoyl)piperidine-1-carbonyl)nicotinamide | 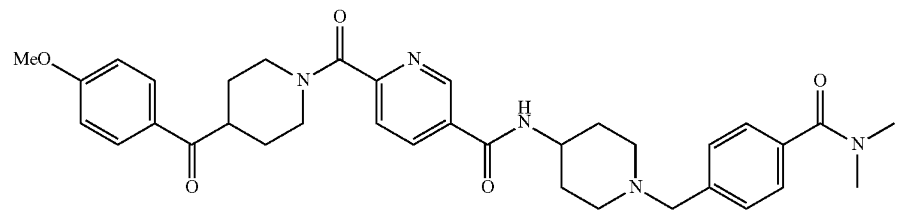 [SMILES: COc1ccc(C(=O)C2CCN(C(=O)c3ccc(C(=O)NC4CCN(Cc5ccc(C(=O)N(C)C)cc5)CC4)cn3)CC2)cc1] |
| 491 | N-(1-(4-cyanobenzyl)piperidin-4-yl)-6-(4-(4-fluorobenzyl)piperazin-1-yl)pyridazine-3-carboxamide | 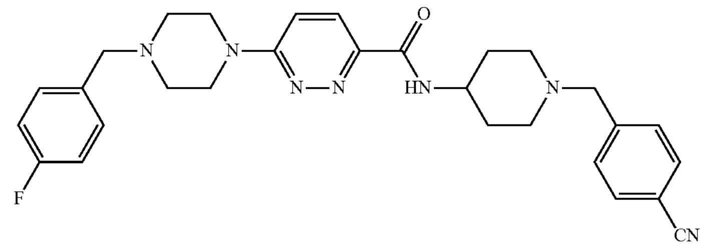 [SMILES: N#Cc1ccc(CN2CCC(NC(=O)c3ccc(N4CCN(Cc5ccc(F)cc5)CC4)nn3)CC2)cc1] |
| 492 | N-(1-(4-cyanobenzyl)piperidin-4-yl)-5-(4-(4-(pentafluorosulfanyl)phenoxy)piperidine-1-carbonyl)picolinamide | 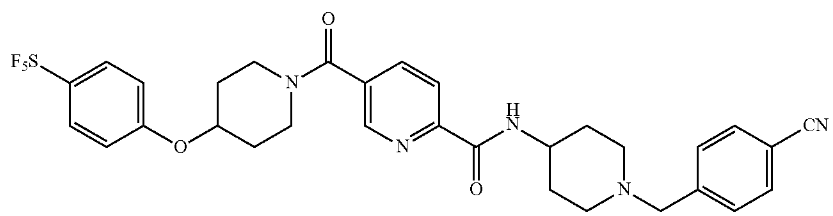 |
| 493 | N-(1-(4-cyanobenzyl)piperidin-4-yl)-6-(4-(4-(pentafluorosulfanyl)phenoxy)piperidine-1-carbonyl)nicotinamide | 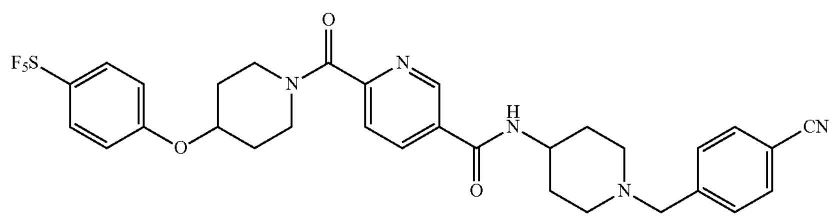 |

TABLE 1-continued

| No. | Name | Structure |
|---|---|---|
| 494 | 6-(4-(4-(pentafluorosulfanyl)phenoxy)piperidine-1-carbonyl)-N-(1-(4-(trifluoromethoxy)benzyl)piperidin-4-yl)nicotinamide | 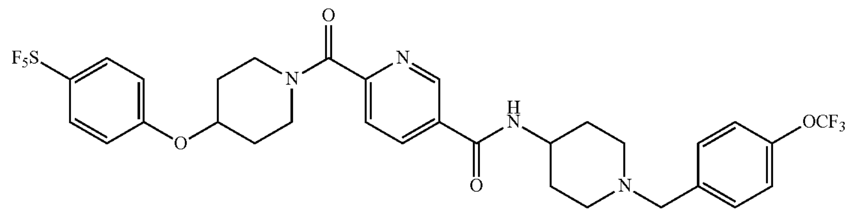 |
| 495 | N-(1-(4-methoxybenzyl)piperidin-4-yl)-6-(4-(4-(pentafluorosulfanyl)phenoxy)piperidine-1-carbonyl)nicotinamide | 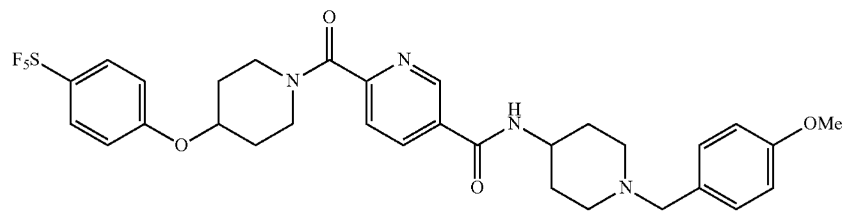 |
| 496 | N-(6-(4-fluorophenoxy)pyridin-3-yl)-6-(4-(4-(pentafluorosulfanyl)phenoxy)piperidine-1-carbonyl)nicotinamide | 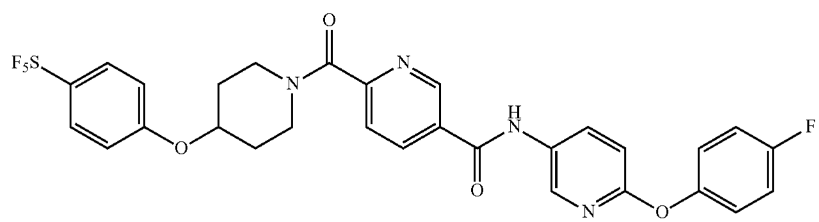 |

TABLE 1-continued

| No. | Name | Structure |
|-----|------|-----------|
| 497 | N-(6-(4-cyanophenoxy)pyridin-3-yl)-6-(4-(4-(pentafluorosulfanyl)phenoxy)piperidine-1-carbonyl)nicotinamide | 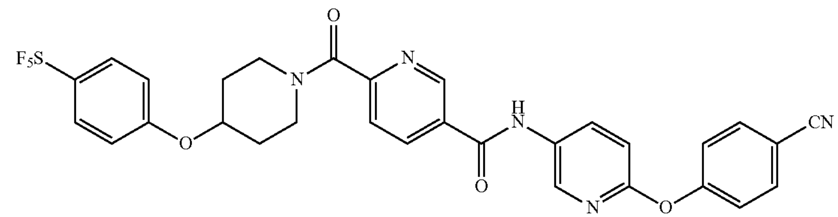 |
| 498 | N-(1-(4-cyanobenzyl)-3,3-difluoropiperidin-4-yl)-6-(4-(4-methoxybenzoyl)piperidine-1-carbonyl)nicotinamide | 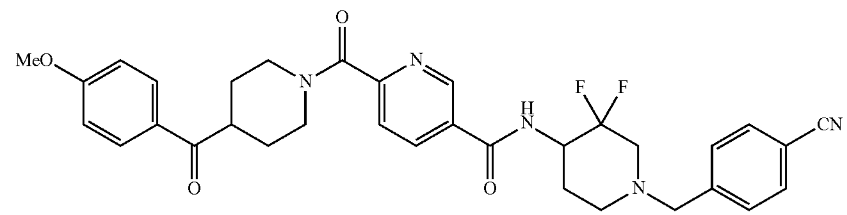 [SMILES: COc1ccc(C(=O)C2CCN(C(=O)c3ccc(C(=O)NC4CCN(Cc5ccc(C#N)cc5)CC4(F)F)cn3)CC2)cc1] |

For simplicity, chemical moieties are defined and referred to throughout primarily as univalent chemical moieties (for example, alkyl, aryl, etc.). Nevertheless, such terms are also used to convey corresponding multivalent moieties under the appropriate structural circumstances clear to those skilled in the art. For example, while an "alkyl" moiety can refer to a monovalent radical (for example $CH_3$—$CH_2$—), in some circumstances a bivalent linking moiety can be "alkyl," in which case those skilled in the art will understand the alkyl to be a divalent radical (for example the $C_2$ alkylene —$CH_2$—$CH_2$— may be described as a $C_2$ alkyl group), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, for example, an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, desirably from 1 to about 12 carbons (i.e., inclusive of 1 and 12). The term "$C_m$-$C_n$ alkyl" means an alkyl group having from m to n carbon atoms (i.e., inclusive of m and n). The term "$C_m$-$C_n$ alkyl" means an alkyl group having from m to n carbon atoms. For example, "$C_1$-$C_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$ alkyl"), the group is simply a single covalent bond if it is a divalent radical or is a hydrogen atom if it is a monovalent radical. For example, the moiety "—($C_0$-$C_6$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "haloalkyl" is an alkyl group substituted with one or more halogen atoms, for example F, Cl, Br and I. A more specific term, for example, "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic carbocyclic ring system having a single ring (for example, phenyl) which is optionally fused to other aromatic hydrocarbon rings or non-aromatic hydrocarbon rings. "Aryl" includes ring systems having multiple condensed rings and in which at least one is aromatic, (for example, 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, 2,3-dihydrobenzofuranyl and 6,7,8,9-tetrahydro-5H-benzo[a]cycloheptenyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings.

Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2 (1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (for example, bridged systems) to other cycloalkyl rings. Preferred cycloalkyl groups have from 3 to 7 members in a single ring. More preferred cycloalkyl groups have 5 or 6 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), —SF$_5$, NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —O$^-$M$^+$, =O, —OR$^{70}$, —SR$^{70}$, —S$^-$M$^+$, =S, —NR$^{80}$R$^{80}$, =NR$^{70}$, =N—OR$^{70}$, trihalomethyl, —CF$_3$, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$. Each R$^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{71}$, —SR$^{71}$, —S$^-$M$^+$, =S, —NR$^{81}$R$^{81}$, =NR$^{71}$, =N—OR$^{71}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —OSO$_2$R$^{71}$, —OSO$_2$R$^{71}$, —OSO$_2$O$^-$M$^+$, —OSO$_2$OR$^{71}$, —P(O)(O$^-$)$_2$(M$^+$)$_2$, —P(O)(OR$^{71}$)O$^-$M$^+$, —P(O)(OR$^{71}$)$_2$, —C(O)R$^{71}$, —C(S)R$^{71}$, —C(NR$^{71}$)R$^{71}$, —C(O)O$^-$M$^+$, —C(O)OR$^{71}$, —C(S)OR$^{71}$, —C(O)NR$^{81}$R$^{81}$, —C(NR$^{71}$)NR$^{81}$R$^{81}$, —OC(O)R$^{71}$, —OC(S)R$^{71}$, —OC(O)O$^-$M$^+$, —OC(O)OR$^{71}$, —OC(S)OR$^{71}$, —NR$^{71}$C(O)R$^{71}$, —NR$^{71}$C(S)R$^{71}$, —NR$^{71}$CO$_2$$^-$M$^+$, —NR$^{71}$CO$_2$R$^{71}$, —NR$^{71}$C(S)OR$^{71}$, —NR$^{71}$C(O)R$^{71}$, —NR$^{71}$C(S)R$^{71}$, —NR$^{71}$CO$_2$$^-$ and —NR$^{71}$C(NR$^{71}$)NR$^{81}$R$^{81}$. Each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M$^+$ is a counter ion with a net single positive charge. Each R$^{71}$ is independently hydrogen or R$^{61}$, in which R$^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, (NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2$$^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each R$^{81}$ is independently R$^{71}$ or alternatively, two R$^{81}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each R$^{72}$ is independently hydrogen, ($C_1$-$C_6$ alkyl) or ($C_1$-$C_6$ fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$ alkyl substitution. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means for example that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl. In certain embodiments, each R$^{60}$ is H or (unsubstituted $C_1$-$C_6$ alkyl). In certain embodiments, each R$^{70}$ is H or (unsubstituted $C_1$-$C_6$ alkyl). In certain embodiments, each R$^{80}$ is H or (unsubstituted $C_1$-$C_6$ alkyl).

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —OCN, —SCN, —NO, —NO$_2$, —SO$_2$R$^{70}$, —SO$_3$$^-$ $M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

Substituent groups for hydrogens on nitrogen atoms in "substituted" heteroalkyl and heterocycloalkyl groups are, unless otherwise specified, —$R^{60}$, —$O^-M^+$, —$OR^{70}$, —$SR^{70}$, —S trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In certain embodiments as described above, the substituent groups on carbon atoms can also or alternatively be —$SF_5$.

In certain embodiments of the compounds disclosed herein, a group that is substituted has 1, 2, 3, or 4 substituents, 1, 2, or 3 substituents, 1 or 2 substituents, or 1 substituent.

In certain embodiments, an "optionally substituted alkyl," unless otherwise specified, is substituted with halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}$SO$_2$R$^{33}$, —(NH)$_{0-1}$COR$^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, "optionally substituted alkyl" is also or alternatively optionally substituted with —$N_3$ or —$SF_5$.

In certain embodiments, an "optionally substituted aryl," unless otherwise specified, is substituted with halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}$SO$_2$R$^{33}$, —(NH)$_{0-1}$COR$^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, "optionally substituted aryl" is also or alternatively optionally substituted with —$N_3$ or —$SF_5$.

In certain embodiments, an "optionally substituted heteroaryl," unless otherwise specified, is substituted with halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}$SO$_2$R$^{33}$, —(NH)$_{0-1}$COR$^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, "optionally substituted heteroaryl" is also or alternatively optionally substituted with —$N_3$ or —$SF_5$.

In certain embodiments, an "optionally substituted cycloalkyl," unless otherwise specified, is substituted with halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}$SO$_2$R$^{33}$, —(NH)$_{0-1}$COR$^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, "optionally substituted cycloalkyl" is also or alternatively optionally substituted with —$N_3$ or —$SF_5$.

In certain embodiments, an "optionally substituted heterocycloalkyl," unless otherwise specified, is substituted with halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N(unsubstituted $C_1$-$C_4$ alkyl)$_2$, —C(O)OH, C(O)O(unsubstituted $C_1$-$C_6$ alkyl), —(NH)$_{0-1}$SO$_2$R$^{33}$, —(NH)$_{0-1}$COR$^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, "optionally substituted heterocycloalkyl" is also or alternatively optionally substituted with —$N_3$ or —$SF_5$.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that requires a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Other specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

Compounds can be assayed for binding to a membrane-bound adiponectin receptor by performing a competitive binding assay with adiponectin. In one such procedure, HEK 293 cellular membrane is coated onto a COSTAR 384 plate, which is then blocked with 1% casein. Polyhistidine-tagged globular adiponectin and a candidate compound is incubated with the membrane in HEPES buffer. Unbound ligands are washed away and the degree of binding of the adiponectin is determined using horseradish peroxidase-conjugated anti-polyhistidine. Compounds that compete with adiponectin binding to the membrane (i.e., give a reduced signal compared to a control performed without a candidate compound) can be chosen as hits and further screened using the below-described functional assays to identify adiponectin receptor agonists.

An in-cell western assay can be performed to demonstrate the activation of the AMPK pathway in human liver cells by globular adiponectin using glutathione S-transferase (GST). AMPK activity can be measured by the relative concentration of phosphorylated acetyl Co-A carboxylase, which is one of the products of AMPK. An increase in pACC correlates with an increase in the rate of fatty acid oxidation.

The compounds of structural formulae (I)-(LXXXVI) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (for example, intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(LXXXVI).

In the pharmaceutical compositions disclosed herein, one or more compounds of structural formulae (I)-(LXXXVI) may be present in association with one or more pharmaceutically acceptable carriers, diluents or excipients, and, if desired, other active ingredients. The pharmaceutical compositions containing compounds of structural formulae (I)-(LXXXVI) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(LXXXVI) can be formulated into lotions, oils or powders for application to the skin according to certain methods described below.

Compounds of structural formulae (I)-(LXXXVI) can also be administered in the form of suppositories, for example, for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(LXXXVI) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compounds disclosed herein can be made using procedures familiar to the person of ordinary skill in the art and as described herein. For example, compounds of structural formula (I) can be prepared according to Schemes 1-6, below, or analogous synthetic schemes:

Scheme 1

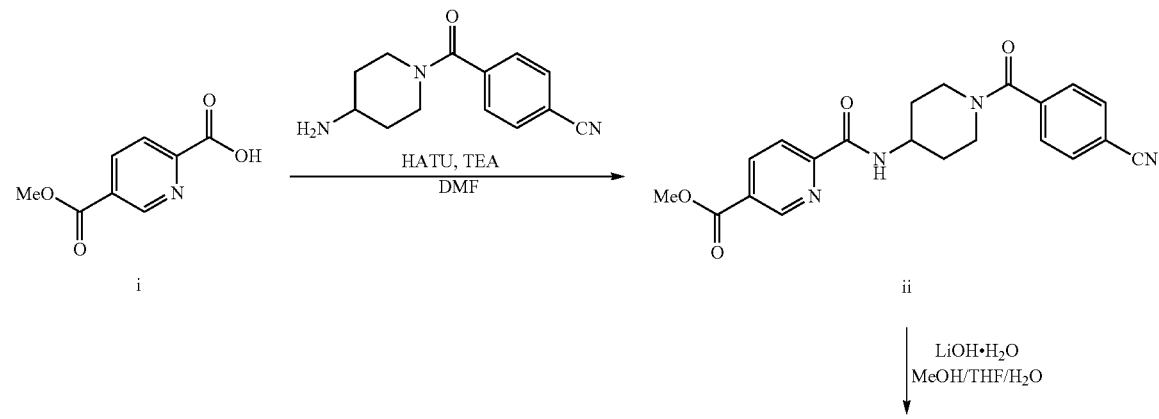

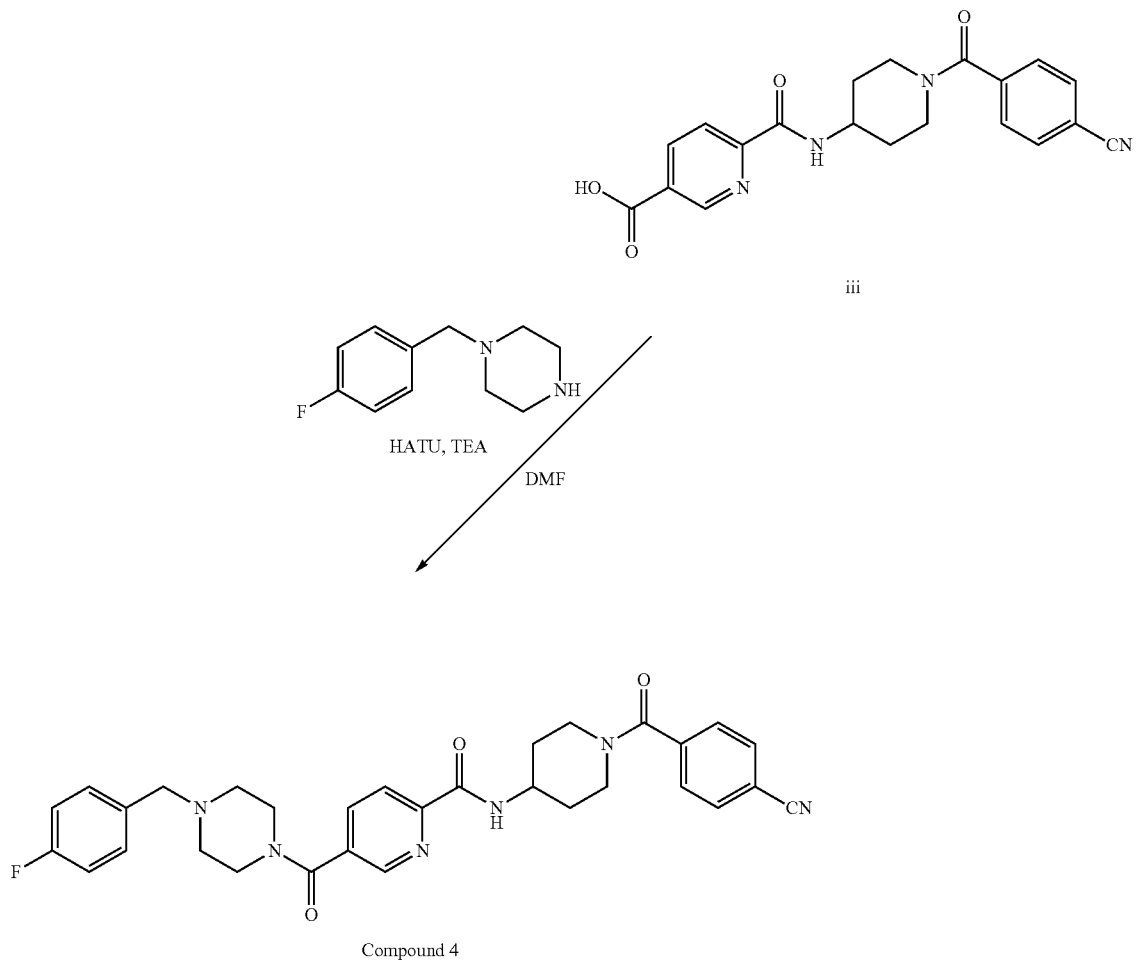

iii

Compound 4

Referring to Scheme 1, a pyridinedicarboxylic acid monomethyl ester (i), for example, is coupled with an amine (here a substituted 1-benzoylpiperidine-4-amine) to form a carboxymethyl-substituted pyridinecarboxamide (ii). The ester is saponified to form the corresponding carboxylic acid (iii), which is then coupled with a suitable amine (in this case, a substituted 1-benzylpiperazine) to form Compound 4 of Table 1.

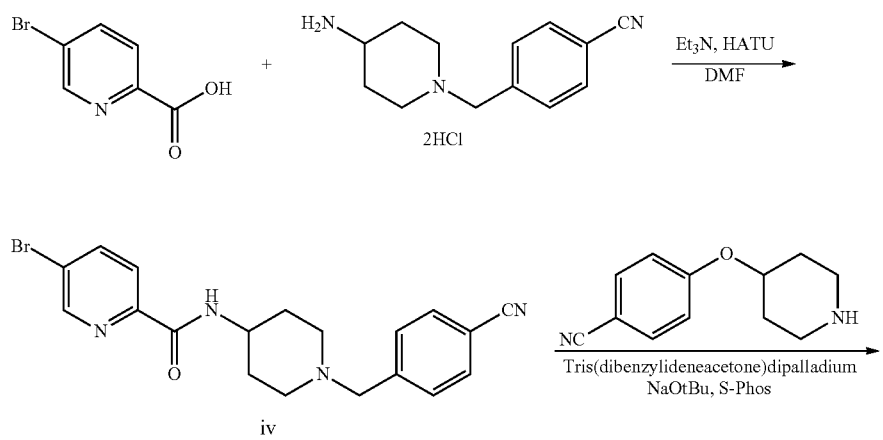

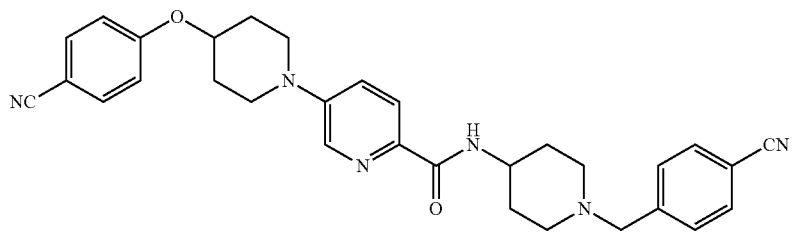
Compound 17
Referring to Scheme 2, a bromopyridinedicarboxylic acid, for example, is coupled with an amine (here a substituted 1-benzylpiperidine-4-amine) to form a bromo-substituted pyridinecarboxamide (iv), which is then coupled with a suitable amine (in this case, a substituted 4-phenoxypiperidine) using a palladium catalyst to form Compound 17 of Table 1.
Scheme 3
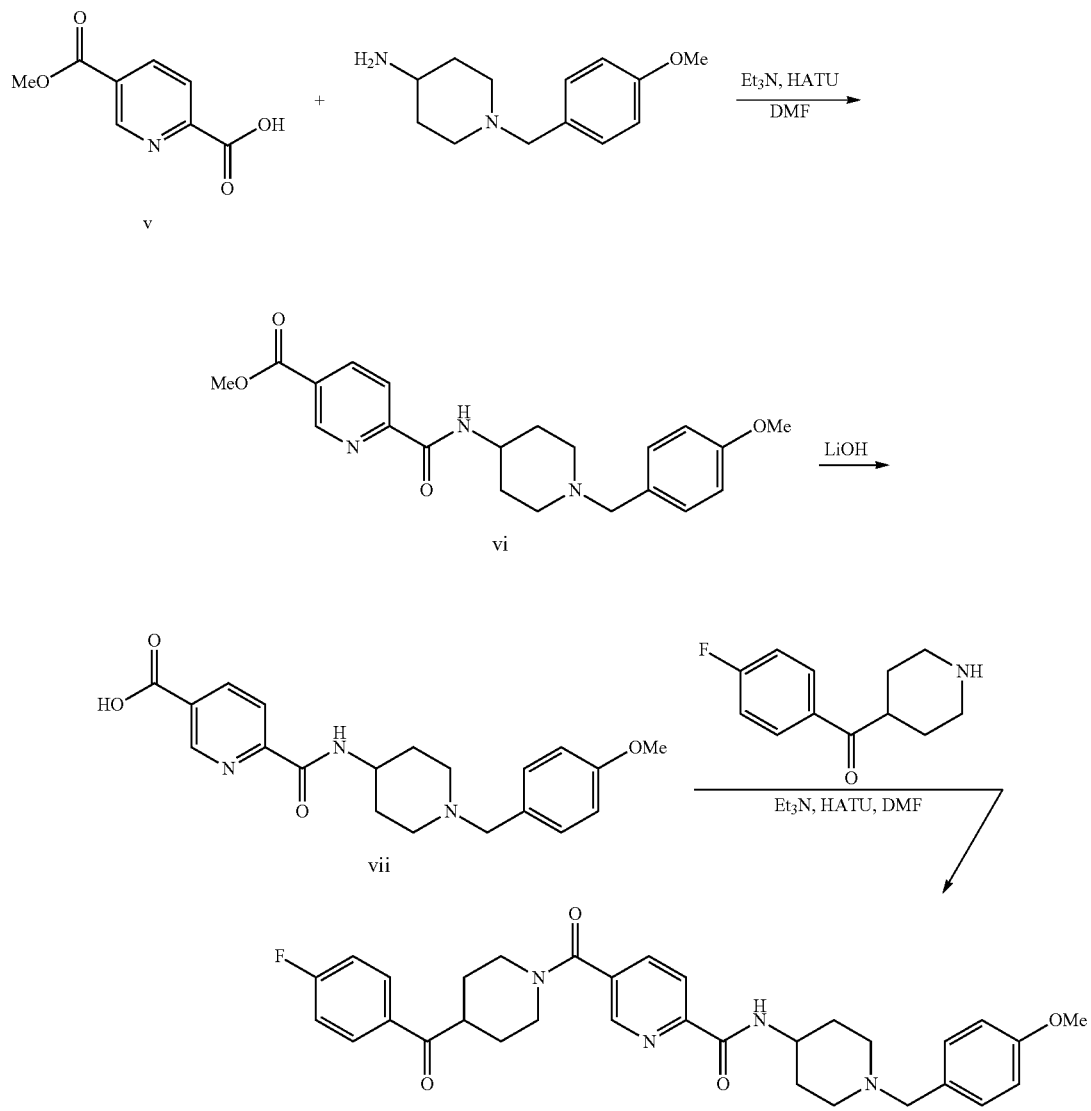

Referring to Scheme 3, a pyridinedicarboxylic acid monomethyl ester (v), for example, is coupled with an amine (here a substituted 1-benzylpiperidine-4-amine) to form a carboxymethyl-substituted pyridinecarboxamide (vi). The ester is saponified to form the corresponding carboxylic acid (vii), which is then coupled with a suitable amine (in this case, a substituted 4-benzoylpiperidine) to form Compound 160 of Table 1.

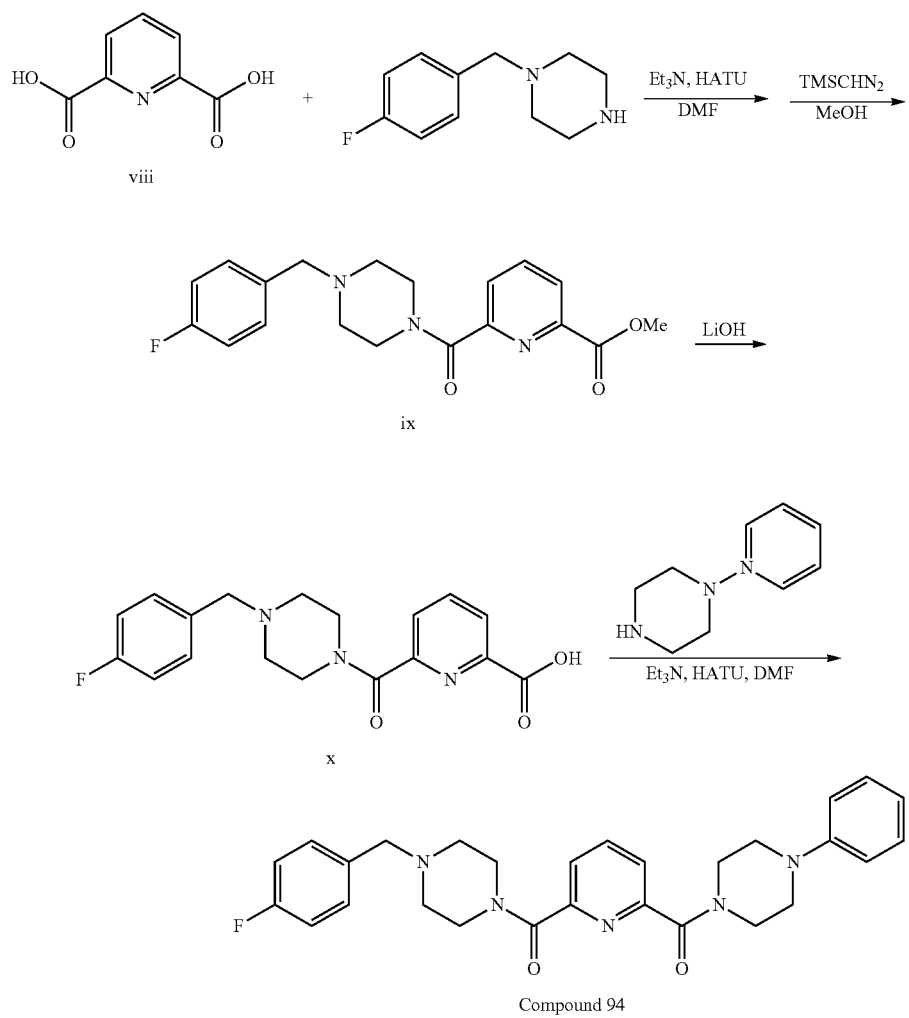

Referring to Scheme 4, a pyridine dicarboxylic acid (viii), for example, is coupled with one equivalent of an amine (here, a substituted 1-benzylepiperizine), then with methanol and trimethylsilyl(diazomethane) to form a carbomethoxy-substituted pyridinecarboxamide (ix), which is saponified to give a carboxylic acid-substituted pyridinecarboxamide (x). An amine (in this case, 1-phenylpiperazine) is coupled with the carboxylic acid-substituted pyridinecarboxamide (x) to form Compound 94 of Table 1.

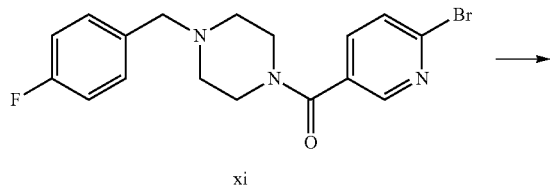

-continued

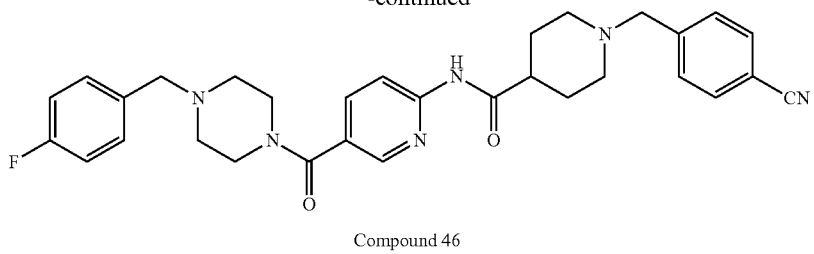

Compound 46

Referring to Scheme 5, a bromopyridinecarboxamide (xi) is coupled with a substituted 1-benzylpiperidine-4-carboxamide using a palladium catalyst to form Compound 46 of Table 1. Reactions of this general type are described in more detail, for example, in Wrona, Iwona E. et al., Journal of Organic Chemistry (2010), 75(9), 2820-2835.

Scheme 6

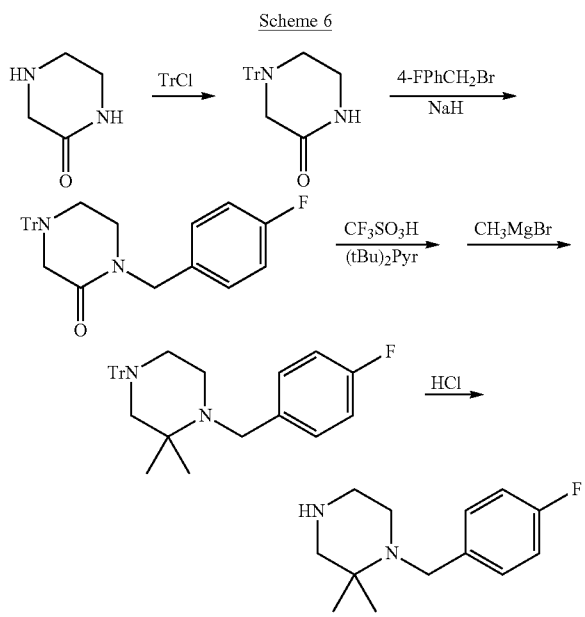

Scheme 6 describes a preparation that can be used to make gem-dimethylpiperazines for use in making compounds analogous to Compound 125 of Table 1. A piperazin-2-one is singly protected with trityl chloride, then coupled with an appropriate bromide (here, a substituted benzyl bromide) to form a 4-protected 1-(substituted benzyl)piperazin-2-one. The oxo is convered to a gem-dimethyl using Grignard chemistry, then the trityl is removed to yield the desired gem-dimethyl piperazine. Details are provided in the Examples below, and in Xiao, K-J.; Luo, J-M.; Ye, K-Y.; Wang, Y.; Huang, P-Q. Angew. Chem. Int. Ed. 2010, 49, 3037-3040.

One of skill in the art can adapt the reaction sequences of Schemes 1-6 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(LXXXVI) can be synthesized using different routes altogether.

Compounds suitable for use in the presently disclosed pharmaceutical compositions include compounds of Table 1, above. These compounds can be made according to the general scheme described above, for example using a procedure similar to that described below in the Examples.

While not intending to be bound by theory, the inventors surmise that compounds of structural formulae (I)-(LXXXVI) activate the AMPK pathway. Activation of the AMPK pathway has the effect of increasing glucose uptake, decreasing glycogen synthesis and increasing fatty acid oxidation, thereby reducing glycogen, intracellular triglyceride and fatty acid concentration and causing an increase in insulin sensitivity. Because they activate the AMPK pathway, compounds of structural formulae (I)-(LXXXVI) should also inhibit the inflammatory processes which occur during the early phases of atherosclerosis. Accordingly, compounds of structural formulae (I)-(LXXXVI) can be useful in the treatment of type II diabetes and in the treatment and prevention of atherosclerosis, cardiovascular disease, obesity and non-alcoholic fatty liver disease.

In one aspect and without limitation to theory, the present compounds exert AMPK activating activity by binding to an adiponectin receptor, acting as effective adiponectin mimetics. Adiponectin is a protein hormone exclusively expressed in and secreted from adipose tissue and is the most abundant adipose-specific protein. Adiponectin has been implicated in the modulation of glucose and lipid metabolism in insulin-sensitive tissues. Decreased circulating adiponectin levels have been demonstrated in some insulin-resistant states, such as obesity and type 2 diabetes mellitus and also in patients with coronary artery disease, atherosclerosis and hypertension. Adiponectin levels are positively correlated with insulin sensitivity, HDL (high density lipoprotein) levels and insulin stimulated glucose disposal and inversely correlated with adiposity and glucose, insulin and triglyceride levels. Thiazolidinedione drugs, which enhance insulin sensitivity through activation of the peroxisome proliferator-activated receptor-γ, increase endogenous adiponectin production in humans.

Adiponectin binds its receptors in liver and skeletal muscle and thereby activates the AMPK pathway. Similarly, in one aspect, the present compounds act as adiponectin receptor agonists. Adiponectin receptors 1 and 2 are membrane-bound proteins found in skeletal muscle and liver tissue.

Accordingly, another aspect of the present disclosure relates to a method of activating the AMPK pathway. According to this aspect, a method for activating the AMPK pathway in a cell includes contacting the cell with an effective amount of a compound, pharmaceutically acceptable salt, prodrug, N-oxide (or solvate or hydrate thereof) or composition of such a compound described above, such as a compound of one of formulas (I)-(LXXXVI).

In one embodiment, a method of increasing fatty acid oxidation in a cell includes contacting the cell with an effective amount of a compound, pharmaceutically acceptable salt, prodrug, N-oxide (or solvate or hydrate thereof) or composition of such a compound described above, such as a compound of one of formulas (I)-(LXXXVI). Acetyl Co-A carboxylase (ACC) catalyzes the formation of malonyl Co-A, a potent inhibitor of fatty acid oxidation; phosphorylation of ACC greatly reduces its catalytic activity, thereby reducing the concentration of malonyl Co-A and increasing the rate of fatty acid oxidation. Because the presently disclosed compounds can increase the rate of phosphorylation of ACC, they can reduce the inhibition of fatty acid oxidation and therefore increase its overall rate.

In another embodiment, a method of decreasing glycogen concentration in a cell includes contacting the cell with an effective amount of a compound, pharmaceutically acceptable salt, prodrug, N-oxide (or solvate or hydrate thereof) or composition of such a compound described above, such as a compound of one of formulas (I)-(LXXXVI).

In another embodiment, a method of increasing glucose uptake in a cell includes contacting the cell with an effective amount of a compound, pharmaceutically acceptable salt, prodrug, N-oxide (or solvate or hydrate thereof) or composition of such a compound described above, such as a compound of one of formulas (I)-(LXXXVI).

In another embodiment, a method of reducing triglyceride levels in a subject includes administering to the subject an effective amount of a compound, pharmaceutically acceptable salt, prodrug, N-oxide (or solvate or hydrate thereof) or composition of such a compound described above, such as a compound of one of formulas (I)-(LXXXVI).

In another embodiment, a method of increasing insulin sensitivity of a subject includes administering to the subject an effective amount of a compound, pharmaceutically acceptable salt prodrug, N-oxide (or solvate or hydrate thereof) or composition of such a compound described above, such as a compound of one of formulas (I)-(LXXXVI).

Accordingly, the compounds and compositions disclosed herein can be used to treat a variety of metabolic disorders. For example, in one embodiment, a method of treating type II diabetes in a subject in need of such treatment includes administering to the subject an effective amount of a compound, pharmaceutically acceptable salt, prodrug, solvate, hydrate, N-oxide or composition described above. In another embodiment, a method of treating or preventing atherosclerosis or cardiovascular disease in a subject includes administering to the subject an effective amount of a compound, pharmaceutically acceptable salt, prodrug prodrug, N-oxide (or solvate or hydrate thereof) or composition of such a compound described above, such as compound of one of formulas (I)-(LXXXVI).

As described above, the compounds disclosed herein can act as activators of the AMPK pathway. Accordingly, in another embodiment, a method comprises modulating the AMPK pathway (either in vitro or in vivo) by contacting a cell with a compound, pharmaceutically acceptable salt, prodrug, N-oxide (or solvate or hydrate thereof) or composition described above, or administering a compound, pharmaceutically acceptable salt, prodrug, N-oxide (or solvate or hydrate thereof) or composition described above to a mammal (for example, a human) in an amount sufficient to modulate the AMPK activity and study the effects thereby induced. Such methods are useful for studying the AMPK pathway and its role in biological mechanisms and disease states both in vitro and in vivo.

In certain embodiments, the compounds disclosed herein affect lipid signaling pathways. For example, in some embodiments, the compounds up-regulate ceramidase activity. Ceramide is a central player in sphingolipid metabolism, and is the immediate precursor of sphingomyelins and glycosphingolipids as well as the bioactive products sphingosine and sphingosine-1-phosphate. Moreover, endogenous ceramide itself mediates, at least in part, the actions of a variety of stimuli on cell differentiation, apoptosis, and growth suppression. Ceramide is deacylated by ceramidase to form sphingosine, which is in turn phosphorylated to sphingosine-1-phosphate by sphingosine kinase.

Elevated ceramide levels have been shown to induce cell apoptosis, differentiation and senescence. Moreover, elevated ceramide levels are linked to a variety of diseases and disorders, including, for example, Batten's disease, inflammatory bowel diseases, diffuse intravascular coagulation, fever, protein catabolism and/or lipid depletion, hepatosplenomegaly associated with inflammatory or metabolic liver diseases, endomyocarditis, endolithial cell and leucocyte activation, capillary thrombosis, meningo-encephalitis due to infectious agents, complications in organ transplantation, rheumatoid arthritis and connective tissue diseases, autoimmune diseases, hyperthyroidism, damage by radiation/chemotherapy agents and chronic fatigue syndrome.

Up-regulating ceramidase function (and therefore reducing the concentration of ceramide) can be used to treat disorders involving deficient cell proliferation (growth) or in which cell proliferation is otherwise desired, for example, degenerative disorders, growth deficiencies, lesions, physical trauma, and diseases in which ceramide accumulates within cells, such as Fabry disease. Other disorders that may benefit from the activation of ceramidase include neurodegenerative disorders such as Alzheimer's disease and amyotrophic lateral sclerosis and disorders of aging such as immune dysfunction, as well as disorders, such as those listed above, linked to elevated ceramide levels.

The compounds, salts, prodrugs, N-oxides, solvates and hydrates described herein can be administered, for example, to a mammalian host to retard cellular responses associated with the activation of the ceramide-mediated signal transduction pathway. The compounds can be useful, for example, in providing protection against cell senescence or apoptosis, such as occurs as a result of trauma (for example, radiation dermatitis) and aging (for example, of the skin or other organs).

Another embodiment is a method for up-regulating ceramidase function in a cell (either in vivo or in vitro), the method including contacting the cell with an effective amount of a compound, pharmaceutically acceptable salt, prodrug, N-oxide (or solvate or hydrate thereof) or composition of such a compound described above, such as a compound of one of formulas (I)-(LXXXVI).

In another embodiment, a method for decreasing ceramide concentration in a cell (either in vivo or in vitro) includes contacting the cell with an effective amount of a compound, pharmaceutically acceptable salt, prodrug, N-oxide (or solvate or hydrate thereof) or composition of such a compound described above, such as a compound of one of formulas (I)-(LXXXVI).

In another embodiment, a method for inhibiting ceramide-activated responses to stimuli in a cell (either in vivo or in vitro) includes contacting the cell with an effective amount of a compound, pharmaceutically acceptable salt, prodrug, N-oxide (or solvate or hydrate thereof) or composition described above. The stimuli can be, for example, stimuli for cell senescence and/or apoptosis.

Another embodiment is a method for treating or preventing a disease or disorder in which cell proliferation is deficient or desired in a subject, the method including administering to the subject an effective amount of a compound, pharmaceutically acceptable salt, prodrug, N-oxide (or solvate or hydrate thereof) or composition of such a compound described above, for example, a compound of one of formulas (I)-(LXXXVI). Various applicable diseases and disorders are described above.

Another embodiment is a method for treating a disease or disorder linked to elevated ceramide levels in a subject, the method including administering to the subject an effective amount of a compound, pharmaceutically acceptable salt, prodrug, N-oxide (or solvate or hydrate thereof) or composition as described herein. Various applicable diseases and disorders are described above. In certain embodiments, the subject has a ceramide level higher than about 50 pmol/$10^6$ cells.

Moreover, since some drugs can induce high levels of ceramide, the compounds, salts, prodrugs, N-oxides, solvates and hydrates described herein can be usefully co-administered with such drugs in order to at least partially ameliorate this effect. For example, in certain embodiments, an effective amount of a compound, pharmaceutically acceptable salt, prodrug, N-oxide (or solvate or hydrate thereof) or composition as described herein is co-administered with a corticosteroid (for example, dexamethasone), an anti-inflammatory (for example, indomethacin), an antiviral (for example, interferon), an immunosuppressant (for example, cyclosporin), a chemotherapy agent (for example, adriamicin), and immunopotentiant (for example, an immunoglobulin or a vaccine), or an andocrinological agent (for example, metimazole). As the person of skill in the art will appreciate, co-administration contemplates not only administration at the same time, but also administration at different times, but with time-overlapping pharmacological effects.

Another embodiment is a method for reducing the effect of aging in the skin of a subject, the method including contacting the skin with a compound, pharmaceutically acceptable salt, prodrug, N-oxide (or solvate or hydrate thereof) or composition as described herein.

Another embodiment is a method for treating or preventing radiation dermatitis in the skin of a subject, the method including contacting the skin with a compound, pharmaceutically acceptable salt, prodrug, N-oxide (or solvate or hydrate thereof) or composition as described herein.

To identify and select therapeutic compounds for use in treating ceramide-associated conditions, cells (or intracellular components such as microsomes) which have not been exposed to a senescence or apoptosis-inducing agent (for example, cytokines such as TNF-α or exogenous stimuli such as heat, radiation or chemical agents) are exposed to such and agent and to the candidate compound. Inhibition of senescence or apoptosis is measured as a function of cell growth. The person of ordinary skill in the art will be familiar with techniques for obtaining such measurements.

For example, inhibition of cell senescence can be measured after serum deprivation in serum-dependent cells. Many cell types are dependent upon serum factors for growth. Thus, deprivation of such cells of serum provides a model for assessment of compounds to modulate cell responses to intracellular ceramide-mediated signal transduction. In particular, withdrawal of serum from serum-dependent cell cultures produces increased intracellular levels of endogenous ceramide and may also increase intracellular levels of endogenous diacyl glycerol (see, e.g., Jayadev, et al., J. Biol. Chem., 270, 2047-2052 (1995)). To evaluate the inhibitory effect of the compounds described herein on ceramide-associated conditions in vitro, the serum withdrawal model can be used. Specifically, 3T3 fibroblast cells can be seeded in 96 well microtiter plates in DMEM in the presence of 10% fetal bovine serum. The cells are incubated to 90% confluence. The medium is removed, and the cells washed and reincubated in serum-free DMEM. A test compound at a variety of concentrations (for example, 0, 4, 40 or 400 μM) and cell permeable ceramide (for example, 0, 5 or 10 μM) are added to the wells. After 24 hrs. incubation, 0.5 μCi of [$^3$H] thymidine is added to each well for 2 hrs. DNA synthesis in the tested cell population is assessed by conventional techniques for detection of [$^3$H] thymidine incorporation. The results of this assay can be used to establish the cell senescence inhibitory efficacy of the test compound.

Inhibition of cell apoptosis can be determined, for example, using CD95 stimulation. Engagement of cell surface receptor CD95 (also known as Fas/Apo-1 antigen) triggers cell apoptosis. DX2 is a functional anti-FAS (CD95) antibody which will, on binding of CD95, activate the sphingomyelinase catalysis of sphingomyelin hydrolysis and production of ceramide (see, with respect to DX2, Cifone, et al., J. Exp. Med., 177, 1547-1552 (1993)). Thus, binding of CD95 is a model for conduction of apoptosis via the sphingomyelin signal transduction pathway. To assess the inhibitory effect of the compounds disclosed herein on ceramide-mediated cell apoptosis, human T lymphoblasts (Jurkat) are suspended at 2×$10^6$ cells/mL in RPMI-1640 supplemented with insulin, transferrin, selenium and glutamine. After incubation for 2 hrs. at room temperature with a test compound, pentoxifylline or a control compound (Ro-1724), 25 ng/mL of anti-FAS antibody is added to each suspension. After another 2 hrs., cell apoptosis is measured as a function of the number of cells (counted by hemocytometer) that excluded the vital dye erythrosin B. The results of the experiment can be used to establish the apoptosis inhibitory efficacy of the test compound.

To assess the inhibitory effect of the compounds disclosed herein on death of human lymphocytes, human peripheral blood lymphocytes are isolated from normal human blood and depleted of monocytes by adherence to a plastic substrate. Lymphocytes are then cultured in RPMI-1640 medium with 10% autologous plasma at an initial concentration of 2×$10^6$ cells/mL. Aliquots of the cell samples are divided and one half of the samples are incubated with a test compound or 6,7-dimethoxy-1(2H)-isoquinoline (Aldrich) for four days. The remaining half of the samples are allowed to rest for four days. Cell viability after four days is determined by erythrosin B dye exclusion in a hemocytometer. The results of the experiment can be used to establish the apoptosis inhibitory efficacy of the test compound on human lymphocytes as compared to untreated lymphocytes.

Ceramide-activated protein kinase (CaPK) is a 97 kDa protein which is exclusively membrane-bound and is believed to serve a role in the sphingomyelin signal transduction pathway. In particular, CaPK is believed to mediate phosphorylation of a peptide derived from the amino acid sequence surrounding Thr.sup.669 of the epidermal growth factor receptor (i.e., amino acids 663-681). This site is also recognized by the mitogen-activated kinase MAP (also known as a family of extracellular signal-regulated kinases). Thus, the effect of the compounds disclosed herein on CaPK activity in cells can be indicative of the effect that the compounds exert on signal transduction in the sphingomyelin pathway. Accordingly, Jurkat cells are suspended at 2×$10^6$ cells/mL in RPMI-1640 medium as described above with respect to the cell apoptosis experiment. After incubation for 2 hrs., either a test compound; 20 μM of ceramide or 25 ng/ml of anti-FAS antibody DX2 are added to each suspension and incubated for 15 mins. After centrifugation and washing, the cells were separately homogenized in a dounce homogenizer. Ceramide kinase levels in each test sample can be assayed as described by Liu, et al., J. Biol. Chem., 269, 3047-3052

(1994), which is hereby incorporated by reference herein in its entirety. Briefly, the membrane fraction is isolated from each test sample of treated cell homogenate by ultracentrifugation and run on a 10% PAGE gel. The gel is washed with guanadine-HCl, and renatured in HEPES buffer. Then [$^{32}$P]-ATP is added to the gel and left there for 10 mins. Thereafter, the gel is extensively washed with 5% TCA. Autophosphorylated kinase is detected by autoradiography. The results of this assay can be used to establish the CaPK inhibitory efficacy of the compounds disclosed herein.

Ceramidase activity can be measured in a variety of ways. For example, a sample from a subject or a sample of cells can be assayed in vitro for RNA or protein levels, structure, and/or activity of the expressed ceramidase RNA or protein. Many methods standard in the art can be thus employed, including but not limited to ceramidase enzyme assays.

Cellular ceramide levels can be monitored directly, or by indirectly monitoring the concentrations of a ceramide metabolite in a cell. For example, ceramide levels can be directly measured by isolating peripheral blood lymphocytes from a subject. The cells are centrifuged to remove supernatant, and lipids are removed from the cell pellet. The organic phase containing the ceramide can be assayed using the diacylglycerase kinase assay for phosphorylating the ceramide which is then evidenced by autoradiography. Methods for performing diacylglycerase kinase assays are described, for example, in Cifone, M. G. et al., J. Exp. Med., 180(4), 1547-52 (1993), Jayadev et al., J. Biol. Chem., 270, 2047-2052. (1995), and Perry, D. K. et al, Methods Enzymology, 312, 22-31 (2000), each of which is hereby incorporated by reference in its entirety.

The presently disclosed AMPK activating compounds are useful for increasing metabolic efficiency, for example by increasing fiber oxidative capacity, endurance and aerobic workload. In particular, the present compounds are useful for treating and regulating disorders of mitochondrial function, including, without limitation, exercise intolerance, chronic fatigue syndrome, muscle weakness, myoclonus, myoclonus epilepsy, such as associated with ragged-red fibers syndrome, Kearns-Sayre syndrome, Leigh's syndrome, mitochondrial myopathy encephalopathy lactacidosis stroke (MELAS) syndrome and stroke like episodes. The disclosed compounds also are useful for treating muscular dystrophic states, such as Duchenne's and Becker's muscular dystrophies and Friedreich's ataxia.

The presently disclosed AMPK activating compounds also function to reduce oxidative stress and secondary effects of such stress. Many diseases, including several of those listed above, have secondary effects caused by damage due to excessive oxidative stress which can be treated using the compounds disclosed herein. For example, free radical damage has been implicated in neurological disorders, such as Parkinson's disease, amyotrophic lateral sclerosis (Lou Gehrig's disease) and Alzheimers disease. Additional diseases in which excessive free radical damage occurs generally include hypoxic conditions and a variety of other disorders. More specifically, such disorders include ischemia, ischemic reperfusion injury (such as coronary or cerebral reperfusion injury), myocardial ischemia or infarction, cerebrovascular accidents (such as a thromboembolic or hemorrhagic stroke) that can lead to ischemia in the brain, operative ischemia, traumatic hemorrhage (for example, a hypovolemic stroke that can lead to CNS hypoxia or anoxia), resuscitation injury, spinal cord trauma, inflammatory diseases, autoimmune disorders (such as rheumatoid arthritis or systemic lupus erythematosis), Down's syndrome, Hallervorden-Spatz disease, Huntingtons chorea, Wilson's disease, diabetic angiopathy (such as peripheral vascular disease or retinal degeneration), uveitis, chronic obstructive pulmonary disease (COPD), including chronic bronchitis and emphysema, asthma, neoplasia, Crohn's disease, inflammatory bowel disease and pancreatitis. Free radical damage is also implicated in a variety of age-related disorders, particularly ophthalmic conditions such as cataracts and age-related macular degeneration.

In particular the present compounds are useful for treating neurological disorders associated with reduced mitochondrial function, oxidative stress, or both. For example, Alzheimer's disease, dementia and Parkinson's disease can be treated using the present AMPK activating compounds.

Metabolic efficiency is enhanced by the disclosed AMPK activating compounds. Thus the compounds can be administered to a subject to improve exercise efficiency and athletic performance. Moreover, conditions including, without limitation, hypoxic states, angina pectoris, coronary ischemia and organ damage secondary to coronary vessel occlusion, intermittent claudication, multi-infarct dementia, myocardial infarction, stroke, high altitude sickness and heart failure, including congestive heart failure can be treated using the disclosed compounds.

Inflammatory disorders and effects can be treated using the present compounds. For example, in one aspect, the present compounds are particularly useful for treating lung inflammation, such as is involved in asthma, COPD and transplant rejection. Similarly, the present compounds are useful in reducing organ inflammation, particularly macrophage-associated inflammation, such as inflammation of the kidney, liver and other organs. The anti-inflammatory activity of the presently disclosed compounds can be assessed as is known to those of skill in the art, for example, by using the mixed lymphocyte response in vitro.

Accordingly, one aspect of the disclosure relates to a method for treating or ameliorating a disorder or condition related to oxidative stress, mitochondrial dysfunction, free radical damage and/or metabolic inefficiency in a subject in need thereof, the method including administering to the subject an effective amount of a compound, pharmaceutically acceptable salt, prodrug, N-oxide (or solvate or hydrate thereof) or pharmaceutical composition described above.

Another aspect of the present disclosure relates to a method for the treatment or amelioration of a disorder of mitochondrial dysfunction in a subject in need thereof, the method including administering to the subject an effective amount of a compound, pharmaceutically acceptable salt, prodrug, N-oxide (or solvate or hydrate thereof) or pharmaceutical composition described above. In certain embodiments, the disorder is selected from the group consisting of exercise intolerance, chronic fatigue syndrome, muscle weakness, myoclonus, myoclonus epilepsy (such as associated with ragged-red fibers syndrome), Kearns-Sayre syndrome, Leigh's syndrome, mitochondrial myopathy encephalopathy lactacidosis stroke (MELAS) syndrome and stroke like episodes.

Another aspect of the disclosure relates to a method of increasing metabolic efficiency in a subject in need thereof, the method including administering to the subject an effective amount of a compound, pharmaceutically acceptable salt, prodrug, N-oxide (or solvate or hydrate thereof) or pharmaceutical composition described above. Such methods can be used to increase fiber oxidative capacity, endurance, aerobic workload, or any combination thereof. These methods can be used, for example, to improve exercise efficiency, exercise endurance and/or athletic performance in a subject.

Another aspect of the present disclosure relates to methods for mimicking the effects of exercise in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for treating or ameliorating a disorder in a subject in need thereof, the disorder being selected from the group consisting of hypoxic states, angina pectoris, coronary ischemia and organ damage secondary to coronary vessel occlusion, intermittent claudication, multi-infarct dementia, myocardial infarction, stroke, high altitude sickness and heart failure, including congestive heart failure, the method including administering to the subject an effective amount of a compound, pharmaceutically acceptable salt, prodrug, N-oxide (or solvate or hydrate thereof) or pharmaceutical composition described above.

Another aspect of the disclosure relates to a method for the treatment of amelioration of a muscular dystrophic state in a subject in need thereof, the method including administering to the subject an effective amount of a compound, pharmaceutically acceptable salt, prodrug, N-oxide (or solvate or hydrate thereof) or pharmaceutical composition described above. In certain embodiments, the muscular dystrophic state is Duchenne's muscular dystrophy, Becker's muscular dystrophy, or Freidreich's ataxia.

Another aspect of the disclosure relates to a method for increasing oxidative capacity of a muscle fiber, the method including contacting the muscle fiber with a compound, pharmaceutically acceptable salt, prodrug, N-oxide (or solvate or hydrate thereof) or pharmaceutical composition described above. The contacting may be performed in vitro or in vivo.

Another aspect of the disclosure relates to a method for reducing oxidative stress in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for reducing free radical damage in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for treating or ameliorating a disorder or condition in a subject in need thereof, the disorder or condition selected from the group consisting of neurological disorders, hypoxic conditions, ischemia, ischemic reperfusion injury, myocardial ischemia or infarction, cerebrovascular accidents, operative ischemia, traumatic hemorrhage, resuscitation injury, spinal cord trauma, inflammatory diseases, autoimmune disorders, Down's syndrome, Hallervorden-Spatz disease, Huntingtons chorea, Wilson's disease, diabetic angiopathy, uveitis, chronic obstructive pulmonary disease (COPD), asthma, neoplasia, Crohn's disease, inflammatory bowel disease, pancreatitis and age-related disorders, the method including administering to the subject an effective amount of a compound, pharmaceutically acceptable salt, prodrug, N-oxide (or solvate or hydrate thereof) or pharmaceutical composition described above. Particular examples of such disorders and conditions are discussed above.

Another aspect of the disclosure is a method for treating or ameliorating a neurological disorder in a subject in need thereof, the neurological disorder being associated with reduced mitochondrial function, oxidative stress, or both, the method including administering to the subject an effective amount of a compound, pharmaceutically acceptable salt, prodrug, N-oxide (or solvate or hydrate thereof) or pharmaceutical composition described above. Particular examples of such neurological disorders are discussed above.

Another aspect of the disclosure relates to a method for reducing oxidative stress in a cell, the method including contacting the cell with a compound, pharmaceutically acceptable salt, prodrug, N-oxide (or solvate or hydrate thereof) or pharmaceutical composition described above. The contacting may be performed in vitro or in vivo.

Another aspect of the disclosure relates to a method for reducing free radical damage in a cell, the method including contacting the cell with a compound, pharmaceutically acceptable salt, prodrug, N-oxide (or solvate or hydrate thereof) or pharmaceutical composition described above. The contacting may be performed in vitro or in vivo.

Another aspect of the disclosure is a method for treating an inflammatory disorder or effect in a subject in need thereof, the method including administering to the subject an effective amount of a compound, pharmaceutically acceptable salt, prodrug, N-oxide (or solvate or hydrate thereof) or pharmaceutical composition described above. For example, in one embodiment, the inflammatory disorder or effect is lung inflammation, such as is involved in asthma, COPD and transplant rejection. In another embodiment, the inflammatory disorder or effect is organ inflammation, particularly macrophage-associated inflammation, such as inflammation of the kidney, liver and other organs.

Another embodiment is the use of a compound, pharmaceutically acceptable salt, prodrug, N-oxide (or solvate or hydrate thereof) or composition as described above in the manufacture of a medicament for any of the therapeutic purposes described above. For example, the medicament can be for the reduction of triglyceride levels in a subject, the treatment of type II diabetes in a subject, or the treatment or prevention of atherosclerosis or cardiovascular disease in a subject. In other embodiments, the medicament can be used to reduce the levels of cellular ceramide in a subject, for example in the treatment of Batten's disease.

The compounds disclosed herein can be linked to labeling agents, for example for use in variety of experiments exploring their receptor binding, efficacy and metabolism. Accordingly, another embodiment is a labeled conjugate comprising a compound as disclosed herein covalently linked to a labeling agent, optionally through a linker. Suitable linker and labeling agents will be readily apparent to those of skill in the art upon consideration of the present disclosure. The labeling agent can be, for example, an affinity label such as biotin or strepavidin, a hapten such as digoxigenin, an enzyme such as a peroxidase, or a fluorophoric or chromophoric tag. Any suitable linker can be used. For example, in some embodiments, an ethylene glycol, oligo(ethylene glycol) or poly(ethylene glycol) linker is used. Other examples of linkers include amino acids, which can be used alone or in combination with other linker groups, such as ethylene glycol, oligoethylene glycol or polyethylene glycol. Suitable linkers include, without limitation, single amino acids, as well as di- and tripeptides.

In one embodiment, the linker includes a glycine residue. The person of skill in the art will realize, of course, that other linkers and labeling agents can be used. In other embodiments, an alkylene chain is the linker. In other embodiments, the linker has the structure —$[(C_0-C_3 \text{ alkyl})-Y^m]_m$—, in which each $Y^m$ is —O—, —N(R$^9$)—, or L, and m is in the range of 1-40. For example, in certain embodiments, a labeled conjugate has structural formula (LXXXVII):

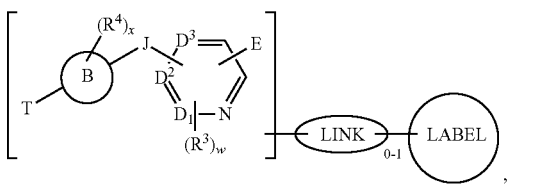

(LXXXVII)

in which the "LINK" moiety is a linker and is optional, and the "LABEL" moiety is a labeling agent, the LINK$_{0-1}$-LABEL moiety is bound to the bracketed compound at any aryl or heteroaryl carbon (for example, of the central pyridine, pyridazine, pyrimidine or pyrazine, of the E moiety (e.g., of an R$^{17}$ group thereof as in compound 403), or of the T moiety (e.g., of an "A" ring thereof as in compounds 371 and 394)), and all other variables are as described above, for example with reference to structural formula (I). Any of the compounds disclosed with reference to structural formulae (I)-(LXXXVI) can be used in the labeled conjugate of structural formula (LXXXVII).

For example, in one particular embodiment, a labeled conjugate has structural formula (LXXXVIII):

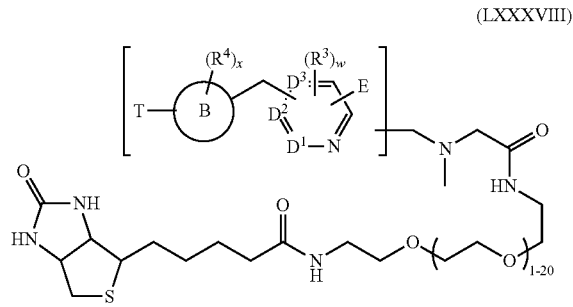

(LXXXVIII)

in which all variables are as described above, for example with reference to any of structural formulae (I)-(LXXXVI). The bond to the bracketed compound can be made, for example, at the central pyridine, pyridazine, pyrimidine or pyrazine.

Another disclosed embodiment of a labeled conjugate has the formula (LXXXIX):

The bond to the bracketed compound can be made, for example, at the central pyridine, pyridazine, pyrimidine or pyrazine.

Compounds of formulae (LXXXIX) can be synthesized by those of skill in the art of organic synthesis, for example by reductive amination of N-Boc-glycine aldehyde with a primary amine H$_2$NR$^2$, to yield R$^2$NHCH$_2$CH$_2$NHBoc, which is can be coupled to a pyridinecarboxylic acid to build up the target structure as described herein. The Boc protecting group can be removed, and the resulting amine further elaborated to provide the labeled species.

In another particular embodiment, a labeled conjugate has structural formula (XC):

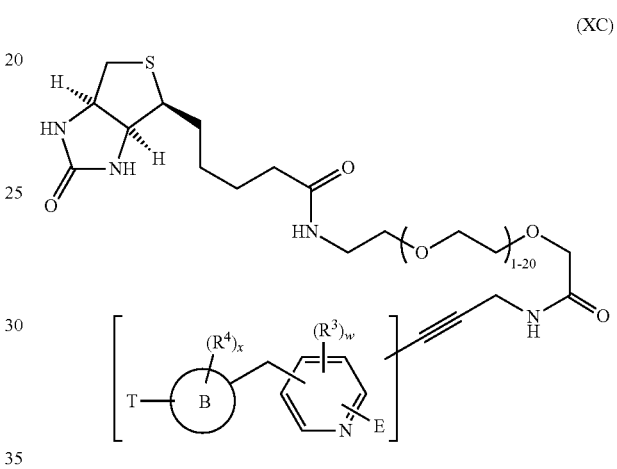

(XC)

in which all variables are as described above, for example with reference to any of structural formulae (I)-(LXXXVI). The bond to the bracketed compound can be made, for example, at the central pyridine, pyridazine, pyrimidine or pyrazine. Compound 159 is an example of an embodiment according to structural formula (XC).

Compounds according to structural formula (XC) can be made according to Scheme 7, below, and as described with respect to Examples 159 and 164.

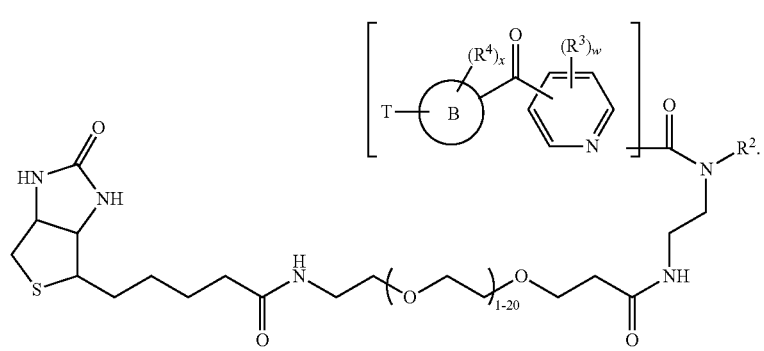

(LXXXIX)

Scheme 7
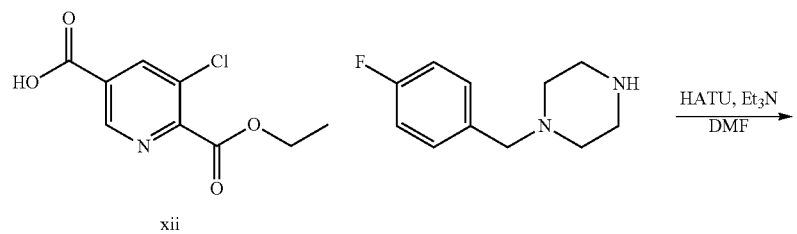
xii
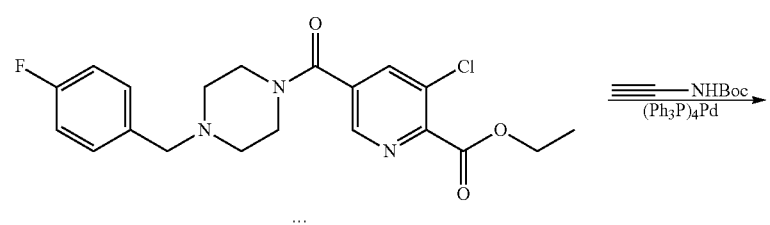
xiii
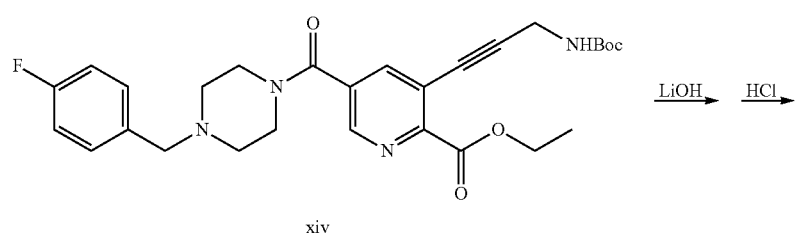
xiv
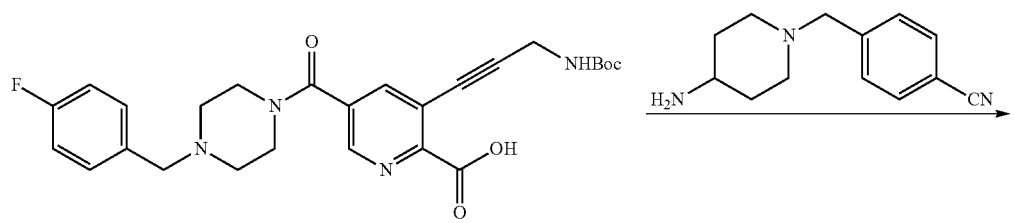
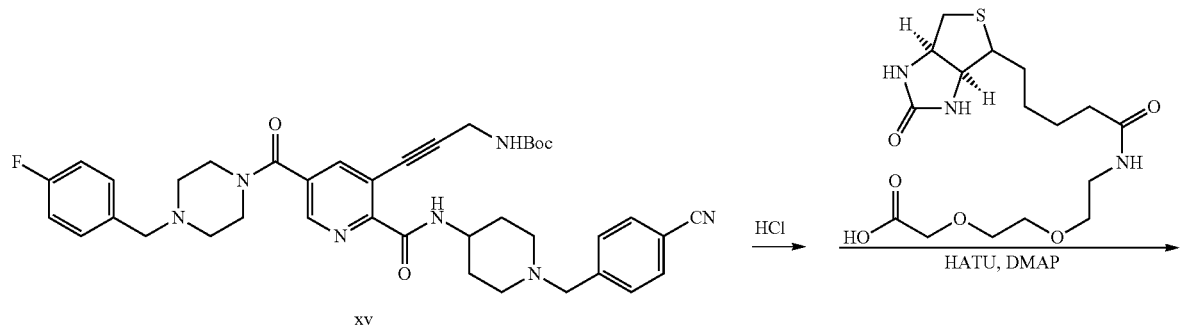
xv -continued

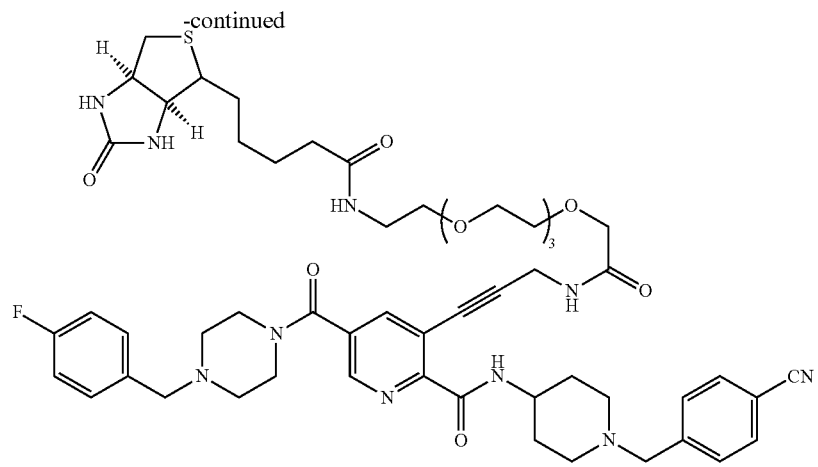

Referring to Scheme 7, a chloropyridinedicarboxylic acid monoethyl ester (xii) is coupled with an amine (here, a substituted 1-benzylpiperazine) to form a carboxymethyl-substituted chloropyridinecarboxamide (xiii), which is coupled with a protected propargyl amine to form a carboxyethyl-substituted alkynylpyridinecarboxamide (xiv). Compound (xiv) is saponified, then coupled with an amine (here, a substituted 1-benzylpiperidine), to form a (3-amino-1-propyne)-substituted pyridinedicarboxamide, Compound 164 of Table 1. Compound 164 is deprotected, and the free amine is coupled with a biotinyl-linked acid to form Compound 159 of Table 1.

The following Examples are intended to further illustrate certain embodiments and are not intended to limit the scope of the disclosure.

EXAMPLES

Example 1

The following compounds were made using methods analogous to those of Schemes 1-7; in certain cases, exemplary synthetic procedures are provided.

Compound 1 N-(4-(4-cyanobenzyl)piperidin-4-yl)-6-(4-(4-fluorobenzyl)piperizine-1-carbonyl)picolinamide. $^1$H nmr (CD$_3$OD) δ 8.96 (1H, s), 8.29 (1H, dd, J 8.0, 2.0 Hz), 7.71-7.64 (3H, m), 7.55 (2H, d, J 8.0 Hz), 7.38-7.32 (2H, m), 7.04 (2H, t, J 8.5 Hz), 3.96-3.85 (1H, m), 3.82-3.76 (2H, m), 3.62 (2H, s), 3.54 (2H, s), 3.48-3.43 (2H, m), 2.91 (2H, m), 2.56 (2H, m), 2.45 (2H, m), 2.19 (2H, m), 1.95 (2H, m), 1.74-1.63 (3H, m); m/z: 542 [M+H]$^+$.

Compound 2: N-(1-(4-cyanobenzyl)piperidin-4-yl)-5-(piperazine-1-carbonyl)picolinamide. $^1$H nmr (CD$_3$OD) δ 8.67 (1H, s), 8.15 (1H, d, J 8.0 Hz), 7.99 (1H, dd, J 8.0, 2.0), 7.68 (2H, d, J 8.0 Hz), 7.54 (2H, d, J 8.0 Hz), 3.97-3.87 (1H, m), 3.75 (2H, m), 3.62 (2H, s), 3.39 (2H, m), 2.97-2.74 (6H, m), 2.23 (2H, m), 1.96-1.91 (2H, m), 1.80-1.66 (3H, m); m/z: 533 [M+H]$^+$.

Compound 3: pyridine-2,5-diylbis((4-(4-fluorobenzyl)piperazin-1-yl)methanone). $^1$H nmr (CD$_3$OD) δ 8.62 (1H, s), 7.97 (1H, dd, J 8.0, 2.0 Hz), 7.66 (1H, d, J 8.0 Hz), 7.38-7.32 (m, 4H), 7.07-7.01 (4H, m), 3.82-3.74 (4H, m), 3.55-3.47 (8H, m), 2.58-2.54 (4H, m), 2.46-2.41 (4H, m); m/z: 520 [M+H]$^+$.

Compound 4: N-(1-(4-cyanobenzoyl)piperidin-4-yl)-5-(4-(4-fluorobenzyl)piperazine-1-carbonyl)picolinamide. $^1$H nmr (CD$_3$OD) δ 8.66 (1H, s), 8.15 (1H, d, J 8.0 Hz), 7.99 (1H, dd, J 8.0, 2.0 Hz), 7.84 (2H, d, J 8.5 Hz), 7.60 (2H, d, J 8.5 Hz), 7.37-7.32 (2H, m), 7.04 (2H, t, J 9.0 Hz), 4.63 (1H, m), 4.24-4.17 (1H, m), 3.79 (2H, m), 3.67-3.52 (4H, m), 3.43 (2H, m), 3.11-3.03 (1H, m), 2.56 (2H, m), 2.43 (2H, m), 2.14-1.85 (2H, m), 1.79-1.62 (2H, m); m/z: 555 [M+H]$^+$.

Compound 5: N$^2$-(1-(4-cyanobenzyl)piperidin-4-yl)-N$^5$-(3-benzylphenyl)pyridine-2,5-dicarboxamide. $^1$H nmr (CDCl$_3$) δ 9.01 (1H, s), 8.26 (2H, s), 7.96 (1H, d, J 8.0 Hz), 7.87 (1H, s), 7.61 (2H, d, J 8.5 Hz), 7.57 (2H, d, J 8.0 Hz), 7.45 (2H, d, J 8.0 Hz), 7.32-7.16 (m, 7H), 3.99 (3H, s), 3.56 (2H, s), 2.84 (2H, m), 2.22 (2H, m), 2.02 (2H, m), 1.72-1.61 (2H, m); m/z: 530 [M+H]$^+$.

Compound 6: N-(4-((4-cyanophenyl)sulfonyl)piperidin-4-yl)-5-(4-(4-fluorobenzyl)piperazine-1-carbonyl)picolinamide. $^1$H nmr (CDCl$_3$) δ 8.57 (1H, br s), 8.17 (1H, m), 7.91-7.83 (m, 6H), 7.28 (1H, m), 7.01 (2H, m), 3.98-3.77 (5H, m), 3.57-3.30 (4H, m), 2.62-2.31 (6H, m), 2.09 (2H, m), 1.78-1.62 (2H, m); m/z: 591 [M+H]$^+$.

Compound 7: N-(1-(cyclohexanecarbonyl)piperidin-4-yl)-5-(4-(4-fluorobenzyl)piperazine-1-carbonyl)picolinamide. m/z: 537 [M+H]$^+$.

Compound 8: N-(1-(benzoyl)piperidin-4-yl)-5-(4-(4-fluorobenzyl)piperazine-1-carbonyl)picolinamide. $^1$H nmr (CD$_3$OD) δ 8.66 (1H, m), 8.15 (1H, d, J 8.0 Hz), 7.98 (1H, dd, J 8.0, 2.0), 7.48-7.40 (5H, m), 7.37-7.31 (2H, m), 7.07-7.01 (2H, m), 4.62 (1H, m), 4.24-4.14 (1H, m), 3.78 (3H, m), 3.54 (2H, s), 3.43 (2H, m), 3.26-3.00 (3H, m), 2.54 (2H, m), 2.42 (m, 2H), 2.10-1.84 (2H, m), 1.69 (2H, m); m/z: 530 [M+H]$^+$.

Compound 9: N-(1-(4-cyanobenzyl)-1H-pyrazol-3-yl)-5-(4-(4-fluorobenzyl)piperazine-1-carbonyl)picolinamide. $^1$H nmr (CD$_3$OD) δ 8.68 (1H, m), 8.23 (1H, d, J 8.0 Hz), 8.02 (1H, dd, J 8.0, 2.0 Hz), 7.71-7.64 (3H, m), 7.38-7.30 (4H, m), 7.02 (2H, m), 6.80 (1H, m), 5.36 (2H, s), 3.76 (2H, m), 3.52 (2H, s), 3.43 (2H, m), 2.53 (2H, m), 2.41 (2H, m); m/z: 524 [M+H]$^+$.

Compound 10: N-(4-benzylphenyl)-5-(4-(4-fluorobenzyl)piperazine-1-carbonyl)picolinamide. $^1$H nmr (CDCl$_3$) δ 9.88 (1H, s), 8.64 (1H, s), 8.32 (1H, d, J 8.0 Hz), 7.92 (1H, dd, J 8.0, 2.0 Hz), 7.69 (2H, d, J 8.5 Hz), 7.33-7.17 (9H, m), 7.02 (2H, m), 3.98 (2H, s), 3.83 (2H, s), 3.55-3.40 (4H, m), 2.62-2.36 (4H, m); m/z: 510 [M+H]$^+$.

Compound 11: 5-(4-(4-fluorobenzyl)piperazine-1-carbonyl-N-(4-phenylphenyl)picolinamide. $^1$H nmr (D$_6$-DMSO) δ 10.79 (1H, s), 8.73 (1H, m), 8.20 (1H, d, J 8.0 Hz), 8.06 (1H, dd, J 8.0, 2.0), 8.00 (2H, d, J 9.0 Hz), 7.67 (4H, m), 7.44 (2H, t, J 8.0 Hz), 7.35-7.29 (3H, m), 7.13 (2H, t, J 9.0 Hz), 3.66 (2H, m), 3.49 (2H, s), 3.33 (2H, m), 2.44 (2H, m), 2.35 (2H, m); m/z: 495 [M+H]$^+$.

Compound 12: 5-(4-(4-fluorobenzyl)piperazine-1-carbonyl-N-(3-phenylphenyl)picolinamide. $^1$H nmr (CDCl$_3$) δ 9.95 (1H, s), 8.60 (1H, m), 8.28 (1H, d, J 8.0 Hz), 7.96 (1H, m), 7.86 (1H, dd, J 8.0, 2.0 Hz), 7.70 (1H, m), 7.57 (2H, d, J 7.0 Hz), 7.42-7.19 (7H, m), 6.95 (2H, m), 3.76 (2H, m), 3.46 (2H, s), 3.37 (2H, m), 2.49 (2H, m), 2.36 (2H, m); m/z: 495 [M+H]$^+$.

Compound 13: N-(1-(cyclohexylmethyl)piperidin-4-yl)-5-(4-(4-fluorobenzyl)piperazine-1-carbonyl)picolinamide. $^1$H nmr (CDCl$_3$) δ 8.56 (1H, s), 8.18 (1H, d, J 8.0 Hz), 7.98 (1H, d, J 8.0 Hz), 7.86 (1H, dd, J 8.0, 2.0 Hz), 7.29-7.24 (2H, m), 7.03-6.95 (2H, m), 4.07 (1H, m), 3.79 (2H, m), 3.50 (2H, s), 3.38 (2H, m), 3.20-3.10 (2H, m), 2.97 (1H, d, J 5.0 Hz), 2.60-2.35 (8H, m), 2.16-2.06 (2H, m), 1.95-1.60 (6H, m), 1.31-1.08 (4H, m), 1.01-0.86 (2H, m); m/z: 522 [M+H]$^+$.

Compound 14: 5-(4-(4-fluorobenzyl)piperazine-1-carbonyl)-N-(1-(phenyl)piperidin-4-yl)picolinamide. $^1$H nmr (D$_6$-DMSO) δ 8.73 (1H, d, J 9.0 Hz), 8.62 (1H, m), 8.06 (1H, d, J 8.0 Hz), 7.98 (1H, dd, J 8.0, 2.0 Hz), 7.35-7.28 (2H, m), 7.21-7.08 (4H, m), 6.96-6.91 (2H, m), 6.73 (1H, m), 3.97 (1H, m), 3.72-3.58 (4H, m), 3.47 (2H, s), 2.82-2.70 (2H, m), 2.41 (2H, m), 2.31 (2H, m), 1.88-1.74 (4H, m); m/z: 503 [M+H]$^+$.

Compound 15: 4-((8-(5-(4-(4-fluorobenzyl)piperazine-1-carbonyl)picolinoyl)-2,8-diazaspiro[4.5]decan-2-yl)methyl)benzonitrile. $^1$H nmr (D$_6$-DMSO) δ 8.56 (1H, s), 7.91 (2H, d, J 8.5 Hz), 7.78 (2H, m), 7.57 (1H, t, J 8.0 Hz), 7.49 (1H, m), 7.32 (2H, m), 7.13 (2H, m), 3.62 (4H, m), 3.47 (4H, m), 3.40-3.20 (8H, m), 2.44-2.37 (6H, m), 1.58 (4H, m); m/z: 582 [M+H]$^+$.

Compound 16: 5-(4-(4-fluorobenzyl)piperazine-1-carbonyl)-N-(4-phenoxyphenyl)picolinamide. $^1$H nmr (CDCl$_3$) δ 9.84 (1H, s), 8.58 (1H, m), 8.26 (1H, d, J 8.0 Hz), 7.85 (1H, dd, J 8.0, 2.0), 7.67 (2H, d, J 9.0 Hz), 7.30-7.18 (4H, m), 7.06-6.90 (7H, m), 3.76 (2H, m), 3.46 (2H, s), 3.37 (2H, m), 2.49 (2H, m), 2.35 (2H, m); m/z: 512 [M+H]$^+$.

Compound 17: (4-(4-fluorobenzyl)piperazin-1-yl)(6-(4-(benzyloxy)phenyl)pyridin-3-yl)methanone. To a mixture of (4-(4-fluorobenzyl)piperazin-1-yl)(6-bromopyridin-3-yl)methanone (0.048 g, 0.13 mmol, 1.0 eq), 4-benzyloxyphenylboronic acid (0.040 g, 0.18 mmol, 1.4 eq), potassium phosphate (0.053 g, 0.25 mmol, 1.9 eq), S-Phos (0.006 g, 0.01 mmol, 0.1 eq), and tris(dibenzylideneacetone)dipalladium(0) (0.012 g, 0.01 mmol, 0.01 eq) was added 1-butanol-water (1.25 mL, 4:1). Following a 5 minute purge of the reaction mixture with argon, the reaction vessel was sealed and heated at 100° C. for 10 hours. The reaction mixture was filtered through Celite®, eluting with 5% MeOH—CH$_2$Cl$_2$ and purified by RP-HPLC to provide Compound 17. $^1$H nmr (D$_6$-DMSO) δ 8.61 (1H, s), 8.06 (2H, d, J 9.0 Hz), 7.95 (1H, d, J 8.0 Hz), 7.83 (1H, dd, J 8.0, 2.0 Hz), 7.48-7.30 (7H, m), 7.16-7.10 (4H, m), 5.16 (2H, s), 3.61 (2H, m), 3.48 (2H, s), 3.37 (2H, m), 2.38 (4H, m); m/z: 483 [M+H]$^+$.

Compound 18: 5-(4-(4-fluorobenzyl)piperazine-1-carbonyl)-N-(1-(1-phenylethyl)piperidin-4-yl)picolinamide. $^1$H nmr (CDCl$_3$) δ 8.50 (1H, s), 8.13 (1H, d, J 8.0 Hz), 7.88 (1H, d, J 8.0 Hz), 7.78 (1H, dd, J 8.0, 2.0 Hz), 7.32-7.18 (7H, m), 6.94 (2H, m), 3.98-3.86 (1H, m), 3.74 (2H, m), 3.44 (2H, s), 3.32 (2H, m), 3.14 (1H, m), 2.98-2.85 (1H, m), 2.47 (2H, m), 2.38-2.14 (4H, m), 1.98 (2H, m), 1.86-1.62 (3H, m), 1.48 (4H, m); m/z: 531 [M+H]$^+$.

Compound 19: 5-(4-(4-fluorobenzyl)piperazine-1-carbonyl)-N-(2-phenylphenyl)picolinamide. $^1$H nmr (CDCl$_3$) δ 10.15 (1H, s), 8.56 (1H, d, J 8.0 Hz), 8.35 (1H, m), 8.22 (1H, d, J 8.0 Hz), 7.78 (1H, dd, J 8.0, 2.0 Hz), 7.46-7.34 (6H, m), 7.29-7.13 (4H, m), 6.95 (2H, m), 3.73 (2H, m), 3.53-3.22 (4H, m), 2.47 (2H, m), 2.32 (2H, m); m/z: 496 [M+H]$^+$.

Compound 20: 5-(4-(4-fluorobenzyl)piperazine-1-carbonyl)-N-(4-(4-nitrophenyl)phenyl)picolinamide. $^1$H nmr (D$_6$-DMSO) δ 10.93 (1H, s), 8.74 (1H, m), 8.28 (2H, d, J 9.0 Hz), 8.20 (1H, d, J 8.0 Hz), 8.11-8.05 (3H, m), 7.97 (2H, d, J 9.0 Hz), 7.82 (2H, d, J 9.0 Hz), 7.35-7.30 (2H, m), 3.65 (2H, m), 3.49 (2H, s), 3.35 (2H, m), 2.43 (2H, m), 2.35 (2H, m); m/z: 541 [M+H]$^+$.

Compound 21: 5-(4-(4-fluorobenzyl)piperazine-1-carbonyl)-N-(3-phenoxyphenyl)picolinamide. $^1$H nmr (CDCl$_3$) δ 9.85 (1H, s), 8.56 (1H, m), 8.24 (1H, d, J 8.0 Hz), 7.84 (1H, dd, J 8.0, 2.0 Hz), 7.47-7.40 (2H, m), 7.32-7.18 (5H, m), 7.00-6.91 (5H, m), 6.77-6.71 (1H, m), 3.76 (2H, m), 3.46 (2H, s), 3.36 (2H, m), 2.49 (2H, m), 2.36 (2H, m); m/z: 512 [M+H]$^+$.

Compound 22: (6-(3-(benzyloxy)phenyl)pyridin-3-yl)(4-(4-fluorobenzyl)piperazin-1-yl)methanone. $^1$H nmr (CDCl$_3$) δ 8.72 (1H, br s), 7.84-7.74 (2H, m), 7.96 (1H, s), 7.58 (1H, d, J 8.0 Hz), 7.48-7.25 (8H, m), 7.08-6.98 (3H, m), 5.16 (2H, s), 3.80 (2H, m), 3.53 (4H, m), 2.50 (4H, m); m/z: 483 [M+H]$^+$.

Compound 23: N-(1-(4-cyanobenzyl)-1H-pyrazol-4-yl)-5-(4-(4-fluorobenzyl)piperazine-1-carbonyl)picolinamide. $^1$H nmr (CDCl$_3$) δ 9.71 (1H, s), 8.56 (1H, m), 8.20 (1H, d, J 8.0 Hz), 8.12 (1H, m), 7.84 (1H, dd, J 8.0, 2.0 Hz), 7.60-7.54 (3H, m), 7.26-7.18 (4H, m), 6.95 (2H, m), 5.29 (2H, s), 3.76 (2H, m), 3.46 (2H, s), 3.36 (2H, m), 2.60-2.27 (4H, m); m/z: 425 [M+H]$^+$.

Compound 24: N-(4-(4-cyanophenyl)phenyl)-5-(4-(4-fluorobenzyl)piperazine-1-carbonyl)picolinamide. $^1$H nmr (CDCl$_3$) δ 10.04 (1H, s), 8.67 (1H, m), 8.36 (1H, d, J 8.0 Hz), 7.97-7.88 (3H, m), 7.75-7.61 (6H, m), 7.29 (2H, m), 7.03 (2H, m), 3.84 (2H, m), 3.60-3.34 (4H, m), 2.49 (4H, m); m/z: 521 [M+H]$^+$.

Compound 25: 5-(4-(4-fluorobenzyl)piperazine-1-carbonyl)-N-(4-(4-trifluoromethylphenyl)phenyl)picolinamide. $^1$H nmr (CDCl$_3$) δ 10.02 (1H, s), 8.68 (1H, m), 8.37 (1H, d, J 8.0 Hz), 7.95 (1H, d, J 9.0 Hz), 7.89 (2H, d, J 8.5 Hz), 7.71-7.61 (6H, m), 7.28 (2H, m), 7.04 (2H, m), 3.84 (2H, m), 3.60-3.38 (4H, m), 2.56 (2H, m), 2.43 (2H, m); m/z: 564 [M+H]$^+$.

Compound 26: N-(4-benzoylphenyl)-5-(4-(4-fluorobenzyl)piperazine-1-carbonyl)picolinamide. $^1$H nmr (CDCl$_3$) δ 10.15 (1H, s), 8.67 (1H, m), 8.35 (1H, d, J 8.0 Hz), 7.95 (1H, dd, J 8.0, 2.0 Hz), 7.90 (4H, m), 7.79 (2H, d, J 7.5 Hz), 7.59 (1H, m), 7.49 (2H, m), 7.29 (2H, m), 7.02 (2H, m), 3.83 (2H, m), 3.54 (2H, s), 3.47 (2H, m), 2.56 (2H, m), 2.43 (2H, m); m/z: 524 [M+H]$^+$.

Compound 27: N-(4-benzyloxyphenyl)-5-(4-(4-fluorobenzyl)piperazine-1-carbonyl)picolinamide. $^1$H nmr (CDCl$_3$) δ 9.75 (1H, s), 8.58 (1H, s), 2.27 (1H, d, J 8.0 Hz), 7.84 (1H, dd, J 8.0, 2.0 Hz), 7.62 (2H, d, J 9.0 Hz), 7.39-7.18 (7H, m), 6.96-6.90 (4H, m), 5.01 (2H, s), 3.76 (2H, m), 3.52-3.28 (4H, m), 2.60-2.24 (4H, m); m/z: 526 [M+H]$^+$.

Compound 28: N-(4-bromophenyl)-5-(4-(4-fluorobenzyl)piperazine-1-carbonyl)picolinamide. $^1$H nmr (CDCl$_3$) δ 9.93 (1H, s), 8.65 (1H, s), 8.33 (1H, d, J 8.0 Hz), 7.93 (1H, dd, J 8.0, 2.0 Hz), 7.68 (2H, d, J 9.0 Hz), 7.50 (2H, d, J 9.0 Hz), 7.28 (2H, m), 7.02 (2H, m), 3.82 (2H, m), 3.52 (2H, s), 3.42 (2H, m), 2.49 (4H, m); m/z: 497, 499 [M+H]$^+$.

Compound 29: N-(4-(4-methoxyphenyl)phenyl)-5-(4-(4-fluorobenzyl)piperazine-1-carbonyl)picolinamide. $^1$H nmr (CDCl$_3$) δ 9.96 (1H, s), 8.66 (1H, m), 8.36 (1H, d, J 8.0 Hz), 7.93 (1H, dd, J 8.0, 2.0 Hz), 7.83 (2H, d, J 9.0 Hz), 7.60-7.51 (4H, m), 7.29 (2H, m), 7.03 (2H, m), 6.97 (2H, d, J 9.0 Hz), 3.85 (5H, m), 3.60-3.36 (4H, m), 2.50 (4H, m); m/z: 526 [M+H]$^+$.

Compound 30: (6-(4-benzylphenylamino)pyridin-3-yl)(4-(4-fluorobenzyl)piperazin-1-yl)methanone. $^1$H nmr (CDCl$_3$) δ 8.26 (1H, s), 7.56 (1H, dd, J 9.0, 1.0), 7.32-7.15 (10H, m), 7.06-6.97 (3H, m), 6.77 (1H, d, J 8.5 Hz), 3.96 (2H, s), 3.66 (4H, m), 3.52 (2H, s), 2.47 (4H, m); m/z: 482 [M+H]$^+$.

Compound 31: 4-((2-(5-(4-(4-fluorobenzyl)piperazine-1-carbonyl)pyridin-2-yl)-2,8-diazaspiro[4.5]decan-8-yl)methyl)benzonitrile. m/z: 554 [M+H]$^+$.

Compound 32: N-(4-(3-cyanophenyl)phenyl)-5-(4-(4-fluorobenzyl)piperazine-1-carbonyl)picolinamide. $^1$H nmr (CDCl$_3$) δ 10.04 (1H, s), 8.67 (1H, s), 8.35 (1H, d, J 8.0 Hz), 7.95 (1H, dd, J 8.0, 2.0), 7.94-7.80 (3H, m), 7.63-7.52 (3H, m), 7.28 (2H, m), 7.02 (2H, m), 3.83 (2H, m), 3.53 (2H, s), 3.44 (2H, m), 2.48 (4H, m); m/z: 521 [M+H]$^+$.

Compound 33: (6-(3-phenylphenylamino)pyridin-3-yl)(4-(4-fluorobenzyl)piperazin-1-yl)methanone. $^1$H nmr (CDCl$_3$) δ 8.23 (1H, s), 7.56-7.47 (4H, m), 7.39-7.18 (9H, m), 6.93 (2H, t, J 9.0 Hz), 6.80 (1H, d, 8.5 Hz), 3.59 (4H, m), 3.43 (2H, s), 2.39 (4H, m)); m/z: 468 [M+H]$^+$.

Compound 34: (4-(4-fluorobenzyl)piperazin-1-yl)(6-(4-phenoxyphenylamino)pyridin-3-yl)methanone. $^1$H nmr (CDCl$_3$) δ 8.26 (1H, s), 7.58 (1H, dd, J 9.0, 2.0 Hz), 7.35-7.25 (6H, m), 7.12-6.97 (8H, m), 6.73 (1H, d, J 9.0 Hz), 3.66 (4H, m), 3.51 (2H, s), 2.46 (4H, m); m/z: 483 [M+H]$^+$.

Compound 35: (6-(4-(4-cyanobenzylcarbamoyl)phenyl)pyridin-3-yl)(4-(4-fluorobenzyl)piperazin-1-yl)methanone. $^1$H nmr (CDCl$_3$) δ 8.64 (1H, br s), 7.96 (2H, d, J 8.0 Hz), 7.83 (2H, d, J 8.0 Hz), 7.75-7.68 (2H, m), 7.56 (2H, d, J 8.0 Hz), 7.40 (2H, d, J 8.0 Hz), 7.26-7.19 (2H, m), 7.01-6.91 (3H, m), 4.65 (2H, d, J 6.0 Hz), 3.73 (2H, m), 3.47 (4H, m), 2.42 (4H, m); m/z: 535 [M+H]$^+$.

Compound 36: (6-(4-(cyanobenzyl)piperidin-4-ylamino)pyridin-3-yl)(4-(4-fluorobenzyl)piperazin-1-yl)methanone. $^1$H nmr (CD$_3$OD) δ 8.06 (1H, s), 7.68 (2H, dd, J 8.0, 2.0 Hz), 7.44 (1H, m), 7.36-7.32 (2H, m), 7.06-6.98 (2H, m), 6.49 (2H, d, J 9.0 Hz), 3.68-3.56 (6H, m), 3.34 (2H, s), 2.84 (2H, m), 2.46 (4H, m), 2.20 (2H, m), 1.96 (2H, m), 1.60-1.47 (2H, m); m/z: 514 [M+H]$^+$.

Compound 37: (6-(4-phenylphenylamino)pyridin-3-yl)(4-(4-fluorobenzyl)piperazin-1-yl)methanone. $^1$H nmr (CDCl$_3$) δ 8.31 (1H, d, J 2.0 Hz), 7.65-7.55 (5H, m), 7.46-7.40 (4H, m), 7.36-7.25 (3H, m), 7.16 (1H, s), 7.01 (2H, t, J 9.0 Hz), 6.87 (1H, d, J 9.0 Hz), 3.68 (4H, m), 3.52 (2H, s), 2.48 (4H, m); m/z: 467 [M+H]$^+$.

Compound 38: N$^5$-(1-(4-cyanobenzyl)-1H-pyrazol-3-yl)-N$^2$-(1-(4-cyanobenzyl)piperidin-4-yl)pyridine-2,5-dicarboxamide. $^1$H nmr (CDCl$_3$) δ 8.98 (1H, s), 8.57 (1H, s), 8.22 (2H, m), 7.92 (1H, m), 7.59-7.54 (4H, m), 7.46 (2H, m), 7.39 (1H, d, J 2.0 Hz), 7.21-7.16 (2H, m), 6.86 (1H, d, J 1.5 Hz), 5.21 (2H, s), 3.96 (1H, m), 3.57 (2H, s), 2.89-2.80 (2H, m), 2.23 (2H, m), 1.97 (2H, m), 1.67 (2H, m); m/z: 546 [M+H]$^+$.

Compound 39: 5-(4-(4-fluorobenzyl)piperazine-1-carbonyl)-N-(4-(1H-pyrrol-3-yl)phenyl)picolinamide. $^1$H nmr (CDCl$_3$) δ 9.85 (1H, s), 8.58 (1H, s), 8.31 (1H, m), 8.27 (1H, d, J 8.0 Hz), 7.85 (1H, dd, J 8.0, 2.0 Hz), 7.68 (2H, d, J 9.0 Hz), 7.48 (2H, d, J 9.0 Hz), 7.24-7.18 (2H, m), 7.02 (1H, m), 6.95 (2H, t, J 8.5 Hz), 6.77 (1H, m), 6.47 (1H, m), 3.76 (2H, m), 3.46-3.32 (4H, m), 2.48 (2H, m), 2.36 (2H, m); m/z: 485 [M+H]$^+$.

Compound 40: 5-(4-(4-fluorobenzyl)piperazine-1-carbonyl)-N-(4-morpholinophenyl)picolinamide. $^1$H nmr (CDCl$_3$) δ 9.74 (1H, s), 8.57 (1H, s), 8.26 (1H, d, J 8.0 Hz), 7.84 (1H, dd, J 8.0, 2.0 Hz), 7.62 (2H, d, J 9.0 Hz), 7.22 (2H, m), 6.94 (2H, t, J 9.0 Hz), 6.88 (2H, d, J 9.0 Hz), 3.83-3.53 (6H, m), 3.45 (2H, s), 3.36 (2H, m), 3.08 (2H, m), 2.48 (2H, m), 2.35 (2H, m); m/z: 505 [M+H]$^+$.

Compound 41: 5-(4-(4-fluorobenzyl)piperazine-1-carbonyl)-N-(4-(4-methylpiperazin-1-yl)phenyl)picolinamide. $^1$H nmr (CDCl$_3$) δ 9.74 (1H, s), 8.57 (1H, m), 8.25 (1H, d, J 8.0 Hz), 7.84 (1H, dd, J 8.0, 2.0), 7.60 (2H, d, J 9.0 Hz), 7.24-7.18 (2H, m), 6.97-6.87 (4H, m), 3.75 (2H, m), 3.45 (2H, s), 3.36 (2H, m), 3.19 (4H, m), 2.60 (4H, m), 2.48 (2H, m), 2.34 (5H, m); m/z: 518 [M+H]$^+$.

Compound 42: (6-(3-(4-cyanobenzylcarbamoyl)phenyl)pyridin-3yl)(4-(4-fluorobenzyl)piperazin-1-yl)methanone. $^1$H nmr (CDCl$_3$) δ 8.64 (1H, br s), 8.40 (1H, s), 8.07 (1H, d, J 8.0 Hz), 7.86 (1H, d, J 8.0 Hz), 7.77 (2H, m), 7.59-7.47 (3H, m), 7.41 (2H, d, J 8.0 Hz), 7.24-7.17 (2H, m), 6.95 (2H, t, J 9.0 Hz), 6.88 (1H, m), 4.66 (2H, d, J 6.0 Hz), 3.74 (2H, m), 3.45 (4H, m), 2.42 (4H, m); m/z: 535 [M+H]$^+$.

Compound 43: N$^5$-(1-(4-cyanobenzyl)-1H-pyrazol-4-yl)-N$^2$-(1-(4-cyanobenzyl)piperidin-4-yl)pyridine-2,5-dicarboxamide. $^1$H nmr (D$_6$-DMSO) δ 10.83 (1H, s), 9.08 (1H, s), 8.70 (1H, d, J 8.0 Hz), 8.43 (1H, dd, J 8.0, 2.0 Hz), 8.25 (1H, s), 8.13 (1H, d, J 8.5 Hz), 7.79 (4H, m), 7.67 (1H, s), 7.49 (2H, d, J 8.0 Hz), 7.33 (2H, d, J 8.0 Hz), 5.45 (2H, s), 3.80 (1H, m), 3.55 (2H, s), 2.76 (2H, m), 2.07 (2H, m), 1.71 (4H, m); m/z: 546 [M+H]$^+$.

Compound 44: (6-(1-(4-fluorobenzyl)-1H-pyrazol-4-ylamino)pyridin-3-yl)(4-(4-fluorobenzyl)piperazin-1-yl)methanone. $^1$H nmr (CDCl$_3$) δ 8.15 (1H, d, J 2.0 Hz), 7.61 (1, 1H), 7.46 (1H, dd, J 8.0, 2.0 Hz), 7.42 (1H, s), 7.24-7.12 (4H, m), 6.99-6.90 (4H, m), 6.70 (1H, s), 6.45 (1H, d, J 8.5 Hz), 5.17 (2H, s), 3.57 (4H, m), 3.44 (2H, m), 2.39 (4H, m); m/z: 489 [M+H]$^+$.

Compound 45: N-(1-(4-cyanobenzyl)piperidin-4-yl)-5-(1-(4-fluorobenzyl)-1H-pyrazol-4-ylamino)picolinamide. $^1$H nmr (CDCl$_3$) δ 7.92 (1H, d, J 3.0 Hz), 7.89 (1H, d, J 9.0 Hz), 7.62 (1H, d, J 8.5 Hz), 7.54 (2H, d, J 8.0 Hz), 7.44-7.38 (3H, m), 7.30 (1H, s), 7.19-7.13 (2H, m), 7.02-6.94 (3H, m), 5.49 (1H, s), 5.19 (2H, s), 3.98-3.84 (1H, m), 3.52 (2H, s), 2.76 (2H, m), 2.17 (2H, m), 1.93 (2H, m), 1.57 (2H, m); m/z: 511 [M+H]$^+$.

Compound 46: (6-(1-(4-cyanobenzyl)piperidine-4-carboxamido)pyridin-3-yl)(4-(4-fluorobenzyl)piperazin-1-yl)methanone. To a mixture of (4-(4-fluorobenzyl)piperazin-1-yl)(6-bromopyridin-3-yl)methanone (0.040 g, 0.11 mmol, 1.0 eq), 1-(4-cyanobenzyl)piperidine-4-carboxamide (0.028 g, 0.12, 1.1 eq), and N,N'-dimethylethylenediamine (0.012 mL, 0.11 mmol, 1.0 eq) was added anhydrous toluene (1.0 mL). This mixture was purged with argon for 5 minutes and copper(I)iodide (0.011 g, 0.058 mmol, 0.5 eq) and potassium carbonate (0.044 g, 0.23 mmol, 2.1 eq) were added. The reaction mixture was heated at 100° C. for 4.5 hours and then absorbed on silica gel. Purification by column chromatography (silica, 0→5% MeOH—CH$_2$Cl$_2$) yielded a green solid (0.070 g). Further purification using preparative TLC (silica, 4% MeOH—CH$_2$Cl$_2$) provided Compound 46 as a white solid (0.040 g, 67%). $^1$H nmr (D$_6$-DMSO) δ 10.64 (1H, s), 8.32 (1H, s), 8.10 (1H, d, J 8.5 Hz), 7.81-7.74 (3H, m), 7.53-7.46 (2H, m), 7.31 (2H, t, J 8.0 Hz), 7.12 (2H, t, J 9.0 Hz), 3.64-3.36 (9H, m), 2.79 (2H, m), 2.35 (m, 4H), 1.99-1.87 (2H, m), 1.79-1.54 (4H, m); m/z: 542 [M+H]$^+$. More information about this type of coupling is provided in Wrona, Iwona E.; Gozman, Alexander; Taldone, Tony; Chiosis, Gabriela; Panek, James S. Journal of Organic Chemistry (2010), 75(9), 2820-2835.

$^1$H nmr (D$_6$-DMSO) δ 10.64 (1H, s), 8.32 (1H, s), 8.10 (1H, d, J 8.5 Hz), 7.81-7.74 (3H, m), 7.53-7.46 (2H, m), 7.31 (2H, t, J 8.0 Hz), 7.12 (2H, t, J 9.0 Hz), 3.64-3.36 (9H, m), 2.79 (2H, m), 2.35 (m, 4H), 1.99-1.87 (2H, m), 1.79-1.54 (4H, m); m/z: 542 [M+H]$^+$.

Compound 47: N-(4-(4-cyanobenzylcarbamoyl)phenyl)-5-(4-(4-fluorobenzyl)piperazine-1-carbonyl)picolinamide. $^1$H nmr (CDCl$_3$) δ 10.03 (1H, s), 8.58 (1H, s), 8.24 (1H, d, J 8.0 Hz), 7.84 (1H, dd, J 8.0, 2.0 Hz), 7.78 (4H, m), 7.57 (1H, d, J 8.0 Hz), 7.40 (2H, d, J 8.0 Hz), 7.26-7.19 (2H, m), 6.95 (2H, t, J 9.0 Hz), 6.68 (1H, m) 4.64 (2H, d, J 6.0 Hz), 3.76 (2H, m), 3.47 (2H, s), 3.37 (2H, m), 2.49 (2H, m), 2.36 (2H, m); m/z: 578 [M+H]$^+$.

Compound 48: (6-(4-(4-cyanobenzylcarbamoyl)phenylamino)pyridin-3-yl)(4-(4-fluorobenzyl)piperazin-1-yl)methanone. $^1$H nmr (CDCl$_3$) δ 8.25 (1H, s), 7.81 (1H, s), 7.70 (1H, d, J 9.0 Hz), 7.53-7.33 (8H, m), 7.28-7.23 (2H, m), 6.99 (2H, t, J 9.0 Hz), 6.73 (1H, d, J 8.5 Hz), 4.60 (2H, d, J 6.0 Hz), 3.60 (4H, m), 3.48 (2H, s), 2.43 (4H, m); m/z: 550 [M+H]$^+$.

Compound 49: N-(1-(3,5-difluorobenzyl)piperidin-4-yl)-5-(4-(4-fluorobenzyl)piperazine-1-carbonyl)picolinamide. $^1$H nmr (CDCl$_3$) δ 8.52 (1H, s), 8.16 (1H, d, J 8.0 Hz), 7.86 (1H, d, J 8.0 Hz), 7.81-7.78 (1H, m), 7.23-7.07 (3H, m), 7.06-6.91 (4H, m), 4.20-3.88 (1H, m), 3.74 (2H, m), 3.44 (2H, s), 3.43 (2H, s), 3.33 (2H, m), 2.78 (2H, m), 2.47 (2H, m), 2.321 (2H, m), 2.16 (2H, m), 1.96 (2H, m), 1.62 (2H, m); m/z: 553 [M+H]$^+$.

Compound 50: 5-(4-(4-fluorobenzyl)piperazine-1-carbonyl)-N-(1-(4-fluoro-3-methylbenzyl)piperidin-4-yl)picolinamide. $^1$H nmr (CDCl$_3$) δ 8.51 (s, 1H), 8.16 (1H, d, J 8.0 Hz), 7.85 (1H, d, J 9.0 Hz), 7.79 (1H, d, J 8.0 Hz), 7.23-7.18 (2H, m), 7.10-7.01 (2H, m), 6.97-6.84 (3H, m), 3.99-3.88 (1H, m), 3.74 (2H, m), 3.44 (2H, s), 3.40 (2H, s), 3.33 (2H, m), 2.79 (2H, m), 2.47 (2H, m), 2.32 (2H, m), 2.20 (3H, s), 2.13 (1H, m), 1.94 (2H, m), 1.60 (3H, m); m/z: 549 [M+H]$^+$.

Compound 51: N-(1-(4-chlorobenzyl)piperidin-4-yl)-5-(4-(4-fluorobenzyl)piperazine-1-carbonyl)picolinamide. $^1$H nmr (CD$_3$OD) δ 8.67 (1H, m, major isomer), 8.63 (1H, m, minor isomer), 8.16 (1H, d, J 8.0 Hz), 8.00 (1H, dd, J 8.0, 2.0 Hz), 7.38-7.32 (2H, m), 7.09-7.00 (5H, m), 6.81 (2H, d, J 9.0 Hz), 4.10 (m), 3.80 (m), 3.57 (s), 3.45 (m), 3.30 (m), 2.96 (s), 2.58-2.44 (m), 1.94-1.60 (m), 1.39-1.28 (m); m/z: 546 [M+H]$^+$.

Compound 52: N-(1-(4-chlorobenzyl)piperidin-4-yl)-5-(4-(4-fluorobenzyl)piperazine-1-carbonyl)picolinamide. $^1$H nmr (CDCl$_3$) δ 8.57 (1H, s), 8.21 (1H, d, J 8.0 Hz), 7.90 (1H, d, J 8.0 Hz), 7.84 (1H, dd, J 8.0, 2.0), 7.28-7.22 (6H, m), 6.99 (2H, m), 4.04-3.92 (1H, m), 3.79 (2H, m), 3.49 (2H, s), 3.46 (2H, s), 3.38 (2H, m), 2.81 (2H, m), 2.52 (2H, m), 2.37 (2H, m), 2.17 (2H, m), 1.98 (2H, m), 1.62 (2H, m); m/z: 551, 553 [M+H]$^+$.

Compound 53: 5-(4-(4-fluorobenzyl)piperazine-1-carbonyl)-N-(4-(4-methylphenoxy)phenyl)picolinamide. $^1$H nmr (CDCl$_3$) δ 9.88 (1H, s), 8.64 (1H, s), 8.33 (1H, d, J 8.0 Hz), 7.91 (1H, dd, J 8.0, 2.0 Hz), 7.71 (2H, d, J 9.0 Hz), 7.30-7.24 (2H, m), 7.13 (2H, d, J 8.0 Hz), 7.03-6.96 (4H, m), 6.91 (2H, d, J 8.5 Hz), 3.82 (2H, m), 3.51 (2H, s), 3.42 (2H, m), 2.54 (2H, m), 2.41 (2H, m), 2.33 (3H, m); m/z: 526 [M+H]$^+$.

Compound 54: 5-(4-(4-fluorobenzyl)piperazine-1-carbonyl)-N-(4-(4-methoxyphenoxy)phenyl)picolinamide. $^1$H nmr (CDCl$_3$) δ 9.87 (1H, m), 8.64 (1H, s), 8.32 (1H, d, J 8.0 Hz), 7.91 (1H, dd, J 8.0, 2.0 Hz), 7.69 (2H, d, J 9.0 Hz), 7.30-7.24 (2H, m), 7.03-6.95 (6H, m), 6.87 (2H, m), 3.80 (5H, m), 3.51 (2H, s), 3.42 (2H, m), 2.54 (2H, m), 2.41 (2H, m); m/z: 541 [M+H]$^+$.

Compound 55: 5-(4-(4-fluorobenzyl)piperazine-1-carbonyl)-N-(4-(3-fluorophenoxy)phenyl)picolinamide. $^1$H nmr (CDCl$_3$) δ 9.86 (1H, s), 8.59 (1H, s), 8.26 (1H, d, J 8.0 Hz), 7.85 (1H, dd, J 8.0, 2.0 Hz), 7.70 (2H, d, J 9.0 Hz), 7.24-7.15 (3H, m), 7.00 (2H, d, J 9.0 Hz), 6.94 (2H, t, J 9.0 Hz), 6.74-6.60 (3H, m), 3.75 (2H, m), 3.45 (2H, s), 3.36 (2H, m), 2.48 (2H, m), 2.34 (2H, m); m/z: 530 [M+H]$^+$.

Compound 56: N-(4-(3-cyanophenoxy)phenyl)-5-(4-(4-fluorobenzyl)piperazine-1-carbonyl)picolinamide. $^1$H nmr (CDCl$_3$) δ 9.90 (1H, s), 8.59 (1H, s), 8.27 (1H, d, J 8.0 Hz), 7.86 (1H, dd, J 8.0, 2.0 Hz), 7.74 (2H, d, J 9.0 Hz), 7.38-7.25 (2H, m), 7.24-7.14 (4H, m), 7.00 (2H, d, J 9.0 Hz), 6.94 (2H, t, J 8.5 Hz), 3.76 (2H, m), 3.45 (2H, s), 3.36 (2H, m), 2.48 (2H, m), 2.35 (2H, m); m/z: 537 [M+H]$^+$.

Compound 57: 5-(4-(4-fluorobenzyl)piperazine-1-carbonyl)-N-(4-(3-methoxyphenoxy)phenyl)picolinamide. $^1$H nmr (CDCl$_3$) δ 9.84 (1H, s), 8.59 (1H, s), 8.26 (1H, d, J 8.0 Hz), 7.85 (1H, dd, J 8.0, 2.0 Hz), 7.67 (2H, d, J 9.0 Hz), 7.24-7.11 (3H, m), 7.01-6.91 (4H, m), 6.60-6.48 (3H, m), 3.76 (2H, m), 3.70 (3H, m), 3.45 (2H, s), 3.37 (2H, m), 2.48 (2H, m), 2.34 (2H, m); m/z: 542 [M+H]$^+$.

Compound 58: 5-(4-(4-fluorobenzyl)piperazine-1-carbonyl)-N-(4-(3-methylphenoxy)phenyl)picolinamide. $^1$H nmr (CDCl$_3$) δ 9.90 (1H, s), 8.65 (1H, s), 8.33 (1H, d, J 8.0 Hz), 7.92 (1H, dd, J 8.0, 2.0 Hz), 7.73 (2H, d, J 9.0 Hz), 7.31-7.25 (2H, m), 7.21 (1H, t, J 7.5 Hz), 7.06-6.96 (4H, m), 6.90 (2H, d, J 7.5 Hz), 6.82 (2H, m), 3.82 (2H, m), 3.51 (2H, s), 3.42 (2H, s), 2.54 (2H, m), 2.41 (2H, m), 2.32 (3H, s); m/z: 526 [M+H]$^+$.

Compound 59: N-(4-(4-cyanophenoxy)phenyl)-5-(4-(4-fluorobenzyl)piperazine-1-carbonyl)picolinamide. $^1$H nmr (CDCl$_3$) δ 9.91 (1H, s), 8.59 (1H, s), 8.27 (1H, d, J 8.5 Hz), 7.87 (1H, dd, J 8.0, 1.5 Hz), 7.76 (2H, d, J 9.0 Hz), 7.53 (2H, d, J 8.5 Hz), 7.24-7.18 (2H, m), 7.04 (2H, d, J 9.0 Hz), 6.98-6.91 (4H, m), 3.76 (2H, m), 3.45 (2H, s), 3.36 (2H, m), 2.49 (2H, m), 2.35 (2H, m); m/z: 537 [M+H]$^+$.

Compound 60: 5-(4-(4-fluorobenzyl)piperazine-1-carbonyl)-N-(4-(4-fluorophenoxy)phenyl)picolinamide. $^1$H nmr (CDCl$_3$) δ 9.84 (1H, s), 8.58 (1H, s), 8.27 (1H, d, J 8.5 Hz), 7.88-7.84 (1H, m), 7.66 (2H, d, J 9.0 Hz), 7.24-7.18 (3H, m), 6.99-6.88 (7H, m), 3.76 (2H, m), 3.45 (2H, s), 3.36 (2H, m), 2.48 (2H, m), 2.34 (2H, m); m/z: 530 [M+H]$^+$.

Compound 61: 5-(4-(4-fluorobenzyl)piperazine-1-carbonyl)-N-(4-(pyridine-3-yl)phenyl)picolinamide. $^1$H nmr (CDCl$_3$) δ 9.97 (1H, s), 8.80 (1H, s), 8.61 (1H, s), 8.51 (1H, d, J 5.0 Hz), 7.90-7.80 (4H, m), 7.56 (2H, d, J 8.5 Hz), 7.33-7.27 (1H, m), 7.25-7.18 (2H, m), 6.95 (2H, t, J 8.5 Hz), 3.76 (2H, m), 3.45 (2H, s), 3.37 (2H, m), 2.49 (2H, m), 2.35 (2H, m); m/z: 497 [M+H]$^+$.

Compound 62: 5-(4-(4-fluorobenzyl)piperazine-1-carbonyl)-N-(4-(thiophen-3-yl)phenyl)picolinamide. $^1$H nmr (CDCl$_3$) δ 9.91 (1H, s), 8.59 (1H, s), 8.28 (1H, d, J 8.0 Hz), 7.86 (1H, dd, J 8.0, 2.0 Hz), 7.75 (2H, d, J 8.5 Hz), 7.56 (2H, d, J 8.5 Hz), 7.38-7.31 (2H, m), 7.24-7.16 (3H, m), 6.94 (2H, t, J 8.5 Hz), 3.76 (2H, m), 3.45 (2H, s), 3.36 (2H, m), 2.48 (2H, m), 2.34 (2H, m); m/z: 502 [M+H]$^+$.

Compound 63: 5-(4-(4-fluorobenzyl)piperazine-1-carbonyl)-(6-(4-cyanophenoxy)pyridin-3-yl)picolinamide. $^1$H nmr (CDCl$_3$) δ 9.89 (1H, s), 8.60 (1H, m), 8.40 (1H, d, J 2.5 Hz), 8.35 (1H, dd, J 9.0, 3.0 Hz), 8.26 (1H, dd, J 8.5, 1.0 Hz), 7.88 (1H, dd, J 8.0, 2.0 Hz), 7.61 (2H, d, J 9.0 Hz), 7.25-7.13 (4H, m), 7.00 (1H, d, J 9.0 Hz), 6.94 (2H, t, J 8.5 Hz), 3.76 (2H, m), 3.45 (2H, s), 3.35 (2H, m), 2.48 (2H, m), 2.35 (2H, m); m/z: 538 [M+H]$^+$.

Compound 64: 5-(4-(4-fluorobenzyl)piperazine-1-carbonyl)-(6-(3-cyanophenoxy)pyridin-3-yl)picolinamide. $^1$H nmr (CDCl$_3$) δ 9.87 (1H, s), 8.60 (1H, m), 8.36 (2H, m), 8.26 (1H, d, J 8.5 Hz), 7.87 (1H, dd, J 8.0, 2.0 Hz), 7.46-7.31 (3H, m), 7.23-7.18 (3H, m), 7.02-6.90 (3H, m), 3.76 (2H, m), 3.45 (2H, s), 3.35 (2H, m), 2.48 (2H, m), 2.35 (2H, m); m/z: 538 [M+H]$^+$.

Compound 65: 5-(4-(4-fluorobenzyl)piperazine-1-carbonyl)-N-(6-(4-fluorophenoxy)pyridin-3-yl)picolinamide. $^1$H nmr (CDCl$_3$) δ 9.83 (1H, s), 8.58 (1H, m), 8.37-8.21 (4H, m), 7.86 (1H, dd, J 8.0, 2.0 Hz), 7.24-7.17 (2H, m), 7.05-6.86 (6H, m), 3.75 (2H, m), 3.44 (2H, s), 3.34 (2H, m), 2.48 (2H, m), 2.34 (2H, m); m/z: 531 [M+H]+.

Compound 66: 5-(4-(4-cyano-2-methoxyphenoxy)piperidine-1-carbonyl)-N-(1-(4-cyanobenzyl)piperidin-4-yl)picolinamide. $^1$H nmr (CDCl$_3$) δ 8.54 (1H, m), 8.18 (1H, d, J 8.0 Hz), 7.87-7.80 (2H, m), 7.55 (2H, d, J 8.5 Hz), 7.39 (2H, d, J 8.0 Hz), 7.21-7.15 (1H, m), 7.05 (1H, m), 6.87 (1H, d, J 8.0 Hz), 4.66-4.58 (1H, m), 3.97-3.78 (6H, m), 3.60 (1H, m), 3.50 (2H, s), 3.41 (2H, m), 3.31 (1H, m), 2.76 (2H, m), 2.16 (2H, m), 2.20-1.57 (4H, m), 1.63-1.52 (2H, m); m/z: 580 [M+H]+.

Compound 67: 5-(4-(4-fluoro-4-fluorobenzoyl)piperidine-1-carbonyl)-N-(6-(4-fluorophenoxy)pyridin-3-yl)picolinamide. $^1$H nmr (CDCl$_3$) δ 9.83 (1H, s), 8.64 (1H, s), 8.36-8.24 (3H, m), 8.11-8.05 (2H, m), 7.92 (1H, dd, J 8.0, 2.0 Hz), 7.11-6.97 (6H, m), 6.89 (1H, d, J 9.0 Hz), 4.62 (1H, m), 3.70-3.41 (3H, m), 2.36-1.91 (4H, m); m/z: 562 [M+H]+.

Compound 68: N-(1-(4-cyanobenzyl)piperidin-4-yl)-5-(4-(4-fluoro-4-fluorobenzoyl)piperidine-1-carbonyl)picolinamide. $^1$H nmr (CDCl$_3$) δ 8.57 (1H, s), 8.19 (1H, d, J 8.0 Hz), 8.09-8.04 (2H, m), 7.88-7.82 (2H, m), 7.54 (2H, d, J 8.5 Hz), 7.39 (2H, d, J 8.0 Hz), 7.08 (2H, t, J 8.5 Hz), 4.60 (1H, m), 3.99-3.90 (1H, m), 3.60-3.30 (4H, m), 2.75 (2H, m), 2.28-2.07 (6H, m), 1.95 (3H, m), 1.65-1.53 (2H, m); m/z: 573 [M+H]+.

Compound 69: 5-(4-(4-methoxybenzoyl)piperidine-1-carbonyl)-N-(6-(4-fluorophenoxy)pyridin-3-yl)picolinamide. $^1$H nmr (CDCl$_3$) δ 9.85 (1H, s), 8.62 (1H, s), 8.37-8.25 (3H, m), 7.92-7.85 (3H, m), 7.06-6.99 (4H, m), 6.90 (3H, m), 4.62 (1H, m), 3.81 (3H, s), 3.72 (1H, m), 3.49 (1H, s), 3.28-2.98 (2H, m), 1.97 (1H, m), 1.77 (3H, m); m/z: 556 [M+H]+.

Compound 70: 5-(4-(4-methoxyphenoxy)piperidine-1-carbonyl)-N-(6-(4-fluorophenoxy)pyridin-3-yl)picolinamide. $^1$H nmr (CDCl$_3$) δ 9.84 (1H, s), 8.61 (1H, s), 8.35-8.25 (2H, m), 7.89 (1H, dd, J 8.0, 2.0 Hz), 7.06-7.01 (4H, m), 6.90 (1H, d, J 9.0 Hz), 6.83-6.75 (4H, m), 4.43 (1H, m), 3.84 (2H, m), 3.70 (3H, m), 3.31 (1H, m), 1.93 (2H, m), 1.79 (2H, m); m/z: 544 [M+H]+.

Compound 71: trans-N-(4-(4-cyanophenoxy)cyclohexyl)-5-(4-(4-fluorobenzyl)piperazine-1-carbonyl)picolinamide. $^1$H nmr (CDCl$_3$) δ 8.53 (1H, s), 8.18 (1H, d, J 8.0 Hz), 7.86-7.80 (2H, m), 7.51 (2H, d, J 9.0 Hz), 7.00 (2H, t, J 8.5 Hz), 4.27 (1H, m), 4.07-3.40 (7H, m), 2.65 (4H, m), 2.13 (4H, m), 1.68-1.57 (2H, m), 1.49-1.38 (2H, m); m/z: 543 [M+H]+.

Compound 94: (4-(4-fluorobenzyl)piperazin-1-yl)(6-(4-phenylpiperazine-1-carbonyl)pyridin-2-yl)methanone. To a suspension of pyridine-2,6-dicarboxylic acid (0.200 g, 1.20 mmol, 1.0 eq) in tetrahydrofuran (6.0 mL) was added 4-fluorobenzylpiperazine (0.116 g, 0.60 mmol, 0.5 eq). Triethylamine (0.33 mL, 2.40 mmol, 2.0 eq) was added followed by HATU (0.319 g, 0.84 mmol, 0.7 eq) and the reaction was stirred at room temperature for 14 hours. The reaction mixture was diluted with methanol (3.0 mL) and (trimethylsilyl)diazomethane (2.0 mL of a 2M solution in hexane, 4.00 mmol). The reaction mixture was stirred at room temperature for 30 minutes before concentrating under reduced pressure. The residue was partitioned between NaHCO$_3$ (50 mL) and EtOAc (50 mL). The organics were washed with brine (50 mL), dried (Na$_2$SO$_4$) and concentrated under reduced pressure. Column chromatography (silica, 2→5% MeOH—CH$_2$Cl$_2$) yielded methyl 6-(4-(4-fluorobenzyl)piperazine-1-carbonyl)picolinate (0.214 g, 50%) as a white solid; m/z: 358 [M+H]+. To a solution of the methyl 6-(4-(4-fluorobenzyl)piperazine-1-carbonyl)picolinate (0.214 g, 0.60 mmol, 1.0 eq) in tetrahydrofuran (4.0 mL) was added a solution of lithium hydroxide monohydrate (0.050 g, 1.20 mmol, 2.0 eq) in water (3.0 mL). The reaction was stirred at room temperature for 25 minutes before neutralizing with HCl (approximately 0.6 mL of a 2M solution). The reaction mixture was concentrated to dryness to yield 6-(4-(4-fluorobenzyl)piperazine-1-carbonyl)picolinic acid, which was used without further purification; m/z: 344 [M+H]+. To a solution of the crude 6-(4-(4-fluorobenzyl)piperazine-1-carbonyl)picolinic acid (approximately 0.200 mmol, 1.0 eq) and triethylamine (0.083 mL, 0.600 mmol, 3.0 eq) in dimethylformamide (2.0 mL) was added 1-phenylpiperazine (0.036 mL, 0.240 mmol, 1.2 eq). HATU was added and the reaction shaken at room temperature for 2.5 hours before partitioning between EtOAc (50 mL) and NaHCO$_3$-water (1:1, 50 mL). The organics were further washed with brine (50 mL), water (50 mL) and brine (50 mL) before drying (Na$_2$SO$_4$) and concentrating under reduced pressure. Column chromatography (silica, 3→7% MeOH—CH$_2$Cl$_2$) yielded Compound 94 as a colourless oil; $^1$H nmr (CDCl$_3$) δ 7.92 (1H, t, J 7.5 Hz, pyH-4), 7.73 (1H, d, J 8.0 Hz, pyH-3 or pyH-5), 7.70 (1H, d, J 7.5 Hz, pyH-3 or pyH-5), 7.33-7.22 (4H, m, 2H of C$_6$H$_4$F and 2H of C$_6$H$_5$), 7.01-6.90 (5H, m, 2H of C$_6$H$_4$F and 3H of C$_6$H$_5$), 3.97 (2H, dd, J 5.5, 5.0 Hz, 2H of piz), 3.81 (2H, dd, J 5.0, 4.5 Hz, 2H of piz), 3.74 (2H, t, J 5.0 Hz, 2H of piz), 3.55 (2H, dd, J 5.0, 4.5 Hz, 2H of piz), 3.46 (2H, s, CH$_2$C$_6$H$_4$F), 3.29 (2H, t, J 5.0 Hz, 2H of piz), 3.17 (2H, dd, J 5.5, 4.5 Hz, 2H of piz), 2.52 (2H, t, J 5.0 Hz, 2H of piz), 2.39 (2H, dd, 5.0, 4.5 Hz, 2H of piz); m/z: 488 [M+H]+.

Compound 140: N-(1-(4-cyanobenzyl)piperidin-4-yl)-5-(4-(3,5-difluorobenzyl)piperazine-1-carbonyl)picolinamide. $^1$H nmr (CDCl$_3$) δ 8.58 (1H, br s, pyH-6), 8.23 (1H, d, J 8.0 Hz, pyH-3), 7.91 (1H, d, J 9.0 Hz, NH), 7.86 (1H, dd, J 8.0, 2.0 Hz, pyH-4), 7.61 (2H, d, J 8.5 Hz, 2H of C$_6$H$_4$CN), 7.45 (2H, d, J 8.0 Hz, 2H of C$_6$H$_4$CN), 6.87 (2H, d, J 6.5 Hz, H-2 and H-6 of C$_6$H$_3$F$_2$), 6.70 (1H, t, J 9.0 Hz, H-4 of C$_6$H$_3$F$_2$), 4.00 (1H, m, pipH-4), 3.82 (2H, m, 2H of piz), 3.56 (2H, s, 1×CH$_2$Ar), 3.51 (2H, s, 1×CH$_2$Ar), 3.41 (2H, m, 2H of piz), 2.81 (2H, m, 2H of pip), 2.55 (2H, m, 2H of piz), 2.40 (2H, m, 2H of piz), 2.22 (2H, t, J 11.0 Hz, 2H of pip), 2.01 (2H, m, 2H of pip), 1.64 (2H, m, 2H of pip); m/z: 560 [M+H]+.

Compound 141: 5-(4-(4-carbamoylbenzyl)piperidine-1-carbonyl)-N-(1-(4-cyanobenzyl)piperidin-4-yl)picolinamide. $^1$H nmr (D$_6$-DMSO) δ 8.65 (2H, m, NH, 1×pyH), 8.04 (1H, m, 2×pyH), 7.81 (1H, d, J 8.5 Hz, 2H of C$_6$H$_4$CN or C$_6$H$_4$CONH$_2$), 7.78 (2H, d, J 8.0 Hz, 2H of C$_6$H$_4$CN or C$_6$H$_4$CONH$_2$), 7.49 (2H, d, J 8.5 Hz, 2H of C$_6$H$_4$CN), 7.01 (2H, d, J 9.0 Hz, 2H of C$_6$H$_4$CONH$_2$), 4.75 (1H, m, oxypipH-4), 4.09 (1H, m, 1H of oxypipH-2, H-6), 3.80 (1H, m, pipH-4), 3.54 (2H, s, CH$_2$C$_6$H$_4$CN), 3.48 (2H, m, 2H of oxypipH-2, H-6), 3.25 (1H, m, 1H of oxypipH-2, H-6), 2.75 (2H, m, 2H of pipH-2, H-6), 2.06 (3H, m, 2H of pipH-2, H-6, 1H of oxypipH-3, H-5), 1.91 (1H, m, 1H of oxypipH-3, H-5), 1.71 (6H, m, 4H of pipH-3, H-5, 2H of oxypipH-3, H-5); m/z: 568 [M+H]+.

Compound 142: N-(1-(4-cyanobenzyl)piperidin-4-yl)-5-(4-((4-fluorophenyl)(hydroxy)methyl)piperidine-1-carbonyl)picolinamide. $^1$H nmr (CDCl$_3$) δ 8.56 (1H, br s, pyH-6), 8.21 (1H, d, J 7.0 Hz, pyH-3), 7.91 (1H, d, J 8.5 Hz, NH), 7.85 (1H, m, pyH-4), 7.61 (2H, d, J 8.0 Hz, 2H of C$_6$H$_4$CN), 7.45 (2H, d, J 8.0 Hz, 2H of C$_6$H$_4$CN), 7.26 (2H, m, 2H of C$_6$H$_4$F), 7.04 (2H, t, J 8.5 Hz, 2H of C$_6$H$_4$F), 4.75 (1H, m, 1H of BnpipH-2, H-6), 4.43 (1H, d, J 7.0 Hz, CH(OH)C$_6$H$_4$F), 3.99 (1H, m, pipH-4), 3.66 (1H, m, 1H of BnpipH-2, H-6), 3.56 (2H, s, CH$_2$C$_6$H$_4$CN), 3.01 (1H, m, 1H of BnpipH-2, H-6), 2.81 (2H, m, 2H of pipH-2, H-6) 2.71 (1H, m, 1H of BnpipH-2, H-6), 2.22 (2H, dd, J 11.5, 10.0 Hz, 2H of pipH-2, H-6), 2.00 (2H, m, 2H of pipH-3, H-5), 1.86 (1H, m, BnpipH-4), 1.62 (2H, m, 2H of pipH-3, H-5), 1.44-1.30 (4H, m, 4H of BnpipH-3, H-5); m/z: 556 [M+H]+.

Compound 143: N-(1-(4-cyanobenzyl)piperidin-4-yl)-5-(4-(4-methoxyphenoxy)piperidine-1-carbonyl)picolinamide. $^1$H nmr (CDCl$_3$) δ 8.60 (1H, d, J 1.5 Hz, pyH-6), 8.24 (1H, d, J 8.0 Hz, pyH-3), 7.92 (1H, d, J 8.5 Hz, NH), 7.88 (1H, dd, J 8.0, 2.0 Hz, pyH-4), 7.61 (2H, d, J 8.5 Hz, 2H of C$_6$H$_4$CN), 7.45 (2H, d, J 8.5 Hz, 2H of C$_6$H$_4$CN), 6.87 (2H, d, J 9.0 Hz, 2H of C$_6$H$_4$OCH$_3$), 6.82 (2H, d, J 9.0 Hz, 2H of C$_6$H$_4$OCH$_3$), 4.47 (1H, m, 1H of oxypip), 4.00 (1H, m, pipH-4), 3.88 (2H, m, 2H of oxypip), 3.77 (3H, s, OCH$_3$), 3.63 (1H, m, 1H of oxypip), 3.56 (2H, s, CH$_2$C$_6$H$_4$CN), 3.35 (1H, m, 1H of oxypip), 2.81 (2H, m, 2H of pip), 2.23 (2H, dd, J 11.0, 10.0 Hz, 2H of pip), 2.01 (4H, m, 2H of pip, 2H of oxypip), 1.82 (2H, m, 2H of oxypip), 1.63 (2H, m, 2H of pip); m/z: 555 [M+H]$^+$.

Compound 144: N2-(2-(4-cyanobenzyl)-1,2,3,4-tetrahydroisoquinolin-7-yl)-N-5-(4-fluorobenzyl)pyridine-2,5-dicarboxamide. $^1$H nmr (CDCl$_3$) δ 9.86 (1H, s, IsoqH-8), 8.99 (1H, d, J 1.0 Hz, pyH-6), 8.28 (1H, d, J 8.0 Hz, pyH-3), 8.22 (1H, dd, J 8.0, 1.5 Hz, pyH-4), 7.51 (2H, d, J 8.0 Hz, 2H of C$_6$H$_4$CN), 7.51 (2H, d, J 8.5 Hz, 2H of C$_6$H$_4$CN), 7.42 (1H, dd, J 8.5, 1.5 Hz, IsoqH-6), 7.33 (2H, m, 2H of C$_6$H$_4$F), 7.12 (1H, d, J 8.5 Hz, IsoqH-5), 7.04 (2H, t, J 8.5 Hz, 2H of C$_6$H$_4$F), 6.71 (1H, t, J 5.5 Hz, NH), 4.63 (2H, d, J 6.0 Hz, NHCH$_2$C$_6$H$_4$F), 3.72 (2H, s, IsoqH-1 of CH$_2$C$_6$H$_4$CN), 3.62 (2H, s, IsoqH-1 or CH$_2$C$_6$H$_4$CN), 2.89 (2H, t, J 5.5 Hz, IsoqH-3 or IsoqH-4), 2.75 (2H, t, J 6.0 Hz, IsoqH-3 or H-4); m/z: 520 [M+H]$^+$.

Compound 145: N-(1-(4-cyanobenzyl)piperidin-4-yl)-5-(4-(4-methylbenzyl)piperidine-1-carbonyl)picolinamide. $^1$H nmr (CDCl$_3$) δ 8.56 (1H, s, pyH-6), 8.21 (1H, d, J 8.0 Hz, pyH-3), 7.93 (1H, d, J 8.5 Hz, NH), 7.84 (1H, dd, J 8.0, 1.5 Hz, pyH-4), 7.61 (2H, d, J 8.5 Hz, 2H of C$_6$H$_4$CN), 7.46 (2H, d, J 8.5 Hz, 2H of C$_6$H$_4$CN), 7.09 (2H, d, J 8.0 Hz, 2H of C$_6$H$_4$CH$_3$), 7.02 (2H, d, J 8.0 Hz, 2H of C$_6$H$_4$CH$_3$), 4.69 (1H, m, 1H of BnpipH-2, H-6), 4.01 (1H, m, pipH-4), 3.60 (1H, m, 1H of BnpipH-2, H-6), 3.58 (2H, s, CH$_2$C$_6$H$_4$CN), 3.00 (1H, m, 1H of BnpipH-2, H-6), 2.82 (2H, m, 2H of pipH-2, H-6), 2.74 (1H, m, 1H of BnpipH-2, H-6), 2.53 (2H, m, CH$_2$C$_6$H$_4$CH$_3$), 2.04 (3H, s, CH$_3$), 2.24 (2H, t, J 11.0 Hz, 2H of pipH-2, H-6), 2.01 (2H, m, 2H of pipH-3, H-5), 1.79-1.63 (4H, m, 2H of pipH-3, H-5, BnpipH-4', 1H of BnpipH-3, H-5), 1.31-1.13 (3H, m, 3H of BnpipH-3, H-5); m/z: 537 [M+H]$^+$.

Compound 146: N-(1-(4-cyanobenzyl)piperidin-4-yl)-5-(4-(3-fluoro-4-methoxybenzyl)piperidine-1-carbonyl)picolinamide. $^1$H nmr (CDCl$_3$) δ 8.56 (1H, m, pyH-6), 8.22 (1H, d, J 8.0 Hz, pyH-3), 7.92 (1H, d, J 8.5 Hz, NH), 7.85 (1H, dd, J 8.0, 2.0 Hz, pyH-4), 7.61 (2H, d, J 8.5 Hz, 2H of C$_6$H$_4$CN), 7.46 (2H, d, J 8.5 Hz, 2H of C$_6$H$_4$CN), 7.20 (1H, t, 8.0 Hz, 1×ArH), 6.73 (1H, dd, J 8.0, 7.0 Hz, 1×ArH), 6.68 (1H, br s, 1×ArH), 4.69 (1H, m, 1H of Bnpip), 4.00 (1H, m, pipH-4), 3.79 (3H, s, OCH$_3$), 3.62 (1H, m, 1H of Bnpip), 3.56 (2H, s, CH$_2$C$_6$H$_4$CN), 3.01 (1H, m, 1H of Bnpip), 2.81 (2H, m, 2H of pip), 2.75 (1H, m, 1H of Bnpip), 2.55 (2H, t, J 6.0 Hz, CH$_2$C$_6$H$_3$FOCH$_3$), 2.23 (2H, dd, J 11.0, 9.5 Hz, 2H of pip), 2.01 (2H, m, 2H of pip), 1.82 (2H, m, 2H of Bnpip), 1.64 (2H, m, 2H of pip), 1.33-1.18 (3H, m, 3H of Bnpip); m/z: 570 [M+H]$^+$.

Compound 147: N-(1-(4-cyanobenzyl)piperidin-4-yl)-5-(4-(3-methoxybenzyl)piperidine-1-carbonyl)picolinamide. $^1$H nmr (CDCl$_3$) δ 8.56 (1H, br s, pyH-6), 8.22 (1H, d, J 8.0 Hz, pyH-3), 7.92 (1H, d, J 8.5 Hz, NH), 7.84 (1H, br d, J 8.0 Hz, pyH-4), 7.61 (2H, d, J 8.0 Hz, 2H of C$_6$H$_4$CN), 7.46 (2H, d, J 8.0 Hz, 2H of C$_6$H$_4$CN), 7.85 (4H, m, 4H of C$_6$H$_4$OCH$_3$), 4.69 (1H, m, 1H of BnpipH-2, H-6), 3.99 (1H, m, pipH-4), 3.86 (3H, s, OCH$_3$), 3.62 (1H, m, 1H of BnpipH-2, H-6), 3.56 (2H, s, CH$_2$C$_6$H$_4$CN), 3.02 (1H, m, 1H of BnpipH-2, H-6), 2.81 (2H, m, 2H of pipH-2, H-6), 2.75 (1H, m, 1H of BnpipH-2, H-6), 2.51 (2H, m, CH$_2$C$_6$H$_4$OCH$_3$), 2.23 (2H, dd, J 11.0, 9.5 Hz, 2H of pipH-2, H-6), 2.01 (2H, m, 2H of pipH-3, H-5), 1.77 (2H, m, 2H of BnpipH-3, H-4, H-5), 1.64 (2H, m, 2H of pipH-3, H-5), 1.30-1.16 (3H, m, 3H of BnpipH-3, H-4, H-5); m/z: 552 [M+H]$^+$.

Compound 148: N-(1-(4-cyanobenzyl)piperidin-4-yl)-5-(4-(4-fluorophenoxy)piperidine-1-carbonyl)picolinamide. $^1$H nmr (CDCl$_3$) δ 8.60 (1H, s, pyH-6), 8.23 (1H, d, J 8.0 Hz, pyH-3), 7.92 (1H, d, J 8.5 Hz, NH), 7.88 (1H, dd, J 8.0, 2.0 Hz, pyH-4), 7.61 (2H, d, J 8.5 Hz, 2H of C$_6$H$_4$CN), 7.46 (2H, d, J 8.0 Hz, 2H of C$_6$H$_4$CN), 6.98 (2H, dd, J 9.5, 8.0 Hz, 2H of C$_6$H$_4$F), 6.86 (2H, m, 2H of C$_6$H$_4$F), 4.52 (1H, m, oxypipH-4), 4.01 (1H, m, pipH-4), 3.88 (2H, m, 2H of oxypipH-2, H-6), 3.64 (1H, m, 1H of oxypipH-2, H-6), 3.58 (2H, s, CH$_2$C$_6$H$_4$CN), 3.32 (1H, m, 1H of oxypipH-2, H-6), 2.83 (2H, m, 2H of pipH-2, H-6), 2.24 (2H, t, J 11.0 Hz, 2H of pipH-2, H-6), 2.01 (3H, m, 2H of pipH-3, H-5, 1H of oxypipH-3, H-5), 1.83 (3H, m, 3H of oxypipH-3, H-5), 1.66 (2H, m, 2H of pipH-3, H-5); m/z: 542 [M+H]$^+$.

Compound 149: N2-(1-(4-cyanobenzyl)piperidin-4-yl)-N-5-(2-(4-fluorophenoxy)ethyl)pyridine-2,5-dicarboxamide. $^1$H nmr (CDCl$_3$) δ 8.94 (1H, s, pyH-6), 8.25 (1H, d, J 8.0 Hz, pyH-3), 8.19 (1H, dd, J 8.0, 2.0 Hz, pyH-4), 7.95 (1H, d, J 8.5 Hz, NHpip), 7.61 (2H, d, J 8.5 Hz, 2H of C$_6$H$_4$CN), 7.45 (2H, d, J 8.5 Hz, 2H of C$_6$H$_4$CN), 6.98 (2H, dd, J 9.5, 8.0 Hz, 2H of C$_6$H$_4$F), 6.85 (2H, dd, J 9.5, 4.5 Hz, 2H of C$_6$H$_4$F), 6.67 (1H, br s, NHCH$_2$CH$_2$O), 4.13 (2H, t, J 5.0 Hz, NHCH$_2$CH$_2$O), 4.00 (1H, m, pipH-4), 3.89 (2H, q, J 5.5 Hz, NHCH$_2$CH$_2$O), 3.56 (2H, s, CH$_2$C$_6$H$_4$CN), 2.81 (2H, m, 2H of pipH-2, H-6), 2.23 (2H, dd, J 11.5, 11.0 Hz, 2H of pipH-2, H-6), 2.02 (2H, m, 2H of pipH-3, H-5), 1.69 (2H, m, 2H of pipH-3, H-5); m/z: 502 [M+H]$^+$.

Compound 150: N-(cis-4-(4-cyanophenoxy)cyclohexyl)-5-(4-(4-fluorobenzyl)piperazine-1-carbonyl)picolinamide. $^1$H nmr (CDCl$_3$) δ 8.58 (1H, m, pyH-6), 8.23 (1H, dd, J 8.0, 1.0 Hz, pyH-3), 7.99 (1H, d, J 8.5 Hz, NH), 7.86 (1H, dd, J 8.0, 2.0 Hz, pyH-4), 7.58 (2H, d, J 9.0 Hz, 2H of C$_6$H$_4$CN), 7.26 (2H, m, 2H of C$_6$H$_4$F), 7.00 (2H, t, J 8.5 Hz, 2H of C$_6$H$_4$F), 6.95 (2H, d, J 9.0 Hz, 2H of C$_6$H$_4$CN), 4.59 (1H, br s, cHexH-1), 4.10 (1H, m, cHexH-4), 3.80 (2H, m, 2H of piz), 3.50 (2H, s, CH2C6H4F), 3.39 (2H, m, 2H of piz), 2.53 (2H, m, 2H of piz), 2.38 (2H, m, 2H of piz), 2.06 (2H, m, 2H of cHexH-2, H-6), 1.90-1.72 (4H, m, 2H of cHexH2, H-6, 2H of cHexH-3, H-5), 1.24 (2H, m, 2H of cHexH-3, H-5); m/z: 542 [M+H]$^+$.

Compound 151: N-(trans-4-(4-cyanophenoxy)cyclohexyl)-5-(4-(4-fluorobenzoyl)piperazine-1-carbonyl)picolinamide. $^1$H nmr (CDCl$_3$) δ 8.60 (1H, m, pyH-6), 8.25 (1H, d, J 8.0 Hz, pyH-3), 8.02-7.96 (3H, m, 2H of C$_6$H$_4$F, NH), 7.89 (1H, dd, J 8.0, 2.0 Hz, pyH-4), 7.58 (2H, d, J 9.0 Hz, 2H of C$_6$H$_4$CN), 7.16 (2H, t, J 8.5 Hz, 2H of C$_6$H$_4$F), 6.96 (2H, d, J 9.0 Hz, 2H of C$_6$H$_4$CN), 4.66 (1H, m, 1H of pipH-2, H-6), 4.60 (1H, br s, cHexH-1), 4.10 (1H, m, cHexH-4), 3.76 (1H, m, 1H of pipH-2, H-6), 3.54 (1H, m, pipH-4), 3.24 (1H, m, 1H of pipH-2, H-6), 3.11 (1H, m, 1H of pipH-2, H-6), 2.07 (3H, m, 3H of cHexH-2, H-6), 1.90-1.79 (8H, m, 1H of cHexH-2, H-6, 3H of cHexH-3, H-5, 4H of pipH-3, H-5), 1.25 (1H, m, 1H of cHexH-3, H-5); m/z: 555 [M+H]$^+$.

Compound 152: N-(1-(4-cyanobenzyl)piperidin-4-yl)-5-(3-(4-fluorobenzyl)piperidine-1-carbonyl)picolinamide. $^1$H nmr (CDCl$_3$) δ 8.48 (1H, br s, pyH-6), 8.17 (1H, d, J 8.0 Hz, NH or pyH-3), 7.87 (1H, d, J 7.5 Hz, NH or pyH-3), 7.80 (1H, m, pyH-4), 7.60 (2H, d, J 8.5 Hz, 2H of C$_6$H$_4$CN), 7.46 (2H, d, J 8.5 Hz, 2H of C$_6$H$_4$CN), 7.03 (2H, m, 2H of C$_6$H$_4$F), 6.93 (2H, m, 2H of C$_6$H$_4$F), 4.52 (1H, br s, 1H of Bnpip), 4.02 (1H, m, pipH-4), 3.57 (2H, s, CH$_2$C$_6$H$_4$CN), 2.95 (1H, m, 1H of Bnpip), 2.81 (2H, m, 2H of pip), 2.68 (1H, dd, J 13.0, 10.5 Hz, 1H of Bnpip), 2.50 (1H, m, 1H of Bnpip), 2.26 (2H, td, J 11.5, 2.0 Hz, 2H of pip), 2.04 (2H, m, 2H of pip), 1.90-1.58 (5H, m, 2H of pip, 3H of Bnpip), 1.27 (2H, m, 2H of Bnpip); m/z: 541 [M+H]+.  2H of Bnpip missing, probably due to broadness of the peak in the 3-5 region

Compound 153: N-(1-(4-cyanobenzyl)piperidin-4-yl)-5-(2-(4-fluorobenzyl)piperidine-1-carbonyl)picolinamide. $^1$H nmr (CDCl$_3$) δ 8.19 (1H, br s, pyH-6), 8.10 (1H, d, J 7.5 Hz, 1H of NH, pyH-3 or pyH-4), 7.86 (1H, d, J 8.0 Hz, 1H of NH, pyH-3 or pyH-4), 7.60 (2H, d, J 8.5 Hz, 2H of C$_6$H$_4$CN), 7.46 (2H, d, J 8.0 Hz, 2H of C$_6$H$_4$CN), 7.05 (2H, m broad, 2H of C$_6$H$_4$F), 6.96 (2H, t, J 8.0 Hz, 2H of C$_6$H$_4$F), 4.00 (1H, m, pipH-4), 3.57 (2H, s, CH2C6H4CN), 3.08 (2H, m, 2H of Bnpip), 2.80 (3H, m, 2H of pip, 1H of Bnpip), 2.25 (2H, m, 2H of pip), 2.02 (2H, m, 2H of pip), 1.76-1.60 (8H, m, 2H of pip, 6H of Bnpip); m/z: 540 [M+H]+. 2H of Bnpip not showing up, probably too broad to observe

Compound 154: 5-(4-(4-chlorobenzoyl)piperidine-1-carbonyl)-N-(1-(4-cyanobenzyl)piperidin-4-yl)picolinamide. $^1$H nmr (CDCl$_3$) δ 8.60 (1H, m, pyH-6), 8.24 (1H, dd, J 8.0, 0.5 Hz, pyH-3), 7.94-7.87 (4H, m, NH, pyH-4, 2H of C$_6$H$_4$Cl), 7.61 (2H, d, J 8.0 Hz, 2H of C$_6$H$_4$CN), 7.46 (4H, m, 2H of C$_6$H$_4$CN, 2H of C$_6$H$_4$Cl), 4.65 (1H, m, 1H of BzpipH-2, H-6), 4.01 (1H, m, pipH-4), 3.77 (1H, m, 1H of BzpipH-2, H-6), 3.58 (2H, s, C$\underline{\text{H}}_2$C$_6$H$_4$CN), 3.53 (1H, m, BzpipH-4), 3.17 (2H, m 2H of BzpipH-2, H-6), 2.83 (2H, m, 2H of pipH-2, H-6), 2.24 (2H, t, J 10.5 Hz, 2H of pipH-2, H-6), 2.02 (2H, m, 2H of BzpipH-3, H-5), 1.82 (2H, m, 2H of pipH-3, H-5), 1.71-1.61 (4H, m, 2H of pipH-3, H-5, 2H of BzpipH-3, H-5); m/z: 570 [M+H]+.

Compound 155: N-(1-(4-cyanobenzyl)piperidin-4-yl)-5-(4-(3-cyanophenoxy)piperidine-1-carbonyl)picolinamide. $^1$H nmr (CDCl$_3$) δ 8.60 (1H, m, pyH-6), 8.24 (1H, d, J 8.0 Hz, pyH-3), 7.92 (1H, d, J 8.5 Hz, NH), 7.89 (1H, dd, J 8.0, 2.0 Hz, pyH-4), 7.61 (2H, d, J 8.5 Hz, 2H of C$_6$H$_4$CN), 7.46 (2H, d, J 8.0 Hz, 2H of C$_6$H$_4$CN), 7.39 (1H, t, J 7.5 Hz, 1H of OC$_6$H$_4$CN), 7.26 (1H, m, 1H of OC$_6$H$_4$CN), 7.14 (2H, m, 2H of OC$_6$H$_4$CN), 4.65 (1H, m, PhoxypipH-4), 4.01 (1H, m, pipH-4), 3.90 (2H, m, 2H of PhoxypipH-2, H-6), 3.63 (1H, m, 1H of PhoxypipH-2, H-6), 3.56 (2H, s, C$\underline{\text{H}}_2$C$_6$H$_4$CN), 3.39 (1H, m, 1H of PhoxypipH-2, H-6), 2.81 (2H, m, 2H of pipH-2, H-6), 2.22 (2H, dd, J 11.0, 10.0 Hz, 2H of pipH-2, H-6), 2.04-1.70 (6H, m, 2H of pipH-3, H-5, PhoxypipH-3, H-5), 1.64 (2H, m, 2H of pipH-3, H-5); m/z: 549 [M+H]+.

Compound 156: 5-(4-(3-chloro-4-cyanophenoxy)piperidine-1-carbonyl)-N-(1-(4-cyanobenzyl)piperidin-4-yl)picolinamide. $^1$H nmr (CDCl$_3$) δ 8.60 (1H, m pyH-6), 8.25 (1H, d, J 8.0 Hz, pyH-3), 7.91 (1H, m, NH), 7.89 (1H, dd, J 8.5, 2.0 Hz, pyH-4), 7.61 (2H, d, J 8.5 Hz, 2H of C$_6$H$_4$CN), 7.59 (1H, d, J 9.0 Hz, H-5 or H-6 of C$_6$H$_3$ClCN), 7.45 (2H, d, J 8.0 Hz, 2H of C$_6$H$_4$CN), 7.03 (1H, d, J 2.0 Hz, H-2 of C$_6$H$_3$ClCN), 6.87 (1H, dd, J 8.5, 2.0 Hz, H-5 or H-6 of C$_6$H$_3$ClCN), 4.69 (1H, m, PhoxypipH-4), 4.01 (1H, m, pipH-4), 3.91 (2H, m, 2H of PhoxypipH-2, H-6), 3.62 (1H, m, 1H of PhoxypipH-2, H-6), 3.56 (2H, s, C$\underline{\text{H}}_2$C$_6$H$_4$CN), 3.42 (1H, m, 1H of PhoxypipH-2, H-6), 2.82 (2H, m, 2H of pipH-2, H-6), 2.23 (2H, dd, J 11.5, 10.0 Hz, 2H of pipH-2, H-6), 2.04-1.69 (6H, m, 2H of pipH-3, H-5, PhoxypipH-3, H-5), 1.64 (2H, m, 2H of pipH-3, H-5); m/z: 583, 585 [M+H]+.

Compound 157: N-(1-(4-cyanobenzyl)piperidin-4-yl)-5-(4-(4-(trifluoromethyl)phenoxy)piperidine-1-carbonyl)picolinamide. $^1$H nmr (CDCl$_3$) δ 8.60 (1H, m, pyH-6), 8.24 (1H, d, J 8.0 Hz, pyH-3), 7.94-7.87 (2H, m, NH, pyH-4), 7.61 (2H, d, J 8.5 Hz, 2H of C$_6$H$_4$CN), 7.55 (2H, m, 2H of C$_6$H$_4$CF$_3$), 7.46 (2H, d, J 8.0 Hz, 2H of C$_6$H$_4$CN), 6.97 (2H, d, J 9.0 Hz, 2H of C$_6$H$_4$CF$_3$), 4.70 (1H, m, 1H of Phoxypip), 4.01 (1H, m, 1H of Phoxypip or pipH-4), 3.95-3.87 (1H, m, 1H of Phoxypip or pipH-4), 3.64 (1H, m, 1H of Phoxypip), 3.58 (2H, s, C$\underline{\text{H}}_2$C$_6$H$_4$CN), 3.50 (1H, m, 1H of Phoxypip), 3.35 (1H, m, 1H of Phoxypip), 2.83 (2H, m, 2H of pip), 2.24 (2H, t, J 11.0 Hz, 2H of pip), 2.14-1.84 (6H, m, 2H of pip, 4H of Phoxypip), 1.65 (2H, m, 2H of pip); m/z: 592 [M+H]+.

Compound 158: N-(1-(4-cyanobenzyl)piperidin-4-yl)-5-(4-(3,4-difluorophenoxy)piperidine-1-carbonyl)picolinamide. $^1$H nmr (CDCl$_3$) δ 8.60 (1H, m, pyH-6), 8.24 (1H, d, J 8.0 Hz, pyH-3), 7.91 (1H, m, NH), 7.88 (1H, dd, J 8.0, 2.0 Hz, pyH-4), 7.61 (2H, d, J 8.0 Hz, 2H of C$_6$H$_4$CN), 7.45 (2H, d, J 8.0 Hz, 2H of C$_6$H$_4$CN), 7.07 (1H, q, J 9.5 Hz, H-5 of C$_6$H$_3$F$_2$), 6.74 (1H, m, H-1 of C$_6$H$_3$F$_2$), 6.61 (1H, m, H-6 of C$_6$H$_3$F$_2$), 4.51 (1H, m, PhoxypipH-4), 4.01 (1H, m, pipH-4), 3.88 (2H, m, 2H of PhoxyH-2, H-6), 3.63 (1H, m, 1H of PhoxypipH-2, H-6), 3.56 (2H, s, C$\underline{\text{H}}_2$C$_6$H$_4$CN), 3.37 (1H, m, 1H of PhoxypipH-2, H-6), 2.82 (2H, m, 2H of pipH-2, H-6), 2.22 (2H, t, J 11.0 Hz, 2H of pipH-2, H-6), 2.04-1.84 (6H, m, 2H of pipH-3, H-5, 4H of PhoxypipH-3, H-5), 1.64 (2H, m, 2H of pipH-3, H-5); m/z: 560 [M+H]+.

Compound 159: N-(1-(4-cyanobenzyl)piperidin-4-yl)-3-(5,20-dioxo-24-((3aS,4S,6aR)-2-oxohexahydro-1H-thieno[3,4-d]imidazol-4-yl)-7,10,13,16-tetraoxa-4,19-diazatetracos-1-ynyl)-5-(4-(4-fluorobenzyl)piperazine-1-carbonyl)picolinamide. Hydrogen chloride (0.054 mL of a 4.0M solution in dioxane, 0.216 mmol, 5.0 eq) was added to a solution of Compound 164 (see below) (0.030 g, 0.043 mmol, 1.0 eq) in dichloromethane (1.0 mL). The reaction mixture was stirred at room temperature for 90 minutes before removing the solvent under a stream of nitrogen. The residue was dried under vacuum to provide 3-(3-aminoprop-1-ynyl)-N-(1-(4-cyanobenzyl)piperidin-4-yl)-5-(4-(4-fluorobenzyl)piperazine-1-carbonyl)picolinamide trihydrochloride, which was used without further purification; m/z 594 [M+H]+. To a suspension of the 3-(3-aminoprop-1-ynyl)-N-(1-(4-cyanobenzyl)piperidin-4-yl)-5-(4-(4-fluorobenzyl)piperazine-1-carbonyl)picolinamide trihydrochloride (0.043 mmol, 1.0 eq) in dichloromethane (1.0 mL) was added triethylamine (0.018 mL, 0.129 mmol, 3.0 eq) forming a brown solution. 15-[(D)-(+)-Biotinylamino]-4,7,10,13-tetraoxapentadecanoic acid (0.023 g, 0.047 mmol, 1.1 eq) and HATU (0.018 g, 0.047 mmol, 1.1 eq) were added followed by dimethylaminopyridine (0.005 g, 0.043 mmol, 1.0 eq). The reaction was stirred at room temperature for 3 hours before pouring into water (20 mL). The organics were extracted with CH$_2$Cl$_2$ (3×25 mL). The combined organics were washed with brine (35 mL), dried (Na$_2$SO$_4$) and concentrated under reduced pressure. The crude material was purified by RP-HPLC to provide Compound 159; m/z 1068 [M+H]+.

Compound 160: 5-(4-(4-fluorobenzoyl)piperidine-1-carbonyl)-N-(1-(4-methoxybenzyl)piperidin-4-yl)picolinamide. To a solution of 5-(methoxycarbonyl)pyridine-2-carboxylic acid (0.209 g, 1.18 mmol, 1.0 eq) and 1-(4-methoxybenzyl)piperidine dihydrochloride (0.373 g, 1.27 mmol, 1.1 eq) in dimethylformamide (10 mL) was added triethylamine (0.40 mL, 2.89 mmol, 2.5 eq) followed by HATU (0.528 g, 1.39 mmol, 1.2 eq). The reaction was stirred at room temperature for 2 days before partitioning between EtOAc (100 mL) and water (80 mL). The organics were further washed with brine (80 mL), water (80 mL) and brine (80 mL), before drying (Na$_2$SO$_4$) and concentrating under reduced pressure to yield methyl 6-(1-(4-methoxybenzyl)piperidin-4-ylcarbamoyl)nicotinate as a white solid (0.378 g, 84%) which was used without further purification; $^1$H nmr (CDCl$_3$) 9.13 (1H, m, pyH-6), 8.43 (1H, dd, J 8.0, 2.0 Hz, pyH-4), 8.25 (1H, d, J 8.0 Hz, pyH-3), 7.98 (1H, d, J 7.5 Hz, NH), 7.26 (2H, d, J 8.5 Hz, 2H of C$_6$H$_4$OCH$_3$), 6.87 (2H, d, J 8.5 Hz, 2H of C$_6$H$_4$OCH$_3$), 4.01 (1H, m, pipH-4), 3.98 (3H, s, 1×OCH$_3$), 3.80 (3H, s, 1×OCH$_3$), 3.53 (2H, s, CH$_2$C$_6$H$_4$OCH$_3$), 2.90 (2H, m, 2H of pip), 2.24 (2H, dd, J 11.0, 10.0 Hz, 2H of pip), 2.02 (2H, m, 2H of pip), 1.69 (2H, m, 2H of pip); m/z 384 [M+H]$^+$. To a solution of the methyl 6-(1-(4-methoxybenzyl)piperidin-4-ylcarbamoyl)nicotinate (0.378 g, 0.987 mmol, 1.0 eq) in tetrahydrofuran (6 mL) and methanol (3 mL) was added a solution of lithium hydroxide monohydrate (0.166 g, 3.948 mmol, 4.0 eq) in water (3 mL). The reaction mixture was stirred at room temperature for 30 minutes before neutralizing with HCl (approximately 2.0 mL of a 2M solution). The reaction was concentrated to dryness to yield 6-(1-(4-methoxybenzyl)piperidin-4-ylcarbamoyl)nicotinic acid as a white solid, which was used without purification. To a mixture of the 6-(1-(4-methoxybenzyl)piperidin-4-ylcarbamoyl)nicotinic acid (0.036 g, 0.098 mmol, 1.0 eq), 4-fluorobenzoylpiperidine hydrochloride (0.029 g, 0.117 mmol, 1.2 eq), and triethylamine (0.034 mL, 0.244 mmol, 2.5 eq) in dimethylformamide (1.0 eq) was added HATU (0.041 g, 0.244 mmol, 1.1 eq). The reaction was shaken at room temperature for 3 hours before adding water (5 mL). A gum formed, which was dissolved in EtOAc-CH$_2$Cl$_2$ (4:1, 50 mL). The solution was washed with NaHCO$_3$-water (1:1, 50 mL), brine (50 mL), water (50 mL) and brine (50 mL). The organics were dried (Na$_2$SO$_4$) and concentrated under reduced pressure. Column chromatography (silica, 3→7% MeOH—CH$_2$Cl$_2$) yielded Compound 160 as a colourless oil (0.037 g, 68%); $^1$H nmr (CDCl$_3$) δ 8.60 (1H, m, pyH-6), 8.24 (1H, d, J 8.0 Hz, pyH-3), 7.98 (2H, dd, J 8.5, 5.5 Hz, 2H of C$_6$H$_4$F), 7.91 (1H, m, NH), 7.88 (1H, dd, J 8.0, 2.0 Hz, pyH-4), 7.24 (2H, d, 2H of C$_6$H$_4$OCH$_3$), 7.16 (2H, t, J 8.5 Hz, 2H of C$_6$H$_4$F), 6.86 (2H, d, J 8.5 Hz, 2H of C$_6$H$_4$OCH$_3$), 4.66 (1H, m, BzpipH-4), 3.99 (1H, m, pipH-4), 3.80 (3H, s, OCH$_3$), 3.77 (1H, m, 1H of BzpipH-2, H-6), 3.54 (1H, m, 1H of BzpipH-2, H-6), 3.48 (2H, s, CH$_2$C$_6$H$_4$OCH$_3$), 3.21-3.11 (2H, m, 2H of BzpipH-2, H-6), 2.86 (2H, m, 2H of pipH-2, H-6), 2.19 (2H, t, J 11.0 Hz, 2H of pipH-2, H-6), 2.00 (2H, m, 2H of pipH-3, H-5), 1.82 (4H, m, BzpipH-3, H-5), 1.64 (2H, m, 2H of pipH-3, H-5); m/z 559 [M+H]$^+$.

Compound 161: 5-(4-(4-fluorophenoxy)piperidine-1-carbonyl)-N-(1-(4-methoxybenzyl)piperidin-4-yl)picolinamide. $^1$H nmr (CDCl$_3$) δ 8.59 (1H, m, pyH-6), 8.23 (1H, d, J 8.0 Hz, pyH-3), 7.91 (1H, m, NH), 7.88 (1H, dd, J 8.5, 2.0 Hz, pyH-4), 7.24 (2H, d, J 8.5 Hz, 2H of C$_6$H$_4$OCH$_3$), 6.98 (2H, dd, J 9.0, 8.5 Hz, 2H of C$_6$H$_4$F), 6.86 (4H, m, 2H of C$_6$H$_4$F, 2H of C$_6$H$_4$OCH$_3$), 4.51 (1H, m, PhOpipH-4), 4.00 (1H, m, pipH-4), 3.88 (2H, m, 2H of PhOpipH-2, H-6), 3.80 (3H, s, OCH$_3$), 3.63 (1H, m, 1H of PhOpipH-2, H-6), 3.49 (2H, s, CH$_2$C$_6$H$_4$OCH$_3$), 3.34 (1H, m, 1H of PhOpipH-2, H-6), 2.87 (2H, m, 2H of pipH-2, H-6), 2.20 (2H, t, J 11.0 Hz, 2H of pipH-2, H-6), 2.06-1.90 (4H, m, 2H of pipH-3, H-5, 2H of PhOpipH-3, H-5), 1.83 (2H, m, 2H of PhOpipH-3, H-5), 1.65 (2H, m, 2H of pipH-3, H-5); m/z 547 [M+H]$^+$.

Compound 162: 5-(4-(4-cyanophenoxy)piperidine-1-carbonyl)-N-(1-(4-methoxybenzyl)piperidin-4-yl)picolinamide. $^1$H nmr (CDCl$_3$) δ 8.59 (1H, d, J 1.0 Hz, pyH-6), 8.24 (1H, d, J 8.0 Hz, pyH-3), 7.90 (1H, m, NH), 7.87 (1H, dd, J 8.0, 2.0 Hz, pyH-4), 7.59 (2H, d, J 9.0 Hz, 2H of C$_6$H$_4$CN or C$_6$H$_4$OCH$_3$), 7.23 (2H, d, J 9.0 Hz, 2H of C$_6$H$_4$CN or C$_6$H$_4$OCH$_3$), 6.96 (2H, d, J 9.0 Hz, 2H of C$_6$H$_4$CN or C$_6$H$_4$OCH$_3$), 6.86 (2H, d, J 9.0 Hz, 2H of C$_6$H$_4$CN or C$_6$H$_4$OCH$_3$), 4.70 (1H, m, PhOpipH-4), 3.99 (1H, m, pipH-4), 3.90 (2H, m, 2H of PhOpipH-2, H-6), 3.80 (3H, s, OCH$_3$), 3.64 (1H, m, 1H of PhOpipH-2, H-6), 3.48 (2H, s, CH$_2$C$_6$H$_4$OCH$_3$), 3.41 (1H, m, 1H of PhOpipH-2, H-6), 2.87 (2H, m, 2H of pipH-2, H-6), 2.19 (2H, t, J 11.0 Hz, 2H of pipH-2, H-6), 2.04-1.82 (6H, m, 2H of pipH-3, H-5 and 4H of PhOpipH-3, H-5), 1.64 (2H, m, 2H of pipH-3, H-5); m/z: 555 [M+H]$^+$.

Compound 163: 5-(4-(4-methoxybenzoyl)piperidine-1-carbonyl)-N-(1-(4-methoxybenzyl)piperidin-4-yl)picolinamide. $^1$H nmr (CDCl$_3$) δ 8.59 (1H, m, pyH-6), 8.23 (1H, d, J 8.0 Hz, pyH-3), 7.94 (1H, d, J 9.0 Hz, 2H of OC$_6$H$_4$CN or CH$_2$C$_6$H$_4$CN), 7.88 (1H, dd, J 8.0, 2.0 Hz, pyH-4), 7.26 (2H, d, J 8.5 Hz, 2H of OC$_6$H$_4$CN or CH$_2$C$_6$H$_4$CN), 6.96 (2H, d, J 9.0 Hz, 2H of OC$_6$H$_4$CN or CH$_2$C$_6$H$_4$CN), 6.86 (2H, d, J 8.5 Hz, 2H of OC$_6$H$_4$CN or CH$_2$C$_6$H$_4$CN), 4.65 (1H, m, PhOpipH-4), 4.01 (1H, m, pipH-4), 3.88 (3H, s, OCH$_3$), 3.80 (1H, m, 1H of PhOpipH-2, H-6), 3.53 (3H, m, 1H of PhOpipH-2, H-6, CH$_2$C$_6$H$_4$OCH$_3$), 3.24-3.11 (2H, m, 2H of PhOpipH-2, H-6), 2.91 (2H, m, 2H of pipH-2, H-6), 2.25 (2H, t, J 11.0 Hz, 2H of pipH-2, H-6), 2.02 (2H, m, 2H of pipH-3, H-5), 1.89-1.76 (4H, m, 4H of PhOpipH-3, H-5), 1.70 (2H, m, 2H of pipH-3, H-5); m/z: 572 [M+H]$^+$.

Compound 164: tert-butyl 3-(2-(1-(4-cyanobenzyl)piperidin-4-ylcarbamoyl)-5-(4-(4-fluorobenzyl)piperazine-1-carbonyl)pyridin-3-yl)prop-2-ynylcarbamate. To a solution of 5-chloro-6-(ethoxycarbonyl)nicotinic acid (0.201 g, 0.875 mmol, 1.0 eq) and 4-fluorobenzylpiperazine (0.204 g, 1.051 mmol, 1.2 eq) in dimethylformamide (4.0 mL) was added triethylamine (0.146 mL, 1.051 mmol, 1.2 eq) followed by HATU (0.366 g, 0.963 mmol, 1.1 eq). The reaction was shaken at room temperature for 3 hours before partitioning between EtOAc (80 mL) and water-NaHCO$_3$ (2:1, 60 mL). The organics were further washed with brine (80 mL), water (80 mL) and brine (80 mL) before drying (Na$_2$SO$_4$) and concentrating under reduced pressure. MPLC (30→95% EtOAc-hexane, 2→25 min) yielded ethyl 3-chloro-5-(4-(4-fluorobenzyl)piperazine-1-carbonyl)picolinate as a white solid (0.265 g, 75%); $^1$H nmr (D$_6$-DMSO) 8.54 (1H, d, J 1.5 Hz, pyH-2 or pyH-4), 7.83 (1H, d, J 1.0 Hz, pyH-2 or pyH-4), 7.26 (2H, m, 2H of C$_6$H$_4$F), 6.99 (2H, t, J 8.5 Hz, 2H of C$_6$H$_4$F), 4.48 (2H, q, J 7.0 Hz, OCH$_2$CH$_3$), 3.55 (4H, m, 4H of piz), 2.45 (4H, m, 4H of piz), 1.43 (3H, t, J 7.0 Hz, OCH$_2$CH$_3$); m/z 406, 408 [M+H]$^+$. A solution of the ethyl 3-chloro-5-(4-(4-fluorobenzyl)piperazine-1-carbonyl)picolinate (0.265 g, 0.654 mmol, 1.0 eq) and N-Boc-propargylamine (0.122 g, 0.785 mmol, 1.2 eq) in dimethylformamide (7.0 mL) was degassed by bubbling argon through it. Triethylamine (0.14 mL, 0.981 mmol, 1.5 eq) was added followed by copper (I) iodide (0.006 g, 0.033 mmol, 0.05 eq) and tetrakis(triphenylphosphine)palladium (0.038 g, 0.033 mmol, 0.05 eq). The reaction mixture was further degassed before heating to 90° C. for 14 hours. The reaction was cooled and filtered through Celite®, eluting with EtOAc (80 mL). The filtrate was washed with water (100 mL), brine (80 mL), water (100 mL) and brine (80 mL). The organics were dried (Na$_2$SO$_4$) and concentrated under reduced pressure. Column chromatography (silica, 70% EtOAc-hexane) yielded the ethyl 3-chloro-5-(4-(4-fluorobenzyl)piperazine-1-carbonyl)picolinate starting material and ethyl 3-(3-(tert-butoxycarbonylamino)prop-1-ynyl)-5-(4-(4-fluorobenzyl)piperazine-1-carbonyl)picolinate as a colourless oil; $^1$H nmr (CDCl$_3$) 8.60 (1H, d, J 2.0 Hz, pyH-2 or pyH-4), 7.87 (1H, d, J 2.0 Hz, pyH-2 or pyH-4), 7.26 (2H, m, 2H of C$_6$H$_4$F), 6.99 (2H, t, J 8.5 Hz, 2H of C$_6$H$_4$F), 4.87 (1H, br s, NH), 4.47 (2H, q, J 7.0 Hz, OCH$_2$CH$_3$), 4.21 (2H, d, J 5.5 Hz, CH$_2$NHBoc), 3.77 (2H, m, 2H of piz), 3.37 (2H, m, 2H of piz), 2.51 (2H, m, 2H of piz), 2.38 (2H, m, 2H of piz), 1.47 (9H, s, C(CH$_3$)$_3$), 1.43 (3H, t, J 7.0 Hz, OCH$_2$CH$_3$); m/z 525 [M+H]$^+$. A solution of lithium hydroxide monohydrate (0.010 g, 0.229 mmol, 2.0 eq) in water (0.5 mL) was added to a solution of the ethyl 3-(3-(tert-butoxycarbonylamino)prop-1-ynyl)-5-(4-(4-fluorobenzyl)piperazine-1-carbonyl)picolinate (0.060 g, 0.115 mmol, 1.0 eq) in tetrahydrofuran-methanol (2:1, 1.5 mL). The reaction was stirred at room temperature for 40 minutes before neutralizing with HCl (approximately 0.2 mL of a 2M solution). The reaction mixture was concentrated to dryness to provide 3-(3-(tert-butoxycarbonylamino)prop-1-ynyl)-5-(4-(4-fluorobenzyl)piperazine-1-carbonyl)picolinic acid, which was used without purification; m/z 497 [M+H]$^+$. To a solution of the crude 3-(3-(tert-butoxycarbonylamino)prop-1-ynyl)-5-(4-(4-fluorobenzyl)piperazine-1-carbonyl)picolinic acid (0.115 mmol, 1.0 eq) in dimethylformamide (2.0 mL) was added 1-(4-cyanobenzyl)-4-aminopiperidine dihydrochloride (0.040 g, 0.138 mmol, 1.2 eq) and HATU (0.052 g, 0.138 mmol, 1.2 eq). Triethylamine (0.056 mL, 0.403 mmol, 3.5 eq) was added and the reaction mixture was stirred at room temperature for 2.5 hours before partitioning between EtOAc (100 mL) and water (100 mL). The organics were further washed with brine (80 mL), water (80 mL) and brine (80 mL), dried ($Na_2SO_4$) and concentrated under reduced pressure. Column chromatography (silica, 3→6% MeOH—$CH_2Cl_2$) yielded Compound 164 as a yellow foam; $^1$H nmr ($CDCl_3$) δ 8.46 (1H, d, J 2.0 Hz, pyH-4 or pyH-6), 7.85 (1H, d, J 2.0 Hz, pyH-4 or pyH-6), 7.80 (1H, d, J 8.0 Hz, CONH), 7.60 (2H, d, J 8.0 Hz, 2H of $C_6H_4CN$), 7.45 (2H, d, J 8.0 Hz, 2H of $C_6H_4CN$), 7.29-7.25 (2H, m, 2H of $C_6H_4F$), 7.00 (2H, t, J 8.5 Hz, 2H of $C_6H_4F$), 4.88 (1H, m, $NHCO_2C$), 4.23 (2H, d, J 5.5 Hz, $CCH_2NH$), 3.99 (1H, m, pipH-4), 3.80-3.40 (4H, br m, 4H of piz), 3.56 (2H, s, $CH_2C_6H_4CN$ or $CH_2C_6H_4F$), 3.51 (2H, s, $CH_2C_6H_4CN$ or $CH_2C_6H_4F$), 2.80 (2H, m, 2H of pip), 2.46 (4H, m, 4H of piz), 2.23 (2H, t, J 11.0 Hz, 2H of pip), 2.01 (2H, m, 2H of pip), 1.63 (2H, m, 2H of pip), 1.46 (9H, s, $C(CH_3)_3$); m/z: 694 [M+H]$^+$.

Compound 165: N-(1-(4-cyanobenzyl)piperidin-4-yl)-5-(4-(4-cyanophenoxy)piperidin-1-yl)picolinamide. To a solution of 5-bromopicolinic acid (0.50 g, 2.48 mmol, 1.0 eq) and 1-(4-cyanobenzyl)-4-aminopiperidine dihydrochloride (0.71 g, 2.48 mmol, 1.0 eq) in dimethylformamide (10 mL) was added triethylamine (1.21 mL, 8.66 mmol, 3.5 eq) and HATU (1.13 g, 2.97 mmol, 1.2 eq). The reaction mixture was stirred at room temperature 14 hours before partitioning between EtOAc (120 mL) and water (100 mL). The organics were washed with brine (100 mL), water (100 mL) and brine (100 mL), dried ($Na_2SO_4$) and concentrated under reduced pressure. MPLC (0%, 5%, 10% MeOH—$CH_2Cl_2$, 0→5→25→35 min) yielded 5-bromo-N-(1-(4-cyanobenzyl)piperidin-4-yl) picolinamide as a waxy brown solid: $^1$H nmr ($CDCl_3$) 8.60 (1H, d, J 2.0 Hz, pyH-6), 8.07 (1H, d, J 8.5 Hz, pyH-3), 7.97 (1H, dd, J 8.5, 2.0 Hz, pyH-4), 7.84 (1H, d, J 7.5 Hz, NH), 7.63 (2H, d, J 8.5 Hz, 2H of $C_6H_4CN$), 7.50 (2H, d, J 8.0 Hz, 2H of $C_6H_4CN$), 4.00 (1H, m, pipH-4), 3.63 (2H, s, $CH_2C_6H_4CN$), 2.88 (2H, m, 2H of pip), 2.30 (2H, m, 2H of pip), 2.04 (2H, m, 2H of pip), 1.70 (2H, m, 2H of pip); m/z 399, 401 [M+H]$^+$. To a mixture of the 5-bromo-N-(1-(4-cyanobenzyl)piperidin-4-yl)picolinamide (0.040 g, 0.100 mmol, 1.0 eq) 4-(4-piperidinyloxy)benzonitrile (0.024 g, 0.120 mmol, 1.2 eq), sodium t-butoxide (0.019 g, 0.201 mmol, 2.0 eq) and S-Phos (0.004 g, 0.010 mmol, 0.1 eq) was added toluene (1.0 mL). The resulting mixture was degassed by bubbling argon through the mixture. Tris(dibenzylideneacetone)dipalladium (0.005 g, 0.005 mmol, 0.05 eq) was added and the mixture further degassed before sealing the reaction and heating to 105° C. for 14 hours. The reaction was filtered through celite, eluting with 5% MeOH—$CH_2Cl_2$ (3×15 mL). The filtrate was concentrated under reduced pressure. The crude material was purified by RP-HPLC to yield Compound 165: $^1$H nmr ($CDCl_3$) δ 8.19 (1H, d, J 3.0 Hz, pyH-6), 8.04 (1H, d, J 9.0 Hz, pyH-3), 7.72 (1H, d, J 8.5 Hz, NH), 7.60 (4H, m, 2H of $OC_6H_4CN$, 2H of $CH_2C_6H_4CN$), 7.45 (2H, d, J 8.0 Hz, 2H of $CH_2C_6H_4CN$), 7.24 (1H, dd, J 8.0, 3.0 Hz, pyH-4), 6.97 (2H, d, J 9.0 Hz, 2H of $OC_6H_4CN$), 4.64 (1H, m, PhOpipH-4), 3.98 (1H, m, pipH-4), 3.63-3.57 (2H, m, 2H of PhOpipH-2, H-6), 3.55 (2H, s, $CH_2C_6H_4CN$), 3.38-3.30 (2H, m, 2H of PhOpipH-2, H-6), 2.80 (2H, m, 2H of pipH-2, H-6), 2.22 (2H, t, J 11.5 Hz, 2H of pipH-2, H-6), 2.16-2.05 (2H, m, 2H of PhOpipH-3, H-5), 2.01-1.92 (4H, m, 2H of pipH-3, H-5, 2H of PhOpipH-3, H-5), 1.62 (2H, m, 2H of pipH-3, H-5); m/z: 522 [M+H]$^+$.

Compound 166: N2-(1-(4-cyanobenzyl)piperidin-4-yl)-N5-(1-(4-cyanophenyl)piperidin-4-yl)pyridine-2,5-dicarboxamide. $^1$H nmr ($CDCl_3$) δ 8.92 (1H, d, J 1.0 Hz, pyH-6), 8.22 (1H, d, J 8.0 Hz, pyH-3), 8.16 (1H, dd, J 8.0, 2.0 Hz, pyH-4), 7.94 (1H, d, J 8.5 Hz, BnpipNH), 7.61 (2H, d, J 8.5 Hz, 2H of $CH_2C_6H_4CN$), 7.47 (4H, m, 2H of $CH_2C_6H_4CN$, 2H of $NC_6H_4CN$), 6.88 (2H, d, J 9.0 Hz, 2H of $NC_6H_4CN$), 6.21 (1H, d, J 7.5 Hz, PhpipNH), 4.26 (1H, m, PhpipH-4), 3.99 (1H, m, BnpipH-4), 3.89 (2H, m, 2H of PhpipH-2, H-6), 3.56 (2H, s, $CH_2C_6H_4CN$), 3.08 (2H, t, J 11.5 Hz, 2H of PhpipH-2, H-6), 2.81 (2H, m, 2H of BnpipH-2, H-6), 2.26-2.16 (4H, m, 2H of PhpipH-3, H-5, 2H of BnpipH-2, H-6), 2.02 (2H, m, 2H of BnpipH-3, H-5), 1.70-1.59 (4H, m, 2H of PhpipH-3, H-5, 2H of BnpipH-3, H-5); m/z: 548 [M+H]$^+$.

Compound 167: N-((cis)-4-(4-cyanophenoxy)cyclohexyl)-5-(4-(4-fluorophenoxy)piperidine-1-carbonyl)picolinamide. $^1$H nmr ($CDCl_3$) δ 8.61 (1H, dd, J 2.0, 1.0 Hz, pyH-6), 8.25 (1H, dd, J 8.0, 1.0 Hz, pyH-3), 7.99 (1H, d, J 8.5 Hz, NH), 7.89 (1H, dd, J 8.0, 2.0 Hz, pyH-4), 7.58 (2H, d, J 9.0 Hz, 2H of $C_6H_4CN$), 7.01-6.94 (4H, m, 2H of $C_6H_4CN$, 2H of $C_6H_4F$), 6.89-6.84 (2H, m, 2H of $C_6H_4F$), 4.60 (1H, br s, cHexH-1 or PhOpipH-4), 4.52 (1H, m, cHexH-1 or PhOpipH-4), 4.10 (1H, m, cHexH-4), 3.88 (2H, m, 2H of PhOpipH-2, H-6), 3.64 (1H, m, 1H of PhOpipH-2, H-6), 3.36 (1H, m, 1H of PhOpipH-2, H-6), 2.11-1.90 (12H, m, cHexH-2, H-3, H-5, H-6, PhOpipH-3, H-5); m/z: 543 [M+H]$^+$.

Compound 265: N-(1-(4-cyanobenzyl)piperidin-4-yl)-5-(3-(4-cyanophenoxy)piperidin-1-yl)picolinamide. $^1$H nmr ($CDCl_3$) δ 8.13 (1H, d, J 3.0 Hz, pyH-6), 8.01 (1H, d, J 9.0 Hz, pyH-3), 7.70 (1H, d, J 8.5 Hz, NH), 7.62-7.57 (4H, 4×ArH), 7.45 (2H, d, J 8.0 Hz, 2H of $CH_2C_6H_4CN$ or $OC_6H_4CN$), 7.19 (1H, dd, J 9.0, 3.0 Hz, pyH-4), 6.94 (2H, d, J 9.0 Hz, 2H of $CH_2C_6H_4CN$ or $OC_6H_4CN$), 4.54 (1H, m, PhOpipH-4), 3.98 (1H, m, pipH-4), 3.75 (1H, dd, J 12.5, 3.0 Hz, 1H of PhOpipH-2, H-6), 3.55 (2H, s, $CH_2C_6H_4CN$), 3.49 (1H, m, 1H of PhOpipH-2, H-6), 3.31 (1H, dd, J 13.0, 7.5 Hz, 1H of PhOpipH-2, H-6), 3.23 (1H, m, 1H of PhOpipH-2, H-6), 2.80 (2H, m, 2H of pip), 2.22 (2H, dd, J 11.0, 10.0 Hz, 2H of pip), 2.14 (1H, m, 1H of PhOpip), 1.99 (3H, m, 2H of pip, 1H of PhOpip), 1.79 (2H, m, 2H of PhOpip), 1.62 (2H, m, 2H of pip); m/z: 521 [M+H]$^+$.

Compound 266: 5-(4-(4-chlorobenzoyl)piperidin-1-yl)-N-(1-(4-cyanobenzyl)piperidin-4-yl)picolinamide. $^1$H nmr ($CDCl_3$) δ 8.18 (1H, br s, 1×py), 7.98 (1H, d, J 8.5 Hz, NH or 1×py), 7.98 (2H, d, J 8.5 Hz, 2H of $C_6H_4CN$ or $C_6H_4Cl$), 7.96 (1H, m, NH or 1×py), 7.90 (2H, d, J 8.5 Hz, 2H of $C_6H_4CN$ or $C_6H_4Cl$), 7.75 (2H, d, J 8.5 Hz, 2H of $C_6H_4CN$ or $C_6H_4Cl$), 7.47 (2H, d, J 8.5 Hz, 2H of $C_6H_4CN$ or $C_6H_4Cl$), 7.25 (1H, m, NH or 1×py), 4.26 (2H, s, $CH_2C_6H_4CN$), 4.19 (1H, m, pipH-4 or BzpipH-4), 3.90 (2H, m, 2H of pip or Bzpip), 3.62 (2H, m, 2H of pip or Bzpip), 3.45 (1H, m, pipH-4 or BzpipH-4), 3.07 (2H, m, 2H of pip or Bzpip), 2.81 (2H, m, 2H of pip or Bzpip), 2.20-1.85 (8H, m, 4H of pip, 4H of Bzpip); m/z: 542, 544 [M+H]$^+$.

Compound 267: N-(1-(4-cyanobenzyl)piperidin-4-yl)-5-(1-(4-cyanophenyl)piperidin-4-ylamino)picolinamide. $^1$H nmr ($CDCl_3$) δ 7.99 (1H, d, J 8.5 Hz, pyH-3), 7.89 (1H, d, J 2.0 Hz, pyH-6), 7.65 (1H, d, J 8.5 Hz, NH), 7.66 (2H, d, J 9.0 Hz, 2H of $CH_2C_6H_4CN$ or $NC_6H_4CN$), 7.60 (2H, d, J 8.5 Hz, 2H of $CH_2C_6H_4CN$ or $NC_6H_4CN$), 7.45 (2H, d, J 7.5 Hz, 2H of $CH_2C_6H_4CN$ or $NC_6H_4CN$), 6.94 (1H, dd, J 9.0, 2.5 Hz, pyH-4), 6.89 (2H, d, J 9.0 Hz, 2H of $CH_2C_6H_4CN$ or $NC_6H_4CN$), 3.99 (2H, m, 2H of pip), 3.85 (2H, m, 2H of pip), 3.60 (1H, m, 1H of pip), 3.55 (2H, s, $C\underline{H}_2C_6H_4CN$), 3.08 (2H, t, J 11.5 Hz, 2H of pip), 2.80 (2H, m, 2H of pip), 2.21 (4H, m, 4H of pip), 1.99 (2H, m, 2H of pip), 1.59 (3H, m, 3H of pip); m/z: 520 $[M+H]^+$.

Compound 268: N-(1-(4-cyanobenzyl)piperidin-4-yl)-5-(4-(2-(4-fluorophenyl)propan-2-yl)piperazine-1-carbonyl)picolinamide. $^1$H nmr (CDCl$_3$) δ 8.57 (1H, m, pyH-6), 8.20 (1H, d, J 8.0 Hz, pyH-3), 7.91 (1H, d, J 8.5 Hz, NH), 7.84 (1H, dd, J 8.0, 2.0 Hz, pyH-4), 7.61 (2H, d, J 8.5 Hz, 2H of $C_6H_4CN$), 7.49-7.29 (4H, m, 2H of $C_6H_4CN$, 2H of $C_6H_4F$), 6.98 (2H, t, J 9.0 Hz, 2H of $C_6H_4F$), 4.00 (1H, m, pipH-4), 3.76 (2H, m, 2H of piz), 3.56 (2H, s, $C\underline{H}_2C_6H_4CN$), 3.33 (2H, m, 2H of piz), 2.81 (2H, m, 2H of pip), 2.57 (2H, m, 2H of piz), 2.40 (2H, m, 2H of piz), 2.22 (2H, dd, J 11.0, 9.5 Hz, 2H of pip), 2.01 (2H, m, 2H of pip), 1.63 (2H, m, 2H of pip), 1.33 (6H, s, C(CH$_3$)$_2$); m/z: 569 $[M+H]^+$.

Compound 269: N-(1-(4-cyanobenzyl)piperidin-4-yl)-5-(4-(pyridin-4-yloxy)piperidine-1-carbonyl)picolinamide. $^1$H nmr (CDCl$_3$) δ 8.60 (1H, m, pyH-6), 8.44 (2H, d, J 6.0 Hz, 2H of Opy), 8.24 (1H, d, J 8.0 Hz, pyH-3), 7.92 (1H, m, NH), 7.89 (1H, dd, J 8.0, 2.0 Hz, pyH-4), 7.60 (2H, d, J 8.5 Hz, 2H of $C_6H_4CN$), 7.45 (2H, d, J 8.5 Hz, 2H of $C_6H_4CN$), 6.81 (2H, d, J 6.5 Hz, 2H of Opy), 4.72 (1H, m, PyOpipH-4), 4.05-3.87 (3H, m, pipH-4, 2H of PyOpipH-2, H-6), 3.63 (1H, m, 1H of PyOpipH-2, H-6), 3.56 (2H, s, $CH_2C_6H_4CN$), 3.41 (1H, m, 1H of PyOpipH-2, H-6), 2.81 (2H, m, 2H of pipH-2, H-6), 2.23 (2H, dd, J 11.0, 10.0, 2H of pipH-2, H-6), 2.02 (2H, m, 2H of pipH-3, H-5), 2.00-1.79 (4H, m, 4H of PyOpipH-3, H-5), 1.64 (2H, m, 2H of pipH-3, H-5); m/z: 525 $[M+H]^+$.

Compound 270: (S)—N-(1-(4-cyanobenzyl)piperidin-4-yl)-5-(3-(4-fluorophenoxy)pyrrolidine-1-carbonyl)picolinamide. $^1$H nmr (CDCl$_3$ @ 50° C.) δ 8.72 (1H, br s, pyH-6), 8.22 (1H, d, J 8.0 Hz, pyH-3), 7.98 (1H, m, NH or pyH-4), 7.90 (1H, d, J 8.0 Hz, NH or pyH-4), 7.59 (2H, d, J 8.0 Hz, 2H of $C_6H_4CN$), 7.45 (2H, d, J 8.5 Hz, 2H of $C_6H_4CN$), 6.97 (2H, m, 2H of $C_6H_4F$), 6.80 (2H, m, 2H of $C_6H_4F$), 4.90 (1H, m, pyrrolidineH-3), 4.01 (1H, m, pipH-4), 3.98-3.86 (2H, m, 1H of pyrrolidineH-2, 1H of pyrrolidineH-5), 3.80-3.50 (2H, m, 1H of pyrrolidineH-2, 1H of pyrrolidineH-5), 3.56 (2H, s, C$\underline{H}_2C_6H_4CN$), 2.80 (2H, m, 2H of pipH-2, H-6), 2.29-2.14 (4H, m, 2H of pipH-2, H-6, pyrrolidineH-4), 2.02 (2H, m, 2H of pipH-3, H-5), 1.66 (2H, m, 2H of pipH-3, H-5); $^{19}$F nmr (CDCl$_3$ @ 50° C.) δ −122.3; m/z: 528 $[M+H]^+$.

Compound 271: N-(1-(4-cyanobenzyl)piperidin-4-yl)-5-(4-(2,4-difluorobenzoyl)piperidine-1-carbonyl)picolinamide. $^1$H nmr (CDCl$_3$) δ 8.58 (1H, m, pyH-6), 8.23 (1H, d, J 8.0 Hz, pyH-3), 7.94-7.84 (3H, m, NH, pyH-4, 1H of BzH-5 or BzH-6), 7.61 (2H, d, J 8.5 Hz, 2H of $C_6H_4CN$), 7.45 (2H, d, J 8.5 Hz, 2H of $C_6H_4CN$), 6.99 (1H, m, BzH-5 or BzH-6), 6.89 (ddd, J 11.0, 8.5, 2.5 Hz, BzH-3), 4.65 (1H, m, 1H of BzpipH-2, H-6), 4.00 (1H, m, pipH-4), 3.75 (1H, m, 1H of BzpipH-2, H-6), 3.56 (2H, s, C$\underline{H}_2C_6H_4CN$), 3.41 (1H, m, BzpipH-4), 3.20 (1H, m, 1H of BzpipH-2, H-6), 3.07 (1H, m, 1H of BzpipH-2, H-6), 2.81 (2H, m, 2H of pipH-2, H-6), 2.22 (2H, d, J 11.0, 10.0 Hz, 2H of pipH-2, H-6), 2.03 (3H, m, 2H of pipH-3, H-5, 1H of BzpipH-3, H-5), 1.86 (1H, m, 1H of BzpipH-3, H-5), 1.75-1.58 (4H, m, 2H of pipH-3, H-5, 2H of BzpipH-3, H-5); m/z: 572 $[M+H]^+$.

Compound 272: 5-(4-(4-fluorobenzoyl)piperidine-1-carbonyl)-N-(6-(4-fluorophenoxy)pyridin-3-yl)picolinamide. $^1$H nmr (CDCl$_3$) δ 9.91 (1H, s, 1×NH or ArH), 8.68 (1H, m, 1×NH or ArH), 8.42-8.33 (3H, m, NH, 2×ArH or 3×ArH), 8.01-7.95 (3H, m, NH, 2×ArH or 3×ArH), 7.20-7.08 (5H, m, NH, 4×ArH or 5×ArH), 6.97 (2H, d, J 9.0 Hz, 2×ArH), 4.67 (1H, m, 1H of BzpipH-2, H-4, H-6), 3.76 (1H, m, 1H of BzpipH-2, H-4, H-6), 3.49 (1H, m, 1H of BzpipH-2, H-4, H-6), 3.26 (1H, m, 1H of BzpipH-2, H-4, H-6), 3.14 (1H, m, 1H of BzpipH-2, H-4, H-6), 2.04 (1H, m, 1H of BzpipH-3, H-5), 1.84 (3H, m, 3H of BzpipH-3, H-5); m/z: 543 $[M+H]^+$.

Compound 273: 5-(4-(4-fluorophenoxy)piperidine-1-carbonyl)-N-(6-(4-fluorophenoxy)pyridin-3-yl)picolinamide. $^1$H nmr (CDCl$_3$) δ 9.90 (1H, s, NH or 1×ArH), 8.68 (1H, m, 1×ArH), 8.41-8.33 (3H, NH, 2×ArH or 3×ArH), 7.96 (1H, dd, J 8.0, 2.0 Hz, 1×ArH), 7.11-7.08 (4H, m, NH, 3×ArH or 4×ArH), 7.02-6.95 (3H, NH, 2×ArH or 3×ArH), 6.89-6.85 (2H, m, 2×ArH), 4.54 (1H, m, PhOpipH-4), 3.91 (2H, m, 2H of PhOpipH-2, H-6), 3.66 (1H, m, 1H of PhOpipH-2, H-6), 3.39 (1H, m, 1H of BzpipH-2, H-6), 2.00 (2H, m, 2H of PhOpipH-3, H-5), 1.86 (2H, m, 2H of PhOpipH-3, H-5); m/z: 531 $[M+H]^+$.

Compound 274: N-(1-(4-cyanobenzyl)piperidin-4-yl)-5-(3-(4-methoxyphenoxy)piperidine-1-carbonyl)picolinamide. $^1$H nmr (CDCl$_3$) δ 8.60 (1H, s, pyH-6), 8.23 and 8.11 (1H, 2m, pyH-3), 7.87 (2H, m, NH, pyH-4), 7.61 (2H, d, J 8.0 Hz, 2H of $C_6H_4CN$), 7.45 (2H, d, J 8.0 Hz, 2H of $C_6H_4CN$), 6.92-6.73 (4H, m, 4H of $C_6H_4OCH_3$), 4.24 (2H, m, 1H of PhOpipH-2, H-6, PhOpipH-3), 3.99 (1H, m, pipH-4), 3.75 (3H, s, OCH$_3$), 3.67 (1H, m, 1H of PhOpipH-2, H-6), 3.56 (2H, s, C$\underline{H}_2C_6H_4CN$), 3.43 (1H, m, 1H of PhOpipH-2, H-6), 3.29 (1H, m, 1H of PhOpipH-2, H-6), 2.81 (2H, m, 2H of pipH-2, H-6), 2.22 (2H, t, J 11.0 Hz, 2H of pipH-2, H-6), 2.01 (4H, m, 2H of pipH-3, H-5, 2H of PhOpipH-4, H-5), 1.82 (1H, m, 1H of PhOpipH-4, H-5), 1.65 (3H, m, 2H of pipH-3, H-5, 1H of PhOpipH-4, H-5); m/z: 555 $[M+H]^+$.

Compound 275: N-(1-(4-cyanobenzyl)piperidin-4-yl)-5-(1-(4-methoxyphenyl)piperidin-4-ylamino)picolinamide. $^1$H nmr (CDCl$_3$) δ 7.98 (1H, d, J 8.5 Hz, pyH-3), 7.88 (1H, d, J 2.0 Hz, pyH-6), 7.68 (1H, d, J 8.5 Hz, NH), 7.61 (2H, d, J 8.5 Hz, 2H of $C_6H_4CN$), 7.47 (2H, d, J 7.5 Hz, 2H of $C_6H_4CN$), 6.93 (3H, m, 2H of $C_6H_4OCH_3$, pyH-4), 6.84 (2H, d, J 9.0 Hz, 2H of $C_6H_4OCH_3$), 4.03-3.97 (2H, m, 2×pipH-4), 3.77 (3H, s, OCH$_3$), 3.58 (2H, s, C$\underline{H}_2C_6H_4CN$), 3.49 (4H, m, 2×2H of pipH-2, H-6), 2.83 (4H, m, 2×2H of pipH-2, H-6), 2.28-2.15 (4H, m, 2×2H of pipH-3, H-5), 2.00 (2H, m, 2H of pipH-3, H-5), 1.66 (2H, m, 2H of pipH-3, H-5); m/z: 525 $[M+H]^+$.

Compound 276: N-(1-(4-cyanobenzyl)piperidin-4-yl)-5-(1-(4-fluorophenyl)piperidin-4-ylamino)picolinamide. $^1$H nmr (CDCl$_3$) δ 8.17 (1H, d, J 3.0 Hz, pyH-6), 8.02 (1H, d, J 8.5 Hz, pyH-3), 7.73 (1H, d, J 8.5 Hz, CONH), 7.61 (2H, d, J 8.0 Hz, 2H of $C_6H_4CN$), 7.45 (2H, d, J 8.5 Hz, 2H of $C_6H_4CN$), 7.22 (1H, dd, J 9.0, 3.0 Hz, pyH-4), 6.89 (2H, t, J 8.5 Hz, 2H of $C_6H_4F$), 6.56 (2H, dd, J 9.0, 4.5 Hz, 2H of $C_6H_4F$), 3.98 (1H, m, pipH-4), 3.79 (2H, m, 2H of Phpip), 3.55 (2H, s, C$\underline{H}_2C_6H_4CN$), 3.44 (1H, m, PhpipH-4), 3.04 (2H, m, 2H of Phpip), 2.80 (2H, m, 2H of pipH-2, H-6), 2.21 (4H, m, 2H of Phpip, 2H of pipH-2, H-6), 1.99 (2H, m, 2H of pipH-3, H-5), 1.76-1.47 (4H, m 2H of pipH-3, H-5, 2H of Phpip); m/z: 513 $[M+H]^+$.

Compound 277: N-(1-(4-cyanobenzyl)piperidin-4-yl)-5-(3-(3-methoxyphenoxy)piperidine-1-carbonyl)picolinamide. $^1$H nmr (CDCl$_3$ @ 50° C.) δ 8.58 (1H, s, pyH-6), 8.12 (1H, br s, pyH-3), 7.87 (1H, d, J 8.5 Hz, NH), 7.83 (1H, m, pyH-4), 7.60 (2H, d, J 8.0 Hz, 2H of $C_6H_4CN$), 7.45 (2H, d, J 8.0 Hz, 2H of $C_6H_4CN$), 7.12 (1H, t, J 7.5 Hz, 1H of $C_6\underline{H}_4OCH_3$), 6.49 (1H, d, J 8.5 Hz, 1H of $C_6\underline{H}_4OCH_3$), 6.40 (2H, m, 2H of $C_6\underline{H}_4OCH_3$), 4.32 (1H, m, PhOpipH-3), 4.00 (1H, m, pipH-4), 3.76 (3H, s, OCH$_3$), 3.59 (1H, m, 1H of PhOpipH-2), 3.56 (2H, s, C$\underline{H}_2C_6H_4CN$), 3.37 (2H, m, PhOpipH-6), 2.80 (3H, m, 2H of pipH-2, H-6, 1H of PhOpipH-2), 2.25 (2H, t, J 11.0 Hz, 2H of pipH-2, H-6), 1.98 (4H, m, 2H of pipH-3, H-5, 2H of PhOpipH-4, H-5), 1.71-1.59 (4H, m, 2H of pipH-3, H-5, 2H of PhOpipH-4, H-5); m/z: 554 [M+H]$^+$.

Compound 278: (R)—N-(1-(4-cyanobenzyl)piperidin-4-yl)-5-(3-(4-fluorophenoxy)pyrrolidine-1-carbonyl)picolinamide. $^1$H nmr (CDCl$_3$ @ 50° C.) δ 8.72 (1H, br s, pyH-6), 8.22 (1H, d, J 7.5 Hz, pyH-3 or H-4), 7.98 (1H, br s, NH), 7.90 (1H, d, J 8.0 Hz, pyH-3 or H-4), 7.59 (2H, d, J 8.5 Hz, 2H of C$_6$H$_4$CN), 7.45 (2H, d, J 8.5 Hz, 2H of C$_6$H$_4$CN), 6.98 (2H, m, 2H of C$_6$H$_4$F), 6.90-6.78 (2H, m, 2H of C$_6$H$_4$F), 4.92 (1H, m, pyrrolidineH-3), 4.01 (1H, m, pipH-4), 3.98-3.85 (2H, m, 1H of pyrrolidineH-2, 1H of pyrrolidineH-5), 3.78-3.50 (2H, m, 1H of pyrrolidineH-2, 1H of pyrrolidineH-5), 3.56 (2H, s, C$\underline{H}_2$C$_6$H$_4$CN), 2.80 (2H, m, 2H of pipH-2, H-6), 2.25 (2H, t, J 11.5 Hz, 2H of pipH-2, H-6), 2.16 (2H, m, pyrrolidineH-4), 2.02 (2H, m, 2H of pipH-3, H-5), 1.65 (2H, m, 2H of pipH-3, H-5); m/z: 528 [M+H]$^+$.

Compound 279: N-(1-(4-cyanobenzyl)piperidin-4-yl)-5-((trans)-4-(4-cyanophenoxy)-3-fluoropiperidine-1-carbonyl)picolinamide. $^1$H nmr (CDCl$_3$) δ 8.62 (1H, m, pyH-6), 8.26 (1H, d, J 8.0 Hz, pyH-3), 7.92 (2H, m, NH, pyH-4), 7.63 (2H, d, J 9.0 Hz, 2H of OC$_6$H$_4$CN), 7.61 (2H, d, J 8.0 Hz, 2H of CH$_2$C$_6$H$_4$CN), 7.46 (2H, d, J 8.5 Hz, 2H of CH$_2$C$_6$H$_4$CN), 7.01 (2H, d, J 9.0 Hz, 2H of OC$_6$H$_4$CN), 4.75 (1H, m, PhOpipH-4), 4.75-4.03 (2H, m, 2H of PhOpipH-2, H-3, H-6), 4.01 (1H, m, pipH-4), 3.78 (1H, m, 1H of PhOpipH-2, H-3, H-6), 3.68-3.37 (2H, m, 2H of PhOpipH-2, H-3, H-6), 3.57 (2H, s, C$\underline{H}_2$C$_6$H$_4$CN), 2.82 (2H, m, 2H of pipH-2, H-6), 2.23 (2H, dd, J 11.0, 10.0 Hz, 2H of pipH-2, H-6), 2.02 (2H, m, 2H of pipH-3, H-5), 1.63 (4H, m, 2H of pipH-3, H-5, 2H of PhOpipH-6); m/z: 567 [M+H]$^+$.

Compound 280: N-(1-(4-cyanobenzyl)piperidin-4-yl)-5-((1R,3r,5S)-3-(4-cyanophenoxy)-8-azabicyclo[3.2.1]octane-8-carbonyl)picolinamide. $^1$H nmr (CDCl$_3$) δ 8.69 (1H, d, J 1.5 Hz, pyH-6), 8.25 (1H, d, J 8.0 Hz, pyH-3), 7.97 (1H, dd, J 8.0, 2.0 Hz, pyH-4), 7.92 (1H, d, J 8.5 Hz, NH), 7.61 (2H, d, J 8.5 Hz, 2H of CH$_2$C$_6$H$_4$CN), 7.57 (2H, d, J 9.0 Hz, 2H of OC$_6$H$_4$CN), 7.45 (2H, d, J 8.0 Hz, 2H of CH$_2$C$_6$H$_4$CN), 6.93 (2H, d, J 9.0 Hz, 2H of OC$_6$H$_4$CN), 4.67 (1H, m, 1H of PhOpipH-2, H-4, H-6), 4.82 (1H, m, 1H of PhOpipH-2, H-4, H-6), 4.13 (1H, m 1H of PhOpipH-2, H-4, H-6), 4.01 (1H, m pipH-4), 3.56 (2H, s, C$\underline{H}_2$C$_6$H$_4$CN), 2.81 (2H, m, 2H of pipH-2, H-6), 2.22 (2H, t, J 11.5 Hz, 2H of pipH-2, H-6), 2.17 (4H, m, 4H of PhOpip), 2.01 (2H, m, 2H of pipH-3, H-5), 1.86 (2H, d, J 7.5 Hz, 2H of PhOpip), 1.68 (4H, m, 2H of pipH-3, H-5, 2H of PhOpip); m/z: 575 [M+H]$^+$.

Compound 281: N-(1-(4-cyanobenzyl)piperidin-4-yl)-5-(4-(3,4-difluorobenzoyl)piperidine-1-carbonyl)picolinamide. $^1$H nmr (CDCl$_3$) δ 8.59 (1H, m, pyH-6), 8.23 (1H, d, J 8.0 Hz, pyH-3), 7.94-7.84 (3H, NH, pyH-4, BzH-5 or H-6), 7.61 (2H, d, J 8.5 Hz, 2H of C$_6$H$_4$CN), 7.46 (2H, d, J 8.5 Hz, 2H of C$_6$H$_4$CN), 6.99 (1H, m, BzH-5 or H-6), 6.89 (1H, ddd, J 11.0, 9.0, 2.0 Hz, BzH-2), 4.63 (1H, m, 1H of BzpipH-2, H-6), 4.01 (1H, m, pipH-4), 3.71 (1H, m, 1H of BzpipH-2, H-6), 3.56 (2H, s, C$\underline{H}_2$C$_6$H$_4$CN), 3.41 (1H, m, BzpipH-4), 3.20 (1H, m 1H of BzpipH-2, H-6), 3.08 (1H, m, BzpipH-2, H-6), 2.81 (2H, m, 2H of pipH-2, H-6), 2.23 (2H, dd, 11.5, 10.0 Hz, pipH-2, H-6), 2.12-1.82 (4H, m, 2H of pipH-3, H-5, 2H of BzpipH-3, H-5), 1.78-1.59 (4H, m, 2H of pipH-3, H-5, 2H of BzpipH-3, H-5); m/z: 572 [M+H]$^+$.

Compound 282: N-(1-(4-cyanobenzyl)piperidin-4-yl)-5-(4-(2,4-difluorophenoxy)piperidine-1-carbonyl)picolinamide. $^1$H nmr (CDCl$_3$) δ 8.60 (1H, m, pyH-6), 8.25 (1H, d, J 8.0 Hz, pyH-3), 7.92 (1H, d, J 9.0 Hz, NH), 7.89 (1H, dd, J 8.0, 2.0 Hz, pyH-4), 7.61 (2H, d, J 8.5 Hz, 2H of C$_6$H$_4$CN), 7.46 (2H, d, J 8.5 Hz, 2H of C$_6$H$_4$CN), 6.98 (1H, td, J 9.0, 5.5 Hz, PhH-5), 6.87 (1H, ddd, J 11.0, 8.5, 3.0 Hz, PhH-2), 6.80 (1H, m, PhH-6), 4.47 (1H, m, PhOpipH-4), 4.00 (1H, m, pipH-4), 3.90 (2H, m, 2H of PhOpipH-2, H-6), 3.68 (1H, m, 1H of PhOpipH-2, H-6), 3.56 (2H, s, C$\underline{H}_2$C$_6$H$_4$CN), 3.49 (1H, m, 1H of PhOpipH-2, H-6), 2.82 (2H, m, 2H of pipH-2, H-6), 2.23 (2H, t, J 11.0 Hz, 2H of pipH-2, H-6), 2.03-1.96 (4H, m, 2H of pipH-3, H-5, 2H of PhOpipH-3, H-5), 1.85 (2H, m, 2H of PhOpipH-3, H-5), 1.65 (2H, m, 2H of pipH-3, H-5); m/z: 560 [M+H]$^+$.

Compound 283: N-(1-(4-cyanobenzyl)piperidin-4-yl)-5-(4-(pyridin-3-yloxy)piperidine-1-carbonyl)picolinamide. $^1$H nmr (CDCl$_3$) δ 8.61 (1H, m, pyH-6), 8.33 (1H, m, OpyH-2), 8.26-8.23 (2H, m, pyH-3, 1H of OpyH), 7.92 (1H, d, J 9.5 Hz, NH), 7.89 (1H, dd, J 8.5, 2.0 Hz, pyH-4), 7.61 (2H, d, J 8.5 Hz, 2H of C$_6$H$_4$CN), 7.45 (2H, d, J 8.0 Hz, 2H of C$_6$H$_4$CN), 7.23 (2H, m, 2H of OpyH), 4.66 (1H, m pyOpipH-4), 4.01 (1H, m, pipH-4), 3.91 (2H, m, 2H of pyOpipH-2, H-6), 3.66 (1H, m, 1H of pyOpipH-2, H-6), 3.40 (1H, m, 1H of pyOpipH-2, H-6), 2.81 (2H, m, 2H of pipH-2, H-6), 2.22 (2H, dd, J 11.0, 10.0 Hz, 2H of pipH-2, H-6), 2.04-1.88 (6H, m, 2H of pipH-3, H-5, 4H of pyOpipH-3, H-5), 3.56 (2H, s, C$\underline{H}_2$C$_6$H$_4$CN), 1.64 (2H, m, 2H of pipH-3, H-5); m/z: 525 [M+H]$^+$.

Compound 284: ethyl 4-(1-(6-(1-(4-cyanobenzyl)piperidin-4-ylcarbamoyl)nicotinoyl)piperidin-4-yloxy)benzoate. $^1$H nmr (CDCl$_3$) δ 8.60 (1H, m, pyH-6), 8.24 (1H, d, J 8.0 Hz, pyH-3), 7.99 (2H, d, J 8.5 Hz, 2H of C$_6$H$_4$CO$_2$Et), 7.92 (1H, d, J 9.5 Hz, NH), 7.89 (1H, dd, J 8.5, 2.0 Hz, pyH-4), 7.61 (2H, d, J 8.5 Hz, 2H of C$_6$H$_4$CN), 7.46 (2H, d, J 8.0 Hz, 2H of C$_6$H$_4$CN), 6.92 (2H, d, J 9.0 Hz, 2H of C$_6$H$_4$CO$_2$Et), 4.72 (1H, m, PhOpipH-4), 4.34 (2H, q, J 7.0 Hz, OC$\underline{H}_2$CH$_3$), 4.02-3.87 (3H, m, pipH-4, 2H of PhOpipH-2, H-6), 3.64 (1H, m, 1H of PhOpipH-2, H-6), 3.57 (2H, s, C$\underline{H}_2$C$_6$H$_4$CN), 3.55 (1H, m, 1H of PhOpipH-2, H-6), 2.83 (2H, m, 2H of pipH-2, H-6), 2.24 (2H, t, J 10.5 Hz, pipH-2, H-6), 2.03-1.88 (6H, m, pipH-3, H-5, 4H of PhOpipH-3, H-5), 1.67 (2H, m, 2H of pipH-3, H-5), 1.37 (3H, t, J 7.0 Hz, OCH$_2$C$\underline{H}_3$); m/z: 597 [M+H]$^+$.

Compound 285: 5-(4-(4-cyanobenzyl)piperazine-1-carbonyl)-N-(1-(4-methoxybenzyl)piperidin-4-yl)picolinamide. $^1$H nmr (CDCl$_3$) δ 8.58 (1H, m, pyH-6), 8.22 (1H, d, J 8.0 Hz, pyH-3), 7.90 (1H, d, J 9.0 Hz, NH), 7.86 (1H, dd, J 8.0, 2.0 Hz, pyH-4), 7.62 (2H, d, J 8.0 Hz, 2H of C$_6$H$_4$CN), 7.45 (2H, d, J 8.0 Hz, 2H of C$_6$H$_4$CN), 7.25 (2H, d, J 8.0 Hz, 2H of C$_6$H$_4$OCH$_3$), 6.86 (2H, d, J 8.5 Hz, 2H of C$_6$H$_4$OCH$_3$), 4.00 (1H, m, pipH-4), 3.80 (5H, m, 2H of piz, OCH$_3$), 3.59 (2H, s, 1×CH$_2$Ar), 3.52 (2H, s, 1×CH$_2$Ar), 3.41 (2H, m, 2H of piz), 2.90 (2H, m, 2H of pipH-2, H-6), 2.54 (2H, m, 2H of piz), 2.41 (2H, m, 2H of piz), 2.22 (2H, t, J 11.0 Hz, 2H of pipH-2, H-6), 2.01 (2H, m, 2H of pipH-3, H-5), 1.67 (2H, m, 2H of pipH-3, H-5); m/z: 553 [M+H]$^+$.

Compound 286: 5-(4-(4-cyano-2-methoxyphenoxy)piperidin-1-yl)-N-(1-(4-cyanobenzyl)piperidin-4-yl)picolinamide. $^1$H nmr (CDCl$_3$) δ 8.18 (1H, d, J 2.5 Hz, pyH-6), 8.02 (1H, d, J 9.0 Hz, pyH-3), 7.73 (1H, d, 8.5 Hz, CONH), 7.61 (2H, d, J 8.5 Hz, 2H of C$_6$H$_4$CN), 7.46 (2H, d, J 8.0 Hz, 2H of C$_6$H$_4$CN), 7.26-7.21 (2H, m, pyH-4, C$_6$H$_3$(OCH$_3$)CNH-5), 7.11 (1H, d, J 1.5 Hz, C$_6$H$_3$(OCH$_3$)CNH-3), 6.95 (1H, d, J 8.5 Hz, C$_6$H$_3$(OCH$_3$)CNH-6), 4.60 (1H, m, PhOpipH-4), 3.99 (1H, m, pipH-4), 3.86 (3H, s, OCH$_3$), 3.69-3.61 (4H, m, 2H of PhOpipH-2, H-6, C$\underline{H}_2$C$_6$H$_4$CN), 3.30 (2H, m, 2H of PhOpipH-2, H-6), 2.84 (2H, m, 2H of pipH-2, H-6), 2.26 (2H, dd, J 11.0, 10.0 Hz, 2H of pipH-2, H-6), 2.14-1.96 (6H, m, 2H of pipH-3, H-5, 4H of PhOpipH-3, H-5), 1.65 (2H, m, 2H of pipH-3, H-5); m/z: 552 [M+H]$^+$.

Compound 287: N-(1-(3,5-difluorobenzyl)piperidin-4-yl)-5-(4-(4-methoxybenzoyl)piperidine-1-carbonyl)picolinamide. $^1$H nmr (CDCl$_3$) δ 8.60 (1H, d, J 2.0 Hz, pyH-6), 8.23 (1H, d, J 8.0 Hz, pyH-3), 7.94 (2H, d, J 9.0 Hz, 2H of C$_6$H$_4$OCH$_3$), 7.92 (1H, m, NH), 7.89 (1H, dd, J 8.0, 2.0 Hz, pyH-4), 6.95 (2H, d, J 9.0 Hz, 2H of C$_6$H$_4$OCH$_3$), 6.88 (2H, d, J 6.0 Hz, C$_6$H$_3$F$_2$-2, H-6), 6.68 (1H, tt, J 9.0, 2.0 Hz, C$_6$H$_3$F$_2$H-4), 4.67 (1H, m, 1H of BzpipH-2, H-6), 4.01 (1H, m, pipH-4), 3.87 (3H, s, OCH$_3$), 3.77 (1H, m, 1H of BzpipH-2, H-6), 3.54 (1H, m, BzpipH-4), 3.49 (2H, s, C$\underline{H}_2$C$_6$H$_3$F$_2$), 3.17 (2H, m, 2H of BzpipH-2, H-6), 2.83 (2H, m, 2H of pipH-2, H-6), 2.23 (2H, dd, J 11.0, 9.5 Hz, 2H of pipH-2, H-6), 2.02 (3H, m, 2H of pipH-3, H-5, 1H of BzpipH-3, H-5), 1.83 (3H, m, 3H of BzpipH-3, H-5), 1.66 (2H, m, 2H of pipH-3, H-5); m/z: 577 [M+H]$^+$.

Compound 288: N-(1-(3,5-difluorobenzyl)piperidin-4-yl)-5-(4-(4-fluorobenzoyl)piperidine-1-carbonyl)picolinamide. $^1$H nmr (CDCl$_3$) δ 8.54 (1H, m, pyH-6), 8.17 (1H, d, J 8.0 Hz, pyH-3), 7.91 (2H, dd, J 9.0, 5.0 Hz, 2H of C$_6$H$_4$F), 7.87 (1H, m, NH), 7.82 (1H, dd, J 8.0, 2.0 Hz, pyH-4), 7.10 (2H, t, J 8.5 Hz, 2H of C$_6$H$_4$F), 6.82 (2H, d, J 6.5 Hz, C$_6$H$_3$F$_2$H-2 and H-6), 6.62 (1H, tt, J 9.0, 2.0 Hz, C$_6$H$_3$F$_2$H-4), 4.60 (1H, m, 1H of BzpipH-2, H-6), 4.00 (1H, m, pipH-4), 3.69 (1H, m, 1H of BzpipH-2, H-6), 3.47 (1H, m, BzpipH-4), 3.44 (2H, s, C$\underline{H}_2$C$_6$H$_3$F$_2$), 3.11 (2H, m, 2H of BzpipH-2, H-6), 2.78 (2H, m, 2H of pipH-2, H-6), 2.17 (2H, dd, J 11.0, 9.5 Hz, 2H of pipH-2, H-6), 1.95 (2H, m, 2H of pipH-3, H-5), 1.76 (4H, m, 4H of BzpipH-3, H-5), 1.60 (2H, m, 2H of pipH-3, H-5); $^{19}$F nmr (CDCl$_3$) δ −104.4, −110.5; m/z: 565 [M+H]$^+$.

Compound 289: 5-(4-(4-cyanophenoxy)piperidine-1-carbonyl)-N-(1-(3,5-difluorobenzyl)piperidin-4-yl)picolinamide. $^1$H nmr (CDCl$_3$) δ 8.60 (1H, m, pyH-6), 8.24 (1H, d, J 8.0 Hz, pyH-3), 7.91 (1H, d, J 8.0 Hz, NH), 7.89 (1H, dd, J 8.0, 2.0 Hz, pyH-4), 7.59 (2H, d, J 9.0 Hz, 2H of C$_6$H$_4$CN), 9.69 (2H, d, J 9.0 Hz, 2H of C$_6$H$_4$CN), 6.87 (2H, d, J 8.0 Hz, C$_6$H$_3$F$_2$H-2, H-6), 6.68 (1H, m, C$_6$H$_3$F$_2$H-4), 4.70 (1H, m, PhOpipH-4), 4.00 (1H, m, pipH-4), 3.89 (2H, m, 2H of PhOpipH-2, H-6), 3.65 (1H, m, 1H of PhOpipH-2, H-6), 3.49 (2H, s, C$\underline{H}_2$C$_6$H$_3$F$_2$), 3.41 (1H, m, 1H of PhOpipH-2, H-6), 2.83 (2H, m, 2H of pipH-2, H-6), 2.22 (2H, t, J 11.5 Hz, 2H of pipH-2, H-6), 2.03-1.1.83 (6H, m, 2H of pipH-3, H-5, 4H of PhOpipH-3, H-5), 1.65 (2H, m, 2H of pipH-3, H-5); $^{19}$F nmr (CDCl$_3$) δ −110.5; m/z: 560 [M+H]$^+$.

Compound 290: tert-butyl 3-(2-(1-(4-cyanobenzyl)piperidin-4-ylcarbamoyl)-5-(4-(4-fluorobenzyl)piperazine-1-carbonyl)pyridin-3-yl)propylcarbamate. $^1$H nmr (CDCl$_3$) δ 8.42 (1H, d, J 1.5 Hz, pyH-6), 8.03 (1H, d, J 8.5 Hz, PyCONH), 7.61 (3H, m, pyH-4, 2H of C$_6$H$_4$CN), 7.45 (2H, d, J 8.5 Hz, 2H of C$_6$H$_4$CN), 7.27 (2H, dd, J 8.6, 6.0 Hz, 2H of C$_6$H$_4$F), 7.01 (2H, t, J 8.5 Hz, 2H of C$_6$H$_4$F), 5.02 (1H, m, NHCO$_2$), 3.93 (1H, m, pipH-4), 3.79 (2H, m, 2H of piz), 3.56 (2H, s, C$\underline{H}_2$C$_6$H$_4$CN or C$\underline{H}_2$C$_6$H$_4$F), 3.50 (2H, s, C$\underline{H}_2$C$_6$H$_4$CN or C$\underline{H}_2$C$_6$H$_4$F), 3.40 (2H, m, 2H of piz), 3.17 (4H, m, PyC$\underline{H}_2$C$\underline{H}_2$CH$_2$NH), 2.81 (2H, m, 2H of pipH-2, H-6), 2.79 (2H, m, 2H of piz), 2.53 (2H, m, 2H of piz), 2.21 (2H, t, J 10.5 Hz, 2H of pipH-2, H-6), 2.00 (2H, m, 2H of pipH-3, H-5), 1.84 (2H, m, PyCH$_2$CH$_2$CH$_2$NH), 1.66 (2H, m, 2H of pipH-3, H-5), 1.43 (9H, s, C(CH$_3$)$_3$); m/z: 699 [M+H]$^+$.

Compound 291: N-(1-(4-cyanobenzyl)piperidin-4-yl)-3-(5,21-dioxo-25-((3aS,4S,6aR)-2-oxohexahydro-1H-thieno[3,4-d]imidazol-4-yl)-8,11,14,17-tetraoxa-4,20-diazapentacosyl)-5-(4-fluorobenzyl)piperazine-1-carbonyl)picolinamide (as its trifluoroacetate salt). m/z: 1072 [M+H]$^+$.

Compound 292: N-(1-(3,5-difluorobenzyl)piperidin-4-yl)-5-(S)-3-(4-fluorophenoxy)pyrrolidine-1-carbonyl)picolinamide. m/z: 539 [M+H]$^+$ (found [M+H]$^+$, 539.2314, C$_{29}$H$_{29}$F$_3$N$_4$O$_3$ requires [M+H]$^+$ 539.2265).

Compound 293: N-(1-(3,5-difluorobenzyl)piperidin-4-yl)-5-(4-(p-tolyloxy)piperidine-1-carbonyl)picolinamide. $^1$H nmr (CDCl$_3$) δ 8.60 (1H, m, pyH-6), 8.24 (1H, d, J 8.0 Hz, pyH-3), 7.93 (1H, d, J 8.5 Hz, NH), 7.88 (1H, dd, J 8.0, 2.0 Hz, pyH-4), 7.09 (2H, d, J 9.0 Hz, 2H of C$_6$H$_4$CH$_3$), 6.88 (2H, d, J 6.5 Hz, C$_6$H$_3$F$_2$-2, H-6), 6.82 (2H, d, J 8.5 Hz, 2H of C$_6$H$_4$CH$_3$), 6.80 (1H, tt, J 9.0, 2.0 Hz, C$_6$H$_3$F$_2$H-4), 4.56 (1H, m, PhOpipH-4), 4.01 (1H, m, pipH-4), 3.89 (2H, m, 2H of PhOpipH-2, H-6), 3.64 (1H, m, 1H of PhOpipH-2, H-6), 3.49 (2H, s, CH$_2$C$_6$H$_3$F$_2$), 2.83 (2H, m, 2H of pipH-2, H-6), 2.29 (3H, s, ArCH3), 2.22 (2H, t, J 11.0 Hz, 2H of pipH-2, H-6), 2.04-1.84 (6H, m, 2H of pipH-3, H-5, PhOpipH-3, H-5), 1.68 (2H, m, 2H of pipH-3, H-5); m/z: 550 [M+H]$^+$.

Compound 294: N-(1-(3,5-difluorobenzyl)piperidin-4-yl)-5-(4-(4-(trifluoromethyl)phenoxy)piperidine-1-carbonyl)picolinamide. $^1$H nmr (CDCl$_3$) δ 8.61 (1H, m, pyH-6), 8.24 (1H, d, J 8.0 Hz, pyH-3), 7.93 (1H, m, NH), 7.88 (1H, dd, J 8.0, 2.0 Hz, pyH-4), 7.55 (2H, d, J 8.5 Hz, 2H of C$_6$H$_4$CF$_3$), 6.98 (2H, d, J 8.5 Hz, 2H of C$_6$H$_4$CF$_3$), 6.88 (2H, d, J 6.0 Hz, C$_6$H$_3$F$_2$-2, H-6), 6.68 (1H, tt, J 9.0, 2.0 Hz, C$_6$H$_3$F$_2$H-4), 4.70 (1H, m, PhOpipH-4), 4.01 (1H, m, pipH-4), 3.87 (2H, m, 2H of PhOpipH-2, H-6), 3.65 (1H, m, 1H of PhOpipH-2, H-6), 3.49 (2H, s, CH$_2$C$_6$H$_3$F$_2$), 3.35 (1H, m, 1H of PhOpipH-2, H-6), 2.82 (2H, m, 2H of pipH-2, H-6), 2.22 (2H, dd, J 11.5, 10.0 Hz, 2H of pipH-2, H-6), 2.12-1.84 (6H, m, 2H of pipH-3, H-5, PhOpipH-3, H-5), 1.65 (2H, m, 2H of pipH-3, H-5); m/z: 603 [M+H]$^+$.

Compound 295: N-(1-(3,5-difluorobenzyl)piperidin-4-yl)-5-(4-(4-fluorophenoxy)piperidine-1-carbonyl)picolinamide. $^1$H nmr (CDCl$_3$) δ 8.60 (1H, m, pyH-6), 8.28 (1H, d, J 8.0 Hz, pyH-3), 7.92 (1H, m, NH), 7.88 (1H, dd, J 8.0, 2.0 Hz, pyH-4), 6.98 (2H, t, J 8.0 Hz, 2H of C$_6$H$_4$F), 6.89-6.84 (4H, m, 2H of C$_6$H$_4$F, C$_6$H$_3$F$_2$-2, H-6), 6.68 (1H, br t, J 8.5 Hz, C$_6$H$_3$F$_2$H-4), 4.52 (1H, m, PhOpipH-4), 4.01 (1H, m, pipH-4), 3.89 (2H, m, 2H of PhOpipH-2, H-6), 3.64 (1H, m, 1H of PhOpipH-2, H-6), 3.49 (2H, s, CH$_2$C$_6$H$_3$F$_2$), 3.36 (1H, m, 1H of PhOpipH-2, H-6), 2.83 (2H, m, 2H of pipH-2, H-6), 2.22 (2H, t, J 11.0 Hz, 2H of pipH-2, H-6), 2.04-1.85 (6H, m, 2H of pipH-3, H-5, PhOpipH-3, H-5), 1.64 (2H, m, 2H of pipH-3, H-5); m/z: 525 [M+H]$^+$.

Compound 296: N-(1-(3,5-difluorobenzyl)piperidin-4-yl)-5-(4-(4-methoxyphenoxy)piperidine-1-carbonyl)picolinamide. $^1$H nmr (CDCl$_3$) δ 8.60 (1H, m, pyH-6), 8.24 (1H, d, J 8.0 Hz, pyH-3), 7.93 (1H, d, J 8.0 Hz, NH), 7.88 (1H, dd, J 8.0, 2.0 Hz, pyH-4), 6.90-6.82 (6H, m, C$_6$H$_4$OCH$_3$, C$_6$H$_3$F$_2$-2, H-6), 6.69 (1H, tt, J 9.0, 2.0 Hz, C$_6$H$_3$F$_2$H-4), 4.47 (1H, m, PhOpipH-4), 4.01 (1H, m, pipH-4), 3.89 (2H, m, 2H of PhOpipH-2, H-6), 3.77 (3H, s, OCH$_3$), 3.64 (1H, m, 1H of PhOpipH-2, H-6), 3.50 (2H, s, CH$_2$C$_6$H$_3$F$_2$), 3.35 (1H, m, 1H of PhOpipH-2, H-6), 2.84 (2H, m, 2H of pipH-2, H-6), 2.24 (2H, t, J 11.0 Hz, 2H of pipH-2, H-6), 2.04-1.83 (6H, m, 2H of pipH-3, H-5, PhOpipH-3, H-5), 1.66 (2H, m, 2H of pipH-3, H-5); m/z: 565 [M+H]$^+$ (found [M+H]$^+$, 565.2657, C$_{31}$H$_{34}$F$_2$N$_4$O$_4$ requires [M+H]$^+$ 565.2621).

Compound 297: N-(1-(3,5-difluorobenzyl)piperidin-4-yl)-5-(4-(3,4-difluorophenoxy)piperidine-1-carbonyl)picolinamide. $^1$H nmr (CDCl$_3$) δ 8.60 (1H, m, pyH-6), 8.24 (1H, d, J 8.0 Hz, pyH-3), 7.94 (1H, d, J 8.5 Hz, NH), 7.89 (1H, dd, J 8.0, 2.0 Hz, pyH-4), 7.07 (1H, q, J 9.5 Hz, 1H of COC$_6$H$_3$F$_2$), 6.91 (2H, d, J 6.0 Hz, C$_6$H$_3$F$_2$H-2, H-6), 6.78-6.17 (2H, m, 2H of COC$_6$H$_3$F$_2$), 6.62 (1H, m, C$_6$H$_3$F$_2$H-4), 4.51 (1H, m, PhOpipH-4), 4.04 (1H, m, pipH-4), 3.88 (2H, m, 2H of PhOpipH-2, H-6), 3.61 (3H, m, CH$_2$C$_6$H$_3$F$_2$, 1H of PhOpipH-2, H-6), 3.37 (1H, m, 1H of PhOpipH-2, H-6), 2.95 (2H, m, 2H of pipH-2, H-6), 2.33 (2H, m, 2H of pipH-2, H-6), 2.08-1.76 (8H, m, pipH-3, H-5, PhOpipH-3, H-5); $^{19}$F nmr (CDCl$_3$) δ −75.8, −134.9, −146.9; m/z: 571 [M+H]$^+$(found [M+H]$^+$, 571.2402, C$_{30}$H$_{30}$F$_4$N$_4$O$_3$ requires [M+H]$^+$ 571.2327).

Compound 298: 5-(4-(3,4-difluorobenzoyl)piperidine-1-carbonyl)-N-(1-(3,5-difluorobenzyl)piperidin-4-yl)picolinamide. $^1$H nmr (CDCl$_3$) δ 8.59 (1H, m, pyH-6), 8.23 (1H, d, J 8.0 Hz, pyH-3), 7.96 (1H, d, J 8.5 Hz, NH), 7.93-7.85 (2H, m, pyH-4, COC$_6$H$_3$F$_2$H-5 or H-6), 6.99 (1H, td, J 7.5, 2.0 Hz, COC$_6$H$_3$F$_2$H-5 or H-6), 6.91-6.85 (3H, m, COC$_6$H$_3$F$_2$H-2, CH$_2$C$_6$H$_3$F$_2$H-2, H-6), 6.72 (1H, br t, J 9.0 Hz, CH$_2$C$_6$H$_3$F$_2$H-4), 4.65 (1H, m, 1H of BzpipH-2, H-6), 4.04 (1H, m, pipH-4), 3.70 (1H, m, 1H of BzpipH-2, H-6), 3.61 (2H, s, CH$_2$C$_6$H$_3$F$_2$), 3.41 (1H, m, BzpipH-4), 3.21 (1H, m, BzpipH-2, H-6), 3.07 (1H, m, BzpipH-2, H-6), 2.95 (2H, m, 2H of pipH-2, H-6), 2.33 (2H, m, 2H of pipH-2, H-6), 2.04 (3H, m, 2H of pipH-3, H-5, 1H of BzpipH-3, H-5), 1.88 (1H, m, 1H of BzpipH-3, H-5), 1.74 (4H, m, 2H of pipH-3, H-5, 2H of BzpipH-3, H-5); $^{19}$F nmr (CDCl$_3$) δ −75.8, −101.2, −106.5; m/z: 583 [M+H]$^+$ (found [M+H]$^+$, 583.2365, C$_{32}$H$_{34}$F$_2$N$_4$O$_4$ requires [M+H]$^+$ 583.2327).

Compound 299: N-((cis)-4-(3,5-difluorophenoxy)cyclohexyl)-5-(4-(4-fluorophenoxy)piperidine-1-carbonyl)picolinamide. $^1$H nmr (CDCl$_3$) δ 8.60 (1H, m, pyH-6), 8.25 (1H, d, J 8.5 Hz, pyH-3), 8.00 (1H, d, J 8.5 Hz, NH), 7.89 (1H, dd, J 8.0, 2.0 Hz, pyH-4), 6.98 (2H, dd, J 9.0, 8.0 Hz, 2H of C$_6$H$_4$F), 6.86 (2H, dd, J 9.5, 4.5 Hz, 2H of C$_6$H$_4$F), 6.45-6.35 (3H, m, C$_6$H$_3$F$_2$), 4.52 (1H, m, 1H of cyHexH-1 or cyHexH-4 or PhOpipH-4), 4.46 (1H, m, 1H of cyHexH-1 or cyHexH-4 or PhOpipH-4), 4.09 (1H, m, 1H of cyHexH-1 or cyHexH-4 or PhOpipH-4), 3.89 (2H, m 2H of PhOpipH-2, H-6), 3.64 (1H, m, PhOpipH-2, H-6), 3.36 (1H, m, PhOpipH-2, H-6), 2.08-1.75 (12H, m, cyHexH-2, H-3, H-5, H-6 and PhOpipH-3, H-5); $^{19}$F nmr (CDCl$_3$) δ −109.4, −122.5; m/z: 525 [M+H]$^+$.

Compound 300: N-((cis)-4-(3,5-difluorophenoxy)cyclohexyl)-5-(4-(4-methoxybenzoyl)piperidine-1-carbonyl)picolinamide. $^1$H nmr (CDCl$_3$) δ 8.60 (1H, m, pyH-6), 8.24 (1H, d, J 8.5 Hz, pyH-3), 8.00 (1H, d, J 8.5 Hz, NH), 7.93 (2H, d, J 9.0 Hz, 2H of C$_6$H$_4$OCH$_3$), 7.89 (1H, dd, J 8.0, 2.0 Hz, pyH-4), 6.95 (2H, d, J 9.0 Hz, 2H of C$_6$H$_4$OCH$_3$), 6.45-6.35 (3H, m, C$_6$H$_3$F$_2$), 4.65 (1H, m, 1H of BzpipH-2, H-6), 4.46 (1H, m, cyHexH-1 or H-4), 4.09 (1H, m, cyHexH-1 or H-4), 3.87 (3H, s, OCH$_3$), 3.77 (1H, m, 1H of BzpipH-2, H-6), 3.53 (1H, m, BzpipH-4), 3.16 (2H, m, 2H of BzpipH-2, H-6), 2.08-2.03 (3H, m, 3H of cyHexH-2, H-3, H-5, H-6 and BzpipH-3, H-5), 1.89-1.71 (9H, m, 9H of cyHexH-2, H-3, H-5, H-6 and BzpipH-3, H-5); $^{19}$F nmr (CDCl$_3$) δ −109.4; m/z: 578 [M+H]$^+$.

Compound 301: N-(1-(4-cyanobenzyl)piperidin-4-yl)-5-(4-(4-(trifluoromethyl)phenoxy)piperidin-1-yl)picolinamide. $^1$H nmr (CDCl$_3$) δ 8.19 (1H, d, J 3.0 Hz, pyH-6), 8.01 (1H, d, J 8.5 Hz, pyH-3), 7.78 (1H, d, J 8.5 Hz, NH), 7.64 (2H, d, J 8.5 Hz, 2H of C$_6$H$_4$CN), 7.55 (2H, d, J 9.0 Hz, 2H of C$_6$H$_4$CF$_3$), 7.50 (2H, d, J 8.5 Hz, 2H of C$_6$H$_4$CN), 7.23 (1H, dd, J 9.0, 3.0 Hz, pyH-4), 6.98 (2H, d, J 9.0 Hz, 2H of C$_6$H$_4$CF$_3$), 4.62 (1H, heptet, J 3.0 Hz, PhOpipH-4), 4.04 (1H, m, pipH-4), 3.78 (2H, s, CH$_2$C$_6$H$_4$CN), 3.59 (2H, ddd, J 12.5, 8.5, 4.0 Hz, 2H of PhOpipH-2, H-6), 3.34 (2H, ddd, J 12.5, 7.0, 3.5 Hz, 2H of PhOpipH-2, H-6), 3.00 (2H, m, 2H of pipH-2, H-6), 2.43 (2H, m, 2H of pipH-2, H-6), 2.14-1.92 (6H, m, PhOpipH-3, H-5, 2H of pipH-3, H-5), 1.77 (2H, m, 2H of pipH-3, H-5); $^{19}$F nmr (CDCl$_3$) δ −61.6; m/z: 564 [M+H]$^+$(found [M+H]$^+$, 564.2539, C$_{31}$H$_{32}$F$_3$N$_5$O$_2$ requires [M+H]$^+$ 564.2581).

Compound 302: N-(1-(4-cyanobenzyl)piperidin-4-yl)-5-(4-(4-methoxybenzoyl)piperidin-1-yl)picolinamide. $^1$H nmr (CDCl$_3$) δ 8.17 (1H, d, J 2.5 Hz, pyH-6), 7.99 (1H, d, J 9.0 Hz, pyH-3), 7.95 (2H, d, J 9.0 Hz, 2H of C$_6$H$_4$OCH$_3$), 7.79 (1H, d, J 8.5 Hz, NH), 7.66 (2H, d, J 8.0 Hz, 2H of C$_6$H$_4$CN), 7.52 (2H, d, J 8.5 Hz, 2H of C$_6$H$_4$CN), 7.22 (1H, dd, J 9.0, 2.5 Hz, pyH-4), 6.96 (2H, d, J 9.0 Hz, 2H of C$_6$H$_4$OCH$_3$), 4.07 (1H, m, pipH-4), 3.94-3.81 (7H, m, 2H of BzpipH-2, H-6, OCH$_3$, CH$_2$C$_6$H$_4$CN), 3.45 (1H, m, BzpipH-4), 3.13 (2H, m, 2H of BzpipH-2, H-6 or 2H of pipH-2, H-6), 3.05 (2H, m, 2H of BzpipH-2, H-6 or 2H of pipH-2, H-6), 2.52 (2H, m, 2H of pipH-2, H-6), 2.10 (2H, m, 2H of pipH-3, H-5), 1.97 (4H, m, BzpipH-3, H-5), 1.91 (2H, m, 2H of pipH-3, H-5); m/z: 538 [M+H]$^+$ (found [M+H]$^+$, 538.2831, C$_{32}$H$_{35}$N$_5$O$_3$ requires [M+H]$^+$ 538.2813).

Compound 303: 5-(4-(4-cyanophenoxy)piperidine-1-carbonyl)-N-((cis)-4-(4-fluorophenoxy)cyclohexyl)picolinamide. $^1$H nmr (CDCl$_3$) δ 8.61 (1H, m, pyH-6), 8.26 (1H, d, J 8.0 Hz, pyH-3), 8.01 (1H, d, J 8.5 Hz, NH), 7.89 (1H, dd, J 8.0, 2.0 Hz, pyH-4), 7.60 (2H, d, J 9.0 Hz, 2H of C$_6$H$_4$OCN), 7.00-6.94 (4H, m, 2H of C$_6$H$_4$CN, 2H of C$_6$H$_4$F), 6.86 (2H, dd, J 9.0, 4.5 Hz, 2H of C$_6$H$_4$F), 4.70 (1H, m, PhOpipH-4), 4.42 (1H, m, cHexH-1), 4.09 (1H, m, cHexH-4), 3.88 (2H, m, 2H of PhOpipH-2, H-6), 3.65 (1H, m, 1H of PhOpipH-2, H-6), 3.41 (1H, m, 1H of PhOpipH-2, H-6), 2.06-2.00 (4H, m, 2H of PhOpipH-2, H-6, 2H of cHexH-2, H-3, H-5, H-6), 1.87-1.75 (8H, 2H of PhOpipH-3, H-5, 6H of cHexH-2, H-3, H-5, H-6); $^{19}$F nmr (CDCl$_3$) δ −123.5; m/z: 553 [M+H]$^+$ (found [M+H]$^+$, 543.2429, C$_{31}$H$_{31}$FN$_4$O$_4$ requires [M+H]$^+$ 543.2402).

Compound 304: 5-(4-(4-fluorobenzoyl)piperidine-1-carbonyl)-N-((cis)-4-(4-fluorophenoxy)cyclohexyl)picolinamide. $^1$H nmr (CDCl$_3$) δ 8.61 (1H, m, pyH-6), 8.25 (1H, d, J 8.0 Hz, pyH-3), 8.01 (1H, m, NH), 7.99 (2H, m, 2H of COC$_6$H$_4$F), 7.89 (1H, dd, J 8.0, 2.0 Hz, pyH-4), 7.16 (2H, t, J 9.0 Hz, 2H of COC$_6$H$_4$F), 6.97 (2H, t, J 9.0 Hz, 2H of OC$_6$H$_4$F), 6.87 (2H, dd, J 9.0, 4.5 Hz, 2H of OC$_6$H$_4$F), 4.66 (1H, m, 1H of BzpipH-2, H-6), 4.42 (1H, m, cHexH-1), 4.09 (1H, m, cHexH-4), 3.76 (1H, m, 1H of BzpipH-2, H-6), 3.54 (1H, m, BzpipH-4), 2.04 (2H, m, 2H of cHexH-2, H-6), 1.88-1.75 (10H, m, BzpipH-3, H-5, 6H of cHexH-2, H-3, H-5, H-6); $^{19}$F nmr (CDCl$_3$) δ −104.4, −123.6; m/z: 548 [M+H]$^+$ (found [M+H]$^+$, 548.2418, C$_{31}$H$_{31}$F$_2$N$_3$O$_4$ requires [M+H]$^+$ 548.2356).

Compound 305: N-(2-(4-fluorophenoxy)ethyl)-5-(4-(4-methoxybenzoyl)piperidine-1-carbonyl)picolinamide. $^1$H nmr (CDCl$_3$) δ 8.62 (1H, m, pyH-6), 8.40 (1H, t, J 6.0 Hz, NH), 8.25 (1H, d, J 8.0 Hz, pyH-3), 7.94 (2H, d, J 8.5 Hz, 2H of C$_6$H$_4$OCH$_3$), 7.90 (1H, dd, J 8.0, 1.5 Hz, pyH-4), 7.00-6.91 (4H, m, 2H of C$_6$H$_4$OCH$_3$, 2H of C$_6$H$_4$F), 6.87 (2H, dd, J 9.0, 4.5 Hz, 2H of C$_6$H$_4$F), 4.66 (1H, m, 1H of BzpipH-2, H-6), 4.12 (2H, t, J 5.0 Hz, CH$_2$OC$_6$H$_4$F), 3.88 (2H, q, J 5.5 Hz, NHCH$_2$), 3.74 (1H, m, BzpipH-2, H-6), 3.53 (1H, pentet, J 7.0 Hz, BzpipH-4), 3.15 (2H, m, 2H of BzpipH-2, H-6), 2.01 (1H, m, 1H of BzpipH-3, H-5), 1.89-1.82 (3H, m, 3H of BzpipH-3, H-5); $^{19}$F nmr (CDCl$_3$) δ −123.6; m/z: 506 [M+H]$^+$.

Compound 306: 5-(4-(4-cyanophenoxy)piperidine-1-carbonyl)-N-(2-(4-fluorophenoxy)ethyl)picolinamide. $^1$H nmr (CDCl$_3$) δ 8.62 (1H, m, pyH-6), 3.39 (1H, t, J 6.0 Hz, NH), 8.26 (1H, d, J 7.5 Hz, pyH-3), 7.90 (1H, dd, J 8.0, 2.0 Hz, pyH-4), 7.60 (2H, d, J 9.0 Hz, 2H of C$_6$H$_4$CN), 7.00-6.95 (4H, m, 2H of C$_6$H$_4$CN, 2H of C$_6$H$_4$F), 6.87 (2H, dd, J 9.0, 4.5 Hz, 2H of C$_6$H$_4$F), 4.70 (1H, m, PhOpipH-4), 4.13 (2H, t, J 5.0 Hz, CH$_2$OC$_6$H$_4$F), 3.89 (4H, m, 2H of PhOpipH-2, H-6, NHCH$_2$), 3.65 (1H, m, 1H of PhOpipH-2, H-6), 3.40 (1H, m, 1H of PhOpipH-2, H-6), 1.94 (4H, m, PhOpipH-3, H-5); $^{19}$F nmr (CDCl$_3$) δ −123.4; m/z: 489 [M+H]$^+$.

Compound 307: N-(1-(4-cyanobenzyl)piperidin-4-yl)-5-(3-(4-fluorobenzyloxy)azetidine-1-carbonyl)picolinamide. $^1$H nmr (CDCl$_3$) δ 8.76 (1H, m, pyH-6), 8.23 (1H, d, J 8.0 Hz, pyH-3), 8.06 (1H, dd, J 8.0, 2.0 Hz, pyH-4), 7.93 (1H, d, J 8.5 Hz, NH), 7.60 (2H, d, J 8.0 Hz, 2H of C$_6$H$_4$CN), 7.46 (2H, d, J 8.0 Hz, 2H of C$_6$H$_4$CN), 7.30 (2H, dd, J 8.5, 5.0 Hz, 2H of C$_6$H$_4$F), 7.05 (2H, t, 8.5 Hz, 2H of C$_6$H$_4$F), 4.46 (2H, m, OCH$_2$C$_6$H$_4$F), 4.44 (1H, m, 1H of AzH-2, H-4), 4.38 (1H, d AB system, J 6.0 Hz, 1H of AzH-2, H-4), 4.21 (1H, m, 1H of AzH-2, H-4), 4.13 (1H, m 1H of AzH-2, H-6), 4.01 (1H, m pipH-4), 3.56 (2H, s, NCH$_2$C$_6$H$_4$CN), 3.48 (1H, d, J 5.5 Hz, AzH-3), 2.81 (2H, m, 2H of pipH-2, H-6), 2.23 (2H, t, J 11.5 Hz, 2H of pipH-2, H-6), 2.02 (2H, m, 2H of pipH-3, H-5), 1.65 (2H, m, 2H of pipH-3, H-5); $^{19}$F nmr (CDCl$_3$) δ −113.6; m/z: 528 [M+H]$^+$.

Compound 308: N-(1-(3,5-difluorobenzyl)piperidin-4-yl)-5-(3-(4-fluorobenzyloxy)azetidine-1-carbonyl)picolinamide. $^1$H nmr (CDCl$_3$) δ 8.70 (1H, dd, J 2.0, 1.0 Hz, pyH-6), 8.16 (1H, dd, J 8.0, 1.0 Hz, pyH-3, 7.99 (1H, dd, J 8.0, 2.0 Hz, pyH-4), 7.87 (1H, d, J 8.0 Hz, NH), 7.24 (2H, dd, J 8.5, 5.0 Hz, 2H of C$_6$H$_4$F), 6.98 (2H, t, J 8.5 Hz, 2H of C$_6$H$_4$F), 6.81 (2H, m, C$_6$H$_3$F$_2$H-2, H-6), 6.62 (1H, tt, J 9.0, 2.5 Hz, C$_6$H$_3$F$_2$H-4), 4.40 (2H, m, 2H of AzH-2, H-4 or CH$_2$C$_6$H$_4$F), 4.37 (1H, m, 1H of AzH-2, H-4 or 1H of CH$_2$C$_6$H$_4$F), 4.31 (1H, d AB system, J 6.0 Hz, 1H of AzH-2, H-4 or 1H of CH$_2$C$_6$H$_4$F), 4.15 (1H, m, 1H of AzH-2, H-4), 4.05 (1H, m, 1H of AzH-2, H-4), 3.94 (1H, m, pipH-4), 3.44 (2H, s, CH$_2$C$_6$H$_3$F$_2$), 2.98 (1H, m, AzH-3), 2.78 (2H, m, 2H of pipH-2, H-6), 2.16 (2H, t, J 11.5 Hz, 2H of pipH-2, H-6), 1.95 (2H, m, pipH-3, H-5), 1.59 (2H, m, 2H of pipH-3, H-5); $^{19}$F nmr (CDCl$_3$) δ −110.5, −113.6; m/z: 539 [M+H]$^+$.

Compound 309: N-(1-(4-cyanobenzyl)piperidin-4-yl)-6-(4-(4-methoxybenzoyl)piperidine-1-carbonyl)nicotinamide. Compound 309 was synthesized as follows:
Coupling of the Benzoylpiperidine

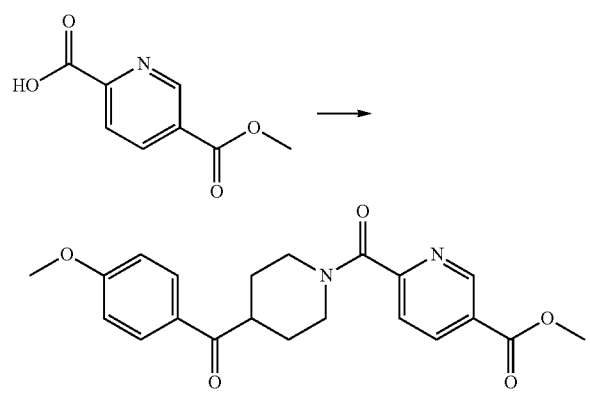

To a mixture of 4-(4-methoxybenzoyl)piperidine hydrochloride (2.00 g, 7.82 mmol, 1.0 eq) and 5-(methoxycarbonyl)pyridine-2-carboxylic acid (1.42 g, 7.82 mmol, 1.0 eq) in dimethylformamide (55 mL) was added triethylamine (2.72 mL, 19.55 mmol, 2.5 eq) followed by HATU (2.97 g, 7.82 mmol, 1.0 eq). The reaction was stirred at room temperature for 4 hours before partitioning between EtOAc (250 mL) and water-NaHCO$_3$ (1:1, 200 mL). The organics were further washed with brine (150 mL), water (150 mL) and brine (150 mL), dried (Na$_2$SO$_4$) and concentrated under reduced pressure. Column chromatography (silica, 4-5% MeOH—CH$_2$Cl$_2$) yielded the coupled product (2.39 g, 80%) as a white foam; $^1$H nmr (CDCl$_3$) δ 9.08 (1H, m, pyH-6), 8.29 (1H, dd, J 8.5, 2.0 Hz, pyH-4), 7.84 (2H, d, J 9.0 Hz, 2H of C$_6$H$_4$OCH$_3$), 7.60 (1H, d, J 8.0 Hz, pyH-3), 6.84 (2H, d, J 9.0 Hz, 2H of C$_6$H$_4$OCH$_3$), 4.60 (1H, m, 1H of BzpipH-2, H-6), 3.87 (3H, s, 1×OCH$_3$), 3.82 (1H, m, 1H of BzpipH-2, H-6), 3.77 (3H, s, 1×OCH$_3$), 3.46 (1H, m, BzpipH-4), 3.19 (1H, ddd, J 14.0, 10.0, 4.0 Hz, 1H of BzpipH-2, H-6), 3.02 (1H, m, 1H of BzpipH-2, H-6), 1.95-1.90 (1H, m, 1H of BzpipH-3, H-5), 1.83-1.79 (3H, m, 3H of BzpipH-3, H-5); $^{13}$C nmr (CDCl$_3$) δ 199.9, 166.6, 165.0, 163.5, 157.7, 149.6, 138.1, 130.5, 128.5, 126.3, 123.1, 113.9, 55.4, 52.5, 46.6, 42.6, 41.8, 28.8, 28.4; m/z: 383 [M+H]$^+$(found [M+H]$^+$, 383.1515, C$_{21}$H$_{22}$N$_2$O$_5$ requires [M+H]$^+$ 383.1602).
Hydrolysis of the Methyl Ester

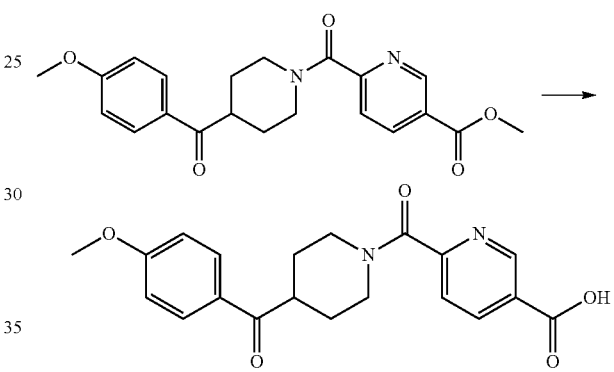

To a solution of the pyridine methyl ester (2.39 g, 6.26 mmol, 1.0 eq) in tetrahydrofuran-methanol (2:1, 50 mL) was added an aqueous solution of lithium hydroxide monohydrate (0.79 g, 18.77 mmol, 3.0 eq in 10 mL of water). The reaction was stirred at room temperature for 20 minutes before neutralizing with HCl (approximately 2.4 mL of a 6M solution). The reaction was concentrated to dryness to yield the crude carboxylic acid (3.08 g) as a white solid, which was used without purification; $^1$H nmr (D$_6$-DMSO) δ 8.97 (1H, m, pyH-6), 8.25 (1H, dd, J 8.0, 2.0 Hz, pyH-4), 7.98 (2H, d, J 9.0 Hz, 2H of C$_6$H$_4$OCH$_3$), 7.51 (1H, dd, J 8.0, 1.0 Hz, pyH-3), 7.04 (2H, d, J 9.0 Hz, 2H of C$_6$H$_4$OCH$_3$), 4.50 (1H, m, 1H of BzpipH-2, H-6), 3.83 (3H, s, 1×OCH$_3$), 3.76-3.62 (2H, m, 1H of BzpipH-2, H-6, BzpipH-4), 3.20 (1H, m, 1H of BzpipH-2, H-6), 3.00 (1H, m, 1H of BzpipH-2, H-6), 1.86 (1H, m, 1H of BzpipH-3, H-5), 1.68 (1H, m, 1H of BzpipH-3, H-5), 1.54 (2H, m, 2H of BzpipH-3, H-5); m/z: 369 [M+H]$^+$.
Coupling of the Benzylaminopiperidine

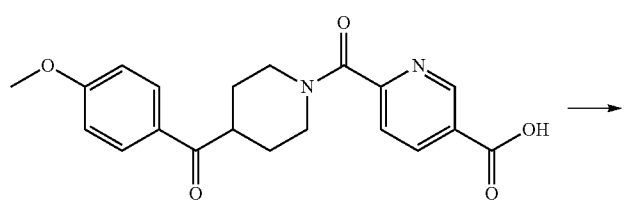

-continued

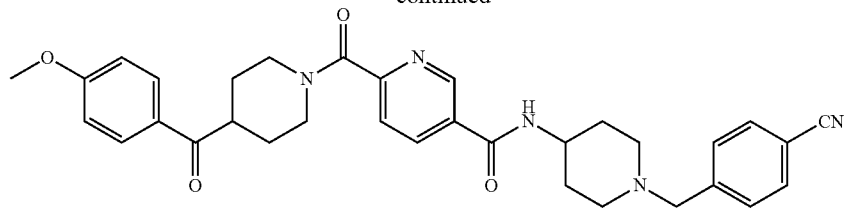

To a suspension of the crude pyridine carboxylic acid (3.08 g, 6.26 mmol, 1.0 eq) and 1-(4-cyanobenzyl)-4-aminopiperidine dihydrochloride (1.80 g, 6.26 mmol, 1.0 eq) in dimethylformamide (50 mL) was added triethylamine (3.05 mL, 21.91 mmol, 3.5 eq). HATU (2.38 g, 6.26 mmol, 1.0 eq) was added forming a yellow solution, which was stirred at room temperature for 6 hours. The reaction was partitioned between EtOAc (200 mL) and water-NaHCO$_3$ (1:1, 200 mL). The organics were washed with brine (150 mL), water (150 mL) and brine (150 mL) before drying (Na$_2$SO$_4$) and concentrating under reduced pressure. MPLC (2→5% MeOH—CH$_2$Cl$_2$) yielded Compound 309 (2.93 g, 83% over two steps) as a white solid; $^1$H nmr (CDCl$_3$) δ 8.84 (1H, d, J 2.0 Hz, pyH-6), 8.06 (1H, dd, J 8.0, 2.0 Hz, pyH-4), 7.88 (2H, d, J 8.5 Hz, 2H of C$_6$H$_4$OCH$_3$), 7.56 (1H, d, J 7.5 Hz, pyH-3), 7.54 (2H, d, J 8.5 Hz, 2H of C$_6$H$_4$CN), 7.38 (2H, d, J 8.0 Hz, 2H of C$_6$H$_4$CN), 6.89 (2H, d, J 9.0 Hz, 2H of C$_6$H$_4$OCH$_3$), 6.24 (1H, d, J 7.5 Hz, NH), 4.63 (1H, m, 1H of BzpipH-2, H-6), 3.98 (1H, m, pipH-4), 3.87 (1H, m, 1H of BzpipH-2, H-6), 3.81 (3H, s, OCH$_3$), 3.50 (2H, s, C$\underline{H}_2$C$_6$H$_4$CN), 3.47 (1H, m, BzpipH-4), 3.19 (1H, m, 1H of BzpipH-2, H-6), 3.04 (1H, ddd, J 11.5, 10.0, 3.0 Hz, 1H of BzpipH-2, H-6), 2.77 (2H, m, 2H of pipH-2, H-6), 2.14 (2H, dd, J 11.5, 10.0 Hz, 2H of pipH-2, H-6), 1.97 (3H, m, 2H of pipH-3, H-5, 1H of BzpipH-3, H-5), 1.85-1.72 (3H, m, 3H of BzpipH-3, H-5), 1.56 (2H, m, 2H of pipH-2, H-6); $^{13}$C nmr (CDCl$_3$) δ 200.0, 167.0, 164.6, 163.7, 155.9, 147.4, 144.6, 135.9, 132.1, 130.9, 130.6, 129.3, 128.5, 122.8, 119.0, 114.0, 110.8, 62.4, 55.5, 52.5, 47.4, 46.7, 42.6, 42.0, 32.0, 28.8, 28.5; m/z: 566 [M+H]$^+$ (found [M+H]$^+$, 566.2749, C$_{33}$H$_{35}$N$_5$O$_4$ requires [M+H]$^+$ 566.2762).

Compound 310: (N-(1-(3,5-difluorobenzyl)piperidin-4-yl)-6-(4-(4-methoxybenzoyl)piperidine-1-carbonyl)nicotinamide. $^1$H nmr (CDCl$_3$) δ 8.90 (1H, d, J 2.0 Hz, pyH-6), 8.11 (1H, dd, J 8.5, 2.0 Hz, pyH-4), 7.94 (2H, d, J 9.0 Hz, 2H of C$_6$H$_4$OCH$_3$), 7.58 (1H, d, J 8.0 Hz, pyH-3), 6.95 (2H, d, J 9.0 Hz, 2H of C$_6$H$_4$OCH$_3$), 6.87 (2H, d, J 6.0 Hz, C$_6$H$_3$F$_2$H-2, H-6), 6.67 (1H, tt, J 9.0, 2.0 Hz, C$_6$H$_3$F$_2$H-4), 6.52 (1H, d, J 7.5 Hz, NH), 4.70 (1H, m, 1H of BzpipH-2, H-6), 4.00 (1H, m, pipH-4), 3.92 (1H, m, 1H, BzpipH-2, H-6), 3.87 (3H, s, OCH$_3$), 3.53 (1H, m, BzpipH-4), 3.48 (2H, s, C$\underline{H}_2$C$_6$H$_3$F$_2$), 3.25 (1H, m, 1H of BzpipH-2, H-6), 3.11 (1H, m, 1H of BzpipH-2, H-6), 2.85 (2H, m, 2H of pipH-2, H-6), 2.19 (2H, dd, J 11.5, 10.0 Hz, 2H of pipH-2, H-6), 2.02 (3H, m, 2H of pipH-3, H-5, 1H of BzpipH-3, H-5), 1.92-1.76 (3H, m, 3H of BzpipH-3, H-5), 1.63 (3H, m, 2H of pipH-3, H-5); $^{19}$F nmr (CDCl$_3$) δ −110.5; m/z: 578 [M+H]$^+$.

Compound 311: N-((cis)-4-(4-fluorophenoxy)cyclohexyl)-5-(4-(4-methoxybenzoyl)piperidine-1-carbonyl)picolinamide. $^1$H nmr (CDCl$_3$) δ 8.61 (1H, d, J 1.5 Hz, pyH-6), 8.25 (1H, d, J 8.0 Hz, pyH-3), 8.01 (1H, d, J 8.5 Hz, NH), 7.94 (2H, d, J 9.0 Hz, 2H of C$_6$H$_4$OCH$_3$), 7.89 (1H, dd, J 8.0, 2.0 Hz, pyH-4), 7.00-6.94 (4H, m, 2H of C$_6$H$_4$OCH$_3$, 2H of C$_6$H$_4$F), 6.87 (2H, dd, J 9.0, 4.5 Hz, 2H of C$_6$H$_4$F), 4.66 (1H, m, 1H of BzpipH-2, H-6), 4.42 (1H, m, cHexH-1), 4.09 (1H, m, cHexH-4), 3.88 (3H, s, OCH$_3$), 3.78 (1H, m, 1H of BzpipH-2, H-6), 3.54 (1H, m, BzpipH-4), 3.16 (2H, m, 2H of BzpipH-2, H-6), 2.07-2.02 (3H, m, 3H of cHexH-2, H-4, H-5, H-6, BzpipH-3, H-5), 1.90-1.75 (9H, m, 9H of cHexH-2, H-3, H-5, H-6, BzpipH-3, H-5); $^{19}$F nmr (CDCl$_3$) δ −123.6; m/z: 560 [M+H]$^+$.

Compound 312: N-((cis)-4-(4-fluorophenoxy)cyclohexyl)-5-(4-(4-fluorophenoxy)piperidine-1-carbonyl)picolinamide. $^1$H nmr (CDCl$_3$) δ 8.61 (1H, m, pyH-6), 8.25 (1H, d, J 8.0 Hz, pyH-3), 8.01 (1H, d, J 8.5 Hz, NH), 7.89 (1H, dd, J 8.0, 2.0 Hz, pyH-4), 7.01-6.94 (4H, m, 2×2H of C$_6$H$_4$F), 6.89-6.84 (4H, m, 2×2H of C$_6$H$_4$F), 4.52 (1H, m, cHexH-1 or PhOpipH-4), 4.42 (1H, m, cHexH-1 or PhOpipH-4), 4.09 (1H, m, cHexH-4)), 3.89 (2H, m, 2H of PhOpipH-2, H-6), 3.65 (1H, m, 1H of PhOpipH-2, H-6), 3.36 (1H, m, 1H of PhOpipH-2, H-6), 2.06-1.75 (12H, m, PhOpipH-3, H-5, cHexH-2, H-3, H-5, H-6); $^{19}$F nmr (CDCl$_3$) δ −122.5, −123.5; m/z: 536 [M+H]$^+$(found [M+H]$^+$, 536.2416, C$_{30}$H$_{31}$F$_2$N$_3$O$_4$ requires [M+H]$^+$ 536.2356).

Compound 313: 5-(3-(4-cyanophenoxy)azetidine-1-carbonyl)-N-(1-(3,5-difluorobenzyl)piperidin-4-yl)picolinamide. $^1$H nmr (CDCl$_3$) δ 8.74 (1H, m, pyH-6), 8.19 (1H, d, J 8.0 Hz, pyH-3), 8.03 (1H, dd, J 8.0, 2.0 Hz, pyH-4), 7.86 (1H, m, NH), 7.55 (2H, d, J 8.0 Hz, 2H of C$_6$H$_4$CN), 6.82 (2H, d, J 6.0 Hz, C$_6$H$_3$F$_2$H-2, H-6), 6.75 (2H, d, J 9.0 Hz, 2H of C$_6$H$_4$CN), 6.62 (1H, tt, J 9.0, 2.0 Hz, C$_6$H$_3$F$_2$H-4), 5.02 (1H, m, AzH-3), 4.61 (2H, dd, J 10.5, 6.0 Hz, 2H of AzH-2, H-4), 4.27 (2H, m, 2H of AzH-2, H-4), 3.94 (1H, m, pipH-4), 3.42 (2H, s, CH$_2$C$_6$H$_3$F$_2$), 2.76 (2H, m, 2H of pipH-2, H-6), 2.15 (2H, t, J 11.0 Hz, 2H of pipH-2, H-6), 1.95 (2H, m, 2H of pipH-3, H-5), 1.58 (2H, m, 2H of pipH-3, H-5); $^{19}$F nmr (CDCl$_3$) δ; m/z: 533 [M+H]$^+$ (found [M+H]$^+$, 532.2160, C$_{29}$H$_{27}$F$_2$N$_5$O$_3$ requires [M+H]$^+$ 532.2155).

Compound 314: 5-(3-(4-cyanophenyl)-5,6,7,8-tetrahydro-[1,2,4]triazolo[4,3-a]pyrazine-7-carbonyl)-N-(1-(3,5-difluorobenzyl)piperidin-4-yl)picolinamide. $^1$H nmr (CDCl$_3$) δ 8.71 (1H, d, J 2.5 Hz, pyH-6), 8.30 (1H, d, J 8.0 Hz, pyH-3), 8.00 (1H, dd, J 8.0, 2.0 Hz, pyH-4), 7.93 (1H, d, J 8.5 Hz, NH), 7.92 (2H, d, J 8.5 Hz, 2H of C$_6$H$_4$CN), 7.86 (2H, d, J 9.0 Hz, 2H of C$_6$H$_4$CN), 6.88 (2H, d, J 6.0 Hz, C$_6$H$_3$F$_2$H-2, H-6), 6.68 (1H, tt, J 9.0, 2.0 Hz, C$_6$H$_3$F$_2$H-4), 5.07 (2H, br s, 2H of triazolopyrazine), 4.27 (2H, br s, 2H of triazolopyrazine), 4.14 (2H, m, 2H of triazolopyrazine), 4.02 (1H, m, pipH-4), 3.49 (2H, s, C$\underline{H}_2$C$_6$H$_3$F$_2$), 2.84 (2H, m, 2H of pipH-2, H-6), 2.23 (2H, dd, J 11.5, 9.5 Hz, 2H of pipH-2, H-6), 2.03 (2H, m, 2H of pipH-3, H-5), 1.68 (2H, m, 2H of pipH-3, H-5); $^{19}$F nmr (CDCl$_3$) δ−110.5; m/z: 583 [M+H]$^+$.

Compound 315: N-((1s,4s)-4-(4-cyanophenoxy)cyclohexyl)-6-(4-(4-methoxybenzoyl)piperidine-1-carbonyl) nicotinamide. $^1$H nmr (CDCl$_3$) δ 8.92 (1H, d, J 1.5 Hz, pyH-6), 8.14 (1H, dd, J 8.0, 2.0 Hz, pyH-4), 7.94 (2H, d, J 9.5 Hz, 2H of C$_6$H$_4$OCH$_3$), 7.61 (1H, d, J 8.0 Hz, pyH-3), 7.57 (2H, d, J 2H of C$_6$H$_4$CN), 6.96 (2H, d, J 9.0 Hz, 2H of C$_6$H$_4$OCH$_3$), 6.95 (2H, d, J 9.0 Hz, 2H of C$_6$H$_4$CN), 6.43 (1H, d, J 8.0 Hz, NH), 4.70 (1H, m, 1H of BzpipH-2, H-6), 4.62 (1H, m, cHexH-1), 4.12 (1H, m, cHexH-4), 3.93 (1H, m, 1H of BzpipH-2, H-6), 3.88 (3H, s, OCH$_3$), 3.53 (1H, m, BzpipH-4), 3.25 (1H, m, 1H of BzpipH-2, H-6), 3.10 (1H, m, 1H of BzpipH-2, H-6), 2.11 (2H, m, 2H of cHexH-2, H-6), 2.04-1.73 (10H, m, 2H of cHexH-2, H-6, cHexH-3, H-5, BzpipH-3, H-5); $^{19}$F nmr (CDCl$_3$) δ −61.6, −114.9; m/z: 568 [M+H]$^+$ (found [M+H]$^+$, 567.2632, C$_{33}$H$_{34}$N$_4$O$_5$ requires [M+H]$^+$ 567.2602).

Compound 316: N-((cis)-4-(4-fluorophenoxy)cyclohexyl)-6-(4-(4-methoxybenzoyl)piperidine-1-carbonyl) nicotinamide. $^1$H nmr (CDCl$_3$) δ 8.93 (1H, d, J 1.5 Hz, pyH-6), 8.15 (1H, dd, J 8.0, 2.0 Hz, pyH-4), 7.94 (2H, d, J 9.0 Hz, 2H of C$_6$H$_4$OCH$_3$), 7.65 (1H, dd, J 8.0, 0.5 Hz, pyH-3), 7.00-6.94 (4H, m, 2H of C$_6$H$_4$OCH$_3$, 2H of C$_6$H$_4$F), 6.86 (2H, dd, J 9.0, 4.5 Hz, 2H of C$_6$H$_4$F), 6.29 (1H, d, J 8.0 Hz, NH), 4.70 (1H, m, 1H of BzpipH-2, H-6), 4.44 (1H, m, cHexH-1), 4.11 (1H, m, cHexH-4), 3.95 (1H, m, 1H of BzpipH-2, H-6), 3.88 (3H, s, OCH$_3$), 3.52 (1H, m, BzpipH-4), 3.26 (1H, ddd, J 10.5, 10.0, 3.5 Hz, 1H of BzpipH-2, H-6), 3.10 (ddd, J 11.5, 10.0, 3.0 Hz, 1H of BzpipH-2, H-6), 2.09-1.73 (12H, m, BzpipH-3, H-5, cHexH-2, H-3, H-5, H-6); $^{19}$F nmr (CDCl$_3$) δ −123.4; m/z: 560 [M+H]$^+$ (found [M+H]$^+$, 560.2511, C$_{32}$H$_{34}$FN$_3$O$_5$ requires [M+H]$^+$ 560.2555).

Compound 317: N-(1-(4-fluorobenzyl)piperidin-4-yl)-6-(4-(4-methoxybenzoyl)piperidine-1-carbonyl)nicotinamide. $^1$H nmr (CDCl$_3$) δ 8.90 (1H, d, J 2.0 Hz, pyH-6), 8.12 (1H, dd, J 8.5, 2.0 Hz, pyH-4), 7.94 (2H, d, J 9.0 Hz, 2H of C$_6$H$_4$OCH$_3$), 7.62 (1H, d, J 8.0 Hz, pyH-3), 7.30-7.25 (2H, m, 2H of C$_6$H$_4$F), 7.02-6.94 (4H, m, 2H of C$_6$H$_4$OCH$_3$, 2H of C$_6$H$_4$F), 6.32 (1H, d, J 8.5 Hz, NH), 4.69 (1H, m, 1H of BzpipH-2, H-6), 4.03 (1H, m, pipH-4), 3.93 (1H, m, 1H of BzpipH-2, H-6), 3.88 (3H, s, OCH$_3$), 3.52 (1H, m, BzpipH-4), 3.47 (2H, s, CH$_2$C$_6$H$_4$F), 3.25 (1H, d, J 11.0, 10.0, 4.0 Hz, 1H of BzpipH-2, H-6), 3.10 (1H, m, 1H of BzpipH-2, H-6), 2.85 (2H, m, 2H of pipH-2, H-6), 2.16 (2H, t, J 11.5 Hz, 2H of pipH-2, H-6), 2.02 (3H, m, 2H of pipH-3, H-5, 1H of BzpipH-3, H-5), 1.93-1.81 (3H, m, 3H of BzpipH-3, H-5), 1.68-1.54 (2H, m, 2H of pipH-3, H-5); $^{19}$F nmr (CDCl$_3$) δ −115.9; m/z: 560 [M+H]$^+$ (found [M+H]$^+$, 559.2708, C$_{32}$H$_{35}$FN$_4$O$_4$ requires [M+H]$^+$ 538.2715).

Compound 318: 6-(4-(4-methoxybenzoyl)piperidine-1-carbonyl)-N-(1-(4-methoxybenzyl)piperidin-4-yl)nicotinamide. $^1$H nmr (CDCl$_3$) δ 8.90 (1H, d, J 2.0 Hz, pyH-6), 8.12 (1H, dd, J 8.5, 2.0 Hz, pyH-4), 7.94 (2H, d, J 9.0 Hz, 2H of COC$_6$H$_4$OCH$_3$), 7.62 (1H, d, J 8.0 Hz, pyH-3), 7.22 (2H, d, J 8.5 Hz, 2H of CH$_2$C$_6$H$_4$OCH$_3$), 6.95 (2H, d, J 9.0 Hz, 2H of COC$_6$H$_4$OCH$_3$), 6.85 (2H, d, J 8.5 Hz, 2H of CH$_2$C$_6$H$_4$OCH$_3$), 6.30 (1H, d, J 8.0 Hz, NH), 4.69 (1H, m, 1H of BzpipH-2, H-6), 4.00 (1H, m, pipH-4), 3.93 (1H, m, 1H of BzpipH-2, H-6), 3.87 (3H, s, 1×OCH$_3$), 3.80 (3H, s, 1×OCH$_3$), 3.52 (1H, m, BzpipH-4), 3.45 (2H, s, CH$_2$C$_6$H$_4$OCH$_3$), 3.25 (1H, m, 1H of BzpipH-2, H-6), 3.10 (1H, ddd, J 12.0, 10.0, 3.0 Hz, 1H of BzpipH-2, H-6), 2.85 (2H, m, 2H of pipH-2, H-6), 2.14 (2H, t, J 11.0 Hz, 2H of pipH-2, H-6), 2.02 (3H, m, 2H of pipH-3, H-5, 1H of BzpipH-3, H-5), 1.92-1.81 (3H, m, 3H of BzpipH-3, H-5), 1.59 (2H, m, 2H of pipH-3, H-5); m/z: 571 [M+H]$^+$ (found [M+H]$^+$, 571.2895, C$_{33}$H$_{38}$N$_4$O$_5$ requires [M+H]$^+$ 571.2915).

Compound 319: 6-(4-(4-cyanophenoxy)piperidine-1-carbonyl)-N-(1-(4-methoxybenzyl)piperidin-4-yl)nicotinamide. $^1$H nmr (CDCl$_3$) δ 8.90 (1H, d, J 1.5 Hz, pyH-6), 8.12 (1H, dd, J 8.0, 2.0 Hz, pyH-4), 7.62 (1H, d, J 8.0 Hz, pyH-3), 7.59 (2H, d, J 9.0 Hz, 2H of C$_6$H$_4$OCH$_3$ or C$_6$H$_4$CN), 7.23 (2H, d, J 9.0 Hz, 2H of C$_6$H$_4$OCH$_3$ or C$_6$H$_4$CN), 6.96 (2H, d, J 9.0 Hz, 2H of C$_6$H$_4$OCH$_3$ or C$_6$H$_4$CN), 6.85 (2H, d, J 8.5 Hz, 2H of C$_6$H$_4$OCH$_3$ or C$_6$H$_4$CN), 6.43 (1H, d, J 7.5 Hz, NH), 4.69 (1H, m, PhOpipH-4), 4.01 (1H, m, pipH-4), 3.90 (2H, m, 2H of PhOpipH-2, H-6), 3.79 (3H, s, OCH$_3$), 3.70 (1H, m, 1H of PhOpipH-2, H-6), 3.51 (1H, m, 1H of PhOpipH-2, H-6), 3.48 (2H, s, CH$_2$C$_6$H$_4$OCH$_3$), 2.88 (2H, m, 2H of pipH-2, H-6), 2.16 (2H, t, J 11.0 Hz, 2H of pipH-2, H-6), 2.03-1.93 (5H, m, 2H of pipH-3, H-5, 3H of PhOpipH-3, H-5), 1.86 (1H, m, 1H of PhOpipH-3, H-5), 1.62 (2H, m, 2H of pipH-3, H-5); m/z: 554 [M+H]$^+$.

Compound 320: 6-(4-(4-cyanophenoxy)piperidine-1-carbonyl)-N-(1-(4-fluorobenzyl)piperidin-4-yl)nicotinamide. $^1$H nmr (CDCl$_3$) δ 8.86 (1H, d, J 1.5 Hz, pyH-6), 8.10 (1H, dd, J 8.5, 2.0 Hz, pyH-4), 7.64 (1H, d, J 8.5 Hz, pyH-3), 7.53 (2H, d, J 9.0 Hz, 2H of C$_6$H$_4$CN), 7.25 (2H, m, 2H of C$_6$H$_4$F), 6.96 (1H, t, J 8.5 Hz, 2H of C$_6$H$_4$F), 6.90 (2H, d, J 9.0 Hz, 2H of C$_6$H$_4$CN), 6.16 (1H, m, NH), 4.63 (1H, m, PhOpipH-4), 3.99 (1H, m, pipH-4), 3.84 (2H, m, 2H of PhOpipH-2, H-6), 3.65 (1H, m, 1H of PhOpipH-2, H-6), 3.51 (2H, s, CH$_2$C$_6$H$_4$F), 3.48 (1H, m, 1H of PhOpipH-2, H-6), 2.88 (2H, m, 2H of pipH-2, H-6), 2.19 (2H, m, 2H of pipH-2, H-6), 2.02-1.92 (6H, m, 2H of pipH-3, H-5, PhOpipH-3, H-5), 1.60 (2H, m, 2H of pipH-3, H-5); m/z: 543 [M+H]$^+$.

Compound 321: N-((cis)-4-(4-cyanophenoxy)cyclohexyl)-6-(4-(4-cyanophenoxy)piperidine-1-carbonyl)nicotinamide. $^1$H nmr (CDCl$_3$) δ 8.93 (1H, d, J 2.0 Hz, pyH-6), 8.15 (1H, dd, J 8.5, 2.0 Hz, pyH-4), 7.62 (1H, d, J 8.5 Hz, pyH-3), 7.58 (1H, d, J 8.5 Hz, 2H of 1×C$_6$H$_4$CN), 7.56 (2H, d, J 9.0 Hz, 2H of 1×C$_6$H$_4$CN), 6.95 (2H, d, J 8.5 Hz, 2H of 1×C$_6$H$_4$CN), 6.93 (2H, d, J 9.0 Hz, 2H of 1×C$_6$H$_4$CN), 6.57 (1H, d, J 8.0 Hz, NH), 4.69 (1H, pentet, J 3.0 Hz, PhOpipH-4), 4.61 (1H, m, cHexH-1), 4.10 (1H, m, cHexH-4), 3.90 (2H, m, 2H of PhOpipH-2, H-6), 3.70 (1H, m, 1H of PhOpipH-2, H-6), 3.49 (1H, m, 1H of PhOpipH-2, H-6), 2.11-2.04 (3H, m, 3H of PhOpipH-3, H-5, cHexH-2, H-3, H-5, H-6), 1.98-1.73 (9H, m, 9H of PhOpipH-3, H-5, cHexH-2, H-3, H-5, H-6); m/z: 550 [M+H]$^+$.

Compound 322: 6-(4-(4-cyanophenoxy)piperidine-1-carbonyl)-N-(1-(3,5-difluorobenzyl)piperidin-4-yl)nicotinamide. $^1$H nmr (CDCl$_3$) δ 8.84 (1H, d, J 2.0 Hz, pyH-6), 8.07 (1H, dd, J 8.0, 2.0 Hz, pyH-4), 7.59 (1H, d, J 8.0 Hz, pyH-3), 7.53 (2H, d, J 9.0 Hz, 2H of C$_6$H$_4$CN), 6.90 (2H, d, J 9.5 Hz, 2H of C$_6$H$_4$CN), 6.80 (2H, m, C$_6$H$_3$F$_2$H-2, H-6), 6.62 (1H, tt, J 9.0, 2.0 Hz, C$_6$H$_3$F$_2$H-4), 6.21 (1H, d, J 8.0 Hz, NH), 4.64 (1H, heptet, J 3.0 Hz, PhOpipH-4), 3.96 (1H, m, pipH-4), 3.85 (2H, m, 2H of PhOpipH-2, H-6), 3.66 (1H, ddd, J 13.0, 9.0, 3.5 Hz, 1H of PhOpipH-2, H-6), 3.47 (1H, m, 1H of PhOpipH-2, H-6), 3.42 (2H, s, CH$_2$C$_6$H$_3$F$_2$), 2.78 (2H, m, 2H of pipH-2, H-6), 2.13 (2H, t, J 11.5 Hz, 2H of pipH-2, H-6), 2.00-1.95 (5H, m, 2H of pipH-3, H-5, 3H of PhOpipH-3, H-5), 1.81 (1H, m, 1H of PhOpipH-3, H-5), 1.56 (2H, m, 2H of pipH-3, H-5); $^{19}$F nmr (CDCl$_3$) δ −110.5; m/z: 560 [M+H]$^+$.

Compound 323: N-(1-(4-cyanobenzyl)piperidin-4-yl)-6-(4-(4-cyanophenoxy)piperidine-1-carbonyl)nicotinamide. $^1$H nmr (CDCl$_3$) δ 8.90 (1H, m, pyH-6), 8.13 (1H, dd, J 8.0, 2.0 Hz, pyH-4), 7.63 (1H, d, J 8.0 Hz, pyH-3), 7.61 (2H, d, J 8.5 Hz, 2H of 1×C$_6$H$_4$CN), 7.58 (2H, d, J 8.5 Hz, 2H of 1×C$_6$H$_4$CN), 7.45 (2H, d, J 8.5 Hz, 1×C$_6$H$_4$CN), 6.96 (2H, d, J 9.0 Hz, 2H of 1×C$_6$H$_4$CN), 6.94 (1H, d, J 8.0 Hz, NH), 4.70 (1H, pentet, J 3.0 Hz, PhOpipH-4), 4.01 (1H, m, pipH-4), 3.90 (2H, m, 2H of PhOpipH-2, H-6), 3.70 (1H, m, 1H of PhOpipH-2, H-6), 3.56 (2H, s, CH$_2$C$_6$H$_4$CN), 2.83 (2H, m, 2H of pipH-2, H-6), 2.20 (2H, t, J 11.5 Hz, 2H of pipH-2, H-6), 2.02 (5H, m, 2H of pipH-3, H-5, 3H of PhOpipH-3, H-5), 1.87 (1H, m, 1H of PhOpipH-3, H-5), 1.61 (2H, m, 2H of pipH-3, H-5); m/z: 549 [M+H]$^+$.

Compound 324: 6-(4-(4-cyanophenoxy)piperidine-1-carbonyl)-N-((cis)-4-(4-fluorophenoxy)cyclohexyl)nicotinamide. $^1$H nmr (CDCl$_3$) δ 8.94 (1H, d, J 1.5 Hz, pyH-6), 8.16

(1H, dd, J 8.0, 2.0 Hz, pyH-4), 7.67 (1H, d, J 8.5 Hz, pyH-3), 7.59 (2H, d, J 9.0 Hz, 2H of $C_6H_4CN$), 6.97 (4H, m, 2H of $C_6H_4CN$, 2H of $C_6H_4F$), 6.85 (2H, m, 2H of $C_6H_4F$), 6.28 (1H, d, J 8.5 Hz, NH), 4.70 (1H, m, PhOpipH-4), 4.44 (1H, br s, cHexH-1), 4.11 (1H, m, cHexH-4), 3.90 (1H, m, 2H of PhOpipH-2, H-6), 3.72 (1H, m, 1H of PhOpipH-2, H-6), 3.54 (1H, m, 1H of PhOpipH-2, H-6), 2.09-1.98 (5H, m, 5H of cHexH-2, H-3, H-5, H-6, PhOpipH-3, -5), 1.90-1.73 (7H, m, 7H of cHexH-2, H-3, H-5, H-6, PhOpipH-3, H-5); $^{19}F$ nmr ($CDCl_3$) δ −123.3; m/z: 543 $[M+H]^+$(found $[M+H]^+$, 543.2511, $C_{31}H_{31}FN_4O_4$ requires $[M+H]^+$ 543.2402).

Compound 325: N-(6-(4-fluorophenoxy)pyridin-3-yl)-6-(4-(4-methoxybenzoyl)piperidine-1-carbonyl)nicotinamide. $^1H$ nmr ($CDCl_3$) δ 9.57 (1H, s, NH), 8.94 (1H, m, pyH-6), 8.47 (1H, d, J 2.5 Hz, N,O-pyH-6), 8.32 (1H, dd, J 9.0, 2.5 Hz, N,O-pyH-4), 8.12 (1H, dd, J 8.0, 2.0 Hz, pyH-4), 7.94 (2H, d, J 9.0 Hz, 2H of $C_6H_4OCH_3$), 7.42 (1H, d, J 8.0 Hz, pyH-3), 7.11-7.06 (4H, m, 2H of $C_6H_4OCH_3$, 2H of $C_6H_4F$), 6.97-6.93 (3H, m, 2H of $C_6H_4F$, N,O-pyH-3), 4.68 (1H, m, 1H of BzpipH-2, H-6), 3.88 (3H, s, $OCH_3$), 3.81 (1H, m, 1H of BzpipH-2, H-6), 3.54 (1H, m, BzpipH-4), 3.28-3.11 (2H, m, 2H of BzpipH-2, H-6), 2.02 (1H, m, 1H of BzpipH-3, H-5), 1.92-1.82 (3H, m, 3H of BzpipH-3, H-5); $^{19}F$ nmr ($CDCl_3$) δ −118.6; m/z: 555 $[M+H]^+$ (found $[M+H]^+$, 555.2267, $C_{31}H_{27}FN_4O_5$ requires $[M+H]^+$ 555.2039).

Compound 326: 6-(4-(4-cyanophenoxy)piperidine-1-carbonyl)-N-(6-(4-fluorophenoxy)pyridin-3-yl)nicotinamide. $^1H$ nmr ($CDCl_3$) δ 9.42 (1H, s, NH), 8.94 (1H, m, pyH-6), 8.42 (1H, d, J 2.5 Hz, N,O-pyH-6), 8.33 (1H, dd, J 9.0, 2.5 Hz, N,O-pyH-4), 8.12 (1H, dd, J 8.0, 2.0 Hz, pyH-4), 7.60 (2H, d, J 9.0 Hz, 2H of $C_6H_4CN$), 7.44 (1H, d, J 8.0 Hz, pyH-3), 7.08 (4H, m, 2H of $C_6H_4CN$, 2H of $C_6H_4F$), 6.97-6.94 (3H, m, 2H of $C_6H_4F$, N, O-pyH-3), 4.71 (1H, m, PhOpipH-4), 3.99 (1H, m, 1H of PhOpipH-2, 6), 3.86 (1H, m, 1H of PhOpipH-2, H-6), 3.65 (1H, m, 1H of PhOpipH-2, H-6), 3.44 (1H, m, 1H of PhOpipH-2, H-6), 2.07-1.94 (3H, m, 3H of PhOpipH-3, H-5), 1.88 (1H, m, 1H of PhOpipH-3, H-5); $^{19}F$ nmr ($CDCl_3$) δ −118.3; m/z: 538 [M+H] (found [M+H] 538.1985, $C_{30}H_{24}FN_5O_4$ requires [M+H] 538.1885).

Compound 327: 6-(4-(4-fluorobenzyl)piperazine-1-carbonyl)-N-(1-(4-methoxybenzyl)piperidin-4-yl)nicotinamide. $^1H$ nmr ($CDCl_3$) δ 8.89 (1H, d, J 1.5 Hz, pyH-6), 8.12 (1H, dd, J 8.5, 2.0 Hz, pyH-4), 7.62 (1H, d, J 7.5 Hz, pyH-3), 7.30-7.21 (4H, m, 2H of $C_6H_4F$, 2H of $C_6H_4OCH_3$), 7.00 (2H, t, J 8.5 Hz, 2H of $C_6H_4OCH_3$), 6.86 (2H, d, J 9.0 Hz, 2H of $C_6H_4OCH_3$), 6.34 (1H, d, J 8.0 Hz, NH), 4.02 (1H, m, pipH-4), 3.80 (5H, m, 2H of piz, $OCH_3$), 3.52 (2H, m, 2H of piz), 3.50 (2H, s, $CH_2C_6H_4F$ or $CH_2C_6H_4OCH_3$), 3.49 (2H, s, $CH_2C_6H_4F$ or $CH_2C_6H_4OCH_3$), 2.89 (2H, m, 2H of pipH-2, H-6), 2.54 (2H, t, J 5.0 Hz, 2H of piz), 2.41 (2H, m, t, J 5.0 Hz, 2H of piz), 2.19 (2H, t, J 11.5 Hz, 2H of pipH-2, H-6), 2.02 (2H, m, 2H of pipH-3, H-5), 1.63 (2H, m, 2H of pipH-3, H-5); $^{19}F$ nmr ($CDCl_3$) δ −115.5; m/z: 546 [M+H]

Compound 328: 6-(4-(4-fluorobenzyl)piperazine-1-carbonyl)-N-(1-(4-fluorobenzyl)piperidin-4-yl)nicotinamide. $^1H$ nmr ($CDCl_3$) δ 8.92 (1H, m, pyH-6), 8.15 (1H, dd, J 8.0, 2.0 Hz, pyH-4), 7.62 (1H, d, J 8.0 Hz, pyH-3), 7.36-7.25 (4H, m, 2×2H of $C_6H_4F$), 7.06-6.97 (4H, m, 2×2H of $C_6H_4.F$), 6.60 (1H, d, J 7.0 Hz, NH), 4.06 (1H, m, pipH-4), 3.80 (2H, t, J 5.0 Hz, 2H of piz), 3.63 (2H, s, 1×$CH_2C_6H_4F$), 3.51 (4H, m, 2H of piz, 1×$CH_2C_6H_4F$), 2.99 (2H, m, 2H of pipH-2, H-6), 2.54 (2H, t, J 5.0 Hz, 2H of piz), 2.41 (2H, t, J 5.0 Hz, 2H of piz), 2.33 (2H, t, J 11.0 Hz, 2H of pipH-2, H-6), 2.06 (2H, m, 2H of pipH-3, H-5), 1.75 (2H, m, 2H of pipH-3, H-5); $^{19}F$ nmr ($CDCl_3$) δ−114.5, −115.4; m/z: 534 [M+H]

Compound 329: 5-(4-(3,4-difluorobenzoyl)piperidine-1-carbonyl)-N-(1-(4-methoxybenzyl)piperidin-4-yl)picolinamide. $^1H$ nmr ($CDCl_3$) δ 8.52 (1H, m, pyH-6), 8.16 (1H, d, J 8.0 Hz, pyH-3), 7.84 (1H, d, J 7.0 Hz, NH), 7.79 (2H, m, pyH-4, 1H of $C_6H_3F_2$), 7.87 (2H, d, J 9.0 Hz, 2H of $C_6H_4OCH_3$), 6.93 (1H, m, 1H of $C_6H_3F_2$), 6.85 (1H, m, 1H of $C_6H_3F_2$), 6.79 (2H, d, J 8.5 Hz, 2H of $C_6H_4OCH_3$), 4.57 (1H, m, BzpipH-4), 3.93 (1H, m, pipH-4), 3.73 (3H, s, $OCH_3$), 3.65 (1H, m, 1H of BzpipH-2, H-6), 3.42 (2H, s, $CH_2C_6H_4OCH_3$), 3.34 (1H, m, BzpipH-4), 3.06 (2H, m, 2H of BzpipH-2, H-6), 2.79 (2H, m, 2H of pipH-2, H-6), 2.13 (2H, dd, J 11.0, 9.5 Hz, 2H of pipH-2, H-6), 1.97-1.80 (4H, m, 2H of pipH-3, H-5, 2H of BzpipH-3, H-5), 1.75-1.52 (4H, m, 2H of pipH-3, H-5, 2H of BzpipH-3, H-5); $^{19}F$ nmr ($CDCl_3$) δ −101.2, −106.6; m/z: 577 [M+H]

Compound 330: 5-(4-(3,4-difluorobenzoyl)piperidine-1-carbonyl)-N-(6-(4-fluorophenoxy)pyridin-3-yl)picolinamide. $^1H$ nmr ($CDCl_3$) δ 8.77 (1H, m, 1×ArH), 8.51 (1H, d, J 2.5 Hz, 1×ArH), 8.45 (2H, dd, J 5.0, 3.5 Hz, 2×ArH), 8.42 (1H, s, 1×ArH), 8.05 (1H, dd, J 8.0, 2.0 Hz, 1×ArH), 7.99 (1H, m, 1×ArH), 7.22-7.18 (4H, m, 4×ArH), 7.15-6.56 (3H, m, 3×ArH), 4.75 (1H, m, 1H of BzpipH-2, H-6), 3.84 (1H, m, 1H of BzpipH-2, H-6), 3.53 (1H, m, BzpipH-4), 3.33-3.22 (2H, m, 2H of BzpipH-2, H-6), 2.07-2.02 (2H, m, 2H of BzpipH-3, H-5), 1.86 (2H, m, 2H of BzpipH-3, H-5); $^{19}F$ nmr ($CDCl_3$) δ −101.1, −106.5, −118.6; m/z: 561 $[M+H]^+$.

Compound 331: 5-(4-(2,4-difluorobenzoyl)piperidine-1-carbonyl)-N-(1-(4-methoxybenzyl)piperidin-4-yl)picolinamide. $^1H$ nmr ($CDCl_3$) δ 8.59 (1H, d, J 1.5 Hz, pyH-6), 8.23 (1H, d, J 8.0 Hz, pyH-3), 7.92-7.84 (3H, m, NH, pyH-4, 1H of $C_6H_3F_2$), 7.24 (2H, d, J 9.0 Hz, 2H of $C_6H_4OCH_3$), 7.00 (1H, m, 1H of $C_6H_3F_2$), 6.88 (1H, m, 1H of $C_6H_3F_2$), 6.86 (2H, d, J 9.0 Hz, 2H of $C_6H_4OCH_3$), 4.64 (1H, m, 1H of BzpipH-2, H-6), 4.00 (1H, m pipH-4), 3.80 (3H, s, $OCH_3$), 3.74 (1H, m, BzpipH-2, H-6), 3.48 (2H, s, $CH_2C_6H_4OCH_3$), 3.41 (1H, m, BzpipH-4), 3.13 (2H, m, 2H of BzpipH-2, H-6), 2.86 (2H, m, 2H of pipH-2, H-6), 2.19 (2H, dd, J 11.0, 8.5 Hz, 2H of pipH-2, H-6), 1.99 (4H, m, 2H of pipH-3, H-5, 2H of BzpipH-3, H-5), 1.76-1.63 (4H, m, 2H of pipH-3, H-5, 2H of BzpipH-3, H-5); $^{19}F$ nmr ($CDCl_3$) δ−101.3, −11.6.5; m/z: 577 $[M+H]^+$.

Compound 332: N-((cis)-4-(4-cyanophenoxy)cyclohexyl)-6-(4-(4-fluorobenzyl)piperazine-1-carbonyl)nicotinamide. $^1H$ nmr ($CDCl_3$) δ 8.91 (1H, d, J 1.5 Hz, pyH-6), 8.14 (1H, dd, J 8.0, 2.0 Hz, pyH-4), 7.67 (1H, d, J 8.0 Hz, pyH-3), 7.58 (2H, d, J 9.0 Hz, $C_6H_4CN$), 7.28 (2H, m, 2H of $C_6H_4F$), 7.00 (2H, t, J 9.0 Hz, 2H of $C_6H_4F$), 6.95 (2H, d, J 8.5 Hz, 2H of $C_6H_4CN$), 6.19 (1H, d, J 8.0 Hz, NH), 4.62 (1H, m, cHexH-1), 4.12 (1H, m, cHexH-4), 3.82 (2H, m, 2H of piz), 3.51 (4H, m, 2H of piz, $CH_2C_6H_4F$), 2.55 (2H, m, 2H of piz), 2.42 (2H, m, 2H of piz), 2.10 (2H, m, 2H of cHexH-2, H-6), 1.94 (2H, m, 2H of cHexH-2, H-6 or 2H of cHexH-3, H-5), 1.84-1.71 (4H, 2H of cHexH-3, H-5, 2H of cHexH-2, H-6 or cHexH-3, H-5); $^{19}F$ nmr ($CDCl_3$) δ −115.5; m/z: 542 $[M+H]^+$.

Compound 333: tert-butyl 4-(6-(4-(4-cyanophenoxy)piperidine-1-carbonyl)nicotinamido)piperidine-1-carboxylate. $^1H$ nmr ($CDCl_3$) δ 8.91 (1H, d, J 2.0 Hz, pyH-6), 8.11 (1H, dd, J 8.5, 2.0 Hz, pyH-4), 7.58 (2H, d, J 9.5 Hz, 2H of $C_6H_4CN$), 7.51 (1H, d, J 8.5 Hz, pyH-3), 7.21 (1H, d, J 8.0 Hz, NH), 6.94 (2H, d, J 9.0 Hz, 2H of $C_6H_4CN$), 4.68 (1H, m, PhOpipH-4), 4.09 (3H, m, 3H of PhOpipH-2, H-6, pipH-2, H-4, H-6), 3.94-3.80 (2H, m, 2H of PhOpipH-2, H-6, pipH-2, H-4, H-6), 3.07-3.62 (1H, m, 1H of PhOpipH-2, H-6, pipH-2, H-4, H-6), 3.44 (1H, m, 1H of PhOpipH-2, H-6, pipH-2, H-4, H-6), 2.85 (2H, t, J 12.0 Hz, 2H of pipH-2, H-6), 2.10-1.80 (8H, m, PhOpipH-3, H-5, pipH-3, H-5), 1.45 (9H, s, $C(CH_3)_3$); m/z: 534 $[M+H]^+$, 478 $[M+H—C_4H_8]^+$.

Compound 334: 6-(4-(4-fluorobenzyl)piperazine-1-carbonyl)-N-(6-(4-fluorophenoxy)pyridin-3-yl)nicotinamide.

$^1$H nmr (CDCl$_3$) δ 9.56 (1H, s, NH), 8.83 (1H, d, J 2.0 Hz, N,O-pyH-6), 8.38 (1H, d, J 2.5 Hz, pyH-6), 8.27 (1H, dd, J 8.5, 2.5 Hz, pyH-4), 8.00 (1H, dd, J 8.5, 2.0 Hz, N,O-pyH-4), 7.31 (1H, d, J 8.0 Hz, N,O-pyH-3), 7.20 (2H, m, 2H of 1×C$_6$H$_4$F), 7.03 (4H, m, 4H of 1×C$_6$H$_4$F), 6.94 (2H, t, J 9.0 Hz, 2H of 1×C$_6$H$_4$F), 6.88 (1H, d, J 9.0 Hz, pyH-3), 3.76 (2H, m, 2H of piz), 3.44 (2H, s, CH$_2$C$_6$H$_4$F), 3.36 (2H, m, 2H of piz), 2.47 (2H, m, 2H of piz), 2.33 (2H, m, 2H of piz); $^{19}$F nmr (CDCl$_3$) δ −115.3, −118.5; m/z: 530 [M+H]$^+$.

Compound 335: 6-(4-(4-cyanophenoxy)piperidine-1-carbonyl)-N-(piperidin-4-yl)nicotinamide. $^1$H nmr (CDCl$_3$) δ 8.90 (1H, d, J 2.0 Hz, pyH-6), 8.12 (1H, dd, J 8.0, 2.0 Hz, pyH-4), 7.58 (3H, m, 2H of C$_6$H$_4$CN, NH), 6.95 (2H, d, J 9.0 Hz, 2H of C$_6$H$_4$CN), 6.68 (1H, d, J 8.0 Hz, pyH-3), 4.69 (1H, m, PhOpipH-4), 4.07 (1H, m, pipH-4), 3.89 (2H, m, 2H of PhOpipH-2, H-6), 3.69 (1H, m, 1H of PhOpipH-2, H-6), 3.47 (1H, m, 1H of PhOpipH-2, H-6), 3.12 (2H, m, 2H of pipH-2, H-6), 2.74 (2H, m, 2H of pipH-2, H-6), 2.10-1.81 (6H, m, PhOpipH-3, H-5, 2H of pipH-3, H-5), 1.48 (2H, m, 2H of pipH-3, H-5); m/z: 434 [M+H]$^+$.

Compound 336: 6-(4-(4-cyanophenoxy)piperidine-1-carbonyl)-N-(1-(4-(pyrrolidin-1-yl)benzyl)piperidin-4-yl)nicotinamide. $^1$H nmr (CDCl$_3$) δ 8.95 (1H, d, J 1.5 Hz, pyH-6), 8.19 (1H, dd, J 8.5, 2.0 Hz, pyH-4), 7.67 (1H, d, J 8.0 Hz, pyH-3), 7.59 (2H, d, J 9.0 Hz, 2H of C$_6$H$_4$CN), 7.20 (2H, d, J 9.0 Hz, 2H of C$_6$H$_4$N), 6.96 (2H, d, J 9.0 Hz, 2H of C$_6$H$_4$CN), 6.72 (1H, d, J 7.0 Hz, NH), 6.53 (2H, d, J 9.0 Hz, 2H of C$_6$H$_4$N), 4.69 (1H, m, PhOpipH-4), 4.08 (1H, m, pipJ-4), 3.93-3.86 (2H, m, 2 h of PhOpipH-2, H-6), 3.71 (1H, m, 1H of PhOpipH-2, H-6), 3.65 (2H, s, CH$_2$C$_6$H$_4$N), 3.50 (1H, m, PhOpipH-2, H-6), 3.28 (4H, m, pyrrolidineH-2, H-5), 3.09 (2H, m, 2H of pipH-2, H-6), 2.35 (6H, m, 2H of pipH-2, H-6, pyrrolidineH-3, H-4), 2.08-1.86 (8H, m, pipH-3, H-5, PhOpipH-3, H-5); m/z: 594 [M+H]$^+$.

Compound 337: 6-(4-(4-cyanophenoxy)piperidine-1-carbonyl)-N-(1-(4-morpholinobenzyl)piperidin-4-yl)nicotinamide. $^1$H nmr (CDCl$_3$) δ 8.92 (1H, m, pyH-6), 8.15 (1H, dd, J 8.0, 2.0 Hz, pyH-4), 7.69 (1H, d, J 8.5 Hz, pyH-3), 7.59 (2H, d, J 9.0 Hz, 2H of C$_6$H$_4$CN), 7.25 (2H, m, 2H of C$_6$H$_4$N), 6.96 (2H, d, J 9.5 Hz, 2H of C$_6$H$_4$CN), 6.88 (2H, d, J 9.0 Hz, 2H of C$_6$H$_4$N), 6.29 (1H, d, J 7.0 Hz, NH), 4.70 (1H, m, PhOpipH-4), 4.04 (1H, m, pipH-4), 3.91 (2H, m, 2H of PhOpipH-2, H-6), 3.87, 3.85 (4H, d AB system, J 5.0 Hz, 2×morpholineH-2, H-6), 3.72 (1H, m, 1H of PhOpipH-2, H-6), 3.55 (3H, m, CH$_2$C$_6$H$_4$N, 1H of PhOpipH-2, H-6), 3.17, 3.15 (4H, d AB system, J 4.5 Hz, 2×morpholineH-3, H-5), 2.96 (2H, m, 2H of pipH-2, H-6), 2.24 (2H, dd, J 12.0, 10.5 Hz, 2H of pipH-2, H-6), 2.02 (4H, m, 2H of pipH-3, H-5, 2H of PhOpipH-3, H-5), 1.81-1.69 (4H, m, 2H of pipH-3, H-5, PhOpipH-3, H-5); m/z: 610 [M+H]$^+$.

Compound 338: 6-(4-(4-cyanophenoxy)piperidine-1-carbonyl)-N-(1-(4-(trifluoromethoxy)benzyl)piperidin-4-yl)nicotinamide. $^1$H nmr (CDCl$_3$) δ 8.92 (1H, d, J 2.0 Hz, pyH-6), 8.16 (1H, dd, J 8.5, 2.0 Hz, pyH-4), 7.69 (1H, d, J 8.0 Hz, pyH-3), 7.59 (2H, d, J 9.0 Hz, 2H of C$_6$H$_4$CN), 7.38 (2H, d, J 8.5 Hz, 2H of C$_6$H$_4$OCF$_3$), 7.18 (2H, d, J 8.5 Hz, 2H of C$_6$H$_4$OCF$_3$), 6.96 (2H, d, J 9.0 Hz, 2H of C$_6$H$_4$CN), 6.22 (1H, m, NH), 4.70 (1H, m, PhOpipH-4), 4.06 (1H, m, pipH-4), 3.94-3.88 (2H, m, 2H of PhOpipH-2, H-6), 3.71 (1H, m, 1H of PhOpipH-2, H-6), 3.58 (2H, s, CH$_2$C$_6$H$_4$OCF$_3$), 3.50 (1H, m, PhOpipH-2, H-6), 2.93 (2H, m, 2H of pipH-2, H-6), 2.25 (2H, dd, J 11.5, 10.5 Hz, 2H of pipH-2, H-6), 2.05 (4H, m, pipH-3, H-5, 2H of PhOpipH-3, H-5), 1.84-1.67 (4H, m, 2H of pipH-3, H-5, 2H of PhOpipH-3, H-5); $^{19}$F nmr (CDCl$_3$) δ −57.9; m/z: 609 [M+H]$^+$.

Compound 339: N-(1-(4-cyanobenzyl)piperidin-4-yl)-5-(4-(4-(trifluoromethyl)phenyl)piperazine-1-carbonyl)picolinamide. $^1$H nmr (CDCl$_3$) δ 8.63 (1H, m, pyH-6), 8.27 (1H, d, J 8.0 Hz, pyH-3), 7.93 (1H, m, NH), 7.92 (1H, dd, J 8.0, 2.0 Hz, pyH-4), 7.61 (2H, d, J 8.5 Hz, 2H of C$_6$H$_4$CN or C$_6$H$_4$CF$_3$), 7.51 (2H, d, J 8.5 Hz, 2H of C$_6$H$_4$CN or C$_6$H$_4$CF$_3$), 7.46 (2H, d, J 8.5 Hz, 2H of C$_6$H$_4$CN or C$_6$H$_4$CF$_3$), 6.94 (2H, d, J 8.5 Hz, 2H of C$_6$H$_4$CN or C$_6$H$_4$CF$_3$), 4.00 (3H, m, pipH-4, 2H of piz), 3.57 (4H, m, CH$_2$C$_6$H$_4$CN, 2H of piz), 3.31 (4H, m, 4H of piz), 2.82 (2H, m, 2H of pipH-2, H-6), 2.24 (2H, dd, J 11.5, 9.5 Hz, 2H of pipH-2, H-6), 2.02 (2H, m, 2H of pipH-3, H-5), 1.65 (2H, m, 2H of pipH-3, H-5); $^{19}$F nmr (CDCl$_3$) δ −61.6; m/z: 577 [M+H]$^+$.

Compound 340: N-(1-(4-cyanobenzyl)piperidin-4-yl)-5-(4-(4-cyanophenyl)piperazine-1-carbonyl)picolinamide. $^1$H nmr (CDCl$_3$) δ 8.63 (1H, m, pyH-6), 8.25 (1H, d, J 8.0 Hz, pyH-3), 7.90 (2H, m, NH, pyH-4), 7.60 (2H, d, J 8.5 Hz, 2H of 1×C$_6$H$_4$CN), 7.52 (2H, d, J 9.0 Hz, 2H of 1×C$_6$H$_4$CN), 7.45 (2H, d, J 8.5 Hz, 2H of 1×C$_6$H$_4$CN), 6.87 (2H, d, J 9.5 Hz, 2H of 1×C$_6$H$_4$CN), 4.03-3.90 (3H, m, pipH-4, 2H of piz), 3.60 (2H, m, 2H of piz), 3.56 (2H, s, CH$_2$C$_6$H$_4$CN), 3.36 (4H, m, 4H of piz), 2.80 (2H, m, 2H of pipH-2, H-6), 2.23 (2H, dd, J 11.0, 10.0 Hz, 2H of pipH-2, H-6), 2.01 (2H, m, 2H of pipH-3, H-5), 1.65 (2H, m, 2H of pipH-3, H-5); m/z: 534 [M+H]$^+$.

Compound 341: N-(1-(4-cyanobenzyl)piperidin-4-yl)-5-(4-(4-fluorophenyl)piperazine-1-carbonyl)picolinamide. $^1$H nmr (CDCl$_3$) δ 8.63 (1H, m, pyH-6), 8.26 (1H, dd, J 8.0, 1.0 Hz, pyH-3), 7.93 (1H, d, J 8.0 Hz, NH), 7.91 (1H, dd, J 8.0, 2.0 Hz, pyH-4), 7.62 (2H, d, J 8.5 Hz, 2H of C$_6$H$_4$CN), 7.46 (2H, d, J 8.0 Hz, 2H of C$_6$H$_4$CN), 6.99 (2H, m, 2H of C$_6$H$_4$F), 6.89 (2H, m, 2H of C$_6$H$_4$F), 3.99 (3H, m, pipH-4, 2H of piz), 3.57 (3H, m, CH$_2$C$_6$H$_4$CN, 2H of piz), 3.18 (2H, m, 2H of piz), 3.07 (2H, m, 2H of piz), 2.82 (2H, m, 2H of pipH-2, H-6), 2.24 (2H, mdd, J 11.0, 10.0 Hz, 2H of pipH-2, H-6), 2.03 (2H, m, 2H of pipH-3, H-5), 1.65 (2H, m, 2H of pipH-3, H-5); $^{19}$F nmr (CDCl$_3$) δ −122.6; m/z: 527 [M+H]$^+$.

Compound 342: 5-(4-(2,4-difluorobenzoyl)piperidine-1-carbonyl)-N-(6-(4-fluorophenoxy)pyridin-3-yl)picolinamide. $^1$H nmr (CDCl$_3$) δ 9.90 (1H, s, NH), 8.67 (1H, m, 1×pyH-6), 8.41 (1H, d, J 2.0 Hz, 1×pyH-6), 8.36-8.33 (2H, m, 2×pyH), 7.95 (1H, dd, J 8.0, 2.0 Hz, 1×pyH-4), 7.89 (1H, m, 1H of C$_6$H$_3$F$_2$), 7.13-7.08 (4H, m, 4H of C$_6$H$_4$F), 7.00 (1H, m, 1H of C$_6$H$_3$F$_2$), 6.97 (1H, d, J 9.0 Hz, 1×pyH-3), 6.90 (1H, ddd, J 11.5, 9.0, 2.5 Hz, 1H of C$_6$H$_3$F$_2$), 4.64 (1H, m, 1H of BzpipH-2, H-6), 3.75 (1H, m, 1H of BzpipH-2, H-6), 3.43 (1H, m, BzpipH-4), 3.19 (1H, m, 1H of BzpipH-2, H-6), 3.12 (1H, m, 1H of BzpipH-2, H-6), 2.08 (1H, m, 1H of BzpipH-3, H-5), 1.90 (1H, m, 1H of BzpipH-3, H-5), 1.78 (2H, m, 2H of BzpipH-3, H-5); $^{19}$F nmr (CDCl$_3$) δ −101.1, −116.5, −118.6; m/z: 562 [M+H]$^+$ (found [M+H]$^+$, 561.1844, C$_{32}$H$_{35}$N$_5$O$_3$ requires [M+H]$^+$ 561.1744).

Compound 343: 6-(4-(2,4-difluorophenoxy)piperidine-1-carbonyl)-N-(6-(4-fluorophenoxy)pyridin-3-yl)nicotinamide. $^1$H nmr (CDCl$_3$) δ 9.79 (1H, s, NH), 8.92 (1H, m, pyH-6), 8.47 (1H, d, J 2.5 Hz, N, O-pyH-6), 8.34 (1H, dd, J 9.0, 2.5 Hz, N, O-pyH-4), 8.08 (1H, dd, J 8.0, 2.0 Hz, pyH-4), 7.36 (1H, d, J 8.0 Hz, pyH-3), 7.11-7.01 (4H, m, C$_6$H$_4$F), 6.99-6.92 (2H, m, N, O-pyH-3, 1H of C$_6$H$_3$F$_2$), 6.90-6.76 (2H, m, 2H of C$_6$H$_3$F$_2$), 4.47 (1H, m, PhOpipH-4), 3.92 (1H, m, 2H of PhOpipH-2, H-6), 3.66 (1H, m, 1H of PhOpipH-2, H-6), 3.35 (1H, m, 1H of PhOpipH-2, H-6), 1.98 (2H, m, 2H of PhOpipH-3, H-5), 1.93-1.80 (2H, m, 2H of PhOpipH-3, H-5); $^{19}$F nmr (CDCl$_3$) δ −117.4, −118.5, −127.3; m/z: 549 [M+H]$^+$.

Compound 344: 6-(4-(2,4-difluorophenoxy)piperidine-1-carbonyl)-N-(1-(4-methoxybenzyl)piperidin-4-yl)nicotinamide. $^1$H nmr (CDCl$_3$) δ 8.91 (1H, m, pyH-6), 8.21 (1H, dd, J 8.0, 2.0 Hz, pyH-4), 7.57 (1H, d, J 8.0 Hz, pyH-3), 7.25 (2H, d, J 9.0 Hz, 2H of C$_6$H$_4$OCH$_3$), 6.97 (1H, td, J 9.0, 5.5 Hz, 1H of C$_6$H$_3$F$_2$), 6.89-6.75 (4H, m, 2H of C$_6$H$_4$OCH$_3$, 2H of C$_6$H$_3$F$_2$), 4.45 (1H, m, PhOpipH-4), 4.03 (1H, m, 1H of pipH-4), 3.92-3.85 (2H, m, 2H of PhOpipH-2, H-6), 3.79 (3H, s, OCH$_3$), 3.71 (1H, m, 1H of PhOpipH-2, H-6), 3.57 (2H, s, CH$_2$C$_6$H$_4$OCH$_3$), 3.44-3.37 (1H, m, 1H of PhOpipH-2, H-6), 2.97 (2H, m, 2H of pipH-2, H-6), 2.27 (2H, dd, J 11.5, 10.5 Hz, 2H of pipH-2, H-6), 2.04-1.90 (5H, m, 2H of pipH-3, H-5, 3H of PhOpipH-3, H-5), 1.83 (1H, m, 1H of PhOpipH-3, H-5), 1.72 (2H, m, 2H of pipH-3, H-5); $^{19}$F nmr (CDCl$_3$) δ −117.7, −127.3; m/z: 565 [M+H]$^+$.

Compound 345: N-(1-(4-cyanobenzyl)piperidin-4-yl)-6-(4-(2,4-difluorophenoxy)piperidine-1-carbonyl)nicotinamide. $^1$H nmr (CDCl$_3$) δ 8.90 (1H, m, pyH-6), 8.13 (1H, dd, J 8.0, 2.0 Hz, pyH-4), 7.65 (1H, d, J 8.5 Hz, pyH-3), 7.61 (2H, d, J 8.5 Hz, 2H of C$_6$H$_4$CN), 7.45 (2H, d, J 8.5 Hz, 2H of C$_6$H$_4$CN), 6.98 (1H, dt, J 5.0, 9.0 Hz, 1H of C$_6$H$_3$F$_2$H-5 or H-6), 6.86 (1H, m, 1H of C$_6$H$_3$F$_2$H-3), 6.79 (1H, m, 1H of C$_6$H$_3$F$_2$H-5 or H-6), 6.24 (1H, d, J 8.0 Hz, NH), 4.47 (1H, m, PhOpipH-4), 4.03 (1H, m, pipH-4), 3.95-3.87 (2H, m, 2H of PhOpipH-2, H-6), 3.75 (1H, m, 1H of PhOpipH-2, H-6), 3.57 (2H, s, CH$_2$C$_6$H$_4$CN), 3.42 (1H, m, 1H of PhOpipH-2, H-6), 2.84 (2H, m, 2H of pipH-2, H-6), 2.21 (2H, dd, J 11.5, 9.5 Hz, 2H of pipH-2, H-6), 2.06-1.92 (5H, m, 2H of pipH-3, H-5, 3H of PhOpipH-3, H-5), 1.86 (1H, m, 1H of PhOpipH-3, H-5), 1.62 (2H, m, 2H of pipH-3, H-5); $^{19}$F nmr (CDCl$_3$) δ−117.6, −127.3; m/z: 560 [M+H]$^+$.

Compound 346: N-(1-(4-cyanobenzyl)piperidin-4-yl)-6-(4-(2,4-difluorobenzoyl)piperidine-1-carbonyl)nicotinamide. $^1$H nmr (CDCl$_3$) δ 8.89 (1H, m, pyH-6), 8.10 (1H, dd, J 8.5, 2.0 Hz, pyH-4), 7.87 (1H, dt, J 6.5, 8.5 Hz, 1H of C$_6$H$_3$F$_2$), 7.61 (2H, d, J 8.5 Hz, 2H of C$_6$H$_4$CN), 7.58 (1H, m, pyH-3), 7.45 (2H, d, J 8.0 Hz, 2H of C$_6$H$_4$CN), 6.99 (1H, ddd, J 9.5, 9.0, 2.5 Hz, 1H of C$_6$H$_3$F$_2$), 6.89 (1H, m, 1H of C$_6$H$_3$F$_2$), 6.50 (1H, d, J 8.0 Hz, NH), 4.67 (1H, m, 1H of BzpipH-2, H-6), 4.02 (1H, m, pipH-4), 3.89 (1H, m, 1H of BzpipH-2, H-6), 3.56 (3H, s, CH$_2$C$_6$H$_4$CN), 3.40 (1H, m, BzpipH-4), 3.21 (1H, m, BzpipH-2, H-6), 3.08 (1H, ddd, J 11.5, 10.5, 3.0 Hz, 1H of BzpipH-2, H-6), 2.83 (2H, m, 2H of pipH-2, H-6), 2.21 (2H, dd, J 11.5, 10.0 Hz, 2H of pipH-2, H-6), 2.08-2.01 (3H, m, 2H of pipH-3, H-5, 1H of BzpipH-3, H-5), 1.89-1.72 (3H, m, 3H of BzpipH-3, H-5), 1.63 (2H, m, 2H of pipH-3, H-5); $^{19}$F nmr (CDCl$_3$) δ −101.5, −106.5; m/z: 572 [M+H]$^+$.

Compound 347: 6-(4-(2,4-difluorobenzoyl)piperidine-1-carbonyl)-N-(1-(4-methoxybenzyl)piperidin-4-yl)nicotinamide. $^1$H nmr (CDCl$_3$) δ 8.88 (1H, d, J 2.0 Hz, pyH-6), 8.11 (1H, dd, J 8.0, 2.0 Hz, pyH-4), 7.86 (1H, dt, J 6.5, 8.5 Hz, 1H of C$_6$H$_3$F$_2$), 7.59 (1H, d, J 8.0 Hz, pyH-3), 7.23 (2H, d, J 9.0 Hz, 2H of C$_6$H$_4$OCH$_3$), 6.98 (1H, m, 1H of C$_6$H$_3$F$_2$), 6.92-6.84 (3H, m, 2H of C$_6$H$_4$OCH$_3$, 1H of C$_6$H$_3$F$_2$), 6.39 (1H, d, J 7.5 Hz, NH), 4.65 (1H, m, 1H of BzpipH-2, H-6), 4.01 (1H, m, pipH-4), 3.89 (1H, m, 1H of BzpipH-2, H-6), 3.80 (3H, s, OCH$_3$), 3.51 (2H, s, CH$_2$C$_6$H$_4$OCH$_3$), 3.39 (1H, m, BzpipH-4), 3.21 (1H, ddd, J 10.5, 9.0, 3.0 Hz, 1H of BzpipH-2, H-6), 3.08 (1H, m, 1H of BzpipH-2, H-6), 2.90 (2H, m, 2H of pipH-2, H-6), 2.21 (2H, dd, J 11.5, 10.0 Hz, 2H of pipH-2, H-6), 2.03 (4H, m, 2H of pipH-3, H-5, 2H of BzpipH-3, H-5), 1.89-1.76 (2H, m, 2H of BzpipH-3, H-5), 1.62 (2H, m, 2H of pipH-3, H-5); $^{19}$F nmr (CDCl$_3$) δ −101.6, −106.5; m/z: 577 [M+H]$^+$.

Compound 348: 6-(4-(2,4-difluorobenzoyl)piperidine-1-carbonyl)-N-(6-(4-fluorophenoxy)pyridin-3-yl)nicotinamide. $^1$H nmr (CDCl$_3$) δ 9.81 (1H, s, NH), 8.91 (1H, m, pyH-6), 8.48 (1H, d, J 2.5 Hz, N,O-pyH-6), 8.34 (1H, dd, J 8.5, 2.5 Hz, N,O-pyH-4), 8.07 (1H, dd, J 8.0, 2.0 Hz, pyH-4), 7.87 (1H, dt, J 8.5, 6.5 Hz, 1H of C$_6$H$_3$F$_2$), 7.35 (1H, d, J 8.0 Hz, pyH-3), 7.10-6.85 (3H, m, N,O-pyH-3, 2H of C$_6$H$_3$F$_2$), 4.65 (1H, m, 1H of BzpipH-2, H-6), 3.78-3.73 (1H, m, 1H of BzpipH-2, H-6), 3.40 (1H, m, BzpipH-4), 3.23-3.07 (2H, m, 2H of BzpipH-2, H-6), 2.08 (1H, m, 1H of BzpipH-3, H-5), 1.90-1.74 (3H, m, 3H of BzpipH-3, H-5); $^{19}$F nmr (CDCl$_3$) δ −101.3, −106.5, −118.6; m/z: 561 [M+H]$^+$.

Synthesis of Compounds 349 and 350

Coupling of the 1-tert-Butyloxycarbonyl-3-Fluoro-4-aminopiperidine

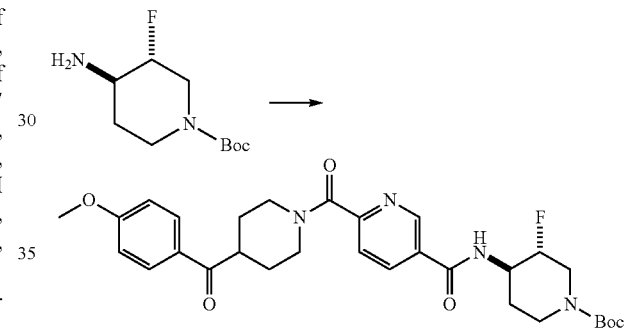

To a mixture of the crude pyridine carboxylic acid (2.15 g of approximately 66% purity, 3.86 mmol, 1.0 eq) and 1-tert-butyl-3-fluoro-4-aminopiperidine (0.84 g, 3.86 mmol, 1.0 eq) was added dimethylformamide (40 mL) followed by triethylamine (1.31 mL, 9.64 mmol, 2.5 eq). After the addition of HATU (1.47 g, 3.86 mmol, 1.0 eq) the reaction was stirred at room temperature for 4 hours before partitioning between EtoAc (300 mL) and water-NaHCO$_3$ (1:1, 300 mL). The organics were further washed with brine (250 mL), water (300 mL) and brine (250 mL) before drying (Na$_2$SO$_4$) and concentrating under reduced pressure. MPLC (0→10% MeOH—CH$_2$Cl$_2$) yielded the coupled material (1.41 g, 64%) as a pale yellow oil; $^1$H nmr (CDCl$_3$) δ 8.90 (1H, m, pyH-6), 8.11 (1H, dt, J 8.0, 2.0 Hz, pyH-4), 7.93 (2H, d, J 9.0 Hz, 2H of C$_6$H$_4$OCH$_3$), 7.56 (1H, d, J 6.0 Hz, NH), 7.50 (1H, dd, J 8.0, 2.0 Hz, pyH-3), 6.95 (2H, d, J 9.0 Hz, 2H of C$_6$H$_4$OCH$_3$), 4.65 (1H, m, 1H of BzpipH-2, H-6), 4.47 (0.5H, m, 0.5H of pipH-3), 4.31 (2.5H, m, 0.5H of pipH-3, pipH-4, 1H of pipH-2), 4.00 (1H, m, 1H of BzpipH-2, H-6), 3.87 (3H, s, OCH$_3$), 3.84 (1H, m, 1H of pipH-6), 3.53 (1H, m, BzpipH-4), 3.23 (1H, m, 1H of pipH-6), 3.11 (1H, m, 1H of BzpipH-2, H-6), 2.90 (2H, m, 1H of pipH-2, 1H of BzpipH-2, H-6), 2.08-1.92 (2H, m, 2H of pipH-5, BzpipH-3, H-5), 1.91-1.80 (4H, m, 4H of pipH-5, BzpipH-3, H-5), 1.47 (9H, s, C(CH$_3$)$_3$); $^{19}$F nmr (CDCl$_3$) δ −189.3 (d, J 47.5 Hz); m/z: 569 [M+H]$^+$.

Deprotection of the Tert-Butyloxycarbonyl Group

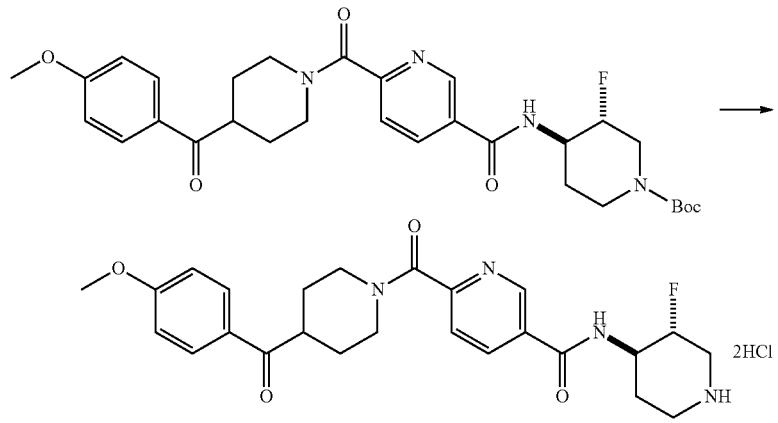

To a solution of the tert-butyloxycarbonylpiperidine (1.41 g, 2.48 mmol, 1.0 eq) in dichloromethane (25 mL) was added hydrogen chloride (2.5 mL of a 4.0M solution in dioxane, 9.93 mmol, 4.0 eq). The reaction was stirred at room temperature for 6 hours. A residue formed over the course of the reaction. Et$_2$O (100 mL) was added resulting in a percipitate after sonication, which was isolated by filtration. The resulting solid was dried under vacuum to yield the fluoropiperidine dihydrochloride as a pale orange solid (1.32 g, quantitative), which was used without further purification; $^1$H nmr (D$_6$-DMSO) δ 8.96 (2H, m, CONH, pyH-6), 8.30 (1H, dt, J 8.0, 2.0 Hz, pyH-4), 7.94 (2H, d, J 9.0 Hz, 2H of C$_6$H$_4$OCH$_3$), 7.62 (1H, dd, J 8.0 Hz, pyH-3), 6.99 (2H, d, J 9.5 Hz, 2H of C$_6$H$_4$OCH$_3$), 4.93, 4.75 (1H, 2 m, pipH-3), 4.46 (1H, m, 1H of BzpipH-2, H-6), 4.32 (1H, m, pipH-4), 3.78 (3H, s, OCH$_3$), 3.69 (1H, m, BzpipH-4), 3.57-3.50 (2H, m, 1H of pipH-2, 1H of BzpipH-2, H-6), 3.28-3.10 (3H, m, 1H of pipH-2, 1H of pipH-6, 1H of BzpipH-2, H-6), 3.08-2.94 (2H, m, 1H of pipH-6, 1H of BzpipH-2, H-6), 2.02 (1H, m, 1H of pipH-5), 1.82 (2H, m, 1H of pipH-5, 1H of BzpipH-3, H-5), 1.63 (1H, m, 1H of BzpipH-3, H-5), 1.55-1.47 (2H, m, 2H of BzpipH-3, H-5); $^{19}$F nmr (D$_6$-DMSO) δ −188.6 (d, J 50.0 Hz); m/z: 469 [M+H]$^+$.

Compound 349

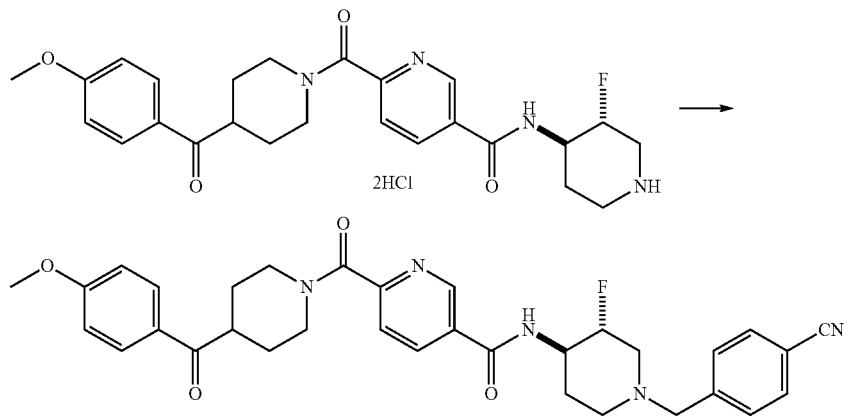

To a suspension of the fluoropiperidine dihydrochloride (0.250 g, 0.462 mmol, 1.0 eq) in dischlormethane (5.0 mL) was added diisopropylethylamine (0.28 mL, 1.617 mmol, 3.5 eq) to form a clear solution. 4-Cyanobenzyl bromide (0.100 g, 0.508 mmol, 1.1 eq) was added and the reaction stirred at room temperature for 5 hours before pouring into NaHCO$_3$ (40 mL). The organics were extracted with CH$_2$Cl$_2$ (3×40 mL), combined, dried (Na$_2$SO$_4$) and concentrated under reduced pressure. MPLC (3→5% MeOH—CH$_2$Cl$_2$) yielded the cyanobenzylpiperidine (0.162 g, 60%) as a white foam; IR (film) 3313, 2953, 1662, 1622, 1599, 1544, 1448, 1259, 1170, 1027, 971, 912, 848, 731 cm$^{-1}$; $^1$H nmr (CDCl$_3$) δ 8.88 (1H, d, J 2.0 Hz, pyH-6), 8.07 (1H, dd, J 8.5, 2.0 Hz, pyH-4), 7.94 (2H, d, J 9.0 Hz, 2H of C$_6$H$_4$OCH$_3$), 7.60 (2H, d, J 8.0 Hz, 2H of C$_6$H$_4$CN), 7.48 (1H, d, J 8.0 Hz, pyH-3), 7.43 (2H, d, J 8.0 Hz, 2H of C$_6$H$_4$CN), 7.33 (1H, m, NH), 6.96 (2H, d, J 9.0 Hz, 2H of C$_6$H$_4$OCH$_3$), 4.70 (1H, m, 1H of BzpipH-2, H-6), 4.70, 4.53 (1H, m, pipH-3), 4.15 (1H, m, pipH-4), 3.88 (3H, s, OCH$_3$), 3.82 (1H, m, 1H of BzpipH-2, H-6), 3.63 (2H, s, CH$_2$C$_6$H$_4$CN), 3.54 (1H, m, BzpipH-4), 3.28-3.09 (3H, m, 2H of BzpipH-2, H-6, 1H of pipH-6), 2.80 (1H, m, 1H of pipH-2), 2.30-2.17 (3H, m, 1H of pipH-6, 1H of pipH-5, 1H of pipH-2), 2.03 (1H, m, 1H of BzpipH-3, H-5), 1.93-1.82 (3H, m, 3H of BzpipH-3, H-5), 1.67 (1H, m, 1H of pipH-5); $^{13}$C nmr (CDCl$_3$) δ 199.9, 167.2, 165.3, 163.7, 155.8, 147.5, 143.8, 136.1, 132.2, 130.8, 130.6, 129.2, 128.5, 122.6, 118.8, 114.0, 111.1, 89.5 (90.7, 88.4, d, J 178.5 Hz), 61.7, 56.5 (56.7, 56.3, J 25.0 Hz), 55.5, 52.3 (52.4, 52.1, J 17.5 Hz), 51.7, 46.7, 42.6, 41.9, 29.9 (29.9, 29.8 J 6.5 Hz), 28.6 (28.8, 28.4, J 28.0

Hz); $^{19}$F nmr (CDCl$_3$) δ −188.5 (d, J 55 Hz); m/z: 584 [M+H]$^+$ (found [M+H]$^+$, 584.2711, C$_{33}$H$_{34}$FN$_5$O$_4$ requires [M+H]$^+$ 584.2668). Compound 350

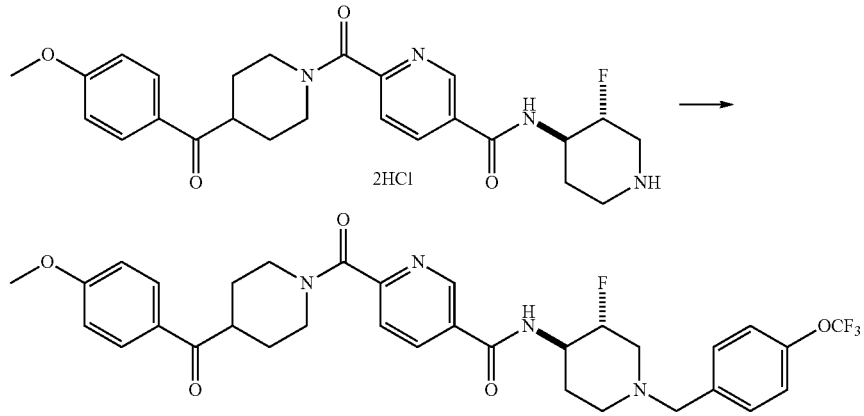

To a suspension of the fluoropiperidine dihydrochloride (0.100 g, 0.185 mmol, 1.0 eq) in dichloromethane (2.0 mL) was added diisopropylethylamine (0.112 mL, 0.647 mmol, 3.5 eq) forming a clear solution. Trifluoromethoxybenzyl bromide (0.035 mL, 0.218 mmol, 1.2 eq) was added and the reaction stirred at room temperature for 4 hours before pouring into NaHCO$_3$ (50 mL). The organics were extracted with CH$_2$Cl$_2$ (3×45 mL), combined, dried (Na$_2$SO$_4$), and concentrated under reduced pressure. MPLC (0→10% MeOH—CH$_2$Cl$_2$) yielded the trifluoromethoxypiperidine (0.076 g, 64%) as a white foam; IR (film) 3314, 3074, 2953, 1665, 1623, 1600, 1509, 1449, 1260, 1221, 1169, 1028, 971, 732 cm$^{-1}$; $^1$H nmr (CDCl$_3$) δ 8.88 (1H, d, J 2.0 Hz, pyH-6), 8.07 (1H, dd, J 8.0, 2.0 Hz, pyH-4), 7.94 (2H, d, J 9.0 Hz, 2H of C$_6$H$_4$OCH$_3$), 7.48 (1H, d, J 8.5 Hz, pyH-3), 7.33 (2H, d, J 8.5 Hz, 2H of C$_6$H$_4$OCF$_3$), 7.15 (2H, d, J 8.0 Hz, 2H of C$_6$H$_4$OCF$_3$), 6.95 (2H, d, J 9.0 Hz, 2H of C$_6$H$_4$OCH$_3$), 4.69 (1H, m, 1H of BzpipH-2, H-6), 4.69, 4.52 (1H, m, pipH-3), 4.15 (1H, m, pipH-4), 3.87 (3H, s, OCH$_3$), 3.82 (1H, m, 1H of BzpipH-2, H-6), 3.58-3.50 (3H, m, CH$_2$C$_6$H$_4$OCF$_3$, BzpipH-4), 3.28-3.08 (3H, m, 2H of BzpipH-2, H-6, 1H of pipH-2 or H-6), 2.82 (1H, m, 1H of pipH-2 or H-6), 2.26-2.14 (3H, m, 1H of pipH-5, 2H of pipH-2, H-6), 2.01 (1H, m, 1H of BzpipH-3, H-5), 1.94-1.80 (3H, m, 3H of BzpipH-3, H-5), 1.66 (1H, m, 1H of pipH-5); $^{13}$C nmr (CDCl$_3$) δ 200.0, 167.2, 165.3, 163.7, 155.8, 148.4, 147.4, 136.7, 136.1, 130.8, 130.0, 128.5, 122.7, 120.9, 114.0, 89.7 (90.9, 88.6 J 178.5 Hz), 61.4, 56.3 (56.5, 56.2 J 25.4 Hz), 55.5, 52.4 (52.5, 52.3 J 18.2 Hz), 51.6, 46.7, 42.6, 41.9, 29.9 (30.0, 29.9 J 6.6 Hz), 28.6 (28.8, 28.4 J 17.7 Hz); $^{19}$F nmr (CDCl$_3$) δ −57.9, −188.4; m/z: 644 [M+H]$^+$ (found [M+H]$^+$, 643.2534, C$_{33}$H$_{34}$F$_4$N$_4$O$_5$ requires [M+H]$^+$ 643.2538).

Compound 349: N-((trans)-1-(4-cyanobenzyl)-3-fluoropiperidin-4-yl)-6-(4-(4-methoxybenzoyl)piperidine-1-carbonyl)nicotinamide. $^1$H nmr (CDCl$_3$) δ 8.88 (1H, d, J 2.0 Hz, pyH-4), 8.07 (1H, dd, J 8.5, 2.0 Hz, pyH-4), 7.94 (2H, d, J 9.0 Hz, 2H of C$_6$H$_4$OCH$_3$), 7.60 (2H, d, J 8.0 Hz, 2H of C$_6$H$_4$CN), 7.48 (1H, d, J 8.0 Hz, pyH-3), 7.43 (2H, d, J 8.0 Hz, 2H of C$_6$H$_4$CN), 7.33 (1H, m, NH), 6.96 (2H, d, J 9.0 Hz, 2H of C$_6$H$_4$OCH$_3$), 4.70 (1H, m, 1H of BzpipH-2, H-6), 4.70, 4.53 (1H, m, pipH-3), 4.15 (1H, m, pipH-4), 3.88 (3H, s, OCH$_3$), 3.82 (1H, m, 1H of BzpipH-2, H-6), 3.63 (2H, s, CH$_2$C$_6$H$_4$CN), 3.54 (1H, m, BzpipH-4), 3.28-3.09 (3H, m, 2H of BzpipH-2, H-6, 1H of pipH-6), 2.80 (1H, m, 1H of pipH-2), 2.30-2.17 (3H, m, 1H of pipH-6, 1H of pipH-5, 1H of pipH-2), 2.03 (1H, m, 1H of BzpipH-3, H-5), 1.93-1.82 (3H, m, 3H of BzpipH-3, H-5), 1.67 (1H, m, 1H of pipH-5); $^{19}$F nmr (CDCl$_3$) δ−188.5; m/z: 584 [M+H]$^+$.

Compound 350: N-((trans)-3-fluoro-1-(4-(trifluoromethoxy)benzyl)piperidin-4-yl)-6-(4-(4-methoxybenzoyl)piperidine-1-carbonyl)nicotinamide. $^1$H nmr (CDCl$_3$) δ 8.88 (1H, d, J 2.0 Hz, pyH-6), 8.07 (1H, dd, J 8.0, 2.0 Hz, pyH-4), 7.94 (2H, d, J 9.0 Hz, 2H of C$_6$H$_4$OCH$_3$), 7.48 (1H, d, J 8.5 Hz, pyH-3), 7.33 (2H, d, J 8.5 Hz, 2H of C$_6$H$_4$OCF$_3$), 7.15 (2H, d, J 8.0 Hz, 2H of C$_6$H$_4$OCF$_3$), 6.95 (2H, d, J 9.0 Hz, 2H of C$_6$H$_4$OCH$_3$), 4.69 (1H, m, 1H of BzpipH-2, H-6), 4.69, 4.52 (1H, m, pipH-3), 4.15 (1H, m, pipH-4), 3.87 (3H, s, OCH$_3$), 3.82 (1H, m, 1H of BzpipH-2, H-6), 3.58-3.50 (3H, m, CH$_2$C$_6$H$_4$OCF$_3$, BzpipH-4), 3.28-3.08 (3H, m, 2H of BzpipH-2, H-6, 1H of pipH-2 or H-6), 2.82 (1H, m, 1H of pipH-2 or H-6), 2.26-2.14 (3H, m, 1H of pipH-5, 2H of pipH-2, H-6), 2.01 (1H, m, 1H of BzpipH-3, H-5), 1.94-1.80 (3H, m, 3H of BzpipH-3, H-5), 1.66 (1H, m, 1H of pipH-5); $^{19}$F nmr (CDCl$_3$) δ −57.9, −188.4; m/z: 644 [M+H]$^+$.]

Compound 351: N-(1-(4-cyanobenzyl)piperidin-4-yl)-6-(4-(4-cyanophenoxy)piperidin-1-yl)pyridazine-3-carboxamide. $^1$H nmr (CDCl$_3$) δ 8.01 (1H, d, J 9.0 Hz, pzH-4 or H-5), 7.86 (1H, d, J 8.5 Hz, NH), 7.62 (2H, d, J 8.0 Hz, 2H of OC$_6$H$_4$CN), 7.61 (2H, d, J 9.0 Hz, 2H of CH$_2$C$_6$H$_4$CN), 7.45 (2H, d, J 8.5 Hz, 2H of CH$_2$C$_6$H$_4$CN), 7.02 (1H, d, J 10.0 Hz, pzH-4 or H-5), 6.97 (2H, d, J 9.0 Hz, 2H of OC$_6$H$_4$CN), 4.72 (1H, m, PhOpipH-4), 3.98 (3H, m, 2H of PhOpipH-2, H-6, pipH-4), 3.86-3.78 (2H, m, 2H of PhOpipH-2, H-6), 3.55 (2H, s, CH$_2$C$_6$H$_4$CN), 2.80 (2H, m, 2H of pipH-2, H-6), 2.22 (dd, J 11.0, 9.0 Hz, 2H of pipH-2, H-6), 2.13-1.93 (6H, m, PhOpipH-3, H-5, 2H of pipH-3, H-5), 1.61 (1H, m, pipH-5); m/z: 522 [M+H]$^+$.

Compound 352: N-((trans)-3-fluoro-1-(4-(pyrrolidin-1-yl)benzyl)piperidin-4-yl)-6-(4-(4-methoxybenzoyl)piperidine-1-carbonyl)nicotinamide. $^1$H nmr (CDCl$_3$) δ 8.89 (1H, m, pyH-6), 8.09 (1H, dd, J 8.0, 2.0 Hz, pyH-4), 7.94 (2H, d, J 8.5 Hz, 2H of C$_6$H$_4$OCH$_3$), 7.52 (1H, d, J 8.0 Hz, pyH-3), 7.13 (2H, d, J 9.0 Hz, 2H of C$_6$H$_4$N), 7.03 (1H, d, J 8.0 Hz, NH), 6.95 (2H, d, J 9.0 Hz, 2H of C$_6$H$_4$OCH$_3$), 6.51 (2H, d, J 9.0 Hz, 2H of C$_6$H$_4$N), 4.68 (1H, m, 1H of BzpipH-2, H-6), 4.65, 4.48 (1H, m, pipH-3), 4.13 (1H, m, pipH-4), 3.87 (4H, m, OCH$_3$, 1H of BzpipH-2, H-6), 3.54-3.47 (3H, m, NCH$_2$C$_6$H$_4$N, BzpipH-4), 3.26 (6H, m, 4H of pyrrolidine, 1H of BzpipH-2, H-6, 1H of pipH-6), 3.11 (1H, m, 1H of BzpipH-2, H-6), 2.84 (1H, d, J 11.5 Hz, 1H of pipH-2), 2.19-2.12 (3H, m, 1H of pipH-2, H-5, H-6), 2.08-1.97 (5H, m, 4H of pyrrolodine, 1H of BzpipH-3, H-5), 2.94-1.80 (3H, m, 3H of BzpipH-3, H-5), 1.61 (1H, 1H of pipH-5); $^{19}$F nmr (CDCl$_3$) δ −188.4; m/z: 528 [M+H]$^+$.

Compound 353: N-((trans)-3-fluoro-1-(4-isopropoxybenzyl)piperidin-4-yl)-6-(4-(4-methoxybenzoyl)piperidine-1-carbonyl)nicotinamide. $^1$H nmr (CDCl$_3$) δ 8.88 (1H, m, pyH-6), 8.07 (1H, dd, J 8.0, 2.0 Hz, pyH-4), 7.94 (2H, d, J 9.0 Hz, 2H of C$_6$H$_4$OCH$_3$), 7.50 (1H, d, J 8.0 Hz, pyH-3), 7.18 (2H, d, J 8.5 Hz, 2H of C$_6$H$_4$OiPr), 7.15 (1H, m, NH), 6.95 (2H, d, J 9.0 Hz, 2H of C$_6$H$_4$OCH$_3$), 6.83 (2H, d, J 8.5 Hz, 2H of C$_6$H$_4$OiPr), 4.67 (1H, m, 1H of BzpipH-2, H-6), 4.67, 4.50 (1H, m, pipH-3), 4.52 (1H, m, OC$\underline{H}$(CH$_3$)$_2$), 4.03 (1H, m, pipH-4), 3.87 (3H, s, OCH$_3$), 3.83 (1H, m, 1H of BzpipH-2, H-6), 3.54, 3.47 (2H, d AB system, J 13.0 Hz, C$\underline{H_2}$C$_6$H$_4$O), 3.52 (1H, m, BzpipH-4), 3.22 (2H, m, 1H of BzpipH-2, H-6, 1H of pipH-6), 3.11 (1H, m, 1H of BzpipH-2, H-6), 2.83 (1H, d, J 11.0 Hz, 1H of pipH-2), 2.21-2.10 (3H, 1H of pipH-2, H-5, H-6), 2.02 (1H, m, 1H of BzpipH-3, H-5), 1.93-1.76 (3H, m, 3H of BzpipH-3, H-5), 1.63 (1H, m, 1H of pipH-5); $^{19}$F nmr (CDCl$_3$) δ −188.4; m/z: 617 [M+H]$^+$.

Compound 354: N-((trans)-1-(4-cyano-3-fluorobenzyl)-3-fluoropiperidin-4-yl)-6-(4-(4-methoxybenzoyl)piperidine-1-carbonyl)nicotinamide. $^1$H nmr (CDCl$_3$) δ 8.88 (1H, m, pyH-6), 8.07 (1H, dd, J 8.0, 2.0 Hz, pyH-4), 7.94 (2H, d, J 8.5 Hz, 2H of C$_6$H$_4$OCH$_3$), 7.57 (1H, dd, J 7.5, 6.5 Hz, 1H of C$_6$H$_3$FCN), 7.49 (1H, d, J 8.0 Hz, pyH-3), 7.30 (1H, d, J 7.0 Hz, NH), 7.23 (2H, m, 2H of C$_6$H$_3$FCN), 6.96 (2H, d, J 9.0 Hz, 2H of C$_6$H$_4$OCH$_3$), 4.71 (1H, m, 1H of BzpipH-2, H-6), 4.71, 4.54 (1H, m, pipH-3), 4.17 (1H, m, pipH-4), 3.88 (3H, s, OCH$_3$), 3.83 (1H, m, 1H of BzpipH-2, H-6), 3.63 (2H, s, CH$_2$C$_6$H$_3$FCN), 3.54 (1H, m, BzpipH-4), 3.28-3.09 (2H, 2H of BzpipH-2, H-6, 1H of pipH-2, H-6), 2.80 (1H, m, 1H of pipH-2, H-6), 2.33-2.17 (3H, m, pipH-2, H-3, H-6), 2.03 (1H, m, 1H of BzpipH-3, H-5), 1.93-1.81 (3H, m, 3H of BzpipH-3, H-5), 1.68 (1H, m, pipH-5); $^{19}$F nmr (CDCl$_3$) δ −106.6, −188.5; m/z: 602 [M+H]$^+$(found [M+H]$^+$, 602.2589, C$_{33}$H$_{33}$F$_2$N$_5$O$_4$ requires [M+H]$^+$ 602.2813).

Compound 355: 6-(4-(4-cyanophenoxy)piperidine-1-carbonyl)-N-(1-(oxazol-4-ylmethyl)piperidin-4-yl)nicotinamide. $^1$H nmr (CDCl$_3$) δ 8.91 (1H, m, pyH-6), 8.15 (1H, dd, J 8.0, 2.0 Hz, pyH-4), 7.86 (1H, d, J 1.0 Hz, 1H of oxazole), 7.61-7.26 (3H, m, 2H of C$_6$H$_4$CN, 1H of oxazole), 6.96 (2H, d, J 9.0 Hz, 2H of C$_6$H$_4$CN), 6.18 (1H, d, J 7.5 Hz, NH), 4.70 (1H, m, PhOpipH-4), 4.02 (1H, m, pipH-4), 3.91 (2H, m, 2H of PhOpipH-2, H-6), 3.72 (1H, m, 1H of PhOpipH-2, H-6), 3.53 (2H, s, CH$_2$oxazole), 3.50 (1H, m, 1H of PhOpipH-2, H-6), 2.96 (2H, m, 2H of pipH-2, H-6), 2.26 (2H, dd, J 11.5, 9.5 Hz, 2H of pipH-2, H-6), 2.07-1.99 (5H, m, 2H of pipH-3, H-5, 3H of PhOpipH-3, H-5), 1.88 (1H, m, 1H of PhOpipH-3, H-5), 1.63 (2H, m, 2H of pipH-3, H-5); m/z: 516 [M+H]$^+$.

Compound 356: 6-(4-(4-cyanophenoxy)piperidine-1-carbonyl)-N-(1-(thiazol-2-ylmethyl)piperidin-4-yl)nicotinamide. $^1$H nmr (CDCl$_3$) δ 8.91 (1H, m, pyH-6), 8.12 (1H, dd, J 8.5, 2.0 Hz, pyH-4), 7.71 (1H, dd, J 6.5, 2.0 Hz, 1H of thiophene), 7.58 (3H, m, pyH-3, 2H of C$_6$H$_4$CN), 7.27 (1H, dd, J 6.5, 3.5 Hz, 1H of thiophene), 6.96 (2H, d, J 9.0 Hz, 2H of C$_6$H$_4$CN), 6.56 (1H, d, J 7.5 Hz, NH), 4.70 (1H, m, PhOpipH-4), 4.05-3.91 (3H, m, pipH-4, 2H of PhOpipH-2, H-6), 3.89 (2H, s, CH$_2$thiophene), 3.69 (1H, m, 1H of PhOpipH-2, H-6), 3.52 (1H, m, 1H of PhOpipH-2, H-6), 2.97 (2H, m, 2H of pipH-2, H-6), 2.37 (2H, t, J 11.5 Hz, 2H of pipH-2, H-6), 2.04 (5H, m, 2H of pipH-3, H-5, 3H of PhOpipH-3, H-5), 1.87 (1H, m, 1H of PhOpipH-3, H-5), 1.67 (2H, m, 2H of pipH-3, H-5); m/z: 531 [M+H]$^+$.

Compound 357: N-(1-(4-cyanobenzyl)piperidin-4-yl)-5-(4-(4-(dimethylcarbamoyl)phenoxy)piperidine-1-carbonyl) picolinamide. $^1$H nmr (CDCl$_3$) δ 8.60 (1H, m, pyH-6), 8.24 (1H, d, J 8.0 Hz, pyH-3), 7.92 (1H, d, J 8.0 Hz, NH), 7.89 (1H, dd, J 8.0, 2.0 Hz, pyH-4), 7.61 (2H, d, J 8.5 Hz, 2H of C$_6$H$_4$CN), 7.47 (2H, d, J 8.5 Hz, 2H of C$_6$H$_4$CN), 7.40 (2H, d, J 9.0 Hz, 2H of C$_6$H$_4$CON(CH$_3$)$_2$), 6.91 (2H, d, J 9.0 Hz, 2H of C$_6$H$_4$CON(CH$_3$)$_2$), 4.66 (1H, m, PhOpipH-4), 4.01 (1H, m, pipH-4), 3.90 (2H, m, 2H of PhOpipH-2, H-6), 3.64 (1H, m, 1H of PhOpipH-2, H-6), 3.57 (2H, s, C$\underline{H_2}$C$_6$H$_4$CN), 3.38 (1H, m, 1H of PhOpipH-2, H-6), 3.05 (6H, s, N(CH$_3$)$_2$), 2.82 (2H, m, 2H of pipH-2, H-6), 2.24 (2H, dd, J 10.5, 10.0 Hz, 2H of pipH-2, H-6), 2.20 (4H, m, 2H of pipH-3, H-5, 2H of PhOpipH-3, H-5), 1.87 (2H, m, 2H of PhOpipH-3, H-5), 1.65 (2H, m, 2H of pipH-3, H-5); m/z: 595 [M+H]$^+$.

Compound 358: 5-(4-(4-acetylphenoxy)piperidine-1-carbonyl)-N-(1-(4-cyanobenzyl)piperidin-4-yl)picolinamide. $^1$H nmr (CDCl$_3$) δ 8.61 (1H, d, J 2.0 Hz, pyH-6), 8.25 (1H, d, J 8.5 Hz, pyH-3), 7.94 (2H, d, J 9.5 Hz, 2H of C$_6$H$_4$COCH$_3$), 7.90 (1H, m, NH), 7.89 (1H, dd, J 8.0, 2.0 Hz, pyH-4), 7.61 (2H, d, J 8.5 Hz, 2H of C$_6$H$_4$CN), 7.45 (2H, d, J 8.0 Hz, 2H of C$_6$H$_4$CN), 6.95 (2H, d, J 8.5 Hz, 2H of C$_6$H$_4$COCH$_3$), 4.73 (1H, m, PhOpipH-4), 4.01 (1H, m, pipH-4), 4.00-76 (2H, m, 2H of PhOpipH-2, H-6), 3.63 (1H, m, 1H of PhOpipH-2, H-6), 3.57 (2H, s, C$\underline{H_2}$C$_6$H$_4$CN), 3.40 (1H, m, 1H of PhOpipH-2, H-6), 2.82 (2H, m, 2H of pipH-2, H-6), 2.55 (3H, s, COCH$_3$), 2.23 (2H, dd, J 11.0, 10.0 Hz, 2H of pipH-2, H-6), 2.04-1.91 (6H, m, 2H of pipH-3, H-5, PhOpipH-3, H-5), 1.65 (2H, m, 2H of pipH-3, H-5); m/z: 566 [M+H]$^+$.

Compound 359: 5-(4-(4-acetylphenoxy)piperidine-1-carbonyl)-N-(6-(4-fluorophenoxy)pyridin-3-yl)picolinamide. $^1$H nmr (CDCl$_3$) δ 9.89 (1H, s, NH), 8.68 (1H, d, J 2.0 Hz, pyH-6), 8.41 (1H, d, 2.5 Hz, N,O-pyH-6), 8.34 (2H, m, pyH-3, N,O-pyH-4), 7.96 (1H, dd, J 8.0, 2.0 Hz, pyH-4), 7.94 (2H, d, J 9.0 Hz, 2H of C$_6$H$_4$COCH$_3$), 7.09 (4H, m, C$_6$H$_4$F), 6.95 (3H, m, 2H of C$_6$H$_4$COCH$_3$, N,O-pyH-3), 4.75 (1H, m, PhOpipH-4), 3.98 (1H, m, 1H of PhOpipH-2, H-6), 3.87 (1H, m, 1H of PhOpipH-2, H-6), 3.68 (1H, m, 1H of PhOpipH-2, H-6), 3.42 (1H, m, 1H of PhOpipH-2, H-6), 2.56 (3H, s, COCH$_3$), 2.04-1.93 (4H, m, PhOpipH-3, H-5); m/z: 555 [M+H]$^+$.

Compound 360: 5-(4-(4-(dimethylcarbamoyl)phenoxy)piperidine-1-carbonyl)-N-(6-(4-fluorophenoxy)pyridin-3-yl) picolinamide. $^1$H nmr (CDCl$_3$) δ 8.90 (1H, s, NH), 8.69 (1H, m, pyH-6), 8.41 (1H, d, J 3.0 Hz, N,O-pyH-6), 8.35 (2H, m, pyH-3, N,O-pyH-4), 7.96 (1H, dd, J 8.0, 2.0 Hz, pyH-4), 7.40 (2H, d, J 9.0 Hz, 2H of C$_6$H$_4$CON(CH$_3$)$_2$), 7.10 (4H, m, C$_6$H$_4$F), 6.97 (1H, d, J 9.0 Hz, N,O-pyH-3), 6.92 (2H, d, J 9.0 Hz, 2H of C$_6$H$_4$CON(CH$_3$)$_2$), 4.68 (1H, m, PhOpipH-4), 3.95 (1H, m, 2H of PhOpipH-2, H-6), 3.89 (1H, m, 2H of PhOpipH-2, H-6), 3.66 (1H, m, 2H of PhOpipH-2, H-6), 3.41 (1H, m, 2H of PhOpipH-2, H-6), 3.06 (6H, s, N(CH$_3$)$_2$), 2.02 (2H, m, 2H of PhOpipH-3, H-5), 1.91 (2H, m, 2H of PhOpipH-3, H-5; $^{19}$F nmr (CDCl$_3$) δ −118.5; m/z: 584 [M+H]$^+$.

Compound 361: N-(1-(4-cyanobenzyl)piperidin-4-yl)-6-(4-(4-(trifluoromethyl)phenoxy)piperidin-1-yl)pyridazine-3-carboxamide. $^1$H nmr (CDCl$_3$) δ 8.00 (1H, d, J 9.5 Hz, pyH-4 or H-5), 7.87 (1H, d, J 8.0 Hz, NH), 7.61 (2H, d, J 8.5 Hz, 2H of C$_6$H$_4$CN), 7.56 (2H, d, J 9.0 Hz, 2H of C$_6$H$_4$CF$_3$), 7.45 (2H, d, J 8.5 Hz, 2H of C$_6$H$_4$CN), 7.01 (2H, d, J 8.5 Hz, pyH-4 or H-5), 7.00 (2H, d, J 9.0 Hz, 2H of C$_6$H$_4$CF$_3$), 4.71 (1H, m, PhOpipH-4), 4.03-3.94 (3H, m, pipH-4, 2H of PhOpipH-2, H-6), 3.86-3.78 (2H, m, 2H of PhOpipH-2, H-6), 3.55 (2H, s, CH$_2$C$_6$H$_4$CN), 2.79 (2H, m, 2H of pipH-2, H-6), 2.22 (2H, dd, J 11.0, 10.0 Hz, 2H of pipH-2, H-6), 2.12-1.93 (6H, m, 2H of pipH-3, H-5, PhOpipH-3, H-5), 1.64 (2H, m, 2H of pipH-3, H-5); $^{19}$F nmr (CDCl$_3$) δ −61.6; m/z: 565 [M+H]$^+$ (found [M+H]$^+$, 565.2567, C$_{30}$H$_{31}$F$_3$N$_6$O$_2$ requires [M+H]$^+$ 565.2533).

Compound 362: N-(1-(4-cyanobenzyl)piperidin-4-yl)-6-(4-(4-methoxybenzoyl)piperidin-1-yl)pyridazine-3-carboxamide. $^1$H nmr (CDCl$_3$) δ 7.99 (1H, d, J 9.5 Hz, pyH-4 or H-5), 7.96 (2H, d, J 9.0 Hz, 2H of C$_6$H$_4$OCH$_3$), 7.87 (1H, d, J 8.5 Hz, NH), 7.61 (2H, d, J 8.0 Hz, 2H of C$_6$H$_4$CN), 7.45 (2H, d, J 8.5 Hz, 2H of C$_6$H$_4$CN), 7.00 (1H, m, pyH-4 or H-5), 6.97 (2H, d, J 9.0 Hz, 2H of C$_6$H$_4$OCH$_3$), 4.52 (2H, m, 2H of BzpipH-2, H-6), 4.01 (1H, m, pipH-4), 3.89 (3H, s, OCH$_3$), 3.58 (1H, m, BzpipH-4), 3.55 (2H, s, CH$_2$C$_6$H$_4$CN), 3.28 (2H, m, 2H of BzpipH-2, H-6), 2.79 (2H, m, 2H of pipH-2, H-6), 2.23 (2H, dd, J 11.0, 9.0 Hz, 2H of pipH-2, H-6), 2.03-1.87 (6H, m, 2H of pipH-3, H-5, BzpipH-3, H-5) 1.63 (2H, m, 2H of pipH-3, H-5); $^{19}$F nmr (CDCl$_3$) δ −61.6, −114.9; m/z: 539 [M+H]$^+$ (found [M+H]$^+$, 539.2782, C$_{31}$H$_{34}$N$_6$O$_3$ requires [M+H]$^+$ 539.2765).

Compound 363: N-(1-(4-cyanobenzyl)piperidin-4-yl)-6-(4-(4-nitrophenoxy)piperidine-1-carbonyl)nicotinamide. $^1$H nmr (CDCl$_3$) δ 8.90 (1H, m, pyH-6), 8.20 (2H, d, J 9.0 Hz, 2H of C$_6$H$_4$NO$_2$), 8.12 (1H, dd, J 8.5, 2.0 Hz, pyH-4), 7.62 (1H, d, J 8.0 Hz, pyH-3), 7.60 (2H, d, J 8.0 Hz, 2H of C$_6$H$_4$CN), 7.44 (2H, d, J 8.0 Hz, 2H of C$_6$H$_4$CN), 6.97 (2H, d, J 9.5 Hz, 2H of C$_6$H$_4$NO$_2$), 6.44 (1H, d, J 8.0 Hz, NH), 4.75 (1H, heptet, J 3.0 Hz, PhOpipH-3), 4.00 (1H, m, pipH-4), 3.92 (2H, m, 2H of PhOpipH-2, H-6), 3.72 (1H, m, 1H of PhOpipH-2, H-6), 3.56 (2H, s, CH$_2$C$_6$H$_4$CN), 3.51 (1H, m, 1H of PhOpipH-2, H-6), 2.83 (2H, m, 2H of pipH-2, H-6), 2.20 (2H, t, J 11.5 Hz, 2H of pipH-2, H-6), 2.12-2.00 (5H, m, 2H of pipH-3, H-5, 3H of PhOpipH-3, H-5), 1.90 (1H, m, 1H of PhOpipH-3, H-5), 1.61 (2H, m, 2H of pipH-3, H-5); m/z: 569 [M+H]$^+$.

Compound 364: 6-(4-(4-aminophenoxy)piperidine-1-carbonyl)-N-(1-(4-cyanobenzyl)piperidin-4-yl)nicotinamide. $^1$H nmr (CD$_3$OD) δ 8.90 (1H, m, pyH-6), 8.33 (1H, dd, J 8.5, 2.0 Hz, pyH-4), 7.80 (2H, d, J 8.5 Hz, 2H of C$_6$H$_4$CN), 7.70 (2H, d, J 9.0 Hz, 2H of C$_6$H$_4$CN), 7.67 (1H, d, J 9.0 Hz, pyH-3), 6.84 (4H, s, C$_6$H$_4$NH$_2$), 4.53 (1H, m, PhOpipH-4), 4.15 (2H, s, CH$_2$C$_6$H$_4$NH$_2$), 4.10 (1H, m, 1H of PhOpipH-2, H-6), 3.97 (1H, m, 1H of PhOpipH-2, H-6), 3.77 (1H, m, 1H of PhOpipH-2, H-6), 3.63 (1H, m, 1H of PhOpipH-2, H-6), 3.37 (2H, m, 2H of pipH-2, H-6), 2.86 (2H, dd, J 11.5, 12.0 Hz, 2H of pipH-2, H-6), 2.13 (2H, m, 2H of PhOpipH-3, H-5 or pipH-3, H-5), 2.04-1.73 (6H, m, 2H or 4H of pipH-3, H-5, 2H or 4H of PhOpipH-3, H-5); m/z: 539 [M+H]$^+$.

Compound 365: N-(1-(4-cyanobenzyl)piperidin-4-yl)-5-(4-(4-(pyrrolidin-1-yl)benzoyl)piperidine-1-carbonyl)picolinamide. $^1$H nmr (CDCl$_3$) δ 8.60 (1H, m, pyH-6), 8.23 (1H, d, J 8.0 Hz, pyH-3), 7.94 (1H, d, J 8.5 Hz, NH), 7.88 (1H, dd, J 8.0, 2.0 Hz, pyH-4), 7.86 (2H, d, J 9.0 Hz, 2H of C$_6$H$_4$N), 7.61 (2H, d, J 8.5 Hz, 2H of C$_6$H$_4$CN), 7.46 (2H, d, J 8.0 Hz, C$_6$H$_4$CN), 6.53 (2H, d, J 9.0 Hz, 2H of C$_6$H$_4$N), 4.66 (1H, m, 1H of BzpipH-2, H-6), 4.01 (1H, m, pipH-4), 3.73 (1H, m, 1H of BzpipH-2, H-6), 3.56 (2H, s, CH$_2$C$_6$H$_4$CN), 3.51 (1H, m, BzpipH-4), 3.37 (4H, m, 4H of pyrrolidine), 3.21-3.13 (2H, m, 2H of BzpipH-2, H-6), 2.80 (2H, m, 2H of pipH-2, H-6), 2.23 (2H, dd, J 11.5, 9.5 Hz, pipH-2, H-6), 2.06-2.00 (7H, m, 4H pyrrolidine, 2H of pipH-3, H-5, 1H of BzpipH-3, H-5), 1.91-1.80 (3H, m, 3H of BzpipH-3, H-5), 1.65 (2H, m, 2H of pipH-3, H-5); m/z: 605 [M+H]$^+$.

Compound 366: 6-(4-(4-acetamidophenoxy)piperidine-1-carbonyl)-N-(1-(4-cyanobenzyl)piperidin-4-yl)nicotinamide. $^1$H nmr (CDCl$_3$) δ 8.91 (1H, m, pyH-6), 8.14 (1H, dd, J 8.0, 2.5 Hz, pyH-4), 7.63 (1H, m, pyH-3), 7.60 (2H, d, J 8.5 Hz, 2H of C$_6$H$_4$CN), 7.46 (2H, d, J 8.0 Hz, 2H of C$_6$H$_4$CN), 7.39 (2H, d, J 9.0 Hz, 2H of C$_6$H$_4$NHAc), 7.15 (1H, s, NHAc), 6.88 (2H, d, J 9.0 Hz, 2H of C$_6$H$_4$NHAc), 6.31 (1H, d, J 8.5 Hz, NHCO), 4.56 (1H, m, PhOpipH-4), 4.03 (1H, m, pipH-4), 3.89 (2H, m, 2H of PhOpipH-2, H-6), 3.70 (1H, m, 1H of PhOpipH-2, H-6), 3.58 (2H, s, CH$_2$C$_6$H$_4$CN), 3.48-3.42 (1H, m, 1H of PhOpipH-2, H-6), 2.85 (2H, m, 2H of pipH-2, H-6), 2.22 (2H, dd, J 11.5, 9.0 Hz, 2H of pipH-2, H-6), 2.15 (3H, s, COCH$_3$), 2.08-1.92 (6H, m, 2H of pipH-3, H-5, PhOpipH-3, H-5), 1.67 (2H, m, 2H of pipH-3, H-5); m/z: 581 [M+H]$^+$.

Compound 367: N-(1-(4-cyanobenzyl)piperidin-4-yl)-6-(4-(4-(methylsulfonamido)phenoxy)piperidine-1-carbonyl)nicotinamide. $^1$H nmr (CDCl$_3$) δ 8.91 (1H, m, pyH-6), 8.14 (1H, dd, J 8.0, 2.0 Hz, pyH-4), 7.64 (1H, d, J 8.5 Hz, pyH-3), 7.60 (2H, d, J 8.5 Hz, 2H of C$_6$H$_4$CN), 7.45 (2H, d, J 8.5 Hz, 2H of C$_6$H$_4$CN), 7.20 (2H, d, J 9.0 Hz, 2H of C$_6$H$_4$NHMs), 6.90 (2H, d, J 9.0 Hz, C$_6$H$_4$NHMs), 6.31 (1H, d, J 8.5 Hz, NHCO), 4.78 (1H, m, PhOpipH-4), 4.03 (1H, m, pipH-4), 3.90 (2H, m, 2H of PhOpipH-2, H-6), 3.71 (1H, m, 1H of PhOpipH-2, H-6), 3.56 (2H, s, CH$_2$C$_6$H$_4$CN), 3.46 (1H, m, 1H of PhOpipH-2, H-6), 2.96 (3H, s, SO$_2$CH$_3$), 2.83 (2H, m, 2H of pipH-2, H-6), 2.21 (2H, t, J 11.5 Hz, 2H of pipH-2, H-6), 2.06-1.94 (5H, m, 2H of pipH-3, H-5, 3H of PhOpipH-3, H-5), 1.85 (1H, m, 1H of PhOpipH-3, H-5), 1.62 (2H, m, 2H of pipH-3, H-5); m/z: 617 [M+H]$^+$.

Compound 412: 6-(4-(3-acetamidophenoxy)piperidine-1-carbonyl)-N-(1-(4-methoxybenzyl)piperidin-4-yl)nicotinamide. $^1$H nmr (CDCl$_3$) δ 8.89 (1H, d, J 2.0 Hz, pyH-6), 8.12 (1H, dd, J 8.0, 2.0 Hz, pyH-4), 7.62 (1H, d, J 7.5 Hz, pyH-3), 7.35 (2H, m, NHAc, C$_6$H$_4$NHAcH-2), 7.22 (2H, d, J 9.0 Hz, 2H of C$_6$H$_4$OCH$_3$), 7.19 (1H, t, J 8.0 Hz, C$_6$H$_4$NHAcH-5), 6.89 (1H, m, C$_6$H$_4$NHAcH-4 or H-6), 6.85 (2H, d, J 9.0 Hz, 2H of C$_6$H$_4$OCH$_3$), 6.66 (1H, dd, J 8.0, 1.5 Hz, C$_6$H$_4$NHAcH-4 or H-6), 6.29 (1H, d, J 8.0 Hz, NH), 4.60 (1H, m, PhOpipH-4), 4.01 (1H, m, pipH-4), 3.89 (2H, m, 2H of PhOpipH-2, H-6), 3.80 (3H, s, OCH$_3$), 3.69 (1H, m, 1H of PhOpipH-2, H-6), 3.48 (2H, s, CH$_2$C$_6$H$_4$OCH$_3$), 3.41 (1H, m, 1H of PhOpipH-2, H-6), 2.86 (2H, m, 2H of pipH-2, H-6), 2.15 (5H, m, NHCOCH$_3$, 2H of pipH-2, H-6), 2.03-1.92 (5H, m, 2H of pipH-3, H-5, 3H of PhOpipH-3, H-5), 1.84 (1H, m, 1H of PhOpipH-3, H-5), 1.59 (2H, m, 2H of pipH-3, H-5); m/z: 587 [M+H]$^+$.

Compound 413: 6-(4-(3-acetamidophenoxy)piperidine-1-carbonyl)-N-(1-(4-fluorobenzyl)piperidin-4-yl)nicotinamide. $^1$H nmr (CDCl$_3$) δ 8.89 (1H, m, pyH-6), 8.10 (1H, dd, J 8.0, 2.0 Hz, pyH-4), 7.56 (1H, d, J 8.0 Hz, pyH-3), 7.54 (1H, br s, C$_6$H$_4$NHAcH-2), 7.36 (1H, s, NHAc), 7.29-7.25 (2H, m, 2H of C$_6$H$_4$F), 7.18 (1H, t, J 8.5 Hz, C$_6$H$_4$NHAcH-5), 6.99 (2H, t, J 8.5 Hz, 2H of C$_6$H$_4$F), 6.90 (1H, d, J 8.5 Hz, C$_6$H$_4$NHAcH-4 or H-6), 6.65 (1H, dd, J 8.5, 2.0 Hz, C$_6$H$_4$NHAcH-4 or H-6), 6.58 (1H, d, J 7.5 Hz, NH), 4.59 (1H, m, PhOpipH-4), 4.00 (1H, m, pipH-4), 3.87 (2H, m, 2H of PhOpipH-2, H-6), 3.66 (1H, m, 1H of PhOpipH-2, H-6), 3.47 (1H, s, CH$_2$C$_6$H$_4$F), 3.43 (1H, m, 1H of PhOpipH-2, H-6), 2.85 (2H, m, 2H of pipH-2, H-6), 2.14 (5H, m, NHCOCH$_3$, 2H of pipH-2, H-6), 2.02-1.90 (5H, m, 2H of pipH-3, H-5, 3H of PhOpipH-3, H-5), 1.83 (1H, m, 1H of PhOpipH-3, H-5), 1.61 (2H, m, 2H of pipH-3, H-5); $^{19}$F nmr (CDCl$_3$) δ −115.8; m/z: 574 [M+H]$^+$.

Compound 414: 6-(4-(3-acetamidophenoxy)piperidine-1-carbonyl)-N-(6-(4-fluorophenoxy)pyridin-3-yl)nicotinamide. $^1$H nmr (CDCl$_3$) δ 9.85 (1H, s, NH), 8.93 (1H, d, J 1.5 Hz, pyH-6), 8.45 (1H, d, J 2.5 Hz, N,O-pyH-6), 8.30 (1H, dd, J 8.5, 2.5 Hz, N,O-pyH-4), 8.11 (1H, dd, J 8.5, 2.0 Hz, pyH-4) 7.66 (1H, s, NHAc), 7.39 (1H, d, J 8.5 Hz, pyH-3), 7.34 (1H, br s, C$_6$H$_4$NHAcH-2), 7.17 (1H, t, J 8.0 Hz, C$_6$H$_4$NHAcH-5), 7.09-7.06 (4H, m, C$_6$H$_4$F), 6.90 (2H, m, C$_6$H$_4$NHAcH-4 or H-6, N,O-pyH-3), 6.64 (1H, d, J 8.0 Hz, C$_6$H$_4$NHAcH-4 or H-6), 4.56 (1H, m, PhOpipH-4), 3.93-3.77 (2H, m, 2H of PhOpipH-2, H-6), 3.59 (1H, m, 1H of PhOpipH-2, H-6), 3.33 (1H, m, 1H of PhOpipH-2, H-6), 2.13 (3H, s, NHCOC$\underline{H}_3$), 1.95-1.89 (3H, m, 3H of PhOpipH-3, H-5), 1.82 (1H, m, 1H of PhOpipH-3, H-5); $^{19}$F nmr (CDCl$_3$) δ –118.5; m/z: 570 [M+H]$^+$.

Compound 415: N-(1-(4-cyanobenzyl)piperidin-4-yl)-5-(4-(4-(trifluoromethylsulfonyl)phenoxy)piperidine-1-carbonyl)picolinamide. $^1$H nmr (CDCl$_3$) δ 8.87 (1H, s, pyH-4 or pyH-6), 8.08 (1H, s, pyH-4 or pyH-6), 7.93 (2H, d, 9.0 Hz, 2H of C$_6$$\underline{H}_4$OCH$_3$), 7.60 (2H, d, J 8.5 Hz, 2H of C$_6$H$_4$CN), 7.45 (2H, d, J 8.5 Hz, 2H of C$_6$H$_4$CN), 6.95 (2H, d, J 9.0 Hz, 2H of C$_6$$\underline{H}_4$OCH$_3$), 6.64 (1H, m, 1×NH), 4.94 (1H, m, 1×NH), 7.72 (1H, m, 1H of BzpipH-2, H-6), 4.05 (1H, m, pipH-4), 3.88 (3H, s, OCH$_3$), 3.56 (2H, s, C$\underline{H}_2$C$_6$H$_4$CN), 3.56-3.41 (3H, m, BzpipH-4, 1H of BzpipH-2, H-6), 3.13 (4H, m, 2H of BzpipH-2, H-6, CH$_2$CH$_2$C$\underline{H}_2$NHCO), 2.83 (2H, m, 2H of pipH-2, H-6), 2.71 (2H, dd, J 7.0, 6.5 Hz, C$\underline{H}_2$CH$_2$CH$_2$NHCO), 2.20 (2H, dd, J 12.0, 9.5 Hz, 2H of pipH-2, H-6), 2.02 (4H, m, 2H of pipH-3, H-5, 2H of BzpipH-3, H-5), 1.89 (2H, m, CH$_2$C$\underline{H}_2$CH$_2$NHCO), 1.76 (2H, m, 2H of BzpipH-3, H-5), 1.67 (2H, m, 2H of pipH-3, H-5), 1.46 (9H, s, C(CH$_3$)$_3$); $^{19}$F nmr (CDCl$_3$) δ –78.7; m/z: 656 [M+H]$^+$.

Compound 416: tert-butyl 3-(5-(1-(4-cyanobenzyl)piperidin-4-ylcarbamoyl)-2-(4-(4-methoxybenzoyl)piperidine-1-carbonyl)pyridin-3-yl)propylcarbamate. $^1$H nmr (CDCl$_3$) δ 8.87 (1H, s, pyH-4 or H-6), 8.08 (1H, s, pyH-4 or H-6), 7.93 (2H, d, J 9.0 Hz, 2H of C$_6$H$_4$OCH$_3$), 7.60 (2H, d, J 8.5 Hz, 2H of C$_6$H$_4$CN), 7.46 (2H, d, J 8.5 Hz, 2H of C$_6$H$_4$CN), 6.95 (2H, d, J 9.0 Hz, 2H of C$_6$H$_4$OCH$_3$), 6.64 (1H, m, NH), 4.94 (1H, m, N$\underline{H}$COOC(CH$_3$)$_3$), 4.71 (1H, m, 1H of BzpipH-2, H-6), 4.04 (1H, m, pipH-4), 3.88 (3H, s, OCH$_3$), 3.56 (2H, s, C$\underline{H}_2$C$_6$H$_4$CN), 3.52-3.41 (2H, m, BzpipH-4, 1H of BzpipH-2, H-6), 3.17-3.08 (4H, m, 2H of BzpipH-2, H-6, CH$_2$CH$_2$C$\underline{H}_2$NHCO), 2.83 (2H, m, 2H of pipH-2, H-6), 2.71 (2H, dd, J 7.0, 6.5 Hz, CH$_2$C$\underline{H}_2$CH$_2$NHCO), 2.20 (2H, dd, J 12.0, 9.5 Hz, 2H of pipH-2, H-6), 2.02 (3H, m, 2H of pipH-3, H-5, 1H of BzpipH-3, H-5), 1.94-1.82 (3H, m, 1H of BzpipH-3, H-5, CH$_2$C$\underline{H}_2$CH$_2$NHCO), 1.76 (2H, m, 2H of BzpipH-3, H-5), 1.67 (2H, m, 2H of pipH-3, H-5), 1.46 (9H, s, C(CH$_3$)$_3$); m/z: 724 [M+H]$^+$, 624 [M+H—CO$_2$—C$_6$H$_4$]$^+$.

Compound 417: N-(1-(4-cyanophenyl)piperidin-4-yl)-6-(4-(4-fluorobenzyl)piperazine-1-carbonyl)nicotinamide. $^1$H nmr (CDCl$_3$) δ 8.86 (1H, d, J 2.0 Hz, pyH-6), 8.05 (1H, dd, J 8.5, 2.0 Hz, pyH-4), 7.49 (1H, d, J 8.0 Hz, pyH-3), 7.57 (2H, d, J 9.0 Hz, 2H of C$_6$H$_4$CN), 7.29-7.24 (2H, m, 2H of C$_6$H$_4$F), 7.00 (2H, t, J 8.5 Hz, 2H of C$_6$H$_4$F), 6.87 (2H, d, J 9.0 Hz, 2H of C$_6$H$_4$CN), 6.85 (1H, m, NH), 4.23 (1H, m, pipH-4), 3.99 (2H, m, 2H of pipH-2, H-6), 3.75, 3.73 (2H, 2 d, AB system, J 5.0 Hz, 2H of piz), 3.48 (2H, s, C$\underline{H}_2$C$_6$H$_4$F), 3.46 (2H, m, 2H of piz), 3.07 (2H, t, J 12.0 Hz, 2H of pipH-2, H-6), 2.49, 2.48 (2H, 2 d AB system, J 5.0 Hz, 2H of piz), 2.38, 2.37 (2H, 2 d AB system, J 5.0 Hz, 2H of piz), 2.13 (2H, m, 2H of pipH-3, H-5), 1.66 (2H, m, 2H of pipH-3, H-5); $^{19}$F nmr (CDCl$_3$) δ–115.4; m/z: 527 [M+H]$^+$.

Compound 418: 6-(4-(4-cyanophenoxy)piperidine-1-carbonyl)-N-(1-(4-cyanophenyl)piperidin-4-yl)nicotinamide. $^1$H nmr (CDCl$_3$) δ 8.90 (1H, m, pyH-6), 8.09 (1H, dd, J 8.0, 2.0 Hz, pyH-4), 7.59 (2H, d, J 9.0 Hz, 2H of 1×C$_6$H$_4$CN), 7.54 (1H, d, J 8.0 Hz, pyH-3), 7.47 (2H, d, J 9.0 Hz, 2H of 1×C$_6$H$_4$CN), 6.95 (2H, d, J 9.0 Hz, 2H of 1×C$_6$H$_4$CN), 6.88 (2H, d, J 9.0 Hz, 2H of 1×C$_6$H$_4$CN), 6.79 (1H, d, J 7.5 Hz, NH), 4.68 (1H, m, PhOpipH-4), 4.25 (1H, m, pipH-4), 3.92-3.81 (4H, m, 2H of pipH-2, H-6, 2H of PhOpipH-2, H-6), 3.67 (1H, m, 1H of PhOpipH-2, H-6), 3.46 (1H, m, 1H of PhOpipH-2, H-6), 3.07 (2H, t, J 12.0 Hz, 2H of pipH-2, H-6), 2.14 (2H, m, 2H of pipH-3, H-5), 2.03-1.94 (3H, m, 3H of PhOpipH-3, H-5), 1.85 (1H, m, 1H of PhOpipH-3, H-5), 1.67 (2H, m, 2H of pipH-3, H-5); m/z: 535 [M+H]$^+$.

Compound 419: N-(1-(4-cyanobenzyl)piperidin-4-yl)-5-(4-(thiophene-2-carbonyl)piperidine-1-carbonyl)picolinamide. $^1$H nmr (CDCl$_3$) δ 8.60 (1H, m, pyH-6), 8.24 (1H, d, J 8.0 Hz, pyH-3), 7.93 (1H, d, J 8.5 Hz, NH), 7.88 (1H, dd, J 8.0, 2.0 Hz, pyH-4), 7.75 (1H, dd, J 3.5, 1.0 Hz, thiopheneH-3 or H-5), 7.68 (1H, dd, J 5.0, 1.0 Hz, thiopheneH-3 or H-5), 7.61 (2H, d, J 8.5 Hz, 2H of C$_6$H$_4$CN), 7.45 (2H, d, J 8.5 Hz, 2H of C$_6$H$_4$CN), 7.16 (1H, dd, J 5.0, 3.5 Hz, thiopheneH-4), 4.68 (1H, m, 1H of BzpipH-2, H-6), 4.01 (1H, m, pipH-4), 3.78 (1H, m, 1H of BzpipH-2, H-6), 3.56 (2H, s, C$\underline{H}_2$C$_6$H$_4$CN), 3.41 (1H, m, BzpipH-4), 3.18 (2H, m, 2H of BzpipH-2, H-6), 2.81 (2H, m, 2H of pipH-2, H-6), 2.23 (2H, dd, J 11.0, 9.5 Hz, 2H of pipH-2, H-6), 2.01 (3H, m, 2H of pipH-3, H-5, 1H of BzpipH-3, H-5), 1.87 (3H, m, 3H of BzpipH-3, H-5), 1.65 (2H, m, 2H of pipH-3, H-5); m/z: 542 [M+H]$^+$.

Compound 420: 6-(4-(4-cyanophenoxy)piperidine-1-carbonyl)-N-(1-(4-(methylsulfonyl)phenyl)piperidin-4-yl)nicotinamide. $^1$H nmr (CDCl$_3$) δ 8.90 (1H, d, J 2.0 Hz, pyH-6), 8.07 (1H, dd, J 8.0, 2.0 Hz, pyH-4), 7.73 (2H, d, J 9.0 Hz, 2H of C$_6$H$_4$CN or C$_6$$\underline{H}_4$SO$_2$CH$_3$), 7.57 (2H, d, J 9.0 Hz, 2H of C$_6$H$_4$CN or C$_6$$\underline{H}_4$SO$_2$CH$_3$), 7.46 (1H, d, J 8.0 Hz, pyH-3), 7.09 (1H, d, J 8.0 Hz, NH), 6.95 (2H, d, J 8.5 Hz, 2H of C$_6$H$_4$CN or C$_6$$\underline{H}_4$SO$_2$CH$_3$), 6.93 (2H, d, J 9.0 Hz, 2H of C$_6$$\underline{H}_4$CN or C$_6$H$_4$SO$_2$CH$_3$), 4.67 (1H, m, PhOpipH-4), 4.26 (1H, m, pipH-4), 3.93 (2H, m, 2H of pipH-2, H-6), 3.78 (2H, m, 2H of PhOpipH-2, H-6), 3.64 (1H, m, 1H of PhOpipH-2, H-6), 3.45-3.37 (1H, m, 1H of PhOpipH-2, H-6), 3.09 (2H, t, J 12.0 Hz, 2H of pipH-2, H-6), 3.00 (3H, s, SO$_2$CH$_3$), 2.10 (2H, m, 2H of pipH-3, H-5), 1.98-1.90 (3H, m, 3H of PhOpipH-3, H-5), 1.84 (1H, m, 1H of PhOpipH-3, H-5), 1.67 (2H, m, 2H of pipH-3, H-5); m/z: 588 [M+H]$^+$.

Compound 421: 6-(4-(4-fluorobenzyl)piperazine-1-carbonyl)-N-(1-(4-(methylsulfonyl)phenyl)piperidin-4-yl)nicotinamide. $^1$H nmr (CDCl$_3$) δ 8.88 (1H, d, J 2.0 Hz, pyH-6), 8.06 (1H, dd, J 8.5, 2.0 Hz, pyH-4), 7.73 (2H, d, J 9.0 Hz, 2H of C$_6$$\underline{H}_4$SO$_2$CH$_3$), 7.46 (1H, d, J 8.0 Hz, pyH-3), 7.25 (2H, m, 2H of C$_6$H$_4$F), 6.99 (3H, m, NH, 2H of C$_6$H$_4$F), 6.93 (2H, d, J 9.0 Hz, 2H of C$_6$$\underline{H}_4$SO$_2$CH$_3$), 4.24 (1H, m, pipH-4), 3.91 (2H, m, 2H of pipH-2, H-6), 3.74, 3.73 (2H, 2 d AB system, J 5.0 Hz, 2H of piz), 3.48 (2H, s, C$\underline{H}_2$C$_6$H$_4$F), 3.46 (2H, m, 2H of piz), 3.08 (2H, t, J 11.5 Hz, 2H of pipH-2, H-6), 3.00 (3H, s, SO$_2$CH$_3$), 2.50, 2.48 (2H, 2 d AB system, J 5.0 Hz, 2H of piz), 2.38, 2.36 (2H, 2 d AB system, J 5.0 Hz, 2H of piz), 2.11 (2H, m, 2H of pipH-3, H-5), 1.68 (2H, m, 2H of pipH-3, H-5); $^{19}$F nmr (CDCl$_3$) δ–115.4; m/z: 581 [M+H]$^+$.

Compound 422: 6-(4-(4-cyanophenoxy)piperidine-1-carbonyl)-N-(1-(4-fluorophenyl)piperidin-4-yl)nicotinamide. $^1$H nmr (CDCl$_3$) δ 8.63 (1H, m, pyH-6), 7.85 (1H, dd, J 8.0, 2.0 Hz, pyH-4), 7.69 (1H, d, J 8.0 Hz, pyH-3), 7.59 (2H, d, J 9.0 Hz, 2H of C$_6$H$_4$CN), 6.96 (2H, d, J 9.0 Hz, 2H of C$_6$H$_4$CN), 6.89 (2H, t, J 8.5 Hz, 2H of C$_6$H$_4$F), 6.55 (2H, m, 2H of C$_6$H$_4$F), 4.70 (1H, m, PhOpipH-4), 4.58 (1H, m, pipH-4), 3.91 (2H, m, 2H of pipH-2, H-6 or PhOpipH-2, H-6), 3.78-3.71 (2H, m, 2H of pipH-2, H-6 or PhOpipH-2, H-6), 3.57-3.47 (2H, m, 2H of pipH-2, H-6 or PhOpipH-2, H-6), 3.17 (2H, m, 2H of pipH-2, H-6 or PhOpipH-2, H-6), 2.21-1.94 (7H, 7H of pipH-3, H-5, PhOpipH-3, H-5), 1.88 (1H, m, 1H of pipH-3, H-5, PhOpipH-3, H-5); $^{19}$F nmr (CDCl$_3$) δ –127.1; m/z: 528 [M+H]$^+$.

Compound 423: 6-(4-(4-cyanophenoxy)piperidine-1-carbonyl)-N-(1-(4-methoxyphenyl)piperidin-4-yl)nicotinamide. $^1$H nmr (CDCl$_3$) δ 8.92 (1H, m, pyH-6), 8.14 (1H, dd, J 8.0, 2.0 Hz, pyH-4), 7.63 (1H, d, J 8.5 Hz, pyH-3), 7.59 (2H, d, J 9.0 Hz, 2H of C$_6$H$_4$CN), 6.95 (2H, d, J 9.0 Hz, 2H of C$_6$$\underline{H}_4$CN), 6.92 (2H, d, J 9.0 Hz, 2H of C$_6$H$_4$OCH$_3$), 6.84 (2H, d, J 9.5 Hz, 2H of C$_6$H$_4$OCH$_3$), 6.45 (1H, d, J 8.0 Hz, NH), 4.69 (1H, m, PhOpipH-4), 4.12 (1H, m, pipH-4), 3.93-3.84 (2H, m, 2H of pipH-2, H-6, PhOpipH-2, H-6), 3.77 (3H, s, OCH$_3$), 3.71 (1H, m, 1H of pipH-2, H-6, PhOpipH-2, H-6), 3.53-3.49 (3H, m, 3H of pipH-2, H-6, PhOpipH-3, H-6), 2.85 (2H, t, J 11.5 z, 2H of pipH2, H-6), 2.15 (2H, m, 2H of pipH-3, H-5), 2.06-1.98 (3H, m, 3H of PhOpipH-3, H-5), 1.87 (1H, m, 1H of PhOpipH-3, H-5), 1.74 (2H, m, 2H of pipH-3, H-5); m/z: 540 [M+H]$^+$.

Compound 424: 6-(4-(4-methoxybenzoyl)piperidine-1-carbonyl)-N-(1-(3-(trifluoromethoxy)benzyl)piperidin-4-yl)nicotinamide. $^1$H nmr (CDCl$_3$) δ 8.91 (1H, m, pyH-6), 8.14 (1H, dd, J 8.0, 2.0 Hz, pyH-4), 7.94 (2H, d, J 8.5 Hz, 2H of C$_6$H$_4$OCH$_3$), 7.65 (1H, d, J 8.0 Hz, pyH-3), 7.33 (1H, t, J 8.0 Hz, C$_6$H$_4$OCF$_3$H-5), 7.24 (2H, m, C$_6$H$_4$OCF$_3$H-2 and H-4 or H-6), 7.10 (1H, d, J 8.5 Hz, C$_6$H$_4$OCF$_3$H-4 or H-6), 6.95 (2H, d, J 9.0 Hz, 2H of C$_6$H$_4$OCH$_3$), 6.22 (1H, d, J 8.0 Hz, NH), 4.69 (1H, m, 1H of BzpipH-2, H-6), 4.03 (1H, m, pipH-4), 3.94 (1H, m, 1H of BzpipH-2, H-6), 3.88 (3H, s, OCH3), 3.54 (3H, m, CH$_2$C$_6$H$_4$OCF$_3$, BzpipH-4), 3.26 (1H, m, 1H of BzpipH-2, H-6), 3.11 (1H, m, 1H of BzpipH-2, H-6), 2.85 (2H, m, 2H of pipH-2, H-6), 2.21 (2H, dd, J 11.0, 9.5 Hz, 2H of pipH-2, H-6), 2.04 (3H, m, 2H of pipH-3, H-5, 1H of BzpipH-3, H-5), 1.93-1.81 (3H, m, 3H of BzpipH-3, H-5), 1.63 (2H, m, 2H of pipH-3, H-5); $^{19}$F nmr (CDCl$_3$) δ −57.7; m/z: 625 [M+H]$^+$.

Compound 425: 6-(4-(4-methoxybenzoyl)piperidine-1-carbonyl)-N-(1-(3-methoxybenzyl)piperidin-4-yl)nicotinamide. $^1$H nmr (CDCl$_3$) δ 8.90 (1H, m, pyH-6), 8.12 (1H, dd, J 8.5, 2.0 Hz, pyH-4), 7.93 (2H, d, J 8.5 Hz, 2H of COC$_6$H$_4$OCH$_3$), 7.57 (1H, d, J 7.5 Hz, pyH-3), 7.22 (1H, t, J 8.0 Hz, C$_6$H$_4$OCH$_3$H-5), 6.95 (2H, d, J 9.0 Hz, 2H of COC$_6$H$_4$OCH$_3$), 6.89 (2H, m, C$_6$H$_4$OCH$_3$H-2 and H-4 or H-6), 6.80 (1H, dd, J 8.5, 2.0 Hz, C$_6$H$_4$OCH$_3$H-4 or H-6), 6.59 (1H, d, J 8.0 Hz, NH), 4.68 (1H, m, 1H of BzpipH-2, H-6), 4.01 (1H, m, pipH-4), 3.89 (1H, m, 1H of BzpipH-2, H-6), 3.87 (3H, s, 1×OCH$_3$), 3.80 (3H, s, 1×OCH$_3$), 3.53 (2H, s, CH$_2$C$_6$H$_4$OCH$_3$), 3.51 (1H, m, BzpipH-4), 3.24 (1H, ddd, J 14.0, 10.0, 4.0 Hz, 1H of BzpipH-2, H-6), 3.10 (1H, m, 1H of BzpipH-2, H-6), 2.91 (2H, m, 2H of pipH-2, H-6), 2.22 (2H, dd, J 11.5, 10.0 Hz, 2H of pipH-2, H-6), 2.04-2.00 (3H, m, 2H of pipH-3, H-5, 1H of BzpipH-3, H-5), 1.91-1.79 (3H, m, 3H of BzpipH-3, H-5), 1.65 (2H, m, 2H of pipH-3, H-5); m/z: 571 [M+H]$^+$.

426: N-((3S,4R)-3-fluoro-1-((5-methylisoxazol-3-yl)methyl)piperidin-4-yl)-6-(4-(4-methoxybenzoyl)piperidine-1-carbonyl)nicotinamide. $^1$H nmr (CDCl$_3$) δ 8.89 (1H, d, J 2.0 Hz, pyH-6), 8.10 (1H, dd, J 8.0, 2.0 Hz, pyH-4), 7.94 (2H, d, J 9.0 Hz, 2H of C$_6$H$_4$OCH$_3$), 7.53 (1H, d, J 8.0 Hz, pyH-3), 7.09 (1H, d, J 7.5 Hz, NH), 6.95 (2H, d, J 9.0 Hz, 2H of C$_6$H$_4$OCH$_3$), 5.97 (1H, d, J 1.0 Hz, isoxazoleH-4), 4.70-4.62 (1.5H, m, 1H of BzpipH-2, H-6, 0.5H of pipH-3), 4.49 (0.5H, dt, J 5.0, 9.5 Hz, 0.5H of pipH-3), 4.12 (1H, m, pipH-4), 3.87 (3H, s, OCH$_3$), 3.84 (1H, m, 1H of BzpipH-2, H-6), 3.64 (2H, s, CH$_2$isoxazole), 3.53 (1H, m, BzpipH-4), 3.26-20 (2H, m, 1H of pipH-6, 1H of BzpipH-2, H-6), 3.11 (1H, t, J 11.0 Hz, 1H of BzpipH-2, H-6), 2.84 (m, 1H of pipH-2), 2.41 (3H, d, J 1.0 Hz, isoxazoleCH3), 2.32 (1H, m, 1H of pipH-6), 2.27-2.18 (2H, m, 1H of pipH-2, 1H of pipH-5), 2.02 (1H, m, BzpipH-3, H-5), 1.92-1.80 (3H, m, 3H of BzpipH-3, H-5) 1.63 (1H, m, 1H of pipH-5); $^{19}$F nmr (CDCl$_3$) δ −188.6; m/z: 565 [M+H]$^+$.

Compound 427: N-((3S,4R)-3-fluoro-1-((2-methylthiazol-4-yl)methyl)piperidin-4-yl)-6-(4-(4-methoxybenzoyl)piperidine-1-carbonyl)nicotinamide. $^1$H nmr (CDCl$_3$) δ 8.94 (1H, m, pyH-6), 8.16 (1H, dd, J 8.5, 2.0 Hz, pyH-4), 7.93 (2H, d, J 9.0 Hz, 2H of C$_6$H$_4$OCH$_3$), 7.59 (1H, d, J 8.0 Hz, pyH-3), 6.96 (2H, J 9.0 Hz, 2H of C$_6$H$_4$OCH$_3$), 6.95 (1H, s, thiazoleH-4), 4.68 (1H, m, 1H of BzpipH-2, H-6), 4.55 (1H, ddt, J 50.0, 5.0, 9.5 Hz, pipH-3), 4.15 (1H, m, pipH-4), 3.92 (1H, m, 1H of BzpipH-2, H-6), 3.87 (3H, s, OCH$_3$), 3.71, 3.64 (2H, 2 d AB system, J 13.0 Hz, CH$_2$thiazole), 3.51 (1H, m, BzpipH-4), 3.29-3.20 (2H, m, 1H of pipH-6, 1H of BzpipH-2, H-6), 3.10 (1H, dd, J 12.5, 11.0 Hz, 1H BzpipH-2, H-6), 2.89 (1H, m, 1H of pipH-2), 2.71 (3H, s, thiazoleCH$_3$), 2.27-2.12 (3H, m, 1H of pipH-2, 1H of pipH-5, 1H of pipH-6), 2.02 (1H, m, 1H of BzpipH-3, H-5), 1.91-1.80 (3H, m, 3H of BzpipH-3, H-5), 1.61 (1H, m, 1H of pipH-5); $^{19}$F nmr (CDCl$_3$) δ −188.6; m/z: 581 [M+H]$^+$.

Compound 428: 6-(4-(4-acetamidophenoxy)piperidine-1-carbonyl)-N-(1-(3-(trifluoromethoxy)benzyl)piperidin-4-yl)nicotinamide. $^1$H nmr (CDCl$_3$) δ 8.90 (1H, m, pyH-6), 8.11 (1H, dd, J 8.5, 2.0 Hz, pyH-4), 7.58 (1H, d, J 8.5 Hz, pyH-3), 7.38 (2H, d, J 9.0 Hz, 2H of C$_6$H$_4$NHAc), 7.32 (1H, t, J 8.0 Hz, C$_6$H$_4$OCF$_3$H-5), 7.31 (1H, m, 1×NH), 7.23 (2H, m, C$_6$H$_4$OCF$_3$H-2, H-4 or H-6), 7.09 (1H, d, J 8.0 Hz, C$_6$H$_4$OCF$_3$H-4 or H-6), 6.86 (2H, d, J 9.0 Hz, 2H of C$_6$H$_4$NHAc), 6.49 (1H, m, 1×NH), 4.54 (1H, m, PhOpipH-4), 4.01 (1H, m, pipH-4), 3.88 (2H, m, 2H of PhOpipH-2, H-6), 3.68 (1H, m, 1H of PhOpipH-2, H-6), 3.52 (2H, s, CH$_2$C$_6$H$_4$OCF$_3$), 3.47-3.40 (1H, m, 1H of PhOpipH-2, H-6), 2.85 (2H, m, 2H of pipH-2, H-6), 2.18 (2H, t, J 11.5 Hz, 2H of pipH-2, H-6), 2.14 (3H, s, NHCOCH$_3$), 2.04-1.90 (5H, m, 2H of pipH-3, H-5, 3H of PhOpipH-3, H-5), 1.80 (1H, m, 1H of PhOpipH-3, H-5), 1.62 (2H, m, 2H of pipH-3, H-5); $^{19}$F nmr (CDCl$_3$) δ −57.7; m/z: 640 [M+H]$^+$.

Compound 429: 6-(4-(3-acetamidophenoxy)piperidine-1-carbonyl)-N-(1-(3-(trifluoromethoxy)benzyl)piperidin-4-yl)nicotinamide. $^1$H nmr (CDCl$_3$) δ 8.89 (1H, m, pyH-6), 8.12 (1H, dd, J 8.0, 2.0 Hz, pyH-4), 7.59 (1H, d, J 8.0 Hz, pyH-3), 7.48 (1H, s, 1×NH), 7.36 (1H, s, C$_6$H$_4$NHAcH-2), 7.32 (1H, m, C$_6$H$_4$NHAcH-5), 7.24-7.16 (3H, m, C$_6$H$_4$OCF$_3$H-2, H-4 or H-6, C$_6$H$_4$NHAcH-5), 7.10 (1H, d, J 8.5 Hz, C$_6$H$_4$OCF$_3$H-4 or H-6), 6.90 (1H, d, J 8.0 Hz, C$_6$H$_4$NHAcH-4 or H-6), 6.65 (1H, d, J 8.0 Hz, C$_6$H$_4$NHAcH-4 or H-6), 6.50 (1H, d, J 8.0 Hz, NH), 4.59 (1H, m, PhOpipH-4), 4.01 (1H, m, pipH-4), 3.88 (2H, m, 2H of PhOpipH-2, H-6), 3.67 (1H, m, 1H of PhOpipH-2, H-6), 3.52 (2H, s, CH$_2$C$_6$H$_4$OCF$_3$), 3.44 (1H, m, 1H of PhOpipH-2, H-6), 2.85 (2H, m, 2H of pipH-2, H-6), 2.18 (2H, t, J 11.0 Hz, 2H of pipH-2, H-6), 2.15 (3H, s, NHCOCH$_3$), 2.08-1.91 (5H, m, 2H of pipH-3, H-5, 3H of PhOpipH-3, H-5), 1.81 (1H, m, 1H of PhOpipH-3, H-5), 1.62 (2H, m, 2H of pipH-3, H-5); $^{19}$F nmr (CDCl$_3$) δ −57.7; m/z: 641 [M+H]$^+$.

Compound 430: 6-(4-(4-methoxybenzoyl)piperidine-1-carbonyl)-N-(1-(4-(trifluoromethoxy)benzyl)piperidin-4-yl)nicotinamide. $^1$H nmr (CDCl$_3$) δ 8.81 (1H, m, pyH-6), 8.14 (1H, dd, J 8.0, 2.0 Hz, pyH-4), 7.94 (2H, d, J 8.5 Hz, 2H of C$_6$H$_4$OCH$_3$), 7.63 (1H, d, J 8.0 Hz, pyH-3), 7.34 (2H, d, J 9.0 Hz, 2H of C$_6$H$_4$OCF$_3$), 7.15 (2H, d, J 8.0 Hz, 2H of C$_6$H$_4$OCF$_3$), 6.96 (2H, d, J 9.5 Hz, 2H of C$_6$H$_4$OCH$_3$), 6.26 (1H, d, J 8.0 Hz, NH), 4.69 (1H, m, 1H of BzpipH-2, H-6), 4.02 (1H, m, pipH-4), 3.94 (1H, m, 1H of BzpipH-2, H-6), 3.88 (3H, s, OCH$_3$), 3.53 (1H, m, BzpipH-4), 3.51 (2H, s, CH$_2$C$_6$H$_4$OCF$_3$), 3.25 (1H, ddd, J 14.0, 10.0, 4.0 Hz, 1H of BzpipH-2, H-6), 3.11 (1H, m, 1H of BzpipH-2, H-6), 2.85 (2H, m, 2H of pipH-2, H-6), 2.18 (2H, dd, J 11.5, 9.5 Hz, 2H of pipH-2, H-6), 2.02 (2H, m, 2H of pipH-3, H-5), 1.93-1.73 (4H, m, BzpipH-3, H-5), 1.61 (2H, m, 2H of pipH-3, H-5); $^{19}$F nmr (CDCl$_3$) δ −57.9; m/z: 626 [M+H]$^+$.

Compound 431: N-(1-(4-cyanobenzyl)piperidin-4-yl)-6-(4-(3-(cyclopropanecarboxamido)phenoxy)piperidine-1-carbonyl)nicotinamide. $^1$H nmr (CDCl$_3$) δ 8.83 (1H, m, pyH-6), 8.05 (1H, dd, J 8.0, 2.0 Hz, pyH-4), 7.56-7.52 (3H, m, 2H of C₆H₄CN, pyH-3), 7.39-3.37 (4H, m, 2H of C₆H₄CN, 1×NH, C₆H₄NH-2), 7.13 (1H, t, J 8.0 Hz, C₆H₄NH-5), 6.79 (1H, dd, J 8.0, 1.5 Hz, C₆H₄NH-4 or H-6), 6.58 (1H, dd, J 8.0, 2.0 Hz, C₆H₄NH-4 or H-6), 6.26 (1H, d, J 7.5 Hz, 1×NH), 4.55 (1H, m, PhOpipH-4), 3.96 (1H, m, pipH-4), 3.82 (2H, m, 2H of PhOpipH-2, H-6), 3.61 (1H, m, 1H of PhOpipH-2, H-6), 3.49 (2H, s, C$\underline{H}_2$C₆H₄CN), 3.42-3.35 (1H, m, 1H of PhOpipH-2, H-6), 2.76 (2H, m, 2H of pipH-2, H-6), 2.14 (2H, dd, J 11.5, 9.5 Hz, 2H of pipH-2, H-6), 1.99-1.82 (5H, m, 2H of pipH-3, H-5, 3H of PhOpipH-3, H-5), 1.78 (1H, m, 1H of PhOpipH-3, H-5), 1.54 (2H, m, 2H of pipH-3, H-5), 1.43 (1H, m cPrH-1), 1.01 (2H, m, 2H of cPrH-2, H-3), 0.79 (2H, m, 2H of cPrH-2, H-3); m/z: 608 [M+H]⁺.

Compound 432: 6-(4-(3-(cyclopropanecarboxamido)phenoxy)piperidine-1-carbonyl)-N-(1-(4-fluorobenzyl)piperidin-4-yl)nicotinamide. ¹H nmr (CDCl₃) δ 8.81 (1H, m, pyH-6), 8.03 (1H, dd, J 8.0, 2.0 Hz, pyH-4), 7.63 (1H, s, 1×NH), 7.50 (1H, d, J 8.5 Hz, pyH-3), 7.36 (1H, s, C₆H₄NH-2), 7.23-7.18 (2H, m, 2H of C₆H₄F), 7.11 (1H, t, J 8.0 Hz, C₆H₄NH-5), 6.92 (2H, t, J 9.0 Hz, 2H of C₆H₄F), 6.82 (1H, dd, J 8.0, 1.0 Hz, C₆H₄NH-4 or H-6), 6.57 (1H, dd, J 8.0, 1.5 Hz, C₆H₄NH-4 or H-6), 6.45 (1H, d, J 8.0 Hz, 1×NH), 4.52 (1H, m, PhOpipH-4), 3.94 (1H, m, pipH-4), 3.80 (2H, m, 2H of PhOpipH-2, H-6), 3.58 (1H, m, 1H of PhOpipH-2, H-6), 3.41 (2H, s, C$\underline{H}_2$C₆H₄F), 3.34 (1H, m, 1H of PhOpipH-2, H-6), 2.77 (2H, m, 2H of pipH-2, H-6), 2.08 (2H, dd, J 11.5, 9.5 Hz, 2H of pipH-2, H-6), 1.95-1.80 (5H, 2H of pipH-3, H-5, 3H of PhOpipH-3, H-5), 1.75 (1H, m, 1H of PhOpipH-3, H-5), 1.53 (2H, m, 2H of pipH-3, H-5), 1.45 (1H, m, cPrH-1), 0.99 (2H, m, 2H of cPrH-2, H-3), 0.77 (2H, m, 2H of cPrH-2, H-3); ¹⁹F nmr (CDCl₃) δ −115.9; m/z: 601 [M+H]⁺.

Compound 433: 6-(4-(3-(cyclopropanecarboxamido)phenoxy)piperidine-1-carbonyl)-N-(6-(4-fluorophenoxy)pyridin-3-yl)nicotinamide. ¹H nmr (CDCl₃) δ 9.56 (1H, s, 1×NH), 8.85 (1H, m, pyH-6), 8.38 (1H, d, J 2.5 Hz, N,O-pyH-6), 8.24 (1H, dd, J 9.0, 2.5 Hz, N,O-pyH-4), 8.04 (1H, dd, J 8.5, 2.0 Hz, pyH-4), 7.56 (1H, s, 1×NH), 7.36 (1H, s, C₆H₄NH-2), 7.34 (1H, d, J 8.5 Hz, pyH-3), 7.11 (1H, t, J 8.0 Hz, C₆H₄NH-5), 7.03-6.99 (4H, m, C₆H₄F), 6.86 (1H, d, J 8.5 Hz, N,O-pyH-3), 6.78 (1H, dd, J 8.0, 1.5 Hz, C₆H₄NH-4 or H-6), 6.57 (1H, dd, J 8.0, 2.0 Hz, C₆H₄NH-4 or H-6), 4.52 (1H, m, PhOpipH-4), 3.87 (1H, m, 1H of PhOpipH-2, H-6), 3.74 (1H, m, 1H of PhOpipH-2, H-6), 3.52 (1H, m, 1H of PhOpipH-2, H-6), 3.27 (1H, m, 1H of PhOpipH-2, H-6), 1.91-1.76 (4H, m, PhOpipH-3, H-5), 1.43 (1H, m, cPrH-1), 0.99 (2H, m, 2H of cPrH-2, H-3), 0.789 (2H, m, 2H of cPrH-2, H-3); ¹⁹F nmr (CDCl₃) δ −118.5; m/z: 596 [M+H]⁺.

Compound 434: N-((cis)-4-(4-cyanophenoxy)cyclohexyl)-6-(4-(3-(cyclopropanecarboxamido)phenoxy)piperidine-1-carbonyl)nicotinamide. ¹H nmr (CDCl₃) δ 8.85 (1H, m, pyH-6), 8.05 (1H, dd, J 8.0, 2.0 Hz, pyH-4), 7.61 (1H, s, 1×NH), 7.48 (2H, d, J 9.0 Hz, 2H of C₆H₄CN), 7.40 (1H, s, C₆H₄NH-2), 7.11 (1H, t, J 8.0 Hz, C₆H₄NH-5), 6.87 (2H, d, J 9.0 Hz, 2H of C₆H₄CN), 6.80 (1H, dd, J 8.0, 1.0 Hz, C₆H₄NH-4 or H-6), 6.64 (1H, d, J 8.0 Hz, 1×NH), 6.57 (1H, dd, J 8.0, 2.0 Hz, C₆H₄NH-4 or H-6), 4.54 (2H, m, cHexH-1, PhOpipH-4), 4.04 (1H, m, cHexH-4), 3.83 (1H, m, 1H of PhOpipH-2, H-6), 3.77 (1H, m, 1H of PhOpipH-2, H-6), 3.58 (1H, m, 1H of PhOpipH-2, H-6), 3.35 (1H, m, 1H of PhOpipH-2, H-6), 2.04 (2H, m, 2H of cHexH-2), 1.94-1.80 (4H, m, 4H of cHexH-2, H-3, H-5, H-6, PhOpipH-3, H-5), 1.80-1.64 (6H, m, 6H of cHexH-2, H-3, H-5, H-6, PhOpipH-3, H-5), 1.45 (1H, m, cPrH-1), 0.99 (2H, m, 2H of cPrH-2, H-3), 0.78 (2H, m, 2H of cPrH-2, H-3); m/z: 609 [M+H]⁺.

Compound 435: 6-(4-(3-(cyclopropanecarboxamido)phenoxy)piperidine-1-carbonyl)-N-(1-(4-methoxybenzyl)piperidin-4-yl)nicotinamide. ¹H nmr (CDCl₃) δ 8.82 (1H, m, pyH-6), 8.04 (1H, dd, J 8.5, 2.0 Hz, pyH-4), 7.54 (1H, s, 1×NH), 7.52 (1H, d, J 8.5 Hz, pyH-3), 7.36 (1H, s, C₆H₄NH-2), 7.15 (2H, d, J 8.5 Hz, 2H of C₆$\underline{H}_4$OCH₃), 7.11 (1H, t, J 8.5 Hz, C₆H₄NH-5), 6.82 (1H, m, C₆H₄NH-4 or H-6), 6.79 (2H, d, J 8.5 Hz, 2H of C₆$\underline{H}_4$OCH₃), 6.57 (1H, dd, J 8.0, 2.0 Hz, C₆H₄NH-4 or H-6), 6.31 (1H, d, J 7.5 Hz, 1×NH), 4.53 (1H, m, PhOpipH-4), 3.93 (1H, m, pipH-4), 3.81 (2H, m, 2H of PhOpipH-2, H-6), 3.73 (3H, s, OCH₃), 3.59 (1H, m, 1H of PhOpipH-2, H-6), 3.39 (2H, s, C$\underline{H}_2$C₆H₄OCH₃), 3.33 (1H, m, 1H of PhOpipH-2, H-6), 2.79 (2H, m, 2H of pipH-2, H-6), 2.08 (2H, dd, J 11.5, 9.5 Hz, 2H of pipH-2, H-6), 1.96-1.71 (6H, m, 2H of pipH-3, H-5, PhOpipH-3, H-5), 1.53 (2H, m, 2H of pipH-3, H-5), 1.47-1.39 (1H, m, cPrH-1), 1.00 (2H, m, 2H of cPrH-2, H-3), 0.77 (2H, m, 2H of cPrH-2, H-3); m/z: 613 [M+H]⁺.

Compound 436: N-(1-(4-cyanobenzyl)piperidin-4-yl)-6-(4-(4-(trifluoromethylthio)phenoxy)piperidine-1-carbonyl)pyridazine-3-carboxamide. ¹H nmr (CDCl₃) δ 8.42 (1H, d, J 9.0 Hz, pyH-5 or H-6), 8.07 (1H, d, J 8.0 Hz, NH), 8.01 (1H, d, J 8.5 Hz, pyH-5 or H-6), 7.62 (2H, d, J 8.0 Hz, 2H of C₆H₄CN), 7.58 (2H, d, J 8.5 Hz, 2H of C₆H₄SCF₃), 7.46 (2H, d, J 8.0 Hz, 2H of C₆H₄CN), 6.95 (2H, d, J 9.0 Hz, 2H of C₆H₄SCF₃), 4.71 (1H, m, PhOpipH-4), 4.10-4.03 (2H, m, pipH-4, 1H of PhOpipH-2, H-6), 3.88 (1H, m, 1H of PhOpipH-2, H-6), 3.82 (1H, ddd, J 13.0, 8.5, 4.5 Hz, 1H of PhOpipH-2, H-6), 3.71-3.64 (1H, m, 1H of PhOpipH-2, H-6), 3.57 (2H, s, C$\underline{H}_2$C₆H₄CN), 2.84 (2H, m, 2H of pipH-2, H-6), 2.24 (2H, dd, J 11.0, 9.5 Hz, 2H of pipH-2, H-6), 2.15-1.97 (6H, m, 2H of pipH-3, H-5, PhOpipH-3, H-5), 1.67 (2H, m, 2H of pipH-3, H-5); ¹⁹F nmr (CDCl₃) δ −43.8; m/z: 625 [M+H]⁺.

Compound 437: 6-(4-(4-acetylphenoxy)piperidine-1-carbonyl)-N-(1-(4-cyanobenzyl)piperidin-4-yl)pyridazine-3-carboxamide. ¹H nmr (CDCl₃) δ 8.43 (1H, d, J 8.5 Hz, pyH-5 or H-6), 8.07 (1H, d, J 8.0 Hz, NH), 8.01 (1H, d, J 9.0 Hz, pyH-5 or H-6), 7.94 (2H, d, J 9.0 Hz, 2H of C₆H₄Ac), 7.62 (2H, d, J 8.5 Hz, 2H of C₆H₄CN), 7.46 (2H, d, J 8.5 Hz, 2H of C₆H₄CN), 6.96 (2H, d, J 9.5 Hz, 2H of C₆H₄Ac), 4.78 (1H, m, PhOpipH-4), 4.11-4.04 (2H, m, pipH-4, 1H of PhOpipH-2, H-6), 3.89 (1H, m, 1H of PhOpipH-2, H-6), 3.83 (1H, m, 1H of PhOpipH-2, H-6), 3.72-3.65 (1H, m, 1H of PhOpipH-2, H-6), 3.57 (2H, s, C$\underline{H}_2$C₆H₄CN), 2.83 (2H, m, 2H of pipH-2, H-6), 2.56 (3H, s, COCH₃), 2.23 (2H, dd, J 11.0, 9.5 Hz, 2H of pipH-2, H-6), 2.16-2.02 (6H, m, 2H of pipH-3, H-5, PhOpipH-3, H-5), 1.67 (2H, m, 2H of pipH-3, H-5); m/z: 568 [M+H]⁺.

Compound 438: 6-(4-(3-(cyclopropanecarboxamido)phenoxy)piperidine-1-carbonyl)-N-(1-(4-(trifluoromethoxy)benzyl)piperidin-4-yl)nicotinamide. ¹H nmr (CDCl₃) δ 8.90 (1H, m, pyH-6), 8.13 (1H, dd, J 8.5, 2.0 Hz, pyH-4), 7.63 (1H, d, J 8.0 Hz, pyH-3), 7.46 (2H, m, C₆H₄NH-2, 1×NH), 7.34 (2H, d, J 8.5 Hz, 2H of C₆H₄OCF₃), 7.19-7.14 (3H, m, 2H of C₆H₄OCF₃, C₆H₄NH-5), 6.86 (1H, d, J 8.5 Hz, C₆H₄NH-4 or H-6), 6.65 (1H, dd, J 8.5, 2.0 Hz, C₆H₄NH-4 or H-6), 6.23 (1H, d, J 8.0 Hz, 1×NH), 4.61 (1H, m, PhOpipH-4), 4.02 (1H, m, pipH-4), 3.95-3.84 (2H, m, 2H of PhOpipH-2, H-6), 3.68 (1H, m, 1H of PhOpipH-2, H-6), 3.51 (2H, s, C$\underline{H}_2$C₆H₄OCF₃), 3.44 (1H, m, 1H of PhOpipH-2, H-6), 2.85 (2H, m, 2H of pipH-2, H-6), 2.18 (2H, t, J 11.5 Hz, 2H of pipH-2, H-6), 2.05-1.92 (5H, m, 2H of pipH-3, H-5, 3H of PhOpipH-3, H-5), 1.84 (1H, m, 1H of PhOpipH-3, H-5), 1.59 (2H, m, 2H of pipH-3, H-5), 1.49 (1H, m, cPrH-1), 1.08 (2H, m, 2H of cPrH-2, H-3), 0.85 (2H, m, 2H of cPrH-2, H-3); ¹⁹F nmr (CDCl₃) δ −57.9; m/z: 666 [M+H]⁺ (found [M+H]⁺, 666.3879, C₃₅H₃₈F₃N₅O₅ requires [M+H]⁺ 666.2898).

Compound 439: N-(1-(4-methoxybenzyl)piperidin-4-yl)-6-(4-(4-(pyrrolidin-1-yl)benzoyl)piperidine-1-carbonyl)nicotinamide. $^1$H nmr (CDCl$_3$) δ 8.90 (1H, m, pyH-6), 8.12 (1H, dd, J 8.0, 2.0 Hz, pyH-4), 7.86 (2H, d, J 8.5 Hz, 2H of C$_6$H$_4$N), 7.61 (1H, d, J 8.5 Hz, pyH-3), 7.22 (2H, d, J 8.5 Hz, 2H of C$_6$H$_4$OCH$_3$), 6.85 (2H, d, J 9.0 Hz, 2H of C$_6$H$_4$OCH$_3$), 6.52 (2H, d, J 9.0 Hz, 2H of C$_6$H$_4$N), 6.32 (1H, m, NH), 4.69 (1H, m, 1H of BzpipH-2, H-6), 4.01 (1H, m, pipH-4), 3.90 (1H, m, 1H of BzpipH-2, H-6), 3.79 (3H, s, OCH$_3$), 3.53 (1H, m, BzpipH-4), 3.49 (2H, s, CH$_2$C$_6$H$_4$OCH$_3$), 3.38, 3.35 (4H, 2 d AB system, J 6.5 Hz, 4H of pyrrolidine), 3.24 (1H, m, 1H of BzpipH-2, H-6), 3.08 (1H, m, 1H of BzpipH-2, H-6), 2.88 (2H, m, 2H of pipH-2, H-6), 2.19 (2H, t, J 11.0 Hz, 2H of pipH-2, H-6), 2.05, 2.02 (4H, 2 d AB system, J 6.5 Hz, 4H of pyrrolidine), 1.98 (2H, m, 2H of pipH-3, H-5), 1.91-1.78 (4H, m, BzpipH-3, H-5), 1.61 (2H, m, 2H of pipH-3, H-5); m/z: 611 [M+H]$^+$.

Compound 440: 6-(4-(4-(pyrrolidin-1-yl)benzoyl)piperidine-1-carbonyl)-N-(1-(4-(trifluoromethyl)benzyl)piperidin-4-yl)nicotinamide. $^1$H nmr (CDCl$_3$) δ 8.92 (1H, m, pyH-6), 8.13 (1H, dd, J 8.0, 2.0 Hz, pyH-4), 7.87 (2H, d, J 9.0 Hz, 2H of C$_6$H$_4$N), 7.56 (1H, d, J 8.5 Hz, pyH-3), 7.34 (2H, d, J 8.5 Hz, 2H of C$_6$H$_4$OCF$_3$), 7.14 (2H, d, J 8.0 Hz, 2H of C$_6$H$_4$OCF$_3$), 6.60 (1H, d, J 7.5 Hz, NH), 6.52 (2H, d, J 9.0 Hz, 2H of C$_6$H$_4$N), 4.69 (1H, m, 1H of BzpipH-2, H-6), 4.01 (1H, m, pipH-4), 3.88 (1H, m, 1H of BzpipH-2, H-6), 3.52 (1H, m, BzpipH-4), 3.50 (2H, s, CH2C6H4OCF3), 3.38, 3.35 (4H, 2 d AB system, J 6.5 Hz, 4H of pyrrolidine), 3.23 (1H, m, 1H of BzpipH-2, H-6), 3.09 (1H, m, 1H of BzpipH-2, H-6), 2.85 (2H, m, 2H of pipH-2, H-6), 2.18 (2H, mdd, J 11.5, 10.0 Hz, 2H of pipH-2, H-6), 2.05, 2.03 (4H, 2 d AB system, J 6.5 Hz, 4H of pyrrolidine), 1.98 (2H, m, 2H of pipH-3, H-5), 1.92-1.76 (4H, m, BzpipH-3, H-5), 1.63 (2H, m, 2H of pipH-3, H-5); $^{19}$F nmr (CDCl$_3$) δ –57.9; m/z: 665 [M+H]$^+$.

Compound 441: 6-(4-(4-(pyrrolidin-1-yl)benzoyl)piperidine-1-carbonyl)-N-(1-(3-(trifluoromethoxy)benzyl)piperidin-4-yl)nicotinamide. $^1$H nmr (CDCl$_3$) δ 8.84 (1H, m, pyH-6), 8.05 (1H, dd, J 8.5, 2.0 Hz, pyH-4), 7.80 (2H, d, J 9.0 Hz, 2H of C$_6$H$_4$N), 7.49 (1H, d, J 8.0 Hz, pyH-3), 7.25 (1H, t, J 7.5 Hz, C$_6$H$_4$OCF$_3$H-5), 7.17 (2H, m, C$_6$H$_4$OCF$_3$H-2, H-4 or H-6), 7.02 (1H, d, J 8.0 Hz, C$_6$H$_4$OCF$_3$H-4 or H-6), 6.54 (1H, d, J 8.0 Hz, NH), 6.46 (2H, d, J 9.0 Hz, 2H of C$_6$H$_4$N), 4.64 (1H, m, 1H of BzpipH-2, H-6), 3.95 (1H, m, pipH-4), 3.82 (1H, m, 1H of BzpipH-2, H-6), 3.46 (2H, s, CH$_2$C$_6$H$_4$OCF$_3$), 3.42 (1H, m, BzzpipH-4), 3.31, 3.29 (4H, 2 d AB system, J 6.5 Hz, 4H of pyrrolidine), 3.17 (1H, m, 1H of BzpipH-2, H-6), 3.02 (1H, m, 1H of BzpipH-2, H-6), 2.78 (2H, m, 2H of pipH-2, H-6), 2.12 (2H, dd, J 11.5, 9.5 Hz, 2H of pipH-2, H-6), 1.99-1.95 (6H, m, 4H of pyrrolidine, 2H of pipH-3, H-5), 1.86-1.72 (4H, m, BzpipH-3, H-5), 1.57 (2H, m, 2H of pipH-3, H-5); $^{19}$F nmr (CDCl$_3$) δ –57.7; m/z: 665 [M+H]$^+$.

Compound 442: N-((cis)-4-(4-cyanophenoxy)cyclohexyl)-6-(4-(4-(pyrrolidin-1-yl)benzoyl)piperidine-1-carbonyl)nicotinamide. $^1$H nmr (CDCl$_3$) δ 8.82 (1H, m, pyH-6), 7.86 (2H, d, J 9.0 Hz, 2H of C$_6$H$_4$N), 7.57-7.52 (3H, m, 2H of C$_6$H$_4$CN, pyH-3), 6.93 (2H, d, J 9.0 Hz, 2H of C$_6$H$_4$CN), 6.77 (1H, d, J 8.0 Hz, NH), 6.53 (2H, d, J 9.0 Hz, 2H of C$_6$H$_4$N), 4.69 (1H, m, 1H of BzpipH-2, H-6), 4.61 (1H, br s, cHexH-1), 4.11 (1H, m, cHexH-4), 3.88 (1H, m, 1H of BzpipH-2, H-6), 3.48 (1H, m BzpipH-4), 3.38, 3.36 (4H, 2 d AB system, J 6.5 Hz, 4H of pyrrolidine), 3.23 (1H, m, 1H of BzpipH-2, H-6), 3.08 (1H, m, 1H of BzpipH-2, H-6), 2.12-2.09 (2H, m, 2H of cHexH-2, H-3, H-5, H-6), 2.05, 2.03 (4H, 2 d AB system, J 6.5 Hz, 4H of pyrrolidine), 1.98-1.90 (2H, m, 2H of cHexH-2, H-3, H-5, H-6), 1.88-1.69 (8H, 8H of cHexH-2, H-3, H-5, H-6, BzpipH-3, H-5); $^{19}$F nmr (CDCl$_3$) δ –118.6; m/z: 607 [M+H]$^+$(found [M+H]$^+$, 606.3158, C$_{36}$H$_{39}$N$_5$O$_4$ requires [M+H]$^+$ 606.3075).

Compound 443: N-(1-(3-fluoro-4-methoxybenzyl)piperidin-4-yl)-6-(4-(4-(pyrrolidin-1-yl)benzoyl)piperidine-1-carbonyl)nicotinamide. $^1$H nmr (CDCl$_3$) δ 8.91 (1H, m, pyH-6), 8.12 (1H, dd, J 8.5, 2.0 Hz, pyH-4), 7.87 (2H, d, J 9.0 Hz, 2H of C$_6$H$_4$N), 7.59 (1H, d, J 8.0 Hz, pyH-3), 7.08 (1H, dd, J 12.0, 2.0 Hz, C$_6$H$_3$FOCH$_3$H-2), 6.99 (1H, d, J 8.5 Hz, C$_6$H$_3$FOCH$_3$H-6), 6.89 (1H, t, J 8.5 Hz, C$_6$H$_3$FOCH$_3$H-5), 6.53 (2H, d, J 9.0 Hz, 2H of C$_6$H$_4$N), 6.49 (1H, d, J 8.5 Hz, NH), 4.70 (1H, m, 1H of BzpipH-2, H-6), 4.01 (1H, m, pipH-4), 3.89 (1H, m, 1H of BzpipH-32, H-6), 3.87 (3H, s, OCH$_3$), 3.50 (1H, m, BzpipH-4), 3.43 (2H, s, CH$_2$C$_6$H$_3$FOCH$_3$), 3.38, 3.36 (4H, 2 d AB system, J 6.5 Hz, 4H of pyrrolidine), 3.24 (1H, m, 1H of BzpipH-2, H-6), 3.09 (1H, m, 1H of BzpipH-2, H-6), 2.84 (2H, m, 2H of pipH-2, H-6), 2.15 (2H, t, J 11.5 Hz, 2H of pipH-2, H-6), 2.05, 2.03 (4H, 2 d AB system, J 6.5 Hz, 4H of pyrrolidine), 1.99 (2H, m, 2H of pipH-3, H-5), 1.90-1.78 (4H, m, BzpipH-3, H-5), 1.62 (2H, m, 2H of pipH-3, H-5); $^{19}$F nmr (CDCl$_3$) δ –135.6; m/z: 629 [M+H]$^+$.

Compound 444: 6-(4-(4-(pyrrolidin-1-yl)benzoyl)piperidine-1-carbonyl)-N-(1-(4-(pyrrolidin-1-yl)benzoyl)piperidin-4-yl)nicotinamide. $^1$H nmr (CDCl$_3$) δ 8.90 (1H, m, pyH-6), 8.12 (1H, dd, J 8.5, 2.0 Hz, pyH-4), 7.87 (2H, d, J 9.0 Hz, 2H of COC$_6$H$_4$N), 7.61 (1H, d, J 8.5 Hz, pyH-3), 7.15 (2H, d, J 9.0 Hz, 2H of CH$_2$C$_6$H$_4$N), 6.53 (2H, d, J 9.0 Hz, 2H of 1×C$_6$H$_4$N), 6.52 (2H, d, J 8.5 Hz, 2H of 1×C$_6$H$_4$N), 6.33 (1H, d, J 8.0 Hz, NH), 4.69 (1H, m, 1H of BzpipH-2, H-6), 4.00 (1H, m, pipH-4), 3.90 (1H, m, 1H of BzpipH-2, H-6), 3.49 (1H, m, BzpipH-4), 3.43 (2H, s, CH$_2$C$_6$H$_4$N), 3.38, 3.35 (4H, 2 d AB system, J 6.5 Hz, 4H of 1×pyrrolidine), 3.28, 3.26 (4H, 2 d AB system, J 6.5 Hz, 4H of 1×pyrrolidine), 3.24 (1H, m, 1H of BzpipH-2, H-6), 3.08 (1H, m, 1H of BzpipH-2, H-6), 2.88 (2H, m, 2H of pipH-2, H-6), 2.14 (2H, dd, J 11.5, 9.5 Hz, 2H of pipH-2, H-6), 2.04-1.96 (10H, m, 2H of pipH-3, H-5, 4H of 2×pyrrolidine), 1.90-1.78 (4H, m, BzpipH-3, H-5), 1.61 (2H, m, 2H of pipH-3, H-5); m/z: 650 [M+H]$^+$.

Compound 445: 6-(4-(4-methoxybenzoyl)piperidine-1-carbonyl)-N-(piperidin-4-yl)nicotinamide (as its dihydrochloride salt). $^1$H nmr (CDCl$_3$) δ 8.99 (1H, s, pyH-6), 8.75 (3H, m, NH, NH$_2$), 8.30 (1H, dt, J 8.5, 2.0 Hz, pyH-4), 7.98 (2H, d, J 9.0 Hz, C$_6$H$_4$OCH$_3$), 7.65 (1H, d, J 8.0 Hz, pyH-3), 7.04 (2H, d, J 8.5 Hz, 2H of C$_6$H$_4$OCH$_3$), 4.50 (1H, m, BzpipH-2, H-6), 4.06 (1H, m, pipH-4), 3.83 (3H, s, OCH3), 3.73 (1H, m, BzpipH-4), 3.60 (1H, m, 1H of BzpipH-2, H-6), 3.33-3.17 (3H, m, 2H of pipH-2, H-6, 1H of BzpipH-2, H-6), 3.06-2.98 (3H, m, 2H of pipH-2, H-6, 1H of BzpipH-2, H-6), 1.99-1.86 (3H, m, 3H of pipH-3, H-5, BzpipH-3, H-5), 1.77-1.65 (3H, m, 3H of pipH-3, H-5, BzpipH-3, H-5), 1.60-1.49 (2H, m, 2H of pipH-3, H-5, BzpipH-3, H-5); m/z: 452 [M+H]$^+$.

Compound 446: N-(1-(4-isopropoxybenzyl)piperidin-4-yl)-6-(4-(4-(pyrrolidin-1-yl)benzoyl)piperidine-1-carbonyl)nicotinamide. $^1$H nmr (CDCl$_3$) d 8.83 (1H, m, pyH-6), 8.05 (1H, dd, J 8.0, 2.0 Hz, pyH-4), 7.80 (2H, d, J 9.5 Hz, 2H of C$_6$H$_4$N), 7.54 (1H, d, J 8.0 Hz, pyH-3), 7.13 (2H, d, J 9.0 Hz, 2H of C$_6$H$_4$OiPr), 6.76 (2H, d, J 9.0 Hz, 2H of C$_6$H$_4$OiPr), 6.46 (2H, d, J 9.0 Hz, 2H of C$_6$H$_4$N), 6.28 (1H, d, J 8.0 Hz, NH), 4.63 (1H, m, 1H of BzpipH-2, H-6), 4.46 (1H, heptet, J 6.0 Hz, OCH(CH$_3$)$_2$), 3.94 (1H, m, pipH-4), 3.84 (1H, m, 1H of BzpipH-2, H-6), 3.43 (1H, m, BzpipH-4), 3.39 (2H, s, CH$_2$C$_6$H$_4$OiPr), 3.31, 3.29 (4H, 2 d AB system, J 6.5 Hz, 4H of pyrrolidine), 3.17 (1H, m, 1H of BzpipH-2, H-6), 3.02 (1H, m, 1H of BzpipH-2, H-6), 2.80 (2H, m, 2H of pipH-2, H-6), 2.09 (2H, t, J 11.0 Hz, 2H of pipH-2, H-6), 1.98, 1.96 (4H, 2 d AB system, J 6.5 Hz, 4H of pyrrolidine), 1.92 (2H, m, 2H of pipH-3, H-5), 1.87-1.67 (4H, m, 4H of BzpipH-3, H-5), 1.55 (2H, m, 2H of pipH-3, H-5); m/z: 638 [M+H]$^+$.

Compound 447: N-(1-(4-cyano-3-fluorobenzyl)piperidin-4-yl)-6-(4-(4-(pyrrolidin-1-yl)benzoyl)piperidine-1-carbonyl)nicotinamide. $^1$H nmr (CDCl$_3$) δ 8.91 (1H, m, pyH-6), 8.12 (1H, dd, J 8.0, 2.0 Hz, pyH-4), 7.87 (2H, d, J 9.0 Hz, 2H of C$_6$H$_4$N), 7.56 (1H, d, J 8.0 Hz, pyH-3), 7.54 (1H, dd, J 8.0, 6.5 Hz, C$_6$H$_3$FCNH—H-5 or H-6), 7.26 (1H, d, J 10.0 Hz, C$_6$H$_3$FCNH-2), 7.22 (1H, d, J 8.5 Hz, C$_6$H$_3$FCNH-5 or H-6), 6.61 (1H, d, J 7.5 Hz, NH), 6.53 (2H, d, J 8.5 Hz, 2H of C$_6$H$_4$N), 4.71 (1H, m, 1H of BzpipH-2, H-6), 4.01 (1H, m, pipH-4), 3.90 (1H, m, 1H of BzpipH-2, H-6), 3.55 (2H, s, CH2C6H4N), 3.51 (1H, m, BzpipH-4), 3.38, 3.36 (4H, 2 d AB system, J 6.5 Hz, 4H of pyrrolidine), 3.24 (1H, m, 1H of BzpipH-2, H-6), 3.09 (1H, m, 1H of BzpipH-2, H-6), 2.83 (2H, m, 2H of pipH-2, H-6), 2.22 (2H, dd, J 11.5, 9.5 Hz, 2H of pipH-2, H-6), 2.05, 2.03 (4H, 2 d AB system, J 6.5 Hz, 4H of pyrrolinine), 2.00 (2H, m, 2H of pipH-3, H-5), 1.95-1.78 (4H, m, BzpipH-3, H-5), 1.65 (2H, m, 2H of pipH-3, H-5); $^{19}$F nmr (CDCl$_3$) δ −106.9; m/z: 624 [M+H]$^+$.

Compound 448: N-(1-(4-cyanobenzyl)piperidin-4-yl)-6-(4-(4-(cyclopropanesulfonamido)phenoxy)piperidine-1-carbonyl)nicotinamide. $^1$H nmr (CDCl$_3$) δ 8.45 (1H, m, pyH-6), 8.08 (1H, dd, J 8.0, 2.0 Hz, pyH-4), 7.61 (1H, d, J 8.5 Hz, pyH-3), 7.54 (2H, d, J 8.5 Hz, 2H of C$_6$H$_4$CN), 7.38 (2H, d, J 8.5 Hz, 2H of C$_6$H$_4$CN), 7.15 (2H, d, J 9.5 Hz, 2H of C$_6$H$_4$NHSO$_2$), 6.82 (2H, d, J 9.0 Hz, 2H of C$_6$H$_4$NHSO$_2$), 6.10 (1H, s, NHSO$_2$), 6.04 (1H, d, J 7.5 Hz, NH), 4.51 (1H, m, PhOpipH-4), 3.97 (1H, m, pipH-4), 3.84 (2H, m, 2H of PhOpipH-2, H-6), 3.66 (1H, m, 1H of PhOpipH-2, H-6), 3.46-3.38 (1H, m, 1H of PhOpipH-2, H-6), 2.76 (2H, m, 2H of pipH-2, H-6), 2.36 (1H, m, cPrH-1), 2.15 (2H, dd, J 11.0, 9.5 Hz, 2H of pipH-2, H-6), 2.00-1.1.86 (5H, m, 2H of pipH-3, H-5, 3H of PhOpipH-3, H-5), 1.79 (1H, m, 1H of PhOpipH-3, H-5), 1.53 (2H, m, 2H of pipH-3, H-5), 1.05 (2H, m, 2H of cPrH-2, H-3), 0.88 (2H, m, 2H of cPrH-2, H-3); m/z: 644 [M+H]$^+$.

Compound 449: 6-(4-(4-(cyclopropanesulfonamido)phenoxy)piperidine-1-carbonyl)-N-(6-(4-fluorophenoxy)pyridin-3-yl)nicotinamide. $^1$H nmr (CDCl$_3$) δ 9.45 (1H, s, 1×NH), 8.95 (1H, m, pyH-6), 8.44 (1H, d, J 2.5 Hz, N,O-pyH-6), 8.33 (1H, dd, J 9.0, 2.5 Hz, N,O-pyH-4), 8.12 (1H, dd, J 8.5, 2.0 Hz, pyH-4), 7.44 (1H, d, J 8.0 Hz, pyH-3), 7.22 (2H, d, J 9.0 Hz, 2H of C$_6$H$_4$NHSO$_2$), 7.20-7.08 (4H, m, C$_6$H$_4$F), 6.94 (1H, d, J 8.5 Hz, N,O-pyH-3), 6.89 (2H, d, J 9.0 Hz, 2H of C$_6$H$_4$NHSO$_2$), 6.29 (1H, s, 1×NH), 4.58 (1H, m, PhOpipH-4), 3.99-3.93 (1H, m, 1H of PhOpipH-2, H-6), 3.88-3.83 (1H, m, 1H of PhOpipH-2, H-6), 3.65 (1H, m, 1H of PhOpipH-2, H-6), 3.41-3.36 (1H, m, 1H of PhOpipH-2, H-6), 2.43 (1H, m, cPrH-1), 2.01-1.91 (3H, m, 3H of PhOpipH-3, H-5), 1.84 (1H, m, 1H of PhOpipH-3, H-5), 1.12 (2H, m, 2H of cPrH-2, H-3), 0.94 (2H, m, 2H of cPrH-2, H-3); $^{19}$F nmr (CDCl$_3$) δ −118.5; m/z: 632 [M+H]$^+$.

Compound 450: N-(1-(4-cyanobenzyl)piperidin-4-yl)-6-(4-(4-(trifluoromethylsulfonyl)phenoxy)piperidine-1-carbonyl)nicotinamide. $^1$H nmr (CDCl$_3$) δ 8.91 (1H, d, J 2.0 Hz, pyH-6), 8.15 (1H, dd, J 8.0, 2.0 Hz, pyH-4), 7.96 (2H, d, J 9.5 Hz, 2H of C$_6$H$_4$SO$_2$), 7.70 (1H, d, J 8.5 Hz, pyH-3), 7.61 (2H, d, J 8.5 Hz, 2H of C$_6$H$_4$CN), 7.45 (2H, d, J 8.5 Hz, 2H of C$_6$H$_4$CN), 7.11 (2H, d, J 9.0 Hz, 2H of C$_6$H$_4$SO$_2$), 6.14 (1H, d, J 7.5 Hz, NH), 4.79 (1H, m, PhOpipH-4), 4.03 (1H, m, pipH-4), 3.94 (2H, m, 2H of PhOpipH-2, H-6), 3.75 (1H, m, 1H of PhOpipH-2, H-6), 3.57 (3H, m, 1H of PhOpipH-2, H-6, CH$_2$C$_6$H$_4$CN), 2.83 (2H, m, 2H of pipH-2, H-6), 2.21 (2H, dd, J 11.5, 9.5 Hz, 2H of pipH-2, H-6), 2.14-1.98 (5H, m, 2H of pipH-3, H-5, 3H of PhOpipH-3, H-5), 1.92 (1H, m, 1H of PhOpipH-3, H-5) 1.62 (2H, m, 2H of pipH-3, H-5); $^{19}$F nmr (CDCl$_3$) δ −78.8; m/z: 656 [M+H]$^+$.

Compound 451: N-((3S,4R)-1-(4-cyanobenzyl)-3-fluoropiperidin-4-yl)-6-(4-(4-(trifluoromethylsulfonyl)phenoxy)piperidine-1-carbonyl)nicotinamide $^1$H nmr (CDCl$_3$) δ 8.91 (1H, m, pyH-6), 8.13 (1H, dd, J 8.0, 2.0 Hz, pyH-4), 7.96 (2H, d, J 8.5 Hz, 2H of C$_6$H$_4$SO$_2$), 7.64 (1H, d, J 8.5 Hz, pyH-3), 7.62 (2H, d, J 8.0 Hz, 2H of C$_6$H$_4$CN), 7.44 (2H, d, J 8.5 Hz, 2H of C$_6$H$_4$CN), 7.11 (2H, d, J 9.0 Hz, 2H of C$_6$H$_4$SO$_2$), 6.64 (1H, d, J 7.5 Hz, NH), 4.79 (1H, m, PhOpipH-4), 4.56 (1H, dtd, J 50.5, 9.5, 4.5 Hz, pipH-3), 4.15 (1H, m, pipH-4), 3.99-3.87 (2H, m, 2H of PhOpipH-2, H-6), 3.71 (1H, m, 1H of PhOpipH-2, H-6), 4.14, 4.09 (2H, 2 d AB system, J 7.5 Hz, CH2C6H4CN), 3.54 (1H, m, 1H of PhOpipH-2, H-6), 3.18 (1H, m, 1H of pipH-2), 2.80 (1H, m, 1H of pipH-6), 2.13-2.18 (3H, m, 1H of pipH2, 1H of pipH-5, 1H of pipH-6), 2.10 (1H, m, 1H of PhOpipH-3, H-5), 2.04 (2H, m, 2H of PhOpipH-3, H-5), 1.91 (1H, m, 1H of PhOpipH-3, H-5), 1.63 (1H, m, 1H of pipH-5); $^{19}$F nmr (CDCl$_3$) δ −78.8, −188.6; m/z: 674 [M+H]$^+$.

Compound 452: N-((3R,4R)-1-(4-cyanobenzyl)-3-fluoropiperidin-4-yl)-6-(4-(4-methoxybenzoyl)piperidine-1-carbonyl)nicotinamide. Compound 452 was separated from the racemic mixture of Compound 349 using chiral chromatography on an (R, R)-Whelk-O 1 25 cm×10 mm column (silica modified with covalently bound 4-(3,5-dinitrobenzamido) tetrahydrophenanthrene), available from Regis Technologies. The instrument was a TharSFC semi-preparative HPLC system, and elution was performed isocratically using 50% MeOH with 0.1% diethylamine in supercritical carbon dioxide at 14 mL/min at 30° C. Compound 452 was the later-eluting peak (at about 21 minutes under the conditions described above). The spectral data agree with Compound 349. Compound 452 was independently enantioselectively synthesized as described in the following scheme:

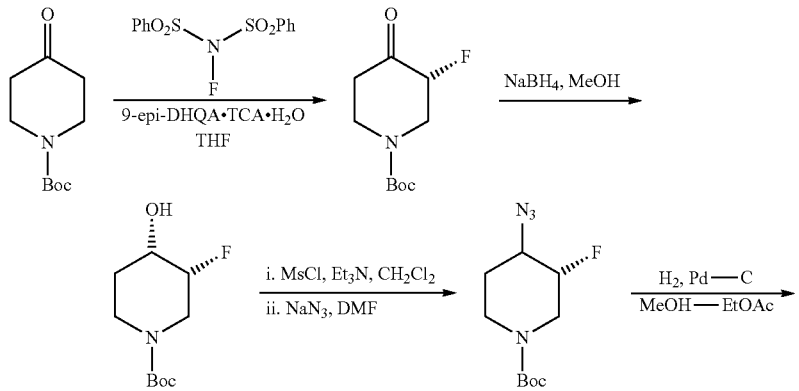

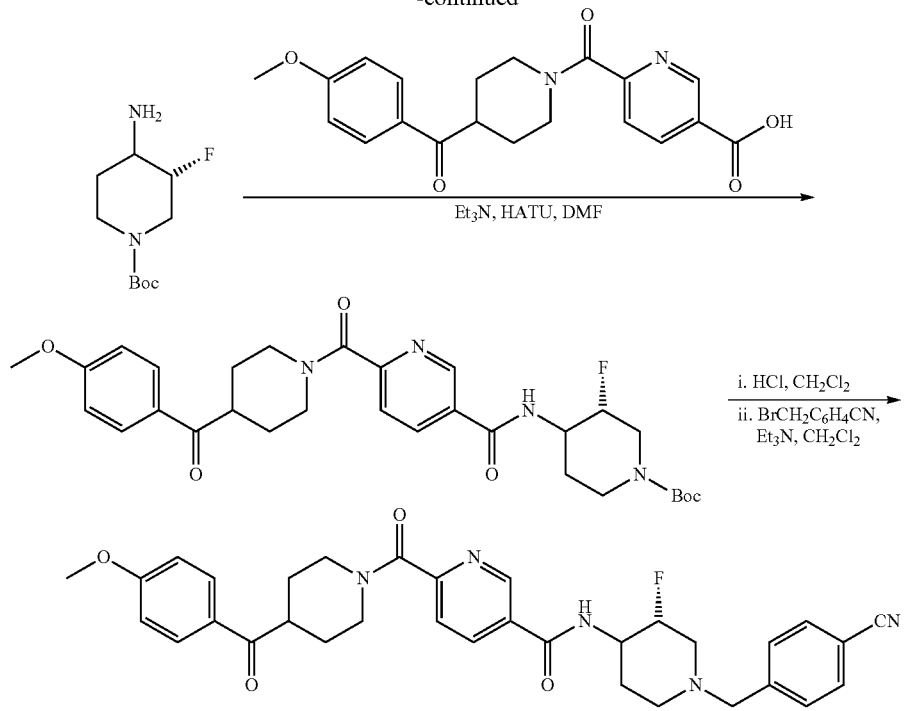

The first step of the synthesis followed the method of Kwiatkowski, P.; Beeson, T. D.; Conrad, J. C.; MacMillan, D. W. C., J. Am. Chem. Soc., 2011, 133(6), 1738-1741, which is hereby incorporated herein by reference in its entirety. 9-Epi-DHQA is (1R)-((2R)-5-ethylquinuclidin-2-yl)(6-methoxyquinolin-4-yl)methanamine. The optical rotation [α] of the (3R,4S)-tert-butyl 3-fluoro-4-hydroxypiperidine-1-carboxylate was −20.0° (c 0.33, $CH_2Cl_2$); the literature value for the corresponding (3S,4R) compound is +21.6°. See International Patent Application Publication no. WO 2010/128425.

Compound 453: N-((3S,4S)-1-(4-cyanobenzyl)-3-fluoropiperidin-4-yl)-6-(4-(4-methoxybenzoyl)piperidine-1-carbonyl)nicotinamide. Compound 453 was separated from the racemic mixture of Compound 349 using chiral chromatography as described above with reference to Compound 452. Compound 452 was the earlier-eluting peak (at about 20 minutes under the conditions described above). The spectral data agree with Compound 349.

Compound 454: N-((cis)-1-(4-cyanobenzyl)-3-fluoropiperidin-4-yl)-6-(4-(4-methoxybenzoyl)piperidine-1-carbonyl)nicotinamide $^1$H nmr ($CDCl_3$) δ 8.94 (1H, d, J 2.0 Hz, pyH-6), 8.14 (1H, dd, J 8.0, 2.0 Hz, pyH-4), 7.93 (2H, d, J 9.0 Hz, 2H of $C_6\underline{H}_4OCH_3$), 7.59 (2H, d, J 8.5 Hz, 2H of $C_6\underline{H}_4CN$), 7.46 (2H, d, J 8.5 Hz, 2H of $C_6\underline{H}_4CN$), 6.94 (2H, d, J 9.0 Hz, 2H of $C_6\underline{H}_4OCH_3$), 6.93 (1H, m, NH), 4.87 (0.5H, m, 0.5H of pipH-3), 4.68 (1.5H, m, 0.5H of pipH-3, 1H of BzpipH-2, H-6), 4.28-4.12 (1H, m, pipH-4), 3.91 (1H, m, 1H of BzpipH-2, H-6), 3.86 (3H, s, $OCH_3$), 3.64, 3.58 (2H, 2 d AB system, J 14.0 Hz, $CH_2C_6H_4CN$), 3.52 (1H, m, BzpipH-4), 3.28-3.16 (2H, m, 1H of pipH-2, 1H of BzpipH-2, H-6), 3.09 (1H, m, 1H of BzpipH-2, H-6), 2.91 (1H, m, 1H of pipH-6), 2.41 (0.5H, d, J 13.0 Hz, 0.5H of pipH-2), 2.26 (1.5H, m, 0.5H of pipH-2, 1H of pipH-6), 2.10-1.98 (2H, m, 2H of pipH-5, BzpipH-3, H-5), 1.91-1.80 (4H, m, 4H of pipH-5, BzpipH-3, H-5); $^{19}$F nmr ($CDCl_3$) δ −200.8 (q, J 63 Hz); m/z: 584 [M+H]$^+$.

Compound 455: 6-(4-(4-(cyclopropanecarbonyl)phenoxy)piperidine-1-carbonyl)-N-(1-(4-(trifluoromethoxy)benzyl)piperidin-4-yl)nicotinamide. $^1$H nmr ($CDCl_3$) δ 8.91 (1H, m, pyH-6), 8.13 (1H, dd, J 8.0, 2.0 Hz, pyH-4), 8.00 (2H, d, J 9.0 Hz, 2H of $C_6H_4OCF_3$ or $C_6H_4COcPr$), 7.64 (1H, d, J 8.0 Hz, pyH-3), 7.34 (2H, d, J 8.5 Hz, 2H of $C_6H_4OCF_3$ or $C_6H_4COcPr$), 7.15 (2H, d, J 8.0 Hz, 2H of $C_6H_4OCF_3$ or $C_6H_4COcPr$), 6.96 (2H, d, J 9.0 Hz, 2H of $C_6H_4OCF_3$ or $C_6H_4COcPr$), 6.30 (1H, d, J 7.5 Hz, NH), 4.73 (1H, m, PhOpipH-4), 4.01 (1H, m, pipH-4), 3.92 (2H, m, 2H of PhOpipH-2, H-6), 3.72 (1H, m, 1H of PhOpipH-2, H-6), 3.51 (3H, m, $C\underline{H}_2C_6H_4OCF_3$, 1H of PhOpipH-2, H-6), 2.86 (2H, m, 2H of pipH-2, H-6), 2.62 (1H, tt, J 7.5, 4.5 Hz, cPrH-1), 2.18 (2H, t, J 11.0 Hz, 2H of pipH-2, H-6), 2.10-1.92 (5H, m, 2H of pipH-3, H-5, 3H of PhOpipH-3, H-5), 1.87 (1H, m, 1H of PhOpipH-3, H-5), 1.60 (2H, m, 2H of pipH-3, H-5), 1.21 (2H, m, 2H of cPrH-2, H-3), 1.00 (2H, m, 2H of cPrH-2, H-3); $^{19}$F nmr ($CDCl_3$) δ −57.2; m/z: 651 [M+H]$^+$.

Compound 456: N-(1-(4-cyanobenzyl)piperidin-4-yl)-6-(4-(4-(cyclopropanecarbonyl)phenoxy)piperidine-1-carbonyl)nicotinamide. $^1$H nmr ($CDCl_3$) δ 8.91 (1H, d, J 2.0 Hz, pyH-6), 8.12 (1H, dd, J 8.5, 2.0 Hz, pyH-4), 8.01 (2H, d, J 9.0 Hz, 2H of $C_6H_4COcPr$), 7.62 (1H, d, J 7.5 Hz, pyH-3), 7.60 (2H, d, J 8.0 Hz, 2H of $C_6H_4CN$), 7.45 (2H, d, J 8.5 Hz, 2H of $C_6H_4CN$), 6.97 (2H, d, J 9.0 Hz, 2H of $C_6H_4COcPr$), 6.40 (1H, d, 8.0 Hz, NH), 4.73 (1H, m, PhOpipH-4), 4.03 (1H, m, pipH-4), 3.96-3.88 (2H, m, 2H of PhOpipH-2, H-6), 3.72 (1H, m, 1H of PhOpipH-2, H-6), 3.56 (2H, s, $C\underline{H}_2C_6H_4CN$), 3.52 (1H, m, 1H of PhOpipH-2, H-6), 2.83 (2H, m, 2H of pipH-2, H-6), 2.62 (tt, J 7.5, 4.5 Hz, cPrH-1), 2.20 (2H, dd, J 11.5, 9.5 Hz, 2H of pipH-2, H-6), 2.05-1.94 (5H, m, 2H of pipH-3, H-5, 3H of PhOpipH-3, H-5), 1.89 (1H, m, 1H of PhOpipH-3, H-5), 1.61 (2H, m, 2H of pipH-3, H-5), 1.21 (2H, m, 2H of cPrH-2, H-3), 1.01 (2H, m, 2H of cPrH-2, H-3); m/z: 593 [M+H]$^+$.

Compound 457: 6-(4-(4-(cyclopropanecarbonyl)phenoxy)piperidine-1-carbonyl)-N-(6-(4-fluorophenoxy)pyridin-3- yl)nicotinamide. $^1$H nmr (CDCl$_3$) δ 9.63 (1H, s, NH), 8.94 (1H, m, pyH-6), 8.46 (1H, d, J 2.5 Hz, N,O-pyH-6), 8.34 (1H, dd, J 8.5, 2.5 Hz, N,O-pyH-4), 8.11 (1H, dd, J 8.0, 2.0 Hz, pyH-4), 8.01 (2H, d, J 9.0 Hz, 2H of C$_6$H$_4$COcPr), 7.41 (1H, d, J 8.0 Hz, pyH-3), 7.10-7.07 (4H, m, C$_6$H$_4$F), 6.96 (2H, d, J 8.5 Hz, 2H of C$_6$H$_4$COcPr), 6.95 (1H, d, J 8.5 Hz, N,O-pyH-3), 4.74 (1H, m, PhOpipH-4), 4.01 (1H, m, 1H of PhOpipH-2, H-6), 3.86 (1H, m, 1H of PhOpipH-2, H-6), 3.65 (1H, m, 1H of PhOpipH-2, H-6), 3.41 (1H, m, 1H of PhOpipH-2, H-6), 2.62 (1H, tt, J 8.0, 4.5 Hz, cPrH-1), 2.11-1.94 (3H, m, 3H of PhOpipH-3, H-5), 1.89 (1H, m, 1H of PhOpipH-3, H-5), 1.21 (2H, m, 2H of cPrH-2, H-3), 1.01 (2H, m, 2H of cPrH-2, H-3); $^{19}$F nmr (CDCl$_3$) δ −118.5; m/z: 581 [M+H]$^+$.

Compound 458: 6-(4-(4-(cyclopropanecarbonyl)phenoxy) piperidine-1-carbonyl)-N-(1-(4-methoxybenzyl)piperidin-4-yl)nicotinamide. $^1$H nmr (CDCl$_3$) δ 8.90 (1H, m, pyH-6), 8.12 (1H, dd, J 8.5, 2.0 Hz, pyH-4), 8.00 (2H, d, J 9.0 Hz, 2H of C$_6$H$_4$COcPr), 7.62 (1H, d, J 8.0 Hz, pyH-3), 7.23 (2H, d, J 8.5 Hz, 2H of C$_6$H$_4$OCH$_3$), 6.96 (2H, d, J 9.0 Hz, 2H of C$_6$H$_4$COcPr), 6.85 (2H, d, J 9.0 Hz, 2H of C$_6$H$_4$OCH$_3$), 6.38 (1H, d, J 7.5 Hz, NH), 4.73 (1H, m, PhOpipH-4), 4.01 (1H, m, pipH-4), 3.95-3.86 (2H, m, 2H of PhOpipH-2, H-6), 3.79 (3H, s, OCH$_3$), 3.71 (1H, m, PhOpipH-2, H-6), 3.50 (3H, m, CH$_2$C$_6$H$_4$OCH$_3$, 1H of PhOpipH-2, H-6), 2.90 (2H, m, 2H of pipH-2, H-6), 2.62 (1H, tt, J 8.0, 4.5 Hz, cPrH-1), 2.20 (2H, t, J 11.0 Hz, 2H of pipH-2, H-6), 2.02 (5H, m, 2H of pipH-3, H-5, 3H of PhOpipH-3, H-5), 1.88 (1H, m, 1H of PhOpipH-3, H-5), 1.21 (2H, m, 2H of cPrH-2, H-3), 1.01 (2H, m, 2H of cPrH-2, H-3); m/z: 597 [M+H]$^+$.

Compound 459: N-(6-(4-cyanophenoxy)pyridin-3-yl)-6-(4-(4-(methylsulfonyl)phenoxy)piperidine-1-carbonyl)nicotinamide. $^1$H nmr (CDCl$_3$) δ 9.64 (1H, s, NH), 8.96 (1H, m, pyH-6), 8.52 (1H, d, J 2.5 Hz, N,O-pyH-6), 8.44 (1H, dd, J 9.0, 2.5 Hz, N,O-pyH-4), 8.12 (1H, dd, J 8.0, 2.0 Hz, pyH-4), 7.87 (2H, d, J 9.0 Hz, 2H of C$_6$H$_4$SO$_2$CH$_3$), 7.68 (2H, d, J 9.0 Hz, 2H of C$_6$H$_4$CN), 7.44 (1H, d, J 8.0 Hz, pyH-3), 7.23 (2H, d, J 9.5 Hz, 2H of C$_6$H$_4$CN), 7.06 (1H, m, N,O-pyH-3), 7.03 (2H, d, J 9.0 Hz, 2H of C$_6$H$_4$SO$_2$CH$_3$), 4.75 (1H, m, PhOpipH-4), 4.02 (1H, m, 1H of PhOpipH-2, H-6), 3.88 (1H, m, 1H of PhOpipH-2, H-6), 3.66 (1H, m, 1H of PhOpipH-2, H-6), 3.45 (1H, m, 1H of PhOpipH-2, H-6), 3.04 (3H, s, SO$_2$CH$_3$), 2.18-1.96 (3H, m, 3H of PhOpipH-3, H-5), 1.90 (1H, m, 1H of PhOpipH-3, H-5); m/z: 598 [M+H]$^+$.

Compound 460: N-(6-(4-cyanophenoxy)pyridin-3-yl)-6-(4-(4-methoxybenzoyl)piperidine-1-carbonyl)nicotinamide. $^1$H nmr (CDCl$_3$) δ 9.95 (1H, s, NH), 8.93 (1H, d, J 2.0 Hz, pyH-6), 8.57 (1H, d, J 2.5 Hz, N,O-pyH-6), 8.46 (1H, dd, J 8.5, 2.5 Hz, N,O-pyH-4), 8.09 (1H, dd, J 8.5, 2.0 Hz, pyH-4), 7.93 (2H, d, J 9.0 Hz, 2H of C$_6$H$_4$OCH$_3$), 7.67 (2H, d, J 8.5 Hz, 2H of C$_6$H$_4$CN), 7.38 (1H, d, J 8.5 Hz, pyH-3), 7.22 (2H, d, J 8.5 Hz, 2H of C$_6$H$_4$CN), 7.06 (1H, d, J 8.5 Hz, N,O-pyH-3), 6.96 (2H, d, J 9.0 Hz, 2H of C$_6$H$_4$OCH$_3$), 4.70 (1H, m, 1H of BzpipH-2, H-6), 3.88 (3H, s, OCH$_3$), 3.79 (1H, m, 1H of BzpipH-2, H-6), 3.55 (1H, m, BzpipH-4), 3.24 (1H, m, 1H of BzpipH-2, H-6), 3.16 (1H, m, 1H of BzpipH-2, H-6), 2.04 (1H, m, 1H of BzpipH-3, H-5), 1.93-1.82 (3H, m, 3H of BzpipH-3, H-5); m/z: 562 [M+H]$^+$.

Compound 461: N-((cis)-3-fluoro-1-(4-(trifluoromethoxy)benzyl)piperidin-4-yl)-6-(4-(4-methoxybenzoyl)piperidine-1-carbonyl)nicotinamide. $^1$H nmr (CDCl$_3$) δ 8.96 (1H, m, pyH-6), 8.17 (1H, dd, J 8.0, 2.0 m Hz, pyH-4), 7.94 (2H, d, J 9.0 Hz, 2H of C$_6$H$_4$OCH$_3$), 7.68 (1H, dd, J 8.0, 0.5 Hz, pyH-3), 7.36 (2H, d, J 9.0 Hz, 2H of C$_6$H$_4$OCF$_3$), 7.17 (2H, d, J 8.0 Hz, 2H of C$_6$H$_4$OCF$_3$), 6.95 (1H, d, J 9.0 Hz, 2H of C$_6$H$_4$OCH$_3$), 6.57 (1H, d, J 9.0 Hz, NH), 4.86 (0.5H, 0.5H of pipH-3), 4.68 (1.5H, m, BzpipH-2, H-6, 0.5H of pipH-3), 4.33-4.15 (1H, m, pipH-4), 3.96 (1H, m, 1H of BzpipH-2, H-6), 3.88 (3H, s, OCH$_3$), 3.60, 3.55 (2H, 2 d AB system, J 14.0 Hz, CH$_2$C$_6$H$_4$OCF$_3$), 3.52 (1H, m, BzpipH-4), 3.31-3.22 (2H, m, 1H of pipH-2, 1H of BzpipH-2, H-6), 3.11 (1H, m, 1H of BzpipH-2, H-6), 2.95 (1H, m, 1H of pipH-6), 2.39 (0.5H, d, J 12.5 Hz, 0.5H of pipH-2), 2.24 (1.5 Hz, 0.5H of pipH-2, 1H of pipH-6), 2.05-1.97 (2H, m, 1H of pipH-5, 1H of BzpipH-3, H-5), 1.93-1.81 (4H, m, 1H of pipH-5, 3H of BzpipH-3, H-5); $^{19}$F nmr (CDCl$_3$) δ −57.9, −200.8; m/z: 644 [M+H]$^+$.

Compound 462: N-(6-(4-acetylphenoxy)pyridin-3-yl)-6-(4-(4-methoxybenzoyl)piperidine-1-carbonyl)nicotinamide. $^1$H nmr (CDCl$_3$) δ 9.98 (1H, s, NH), 8.93 (1H, m, pyH-6), 8.56 (1H, d, J 2.5 Hz, N,O-pyH-6), 8.42 (1H, dd, J 9.0, 2.5 Hz, N,O-pyH-4), 8.10 (1H, dd, J 8.0, 2.0 Hz, pyH-4), 7.99 (2H, d, J 9.0 Hz, 2H of C$_6$H$_4$COCH$_3$), 7.93 (2H, d, J 9.0 Hz, 2H of C$_6$H$_4$OCH$_3$), 7.38 (1H, d, J 8.0 Hz, pyH-3), 7.18 (2H, d, J 8.5 Hz, 2H of C$_6$H$_4$COCH$_3$), 7.03 (1H, d, J 9.0 Hz, N,O-pyH-3), 6.95 (2H, d, J 9.0 Hz, 2H of C$_6$H$_4$OCH$_3$), 7.68 (1H, m, 1H of BzpipH-2, H-6), 3.88 (3H, s, OCH$_3$), 3.78 (1H, m, 1H of BzpipH-2, H-6), 3.54 (1H, m, BzpipH-4), 3.23 (1H, m, 1H of BzpipH-2, H-6), 3.15 (1H, m, 1H of BzpipH-2, H-6), 2.59 (3H, s, COCH$_3$), 2.03 (1H, m, 1H of BzpipH-3, H-5), 1.92-1.81 (3H, m, 3H of BzpipH-3, H-5); m/z: 579 [M+H]$^+$.

Compound 463: N-(6-(4-cyanophenoxy)pyridin-3-yl)-6-(4-(2,4-difluorobenzoyl)piperidine-1-carbonyl)nicotinamide. $^1$H nmr (CDCl$_3$) δ 9.99 (1H, s, NH), 8.90 (1H, m, pyH-6), 8.57 (1H, d, J 2.5 Hz, N,O-pyH-6), 8.46 (1H, dd, J 9.0, 2.5 Hz, N,O-pyH-4), 8.07 (1H, dd, J 8.0, 2.0 Hz, pyH-4), 7.87 (1H, dt, J 6.5, 8.5 Hz, C$_6$H$_3$F$_2$H-6), 7.68 (2H, d, J 9.0 Hz, 2H of C$_6$H$_4$CN), 7.34 (1H, d, J 8.0 Hz, pyH-3), 7.22 (2H, d, J 9.0 Hz, 2H of C$_6$H$_4$CN), 7.05 (1H, d, J 9.0 Hz, N,O-pyH-3), 7.00 (1H, m, C$_6$H$_3$F$_2$H-3 or H-5), 6.89 (1H, ddd, J 11.0, 8.5, 2.5 Hz, C$_6$H$_3$F$_2$H-3 or H-5), 4.67 (1H, m, 1H of BzpipH-2, H-6), 3.75 (1H, m, 1H of BzpipH-2, H-6), 3.42 (1H, m, BzpipH-4), 3.24-3.09 (2H, m, 2H of BzpipH-2, H-6), 2.09 (1H, m, 1H of BzpipH-3, H-5), 1.91-1.72 (3H, m, 3H of BzpipH-3, H-5); $^{19}$F nmr (CDCl$_3$) δ −101.1, −106.5; m/z: 568 [M+H]$^+$.

Compound 464: N-(6-(4-acetylphenoxy)pyridin-3-yl)-6-(4-(2,4-difluorobenzoyl)piperidine-1-carbonyl)nicotinamide. $^1$H nmr (CDCl$_3$) δ 9.62 (1H, s, NH), 8.94 (1H, pyH-6), 8.41 (1H, dd, J 8.0, 2.5 Hz, N,O-pyH-4), 8.11 (1H, dd, J 8.0, 2.0 Hz, pyH-4), 8.01 (2H, d, J 9.0 Hz, 2H of C$_6$H$_4$COCH$_3$), 7.87 (1H, dt, J 6.5, 8.5 Hz, C$_6$H$_3$F$_2$H-6), 7.42 (1H, d, J 8.0 Hz, pyH-3), 7.19 (2H, d, J 9.0 Hz, 2H of C$_6$H$_4$COCH$_3$), 7.04 (1H, d, J 9.0 Hz, N,O-pyH-3), 6.99 (1H, m, C$_6$H$_3$F$_2$H-3 or H-5), 6.89 (1H, ddd, J 11.0, 8.4, 2.0 Hz, C$_6$H$_3$F$_2$H-3 or H-5), 4.67 (1H, m, 1H of BzpipH-2, H-6), 3.79 (1H, m, 1H of BzpipH-2, H-6), 3.41 (1H, m, BzpipH-4), 3.25-3.08 (2H, m, 2H of BzpipH-2, H-6), 2.60 (3H, s, COCH$_3$), 2.08 (1H, m, 1H of BzpipH-3, H-5), 1.91-1.74 (3H, m, 3H of BzpipH-3, H-5); $^{19}$F nmr (CDCl$_3$) δ−101.3, −106.5; m/z: 585 [M+H]$^+$.

Compound 465: 6-(4-(4-methoxybenzoyl)piperidine-1-carbonyl)-N-(6-(4-(methylsulfonyl)phenoxy)pyridin-3-yl) nicotinamide. $^1$H nmr (CDCl$_3$) δ 9.92 (1H, s, NH), 8.94 (1H, m, pyH-6), 8.59 (1H, d, J 2.5 Hz, N,O-pyH-6), 8.45 (1H, dd, J 9.0, 2.5 Hz, N,O-pyH-4), 8.11 (1H, dd, J 8.0, 2.0 Hz, pyH-4), 7.95 (2H, d, J 8.5 Hz, 2H of C$_6$H$_4$OCH$_3$ or C$_6$H$_4$SO$_2$CH$_3$), 7.93 (2H, d, J 9.0 Hz, 2H of C$_6$H$_4$OCH$_3$ or C$_6$H$_4$SO$_2$CH$_3$), 7.39 (1H, d, J 8.0 Hz, pyH-3), 7.30 (2H, d, J 9.0 Hz, 2H of C$_6$H$_4$SO$_2$CH$_3$), 7.07 (1H, d, J 9.0 Hz, N,O-pyH-3), 6.96 (2H, d, J 9.0 Hz, 2H of C$_6$H$_4$OCH$_3$), 7.69 (1H, m, 1H of BzpipH-2, H-6), 3.88 (3H, s, OCH$_3$), 3.79 (1H, m, 1H of BzpipH-2, H-6), 3.55 (1H, m, BzpipH-4), 3.29-3.13 (2H, m, 2H of BzpipH-2, H-6), 3.07 (3H, s, SO₂CH₃), 2.03 (1H, m, 1H, m, 1H of BzpipH-3, H-5), 1.93-1.81 (3H, m, 3H of BzpipH-3, H-5); m/z: 615 [M+H]⁺.

Compound 466: 6-(4-(2,4-difluorobenzoyl)piperidine-1-carbonyl)-N-(6-(4-(methylsulfonyl)phenoxy)pyridin-3-yl)nicotinamide. ¹H nmr (CDCl₃) δ 10.00 (1H, s, NH), 8.91 (1H, m, pyH-6), 8.60 (1H, d, J 2.5 Hz, N,O-pyH-6), 8.46 (1H, dd, J 8.5, 2.5 Hz, N,O-pyH-4), 8.07 (1H, dd, J 8.0, 2.0 Hz, pyH-4), 7.96 (2H, d, J 8.5 Hz, 2H of C₆H₄SO₂CH₃), 7.87 (1H, dt, J 6.5, 9.0 Hz, C₆H₃F₂H-6), 7.35 (1H, d, J 8.0 Hz, pyH-3), 7.30 (2H, d, J 8.5 Hz, 2H of C₆H₄SO₂CH₃), 7.07 (1H, d, J 8.5 Hz, N,O-pyH-3), 6.99 (1H, m, C₆H₃F₂H-3 or H-5), 6.89 (1H, ddd, J 11.0, 8.5, 2.0 Hz, C₆H₃F₂H-3 or H-5), 4.67 (1H, m, 1H of BzpipH-2, H-6), 3.75 (1H, m, 1H of BzpipH-2, H-6), 3.42 (1H, m, BzpipH-4), 3.25-3.09 (2H, m, 2H of BzpipH-2, H-6), 3.07 (3H, s, SO₂CH₃), 2.09 (1H, m, 1H of BzpipH-3, H-5), 1.91-1.75 (3H, m, 3H of BzpipH-3, H-5); ¹⁹F nmr (CDCl₃) δ −101.2, −106.5; m/z: 621 [M+H]⁺.

Compound 467: N-(6-(4-fluorophenylsulfonyl)pyridin-3-yl)-6-(4-(4-methoxybenzoyl)piperidine-1-carbonyl)nicotinamide. ¹H nmr (CDCl₃) δ 10.11 (1H, s, NH), 8.98 (1H, d, J 2.5 Hz, N,O-pyH-6), 8.90 (1H, m, pyH-6), 8.63 (1H, dd, J 8.5, 2.5 Hz, N,O-pyH-4), 8.20 (1H, d, J 8.5 Hz, N,O-pyH-3), 8.10-8.06 (3H, m, pyH-4, 2H of C₆H₄F), 7.94 (2H, d, J 9.0 Hz, 2H of C₆H₄OCH₃), 7.39 (1H, d, J 8.5 Hz, pyH-3), 7.20 (2H, t, J 8.5 Hz, 2H of C₆H₄F), 6.97 (2H, d, J 9.0 Hz, 2H of C₆H₄OCH₃), 4.69 (1H, m, 1H of BzpipH-2, H-6), 3.89 (3H, s, OCH₃), 3.76 (1H, m, 1H of BzpipH-2, H-6), 3.55 (1H, m, BzpipH-4), 3.21 (2H, m, 2H of BzpipH-2, H-6), 2.04 (1H, m, 1H of BzpipH-3, H-5), 1.94-1.76 (3H, m, 3H of BzpipH-3, H-5); ¹⁹F nmr (CDCl₃) δ −103.6; m/z: 603 [M+H]⁺ (found [M+H]⁺, 603.1692, C₃₁H₂₇FN₄O₆S requires [M+H]⁺ 603.1708).

Compound 468: N-(5-(4-cyanophenoxy)pyridin-2-yl)-6-(4-(4-methoxybenzoyl)piperidine-1-carbonyl)nicotinamide. ¹H nmr (CDCl₃) δ 9.32 (1H, s, NH), 8.97 (1H, d, J 2.0 Hz, pyH-6), 8.50 (1H, d, J 2.5 Hz, N,O-pyH-6), 8.41 (1H, dd, J 9.0, 2.5 Hz, N,O-pyH-4), 8.16 (1H, dd, J 8.0, 2.0 Hz, pyH-4), 7.94 (2H, d, J 9.0 Hz, 2H of C₆H₄OCH₃), 7.68 (2H, d, J 9.0 Hz, 2H of C₆H₄CN), 7.50 (1H, d, J 8.0 Hz, pyH-3), 7.23 (2H, d, J 9.0 Hz, 2H of C₆H₄CN), 7.07 (1H, d, J 9.0 Hz, N,O-pyH-3), 6.96 (2H, d, J 8.5 Hz, 2H of C₆H₄OCH₃), 4.69 (1H, m, 1H of BzpipH-2, H-6), 3.89 (3H, s, OCH₃), 3.85 (1H, m, 1H of BzpipH-2, H-6), 3.55 (1H, m, BzpipH-4), 3.22-3.10 (2H, m, 2H of BzpipH-2, H-6), 2.02 (1H, m, 1H of BzpipH-3, H-5), 1.93-1.80 (3H, m, 3H of BzpipH-3, H-5); m/z: 562 [M+H]⁺.

Compound 469: N-(5-(4-cyanophenoxy)pyridin-2-yl)-6-(4-(2,4-difluorobenzoyl)piperidine-1-carbonyl)nicotinamide. ¹H nmr (CDCl₃) δ 9.72 (1H, s, NH), 8.93 (1H, m, pyH-6), 8.54 (1H, d, J 2.5 Hz, N,O-pyH-6), 8.44 (1H, dd, J 9.0, 3.0 Hz, N,O-pyH-4), 8.10 (1H, dd, J 8.0, 2.0 Hz, pyH-4), 7.88 (1H, dt, J 6.5, 9.0 Hz, C₆H₃F₂H-6), 7.68 (2H, d, J 9.0 Hz, 2H of C₆H₄CN), 7.40 (1H, d, J 8.0 Hz, pyH-3), 7.23 (2H, d, J 9.0 Hz, 2H of C₆H₄CN), 7.06 (1H, d, J 9.0 Hz, N,O-pyH-3), 7.00 (1H, m, C₆H₃F₂H-3 or H-5), 6.90 (1H, ddd, J 11.0, 8.5, 2.0 Hz, C₆H₃F₂H-3 or H-5), 4.67 (1H, m, 1H of BzpipH-2, H-6), 3.77 (1H, m, 1H of BzpipH-2, H-6), 3.42 (1H, m, BzpipH-4), 3.25-3.08 (2H, m, 2H of BzpipH-2, H-6), 2.09 (1H, m, 1H of BzpipH-3, H-5), 1.91-1.75 (3H, m, 3H of BzpipH-3, H-5); ¹⁹F nmr (CDCl₃) δ −101.2, −106.5; m/z: 568 [M+H]⁺.

Compound 470: 6-(4-(4-fluorophenylsulfonyl)piperidine-1-carbonyl)-N-(1-(4-(trifluoromethoxy)benzyl)piperidin-4-yl)nicotinamide. ¹H nmr (CDCl₃) δ 8.88 (1H, m, pyH-6), 8.11 (1H, dd, J 8.5, 2.0 Hz, pyH-4), 7.89 (1H, dd, J 9.0, 5.0 Hz, 2H of C₆H₄F), 7.63 (1H, d, J 7.5 Hz, pyH-3), 7.34 (2H, d, J 8.5 Hz, 2H of C₆H₄OCF₃), 7.26 (2H, t, J 8.5 Hz, 2H of C₆H₄F), 7.16 (2H, d, J 7.5 Hz, 2H of C₆H₄OCF₃), 6.31 (1H, d, J 8.0 Hz, NH), 4.83 (1H, m, 1H of BzpipH-2, H-6), 4.13 (1H, m, 1H of BzpipH-2, H-6), 4.01 (1H, m, pipH-4), 3.52 (2H, s, CH₂C₆H₄OCF₃), 3.16 (1H, tt, J 12.0, 3.5 Hz, BzpipH-4), 3.04 (1H, m, 1H of BzpipH-2, H-6), 2.87-2.75 (3H, m, 2H of pipH-2, H-6, 1H of BzpipH-2, H-6), 2.17 (2H, t, J 11.5 Hz, 2H of pipH-2, H-6), 2.01 (4H, m, 2H of pipH-3, H-5, 2H of BzpipH-3, H-5), 1.79 (2H, qd, J 12.5, 4.0 Hz, 2H of BzpipH-3, H-5), 1.59 (2H, m, 2H of pipH-3, H-5); ¹⁹F nmr (CDCl₃) δ−57.9, −102.6; m/z: 649 [M+H]⁺.

Compound 471: N-(1-(4-cyanobenzyl)piperidin-4-yl)-6-(4-(4-fluorophenylsulfonyl)piperidine-1-carbonyl)nicotinamide. ¹H nmr (CDCl₃) δ 8.88 (1H, d, J 2.0 Hz, pyH-6), 8.12 (1H, dd, J 8.0, 2.0 Hz, pyH-4), 7.89 (dd, J 9.0, 5.0 Hz, 2H of C₆H₄F), 7.63 (1H, m, pyH-3), 7.61 (2H, d, J 8.0 Hz, 2H of C₆H₄CN), 7.45 (2H, d, J 8.0 Hz, 2H of C₆H₄CN), 7.27 (2H, t, J 8.5 Hz, 2H of C₆H₄F), 6.36 (1H, d, J 7.5 Hz, NH), 4.83 (1H, m, 1H of BzpipH-2, H-6), 4.13 (1H, m, 1H of BzpipH-2, H-6), 4.01 (1H, m, pipH-4), 3.56 (2H, s, CH₂C₆H₄CN), 3.17 (1H, tt, J 12.0, 4.0 Hz, BzpipH-4), 3.04 (1H, t, J 12.0 Hz, 1H of BzpipH-2, H-6), 2.85-2.74 (3H, m, 2H of pipH-2, H-6, 1H of BzpipH-2, H-6), 2.20 (2H, dd, J 11.5, 9.5 Hz, 2H of pipH-2, H-6), 2.11-1.95 (4H, m, 2H of pipH-3, H-5, 2H of BzpipH-3, H-5), 1.80 (qd, J 12.5, 4.0 Hz, 2H of BzpipH-3, H-5), 1.60 (2H, m, 2H of pipH-3, H-5); ¹⁹F nmr (CDCl₃) δ −102.6; m/z: 590 [M+H]⁺.

Compound 472: N-(6-(4-cyanophenoxy)pyridin-3-yl)-6-(4-(4-fluorophenylsulfonyl)piperidine-1-carbonyl)nicotinamide. ¹H nmr (CDCl₃) δ 9.61 (1H, s, NH), 8.92 (1H, d, J 2.0 Hz, pyH-6), 8.49 (1H, d, J 2.5 Hz, N,O-pyH-6), 8.42 (1H, dd, J 9.0, 2.5 Hz, N,O-pyH-4), 8.11 (1H, dd, J 8.0, 2.0 Hz, pyH-4), 7.89 (2H, dd, J 9.0, 5.0 Hz, 2H of C₆H₄F), 7.69 (2H, d, J 9.0 Hz, 2H of C₆H₄CN), 7.44 (1H, d, J 8.0 Hz, pyH-3), 7.27 (2H, m, 2H of C₆H₄F), 7.23 (2H, d, J 8.5 Hz, 2H of C₆H₄CN), 7.06 (1H, d, J 8.5 Hz, N,O-pyH-3), 4.83 (1H, m, 1H of BzpipH-2, H-6), 3.96 (1H, m, 1H of BzpipH-2, H-6), 3.17 (1H, m, BzpipH-4), 3.09 (1H, m, 1H of BzpipH-2, H-6), 2.84 (1H, m, 1H of BzpipH-2, H-6), 2.10 (1H, d, J 12.0 Hz, 1H of BzpipH-3, H-5), 1.99 (1H, d, J 11.5 Hz, 1H of BzpipH-3, H-5), 1.82 (2H, m, 2H of BzpipH-3, H-5); ¹⁹F nmr (CDCl₃) δ −102.2; m/z: 586 [M+H]⁺.

Compound 473: N-(6-(4-acetylphenoxy)pyridin-3-yl)-6-(4-(4-fluorophenylsulfonyl)piperidine-1-carbonyl)nicotinamide. ¹H nmr (CDCl₃) δ 9.31 (1H, s, NH), 8.95 (1H, m, pyH-6), 8.45 (1H, d, J 2.5 Hz, N,O-pyH-6), 8.38 (1H, dd, J 9.0, 2.5 Hz, N, O-pyH-4), 8.14 (1H, dd, J 8.5, 2.0 Hz, pyH-4), 8.02 (2H, d, J 9.0 Hz, 2H of C₆H₄Ac), 7.89 (2H, dd, J 9.0, 5.0 Hz, 2H of C₆H₄F), 7.49 (1H, d, J 8.0 Hz, pyH-3), 7.27 (2H, t, J 8.5 Hz, 2H of C₆H₄F), 7.20 (2H, d, J 9.0 Hz, 2H of C₆H₄Ac), 7.05 (1H, d, J 9.0 Hz, N,O-pyH-3), 4.83 (1H, m, 1H of BzpipH-2, H-6), 4.01 (1H, m, 1H of BzpipH-2, H-6), 3.17 (1H, m, BzpipH-4), 3.06 (1H, m, 1H of BzpipH-2, H-6), 2.83 (1H, m, 1H of BzpipH-2, H-6), 2.60 (3H, s, COCH₃), 2.10 (1H, d, J 12.5 Hz, 1H of BzpipH-3, H-5), 2.01 (1H, d, J 12.5 Hz, 1H of BzpipH-3, H-5), 1.82 (2H, qd, J 12.5, 4.0 Hz, 2H of BzpipH-3, H-5); ¹⁹F nmr (CDCl₃) δ−102.3; m/z: 603 [M+H]⁺ (found [M+H]⁺, 603.1689, C₃₁H₂₇FN₄O₆S requires [M+H]⁺ 603.1708).

Compound 474: 6-(4-(4-fluorophenylsulfonyl)piperidine-1-carbonyl)-N-(1-(4-methoxybenzyl)piperidin-4-yl)nicotinamide. ¹H nmr (CDCl₃) δ 8.90 (1H, m, pyH-6), 8.13 (1H, dd, J 8.5, 2.0 Hz, pyH-4), 7.91 (2H, dd, J 9.0, 5.0 Hz, 2H of C₆H₄F), 7.66 (1H, d, J 8.0 Hz, pyH-3), 7.29 (2H, t, J 9.0 Hz, 2H of C₆H₄F), 7.24 (2H, d, J 8.5 Hz, 2H of C₆H₄OCH₃), 6.88 (2H, d, J 8.5 Hz, 2H of C₆H₄OCH₃), 6.31 (1H, d, J 8.0 Hz, NH), 4.85 (1H, m, 1H of BzpipH-2, H-6), 4.16 (1H, m, 1H of BzpipH-2, H-6), 4.02 (1H, m, pipH-4), 3.83 (3H, s, OCH₃), 3.48 (2H, s, CH$_2$C$_6$H$_4$OCH$_3$), 3.19 (1H, tt, J 12.0, 3.5 Hz, BzpipH-4), 3.07 (1H, t, J 12.0 Hz, 1H of BzpipH-2, H-6), 2.90-2.77 (3H, m, 2H of pipH-2, H-6, 1H of BzpipH-2, H-6), 2.17 (2H, dd, J 11.5, 10.0 Hz, 2H of pipH-2, H-6), 2.03 (4H, m, 2H of pipH-3, H-5, 2H of BzpipH-3, H-5), 1.81 (2H, qd, J 12.5, 4.0 Hz, 2H of BzpipH-3, H-5), 1.60 (2H, m, 2H of pipH-3, H-5); $^{19}$F nmr (CDCl$_3$) δ −102.6; m/z: 595 [M+H]$^+$.

Compound 475: 6-(4-(4-fluorophenylsulfonyl)piperidine-1-carbonyl)-N-(1-(3-methoxybenzyl)piperidin-4-yl)nicotinamide. $^1$H nmr (CDCl$_3$) δ 8.88 (1H, d, J 2.0 Hz, pyH-6), 8.11 (1H, dd, J 8.5, 2.0 Hz, pyH-4), 7.88 (2H, dd, J 9.0, 5.0 Hz, 2H of C$_6$H$_4$F), 7.62 (1H, d, J 8.0 Hz, pyH-3), 7.29-7.20 (3H, m, 2H of C$_6$H$_4$F, 1H of C$_6$H$_4$OCH$_3$), 6.91-6.88 (2H, m, 2H of C$_6$H$_4$OCH$_3$), 6.79 (1H, m, 1H of C$_6$H$_4$OCH$_3$), 6.35 (1H, d, J 7.5 Hz, NH), 4.83 (1H, m, 1H of BzpipH-2, H-6), 4.12 (1H, m, 1H of BzpipH-2, H-6), 4.03 (1H, m, pipH-4), 3.81 (3H, s, OCH$_3$), 3.49 (2H, s, CH$_2$C$_6$H$_4$OCH$_3$), 3.16 (1H, tt, J 12.0, 3.5 Hz, BzpipH-4), 3.04 (1H, t, J 11.5 Hz, 1H of BzpipH-2, H-6), 2.88-2.74 (3H, m, 2H of pipH-2, H-6, 1H of BzpipH-2, H-6), 2.16 (2H, t, J 11.5 Hz, 2H of pipH-2, H-6), 2.01 (4H, m, 2H of pipH-3, H-5, 2H of BzpipH-3, H-5), 1.78 (2H, qd, J 12.5, 4.5 Hz, 2H of BzpipH-3, H-5), 1.59 (2H, m, 2H of pipH-3, H-5); $^{19}$F nmr (CDCl$_3$) δ −102.6; m/z: 595 [M+H]$^+$.

Compound 476: N-(6-(4-cyanophenoxy)pyridin-3-yl)-6-(4-(4-fluorobenzyl)piperazine-1-carbonyl)nicotinamide. $^1$H nmr (CDCl$_3$) δ 9.87 (1H, s, NH), 8.89 (1H, m, pyH-6), 8.54 (1H, d, J 2.5 Hz, N,O-pyH-6), 8.44 (1H, dd, J 9.0, 2.5 Hz, N,O-pyH-4), 8.06 (1H, dd, J 8.0, 2.0 Hz, pyH-4), 7.68 (2H, d, J 9.0 Hz, 2H of C$_6$H$_4$CN), 7.35 (1H, d, J 7.5 Hz, pyH-3), 7.25 (2H, m, 2H of C$_6$H$_4$F), 7.22 (2H, d, J 8.5 Hz, 2H of C$_6$H$_4$CN), 7.03 (2H, t, J 8.5 Hz, 2H of C$_6$H$_4$F), 6.99 (1H, d, J 8.5 Hz, N,O-pyH-3), 3.83 (2H, m, 2H of piz), 3.50 (2H, s, CH$_2$C$_6$H$_4$F), 3.42, 3.41 (2H, 2 d AB system, J 4.5 Hz, 2H of piz), 2.55, 2.53 (2H, 2d AB system, J 4.5 Hz, 2H of piz), 2.40, 2.38 (2H, 2 d AB system, J 4.5 Hz, 2H of piz); $^{19}$F nmr (CDCl$_3$) δ −115.2; m/z: 537 [M+H]$^+$.

Compound 491: N-(1-(4-cyanobenzyl)piperidin-4-yl)-6-(4-(4-fluorobenzyl)piperazin-1-yl)pyridazine-3-carboxamide. Compound 491 was prepared as follows:
Step 1

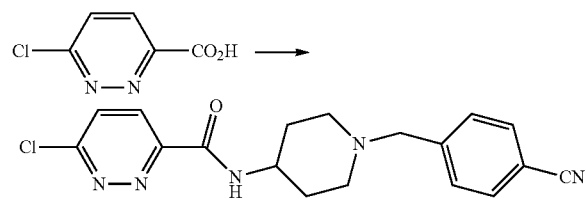

6-Chloropyridazine-3-carboxylic acid (0.96 g, 6.2 mMol) was dissolved in dichloromethane (20 mL) and treated with 4-amino-1-(4-cyanobenzyl)piperidine dihydrochloride (1.79 g, 6.2 mMol), HATU (2.37 g, 6.2 mMol) and DIEA (3.6 mL, 3.3 eq.). The reaction stirred at RT for 3d. The reaction mixture was diluted with dichloromethane and washed with saturated aqueous sodium bicarbonate and brine and then dried over anhydrous sodium sulfate and concentrated under reduced pressure.

The crude product was purified by flash chromatography on silica gel, eluting with 2% methanol in dichloromethane. $^1$H NMR (300 MHz, CDCl$_3$) δ 8.26 (d, J 8.8 Hz, 1H), 7.96 (d, J 10.0 Hz, 1H, NH), 7.68 (d, J 8.8 Hz, 1H), 7.61 (d, J 8.2 Hz, 2H), 7.46 (d, J 8.0 Hz, 2H), 4.02 (m, 1H), 3.15 (m, 2H), 2.81 (m, 2H), 2.29 (m, 2H), 2.12 (m, 2H); m/z=356.05 (M+H)$^+$; m/z=354.11 (M−H)$^+$
Step 2

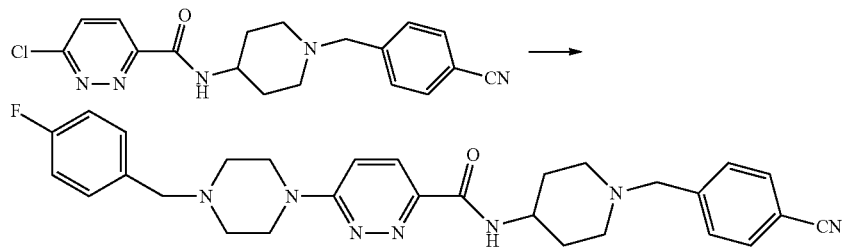

The product from step 1 (109 mg, 0.306 mMol) was dissolved in CH$_3$CN (3 mL) and treated with 4-Fluorobenzylpiperazine (1.2 eq.), tetrabutylammonium iodide (24 mg) and DBU (100 μl). The reaction mixture was then heated at 82° C. for 1.5 h. The reaction mixture was concentrated to dryness and purified by silica gel radial chromatography eluting with 5% methanol in dichloromethane to give Compound 491. $^1$H NMR (300 MHz, CDCl$_3$) δ 7.94 (dd, J 9.6, 1.4 Hz, 1H), 7.84 (d, J 8.3 Hz, 1H, NH), 7.58 (d, J 8.0 Hz, 2H), 7.43 (d, J 8.3 Hz, 2H), 7.26-7.30 (m, 2H), 6.92-7.02 (m, 3H), 3.97 (m, 1H), 3.73 (m, 4H), 3.52 (s, 2H), 3.49 (s, 2H), 3.12 (m, 2H), 2.77 (m, 2H), 2.54 (m, 4H), 2.20 (m, 2H), 1.97 (m, 2H); m/z=514.18 (M+H)$^+$;

For use in the synthesis of Compound 125, 1-(4-fluorobenzyl)-2,2-dimethylpiperazine was synthesized. To a solution of piperazin-2-one (0.500 g, 5.00 mmol, 1.0 eq) in dichloromethane (50 mL) was added trityl chloride (1.533 g, 5.50 mmol, 1.1 eq). The reaction was stirred at room temperature for 18 hours before diluting with CH$_2$Cl$_2$ (50 mL). The reaction was washed with NaHCO$_3$ (100 mL) and brine (100 mL), dried (Na$_2$SO$_4$) and concentrated under reduced pressure to yield 4-tritylpiperazin-2-one as a white foam, which was used without further purification; $^1$H nmr (CDCl$_3$) 7.48 (6H, d, J 7.5 Hz, 6H of trityl), 7.28 (6H, m, 6H of trityl), 7.18 (3H, m, 3H of trityl), 5.95 (1H, m, NH), 3.45 (2H, br s, 2H of oxopip), 3.06 (2H, s, 2H of oxopip), 2.46 (2H, br s, 2H of oxopip). A suspension of the 4-tritylpiperazin-2-one (0.405 g, 1.18 mmol, 1.0 eq) in tetrahydrofuran (11 mL) was cooled to 0° C. and 4-fluorobenzyl bromide (0.246 g, 0.16 mL, 1.30 mmol, 1.1 eq) was added followed by sodium hydride (0.057 g of a 60% suspension in oil, 1.42 mmol, 1.2 eq). Dimethylformamide (3 mL) was added to aid dissolution. The reaction mixture was allowed to warm to room temperature with stirring for 14 hours. Additional 4-fluorobenzyl bromide (0.16 mL, 1.1 eq) and sodium hydride (0.057 g, 1.2 eq) was added and the reaction stirred at room temperature for 3 hours and 60° C. for 15 hours. The reaction was cooled and partitioned between EtOAc (50 mL) and water (50 mL). The organic phase was washed with brine (50 mL), water (50 mL) and brine (50 mL), dried (Na$_2$SO$_4$) and concentrated under reduced pressure. MPLC (10→30% EtOAc-hexane, 0→15 min then 30→70% EtOAc-hexane 15→25 min) yielded 4-tritylpiperazin-2-one as a white solid (0.374 g, 70%); $^1$H nmr (CDCl$_3$) 7.48 (6H, d, J 7.5 Hz, 3×2H of C$_6$H$_5$), 7.28 (6H, t, J 7.5 Hz, 3×2H of C$_6$H$_5$), 7.23-7.15 (5H, m, 3×1H of C$_6$H$_5$, 2H of C$_6$H$_4$F), 7.01 (2H, t, J 8.5 Hz, 2H of C$_6$H$_4$F), 4.78 (2H, s, CH$_2$C$_6$H$_4$F), 3.31 (2H, t, J 5.5 Hz, 2H of oxopip), 3.15 (2H, s, 2H of oxopip), 2.43 (2H, m, 2H of oxopip); m/z 451 [M+H]$^+$. A solution of the 4-tritylpiperazin-2-one (0.165 g, 0.367 mmol, 1.0 eq) and di-t-butylpyridine (0.097 mL, 0.440 mmol, 1.2 eq) in dichloromethane (3.5 mL) was cooled to −78° C. Trifluoromethanesulfonic acid (0.074 mL, 0.440 mmol, 1.2 eq) was added and the reaction stirred at −78° C. for 45 minutes before adding methylmagnesium bromide (0.79 mL of a 1.4M solution in toluene, 1.100 mmol, 3.0 eq). The reaction mixture was allowed to stir at −78° C. for 2 hours and warmed to 0° C. over 2 hours before quenching with NH$_4$Cl (3 mL). The reaction was partitioned between NH$_4$Cl (50 mL) and CH$_2$Cl$_2$ (70 mL). The aqueous phase was extracted with CH$_2$Cl$_2$ (2×50 mL) and the combined organics dried (Na$_2$SO$_4$) before concentrating under reduced pressure. MPLC (10→30% EtOAc-hexane, 5→18 min) yielded 1-(4-fluorobenzyl)-2,2-dimethyl-4-tritylpiperazine (0.126 g, 74%) as a white solid; m/z 451 [M+H]$^+$. To a solution of the 1-(4-fluorobenzyl)-2,2-dimethyl-4-tritylpiperazine (0.126 g, 0.272 mmol, 1.0 eq) in dichloromethane (3.0 mL) was added hydrogen chloride (0.27 mL of a 4M solution in dioxane, 1.086 mmol, 4.0 eq). The reaction was stirred at room temperature for 4 hours. Further hydrogen chloride (0.27 mL of a 4M solution in dioxane, 1.086 mmol, 4.0 eq) was added and the reaction stirred at room temperature for 1 hour before concentrating under reduced pressure. The residue was tritutated with Et$_2$O (2×10 mL) to yield 1-(4-fluorobenzyl)-2,2-dimethylpiperazine as a white solid, which was dried under vacuum and used without further purification; $^1$H nmr (CD$_3$OD) 7.62 (2H, m, 2H of C$_6$H$_4$F), 7.23 (2H, t, J 8.5 Hz, 2H of C$_6$H$_4$F), 3.53 (2H, s, 2H of piz), 3.44 (4H, m, 4H of piz), 1.68 (6H, s, C(CH$_3$)$_2$); m/z 223 [M+H]$^+$. Syntheses of gem-dimethyl compounds are also generally described in Xiao, K.-J.; Luo, J.-M.; Ye, K.-Y.; Wang, Y.; Huang, P.-Q. *Angew. Chem. Int. Ed.* 2010, 49, 3037-3040.

Synthesis of
1-tent-Butyloxycarbonyl-4-N-methylaminopiperidine

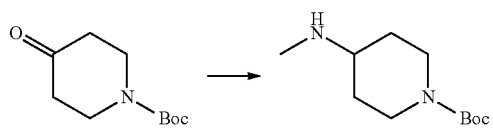

To a solution of 1-tert-butyloxycarbonyl-4-oxopiperidine (0.45 g, 2.26 mmol, 1.0 eq) in dichloromethane (20 mL) was added methylamine (2.26 mL of a 2M solution in tetrahydrofuran, 4.52 mmol, 2.0 eq). After equilibrating at room temperature for 10 minutes, sodium triacetoxyborohydride (0.72 g, 3.39 mmol, 1.5 eq) was added and the reaction stirred at room temperature for 30 minutes. Rochelle's salt (20 mL) was added and the reaction stirred for 1 hour before adding NaHCO$_3$ (50 mL). The organics were extracted with CH$_2$Cl$_2$ (2×100 mL), combined, washed with brine (50 mL), dried (Na$_2$SO$_4$) and concentrated under reduced pressure to yield the title compound as a colourless oil; $^1$H nmr (CDCl$_3$) δ 4.03 (2H, m), 2.79 (2H, t, J 12.0 Hz), 2.50 (1H, tt, J 12.0, 3.0 Hz), 2.43 (3H, s), 1.85 (2H, m), 1.47 (9H, s,), 1.22 (2H, m); m/z: 215 [M+H]$^+$.

Coupling of the 4-N-methylpiperidine

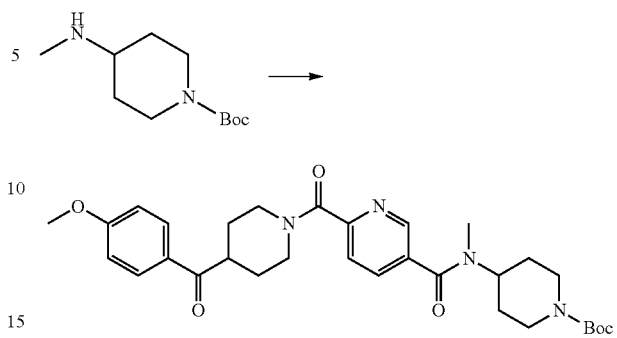

To a mixture of 1-tert-butyloxycarbonyl-4-N-methylaminopiperidine (0.136 g, 0.636 mmol, 1.0 eq) and the pyridine carboxylic acid (0.231 g, 0.636 mmol, 1.0 eq) in dimethylformamide (6 mL) was added triethylamine (0.13 mL, 0.953 mmol, 1.5 eq) followed by HATU (0.214 g, 0.636 mmol, 1.0 eq). The reaction was stirred at room temperature for 4 hours before partitioning between EtOAc (100 mL) and NaHCO3-water (1:1, 100 mL). The organics were further washed with brine (100 mL), water (100 mL) and brine (100 mL) before drying (Na$_2$SO$_4$) and concentrating under reduced pressure. MPLC (0 10% MeOH—CH$_2$Cl$_2$) yielded the coupled material (0.215 g, 61%) as a white foam; $^1$H nmr (CDCl$_3$) δ 8.60 (1H, s, pyH-6), 7.92 (2H, d, J 9.0 Hz, 2H of C$_6$H$_4$OCH$_3$), 7.80 (1H, d, J 9.0 Hz, pyH-3 or pyH-6), 7.67 (1H, d, J 9.0 Hz, pyH-3 or pyH-4), 6.94 (2H, d, J 9.0 Hz, 2H of C$_6$H$_4$OCH$_3$), 4.63 (1H, m, 1H of BzpipH-2, H-6), 4.23 (1H, m, pipH-4), 3.98 (1H, m, 1H of BzpipH-2, H-6), 3.86 (3H, s, OCH$_3$), 3.52 (1H, m, BzpipH-4), 3.25 (1H, m, 1H of BzpipH-2, H-6), 3.09 (1H, m, 1H of BzpipH-2, H-6), 2.97 (1H, m, 1H of pipH-2, H-3, H-5, H-6), 2.82 (3H, br s, NCH$_3$), 2.55 (1H, m, 1H of pipH-2, H-3, H-5, H-6), 1.97 (1H, m, 1H of pipH-2, H-3, H-5, H-6, BzpipH-3, H-5), 1.92-1.66 (9H, m, 9H of pipH-2, H-3, H-5, H-6, BzpipH-3, H-5), 1.45 (9H, s, C(CH$_3$)$_3$); m/z: 565 [M+H]$^+$.

Synthesis of 1-tert-Butyloxycarbonyl-3,3-difluoro-4-aminopiperidine 1-tert-Butyloxycarbonyl-3,3-difluoro-4-benzylaminopiperidine

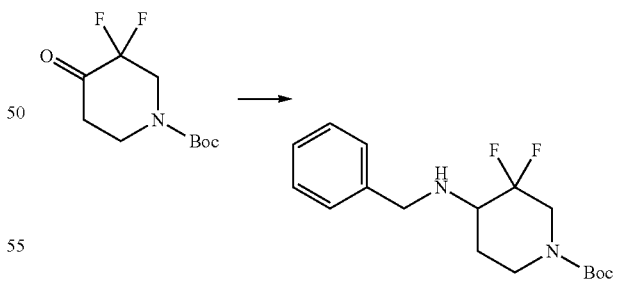

To a solution of 1-tert-butyloxycarbonyl-3,3-difluoro-4-oxopiperidine (Synthonix, 0.100 g, 0.426 mmol, 1.0 eq) in dichloromethane (1.5 mL) was added benzylamine (0.070 mL, 0.638 mmol, 1.5 eq) followed by sodium triacetoxyborohydride (0.180 g, 0.851 mmol, 2.0 eq). The reaction was stirred at room temperature for 16 hours before adding Rochelle's salt (2 mL) and stirring for 1 hour. The reaction mixture was partitioned between NaHCO$_3$ (50 mL) and CH$_2$Cl$_2$ (50 mL). The aqueous phase was extracted with CH$_2$Cl$_2$ (2×50 mL). The combined organics were washed with brine (50 mL), dried (Na$_2$SO$_4$) and concentrated under reduced pressure. MPLC (30→70% EtOAc-hexane) yielded the title compound (0.045 g, 32%) as a colourless oil; $^1$H nmr (CDCl$_3$) δ 7.33 (4H, m, 4H of C$_6$H$_5$), 7.27 (1H, m, 1H of C$_6$H$_5$), 4.02 (1H, m), 3.92 (2H, s, CH$_2$C$_6$H$_5$), 3.76 (1H, m), 3.32 (1H, ddd, J 21.5, 14.0, 4.5 Hz), 3.11 (1H, m), 2.97 (1H, m), 1.90 (1H, m), 1.67-1.59 (1H, m), 1.46 (9H, s, C(CH$_3$)$_3$); $^{19}$F nmr (CDCl$_3$) δ −109.0 (dd, J 243.0, 115.5 Hz), −119.5 (d, J 251.0 Hz); m/z: 327 [M+H]$^+$.

1-tert-Butyloxy-3,3-difluoro-4-aminopiperidine

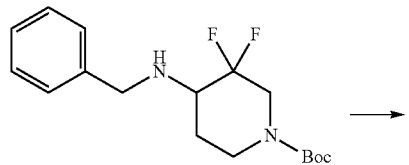

Palladium hydroxide (approx. 0.030 g) was added to a solution of the benzylaminopiperidine (0.045 g, 0.138 mmol) in ethanol (3.0 mL). The flask was purged with hydrogen and the reaction stirred under an atmosphere of hydrogen for 2 hours. The flask was purged with nitrogen and the reaction filtered through celite, eluting with 5% MeOH—CH$_2$Cl$_2$ (4×5 mL). The filtrate was concentrated under reduced pressure to yield the title compound as a colourless oil, which was used without purification;

Coupling of the 3,3-difluoro-4-aminopiperidine to the pyridine carboxylic acid

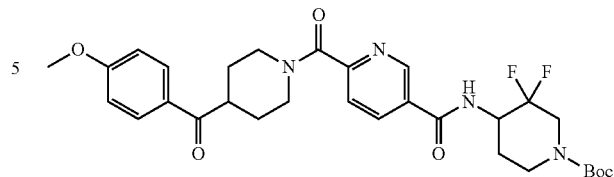

To a solution of the difluoroaminopiperidine (0.035 g, 0.148 mmol, 1.0 eq) and the pyridine carboxylic acid (0.055 g, 0.148 mmol, 1.0 eq) in dimethylformamide (1.5 mL) was added triethylamine (0.031 mL, 0.222 mmol, 1.5 eq) followed by HATU (0.056 g, 0.148 mmol, 1.0 eq). The resulting yellow solution was stirred at room temperature for 5 hours before partitioning between EtOAc (100 mL) and NaHCO$_3$-water (1:1, 100 mL). The organics were further washed with brine (100 mL), water (100 mL) and brine (100 mL) before drying (Na$_2$SO$_4$) and concentrating under reduced pressure. MPLC (0→10% MeOH—CH$_2$Cl$_2$) yielded the diamide (0.057 g, 67%) as a white foam; $^1$H nmr (CDCl$_3$) δ 8.97 (1H, s, pyH-6), 8.17 (1H, dd, J 8.0, 2.0 Hz, pyH-4), 7.93 (2H, d, J 9.5 Hz, 2H of C$_6$H$_4$OCH$_3$), 7.60 (1H, d, J 8.5 Hz, pyH-4), 7.07 (1H, m, NH), 6.94 (2H, d, J 9.0 Hz, 2H of C$_6$H$_4$OCH$_3$), 4.66 (1H, m, 1H of BzpipH-2, H-6), 4.55 (1H, m, 1H of pipH-2), 4.42 (1H, m, 1H of pipH-2), 4.19 (1H, m, pipH-4), 3.90 (1H, m, 1H of BzpipH-2, H-6), 3.87 (3H, s, OCH$_3$), 3.52 (1H, m, BzpipH-4), 3.24 (1H, m, 1H of BzpipH-2, H-6), 3.09 (1H, m, 1H of BzpipH-2, H-6), 3.05-2.87 (2H, m, pipH-6), 2.04-1.99 (2H, m, 2H of pipH-5, BzpipH-3, H-5), 1.91-1.67 (4H, m, 4H of pipH-5, BzpipH-3, H-5), 1.46 (9H, s, C(CH$_3$)$_3$); m/z: 587 [M+H]$^+$.

Syntheses of (cis)- and (trans)-tert-butyl 4-amino-3-fluoropiperidine-1-carboxylate For use in the synthesis of various compounds described above, (cis)- and (trans)-tert-butyl 4-amino-3-fluoropiperidine-1-carboxylate were prepared as described in the scheme below:

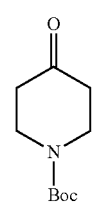

i. TMSCl, Et$_3$N, DMF
ii. Selectfluor, CH$_3$CN

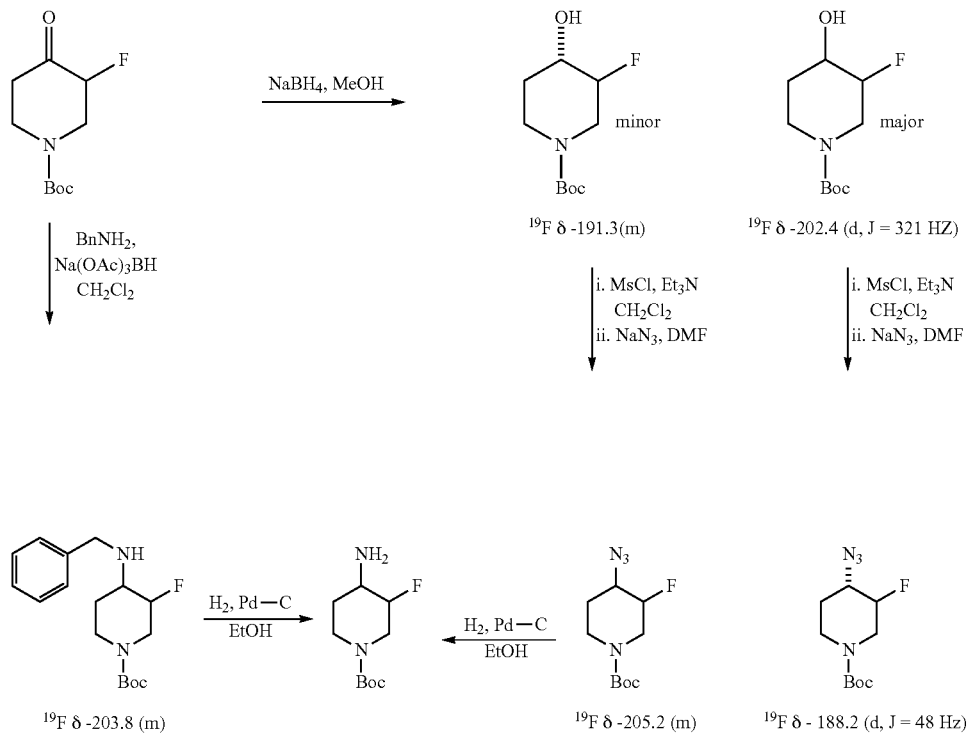

Example 2

Increase in AMPK Activity

Compounds were assayed for their ability to activate AMPK using an enzyme-linked immunosorbent assay. Reagents and procedures for measuring AMPK activation are well known and kits for AMPK activation assays are commercially available. The $EC_{50}$ values for AMPK activation for compounds 1-498 are presented in Table 2 below, in which "A" is less than 0.5 µM; "B" is 0.5-1 µM; "C" is 1-5 µM; and "D" is 5-10 µM; and "E" is >10 µM:

TABLE 2

| Cpd No. | AMPK $EC_{50}$ |
|---|---|
| 1 | A |
| 2 | E |
| 3 | B |
| 4 | B |
| 5 | B |
| 6 | B |
| 7 | A |
| 8 | A |
| 9 | A |
| 10 | A |
| 11 | A |
| 12 | D |
| 13 | C |
| 14 | B |
| 15 | C |
| 16 | A |
| 17 | E |

TABLE 2-continued

| Cpd No. | AMPK $EC_{50}$ |
|---|---|
| 18 | A |
| 19 | F |
| 20 | F |
| 21 | A |
| 22 | A |
| 23 | A |
| 24 | A |
| 25 | A |
| 26 | A |
| 27 | B |
| 28 | B |
| 29 | B |
| 30 | C |
| 31 | A |
| 32 | B |
| 33 | D |
| 34 | C |
| 35 | B |
| 36 | B |
| 37 | D |
| 38 | B |
| 39 | C |
| 40 | C |
| 41 | E |
| 42 | C |
| 43 | C |
| 47 | A |
| 48 | B |
| 49 | A |
| 50 | A |
| 51 | A |
| 52 | A |
| 53 | A |

TABLE 2-continued

| Cpd No. | AMPK EC$_{50}$ |
|---|---|
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 72 | A |
| 73 | D |
| 74 | A |
| 75 | C |
| 76 | A |
| 77 | A |
| 78 | A |
| 79 | B |
| 80 | C |
| 81 | B |
| 82 | B |
| 83 | E |
| 84 | C |
| 85 | C |
| 86 | C |
| 87 | C |
| 88 | C |
| 89 | C |
| 90 | E |
| 91 | E |
| 92 | E |
| 93 | E |
| 94 | E |
| 95 | A |
| 96 | E |
| 97 | C |
| 98 | C |
| 99 | D |
| 100 | A |
| 101 | A |
| 102 | D |
| 103 | A |
| 104 | A |
| 105 | E |
| 106 | D |
| 107 | D |
| 108 | B |
| 109 | D |
| 110 | C |
| 111 | C |
| 112 | C |
| 113 | C |
| 114 | C |
| 115 | D |
| 116 | C |
| 117 | A |
| 118 | A |
| 119 | C |
| 120 | E |
| 121 | C |
| 122 | A |
| 123 | A |
| 124 | A |
| 125 | A |
| 126 | A |
| 127 | A |
| 128 | A |
| 129 | A |
| 130 | A |
| 131 | A |
| 132 | A |

TABLE 2-continued

| Cpd No. | AMPK EC$_{50}$ |
|---|---|
| 133 | A |
| 134 | A |
| 135 | A |
| 136 | A |
| 137 | A |
| 138 | A |
| 139 | A |
| 140 | A |
| 141 | B |
| 142 | A |
| 143 | A |
| 144 | B |
| 145 | A |
| 146 | A |
| 147 | A |
| 149 | B |
| 150 | A |
| 151 | A |
| 152 | A |
| 153 | C |
| 154 | A |
| 155 | A |
| 156 | A |
| 157 | A |
| 158 | A |
| 159 | C |
| 160 | A |
| 161 | A |
| 162 | A |
| 163 | A |
| 164 | B |
| 165 | A |
| 166 | A |
| 167 | A |
| 168 | A |
| 169 | B |
| 170 | E |
| 171 | A |
| 172 | A |
| 173 | A |
| 174 | A |
| 175 | A |
| 176 | C |
| 177 | C |
| 178 | A |
| 179 | A |
| 180 | A |
| 181 | A |
| 182 | A |
| 183 | A |
| 184 | A |
| 185 | A |
| 186 | A |
| 187 | C |
| 188 | B |
| 189 | C |
| 190 | A |
| 191 | A |
| 192 | A |
| 193 | A |
| 194 | A |
| 195 | A |
| 196 | A |
| 197 | A |
| 198 | A |
| 199 | A |
| 200 | A |
| 201 | B |
| 202 | A |
| 203 | A |
| 204 | A |
| 205 | A |
| 206 | A |
| 207 | A |
| 208 | A |
| 209 | A |
| 210 | E |
| 211 | A |

TABLE 2-continued

| Cpd No. | AMPK EC$_{50}$ |
|---|---|
| 212 | A |
| 213 | A |
| 214 | E |
| 215 | E |
| 216 | E |
| 217 | E |
| 218 | A |
| 219 | A |
| 220 | A |
| 221 | C |
| 222 | C |
| 223 | C |
| 224 | A |
| 225 | A |
| 226 | A |
| 227 | A |
| 228 | A |
| 229 | C |
| 230 | B |
| 231 | A |
| 232 | A |
| 233 | A |
| 234 | A |
| 235 | A |
| 236 | A |
| 237 | C |
| 238 | C |
| 239 | C |
| 240 | A |
| 241 | A |
| 242 | A |
| 243 | A |
| 244 | D |
| 245 | A |
| 246 | A |
| 247 | A |
| 248 | A |
| 249 | A |
| 250 | A |
| 251 | A |
| 252 | B |
| 253 | B |
| 254 | A |
| 255 | A |
| 256 | A |
| 257 | A |
| 258 | A |
| 259 | A |
| 260 | A |
| 261 | A |
| 262 | A |
| 263 | A |
| 264 | D |
| 265 | C |
| 266 | A |
| 267 | A |
| 268 | A |
| 269 | A |
| 270 | A |
| 271 | A |
| 272 | A |
| 273 | A |
| 274 | E |
| 275 | A |
| 276 | A |
| 277 | A |
| 278 | A |
| 279 | A |
| 280 | A |
| 281 | A |
| 282 | A |
| 283 | A |
| 284 | A |
| 285 | A |
| 286 | A |
| 287 | A |
| 288 | A |
| 289 | A |

TABLE 2-continued

| Cpd No. | AMPK EC$_{50}$ |
|---|---|
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | A |
| 304 | A |
| 305 | A |
| 306 | A |
| 307 | B |
| 308 | A |
| 309 | A |
| 310 | A |
| 311 | A |
| 312 | A |
| 313 | A |
| 314 | E |
| 315 | A |
| 316 | A |
| 317 | A |
| 318 | A |
| 319 | A |
| 320 | A |
| 321 | A |
| 322 | A |
| 323 | A |
| 324 | A |
| 325 | A |
| 326 | A |
| 327 | A |
| 328 | A |
| 329 | A |
| 330 | B |
| 331 | A |
| 332 | A |
| 333 | A |
| 334 | A |
| 335 | E |
| 336 | A |
| 337 | A |
| 338 | A |
| 339 | A |
| 340 | A |
| 341 | A |
| 342 | A |
| 343 | A |
| 344 | A |
| 345 | A |
| 346 | A |
| 347 | A |
| 348 | A |
| 349 | A |
| 350 | A |
| 351 | A |
| 352 | A |
| 353 | A |
| 354 | A |
| 355 | E |
| 356 | A |
| 357 | A |
| 358 | A |
| 359 | A |
| 360 | A |
| 361 | A |
| 362 | A |
| 363 | A |
| 364 | A |
| 365 | A |
| 366 | A |
| 367 | E |

TABLE 2-continued

| Cpd No. | AMPK EC$_{50}$ |
|---|---|
| 368 | A |
| 369 | A |
| 370 | A |
| 371 | E |
| 372 | A |
| 373 | A |
| 374 | E |
| 375 | A |
| 376 | A |
| 377 | A |
| 378 | A |
| 379 | A |
| 380 | A |
| 381 | A |
| 382 | A |
| 383 | E |
| 384 | B |
| 385 | E |
| 386 | E |
| 387 | A |
| 388 | A |
| 389 | C |
| 390 | A |
| 391 | A |
| 392 | A |
| 393 | A |
| 394 | E |
| 395 | A |
| 396 | C |
| 397 | A |
| 398 | A |
| 399 | A |
| 400 | C |
| 401 | C |
| 402 | A |
| 403 | E |
| 404 | C |
| 405 | A |
| 406 | B |
| 407 | A |
| 408 | A |
| 409 | A |
| 410 | A |
| 411 | C |
| 412 | C |
| 413 | C |
| 414 | C |
| 415 | A |
| 416 | C |
| 417 | A |
| 418 | A |
| 419 | A |
| 420 | C |
| 421 | C |
| 422 | C |
| 423 | A |
| 424 | A |
| 425 | A |
| 426 | A |
| 427 | C |
| 428 | B |
| 429 | B |
| 430 | A |
| 431 | B |
| 432 | B |
| 433 | A |
| 434 | A |
| 435 | A |
| 436 | A |
| 437 | A |
| 438 | A |
| 439 | A |
| 440 | A |
| 441 | A |
| 442 | A |
| 443 | A |
| 444 | A |
| 445 | E |
| 446 | A |
| 447 | A |
| 448 | C |
| 449 | C |
| 450 | A |
| 451 | A |
| 452 | A |
| 453 | A |
| 454 | A |
| 455 | A |
| 456 | A |
| 457 | A |
| 458 | A |
| 459 | A |
| 460 | A |
| 461 | A |
| 462 | A |
| 463 | A |
| 464 | A |
| 465 | A |
| 466 | A |
| 467 | C |
| 468 | A |
| 469 | A |
| 470 | A |
| 471 | C |
| 472 | C |
| 473 | C |
| 474 | C |
| 475 | C |
| 476 | A |
| 477 | A |
| 478 | A |
| 479 | A |
| 480 | A |
| 481 | A |
| 482 | A |
| 483 | A |
| 484 | A |
| 485 | A |
| 486 | A |
| 487 | C |
| 488 | A |
| 489 | A |
| 490 | C |
| 491 | C |
| 492 | A |
| 493 | A |
| 494 | A |
| 495 | A |
| 496 | A |
| 497 | A |
| 498 | A |

What is claimed is:

1. N-((trans)-1-(4-cyanobenzyl)-3-fluoropiperidin-4-yl)-6-(4-(4-methoxybenzoyl)piperidine-1-carbonyl)nicotinamide or a pharmaceutically acceptable salt or N-oxide thereof.

2. A pharmaceutical composition comprising:
at least one pharmaceutically acceptable carrier, diluent or excipient; and
a compound according to claim 1 or a pharmaceutically acceptable salt or N-oxide thereof.

3. A method for activating the AMPK pathway in a cell, the method comprising contacting the cell with an effective amount of a compound according to claim 1 or a pharmaceutically acceptable salt or N-oxide thereof.

4. A method for treating type II diabetes in a subject, the method comprising administering to the subject an effective amount of a compound according to claim 1 or a pharmaceutically acceptable salt or N-oxide thereof.

5. A method for treating atherosclerosis in a subject, the method comprising administering to the subject an effective amount of a compound according to claim 1 or a pharmaceutically acceptable salt or N-oxide thereof.

6. A method for improving exercise efficiency in a subject, the method comprising administering to the subject an effective amount of a compound according to claim 1 or a pharmaceutically acceptable salt or N-oxide thereof.

7. A method for treating intermittent claudication, the method comprising administering to the subject an effective amount of a compound according to claim 1 or a pharmaceutically acceptable salt or N-oxide thereof.

8. The compound of claim 1, having the structural formula

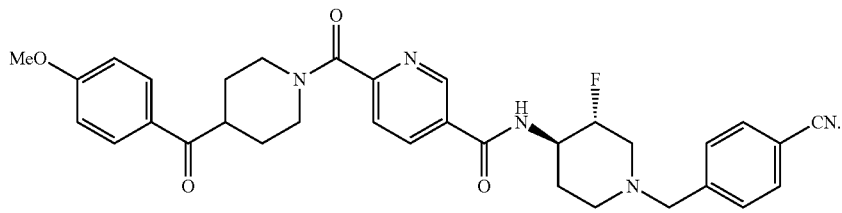 [SMILES: COc1ccc(C(=O)C2CCN(C(=O)c3ccc(C(=O)N[C@@H]4CCN(Cc5ccc(C#N)cc5)C[C@H]4F)cn3)CC2)cc1]

9. A pharmaceutical composition comprising:
at least one pharmaceutically acceptable carrier, diluent or excipient; and
a compound according to claim 8 or a pharmaceutically acceptable salt or N-oxide thereof.

10. A method for activating the AMPK pathway in a cell, the method comprising contacting the cell with an effective amount of a compound according to claim 8 or a pharmaceutically acceptable salt or N-oxide thereof.

11. A method for treating type II diabetes in a subject, the method comprising administering to the subject an effective amount of a compound according to claim 8 or a pharmaceutically acceptable salt or N-oxide thereof.

12. A method for treating atherosclerosis in a subject, the method comprising administering to the subject an effective amount of a compound according to claim 8 or a pharmaceutically acceptable salt or N-oxide thereof.

13. A method for improving exercise efficiency in a subject, the method comprising administering to the subject an effective amount of a compound according to claim 8 or a pharmaceutically acceptable salt or N-oxide thereof.

14. A method for treating intermittent claudication, the method comprising administering to the subject an effective amount of a compound according to claim 8 or a pharmaceutically acceptable salt or N-oxide thereof.

15. The compound of claim 1, having the structural formula

16. A pharmaceutical composition comprising:
at least one pharmaceutically acceptable carrier, diluent or excipient; and a compound according to claim 15 or a pharmaceutically acceptable salt or N-oxide thereof.

17. A method for activating the AMPK pathway in a cell, the method comprising contacting the cell with an effective amount of a compound according to claim 15 or a pharmaceutically acceptable salt or N-oxide thereof.

18. A method for treating type II diabetes in a subject, the method comprising administering to the subject an effective amount of a compound according to claim 15 or a pharmaceutically acceptable salt or N-oxide thereof.

19. A method for treating atherosclerosis in a subject, the method comprising administering to the subject an effective amount of a compound according to claim 15 or a pharmaceutically acceptable salt or N-oxide thereof.

20. A method for improving exercise efficiency in a subject, the method comprising administering to the subject an effective amount of a compound according to claim 15 or a pharmaceutically acceptable salt or N-oxide thereof.

21. A method for treating intermittent claudication, the method comprising administering to the subject an effective amount of a compound according to claim 15 or a pharmaceutically acceptable salt or N-oxide thereof.

22. A compound according to claim 1, wherein the compound is racemic.

23. A compound according to claim 8, wherein the compound is substantially enantiomerically pure.

24. A compound according to claim 15, wherein the compound is substantially enantiomerically pure.

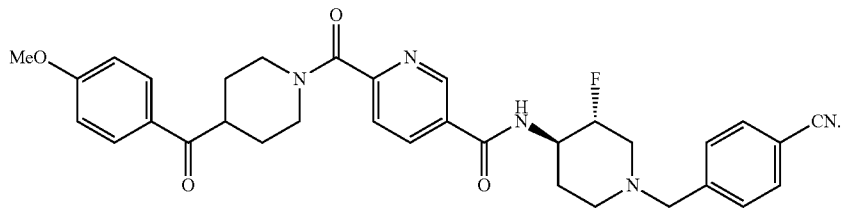 [SMILES: COc1ccc(C(=O)C2CCN(C(=O)c3ccc(C(=O)N[C@@H]4CCN(Cc5ccc(C#N)cc5)C[C@H]4F)cn3)CC2)cc1]

* * * * *